(12) United States Patent
Casarez et al.

(10) Patent No.: US 7,893,264 B2
(45) Date of Patent: *Feb. 22, 2011

(54) ANTIVIRAL PHOSPHINATE COMPOUNDS

(75) Inventors: Anthony Casarez, Princeton, NJ (US);
Kleem Chaudhary, Concord, MA (US);
Aesop Cho, Mountain View, CA (US);
Michael Clarke, Redwood City, CA (US); Edward Doerffler, Foster City, CA (US); Maria Fardis, San Carlos, CA (US); Choung U. Kim, San Carlos, CA (US); Hyungjung Pyun, Fremont, CA (US); Xiaoning C. Sheng, Foster City, CA (US); Jianying Wang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 396 days.

This patent is subject to a terminal disclaimer.

(21) Appl. No.: 11/825,606

(22) Filed: Jul. 6, 2007

(65) Prior Publication Data

US 2008/0057031 A1    Mar. 6, 2008

Related U.S. Application Data

(60) Provisional application No. 60/819,488, filed on Jul. 7, 2006, provisional application No. 60/832,908, filed on Jul. 24, 2006.

(51) Int. Cl.
*C07D 221/18* (2006.01)
*C07F 9/02* (2006.01)
*A61K 38/12* (2006.01)

(52) U.S. Cl. .................. 546/23; 544/243; 530/317

(58) Field of Classification Search .................. 546/23; 544/243; 530/317
See application file for complete search history.

(56) References Cited

U.S. PATENT DOCUMENTS

| | | |
|---|---|---|
| 4,816,570 A | 3/1989 | Farquhar |
| 4,968,788 A | 11/1990 | Farquhar |
| 5,496,592 A | 3/1996 | Saito |
| 5,663,159 A | 9/1997 | Starrett, Jr. et al. |
| 5,792,756 A | 8/1998 | Starrett, Jr. et al. |
| 6,004,977 A | 12/1999 | Kurys et al. |

FOREIGN PATENT DOCUMENTS

| | | |
|---|---|---|
| EP | 0 632 048 | 3/2001 |
| WO | WO 91/19721 | 12/1991 |
| WO | WO 94/21604 | 9/1994 |
| WO | WO 95/07920 | 3/1995 |
| WO | WO 96/15111 | 5/1996 |
| WO | WO 2006/020276 | 2/2006 |
| WO | WO-2006/109085 | 10/2006 |
| WO | WO-2007/014922 | 2/2007 |

OTHER PUBLICATIONS

Fray et all. (2006) "Synthesis of Substituted 5-aminomethyl tetrahydro-isoquinolines and dihydro-isoindoles," Tetrahedron 62(29):6869-6875.

Alexander et al. "Investigation of (Oxodioxolenyl)methyl Carbamates as Nonchiral Bioreversible Prodrug Moieties for Chiral Amines. "39:480-486; J Med Chem., 1996.

Benzaria et al. "Synthesis, In Vitro Antiviral Evaluation, and Stability Studies of Bis(S-acyl-2-thioethyl) Ester Derviatives . . . "39:4958-4965;J Med Chem., 1996.

Bundgaard et al. "Design and Application of Prodrugs."pp. 113-191;Textbook of Drug Design and Development., 1991.

De Lombaert et al. "N-Phosphonomethyl dipeptides and Their Phosphonate Prodrugs, a New Generation of Neutral Endopeptidase . . . "37:498-511;J Med Chem.,1994.

Eliel et al. "Separation of Enantiomers Via Diastereomers," pp. 322-381;Stereochem Org Comp., 1994.

Farquhar et al. "Biologically Reversible Phosphate-Protective Groups." 72:324-325;J Pharm Sci.,1983.

Jacob III, Peyton "Resolution of ( )-5-Bromonornicotine. Synthesis of (R)- and (S)- Nornicotine of High Enantiomeric Purity." 47:4165-4167;J Org Chem.,1982.

Khamnei et al. "Neighboring Group Catalysis in the Design of Nucleotide Prodrugs."39:4109-4115; J Med Chem., 1996.

Lochmuller et al."Chromatographic Resolution of Enantiomers Selective Review." 113:283-302;J Chromatog., 1975.

Mitchell et al. "Bioreversible Protection for the Phospho Group: Bioactivation of the Di(4 acyloxybenzyl) and Mono(4-acyloxybenzy. "2345;J Chem Soc Perkin Trans I., 1992.

Okamoto "Optical resolution of dihydropyridine enantiomers by High-performance liquid chromatography using phenycarbamates ." 513:375-378;Journal of Chromatography., 1990.

Paquette, Leo A. "Three-Membered Rings with One Hetero Atom. "Chptr:1;Principals of Modern Heterocyclic Chemistry.,1968.

Paquette, Leo A. "The Four-Membered Heterocycles. "Chptr:3;Principals of Modern Heterocyclic Chemistry.,1968.

Paquette, Leo A. "Furan, Pyrrole, and Thiophene" Chptr:4;Principals of Modern Heterocyclic Chemistry.,1968.

Paquette, Leo A. "The Azoles." Chptr:6;Principals of Modern Heterocyclic Chemistry.,1968.

Paquette, Leo A. "The Pyridine Group." Chptr:7;Principals of Modern Heterocyclic Chemistry.,1968.

Paquette, Leo A."The Diazines and S-Triazine." Chptr:9;Principals of Modern Heterocyclic Chemistry.,1968.

Puech et al. "Intracellular delivery of nucleoside monophosphates through a reuctase-mediated activation process." 22:155-174;Antiviral Res.,1993.

Sakamoto et al. "Studies on Prodrugs. II. Preparation and Characterization of (5-Substituted 2-Oxo-1,3-dioxolen-4-yl)methyl . . . " 32(6):2241-2248;Chem Pharm Bull.,1983.

(Continued)

Primary Examiner—Nizal S Chandrakumar

(57) ABSTRACT

The invention is related to anti-viral phosphinate compounds, compositions containing such compounds, and therapeutic methods that include the administration of such compounds, as well as to processes and intermediates useful for preparing such compounds.

47 Claims, No Drawings

OTHER PUBLICATIONS

Stuttgart, Georg Thieme Verlag "An Overview." p. 1-20;Protecting Groups.,1994.
Stuttgart, Georg Thieme "Hydroxyl Protecting Groups." p. 21-94;Protecting Groups.,1994.
Stuttgart, Georg Thieme "Diol Protecting Groups." p. 95-117;Protecting Groups.,1994.
Stuttgart, Georg Thieme "Carboxyl Protecting Groups." p. 118-154;Protecting Groups.,1994.
Stuttgart, Georg Thieme "Carbonyl Protecting Groups." p. 155-184;Protecting Groups., 1994.

ANTIVIRAL PHOSPHINATE COMPOUNDS

PRIORITY OF INVENTION

This application claims priority to U.S. Provisional Application No. 60/832,908 filed 24 Jul. 2006, and to U.S. Provisional Application No. 60/819,488 filed 7 Jul. 2006.

FIELD OF THE INVENTION

The invention relates generally to phosphinate compounds with HCV inhibitory activity.

BACKGROUND OF THE INVENTION

Hepatitis C is recognized as a chronic viral disease of the liver which is characterized by liver disease. Although drugs targeting the liver are in wide use and have shown effectiveness, toxicity and other side effects have limited their usefulness. Inhibitors of HCV are useful to limit the establishment and progression of infection by HCV as well as in diagnostic assays for HCV.

There is a need for new HCV therapeutic agents.

SUMMARY OF THE INVENTION

In one embodiment the invention provides a compound of the invention which is a compound of formula I:

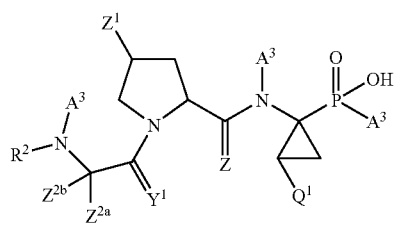

(I)

or a pharmaceutically acceptable salt, or prodrug thereof, wherein:

$R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is selected from,
a) —C($Y^1$)($A^3$),
b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or
  where said alkyl, cycloalkyl and alkyl-cycloalkyl may optionally be mono- or di-substituted with substituents selected from hydroxy and O—(C1-4)alkyl, or
  where each of said alkyl-groups may optionally be mono-, di- or tri-substituted with halogen, or
  where each of said cycloalkyl groups being 5-, 6- or 7-membered, one or two —CH$_2$— group not being directly linked to each other may be optionally substituted replaced by —O— such that the O-atom is linked to the N atom to which $R^2$ is attached via at least two C-atoms, c) phenyl, (C1-3)alkyl-phenyl, heteroaryl or (C1-3)alkyl-heteroaryl,
  wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3)alkyl may optionally be substituted with one or more halogen; or d) —S(O)$_2$($A^3$);

$R^3$ is H or (C1-6)alkyl;

$Y^1$ is independently O, S, N($A^3$), N(O)($A^3$), N(O$A^3$), N(O)(O$A^3$) or N(N($A^3$)($A^3$));

Z is O, S, or N$R^3$;

$Z^1$ is selected from the following structures:

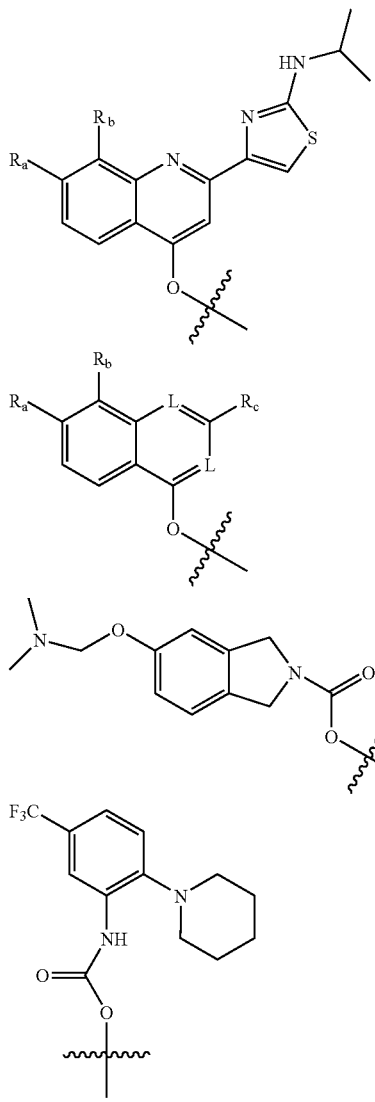

$R_a$ is H or (C1-6)alkoxy;
$R_b$ is H, F, Cl, Br, I, or (C1-6)alkyl;
$R_c$ is H, cyano, F, Cl, Br, I, —C(=O)N$R_d R_e$, (C1-6)alkoxy, or phenyl that is optionally substituted with one or more F, Cl, Br, I, (C1-6)alkyl, or (C1-6)alkoxy;
$R_d$ and $R_e$ are each independently H or (C1-6)alkyl;

each L is independently CH or N;

$Z^{2a}$ is H, (C1-10)alkyl, (C2-10)alkenyl, (C2-10)alkynyl, wherein any carbon atom may optionally be replaced with a heteroatom selected from O, S or N, or $Z^{2a}$ optionally forms a heterocycle with one or more $R^1$, $R^2$, $Q^1$, or $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl; or $Q^1$ and $Z^{2a}$ taken together with the atoms to which they are attached form a heterocycle, which heterocycle may optionally be substituted with one or more oxo (=O) or $A^3$;

$A^3$ is independently selected from PRT, H, —OH, —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, —C($A^2$)$_3$, —C($A^2$)$_2$—C(O)$A^2$, —C(O)$A^2$, —C(O)O$A^2$, —O($A^2$), —N($A^2$)$_2$, —S($A^2$), —$CH_2$P($Y^1$)($A^2$)(O$A^2$), —$CH_2$P($Y^1$)($A^2$)(N($A^2$)$_2$), —$CH_2$P($Y^1$)(O$A^2$)(O$A^2$), —O$CH_2$P($Y^1$)(O$A^2$)(O$A^2$), —O$CH_2$P($Y^1$)($A^2$)(O$A^2$), —O$CH_2$P($Y^1$)($A^2$)(N($A^2$)$_2$), —C(O)O$CH_2$P($Y^1$)(O$A^2$)(O$A^2$), —C(O)O$CH_2$P($Y^1$)($A^2$)(O$A^2$), —C(O)O$CH_2$P($Y^1$)($A^2$)(N($A^2$)$_2$), —$CH_2$P($Y^1$)(O$A^2$)(N($A^2$)$_2$), —O$CH_2$P($Y^1$)(O$A^2$)(N($A^2$)$_2$), —C(O)O$CH_2$P($Y^1$)(O$A^2$)(N($A^2$)$_2$), —$CH_2$P($Y^1$)(N($A^2$)$_2$)(N($A^2$)$_2$), —C(O)O$CH_2$P($Y^1$)(N($A^2$)$_2$)(N($A^2$)$_2$), —O$CH_2$P($Y^1$)(N($A^2$)$_2$)(N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide, wherein each $A^3$ may be optionally substituted with 1 to 4 —$R^1$, —P($Y^1$)(O$A^2$)(O$A^2$), —P($Y^1$)(O$A^2$)(N($A^2$)$_2$), —P($Y^1$)($A^2$)(O$A^2$), —P($Y^1$)($A^2$)(N($A^2$)$_2$), or P($Y^1$)(N($A^2$)$_2$)(N($A^2$)$_2$), —C(=O)N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with $R^1$;

Optionally each independent instance of $A^3$ and $Q^1$ can be taken together with one or more $A^3$ or $Q^1$ groups to form a ring;

$A^2$ is independently selected from PRT, H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention also provides a pharmaceutical composition comprising a compound of the invention and at least one pharmaceutically acceptable carrier.

The present invention also provides a pharmaceutical composition for use in treating disorders associated with HCV.

The present invention also provides a pharmaceutical composition further comprising a nucleoside analog.

The present invention also provides for a pharmaceutical composition further comprising an interferon or pegylated interferon.

The present invention also provides for a pharmaceutical composition wherein said nucleoside analogue is selected from ribavirin, viramidine levovirin, a L-nucleoside, and isatoribine and said interferon is α-interferon or pegylated interferon.

The present invention also provides for a method of treating disorders associated with hepatitis C, said method comprising administering to an individual a pharmaceutical composition which comprises a therapeutically effective amount of a compound of the invention.

The present invention also provides a method of inhibiting HCV, comprising administering to a mammal afflicted with a condition associated with HCV activity, an amount of a compound of the invention, effective to inhibit HCV.

The present invention also provides a compound of the invention for use in medical therapy (preferably for use in inhibiting HCV or treating a condition associated with HCV activity), as well as the use of a compound of the invention for the manufacture of a medicament useful for inhibiting HCV or the treatment of a condition associated with HCV activity in a mammal.

The present invention also provides synthetic processes and novel intermediates disclosed herein which are useful for preparing compounds of the invention. Some of the compounds of the invention are useful to prepare other compounds of the invention.

In another aspect the invention provides a method of inhibiting HCV activity in a sample comprising treating the sample with a compound of the invention.

In one embodiment the invention provides a compound having improved inhibitory or pharmacokinetic properties, including enhanced activity against development of viral resistance, improved oral bioavailability, greater potency or extended effective half-life in vivo. Certain compounds of the invention may have fewer side effects, less complicated dosing schedules, or be orally active.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Compounds of the Invention

The compounds of the invention exclude compounds heretofore known. However it is within the invention to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

Whenever a compound described herein is substituted with more than one of the same designated group, e.g., "$R^1$" or "$A^3$", then it will be understood that the groups may be the same or different, i.e., each group is independently selected.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$).

"Alkenyl" is C$_2$-C$_{18}$ hydrocarbon containing normal, secondary, tertiary or cyclic carbon atoms with at least one site of unsaturation, i.e. a carbon-carbon, sp$^2$ double bond. Examples include, but are not limited to, ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkynyl" is C$_2$-C$_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH$_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O$^-$, —OR, —SR, —S$^-$, —NR$_2$, —NR$_3$, ═NR, —CX$_3$, —CN, —OCN, —SCN, —N═C═O, —NCS, —NO, —NO$_2$, ═N$_2$, —N$_3$, NC(═O)R, —C(═O)R, —C(═O)NRR —S(═O)$_2$O$^-$, —S(═O)$_2$OH, —S(═O)$_2$R, —OS(═O)$_2$OR, —S(═O)$_2$NR, —S(═O)R, —OP(═O)O$_2$RR, —P(═O)O$_2$RR —P(═O)(O$^-$)$_2$, —P(═O)(OH)$_2$, —C(═O)R, —C(═O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

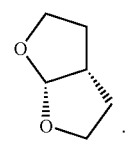

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo [4,5], [5,5], [5,6] or [6,6] system, or 9 or 10 ring atoms arranged as a bicyclo [5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. When $Q^1$ and $Z^{2a}$ taken together with the atoms to which they are attached form a heterocycle, the heterocycle formed by $Q^1$ and $Z^{2a}$ taken together with the atoms to which they are attached may typically comprise up to about 25 atoms.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The term "PRT" is selected from the terms "prodrug moiety" and "protecting group" as defined herein.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (-) are employed to designate the sign of rotation of plane-polarized light by the compound, with (-) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The invention includes all stereoisomers of the compounds described herein.

Prodrugs

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2C(=O)R^9$ and acyloxymethyl carbonates —$CH_2C(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC)—$CH_2C(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

$A^3$ and $A^2$ may be H, alkyl, or an ether- or ester-forming group. "Ether-forming group" means a group which is capable of forming a stable, covalent bond between the parental molecule and a group having the formula:

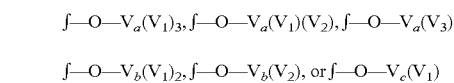

Wherein $V_a$ is a tetravalent atom typically selected from C and Si; $V_b$ is a trivalent atom typically selected from B, Al, N, and P, more typically N and P; $V_c$ is a divalent atom typically selected from O, S, and Se, more typically S; $V_1$ is a group bonded to $V_a$, $V_b$ or $V_c$ by a stable, single covalent bond, typically $V_1$ is $A^2$ groups; $V_2$ is a group bonded to $V_a$ or $V_b$ by a stable, double covalent bond, provided that $V_2$ is not =O, =S or =N—, typically $V_2$ is =C(V_1)_2 wherein $V_1$ is as described above; and $V_3$ is a group bonded to $V_a$ by a stable, triple covalent bond, typically $V_3$ is ʃC(V_1) wherein $V_1$ is as described above.

"Ester-forming group" means a group which is capable of forming a stable, covalent bond between the parental molecule and a group having the formula:

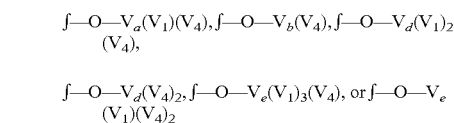

Wherein $V_a$, $V_b$, and $V_1$, are as described above; $V_d$ is a pentavalent atom typically selected from P and N; $V_e$ is a hexavalent atom typically S; and $V_4$ is a group bonded to $V_a$, $V_b$, $V_d$ or $V_e$ by a stable, double covalent bond, provided that at least one $V_4$ is =O, =S or =N—$V_1$, typically $V_4$, when other than =O, =S or =N—, is =C($V_1$)$_2$ wherein $V_1$ is as described above.

Protecting groups for —OH functions (whether hydroxy, acid or other functions) are embodiments of "ether- or ester-forming groups". Particularly of interest are ether- or ester-forming groups that are capable of functioning as protecting groups in the synthetic schemes set forth herein. However, some hydroxyl and thio protecting groups are neither ether- nor ester-forming groups, as will be understood by those skilled in the art, and are included with amides, discussed below, and are capable of protecting hydroxyl or thio groups such that hydrolysis from the parental molecule yields hydroxyl or thio.

In its ester-forming role, $A^3$ or $A^2$ typically is bound to any acidic group such as, by way of example and not limitation, a —CO$_2$H or —C(S)OH group, thereby resulting in —CO$_2$A$^2$ or —CO$_2$A$^3$. $A^2$ for example is deduced from the enumerated ester groups of WO 95/07920.

Examples of $A^2$ include $C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R_1$—O—$C_1$-$C_{12}$ alkylene, $C_1$-$C_{12}$ alkoxy, CN, NO$_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-, 3- and 4-acetylphenyl, 1,8-dihydroxynaphthyl(—$C_{10}H_6$—OH) and aryloxy ethyl [$C_6$-$C_9$ aryl (including phenoxy ethyl)], 2,2'-dihydroxybiphenyl, 2-, 3- and 4-N,N-dialkylaminophenol, —$C_6H_4CH_2$—N(CH$_3$)$_2$, trimethoxybenzyl, triethoxybenzyl, 2-alkyl pyridinyl ($C_{1-4}$ alkyl);

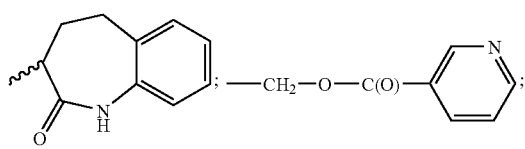

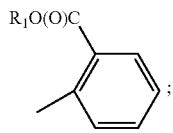

$C_4$-$C_8$ esters of 2-carboxyphenyl; and $C_1$-$C_4$ alkylene-$C_3$-$C_6$ aryl (including benzyl, —CH$_2$-pyrrolyl, —CH$_2$-thienyl, —CH$_2$-imidazolyl, —CH$_2$-oxazolyl, —CH$_2$-isoxazolyl, —CH$_2$-thiazolyl, —CH$_2$-isothiazolyl, —CH$_2$-pyrazolyl, —CH$_2$-pyridinyl and —CH$_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —CH$_2$—CCl$_3$), $C_1$-$C_{12}$ alkyl (including methyl and ethyl), $C_2$-$C_{12}$ alkenyl or $C_2$-$C_{12}$ alkynyl;

alkoxy ethyl [$C_1$-$C_6$ alkyl including —CH$_2$—CH$_2$—O—CH$_3$ (methoxy ethyl)];

alkyl substituted by any of the groups set forth above for aryl, in particular OH or by 1 to 3 halo atoms (including —CH$_3$, —CH(CH$_3$)$_2$, —C(CH$_3$)$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, CH$_2$CH$_2$F, —CH$_2$CH$_2$Cl, —CH$_2$CF$_3$, and —CH$_2$CCl$_3$);

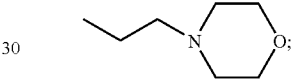

—N-2-propylmorpholino, 2,3-dihydro-6-hydroxyindene, sesamol, catechol monoester, —CH$_2$—C(O)—N(R$^1$)$_2$, —CH$_2$—S(O)(R$^1$), —CH$_2$—S(O)$_2$(R$^1$), —CH$_2$—CH(OC(O)CH$_2$R$^1$)—CH$_2$(OC(O)CH$_2$R$^1$), cholesteryl, enolpyruvate (HOOC—C(=CH$_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* 5(6):670-671 [1974]);

cyclic carbonates such as (5-R$_d$-2-oxo-1,3-dioxolen-4-yl) methyl esters (Sakamoto et al., *Chem. Pharm. Bull.* 32(6) 2241-2248 [1984]) where R$_d$ is R$_1$, R$_4$ or aryl; and

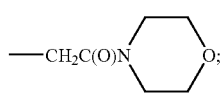

The hydroxyl groups of the compounds of this invention optionally are substituted with one of groups III, IV or V disclosed in WO94/21604, or with isopropyl.

As further embodiments, Table A lists examples of $A^2$ ester moieties that for example can be bonded via oxygen to —C(O)O— and —P(O)(R)(O—) groups. Several amidates also are shown, which are bound directly to —C(O)— or —P(O)$_2$. Esters of structures 1-5, 8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, CsCO$_3$, N,N-dimethylaniline and the like) in DMF (or other solvent such as acetonitrile or N-methylpyrrolidone). When A$^3$ is phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

1. —CH$_2$—C(O)—N(R$_1$)$_2$*
2. —CH$_2$—S(O)(R$_1$)
3. —CH$_2$—S(O)$_2$(R$_1$)
4. —CH$_2$—O—C(O)—CH$_2$—C$_6$H$_5$
5. 3-chloesteryl
6. 3-pyridyl
7. N-ethylmorpholino
8. —CH$_2$—O—C(O)—C$_6$H$_5$
9. —CH$_2$—O—C(O)—CH$_2$CH$_3$
10. —CH$_2$—O—C(O)—C(CH$_3$)$_3$
11. —CH$_3$—CCl$_3$
12. —C$_6$H$_5$
13. —NH—CH$_2$—C(O)O—CH$_2$CH$_3$
14. —N(CH$_3$)—CH$_2$—C(O)O—CH$_2$CH$_3$
15. —NHR$_1$
16. —CH$_2$—O—C(O)—C$_{10}$H$_{15}$
17. —CH$_2$—O—C(O)—CH(CH$_3$)$_2$
18. —CH$_2$—C#H(OC(O)CH$_2$R$_1$)—CH$_2$—(OC(O)CH$_2$R$_1$)*

19.

—CH$_2$C(O)N⟨tetrahydropyran⟩

20.

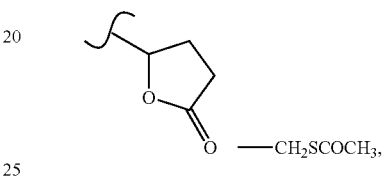

21. HO—⟨cyclohexane with OH, HO, HO⟩

22.

—CH$_2$—O—C(O)—⟨3-pyridyl⟩

23.

—CH$_2$CH$_2$—⟨2-pyridyl⟩

24. CH$_3$O(O)C—⟨2-methylphenyl⟩

25. CH$_3$CH$_2$O(O)C—⟨2-methylphenyl⟩

TABLE A-continued

26.

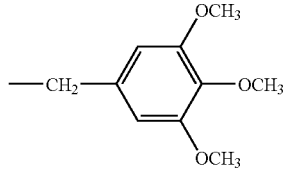

-chiral center is (R), (S) or racemate.

Other esters that are suitable for use herein are described in European Patent No. 632,048.

A$^2$ also includes "double ester" forming profunctionalities such as —CH$_2$OC(O)OCH$_3$,

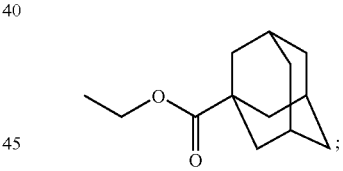

—CH$_2$OCON(CH$_3$)$_2$, or alkyl- or aryl-acyloxyalkyl groups of the structure —CH(R$^1$)O((CO)R$_{37}$) or —CH(R$^1$)((CO)OR$_{38}$) (linked to oxygen of the acidic group) wherein R$_{37}$ and R$_{38}$ are alkyl, aryl, or alkylaryl groups (see U.S. Pat. No. 4,968,788). Frequently R$_{37}$ and R$_{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful A$^2$ groups are alkylacyloxymethyl esters and their derivatives, including —CH(CH$_2$CH$_2$OCH$_3$)OC(O)C(CH$_3$)$_3$, ⟨ethyl adamantane carboxylate structure⟩;

—CH$_2$OC(O)C$_{10}$H$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

For prodrug purposes, the ester typically chosen is one heretofore used for antiviral drugs, in particular the cyclic carbonates, double esters, or the phthalidyl, aryl or alkyl esters.

As noted A$^3$ or A$^2$ groups optionally are used to prevent side reactions with the protected group during synthetic procedures, so they function as protecting groups (PRT) during synthesis. For the most part the decision as to which groups to protect, when to do so, and the nature of the PRT will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect carboxyl, hydroxyl or amino groups. The order of deprotection to yield free groups is dependent upon the intended direction of the synthesis and the reaction conditions to be encountered, and may occur in any order as determined by the artisan.

In some embodiments the $A^2$ protected acidic group is an ester of the acidic group and $A^2$ is the residue of a hydroxyl-containing functionality. In other embodiments, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical $A^2$ esters for protecting $A^3$ acidic functionalities are also described in WO 95/07920, again understanding that the same esters can be formed with the acidic groups herein as with the phosphonate of the '920 publication. Typical ester groups are defined at least on WO 95/07920 pages 89-93 (under $R^{31}$ or $R^{35}$), the table on page 105, and pages 21-23 (as $R^1$). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or $C_1$-$C_4$ alkylestercarboxyphenyl (salicylate $C_1$-$C_{12}$ alkylesters).

The protected acidic groups $A^3$, particularly when using the esters or amides of WO 95/07920, are useful as prodrugs for oral administration. However, it is not essential that the $A^3$ acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical $A^2$ hydroxy protecting groups described in Greene (pages 14-118) include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Chloroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, $A^2$ hydroxy protecting groups include substituted methyl ethers, substituted benzyl ethers, silyl ethers, and esters including sulfonic acid esters, still more typically, trialkylsilyl ethers, tosylates and acetates.

Typical 1,2-diol protecting groups (thus, generally where two OH groups are taken together with the $A^2$ protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

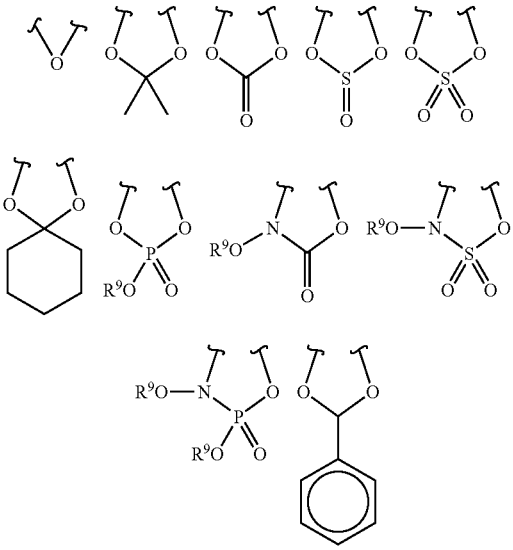

wherein $R^9$ is $C_1$-$C_6$ alkyl.

$A^2$ is also H, a protecting group for amino or the residue of a carboxyl-containing compound, in particular H, —C(O)$R^4$, an amino acid, a polypeptide or a protecting group not —C(O)$R_4$, amino acid or polypeptide. Amide-forming $A^2$ are found for instance in group $A^3$. When $A^2$ is an amino acid or polypeptide it has the structure $R_{15}$NHCH($R_{16}$)C(O)—, where $R_{15}$ is H, an amino acid or polypeptide residue, or $R_{15}$, and $R_{16}$ is defined below.

$R_{16}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R_{10}$ also is taken together with the amino acid αN to form a proline residue ($R_{10}$=—($CH_2$)$_3$—). However, $R_{10}$ is generally the side group of a naturally-occurring amino acid such as H, —$CH_3$, —CH($CH_3$)$_2$, —$CH_2$—CH($CH_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. $R_{10}$ also includes 1-guanidinoprop-3-yl, benzyl, 4-hydroxybenzyl, imidazol-4-yl, indol-3-yl, methoxyphenyl and ethoxyphenyl. $A^2$ are residues of carboxylic acids for the most part, but any of the typical amino protecting groups described by Greene at pages 315-385 are useful. They include Carbamates (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl); Substituted Ethyl (2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido) propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl) ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy) propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N-oxide), Imine Derivatives (N-1,1-dimethylthiomethylene, N-benzylidene, N-p-methoxybenzylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N—N Derivatives (N-nitro, N-nitroso, N-oxide); N—P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N—Si Derivatives; N—S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-☐-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)R$^1$ or —N═CR$^1$N(R$^1$)$_2$. Another protecting group, also useful as a prodrug at the A$^3$ site, particularly for amino or —NH(R$_5$), is:

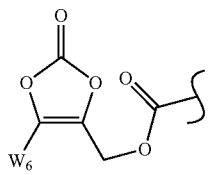

see for example Alexander, J. et al.; J. Med. Chem. 1996, 39, 480-486.

A$^2$ is also H or the residue of an amino-containing compound, in particular an amino acid, a polypeptide, a protecting group, —NHSO$_2$R$_4$, NHC(O)R$_4$, —N(R$_4$)$_2$, NH$_2$ or —NH(R$_4$)(H), whereby for example the carboxyl or phosphonic acid groups of A$^3$ are reacted with the amine to form an amide, as in —C(O) A$^2$, —P(O)(A$^2$)$_2$ or —P(O)(OH)(A$^2$). In general, A$^2$ has the structure R$_{17}$C(O)CH(R$_{16}$)NH—, where R$_{17}$ is OH, O A$^2$, OR$_5$, an amino acid or a polypeptide residue.

Amino acids are low molecular weight compounds, on the order of less than about 1,000 MW, that contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline.

When A$^2$ are single amino acid residues or polypeptides they usually are substituted at A$^3$. These conjugates are produced by forming an amide bond between a carboxyl group of the amino acid (or C-terminal amino acid of a polypeptide for example) and amino nitrogen. Similarly, conjugates are formed between A$^3$ and an amino group of an amino acid or polypeptide. Generally, only one of any site in the parental molecule is amidated with an amino acid as described herein, although it is within the scope of this invention to introduce amino acids at more than one permitted site. Usually, a carboxyl group of A$^3$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g. by A$^2$, esterified with A$^2$ or amidated with A$^2$. Similarly, the amino side chains R$_{16}$ optionally will be blocked with A$^2$ or substituted with R$_5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by A$^2$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid; β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, γ-hydroxynorvaline, δ-hydroxynorvaline and epsilon-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In embodiments where $A^3$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as $A^2$. When $A^3$ is phosphonate, the sequence -$X^4$-pro-$X^5$- (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., "Pharm Res." 9:969-978 (1992). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N (EC 3.4.11.2). In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A (EC 3.4.11.7), di- or tripeptides lacking amino acid residues on the N-terminal side of hydrophobic amino acids (leu, tyr, phe, val, trp) are poor substrates for endopeptidase 24.11 (EC 3.4.24.11), and peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

HCV-Inhibitory Compounds

The compounds of the invention include those with HCV-inhibitory activity as well as intermediate compounds that are useful for preparing the active compounds. The term "HCV-inhibitory compound" includes those compounds that inhibit HCV.

Typically, compounds of the invention have a molecular weight of from about 200 amu to about 10,000 amu; in a specific embodiment of the invention, compounds have a molecular weight of less than about 5000 amu; in another specific embodiment of the invention, compounds have a molecular weight of less than about 2500 amu; in another specific embodiment of the invention, compounds have a molecular weight of less than about 1000 amu; in another specific embodiment of the invention, compounds have a molecular weight of less than about 800 amu; in another specific embodiment of the invention, compounds have a molecular weight of less than about 600 amu; and in another specific embodiment of the invention, compounds have a molecular weight of less than about 600 amu and a molecular weight of greater than about 400 amu.

The compounds of the invention also typically have a log D(polarity) less than about 5. In one embodiment the invention provides compounds having a log D less than about 4; in another one embodiment the invention provides compounds having a log D less than about 3; in another one embodiment the invention provides compounds having a log D greater than about −5; in another one embodiment the invention provides compounds having a log D greater than about −3; and in another one embodiment the invention provides compounds having a log D greater than about 0 and less than about 3.

Selected substituents within the compounds of the invention are present to a recursive degree. In this context, "recursive substituent" means that a substituent may recite another instance of itself. Because of the recursive nature of such substituents, theoretically, a large number may be present in any given embodiment. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $A^3$, $A^2$ and $R^1$ are all recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. Whenever a compound described herein is substituted with more than one of the same designated group, e.g., "$R^1$" or "$A^3$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Cellular Accumulation

In one embodiment, the invention provides compounds capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. et al (2003) *Blood* 102(7):2532-2540). The compounds of this embodiment may further comprise a phosphonate or phosphonate prodrug. More typically, the phosphonate or phosphonate prodrug can have the structure $A^3$ as described herein.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the invention relates to methods of inhibiting the activity of HCV comprising the step of treating a sample suspected of containing HCV with a compound or composition of the invention.

Compounds of the invention may act as inhibitors of HCV, as intermediates for such inhibitors or have other utilities as described below. The inhibitors will generally bind to locations on the surface or in a cavity of the liver. Compounds binding in the liver may bind with varying degrees of reversibility. Those compounds binding substantially irreversibly are ideal candidates for use in this method of the invention. Once labeled, the substantially irreversibly binding compounds are useful as probes for the detection of HCV. Accordingly, the invention relates to methods of detecting NS3 in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino. In one embodiment the invention provides a compound of formula (I) that comprises or that is bound or linked to one or more detectable labels.

Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the compound of the invention to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in man.

However, in screening compounds capable of inhibiting HCV it should be kept in mind that the results of enzyme assays may not always correlate with cell culture assays. Thus, a cell based assay should typically be the primary screening tool.

Screens for HCV Inhibitors

Compounds of the invention are screened for inhibitory activity against HCV by any of the conventional techniques for evaluating enzyme activity. Within the context of the invention, typically compounds are first screened for inhibition of HCV in vitro and compounds showing inhibitory activity are then screened for activity in vivo. Compounds having in vitro Ki (inhibitory constants) of less then about $5 \times 10^{-6}$ M, typically less than about $1 \times 10^{-7}$ M and preferably less than about $5 \times 10^{-8}$ M are preferred for in vivo use. Useful in vitro screens have been described in detail.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention can also be used in combination with other active ingredients. Such combinations are selected based on the condition to be treated, cross-reactivities of ingredients and pharmaco-properties of the combination.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV-inhibitory activity of their own.

Methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing). Other methods suitable for preparing compounds of the invention are described in International Patent Application Publication Number WO 2006/020276.

A number of exemplary methods for the preparation of the compositions of the invention are provided below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

SPECIFIC EMBODIMENTS OF THE INVENTION

International Patent Application Publication Number WO 2006/020276 relates to certain specific compounds. In one specific embodiment of the invention, the compounds of the invention exclude the following compounds:

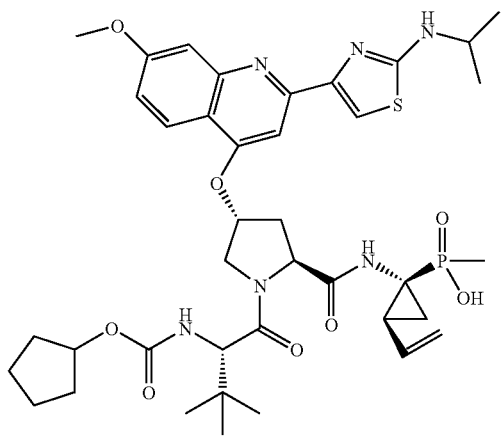

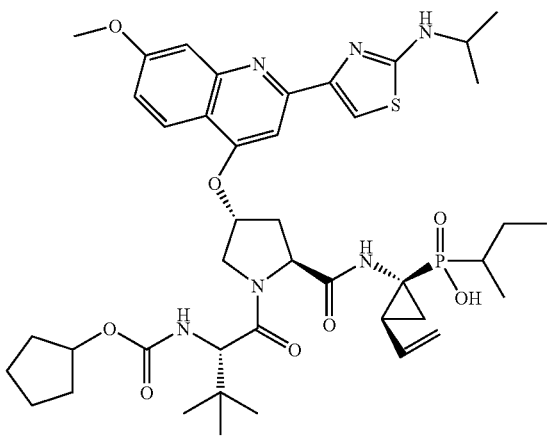

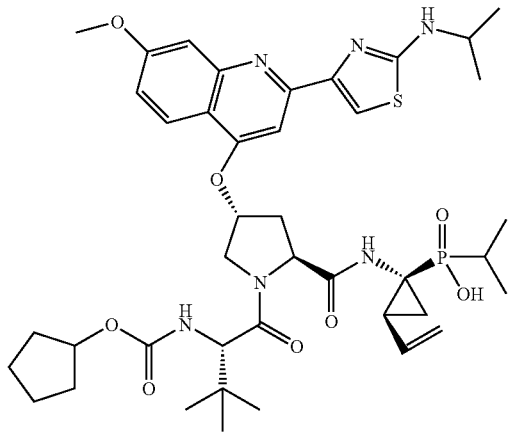

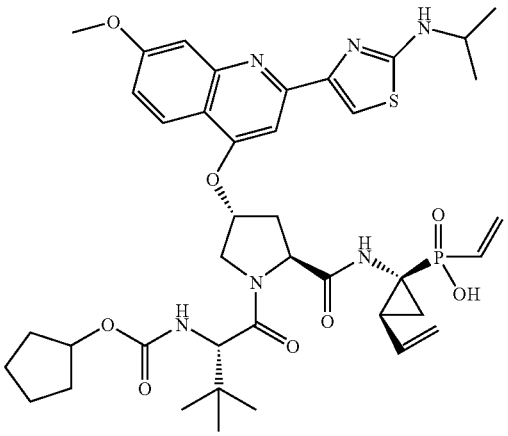

37
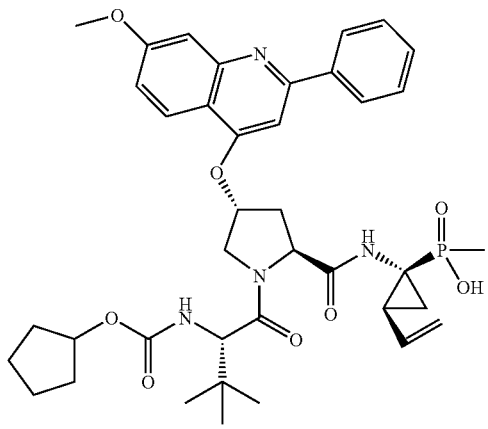
38
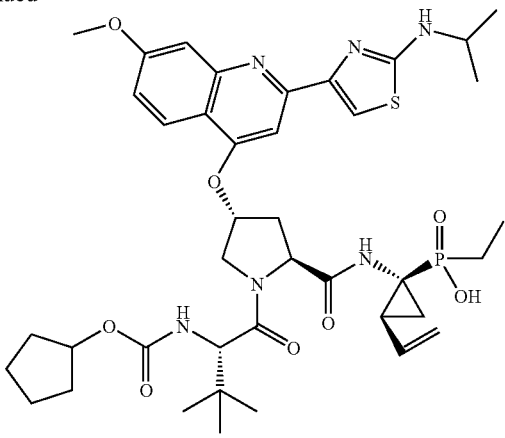
-continued
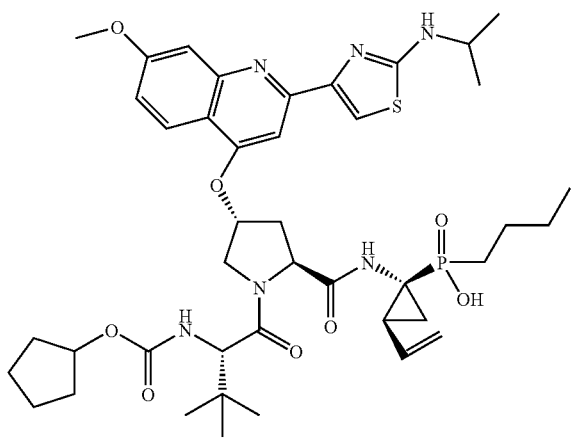
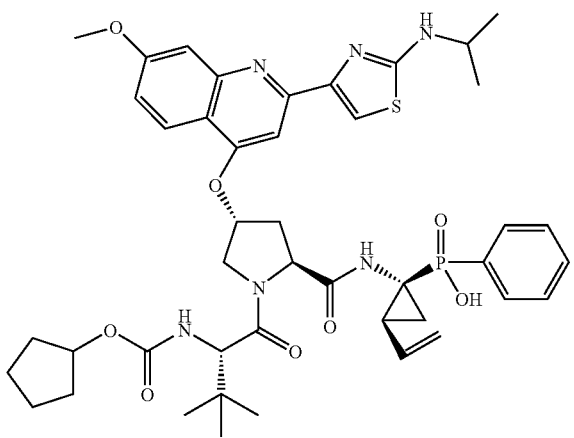
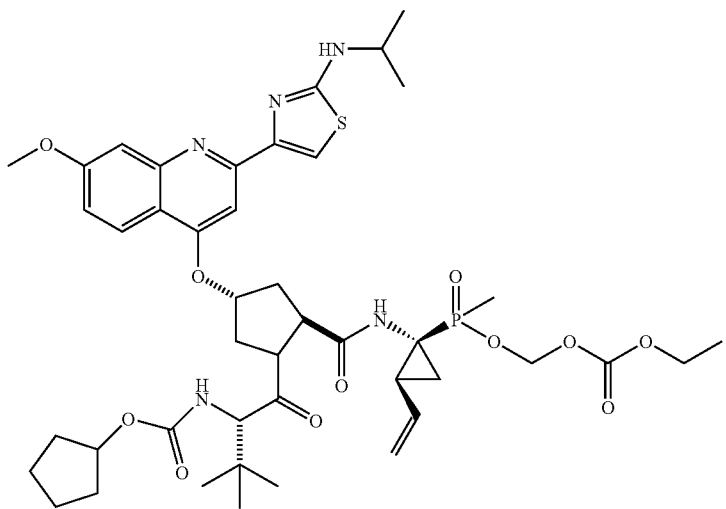

-continued
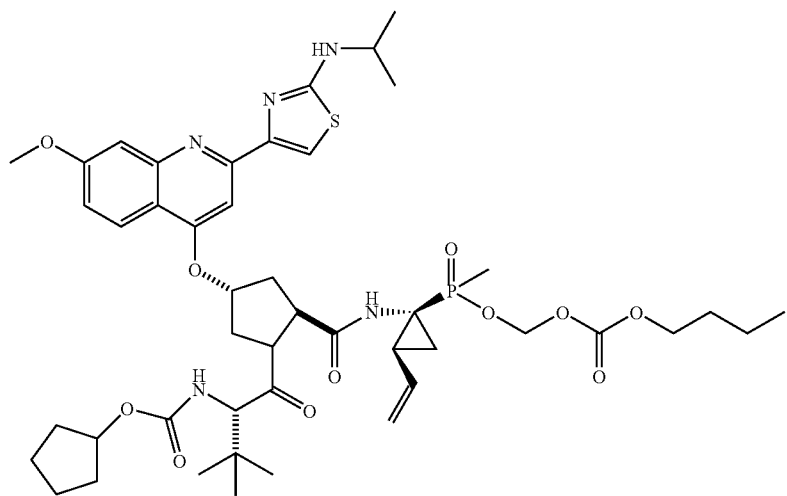
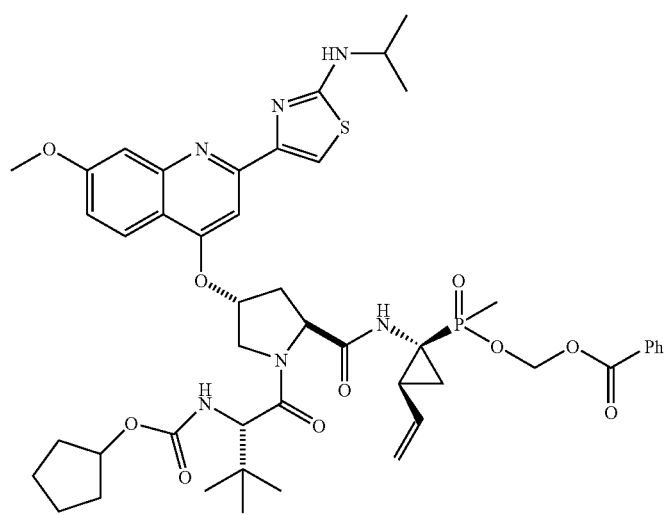
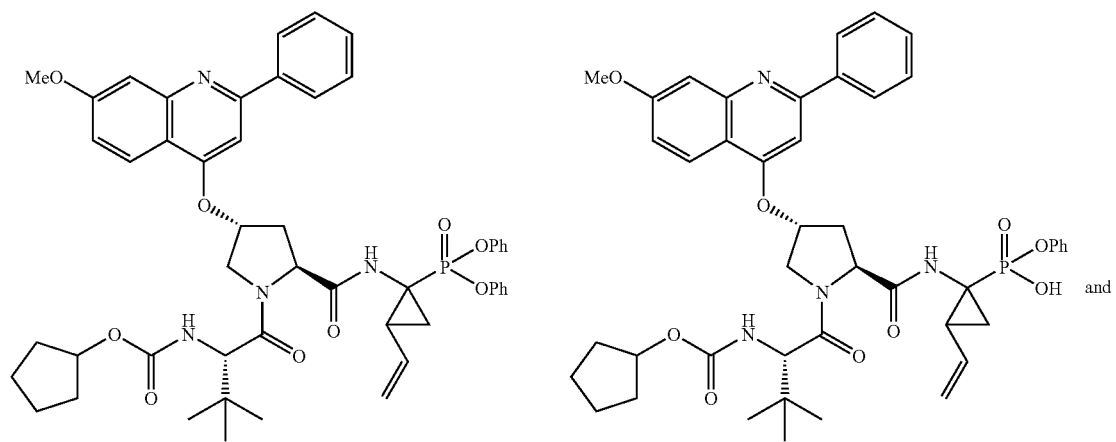

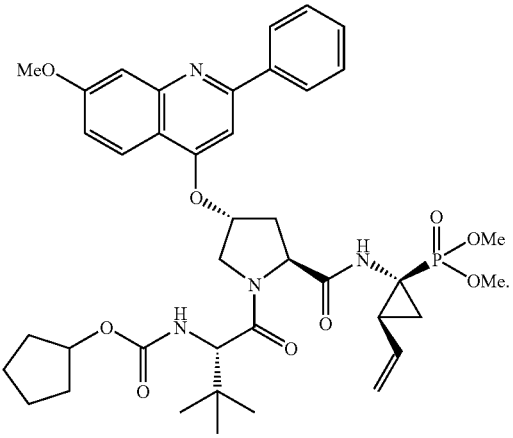

In another embodiment of the invention the compounds of the invention exclude the following compound:

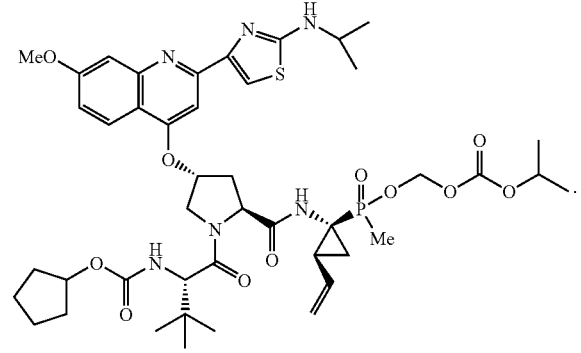

In another embodiment of the invention the compounds of the invention exclude a compound of formula (X):

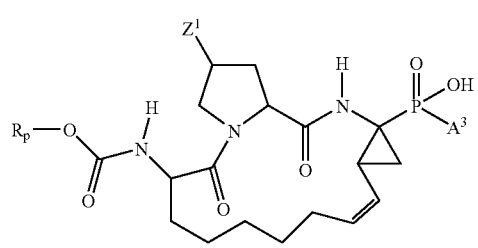

or a pharmaceutically acceptable salt, or prodrug thereof, wherein:

$R_p$ is cyclopentyl or tert-butyl;
$Z^1$ is selected from the following structures:

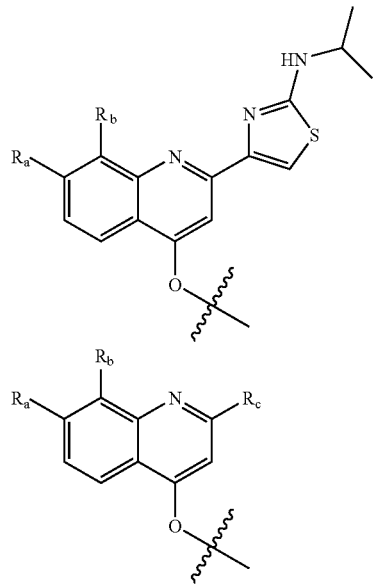

$R_a$ is methoxy;
$R_b$ is H;
$R_c$ is phenyl that is optionally substituted with one or more F, Cl, Br, I, (C1-6)alkyl, or (C1-6)alkoxy; and
$A^3$ has any of the values defined herein.

In another embodiment of the invention the compounds of the invention exclude a compound of formula (X):

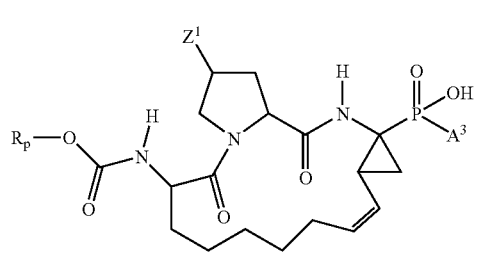

or a pharmaceutically acceptable salt, or prodrug thereof, wherein:

$R_p$ is (C1-6)alkyl or (C3-6)cycloalkyl;
$Z^1$ is selected from the following structures:

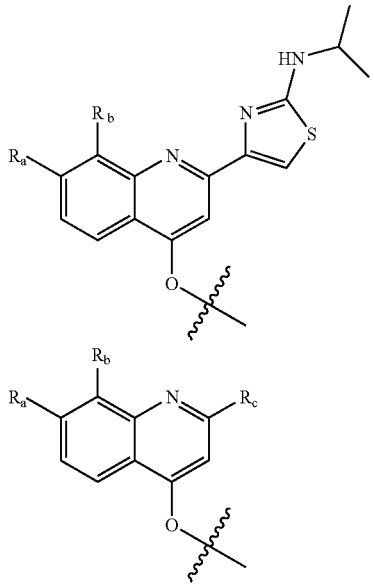

$R_a$ is methoxy;
$R_b$ is H;
$R_c$ is phenyl that is optionally substituted with one or more F, Cl, Br, I, (C1-6)alkyl, or (C1-6)alkoxy; and $A^3$ has any of the values defined herein.

In another embodiment of the invention the compounds of the invention exclude a compound of formula (X):

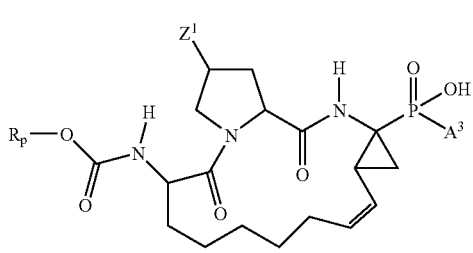

(X)

or a pharmaceutically acceptable salt, or prodrug thereof, wherein:

$R_p$ is cyclopentyl or tert-butyl;
$Z^1$ is selected from the following structures:

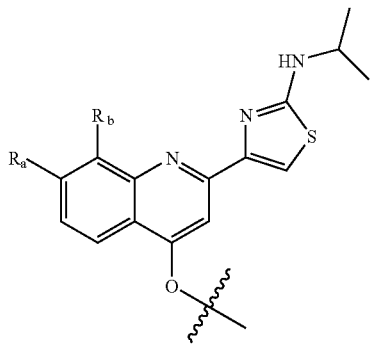

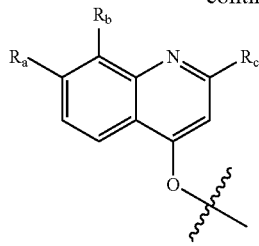

$R_a$ is (C1-6)alkoxy;
$R_b$ is H;
$R_c$ is phenyl that is optionally substituted with one or more F, Cl, Br, I, (C1-6)alkyl, or (C1-6)alkoxy; and
$A^3$ has any of the values defined herein.

In another embodiment of the invention the compounds of the invention exclude a compound of formula (X):

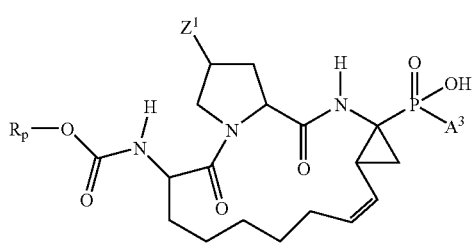

(X)

or a pharmaceutically acceptable salt, or prodrug thereof, wherein:

$R_p$ is (C1-6)alkyl or (C$_{3-6}$)cycloalkyl;
$Z^1$ is selected from the following structures:

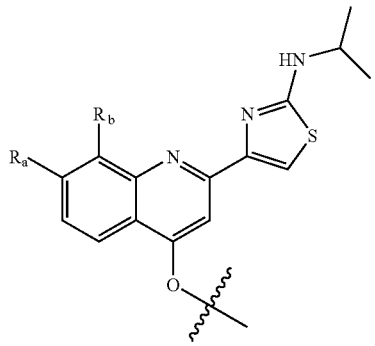

$R_a$ is (C1-6)alkoxy;
$R_b$ is H;
$R_c$ is phenyl that is optionally substituted with one or more F, Cl, Br, I, (C1-6)alkyl, or (C1-6)alkoxy; and
$A^3$ has any of the values defined herein.

In another embodiment of the invention the compounds of the invention exclude a compound of formula (XI):

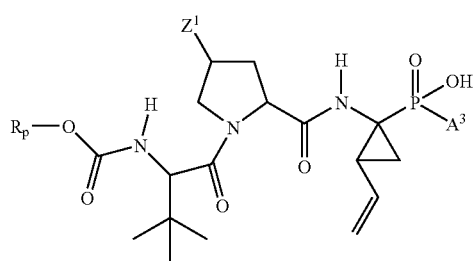

or a pharmaceutically acceptable salt, or prodrug thereof, wherein:
$R_p$ is cyclopentyl or tert-butyl;
$Z^1$ is selected from the following structures:

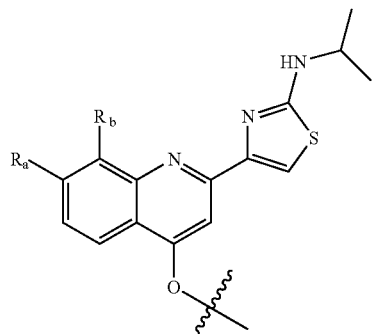

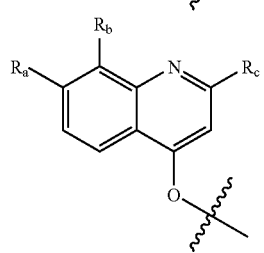

$R_a$ is methoxy;
$R_b$ is H;
$R_c$ is phenyl that is optionally substituted with one or more F, Cl, Br, I, (C1-6)alkyl, or (C1-6)alkoxy; and
$A^3$ has any of the values defined herein.

In another embodiment of the invention the compounds of the invention exclude a compound of formula (XI):

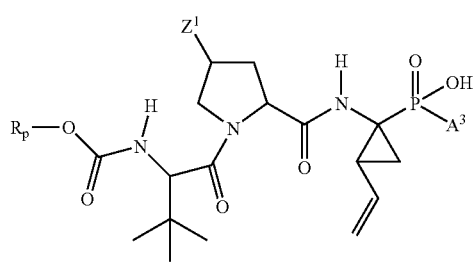

or a pharmaceutically acceptable salt, or prodrug thereof, wherein:
$R_p$ is (C1-6)alkyl or (C3-6)cycloalkyl;
$Z^1$ is selected from the following structures:

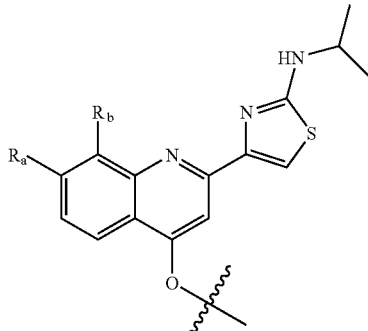

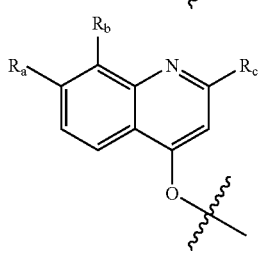

$R_a$ is methoxy;
$R_b$ is H;
$R_c$ is phenyl that is optionally substituted with one or more F, Cl, Br, I, (C1-6)alkyl, or (C1-6)alkoxy; and
$A^3$ has any of the values defined herein.

In another embodiment of the invention the compounds of the invention exclude a compound of formula (XI):

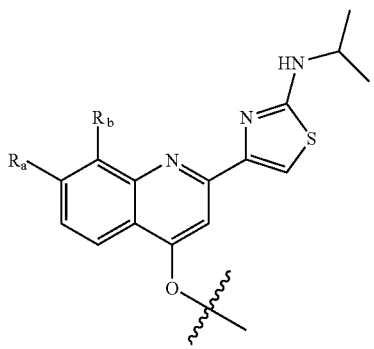

or a pharmaceutically acceptable salt, or prodrug thereof, wherein:
$R_p$ is cyclopentyl or tert-butyl;
$Z^1$ is selected from the following structures:

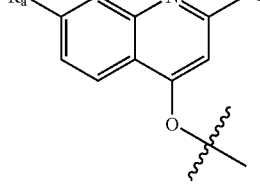

-continued

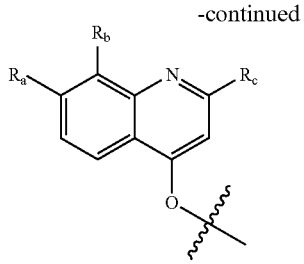

$R_a$ is (C1-6)alkoxy;
$R_b$ is H;
$R_c$ is phenyl that is optionally substituted with one or more F, Cl, Br, I, (C1-6)alkyl, or (C1-6)alkoxy; and
$A^3$ has any of the values defined herein.

In another embodiment of the invention the compounds of the invention exclude a compound of formula (XI):

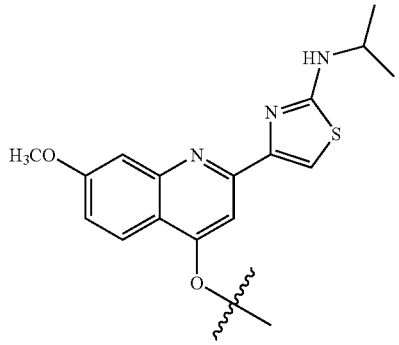

or a pharmaceutically acceptable salt, or prodrug thereof, wherein:
$R_p$ is (C1-6)alkyl or (C3-6)cycloalkyl;
$Z^1$ is selected from the following structures:

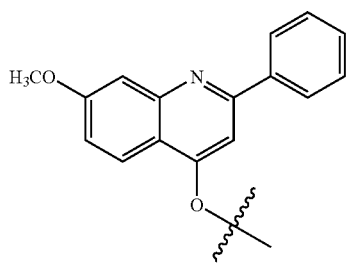

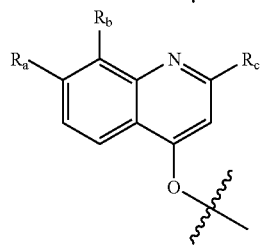

$R_a$ is (C1-6)alkoxy;
$R_b$ is H;
$R_c$ is phenyl that is optionally substituted with one or more F, Cl, Br, I, (C1-6)alkyl, or (C1-6)alkoxy; and
$A^3$ has any of the values defined herein.

In a specific embodiment of the invention $Z^1$ is selected from the following structures:

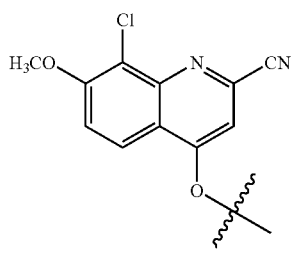

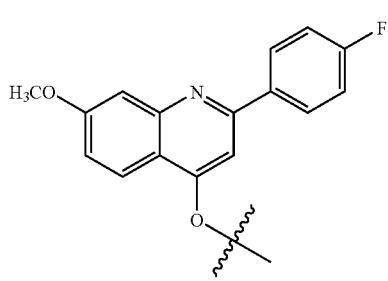

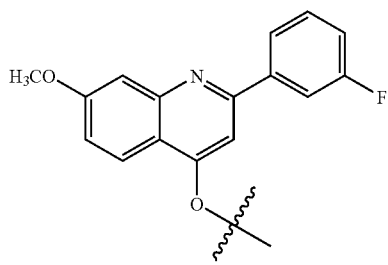

-continued
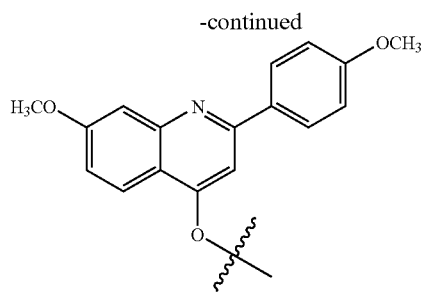
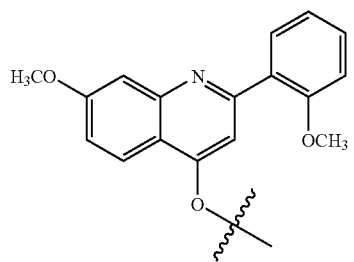
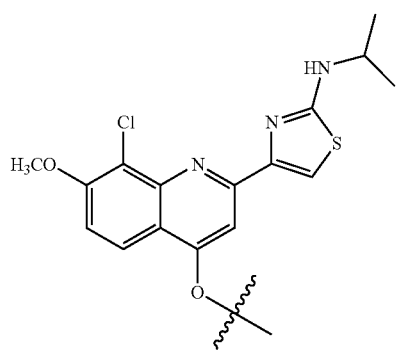
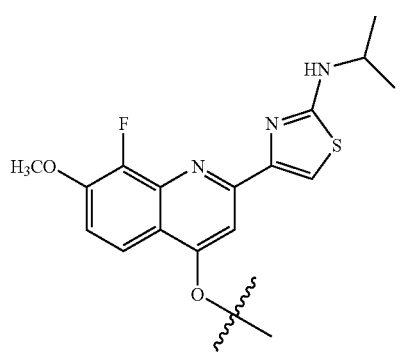
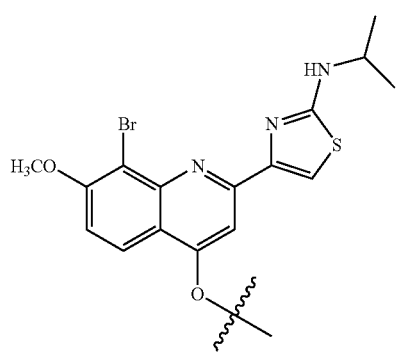
-continued
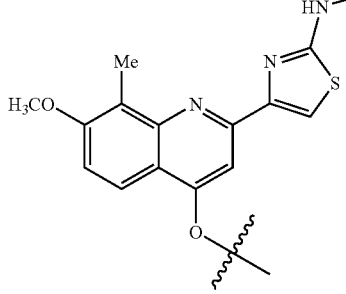
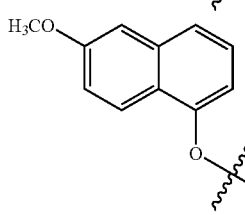
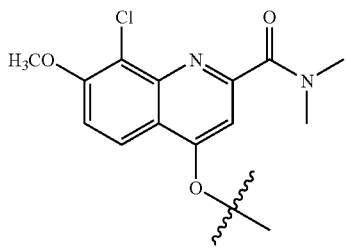
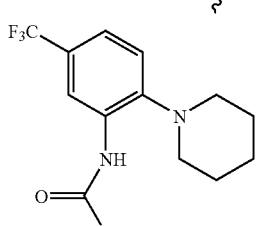
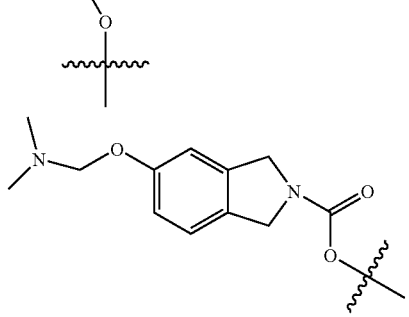
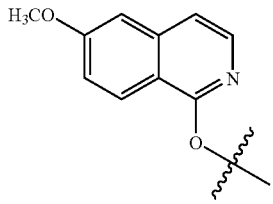
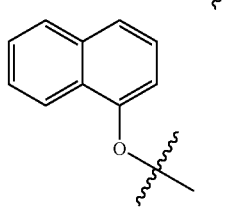

-continued

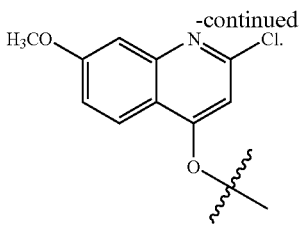

In a specific embodiment of the invention $Z^1$ is:

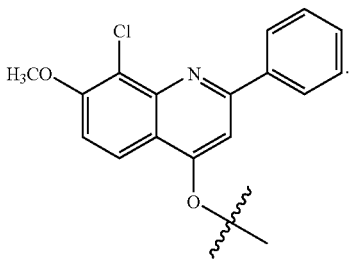

In a specific embodiment of the invention $Z^1$ is selected from the following structures:

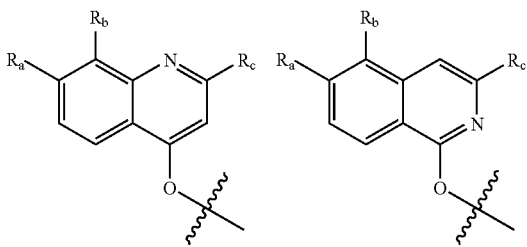

In a specific embodiment the invention provides a compound of formula (II):

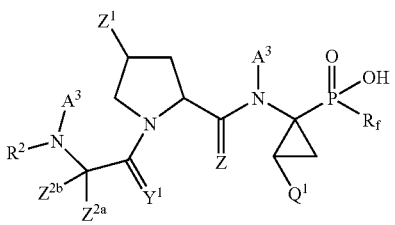

(II)

or a pharmaceutically acceptable salt, or prodrug thereof, wherein: wherein:

$R_f$ is H, alkyl, alkenyl, alkynyl, aryl, heteroaryl, or cycloalkyl, which $R_f$ is optionally substituted with one or more $R_g$;

each $R_g$ is independently halo, hydroxy, cyano, arylthio, cycloalkyl, aryl, heteroaryl, alkoxy, $NR_hR_i$, —C(=O) $NR_hR_i$, wherein each aryl and heteroaryl is optionally substituted with one or more alkyl, halo, hydroxy, cyano, nitro, amino, alkoxy, haloalkyl, or haloalkoxy; and each $R_h$ and $R_i$ is independently H, alkyl, or haloalkyl.

In a specific embodiment of the invention $R_f$ is alkyl, alkenyl, or alkynyl, which $R_f$ is substituted with aryl that is optionally substituted with one or more alkyl, halo, hydroxy, cyano, nitro, amino, alkoxy, alkoxycarbonyl, alkanoyloxy, haloalkyl, or haloalkoxy.

In a specific embodiment of the invention $R_f$ is alkyl, which is substituted with aryl that is optionally substituted with one or more alkyl, halo, hydroxy, cyano, nitro, amino, alkoxy, alkoxycarbonyl, alkanoyloxy, haloalkyl, or haloalkoxy.

In a specific embodiment of the invention $R_f$ is (C1-6)alkyl substituted with a phenyl ring that is optionally substituted with 1, 2, or 3 alkyl, halo, hydroxy, cyano, nitro, amino, alkoxy, alkoxycarbonyl, alkanoyloxy, haloalkyl, or haloalkoxy.

In a specific embodiment of the invention $R_f$ is benzyl or phenethyl that is optionally substituted with 1, 2, or 3 alkyl, halo, hydroxy, cyano, nitro, amino, alkoxy, alkoxycarbonyl, alkanoyloxy, haloalkyl, or haloalkoxy.

In a specific embodiment of the invention $R_f$ is H, methyl, ethyl, propyl, butyl, cyclopropylmethyl, 3-butenyl, 2-methylpropyl, isopropyl, vinyl, cis-1-propenyl, trans-1-propenyl, cis-1-butenyl, 2-methylpropenyl, 2-phenylvinyl, 2-phenylethynyl, 3-methyl-2-butenyl, 2-hydroxyethyl, 2-hydroxy-2-methylpropyl, cyanomethyl, methoxymethyl, N-(2,2,2-trifluoroethyl)-2-aminoethyl, phenethyl, 2-chlorophenethyl, 2-fluorophenethyl, 2-methylphenethyl, 2-chloro-6-fluorophenethyl, phenylthiomethyl, benzyl, 4-fluorobenzyl, 3-fluorobenzyl, 2-fluorobenzyl, 4-cyanobenzyl, 3-cyanobenzyl, 2-cyanobenzyl, 4-methoxybenzyl, 3-methoxybenzyl, 2-methoxybenzyl, 2-bromobenzyl, 2-trifluoromethoxybenzyl, 2-isopropoxybenzyl, 2-methylbenzyl, 3-methylbenzyl, 4-methylbenzyl, 2-ethylbenzyl, 4-trifluoromethylbenzyl, 3-trifluoromethylbenzyl, 2-trifluoromethylbenzyl, 4-chlorobenzyl, 3-chlorobenzyl, 2-chlorobenzyl, 2,6-difluorobenzyl, 2-chloro-6-fluorobenzyl, 2,6-dichlorobenzyl, 2-methoxy-6-fluorobenzyl, 2,6-dimethylbenzyl, 2,6-difluoro-3-chlorobenzyl, 2,6-difluoro-4-chlorobenzyl, 2-chloro-3,6-difluorobenzyl, 2,3,6-trifluorobenzyl, 3-chloro-2,4-difluorobenzyl, 2-chloro-3,6-difluorobenzyl, 2,3-dichloro-6-fluorobenzyl, 2-nitrobenzyl, 2-aminobenzyl, 2-thienylmethyl, 2-furylmethyl, 3-furylmethyl, 5-trifluoromethylfur-2-ylmethyl 5-pyrazolylmethyl, 2-oxazolylmethyl, 4-methylthiazol-2-ylmethyl, 3-pyridyl, 2-pyridylmethyl, 3-hydroxy-2-pyridylmethyl, 6-chloro-2-pyridylmethyl, 2-pyrazinylmethyl, 5-pyrimidinylmethyl, 2-pyrimidinylmethyl, 4-pyrimidinylmethyl, phenyl, 2-thiazolyl, N,N-dimethylaminocarbonylmethyl, N-methylaminocarbonylmethyl, aminocarbonylmethyl, 1-propynyl, or 2-methylthiazol-4-ylmethyl.

In a specific embodiment the invention provides a compound of formula (III):

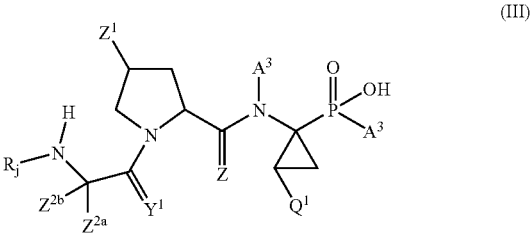

(III)

or a pharmaceutically acceptable salt, or prodrug thereof, wherein:

$R_j$ is 1-[N-(2,2,2-trifluoroethyl)imino]ethyl, α,α-difluorophenethyl, cyclopropylacetyl, butanoyl, 4,4,4-trifluorobutanoyl, 3,3,3-trifluoropropylsulfonyl, 3,3-dimethylbutanoyl, cyclopentylamino-carbonyl, cyclopropylacetyl, 2-norbornanylacetyl, 2-amino-3,3-dimethylbutanoyl, 4-methylphenyl, 4-trifluoromethylphenyl, 3-trifluoromethylphenyl, 2-trifluoromethylphenyl, or 4-tert-butylthiazol-2-yl.

In a specific embodiment of the invention for a compound of formula (III), Z is O; $Y^1$ is O; and $Z^{2a}$ and $Z^{2b}$ are each hydrogen.

In a specific embodiment of the invention $Q^1$ is vinyl.

In a specific embodiment the invention provides a compound of formula (IV):

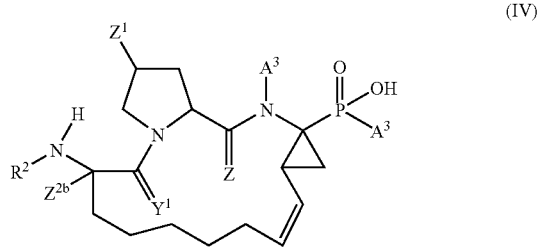

(IV)

or a pharmaceutically acceptable salt, or prodrug thereof.

In a specific embodiment the invention provides a compound of formula (V):

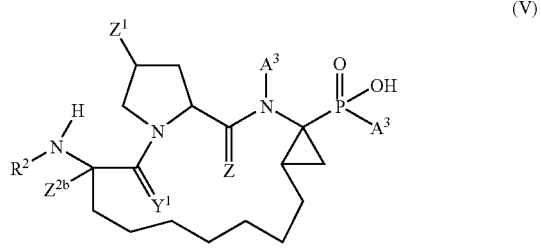

(V)

or a pharmaceutically acceptable salt, or prodrug thereof.

In a specific embodiment the invention provides a compound of formula (VI):

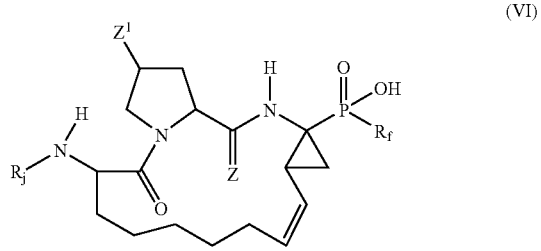

(VI)

or a pharmaceutically acceptable salt, or prodrug thereof, wherein:

$R_f$ is H, alkyl, alkenyl, alkynyl, aryl, heteroaryl, or cycloalkyl, which $R_f$ is optionally substituted with one or more $R_g$;

each $R_g$ is independently halo, hydroxy, cyano, arylthio, cycloalkyl, aryl, heteroaryl, alkoxy, $NR_hR_i$, —C(=O) $NR_hR_i$, wherein each aryl and heteroaryl is optionally substituted with one or more alkyl, halo, hydroxy, cyano, nitro, amino, alkoxy, haloalkyl, or haloalkoxy; and each $R_h$ and $R_i$ is independently H, alkyl, or haloalkyl; and $R_j$ is 1-[N-(2,2,2-trifluoroethyl)imino]ethyl, α,α-difluorophenethyl, cyclopropylacetyl, butanoyl, 4,4,4-trifluorobutanoyl, 3,3,3-trifluoropropylsulfonyl, 3,3-dimethylbutanoyl, cyclopentylaminocarbonyl, cyclopropylacetyl, 2-norbornanylacetyl, 2-amino-3,3-dimethylbutanoyl, 4-methylphenyl, 4-trifluoromethylphenyl, 3-trifluoromethylphenyl, 2-trifluoromethylphenyl, or 4-tert-butylthiazol-2-yl.

In a specific embodiment the invention provides a compound of formula (VII):

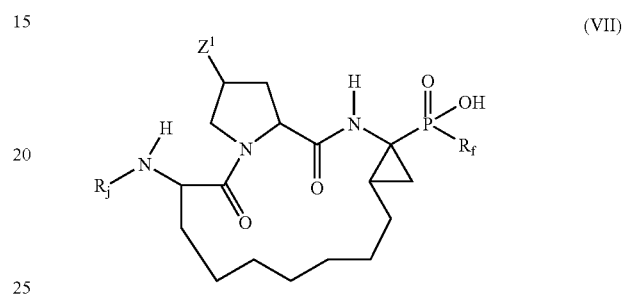

(VII)

or a pharmaceutically acceptable salt, or prodrug thereof, wherein:

$R_f$ is H, alkyl, alkenyl, alkynyl, aryl, heteroaryl, or cycloalkyl, which $R_f$ is optionally substituted with one or more $R_g$;

each $R_g$ is independently halo, hydroxy, cyano, arylthio, cycloalkyl, aryl, heteroaryl, alkoxy, $NR_hR_i$, —C(=O) $NR_hR_i$, wherein each aryl and heteroaryl is optionally substituted with one or more alkyl, halo, hydroxy, cyano, nitro, amino, alkoxy, haloalkyl, or haloalkoxy; and each $R_h$ and $R_i$ is independently H, alkyl, or haloalkyl; and $R_j$ is 1-[N-(2,2,2-trifluoroethyl)imino]ethyl, α,α-difluorophenethyl, cyclopropylacetyl, butanoyl, 4,4,4-trifluorobutanoyl, 3,3,3-trifluoropropylsulfonyl, 3,3-dimethylbutanoyl, cyclopentylaminocarbonyl, cyclopropylacetyl, 2-norbornanylacetyl, 2-amino-3,3-dimethylbutanoyl, 4-methylphenyl, 4-trifluoromethylphenyl, 3-trifluoromethylphenyl, 2-trifluoromethylphenyl, or 4-tert-butylthiazol-2-yl.

In a specific embodiment the invention provides a compound which is a prodrug or a pharmaceutically acceptable salt thereof.

In a specific embodiment the invention provides a prodrug of formula (VIII):

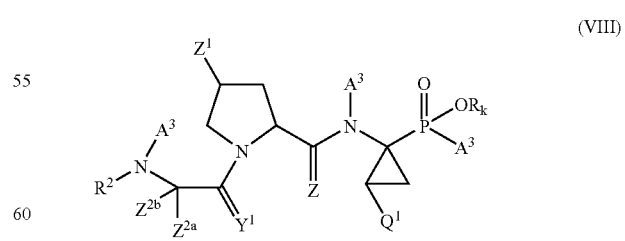

(VIII)

or a pharmaceutically acceptable salt thereof, wherein:

$R_k$ is a prodrug moiety.

In a specific embodiment of the invention $R_k$ is benzyloxymethyl, pivaloyloxymethylcarbonate, 2-methylpropyloxy-carbonyloxymethyl, 4-hydroxy-2-butenyl, benzoyloxymethyl, ethoxycarbonyloxymethyl, or a group of the following formula:

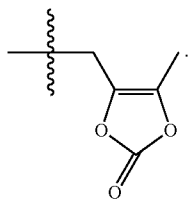

In a specific embodiment the invention provides a compound of formula I, II, III, or VIII wherein $Q^1$ and $Z^{2a}$ taken together with the atoms to which they are attached form a 12-18 membered heterocycle, which heterocycle may optionally be substituted with one or more oxo (=O) or $A^3$.

In a specific embodiment the invention provides a compound of formula (IX):

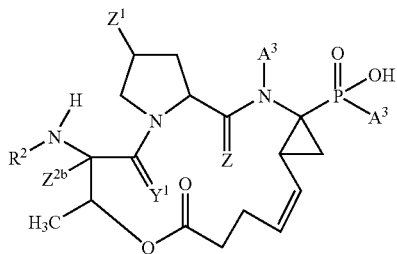

(IX)

or a pharmaceutically acceptable salt, or prodrug thereof.

In a specific embodiment the invention provides a compound of formula (X):

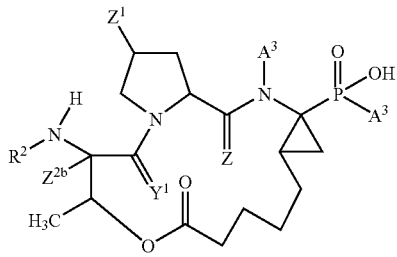

(X)

or a pharmaceutically acceptable salt, or prodrug thereof.

In a specific embodiment the invention provides a compound of formula (XI):

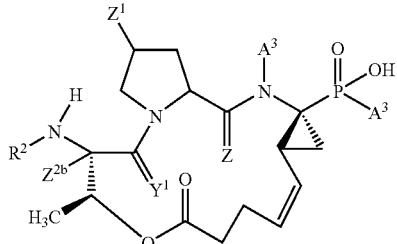

(XI)

or a pharmaceutically acceptable salt, or prodrug thereof.

In a specific embodiment the invention provides a compound of formula (XII):

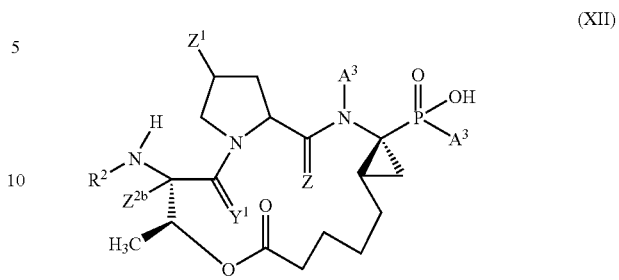

(XII)

or a pharmaceutically acceptable salt, or prodrug thereof.

In a specific embodiment the invention provides a compound of formula (XIII):

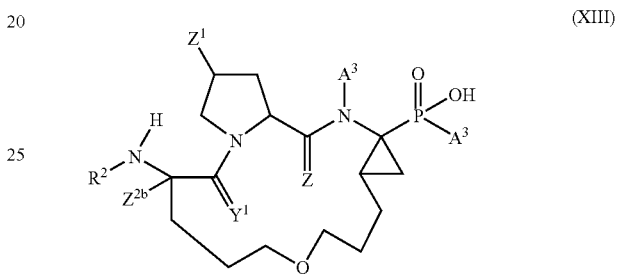

(XIII)

or a pharmaceutically acceptable salt, or prodrug thereof.

In a specific embodiment the invention provides a compound of formula (XIV):

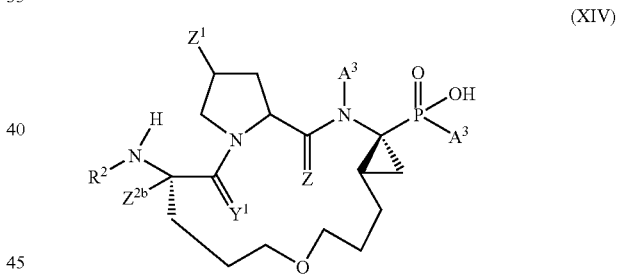

(XIV)

or a pharmaceutically acceptable salt, or prodrug thereof.

In a specific embodiment the invention provides a compound of formula (XV):

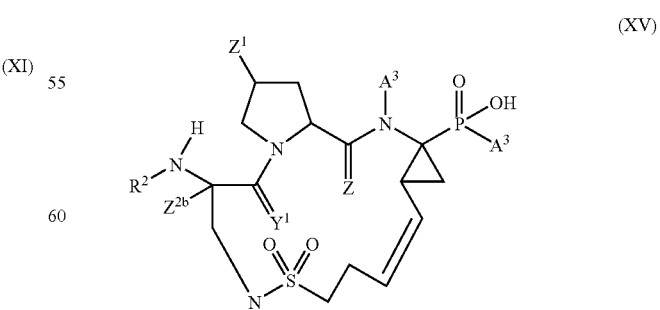

(XV)

or a pharmaceutically acceptable salt, or prodrug thereof.

In a specific embodiment the invention provides a compound of formula (XVI):

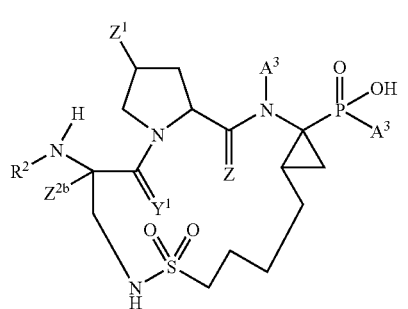

(XVI)

or a pharmaceutically acceptable salt, or prodrug thereof.

In a specific embodiment the invention provides a compound of formula (XVII):

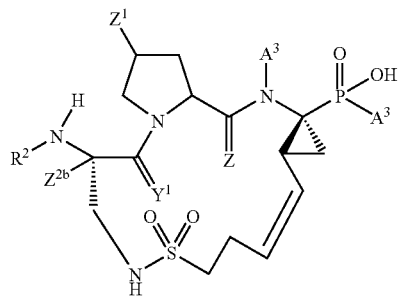

(XVII)

or a pharmaceutically acceptable salt, or prodrug thereof.

In a specific embodiment the invention provides a compound of formula (XVIII):

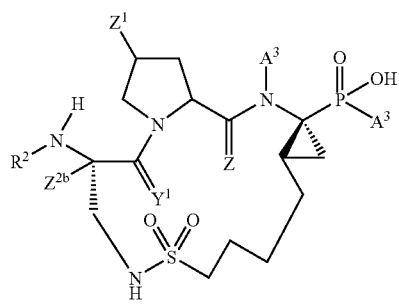

(XVIII)

or a pharmaceutically acceptable salt, or prodrug thereof.

In a specific embodiment the invention provides a compound of formula (XXIV):

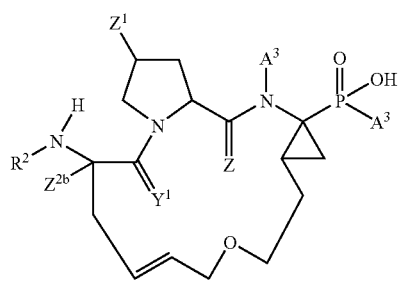

(XXIV)

or a pharmaceutically acceptable salt, or prodrug thereof.

In a specific embodiment the invention provides a compound of formula (XXV):

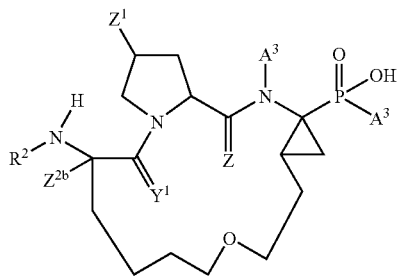

(XXV)

or a pharmaceutically acceptable salt, or prodrug thereof.

In a specific embodiment the invention provides a compound of formula (XXVI):

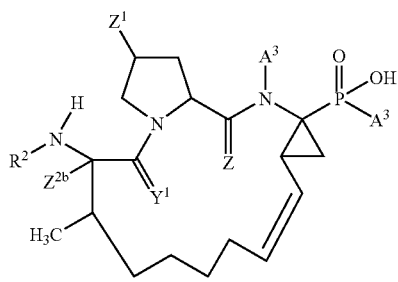

(XXVI)

or a pharmaceutically acceptable salt, or prodrug thereof.

In a specific embodiment the invention provides a compound of formula I:

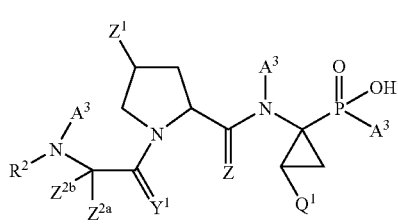

(I)

or a pharmaceutically acceptable salt, or prodrug thereof, wherein:

$R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is selected from, d) —C($Y^1$)($A^3$), e) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or where said alkyl, cycloalkyl and alkyl-cycloalkyl may optionally be mono- or di-substituted with substituents selected from hydroxy and O—(C1-4)alkyl, or where each of said alkyl-groups may optionally be mono-, di- or tri-substituted with halogen, or where each of said cycloalkyl groups being 5-, 6- or 7-membered, one or two —CH$_2$— group not being directly linked to each other may be optionally substituted replaced by —O— such that the O-atom is linked to the N atom to which R$^2$ is attached via at least two C-atoms, f) phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4) alkyl, O—(C1-4)alkyl, S—(C1-4)alkyl, —NH$_2$, —CF$_3$, —NH((C1-4)alkyl) and —N((C1-4)alkyl)$_2$, —CONH$_2$ and —CONH—(C1-4)alkyl; and wherein said (C1-3) alkyl may optionally be substituted with one or more halogen; or d) —S(O)$_2$(A$^3$);

R$^3$ is H or (C1-6)alkyl;

Y$^1$ is independently O, S, N(A$^3$), N(O)(A$^3$), N(OA$^3$), N(O)(OA$^3$) or N(N(A$^3$)(A$^3$));

Z is O, S, or NR$^3$;

Z$^1$ is selected from the following structures:

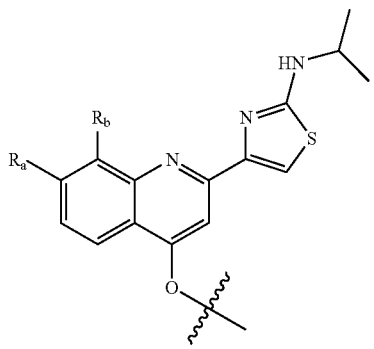

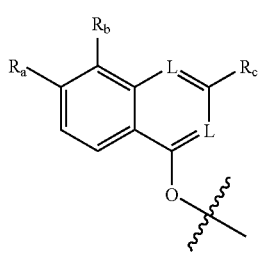

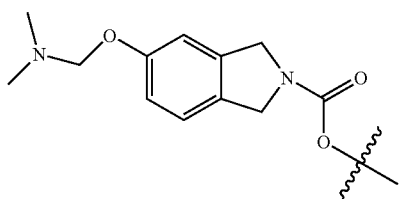

-continued

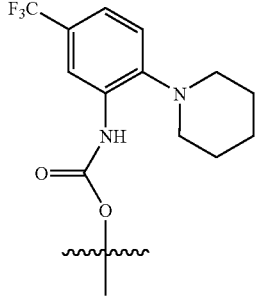

R$_a$ is H or (C1-6)alkoxy;

R$_b$ is H, F, Cl, Br, I, or (C1-6)alkyl;

R$_c$ is H, cyano, F, Cl, Br, I, —C(=O)NR$_d$R$_e$, or phenyl that is optionally substituted with one or more F, Cl, Br, I, (C1-6)alkyl, or (C1-6) alkoxy;

R$_d$ and R$_e$ are each independently H or (C1-6)alkyl;

each L is independently CH or N;

Z$^{2a}$ is H, (C1-10)alkyl, (C2-10)alkenyl, (C2-10)alkynyl, wherein any carbon atom may be replaced with a heteroatom selected from O, S or N, or Z$^{2a}$ optionally forms a carbocycle or heterocycle with one or more R$^1$, R$^2$, Q$^1$, or A$^3$;

Z$^{2b}$ is H, (C1-6)alkyl, (C2-8)alkenyl, (C2-8)alkynyl;

Q$^1$ is (C1-8)alkyl, (C2-8)alkenyl, or (C2-8)alkynyl; or Q$^1$ and Z$^{2a}$ taken together with the atoms to which they are attached form a carbocycle or heterocycle, which carbocycle or heterocycle may optionally be substituted with one or more oxo (=O) or A$^3$;

A$^3$ is independently selected from PRT, H, —OH, —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, —C(A$^2$)$_3$, —C(A$^2$)$_2$—C(O)A$^2$, —C(O)A$^2$, —C(O)OA$^2$, —O(A$^2$), —N(A$^2$)$_2$, —S(A$^2$), —CH$_2$P(Y$^1$)(A$^2$)(OA$^2$), —CH$_2$P(Y$^1$)(A$^2$)(N(A$^2$)$_2$), —CH$_2$P(Y$^1$)(OA$^2$)(OA$^2$), —OCH$_2$P(Y$^1$)(OA$^2$)(OA 2), —OCH$_2$P(Y$^1$)(A$^2$)(OA$^2$), —OCH$_2$P(Y$^1$)(A 2)(N(A$^2$)$_2$), —C(O)OCH$_2$P(Y$^1$)(OA$^2$)(OA$^2$), —C(O)OCH$_2$P(Y$^1$)(A$^2$)(OA$^2$), —C(O)OCH$_2$P(Y$^1$)(A$^2$)(N(A$^2$)$_2$), —CH$_2$P(Y$^1$)(OA$^2$)(N(A$^2$)$_2$), —OCH$_2$P(Y$^1$)(OA$^2$)(N(A 2)$_2$), —C(O)OCH$_2$P(Y$^1$)(OA$^2$)(N(A$^2$)$_2$), —CH$_2$P(Y$^1$)(N(A$^2$)$_2$)(N(A$^2$)$_2$), —C(O)OCH$_2$P(Y$^1$)(N(A$^2$)$_2$)(N(A$^2$)$_2$), —OCH$_2$P(Y$^1$)(N(A$^2$)$_2$)(N(A$^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_m$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide, wherein each A$^3$ maybe optionally substituted with 1 to 4

—R$^1$, —P(Y$^1$)(OA$^2$)(OA$^2$), —P(Y$^1$)(OA$^2$)(N(A$^2$)$_2$), —P(Y$^1$)(A$^2$)(OA$^2$), —P(Y$^1$)(A$^2$)(N(A$^2$)$_2$), or P(Y$^1$)(N(A$^2$)$_2$)(N(A$^2$)$_2$), —C(=O)N(A$^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)

C(CH₃)C(O)O-alkyl, or alkoxy arylsulfonamide, optionally substituted with R¹;
Optionally each independent instance of A³ and Q¹ can be taken together with one or more A³ or Q¹ groups to form a ring;
A² is independently selected from PRT, H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³; and m is 0 to 6;

provided the compound is not a compound of any of the following formulae:

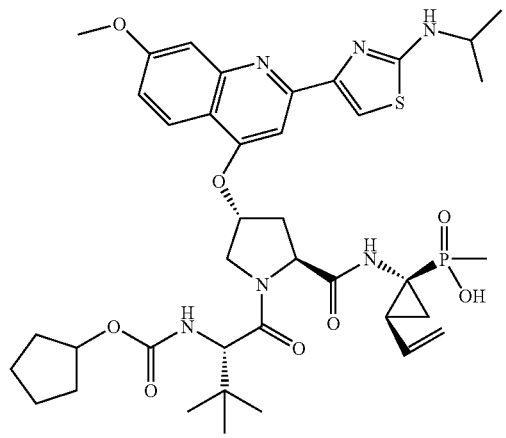 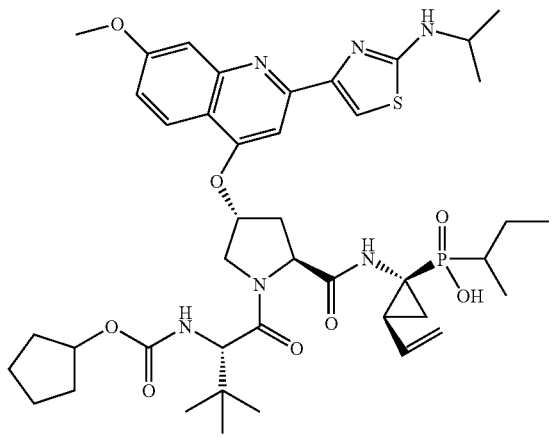

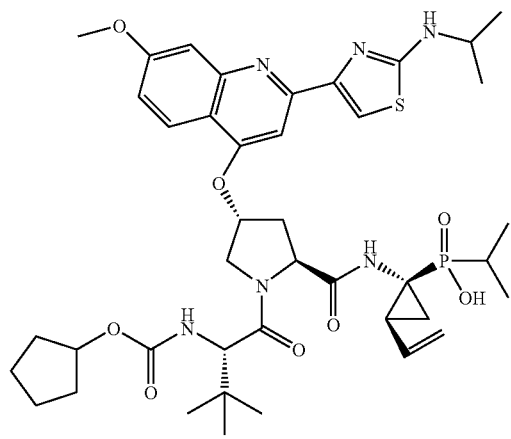 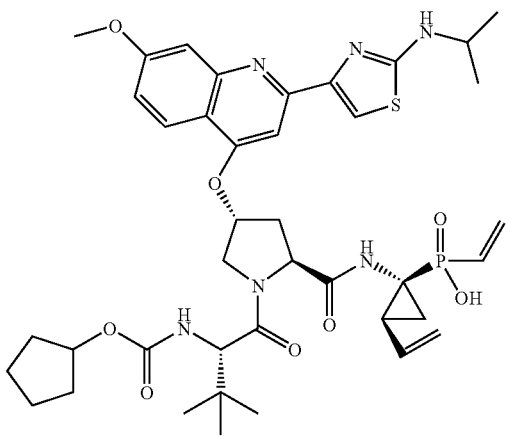

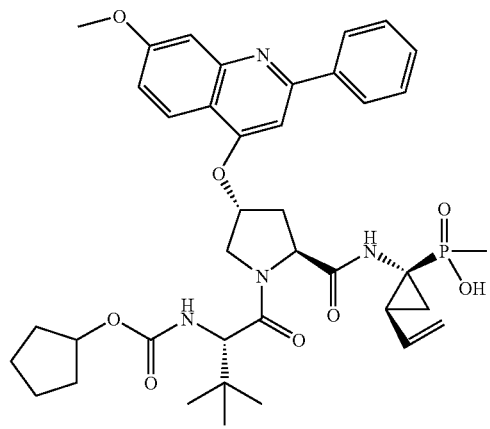 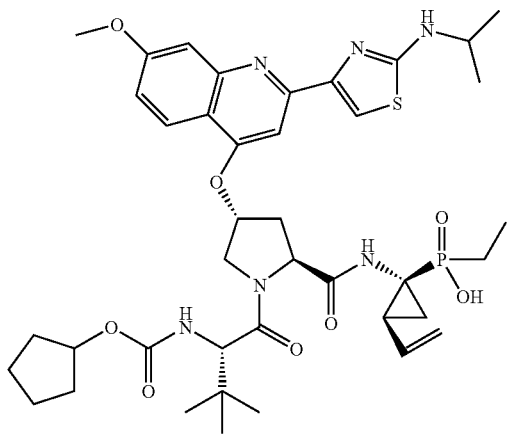

-continued
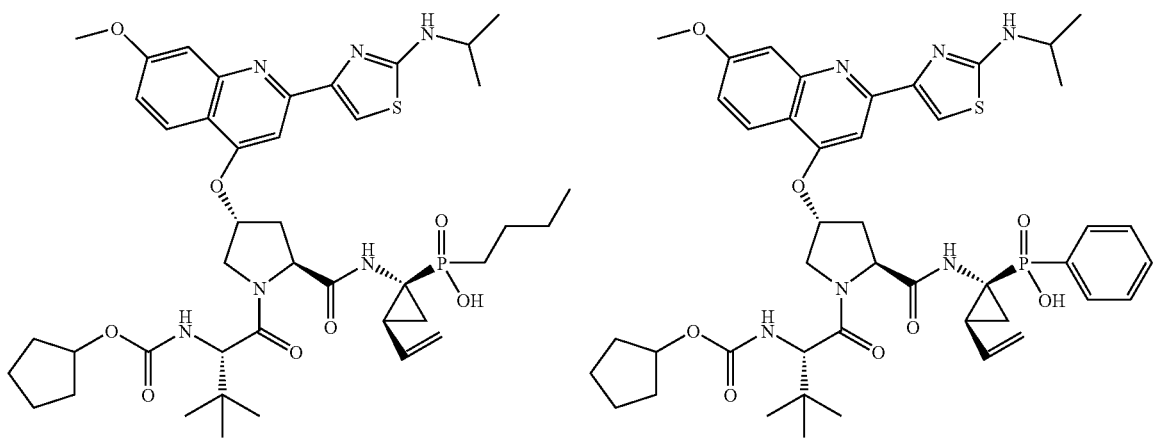
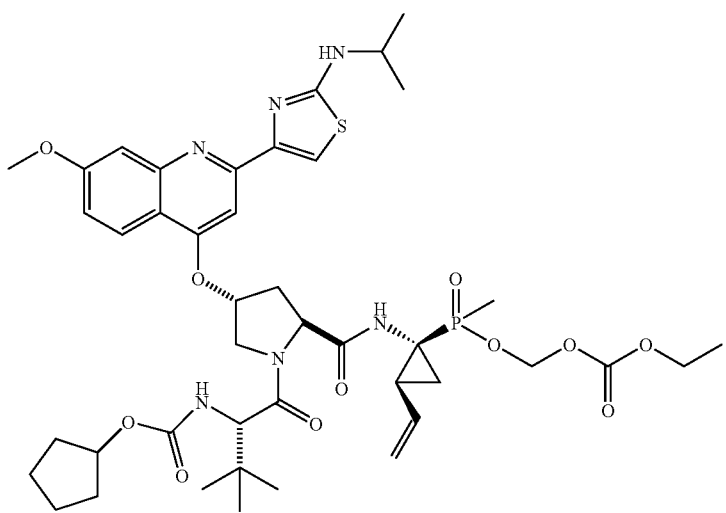
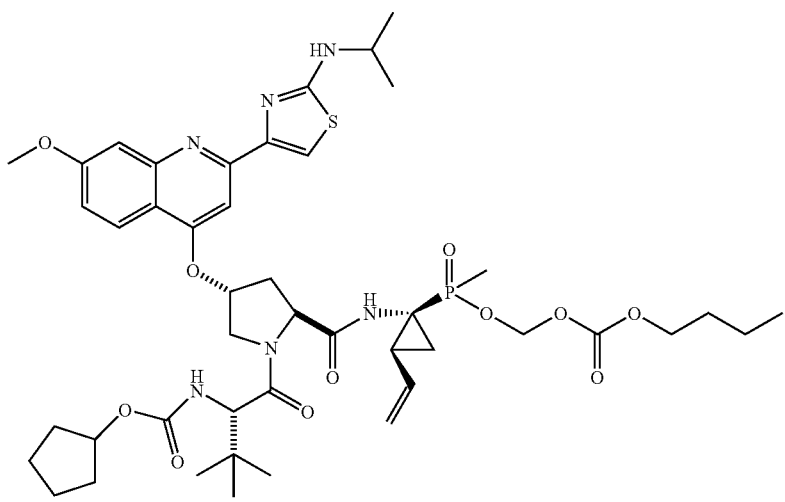

-continued
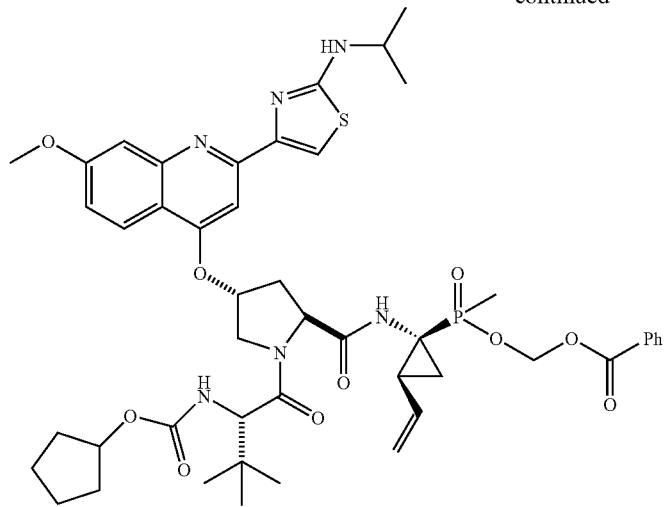
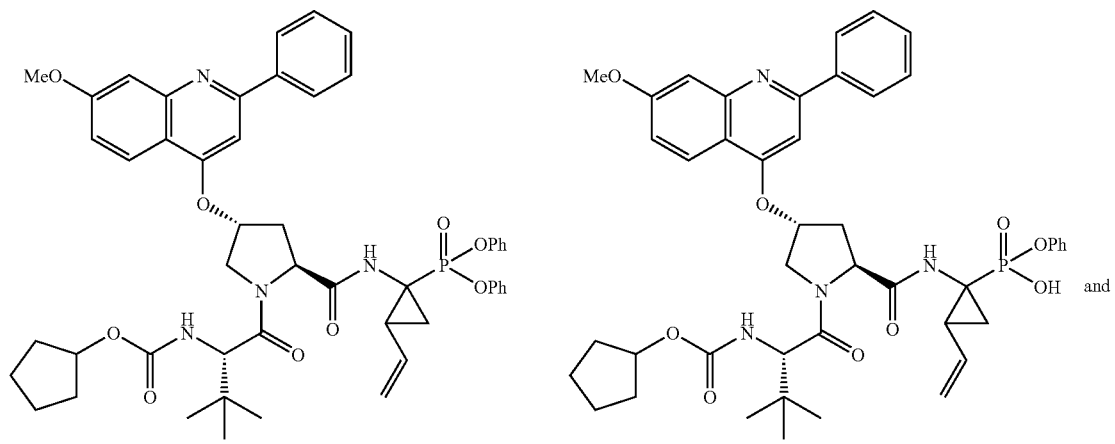
and
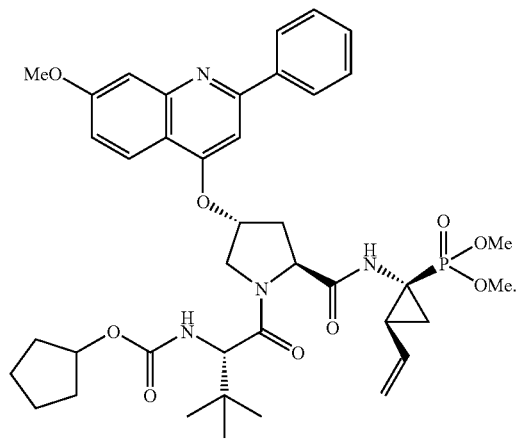

Schemes and Examples

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention. For example, the interconversion of various phosphonate compounds of the invention is illustrated below.

Preparation of Intermediates

Preparation of Phosphonic Acid Intermediates

1. Synthesis and Resolution of Diethyl (1S,2R)-1-amino-2-ethenylcyclopropane-1-phosphonate dibenzoyl-L-tartaric Acid Salt

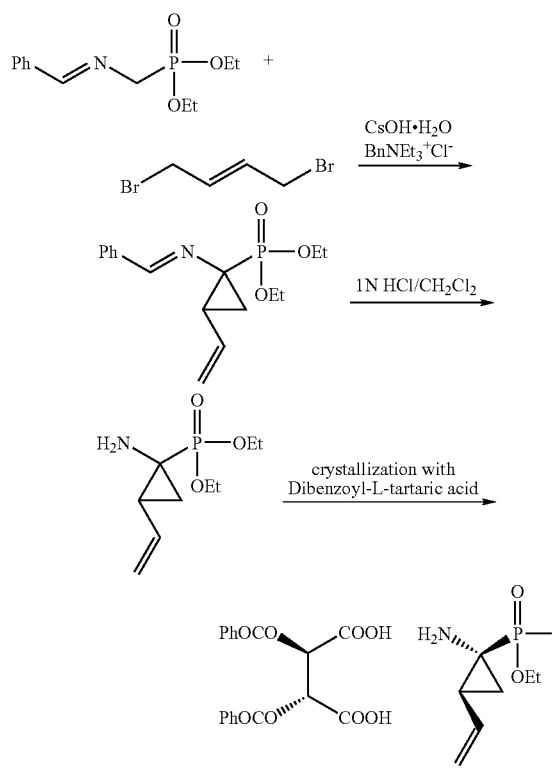

A solution of diethyl-(N-benzylideneaminomethyl)-phosphonate (50 g, 196 mmol), trans-1,4-dibromo-2-butene (50 g, 235 mmol), and benzyltriethylammonium chloride (4.5 g, 19.6 mmol) in dichloromethane (1.0 L) was stirred at rt using a mechanical stirrer when cesium hydroxide monohydrate (82 g, 490 mmol) was added. The resulting mixture was stirred for 18 hr after which another portion of cesium hydroxide monohydrate (82 g, 490 mmol) was added. The resulting mixture was stirred for 24 hr. The salts were then filtered off through a celite 521 pad and the filtrate was allowed to stir with 1N aq. HCl at rt for 3 h. The resulting mixture was filtered through another celite 521 pad and the two phases of the filtrate were separated. The organic fraction was extracted with 1 N aq. HCl (250 mL×1). The aqueous fractions were washed with dichloromethane (250 mL×1) and the combined aq. fractions were stirred with ethyl acetate (500 mL) while 84 g (1 mol) of NaHCO$_3$ was added cautiously, followed by excess NaCl until saturated. After the resulting mixture was filtered through a celite 521 pad to remove excess NaCl and some black tar, the two layers were separated and the aqueous fraction was extracted further with ethyl acetate (250 mL×2). The organic extracts were washed with a saturated NaCl solution (250 mL×1), combined, dried (MgSO$_4$), and concentrated to obtain ~16.5-17 g of the crude amine.

The crude amine was partially purified by column chromatography using 165-170 g of silica gel by eluting with ethyl acetate (100%, ~500 mL), followed by 5% methanol in ethyl acetate (~1200 mL). The product containing fractions were pooled and concentrated, which resulted 11.5-12 g of partially purified amine.

To this amine was added a solution of 18.8-19.6 g (1 mole eq.) of dibenzoyl-L-tartaric acid in 151.5-158 mL of acetonitrile (5 times the amount of the salt). The mixture was heated until it became a solution and cooled slowly at rt to obtain solids. After overnight, the solids were collected by filtration and washed with acetonitrile. The solids were recrystallized from the same amount of acetonitrile again at rt to afford 11.5 g of optically pure salt. $^1$H NMR (300 MHz, CD$_3$OD) δ 8.14 (br, 2H), 8.11 (d, J=1.2 Hz, 2H), 7.64 (tt, J=7.5 and 1.2 Hz, 2H), 7.51 (br t, J=7.5 Hz, 4H), 5.94 (s, 2H), 5.82 (dt, J=17.1 and 9.9 Hz, —H), 5.32 (dd, J=17.1 and 1.2 Hz, 1H), 5.13 (dd, J=10.5 and 1.2 Hz, 1H), 4.11-4.26 (m, 4H), 2.11 (m, 1H), 1.33-1.47 (m, 2H), 1.37 (dt, J=10.2 and 7.2 Hz, 6H); $^{31}$P NMR (121.4 MHz, CD$_3$OD) δ 22.55.

Analytical: The optical purity of the amine can be determined by $^{31}$P NMR of Mosher's amide in DMSO-d$_6$. The recrystallized material (25 mg) was dissolved in a mixture of saturated aq. NaHCO$_3$ (5 mL) and saturated aq. NaCl (5 mL), and the free amine was extracted using dichloromethane (10 mL×2). The extracts were washed once with a mixture of saturated aq. NaHCO$_3$ (5 mL) and saturated aq. NaCl (5 mL), dried (MgSO$_4$), and concentrated.

To a solution of the residue and N,N-dimethylaminopyridine (~3.5 mg) in pyridine (0.1 mL) was added (R)-(-)-α-methoxy-α-(trifluoromethyl)phenylacetyl chloride at rt. After stirring for 1.5 h, the pyridine was evaporated and the residue was dissolved in 0.5 N HCl (10 mL) and ethyl acetate (10 mL). After the separation of the two layers, the organic layer was washed with water (10 mL×1) and saturated aq. NaHCO$_3$ (10 mL×1), dried (MgSO$_4$), and concentrated. In the $^{31}$P NMR of the residue in DMSO-d$_6$, the desired amide appears at 23.00 ppm whereas the undesired amide comes at 22.79 ppm.

2. Preparation of Phosphonic Acid Intermediates

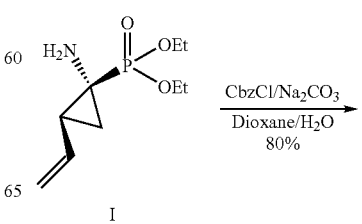

I

-continued

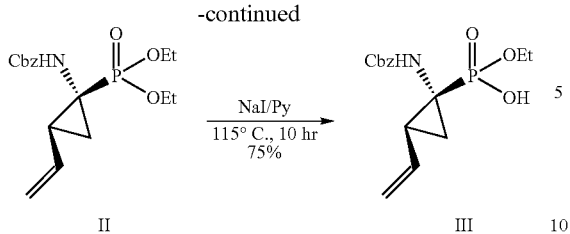

Amine I (9.0 g, 41.1 mmol) was dissolved in 1,4-dioxane (100 mL). A solution of Na$_2$CO$_3$ (13.1 g, 123.3 mmol) in H$_2$O (50 mL) was added to the reaction mixture and stirred for 5 minutes at rt. After benzyl chloroformate (8.4 g, 49.3 mmol) was added, the reaction solution was stirred at rt overnight. The organic phase was diluted with EtOAc and extracted with H$_2$O and brine. The organic phase was dried over MgSO$_4$. Concentration of the filtrate from vacuum filtration removal of the MgSO$_4$ yielded an oil from which II was isolated by column chromatography (SiO$_2$, 20% EtOAc in hexane) as a clear oil (11.6 g, 80%). $^1$H NMR (300 MHz, CDCl$_3$) δ 7.33 (s, 5H), 6.05 (dt, J=9.9, 17.1 Hz, 1H), 5.65 (d, J=23.7 Hz, 1H), 5.$^{31}$ (d, J=17.1 Hz, 1H), 5.06 (m, 3H), 4.06 (m, 4H), 2.09 (m, 1H), 1.73 (m, 2H), 1.15 (dt, J=8.1, 26.4 Hz, 6H). $^{31}$P NMR (121.4 MHz, CDCl$_3$) δ 23.7

Intermediate II (11.6 g, 32.9 mmol) and NaI (24.5 g, 164.3 mmol) were dissolved in pyridine (110 mL). The reaction solution was heated to 115° C. for 10 hours. After cooling back to rt, the reaction solution was concentrated to remove pyridine. H$_2$O (50 mL) was added to the crude. The aqueous was washed by diethyl ether (2×100 mL). Then the aqueous phase was adjusted to pH=2 by adding 1 M HCl$_{(aq.)}$. Product III (7.5 g, 23.0 mmol) was isolated by extracting with dichloromethane and used for next step without further purification. $^1$H NMR (300 MHz, CDCl$_3$) δ 8.63 (br, 1H), 7.33 (s, 5H), 5.95 (dt, J=9.9, 17.1 Hz, 1H), 5.65 (d, J=23.7 Hz, 1H), 5.31 (d, J=17.1 Hz, 1H), 5.06 (m, 3H), 4.06 (m, 2H), 2.09 (m, 1H), 1.73 (m, 2H), 1.23 (dt, J=8.1, 26.4 Hz, 3H) $^{31}$P NMR (121.4 MHz, CDCl$_3$) δ 24.6. LC/MS=326 (M$^+$+1), 348 (M$^+$+Na)

3. Preparation of Phosphinic Acid Intermediates

A general scheme for the preparation of phosphinic acid is shown below starting from compound III (Scheme 1).

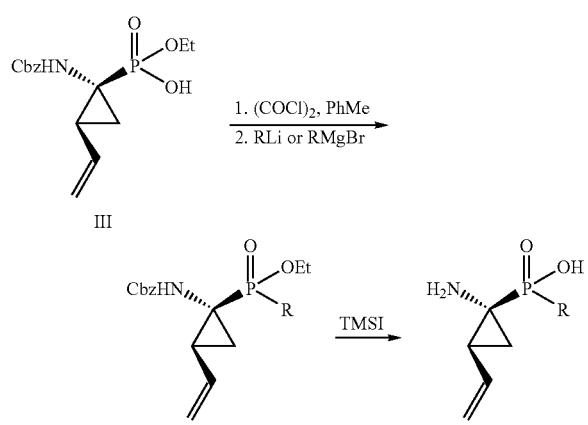

An alternative scheme (Scheme 2) for the preparation of phosphinic acid is shown below.

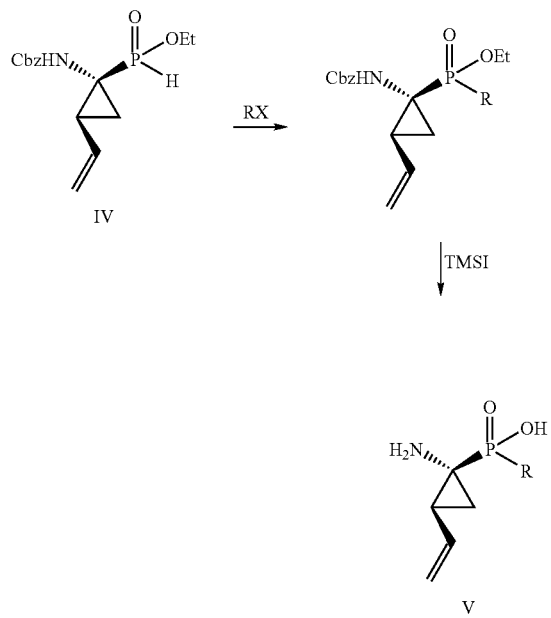

Phosphonic acid intermediate III (1.0 g, 3.1 mmol) was dissolved in toluene (6 mL). This solution was then added dropwise to (COCl)$_2$ (1.1 mL, 12.4 mmol) and DMF (47 μL, 0.6 mmol) dissolved in 6 mL of toluene at rt. After 1 hour of stirring at rt, the reaction was concentrated and azeotroped three times with toluene to afford crude IV as an oil.

The resulting dark, viscous residue in THF (20 mL) was stirred at −78° C. as 1.0 M LiAlH(O-tBu)$_3$ (23.5 mL, 23.5 mmol) was added over 10 minutes. The solution was warmed to r.t. over minutes. The reaction mixture was cooled to 0° C. and quenched with ice cold 1 N HCl (200 mL). The product was extracted with ether (200 mL×2) and the organic fractions were washed with ice cold 1 N HCl (100 mL) and H$_2$O (100 mL). After the organic fraction was dried (MgSO$_4$) and concentrated, the residue was purified by combi-flash column chromatography using hexane/ethyl acetate as eluent to obtain IV (1.89 g, 78.3%). $^1$H NMR (300 MHz, CDCl$_3$): δ 8.14 (bs, 1H), 7.35 (s, 5H), 6.22 (s, 1H), 5.89 (m, 2H), 5.39 (bd, J=11.7 Hz, 1H), 5.30 (s, 2H), 5.21-5.104 (m, 3H), 4.13 (m, 2H), 2.16 (m, 1H), 1.72-1.66 (m, 2H), 1.31 (m, 3H). $^{31}$P (121.4 MHz, CD$_3$OD): δ32.311, 29.241

The resulting phosphinic acid is coupled with dipeptide intermediate as shown in Scheme 3.
Scheme 3
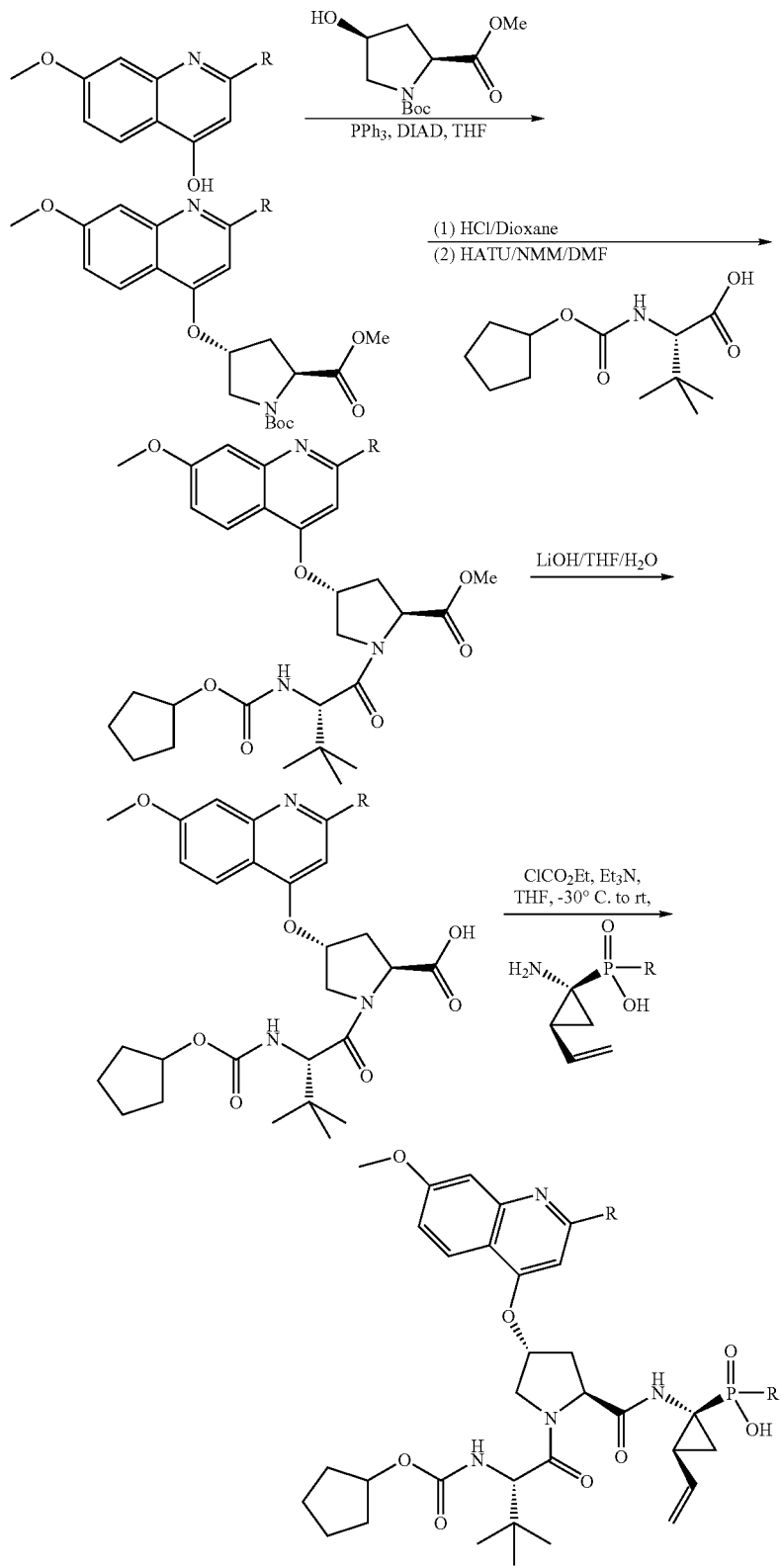

4. Preparation of Dipeptide Intermediates

A. Synthesis of Phenyl Quinoline Dipeptide Intermediate

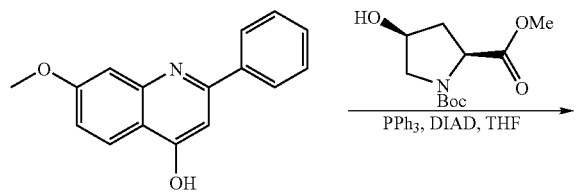

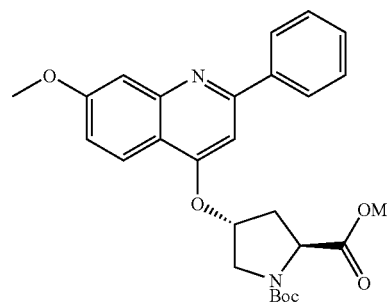

Step 1. Quinoline (7.6 g, 30.1 mmol), N-t-Boc-cis-4-hydroxy-L-proline methyl ester (8.9 g, 36.3 mmol) and triphenylphosphine (17.4 g, 66.3 mmol) were dissolved in THF (250 mL). After cooling the reaction solution to 0° C., DIAD (13.4 g, 66.3 mmol) was added over 15 minutes. The reaction was stirred at rt for 12 hours and was diluted with EtOAc (700 mL) and washed with NaHCO$_3$ $_{(aq.)}$, H$_2$O and brine. The organic phase was dried over MgSO$_4$. After concentration, a crystallization was used to remove most of the triphenylphosphine oxide by using EtOAc (100 mL) and hexane (50 mL) and desired product was isolated by column chromatography (SiO$_2$, 70% EtOAc in hexane) as an oil (11.9 g, 85%). $^1$H NMR (300 MHz, CDCl$_3$) δ 8.03 (m, 2H), 7.50 (m, 5H), 7.18 (m, 1H), 6.97 (m, 1H), 5.15 (m, 1H), 4.99 (m, 2H), 4.06 (s, 3H), 3.99 (m, 1H), 3.75 (s, 3H), 2.79 (dd, J=8.7, 14.3 Hz, 1H), 2.45 (ddd, J=3.5, 10.7, 13.8 Hz, 1H), 1.15 (s, 9H). LC/MS=479 (M$^+$+1), 501 (M$^+$+Na)

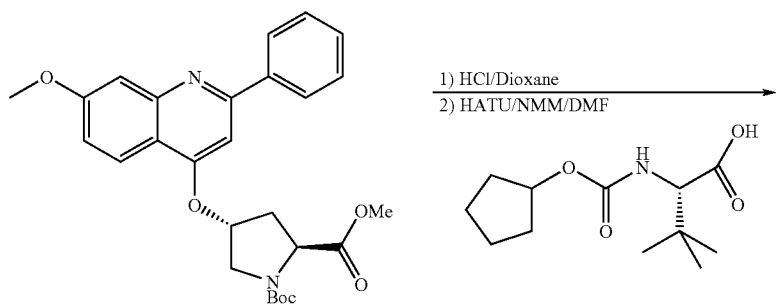

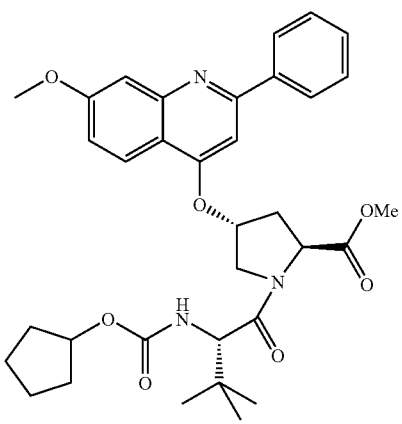

Step 2. Product from the above reaction (9.6 g, 20.8 mmol) was dissolved in dichloromethane (20 mL). 4.0 M HCl in 1,4-dioxane (50 mL) was added to the reaction solution slowly and the reaction solution was allowed to stir at rt for 5 hours. After concentration under high vacuum for 30 minutes, the crude was dissolved in DMF (70 mL). Acid (6.1 g, 25.0 mmol), HATU (11.9 g, 31.0.2 mmol) and N-methylmorpholine (10.5 g, 104.0 mmol) were added to the reaction solution. The reaction solution was stirred at rt overnight and was diluted with EtOAc (500 mL) and washed with $NH_4Cl_{(aq.)}$, $NaHCO_{3\;(aq.)}$ and brine. The organic phase was dried over $MgSO_4$. After concentration, the desired product (10.0 g, 80%) was isolated by column chromatography ($SiO_2$, 90% EtOAc in hexane) as a solid. $^1$H NMR (300 MHz, $CD_3OD$) δ 8.33 (d, J=9.6 Hz, 1H), 8.09 (m, 2H), 7.74 (m, 3H), 7.65 (m 1H), 7.52 (m 1H), 7.24 (dd, J=2.1, 9.6 Hz, 1H), 5.91 (m, 1H), 5.04 (m, 1H), 4.81 (d, J=9.0 Hz, 1H), 4.76 (d, J=9.0 Hz, 1H), 4.46 (m, 1H), 4.23 (m, 1H), 4.06 (s, 3H), 3.99 (m, 1H), 3.75 (s, 3H), 2.99 (dd, J=9.0, 14.7 Hz, 1H), 2.53 (ddd, J=3.3, 10.5, 13.8 Hz, 1H), 1.42-1.78 (m, 8H), 1.05 (s, 9H). LC/MS=604 ($M^+$+1), 626 ($M^+$+Na).

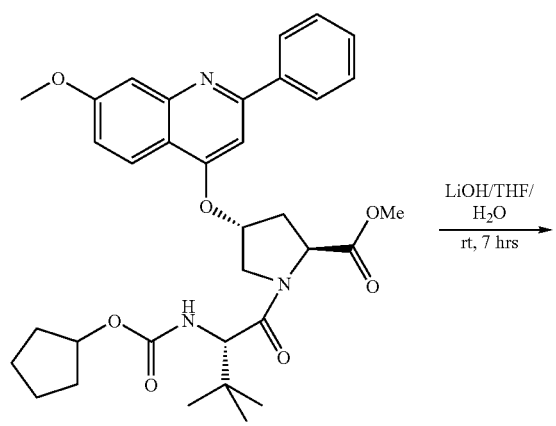

LiOH/THF/
$H_2O$ rt, 7 hrs

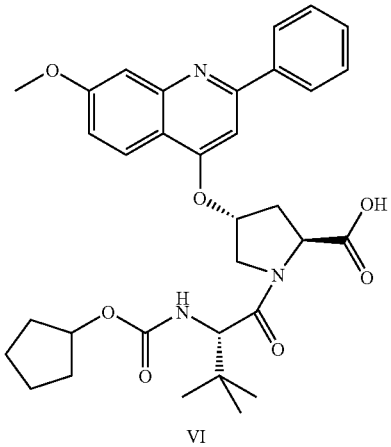

VI

Step 3. The methyl ester (9.2 g, 15.3 mmol) was dissolved in THF (30 mL), MeOH (10 mL) and $H_2O$ (10 mL). LiOH (1.8 g, 76.5 mmol) was added to the reaction solution and the reaction solution was allowed to stir at rt for 7 hours. After EtOAc (150 mL) was added to dilute the reaction solution, the aqueous phase was adjusted to pH=2 by adding 1 M $HCl_{(aq.)}$. Dipeptide acid VI (8.6 g, 95%) was isolated by extracting with EtOAc (2×100 mL) and used for next step without further purification. $^1$H NMR (300 MHz, $CD_3OD$) δ 8.38 (d, J=9.6 Hz, 1H), 8.11 (m, 2H), 7.76 (m, 3H), 7.65 (m 1H), 7.55 (m 1H), 7.24 (dd, J=2.1, 9.6 Hz, 1H), 5.89 (m, 1H), 5.04 (m, 1H), 4.81 (d, J=8.7 Hz, 1H), 4.76 (d, J=8.7 Hz, 1H), 4.46 (m, 1H), 4.23 (m, 1H), 4.06 (s, 3H), 3.99 (m, 1H), 2.99 (dd, J=9.0, 14.7 Hz, 1H), 2.53 (ddd, J 3.3, 10.5, 13.8 Hz, 1H), 1.42-1.78 (m, 8H), 1.05 (s, 9H)

LC/MS=590 ($M^+$+1), 612 ($M^+$+Na).

B. Synthesis of 1-(2-Cyclopentyloxycarbonylamino-3,3-dimethyl-butyryl)-4-[2-(2-isopropylamino-thiazol-4-yl)-7-methoxy-quinolin-4-yloxy]-pyrrolidine-2-carboxylic Acid

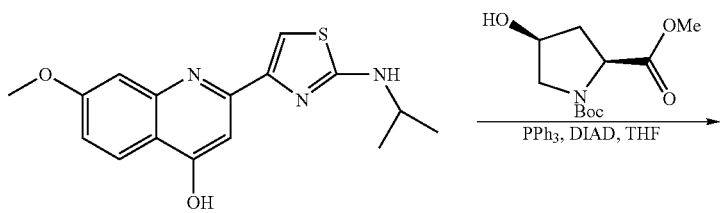

PPh₃, DIAD, THF

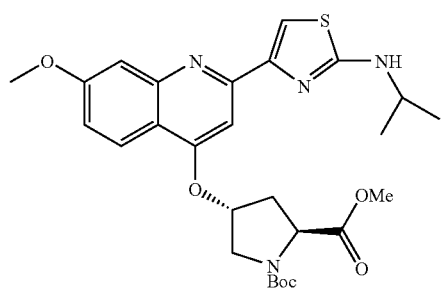

Step 1. To a solution of hydroxythiazole quinoline (20.0 g, 63.5 mmol) in THF (400 mL), was added cis-Boc-hydroxyproline methyl ester (18.7 g, 76.2 mmol), and triphenylphosphine (36.6 g, 139.7 mmol). The solution was cooled to 0° C. and DIAD (27 mL, 139.7 mmol) was added slowly. The solution was allowed to warm to rt over a period of 1 h and stirred overnight. The solvent was removed under reduced pressure and the crude reaction mixture was dissolved in ethyl acetate and extracted with water followed by brine. The organics were dried over MgSO$_4$, filtered and the solvent was removed under reduced pressure. The crude material was eluted through a plug of silica using a quick gradient of (25%-100%) ethyl acetate/hexane to afford 32.5 g of desired product as a yellow solid that has 10%-15% triphenylphosphineoxide contamination. $^1$H NMR (300 MHz, CDCl$_3$): δ 7.98, (d, J=9.2 Hz, 1H), 7.46 (m, 2H), 7.37 (d, J=2.4 Hz, 1H), 7.3 (s, 1H), 7.09 (d, J=9.1 Hz, 1H), 5.26 (m, 1H), 4.96 (m, 1H), 4.62 (t, J=7.3 Hz, 1H), 5.57 (t, J=15 Hz, 1H), 3.97-3.84 (bs, 5H), 3.76-3.66 (bs, 5H), 2.77 (m, 1H), 2.42 (m, 1H), 2.03 (s, 1H), 1.43 (s, 9H), 1.33 (d, J=6.4 Hz, 6H). LC/MS: 543 (M$^+$+1).

amine (20.67 g, 78%) as a crystalline yellow solid. $^1$H NMR (300 MHz, CD$_3$OD): δ 8.45 (d, J=9.2 Hz, 1H), 8.35 (s, 1H), 7.85 (s, 1H), 7.79 (s, 1H), 7.45 (d, J=9.5 Hz, 1H), 6.02 (m, 1H), 4.22 (m, 1H), 4.07 (s, 3H), 4.02 (d, J=3.9 Hz, 1H), 3.98 (s, 1H), 3.92 (s, 3H), 3.66 (s, 1H), 3.03 (m, 1H), 2.82 (m, 1H), 1.36 (d, J=6.4 Hz, 6H), 1.33 (d, J=6.4 Hz, 6H). LC/MS: 443 (M$^+$+1). To a solution of the HCl amine salt (20.96 g, 43.8 mmol) in DMF (300 mL) at rt was added cyclopentylcarbamate-tert-leucine carboxylic acid (13.0 g, 52.6 mmol), and HATU (25.0 g, 65.7 mmol). The reaction was stirred for 10 min at rt and then Hunig's base (45 mL, 262 mmol) was added over 5 min. The reaction was stirred at rt for 1 h, monitoring by LCMS. Solvent was removed under reduced pressure and the residue was diluted with ethyl acetate. The reaction was extracted with sat. NaHCO$_3$, followed by water and brine. The organics were dried over MgSO$_4$, the solids were removed by filtration and then the solvent was removed under reduced pressure. The crude material was eluted through a silica plug to remove excess salts. The solvent was removed, and the product was recrystallized from ethyl acetate and

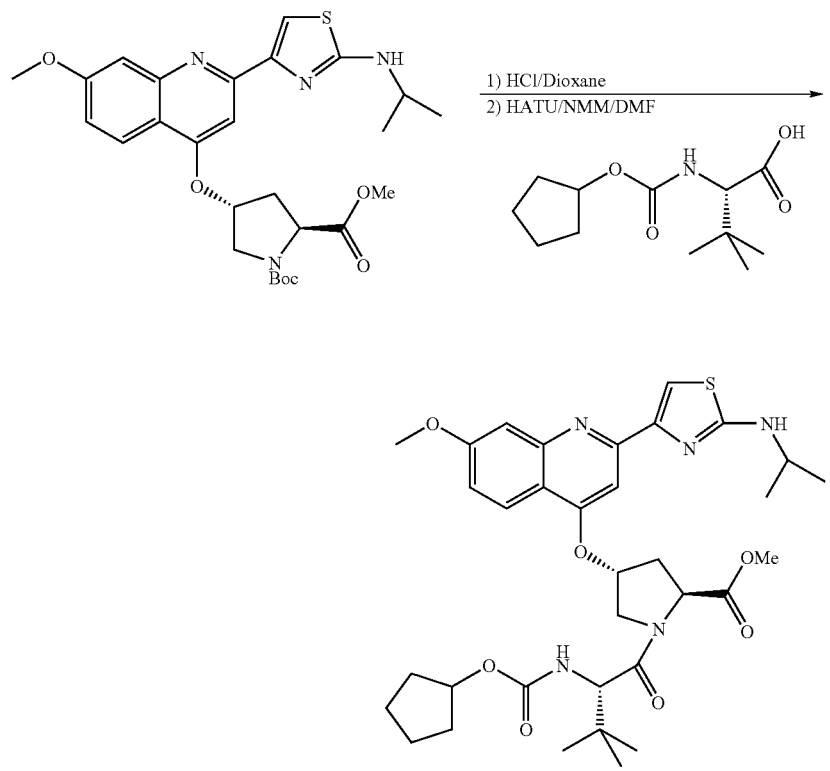

Step 2. To a solution of methyl ester (30.0 g, 55 mmol) in methylene chloride (150 mL) at 0° C., was added 4 N HCl in dioxane (150 mL). The reaction was allowed to warm to rt over 1 hr. As the reaction proceeds, the product precipitates out of solution. The solids were filtered off and then washed repeatedly with diethyl ether to afford the HCl salt of the hexane to afford dipeptide methyl ester (23.5 g, 81%) as a yellow crystalline solid. $^1$H NMR (300 MHz, CDCl$_3$): δ 7.98, (d, J=9.1 Hz, 1H), 7.67 (s, 1H), 7.51 (s, 1H), 7.27 (s, 1H), 7.16 (d, J=7.3 Hz, 1H), 5.62 (m, 1H), 5.54 (m, 1H), 5.27 (d, J=9.7 Hz, 1H), 4.81-4.71 (bs, 2H), 4.49 (d, J=12.5 Hz, 1H), 4.28 (d, J=10 Hz, 1H), 4.14 (m, 1H), 4.04 (s, 3H), 3.78 (s, 3H), 3.60

(m, 1H), 2.76 (m, 2H), 2.51 (m, 2H), 1.63-1.50 (m, 10H) 1.26 (d, J=6.4 Hz, 6H), 1.07 (s, 9H). LC/MS: 668 (M⁺+1).

MHz, CD₃OD): δ 8.29 (d, J=9.5 Hz, 1H), 8.17 (s, 1H), 7.72 (s, 2H), 7.33 (d, J=7.6 Hz, 1H), 5.77 (s, 1H), 4.80 (t, J=9.1 Hz, 1H), 4.77 (d, J=12 Hz, 1H), 4.44 (m, 1H), 4.19-4.04 (bs, 6H), 2.96 (m, 1H), 2.50 (m, 1H), 1.62-1.50 (bs, 8H), 1.35 (d, J=6.7 Hz, 6H), 1.05 (s, 9H). LC/MS: 655 (M⁺+1).

5. Preparation of Dipeptide Intermediates

Synthesis of dipeptide intermediates is shown in Scheme 4 and Scheme 5.

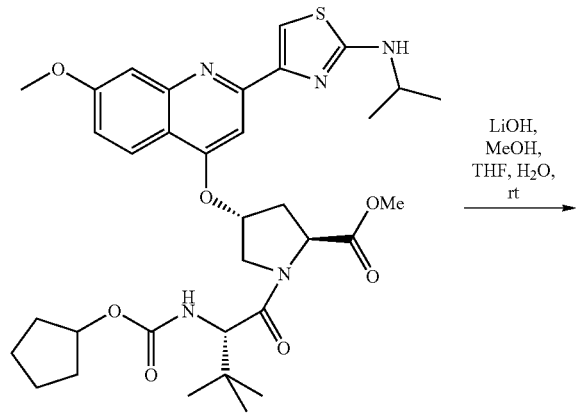

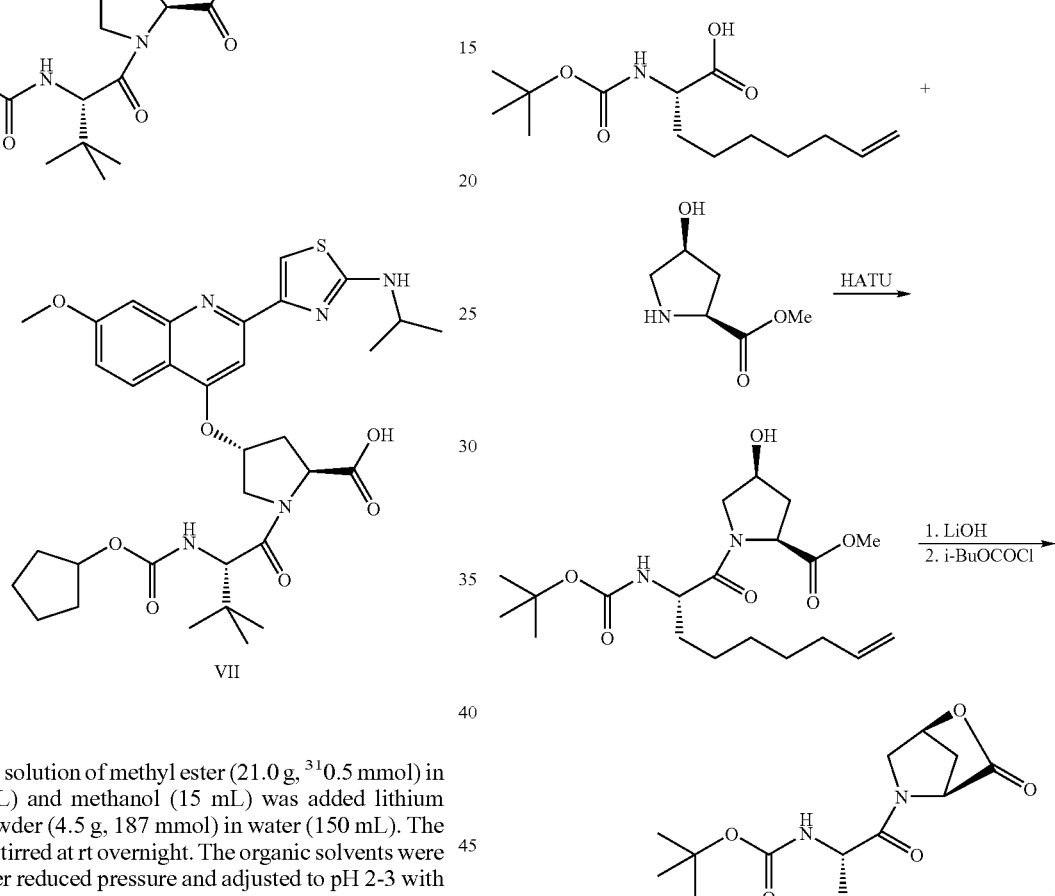

Step 3. To a solution of methyl ester (21.0 g, ³¹0.5 mmol) in THF (300 mL) and methanol (15 mL) was added lithium hydroxide powder (4.5 g, 187 mmol) in water (150 mL). The reaction was stirred at rt overnight. The organic solvents were removed under reduced pressure and adjusted to pH 2-3 with 10% HCl in water. The solution was extracted with ethyl acetate, (2×250 mL). The combined organics were dried over MgSO₄, which was removed by filtration, and the solvent was removed under reduced pressure to afford dipeptide carboxylic acid VII (19.3 g, 94%) as a yellow solid. ¹H NMR (300

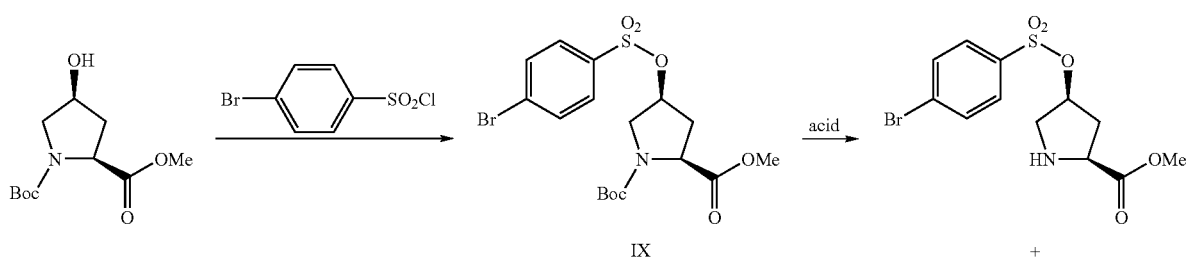

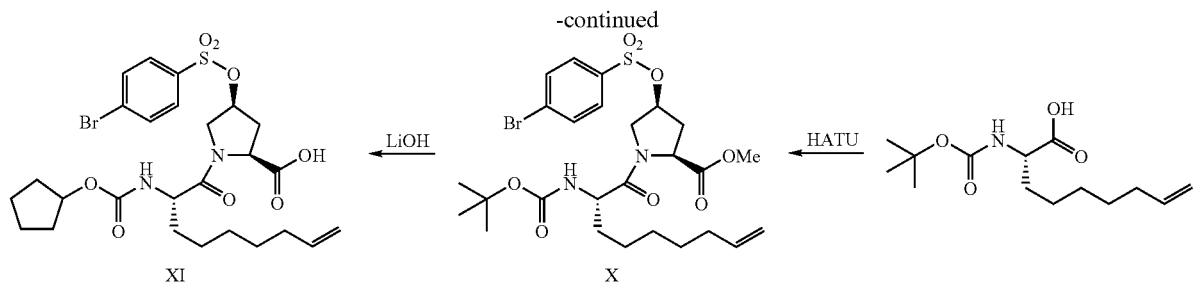

Amine (7.00 g, 28.55 mmol) and DABCO (5.13 g, 45.94 mmol) were dissolved in toluene (30 mL). A toluene (11 mL) solution of brosylchloride (10.22 g, 40.01 mmol) was added. The reaction mixture was stirred at rt overnight. The reaction was diluted with EtOAc (210 mL) and 0.5 N HCl (200 mL) was added. The two layers were separated and the aqueous layer was extracted with EtOAc (2×200 mL). The combined organic layers were washed with brine (200 mL), dried with $Na_2SO_4$, filtered, and concentrated. The crude product was purified by combi-flash to give 12.23 g of intermediate IX in 92% yield.

To a solution of X (12.8 g, 20.7 mmol) in $CH_2Cl_2$ (50 mL) was added 4 N HCl in 1,4-dioxane (50 mL, 200 mmol). The reaction mixture was stirred at r.t. for 2 h, concentrated, dried under vacuum for 20 minutes, and then dissolved in $CH_3CN$ (50 mL). Saturated $NaHCO_3$ in $H_2O$ (50 mL) was added and stirred for 5 minutes. Freshly prepared cyclopentylchloroformate in THF (50 mL) was added. The reaction was complete within 1 h. The solvent was removed under reduced pressure and the residue was diluted with EtOAc. The mixture was brought to pH=2 with 1 N HCl and the two layers were separated. The organic layers were washed with brine, dried with $Na_2SO_4$, filtered, and concentrated to give crude product (3.18 g).

The crude ester (3.18 g, 5.07 mmol) was dissolved in THF (25 mL), $H_2O$ (25 mL), and then MeOH (6 mL) and LiOH (660 mg, 25.4 mmol) was added. The reaction mixture was stirred at rt for 1 h and diluted with EtOAc. The reaction mixture was acidified to pH 2 with 1 N HCl and the two layers were separated. The aqueous layer was extracted with EtOAc (2×). The combined organic layers were washed with brine, dried with $Na_2SO_4$, concentrated and dried under vacuum to give 3.09 g of acid XI.

The proline could be coupled to phosphinate to provide dipeptide as shown in Scheme 6.

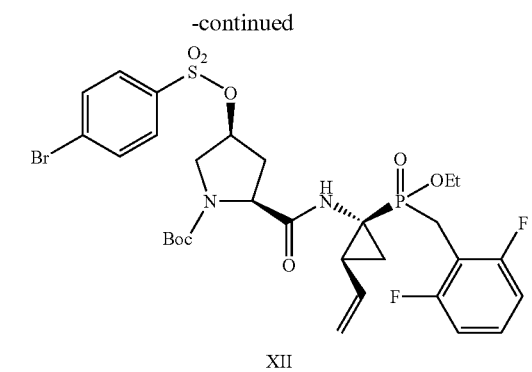

6. Preparation of 8-Chloro-2-(2-isopropylamino-thiazol-4-yl)-7-methoxy-quinolin-4-ol The synthesis of 8-chloro quinoline is shown in scheme 7. The same synthesis is used to prepare 8-bromo, fluoro and methyl analogs.

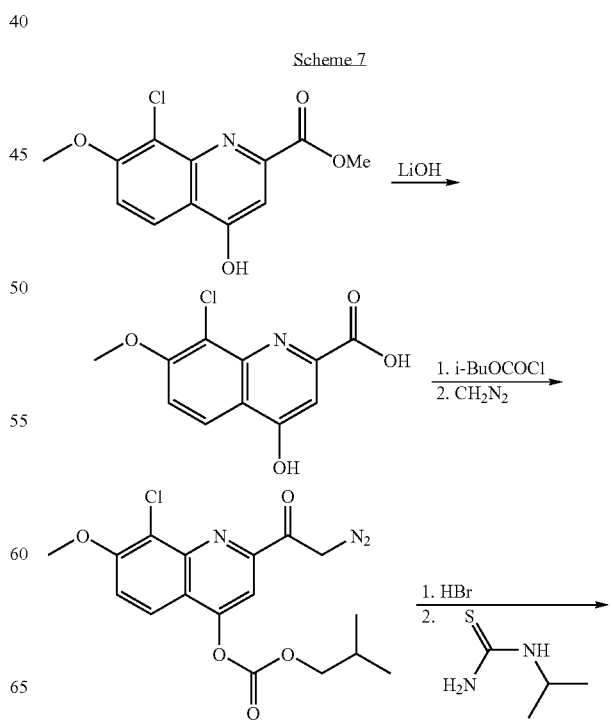

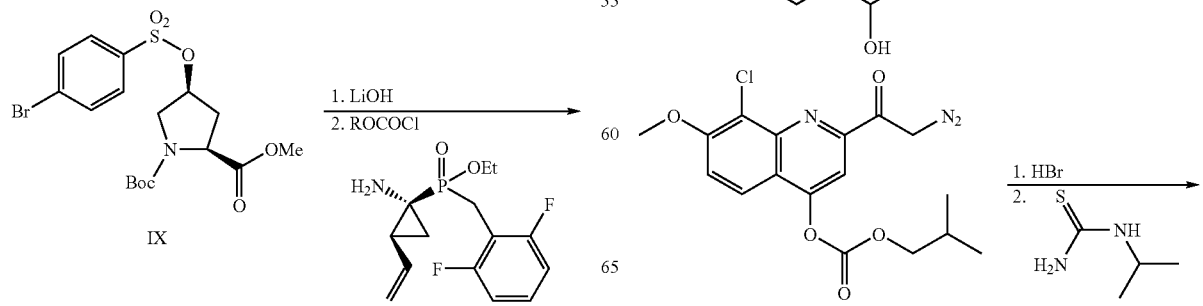

-continued

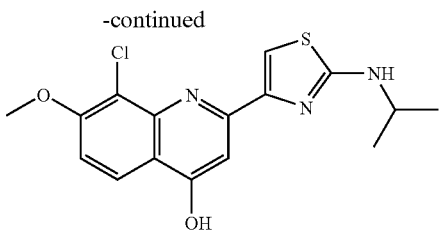

8-chloro-4-hydroxy-7-methoxyquinoline-2-carboxylic acid: To a solution of methyl 8-chloro-4-hydroxy-7-methoxyquinoline-2-carboxylate (36.5 g, 0.145 mol) in a mixture of 1:1 of MeOH: THF (160 mL total) was added a solution of LiOH (30.5 g, 0.725 mol) in H$_2$O (80 mL). The mixture was stirred at room temperature for an hour when LCMS analysis showed complete conversion to the carboxylic acid. The reaction was worked up by removal of the volatiles and adjusting the pH of the solution to 6 using aqueous 6N HCl. The resulted gummy residue was filtered and dried on the lypholizer for 2 days to provide 34.4 g (99.6%) of the product as a white solid. EI MS (m/z) 253.9 [M+H].

2-(2-diazo-1-oxo)-8-chloro-7-methoxyquinolin-4-yl isobutyl carbonate: To a solution of 8-chloro-4-hydroxy-7-methoxyquinoline-2-carboxylic acid (10.2 g, 0.04 mol) in THF (400 mL) was added triethyl amine (12.3 mL, 0.088 mol) and i-Butylchloroformate (11.6 mL, 0.088 mol) at 0° C. under an argon atmosphere. The mixture was stirred at 0° C. for 1 hour when LCMS analysis demonstrated completion of the reaction to provide the desired mixed anhydride. EI MS (m/z) 454.0 [M+H].

To the reaction mixture of the anhydride was added a 1M solution of diazomethane (121 mL, 0.121 mol) in diethyl ether via a plastic funnel at 0° C. This mixture was allowed to stir while warming up to room temperature for additional 2 hours. Analysis of the mixture by LCMS demonstrated completion of the reaction. The septum was removed and the reaction was stirred for additional 20 minutes before removal of the solvent. The residue resulted was dried further under high vacuum and carried on to the next step. EI MS (m/z) 377.9 [M+H].

Preparation of diazomethane from MNNG: To a solution of 130 mL of 40% aqueous KOH and 130 mL of diethyl ether on ice was added a slurry of N-methyl-N'-nitro-N-nitrosoguanidine (18 g, 0.121 mol) over 15 minutes. The mixture was stirred on ice for additional 15 minutes when no further bubbling was observed. The organic layer was decanted to another flask and stored over KOH pellets for subsequent use.

8-chloro-2-(2-(isopropylamino)thiazol-4-yl)-7-methoxyquinolin-4-ol: To a cooled solution of 2-(2-diazo-1-oxo)-8-chloro-7-methoxyquinolin-4-yl isobutyl carbonate (15.2 g, 0.040 mol) at 0° C. in THF (268 mL) was added 48% HBr (23 mL, 0.201 mol) slowly over 15 minutes. The solution was stirred at 0° C. for an additional 40 minutes when LCMS analysis demonstrated complete reaction. The reaction was worked up by addition of aqueous 1N NaOH (180 mL) at 0° C. to adjust the pH of the aqueous layer to 9. The layers were separated and the aqueous layer was washed with EtOAc (2×200 mL). Combined organic extracts were washed with brine and dried over MgSO$_4$. The solvent was removed in vacuo to provide 17.7 g of a yellow solid. EI MS (m/z) 4$^{31}$0.9 [M+H].

The solution of the bromoketone obtained from the previous reaction was suspended in i-propanol (270 mL) and heated at 72° C. for 2 hours when LCMS analysis of the reaction demonstrated complete conversion to the desired product. The reaction was allowed to cool to room temperature to allow for the product to precipitate out of the solution. The reaction was further cooled to 0° C. for 12 hours before filtration. The filtrate was washed with ether and dried on lypholizer to provide 8.03 g of the desired product as an orange solid. $^1$H NMR (500 MHz, CDCl$_3$): δ 8.21 (d, J=9 Hz, 1H), 7.74 (s, 1H), 7.44 (d, J=10 Hz, 1H), 7.07 (s, 1H), 4.05 (s, 3H), 3.92 (pentet, J=6 Hz, 1H), 1.25 (d, J=7 Hz, 6H). EI MS (m/z) 350.0 [M+H].

Example 1

Preparation of Compound 1

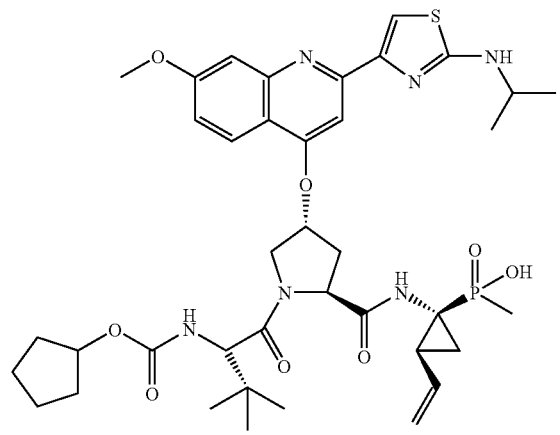

Phosphonic acid intermediate (1-benzyloxycarbonylamino-2-vinyl-cyclopropyl)-phosphonic acid monoethyl ester III (415 mg, 1.28 mmol) was dissolved in toluene (8 mL). This solution was cooled to 0° C. and (COCl)$_2$ (222 µL, 2.56 mmol) was added in a drop-wise fashion. DMF (44 µL, 0.56 mmol) was then added. The reaction was run for 2 h at 0° C. and determined to be complete by $^{31}$P NMR. $^{31}$P NMR (121.4 MHz, CDCl$_3$): δ 39.0, 38.5, 37.4, 36.5, 17.0, 16.2, 16.0, 15.4.

The reaction was concentrated to orange-yellow oil and then placed under high vacuum for 1 h. The resulting residue was dissolved in THF (6.4 mL) and this solution was cooled to −78° C. A 1.4 M solution of methyllithium in diethyl ether (1.37 mL, 1.92 mmol) was added drop-wise. After 40 min, more methyllithium (456 µL, 0.64 mmol) was added drop-wise. After 10 min, the reaction was quenched at −78° C. by the addition of sat. NH$_4$Cl (aq.). The organic phase was diluted with EtOAc and extracted with sat. NH$_4$Cl (aq.) and brine. The organic phase was dried over MgSO$_4$. Concentration of the filtrate after removal of the MgSO$_4$ by vacuum filtration yielded an orange oil from which the product was isolated by column chromatography (SiO$_2$, 100% EtOAc) as a clear oil (214 mg, 52% over 2 steps). $^1$H NMR (300 MHz, CDCl$_3$): δ 7.33 (s, 5H), 6.09 (dt, J=9.9, 17.1 Hz, 1H), 5.65 (d, J=23.7 Hz, 1H), 5.$^{31}$ (d, J=17.1 Hz, 1H), 5.06 (m, 3H), 4.06 (m, 2H), 2.09 (m, 1H), 1.73 (m, 2H), 1.40 (d, 3H), 1.13 (dt, J=8.1, 26.4 Hz, 3H). $^{31}$P NMR (121.4 MHz, CDCl$_3$): δ 53.7, 50.8. LC/MS=324 (M$^+$+1), 346 (M$^+$+Na)

A solution of (1-benzyloxycarbonylamino-2-vinyl-cyclopropyl)-methyl-phosphinic acid ethyl ester (100 mg, 0.308 mmol) in CH$_3$CN (7.7 mL) was cooled to 0° C. and TMSI (220 µL, 1.54 mmol) was added in a drop-wise fashion. The reaction was warmed to rt and stirred for an hour. The reaction was then cooled to 0° C. and additional TMSI (110 µL, 0.77 mmol) was added in a drop-wise fashion. The reaction was warmed to rt and stirred for 30 min. The reaction was cooled back to 0° C. and 2,6-lutidine (360 µL, 3.1 mmol) was added in a drop-wise fashion. This was followed by the addition of Et$_3$N (1 mL, 7.2 mmol) and MeOH (4 mL). The reaction was then concentrated in vacuo and the crude amino phosphinic acid was used directly in the next reaction.

A solution of dipeptide VII (81 mg, 0.123 mmol) in THF (2 mL) was cooled to −30° C. Et$_3$N (34 µL, 0.246 mmol) was added to this solution followed by ClCO$_2$Et (18 µL, 0.185 mmol). The reaction was stirred at a temperature between −20° C. and −30° C. for 30 min. Additional Et$_3$N (34 µL, 0.246 mmol) and ClCO$_2$Et (18 µL, 0.185 mmol) were added. The reaction mixture was stirred for an additional 30 min at a temperature between −20° C. and −30° C. A solution of the crude amino phosphinic acid in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and washed sequentially with sat. NH$_4$Cl$_{(aq.)}$, H$_2$O, and brine. The organic phase was then dried over Na$_2$SO$_4$, which was subsequently removed by vacuum filtration. The filtrate was concentrated in vacuo and the residue was dissolved in MeOH (1.5 mL). Compound 1 was isolated from this solution by reverse-phase HPLC as a yellow solid (37 mg, 37%). $^1$H NMR (300 MHz, CD$_3$CN): δ 8.50 (m, 1H), 8.11 (d, J=9.6 Hz, 1H), 8.02 (s, 1H), 7.75 (s, 1H), 7.38 (s, 1H), 7.21 (dd, J=2.1, 9.3 Hz, 1H), 7.00 (m, 1H), 6.03 (m, 1H), 5.97 (dt, J=6.9, 17.1 Hz, 1H), 5.67 (s, 1H), 5.14 (d, J=17.1 Hz, 1H), 5.01 (d, J=11.4 Hz, 1H), 4.63 (m, 2H), 4.44 (s, 1H), 4.17 (m, 2H), 4.08 (s, 1H), 4.04 (s, 3H), 2.74 (dd, J=7.2, 14.1 Hz, 1H), 2.43 (ddd, J=3.3, 10.5, 13.8 Hz, 1H), 2.08 (m, 1H), 1.24-1.75 (m, 19H), 1.15 (m, 1H), 1.04 (s, 9H). $^{31}$P NMR (121.4 MHz, CD$_3$CN) δ 46.6. LC/MS=797 (M$^+$+1), 819 (M$^+$+Na)

Example 2

Preparation of Compound 2

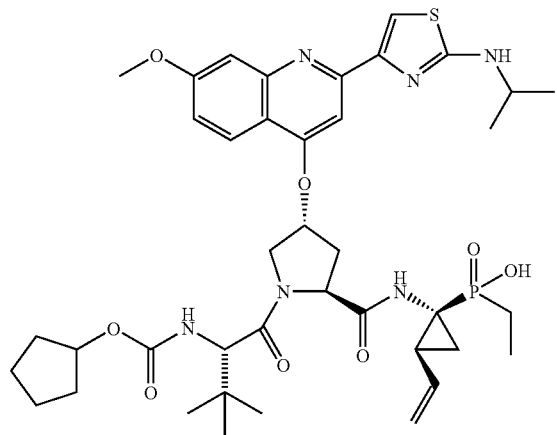

Phosphonic acid intermediate III (208 mg, 0.64 mmol) was dissolved in toluene (8 mL). This solution was cooled to 0° C. and (COCl)$_2$ (111 µL, 1.28 mmol) was added in a drop-wise fashion. DMF (22 µL, 0.28 mmol) was then added. The reaction was run for 2 h at 0° C. and determined to be complete by $^{31}$P NMR.

$^{31}$P NMR (121.4 MHz, CDCl$_3$): δ 39.0, 38.5, 37.4, 36.5, 17.0, 16.2, 16.0, 15.4.

The reaction was concentrated to orange-yellow oil and then placed under high vacuum for 1 h. The resulting residue was dissolved in THF (6.4 mL) and this solution was cooled to −78° C. A solution of EtLi in dibutyl ether (1.7 M, 566 µL, 0.96 mmol) was added drop-wise. After 40 min, more EtLi (189 µL, 0.32 mmol) was added drop-wise. After 10 min, the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate, after vacuum filtration removal of MgSO$_4$, yielded an orange oil from which the desired product was isolated by column chromatography (SiO$_2$, 100% EtOAc) as a clear oil (67 mg, 31% over 2 steps). $^1$H NMR (300 MHz, CDCl$_3$) δ 7.33 (s, 5H), 6.09 (dt, J=9.9, 17.1 Hz, 1H diastereomer 1), 5.94 (dt, J 9.9, 17.1 Hz, 1H diastereomer 2), 5.65 (d, J=23.7 Hz, 1H), 5.31 (d, J=17.1 Hz, 1H), 5.06 (m, 3H), 4.06 (m, 2H), 2.09 (m, 1H), 1.73 (m, 2H), 1.50 (m, 2H), 1.25 (m, 4H), 1.13 (dt, J=8.1, 26.4 Hz, 3H). $^{31}$P NMR (121.4 MHz, CDCl$_3$) δ 54.0, 53.6, 51.3, 50.8 LC/MS=338 (M$^+$+1), 360 (M$^+$+Na)

A solution of (1-benzyloxycarbonylamino-2-vinyl-cyclopropyl)-ethyl-phosphinic acid ethyl ester (104 mg, 0.308 mmol) in CH$_3$CN (7.7 mL) was cooled to 0° C. and TMSI (220 µL, 1.54 mmol) was added in a drop-wise fashion. The reaction was warmed to rt and stirred for an hour. The reaction was then cooled to 0° C. and additional TMSI (110 µL, 0.77 mmol) was added in a drop-wise fashion. The reaction was warmed to rt and stirred for 30 min. The reaction was cooled back to 0° C. and 2,6-lutidine (360 µL, 3.1 mmol) was added in a drop-wise fashion. This was followed by the addition of Et$_3$N (1 mL, 7.2 mmol) and MeOH (4 mL). The reaction was then concentrated in vacuo and the crude amino phosphinic acid, which was used directly in the next reaction.

A solution of dipeptide VII (81 mg, 0.123 mmol) in THF (2 mL) was cooled to −30° C. Et$_3$N (34 µL, 0.246 mmol) was added to this solution followed by ClCO$_2$Et (18 µL, 0.185 mmol). The reaction was stirred at a temperature between −20° C. and −30° C. for 30 min. Additional Et$_3$N (34 µL, 0.246 mmol) and ClCO$_2$Et (18 µL, 0.185 mmol) was added to the reaction. The reaction was stirred for an additional 30 min at a temperature between −20° C. and −30° C. A solution of the crude amino phosphinic acid in CH$_2$Cl$_2$ (2 mL) was added in a drop-wise fashion at −30° C. and the reaction was warmed to rt. The reaction was quenched by the addition of sat. NH$_4$Cl$_{(aq.)}$. The organic phase was diluted with EtOAc and washed with sat. NH$_4$Cl$_{(aq.)}$, H$_2$O, and brine. The organic phase was then dried over Na$_2$SO$_4$, which was subsequently removed by vacuum filtration. The filtrate was concentrated in vacuo and the residue was dissolved in MeOH (1.5 mL). Compound 2 was isolated from this solution by reverse-phase HPLC as a yellow solid (37 mg, 37%). $^1$H NMR (300 MHz, CDCl$_3$): δ 8.27 (d, J=9.6 Hz, 1H), 8.18 (s, 1H), 7.75 (d, J=2.1 Hz, 1H), 7.73 (d, J=3.9 Hz, 1H), 7.31 (dd, J=2.1, 9.3 Hz, 1H), 5.97 (dt, J=6.9, 17.1 Hz, 1H), 5.77 (s, 1H), 5.26 (d, J=17.1 Hz, 1H), 5.08 (d, J=11.4 Hz, 1H), 4.63 (m, 2H), 4.44 (s, 1H), 4.17 (m, 2H), 4.08 (s, 1H), 4.04 (s, 3H), 2.74 (dd, J=7.2, 14.1 Hz, 1H), 2.43 (ddd, J=3.3, 10.5, 13.8 Hz, 1H), 2.08 (m, 1H), 1.84 (m, 2H), 1.54 (m, 8H), 1.34 (d, J=6.3 Hz, 6H), 1.34 (m, 2H), 1.15 (dt, J=7.8, 18.3 Hz, 3H), 1.04 (s, 9H). $^{31}$P NMR (121.4 MHz, CDCl$_3$): δ 50.6. LC/MS=811 (M$^+$+1), 834 (M$^+$+Na)

Example 3

Preparation of Compound 3

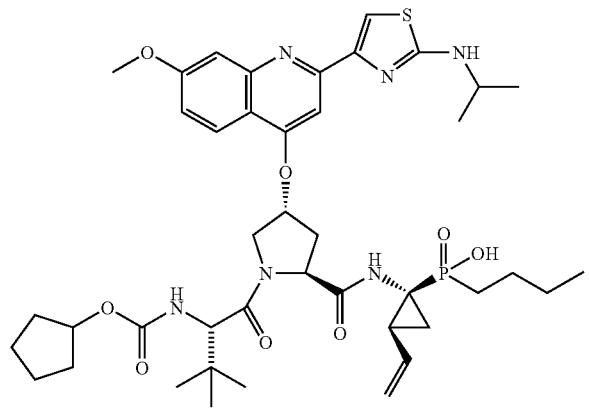

Phosphonic acid intermediate III (386 mg, 1.19 mmol) was dissolved in toluene (14.9 mL). This solution was cooled to 0° C. and (COCl)$_2$ (155 µL, 1.78 mmol) was added in a drop-wise fashion. DMF (20 µL, 0.26 mmol) was then added. The reaction was run for 2 h at 0° C. and determined to be complete by $^{31}$P NMR. $^{31}$P NMR (121.4 MHz, CDCl$_3$): δ 39.0, 38.5, 37.4, 36.6, 17.0, 16.2, 16.1, 15.4.

The reaction was concentrated to a yellow-orange oil and then placed under high vacuum for 1 h. The resulting residue was dissolved in THF (11.9 mL) and this solution was cooled to –78° C. A 2.0 M solution of n-BuLi in pentane (595 µL, 1.19 mmol) was added drop-wise. After 40 min more n-BuLi (520 µL, 1.04 mmol) was added drop-wise. After 10 min the reaction was quenched at –78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate after vacuum filtration removal of the MgSO$_4$ yielded an orange oil from which the product was isolated by column chromatography (SiO$_2$, 7/3 EtOAc:hexane) as a clear oil (243 mg, 56% over 2 steps). $^1$H NMR (300 MHz, CDCl$_3$): δ 7.35 (s, 5H), 6.12 (dt, J=9.9, 16.8 Hz, 1H diastereomer 1), 5.96 (dt, J=10.2, 16.8 Hz, 1H diastereomer 2), 5.33 (m, 2H), 5.09 (m, 3H), 4.11 (m, 2H), 2.01 (brd, J=6.6 Hz, 1H), 1.50-1.90 (m, 6H), 1.37 (brd, J=5.1 Hz, 2H), 1.26 (quart., J=6.2 Hz, 3H), 0.9 (m, 3H) $^{31}$P NMR (121.4 MHz, CDCl$_3$): δ 52.8, 52.4, 50.2, 49.7 LC/MS=366 (M$^+$+1), 388 (M$^+$+Na)

A solution of (1-benzyloxycarbonylamino-2-vinyl-cyclopropyl)-butyl-phosphinic acid ethyl ester (364 mg, 0.996 mmol) in CH$_3$CN (25 mL) was cooled to 0° C. and TMSI (220 µL, 1.54 mmol) was added in a drop-wise fashion. The reaction was warmed to rt and stirred for an hour. The reaction was then cooled to 0° C. and additional TMSI (711 µL, 4.98 mmol) was added in a drop-wise fashion. The reaction was warmed to rt and stirred for 1 h. The reaction was cooled back to 0° C. and 2,6-lutidine (1 mL, 10.1 mmol) was added in a drop-wise fashion. This was followed by the addition of Et$_3$N (1 mL, 7.2 mmol) and MeOH (4 mL). The reaction was warmed to rt and then concentrated in vacuo. The crude mixture was used directly in the next reaction.

A solution of the starting dipeptide VII (100 mg, 0.153 mmol) in THF (2 mL) was cooled to –30° C. Et$_3$N (32 µL, 0.230 mmol) was added to this solution followed by ClCO$_2$Et (22 µL, 0.23 mmol). The reaction was stirred at a temperature between –20° C. and –30° C. for 30 min. Additional Et$_3$N (32 µL, 0.23 mmol) and ClCO$_2$Et (22 µL, 0.23 mmol) was added to the reaction. The reaction was stirred for an additional 30 min at a temperature between –20° C. and –30° C. A solution of crude product from step 1 in CH$_2$Cl$_2$ (2 mL) was added in a drop-wise fashion at –30° C. and the reaction was warmed to rt. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuo and the residue was dissolved in MeOH (1.5 mL). The desired product from the coupling was isolated by reverse-phase HPLC. This coupling reaction was repeated once more on the same scale and the isolated mixture of products from both reaction runs were combined.

The combined products from the coupling reactions were dissolved in CH$_3$CN (5.4 mL) and 2,6-lutidine (149 µL, 1.29 mmol) was then added. This solution was cooled to 0° C. and TMSI (184 µL, 1.29 mmol) was added in a drop-wise fashion. The reaction was stirred at rt for 1 h and then cooled to 0° C. Additional 2,6-lutidine (125 µL, 0.645 mmol) and TMSI (92 µL, 0.645 mmol) was added and the reaction was warmed to rt. The reaction was then cooled to 0° C. and Et$_3$N (1.5 mL, 20.4 mmol) was added in a drop-wise fashion followed by MeOH (5 mL). The reaction was evaporated in vacuo and then dissolved in MeOH (1.5 mL). Compound 3 was isolated from this solution by reverse-phase HPLC as a yellow solid (86 mg, 33% over 2 steps). $^1$H NMR (300 MHz, CDCl$_3$): δ 8.26 (d, J=9 Hz, 1H), 8.15 (s, 1H), 7.70 (d, J=2.1 Hz, 2H), 7.24 (dd, J=2.1, 9 Hz, 1H), 5.93 (dt, J=9.6, 19.5 Hz, 1H), 5.71 (s, 1H), 5.11 (d, J=16.8 Hz, 1H), 4.95 (d, J=12.3 Hz, 1H), 4.70 (d, J=12.3 Hz, 1H), 4.62 (dd, J=7.2, 9.3 Hz, 1H), 4.51 (s, 1H), 4.21 (s, 1H), 4.14 (q, J=6.6 Hz, 1H), 4.07 (dd, J=2.4, 9.9 Hz, 1H), 4.02 (s, 3H), 2.82 (dd, J=7.5, 14.4 Hz, 1H), 2.45 (ddd, J=3.9, 10.2, 14.1 Hz, 1H), 1.98 (m, 1H), 1.40-1.80 (m, 13H), 1.34 (d, J=6.3 Hz, 6H), 1.14-1.32 (m, 3H), 1.01 (s, 9H), 0.86 (t, J=7.2 Hz, 3H). $^{31}$P NMR (121.4 MHz, CDCl$_3$): δ 43.1. LC/MS=839 (M$^+$+1), 861 (M$^+$+Na).

Example 4

Preparation of Compound 4

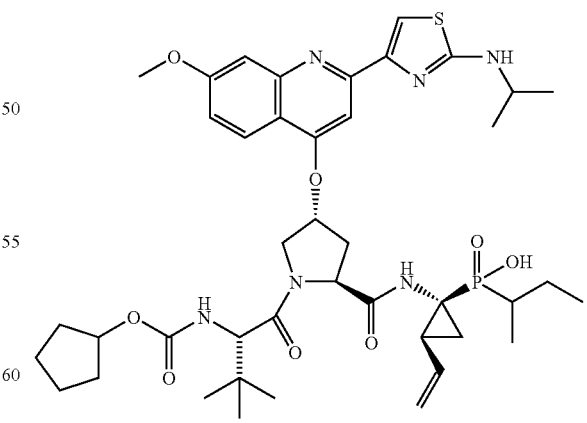

Phosphonic acid intermediate III (415 mg, 1.28 mmol) was dissolved in toluene (8 mL). This solution was cooled to 0° C. and (COCl)$_2$ (222 µL, 2.56 mmol) was added in a drop-wise fashion. DMF (44 µL, 0.56 mmol) was then added. The reaction was run for 2 h at 0° C. and determined to be complete by $^{31}$P NMR. $^{31}$P NMR (121.4 MHz, CDCl$_3$): δ 39.0, 38.5, 37.4, 36.5, 17.0, 16.2, 16.0, 15.4.

The reaction was concentrated to an orange-yellow oil and then placed under high vacuum for 1 h. The resulting residue was dissolved in THF (6.4 mL) and this solution was cooled to −78° C. A 1.4 M solution of sec-butyllithium in cyclohexane (1.37 mL, 1.92 mmol) was added drop-wise. After 40 min more sec-butyllithium in cyclohexane (456 μL, 0.64 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate after vacuum filtration removal of the MgSO$_4$ yielded an orange oil from which the product was isolated by column chromatography (SiO$_2$, 60% EtOAc in Hexane) as a clear oil (146 mg, 31% over 2 steps). $^1$H NMR (300 MHz, CDCl$_3$): δ 7.33 (s, 5H), 6.07 (dt, J=9.9, 17.1 Hz, 1H), 5.55 (d, J=23.7 Hz, 1H), 5.31 (d, J=17.1 Hz, 1H), 5.06 (m, 3H), 4.06 (m, 2H), 2.09 (m, 1H), 1.65-1.83 (m, 3H), 1.58 (m, 1H) 1.41 (m, 1H), 1.03-1.32 (m, 6H), 0.97 (dt, J=8.1, 26.4 Hz, 3H). $^{31}$P NMR (121.4 MHz, CDCl$_3$): δ 54.9, 54.3, 50.8, 50.0 LC/MS=366 (M$^+$+1), 388 (M$^+$+Na)

A solution of (1-benzyloxycarbonylamino-2-vinyl-cyclopropyl)-sec-butyl-phosphinic acid ethyl ester (112 mg, 0.308 mmol) in CH$_3$CN (7.7 mL) was cooled to 0° C. and TMSI (220 μL, 1.54 mmol) was added in a drop-wise fashion. The reaction was warmed to rt and stirred for an hour. The reaction was then cooled to 0° C. and additional TMSI (110 μL, 0.77 mmol) was added in a drop-wise fashion. The reaction was warmed to rt and stirred for 30 min. The reaction was cooled back to 0° C. and 2,6-lutidine (360 μL, 3.1 mmol) was added in a drop-wise fashion. This was followed by the addition of Et$_3$N (1 mL, 7.2 mmol) and MeOH (4 mL). The reaction was then concentrated in vacuo and the resulting crude product was used directly in the next reaction. A solution of dipeptide VII (81 mg, 0.123 mmol) in THF (2 mL) was cooled to −30° C. Et$_3$N (34 μL, 0.246 mmol) was added to this solution followed by ClCO$_2$Et (18 μL, 0.185 mmol). The reaction was stirred at a temperature between −20° C. and −30° C. for 30 min. Additional Et$_3$N (34 μL, 0.246 mmol) and ClCO$_2$Et (18 μL, 0.185 mmol) was added to the reaction. The reaction was stirred for an additional 30 min at a temperature between −20° C. and −30° C. A solution of crude product from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was dried over Na$_2$SO$_4$, which was subsequently removed by vacuum filtration. The filtrate was concentrated in vacuo and the residue was dissolved in MeOH (1.5 mL). Compound 4 was isolated from this solution by reverse-phase HPLC as a yellow solid (42 mg, 41%). $^1$H NMR (300 MHz, CD$_3$OD): δ 8.27 (d, J=9.6 Hz, 1H), 8.18 (s, 1H), 7.75 (d, J=2.1 Hz, 1H), 7.39 (d, J=3.9 Hz, 1H), 7.31 (dd, J=2.1, 9.3 Hz, 1H), 6.01 (dt, J=6.9, 17.1 Hz, 1H), 5.77 (s, 1H), 5.26 (d, J=17.1 Hz, 1H), 5.08 (d, J=11.4 Hz, 1H), 4.63 (m, 2H), 4.44 (s, 1H), 4.17 (m, 2H), 4.08 (s, 1H), 4.04 (s, 3H), 2.76 (dd, J=7.2, 14.1 Hz, 1H), 2.43 (ddd, J=3.3, 10.5, 13.8 Hz, 1H), 2.08 (m, 1H), 1.96 (m, 2H), 1.60-1.82 (m, 9H), 1.34 (d, J=6.3 Hz, 6H), 1.22 (m, 6H), 1.04 (s, 9H), 0.99 (m, 3H). $^{31}$P NMR (121.4 MHz, CD$_3$OD) δ 52.4, 52.2 LC/MS=839 (M$^+$+1), 861 (M$^+$+Na)

Example 5

Preparation of Compound 5

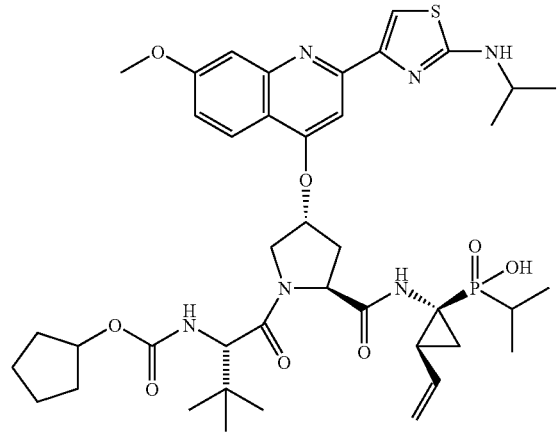

Phosphonic acid intermediate III (415 mg, 1.28 mmol) was dissolved in toluene (8 mL). This solution was cooled to 0° C. and (COCl)$_2$ (222 μL, 2.56 mmol) was added in a drop-wise fashion. DMF (44 μL, 0.56 mmol) was then added. The reaction was run for 2 h at 0° C. and determined to be complete by $^{31}$P NMR. $^{31}$P NMR (121.4 MHz, CDCl$_3$): δ 39.0, 38.5, 37.4, 36.5, 17.0, 16.2, 16.0, 15.4.

The reaction was concentrated to an orange-yellow oil and then placed under high vacuum for 1 h. The resulting residue was dissolved in THF (6.4 mL) and this solution was cooled to −78° C. A 0.7 M solution of isopropyllithium in pentane (2.74 mL, 1.92 mmol) was added drop-wise. After 40 min more isopropyllithium (912 μL, 0.64 mmol) was added drop-wise. After 10 min the reaction was quenched at −78° C. by the addition of sat. NH$_4$Cl $_{(aq.)}$. The organic phase was diluted with EtOAc and extracted with sat. NH$_4$Cl $_{(aq.)}$ and brine. The organic phase was dried over MgSO$_4$. Concentration of the filtrate after vacuum filtration removal of the MgSO$_4$ yielded an orange oil from which the product was isolated by column chromatography (SiO$_2$, 100% EtOAc) as a clear oil (200 mg, 45% over 2 steps). $^1$H NMR (300 MHz, CD$_3$CN): δ 7.38 (s, 5H), 6.69 (m, 1H), 6.12 (m, 1H), 5.35 (m, 1H), 5.06 (m, 4H), 4.06 (m, 2H), 2.09 (m, 1H), 1.55 (m, 1H) 1.41 (m, 1H), 1.02-1.35 (m, 9H). $^{31}$P NMR (121.4 MHz, CD$_3$CN): δ 56.0, 53.8. LC/MS=352 (M$^+$+1), 374 (M$^+$+Na)

A solution of (1-benzyloxycarbonylamino-2-vinyl-cyclopropyl)-isopropyl-phosphinic acid ethyl ester (108 mg, 0.308 mmol) in CH$_3$CN (7.7 mL) was cooled to 0° C. and TMSI (220 μL, 1.54 mmol) was added in a drop-wise fashion. The reaction was warmed to rt and stirred for an hour. The reaction was then cooled to 0° C. and additional TMSI (110 μL, 0.77 mmol) was added in a drop-wise fashion. The reaction was warmed to rt and stirred for 30 min. The reaction was cooled back to 0° C. and 2,6-lutidine (360 μL, 3.1 mmol) was added in a drop-wise fashion. This was followed by the addition of Et$_3$N (1 mL, 7.2 mmol) and MeOH (4 mL). The reaction was then concentrated in vacuo and the crude product was used directly in the next reaction.

A solution of VII (81 mg, 0.123 mmol) in THF (2 mL) was cooled to −30° C. Et$_3$N (34 μL, 0.246 mmol) was added to this solution followed by ClCO$_2$Et (18 µL, 0.185 mmol). The reaction was stirred at a temperature between −20° C. and −30° C. for 30 min. Additional Et$_3$N (34 µL, 0.246 mmol) and ClCO$_2$Et (18 µL, 0.185 mmol) was added to the reaction. The reaction was stirred for an additional 30 min at a temperature between −20° C. and −30° C. A solution of crude product from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuo and the residue was dissolved in MeOH (1.5 mL). Compound 5 was isolated from this solution by reverse-phase HPLC as a yellow solid (40 mg, 40%). $^1$H NMR (300 MHz, CD$_3$CN): δ 8.27 (d, J=9.6 Hz, 1H), 8.11 (m, 1H), 8.05 (s, 1H), 7.75 (d, J=2.1 Hz, 1H), 7.53 (d, J=3.9 Hz, 1H), 7.31 (dd, J=2.1, 9.3 Hz, 1H), 6.75 (m, 1H), 6.06 (dt, J=6.9, 17.1 Hz, 1H), 5.77 (m, 2H), 5.26 (d, J=17.1 Hz, 1H), 5.08 (d, J=11.4 Hz, 1H), 4.63 (m, 2H), 4.17 (m, 2H), 4.08 (s, 1H), 4.04 (s, 3H), 2.74 (dd, J=7.2, 14.1 Hz, 1H), 2.53 (ddd, J=3.3, 10.5, 13.8 Hz, 1H), 2.21 (m, 1H), 2.08 (m, 1H), 1.42-1.78 (m, 8H), 1.34 (d, J=6.3 Hz, 6H), 1.34 (m, 2H) 1.15 (m, 5H), 1.04 (s, 9H), 0.99-1.03 (m, 3H). $^{31}$P NMR (121.4 MHz, CD$_3$CN): δ 50.6. LC/MS=825 (M$^+$+1), 847 (M$^+$+Na)

Example 6

Preparation of Compound 6

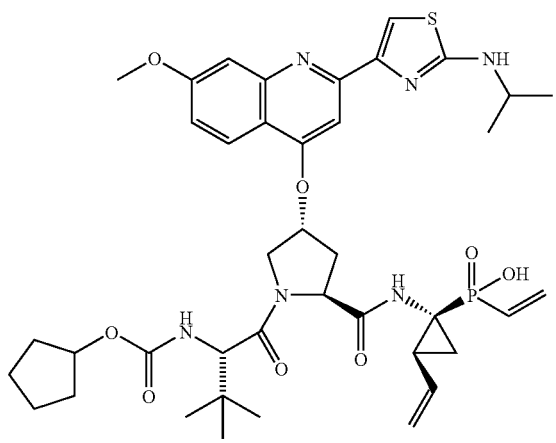

Phosphonic acid intermediate III (415 mg, 1.28 mmol) was dissolved in toluene (8 mL). This solution was cooled to 0° C. and (COCl)$_2$ (222 µL, 2.56 mmol) was added in a drop-wise fashion. DMF (44 µL, 0.56 mmol) was then added. The reaction was run for 2 h at 0° C. and determined to be complete by $^{31}$P NMR.

$^{31}$P NMR (121.4 MHz, CDCl$_3$): δ 39.0, 38.5, 37.4, 36.5, 17.0, 16.2, 16.0, 15.4.

The reaction was concentrated to an orange-yellow oil and then placed under high vacuum for 1 h. The resulting residue was dissolved in THF (6.4 mL) and this solution was cooled to −78° C. A 1.0 M solution of vinylmagnesium bromide in tetrahydrofuran (2.6 mL, 2.6 mmol) was added drop-wise. After 40 min more vinylmagnesium bromide (2.6 mL, 2.6 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate after vacuum filtration removal of the MgSO$_4$ yielded an orange oil from which the product was isolated by column chromatography (SiO$_2$, 100% EtOAc) as a clear oil (214 mg, 40% over 2 steps). $^1$H NMR (300 MHz, CDCl$_3$): δ 7.33 (s, 5H), 6.09-6.15 (m, 2H), 5.55 (m, 1H), 5.31 (m, 1H), 5.05 (m, 4H), 4.06 (m, 2H), 2.09 (m, 1H), 1.73 (m, 1H), 1.60 (m, 1H), 1.43 (m, 1H), 1.13 (dt, J=8.1, 26, 4 Hz, 3H) $^{31}$P NMR (121.4 MHz, CDCl$_3$): δ 36.5, 34.6. LC/MS=336 (M$^+$+1), 358 (M$^+$+Na).

A solution of (1-benzyloxycarbonylamino-2-vinyl-cyclopropyl)-vinyl-phosphinic acid ethyl ester (103 mg, 0.308 mmol) in CH$_3$CN (7.7 mL) was cooled to 0° C. and TMSI (220 µL, 1.54 mmol) was added in a drop-wise fashion. The reaction was warmed to rt and stirred for an hour. The reaction was then cooled to 0° C. and additional TMSI (110 µL, 0.77 mmol) was added in a drop-wise fashion. The reaction was warmed to rt and stirred for 30 min. The reaction was cooled back to 0° C. and 2,6-lutidine (360 µL, 3.1 mmol) was added in a drop-wise fashion. This was followed by the addition of Et$_3$N (1 mL, 7.2 mmol) and MeOH (4 mL). The reaction was then concentrated in vacuo and crude was used directly in the next reaction.

A solution of dipeptide VII (81 mg, 0.123 mmol) in THF (2 mL) was cooled to −30° C. Et$_3$N (34 µL, 0.246 mmol) was added to this solution followed by ClCO$_2$Et (18 µL, 0.185 mmol). The reaction was stirred at a temperature between −20° C. and −30° C. for 30 min. Additional Et$_3$N (34 µL, 0.246 mmol) and ClCO$_2$Et (18 µL, 0.185 mmol) was added to the reaction. The reaction was stirred for an additional 30 min at a temperature between −20° C. and −30° C. A solution of crude from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuo and the residue was dissolved in MeOH (1.5 mL). Compound 6 was isolated from this solution by reverse-phase HPLC as a yellow solid (45 mg, 45%). $^1$H NMR (300 MHz, CD$_3$CN) δ 8.25 (br, 1H), 8.20 (d, J=9.6 Hz, 1H), 8.02 (s, 1H), 7.75 (s, 1H), 7.39 (s, 1H), 7.23 (dd, J=2.1, 9.3 Hz, 1H), 6.84 (br, 1H), 6.35 (m, 2H), 5.97 (m, 3H), 5.77 (m, 1H), 5.61 (s, 1H), 5.26 (d, J=17.1 Hz, 1H), 5.08 (d, J=11.4 Hz, 1H), 4.63 (m, 2H), 4.44 (s, 1H), 4.17 (m, 2H), 4.08 (s, 1H), 4.04 (s, 3H), 2.74 (dd, J=7.2, 14.1 Hz, 1H), 2.43 (ddd, J=3.3, 10.5, 13.8 Hz, 1H), 1.41-1.78 (m, 8H), 1.34 (d, J=6.3 Hz, 6H), 1.34 (m, 2H), 1.15 (m, 1H), 1.04 (s, 9H)

$^{31}$P NMR (121.4 MHz, CD$_3$CN) δ 30.2. LC/MS=809 (M$^+$+1), 831 (M$^+$+Na).

Example 7

Preparation of Compound 7

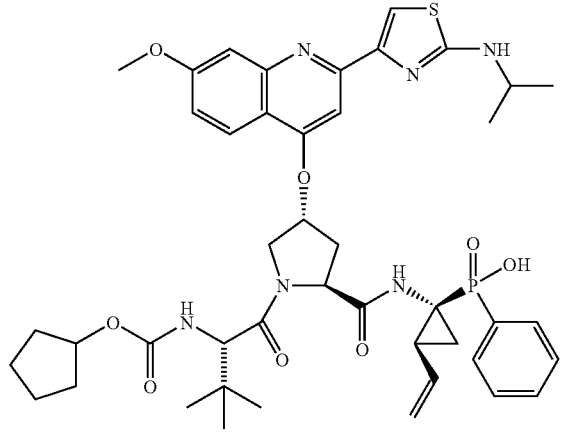

Phosphonic acid intermediate III (451 mg, 1.39 mmol) was dissolved in toluene (17.4 mL). This solution was cooled to 0° C. and (COCl)$_2$ (1.21 mL, 13.87 mmol) was added in a drop-wise fashion. DMF (24 µL, 0.306 mmol) was then added. The reaction was run for 2 h at 0° C. and then 18 h at rt. The reaction was determined to be complete by $^{31}$P NMR. $^{31}$P NMR (121.4 MHz, CDCl$_3$) δ 39.3, 38.8, 37.6, 36.8, 17.2, 16.4, 16.3, 15.6.

The reaction was concentrated to an orange-yellow oil and then placed under high vacuum for 1 h. The resulting residue was dissolved in THF (13.9 mL) and this solution was cooled to −78° C. A 1.8M solution of PhLi in Et$_2$O (1.2 mL, 2.17 mmol) was added drop-wise. After 30 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$ which was subsequently removed by vacuum filtration. Concentration of the filtrate yielded an orange oil from which the desired product was isolated by column chromatography (SiO$_2$, 7/3 EtOAc:hexane) as a clear oil (243 mg, 56% over 2 steps) in 73% purity by $^{31}$P NMR. $^1$H NMR (300 MHz, CDCl$_3$) δ 7.75 (m, 2H), 7.56 (m, 1H), 7.20-7.44 (m, 7H), 6.18 (m, 1H), 5.39 (d, J=17.1 Hz, 1H), 4.80-5.30 (m, 4H), 4.0-4.3 (m, 2H), 1.91 (m, 1H), 1.69 (m, 1H), 1.2-1.4 (m, 4H). $^{31}$P NMR (121.4 MHz, CDCl$_3$) δ 37.8, 37.4, 36.2, 36.0, 35.0, 34.7, 33.4, 33.3.

LC/MS=386 (M$^+$+1), 408 (M$^+$+Na).

A solution of (1-benzyloxycarbonylamino-2-vinyl-cyclopropyl)-phenyl-phosphinic acid ethyl ester (150 mg, 0.389 mmol) in ACN (10 mL) was cooled to 0° C. and TMSI (278 µL, 1.95 mmol) was added in a drop-wise fashion. The reaction was warmed to rt and stirred for an hour. The reaction was cooled back to 0° C. and Et$_3$N (1.5 mL, 20.4 mmol) and MeOH (5 mL) were added in a drop-wise fashion. The reaction was then concentrated in vacuo and the crude product was used directly in the next reaction.

A solution of dipeptide VII (50 mg, 0.076 mmol) in THF (2 mL) was cooled to −30° C. Et$_3$N (16 µp L, 0.114 mmol) was added to this solution followed by ClCO$_2$Et (15 µL, 0.114 mmol). The reaction was stirred at a temperature between −20° C. and −30° C. for 30 min. Additional Et$_3$N (16 µL, 0.114 mmol) and ClCO$_2$Et (15 µL, 0.114 mmol) was added to the reaction. The reaction was stirred for an additional 30 min at a temperature between −20° C. and −30° C. A solution of the crude product from step 1 in CH$_2$Cl$_2$ (2 mL) was added in a drop-wise fashion at −30° C. and the reaction was warmed to rt. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuo and the residue was dissolved in MeOH (1.5 mL). Compound 7 was isolated from this solution by reverse-phase HPLC as a yellow solid (17 mg, 25%). $^1$H NMR (300 MHz, CDCl$_3$) δ 8.22 (d, J=9.6 Hz, 1H), 8.18 (s, 1H), 7.89 (dd, J=6.9, 11.7 Hz, 2H), 7.74 (d, J=2.1 Hz, 1H), 7.72 (s, 1H), 7.53 (m, 3H), 7.30 (dd, J=2.1, 9 Hz, 1H), 6.14 (dt, J=10.2, 19.5 Hz, 1H), 5.71 (s, 1H),), 5.22 (d, J=17.1 Hz, 1H), 5.02 (d, J=10.2 Hz, 1H), 4.55 (m, 2H), 4.40 (s, 1H), 4.18 (quint., J=6.6 Hz, 1H), 4.11 (s, 1H), 4.04 (m, 4H), 5.60 (dd, J=6.9, 14.1 Hz, 1H), 2.23 (ddd, J=3.6, 10.2, 13.8 Hz, 1H), 2.12 (m, 1H), 1.72 (m, 1H), 1.40-1.66 (m, 9H), 1.34 (d, J=6.3 Hz, 6H), 1.03 (s, 9H). $^{31}$P NMR (121.4 MHz, CDCl$_3$) δ 34.0

LC/MS=859 (M$^+$+1), 881 (M$^+$+Na).

Example 8

Preparation of Compound 8

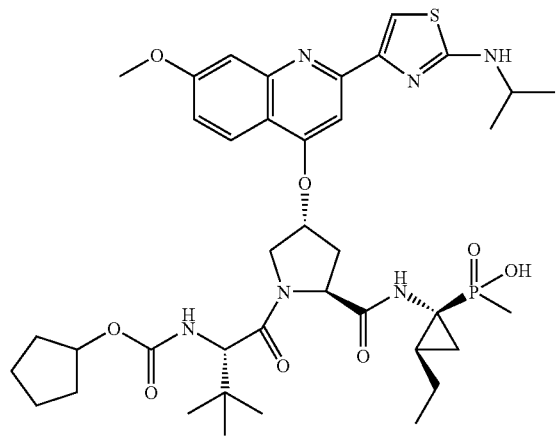

To a solution of 1 (677 mg, 0.79 mmol) in DME (5 mL) and H$_2$O (0.4 mL) was added p-tosylhydrazide (737 mg, 3.96 mmol) and NaOAc (650 mg, 7.93 mmol). The reaction mixture was heated to 95° C. for 1.5 h and cooled to rt. A few drops of 3 N HCl was added to adjust the pH to 2. The crude product was purified by HPLC to give 8 (587 mg, 76%) as a yellow solid. $^1$H NMR (300 MHz, CD$_3$CN): δ 8.16 (m, 1H), 8.06 (s, 1H), 7.71 (s, 1H), 7.44 (s, 1H), 7.25 (m, 1H), 6.83 (m, 1H), 5.92 (m, 1H), 5.61 (br, 1H), 4.58 (m, 2H), 4.41 (m, 1H), 4.14 (m, 2H), 4.05 (m, 4H), 2.76 (m, 1H), 2.45 (m, 1H), 1.80 (m, 2H), 1.65 (m, 10H) 1.38 (d, J=6.3, 6H), 1.21 (m, 1H), 0.98 (m, 12H). $^{31}$P NMR (121.4 MHz, CD$_3$CN): δ46.569. LC/MS=799 (M$^+$+1)

Example 9

Preparation of Compound 9

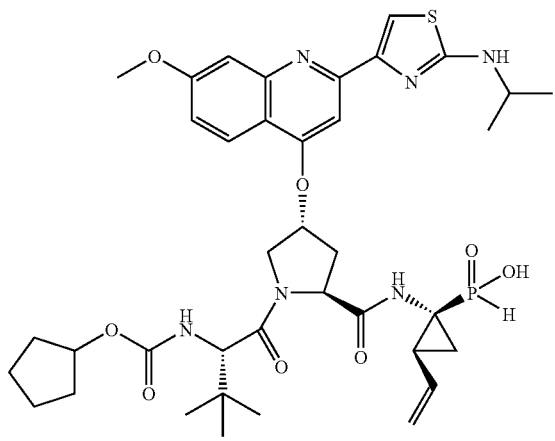

A solution of phosphonous acid (IV) (150 mg, 0.48 mmol) in CH$_3$CN (1 mL) was stirred at 0° C. as iodotrimethylsilane (345 μl, 2.42 mmol) was added. The solution stirred at rt for 45 min. and was cooled again to 0° C. and triethylamine (1 mL, 7.33 mmol) and MeOH (2 mL) was added. The solution was warmed to rt and stirred for an additional 20 minutes. The solution was then concentrated, azeotroped with toluene (×2) and dried on high vacuum for 30 minutes. The crude was coupled with VII (209 mg, 0.32 mmol), using HATU (304 mg, 0.80 mmol), and NMM (176 μl, 1.60 mmol) in DMF (1 mL) overnight at rt. The reaction was concentrated and purified with a Gilson HPLC to obtain 9 as a yellow solid. $^1$H NMR (300 MHz, CD$_3$OD): δ 8.18 (s, 1H), 8.20 (m, 2H), 7.78 (s, 1H), 7.38 (m, 1H), 6.20 (s, J=9.2 Hz, 1H), 5.90 (m, 1H), 5.80 (bs, 1H), 5.23 (dd, 1H), 5.18 (d, J=9.0 Hz, 1H) 4.78 (s, 1H), 4.58 (m, 1H), 4.30 (m, 1H), 4.20 (q, 2H), 4.05 (m, 2H), 4.01 (s, 3H), 2.79 (m, 1H), 2.57 (m, 1H), 2.15 (m, 1H), 1.62 (m, 2H), 1.50 (m, 2H) 1.30 (d, 3H), 1.05 (s, 9H). $^{31}$P (121.4 MHz, CD$_3$OD): δδ22.768, 22.682

Example 10

Preparation of Compound 10

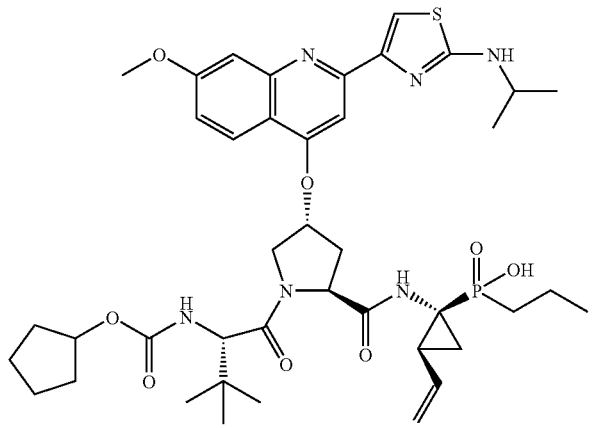

Same procedures as described for example 6 was used to provide compound 10. $^1$H NMR (300 MHz, CD$_3$OD) δ8.25 (d J=9 Hz, 1H), 8.18 (s, 1H), 7.75 (m, 2H), 7.30 (dd, J=9.3, 2.1 Hz, 1H), 5.96 (dt, J=6.9, 19.8 Hz, 1H), 5.77 (s, 1H), 5.25 (d, J=17.1 Hz, 1H), 5.06 (d, J=10.5 Hz, 1H), 4.64 (m, 2H), 4.44 (s, 1H), 4.15 (m, 3H), 4.04 (m, 3H), 2.76 (dd, J=7.5, 14.1 Hz, 1H), 2.43 (ddd, J=3.9, 10.2, 13.8 Hz, 1H), 2.08 (m, 1H), 1.4-1.9 (brm, 14H), 1.34 (d, J=6.3 Hz, 6H), 1.04 (s, 9H), 1.02 (m, 3H).

$^{31}$P NMR (121.4 MHz, CD$_3$OD) δ 48.8
LC/MS 825.3 (M$^+$+1), 847.2 (M$^+$+Na)

Example 11

Preparation of Compound 11

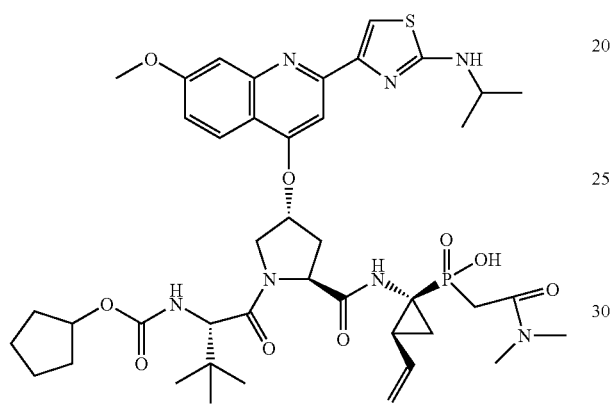

A solution of the phosphonous acid IV (499 mg, 1.61 mmol), Hunig's Base (794 µL, 3.88 mmol), and chlorotrimethylsilane (590 µL, 3.57 mmol) in CH$_2$Cl$_2$ (7.5 mL) was stirred at r.t. for 30 minutes before ethyl 2-bromoacetate (395 µL, 3.65 mmol) was added. The solution was heated at 40° C. for 7.5 h. The solution was concentrated and the residue was dissolved in ethyl acetate (30 mL) and then washed with H$_2$O (30 mL×2). The aqueous layers were extracted with ethyl acetate (30 mL). The combined organic layers were dried (MgSO$_4$) and concentrated. The residue was purified by column chromatography using hexane:ethyl acetate as eluent to obtain [(1-benzyloxycarbonylamino-2-vinyl-cyclopropyl)-ethoxy-phosphinoyl]-acetic acid ethyl ester (344 mg, 54%). $^1$H NMR (300 MHz, CDCl$_3$): δ 7.34 (s, 5H), 6.04 (m, 0.39H), 5.91 (m, 0.53H), 5.72 (d, 1H), 5.42 (s, 1H), 5.36 (s, 1H), 5.30 (s, 2H), 5.09 (m, 3H), 4.18 (m, 4H), 3.04 (m, 2H), 2.30 (m, 1H), 2.03 (m, 1H), 1.85 (m, 2H), 1.70 (m, 2H), 1.58 (m, 2H), 1.38 (m, 2H), 1.25 (m, 6H). $^{31}$P (121.4 MHz, CDCl$_3$): δ43.406, 42.646, 39.087

A solution of [(1-benzyloxycarbonylamino-2-vinyl-cyclopropyl)-ethoxy-phosphinoyl]-acetic acid ethyl ester (352 mg, 0.89 mmol) in THF (3 mL) was stirred at 0° C. as 1 N NaOH (980 µL, 0.98 mmol) was added. The solution was stirred overnight at r.t. and then concentrated, diluted with H$_2$O (10 mL) and washed with ethyl acetate. The aqueous layer was acidified with 1 N HCl (5 mL) and extracted with ethyl acetate (×2). The organic extracts were washed with H$_2$O, dried (MgSO$_4$) and concentrated to yield [(1-Benzyloxycarbonylamino-2-vinyl-cyclopropyl)-ethoxy-phosphinoyl]-acetic acid (224 mg, 69%). $^1$H NMR (300 MHz, CDCl$_3$): δ 7.34 (s, 5H), 5.91 (m, 2H), 5.20 (m, 2H), 4.21 (m, 2H), 3.11 (m, 2H), 2.30 (m, 1H), 2.03 (m, 1H), 1.85 (m, 2H), 1.70 (m, 2H), 1.38 (m, 2H), 1.25 (m, 3H). $^{31}$P (121.4 MHz, CDCl$_3$): δ45.109, 41.119, 40.965, 39.514

A solution of the acid (224 mg, 0.61 mmol), dimethylammonium chloride (125 mg, 1.53 mmol), HATU (697 mg, 1.83 mmol) and N-methylmorpholine (600 µl, 5.46 mmol) was stirred in DMF (3 mL) at rt for 2.5 h. The solution was concentrated and the residue was dissolved in ethyl acetate (30 mL) and washed with H$_2$O (2×30 mL) and brine. The aqueous layer was extracted with ethyl acetate (30 mL) and the combined organic extracts were dried (MgSO$_4$) and concentrated. The residue was triturated with CH$_2$Cl$_2$ (10 mL) and filtered. The filtrate was concentrated and the residue treated with CH$_2$Cl$_2$ and then filtered. The desired product (240 mg, 99%) was isolated by column chromatography using hexane:ethyl acetate as eluent. $^1$H NMR (300 MHz, CDCl$_3$): δ 7.33 (s, 5H), 6.38 (s, 1H), 6.00 (m, 1H), 5.44 (s, 1H), 5.38 (s, 1H), 5.30 (s, 2H), 5.04 (m, 4H), 4.23 (m, 2H), 3.18 (s, 1.08H), 3.09 (s, 1.62H), 2.88 (s, 1.08H), 2.81 (s, 1.62H), 2.38 (m, 1H), 1.87 (m, 1H), 1.76 (m, 1H), 1.45 (m, 1H), 1.23 (m, 3H). $^{31}$P (121.4 MHz, CDCl$_3$): δ46.664, 45.538, 42.765, 42.417. Deprotection and coupling to intermediate VII gave 11. LC/MS=868 (M$^+$+1), Example 12

Preparation of Compound 12

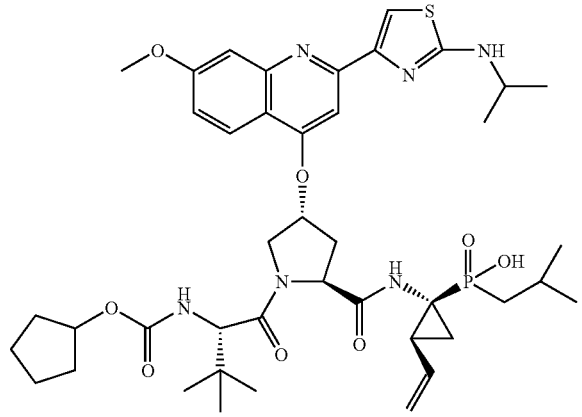

Intermediate IV (840 mg, 2.7 mmol) was dissolved in 8 mL of dry THF and cooled to −40° C. 1N NaHMDS (4.1 mL, 4.1 mmol) in THF was added dropwise and the reaction was stirred at −40° C. for 30 minutes. 1-bromo-2-methyl-propene (446 µl, 4.1 mmol) was dissolved in 1 mL of THF and then added dropwise. The reaction was allowed to warm to rt. After stirring at rt overnight, the reaction was cooled to 0° C. and 300 µl of acetic acid was added to quench the reaction. The mixture was then concentrated in vacuo and diluted with ethyl acetate. The organic was then extracted once with water and once with brine. The organic was then dried over Mg$_2$SO$_4$ and concentrated in vacuo to afford an oily residue. The product (83 mg, 9%) was then isolated from the residue by silica gel chromatography (3:1-ethyl acetate:hexane). $^1$H NMR (300 MHz, CDCl$_3$) δ 7.36 (s, 3H), 6.0 (m, 1H), 5.30 (m, 2H), 5.10 (b, 4H), 4.13 (m, 2H), 2.13 (m, 2H), 1.79 (m, 3H), 1.54-1.39 (m, 4H), 1.28 (m, 3H), 1.03 (m, 6H). $^{31}$P NMR (121.4 MHz, CDCl$_3$) δ 50.26, 47.54. LC/MS=366 (M$^+$+1)

Coupling to dipeptide VII as described above gave compound 12 (28 mg, 28%). $^1$H NMR (300 MHz, CD$_3$OD) 8.27 (d, J=9.3 Hz, 1H), 8.22 (s, 1H), 7.76 (s, 2H), 7.3 (d, J=9.0 Hz, 1H), 5.94 (m, 1H), 5.79 (b, 1H), 5.25 (d, J=17.1 Hz, 1H), 5.07 (d, J=9.9 Hz, 1H), 4.64 (m, 2H), 4.43 (s, 1H), 4.15 (m, 2H), 4.11 (s, 1H), 4.04 (s, 3H), 2.80 (m, 2H), 2.45 (m, 1H), 2.15 (m, 1H), 1.75 (m, 1H), 1.60-1.40 (m, 8H), 1.35 (d, J=6.3 Hz, 12H), 1.04 (s, 10H). $^{31}$P NMR (121.4 MHz, CD$_3$OD) δ 24.48. LC/MS=839 (M$^+$+1)

Example 13

Preparation of Compound 13

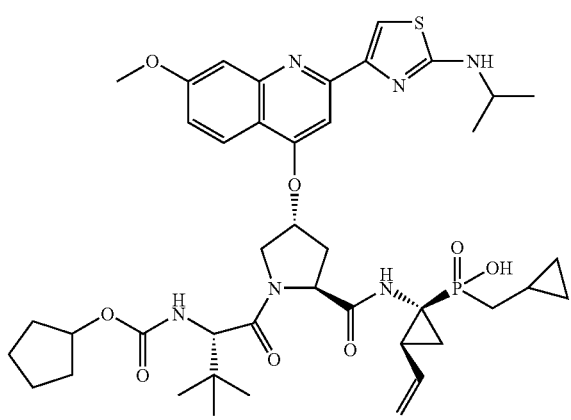

Examples 13 through 15 were prepared by the same method as example 12. $^1$H NMR (300 MHz, CD$_3$OD): δ 8.26 (m, 1H), 8.17 (m, 1H), 7.76 (s, 2H), 7.32 (m, 1H), 5.95 (m, 1H), 5.80 (br, 1H), 5.36 (m, 1H), 5.13 (m, 1H), 4.63 (m, 2H), 4.41 (m, 1H), 4.15 (m, 2H), 4.04 (m, 4H), 2.66 (m, 1H), 2.33 (m, 1H), 1.94 (m, 2H), 1.65 (m, 13H) 1.38 (d, J=6.3 Hz, 6H), 1.04 (s, 9H). $^{31}$P (121.4 MHz, CD$_3$OD): δ33.642. LC/MS=837 (M$^+$+1)

Example 14

Preparation of Compound 14

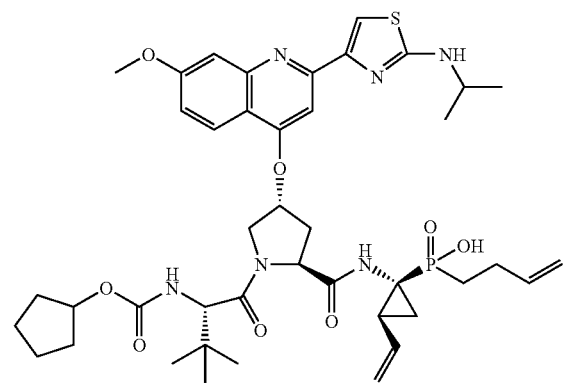

$^1$H NMR (300 MHz, CD$_{30}$D): δ 8.27 (d, J=9.6 Hz, 1H), 8.18 (m, 1H), 7.74 (s, 2H), 7.32 (m, 1H), 5.89 (m, 2H), 5.78 (br, 1H), 5.26 (m, 1H), 5.09 (m, 2H), 4.97 (m, 1H), 4.65 (m, 2H), 4.44 (m, 1H), 4.17 (m, 2H), 4.04 (m, 4H), 2.75 (m, 1H), 2.38 (m, 2H), 2.09 (m, 1H), 1.91 (m, 1H), 1.65 (m, 8H) 1.34 (d, J=6.3 Hz, 6H), 1.04 (s, 9H). $^{31}$P (121.4 MHz, CD$_{30}$D): δ31.453. LC/MS=837 (M$^+$+1)

Example 15

Preparation of Compound 15

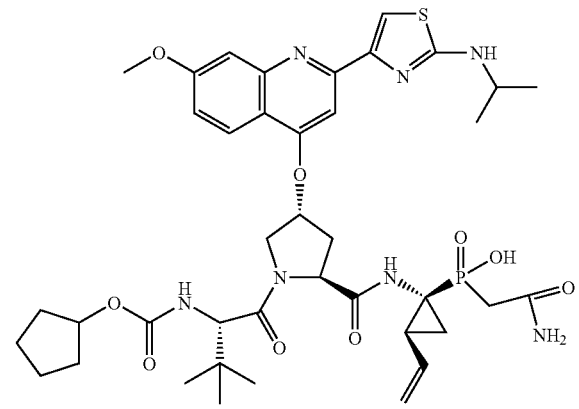

The [(1-Benzyloxycarbonylamino-2-vinyl-cyclopropyl)-ethoxy-phosphinoyl]-acetic acid from example 11 (340 mg, 0.92 mmol) was suspended in 5 mL of DMF. HATU (1.04 g, 2.76 mmol), ammonium chloride (123 mg, 2.32 mmol), followed by NMM (910 µl, 8.28 mmol) was added. After 2 hours, the reaction was concentrated and partitioned with EtOAc and H$_2$O. The aqueous layer was extracted 3× with EtOAc. The organic layer was dried over MgSO$_4$, filtered and concentrated. The product, (1-benzyloxycarbonylamino-2-vinyl-cyclopropyl)-carbamoylmethyl-phosphinic acid ethyl ester as brown oil (214 mg, 64%) was used as crude.

The crude (1-benzyloxycarbonylamino-2-vinyl-cyclopropyl)-carbamoylmethyl-phosphinic acid ethyl ester (107 mg, 0.29 mmol) was suspended in 1 mL of CH$_3$CN and cooled to 0° C. Iodotrimethylsilyl (TMSI) (208 µl 1.46 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The residue was coupled with VII (94 mg, 0.14 mmol), HATU (133 mg, 0.35 mmol) and NMM (77 µl, 0.70 mmol). The mixture was purified via Gilson HPLC to obtain 15 (15.4 mg, 13%) as a yellow solid. $^{1H}$ NMR (300 MHz, CD$_3$OD): δ 8.23 (d, J=9.5 Hz, 1H), 8.20 (s, 1H), 7.79 (s, 2H), 7.33 (d, J=8.8 Hz, 1H), 5.95 (m, 1H), 5.78 (s, 1H), 5.22 (d, J=9.6 Hz, 2H), 5.13 (d, J=9.0 Hz, 2H), 4.63 (m, 2H), 4.45 (bs, 1H), 4.20 (s, 2H), 4.05 (s, 3H), 3.25 (m, 1H), 2.80 (m, 2H), 2.45 (m, 1H), 2.15 (m, 1H), 1.62 (m, 6H), 1.38 (d, 6H), 1.05 (s, 9H). $^{31}$P (121.4 MHz, CD$_3$OD): δ37.283

Example 16

Preparation of Compound 16

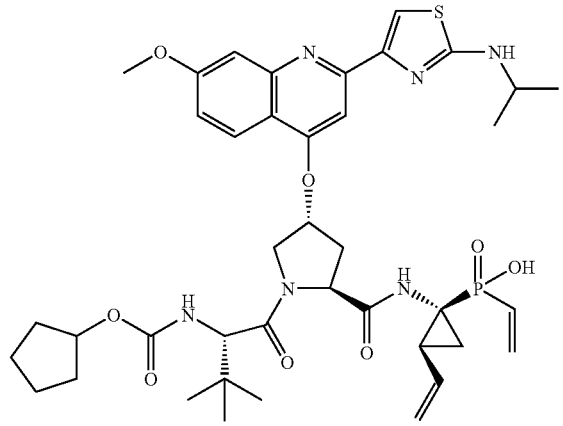

Examples 16-23 were prepared using Grignard reagents. A detailed procedure is described in example 19. $^1$H NMR (300 MHz, CD$_3$CN): δ 8.25 (m, 1H), 8.20 (m, 1H), 7.63 (s, 1H), 7.41 (m, 1H), 7.23 (m, 1H), 6.81 (br, 1H), 6.37 (m, 1H), 6.02 (m, 3H), 5.60 (br, 1H), 5.13 (m, 1H), 4.98 (m, 1H), 4.60 (m, 2H), 4.19 (m, 2H), 4.05 (m, 2H), 4.00 (s, 3H), 2.70 (m, 1H), 2.43 (m, 1H), 1.65 (m, 8H) 1.38 (d, 6H), 1.21 (m, 1H), 1.05 (s, 9H). $^{31}$P (121.4 MHz, CD$_3$CN): δ30.642

LC/MS=809 (M$^+$+1)

Example 17

Preparation of Compound 17

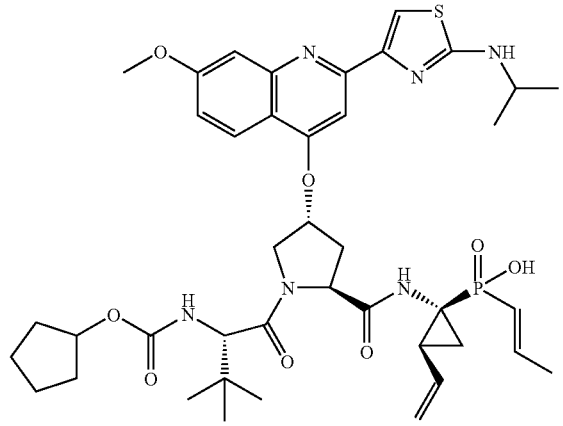

$^1$H NMR (300 MHz, CD$_3$OD): δ 8.27 (d, J=9.6 Hz, 1H), 8.18 (s, 1H), 7.75 (s, 2H), 7.3 (m, 1H), 6.67 (m, 1H), 5.93 (m, 2H), 5.77 (bs, 1H), 5.24 (d, J=17.1 Hz, 1H), 5.07 (d, J=11.4 Hz, 1H), 4.63 (m, 2H), 4.43 (bs, 1H), 4.20 (m, 2H), 4.04 (m, 5H), 3.23 (m, 1H), 2.76 (m, 1H), 2.40 (m, 1H), 2.08 (m, 1H), 1.90 (m, 3H), 1.72-1.40 (m, 8H), 1.38 (d, 6H), 1.05 (m, 9H). $^{31}$P (121.4 MHz, CD$_3$OD): δ33.223. LC/MS=823 (M$^+$+1)

Example 18

Preparation of Compound 18

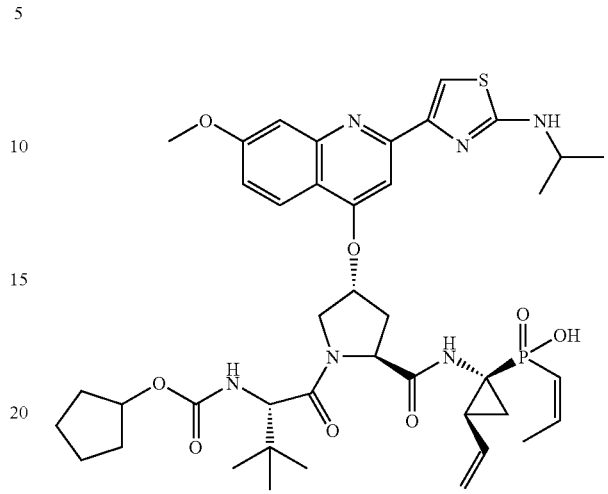

$^1$H NMR (300 MHz, CD$_3$OD): δ 8.27 (d, J=9.6 Hz, 1H), 8.17 (s, 1H), 7.74 (s, 2H), 7.32 (m, 1H), 6.63-6.41 (m, 1H), 5.98 (m, 2H), 5.77 (bs, 1H), 5.24 (d, J=17.1 Hz, 1H), 5.07 (d, J=11.4 Hz, 1H), 4.63 (m, 2H), 4.43 (bs, 1H), 4.17 (m, 2H), 4.07 (m, 4H), 2.75 (m, 1H), 2.42 (m, 1H), 2.10 (m, 1H), 2.07 (m, 3H), 1.72-1.40 (m, 8H), 1.34 (d, J=6.3 Hz, 6H), 1.04 (m, 9H). $^{31}$P (121.4 MHz, CD$_3$OD): δ33.781. LC/MS=823 (M$^+$+1)

Example 19

Preparation of Compound 19

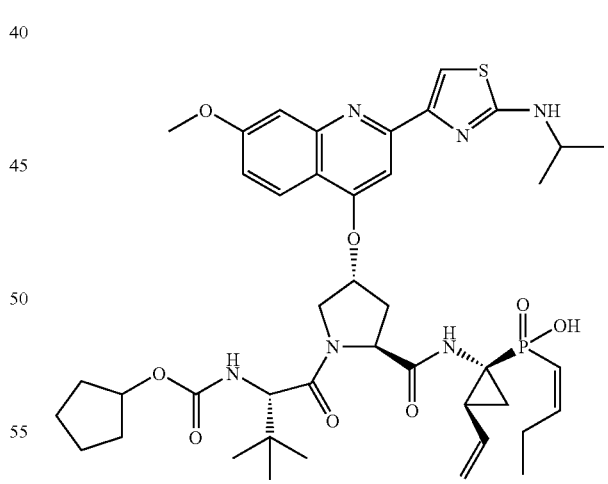

Intermediate III (1.0 g, 3.1 mmol) was dissolved in toluene (20 mL). This solution was cooled to 0° C. and (COCl)$_2$ (1.6 g, 12.4 mmol) was added in a drop-wise fashion. DMF (45 mg, 0.62 mmol) was then added. The reaction was run for 2 h at 0° C. and determined to be complete by $^{31}$P NMR. The reaction was concentrated to an orange-yellow oil and then placed under high vacuum for 1 h. The resulting residue was dissolved in THF (6.4 mL) and this solution was cooled to −78° C. A 1.0M solution of cis-1-butenemagnesium bromide in THF (9.1 mL, 9.1 mmol) was added drop-wise. The reaction mixture was warmed to rt and stirred for 3 hours. The reaction was quenched at 0° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate after vacuum filtration removal of the MgSO$_4$ yielded an orange oil from which (1-Benzyloxycarbonylamino-2-vinyl-cyclopropyl)-but-1-enyl-phosphinic acid ethyl ester was isolated by column chromatography (SiO$_2$, 100% EtOAc) as a clear oil (100 mg, 8% over 2 steps). $^1$H NMR (300 MHz, CDCl$_3$): δ 7.33 (m, 5H), 6.60-6.35 (m, 1H) 6.18-5.83 (m, 1H), 5.68 (m, 1H), 5.38 (m, 2H), 5.10 (m, 3H), 4.05 (m, 2H), 2.57 (m, 2H), 2.01 (m, 1H), 1.78 (m, 1H), 1.50 (m, 1H), 1.23 (m, 3H), 1.00 (m, 3H). $^{31}$P (121.4 MHz, CDCl$_3$): δ37.397, 35.875 diastereomers The phosphinate (100 mg, 0.275 mmol) was suspended in 1 mL of CH$_3$CN and cooled to 0° C. Iodotrimethylsilane (TMSI) (190 μl, 1.38 mmol) was added and the solution was warmed to rt. After 45 minutes, the solution was cooled again to 0° C. and triethylamine (0.5 mL, 3.6 mmol) and 0.5 mL of MeOH was added to the reaction. The reaction was warmed to rt and stirred for an additional 20 minutes. The reaction was concentrated, azeotroped twice with toluene and put on high vacuum for 30 minutes. The solid was coupled to VII to give compound 19 after reverse phase HPLC purification. $^1$H NMR (300 MHz, CD$_3$OD): δ 8.25 (d, J=9.0 Hz, 1H), 8.19 (s, 1H), 7.73 (s, 2H), 7.35 (m, 1H), 6.52-6.28 (m, 1H), 5.95 (m, 2H), 5.77 (s, 1H), 5.24 (d, J=17.9 Hz, 1H), 5.06 (d, J=11.1 Hz, 1H), 4.65 (m, 4H), 4.44 (bs, 1H), 4.20 (m, 2H), 4.04 (m, 4H), 2.76 (m, 1H), 2.52 (m, 3H), 2.43 (m, 1H), 2.13 (m, 1H), 1.62-1.35 (m, 10H) 1.38 (d, J=6.3 Hz, 6H), 1.03 (m, 12H). $^{31}$P (121.4 MHz, CD$_3$OD): δ34.248. LC/MS=837 (M$^+$+1)

Example 20

Preparation of Compound 20

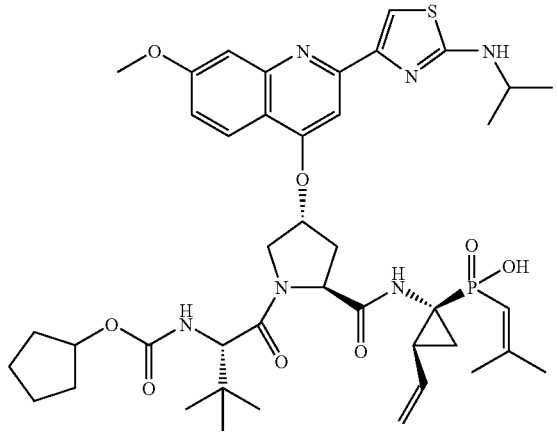

$^1$H NMR (300 MHz, CD$_3$OD): δ 8.27 (d, J=9.6 Hz, 1H), 8.18 (s, 1H), 7.74 (s, 2H), 7.32 (m, 1H), 5.97 (m, 1H), 5.72 (m, 2H), 5.24 (d, J=16.5 Hz, 1H), 5.07 (d, J=10.5 Hz, 1H), 4.66 (m, 2H), 4.43 (bs, 1H), 4.20 (m, 2H), 4.06 (m, 5H), 2.75 (m, 1H), 2.43 (m, 1H), 2.11 (m, 4H), 1.91 (m, 3H), 1.72-1.40 (m, 10H), 1.38 (d, J=6.2 Hz, 6H), 1.04 (m, 9H). $^{31}$P (121.4 MHz, CD$_3$OD): δ33.786 LC/MS=837 (M$^+$+1).

Example 21

Preparation of Compound 21

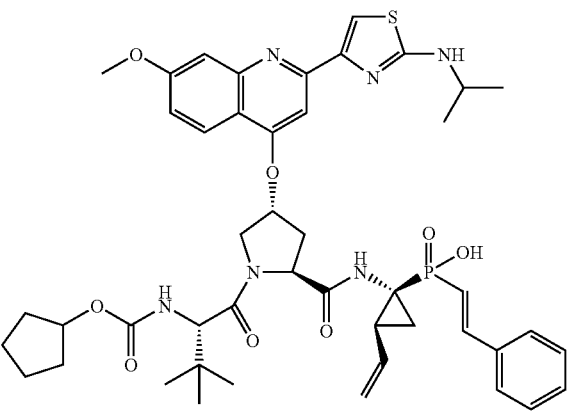

$^1$H NMR (300 MHz, CD$_3$OD): δ 8.25 (d, J=9.0 Hz, 1H), 8.15 (s, 1H), 7.74 (m, 1H), 7.68 (m, 1H), 7.57 (m, 2H), 7.40 (m, 4H), 6.57 (m, 1H), 5.98 (m, 1H), 5.68 (bs, 1H), 5.27 (d, J=17.1 Hz, 1H), 5.10 (d, J=9.0 Hz, 1H), 4.63 (m, 2H), 4.44 (bs, 1H), 4.18 (m, 2H), 4.04 (m, 4H), 3.1 (m, 1H), 2.70 (m, 1H), 2.38 (m, 1H), 2.15 (m, 1H), 1.72-1.40 (m, 8H), 1.38 (d, J=6.3 Hz, 6H), 1.03 (m, 9H). $^{31}$P (121.4 MHz, CD$_3$OD): δ33.372. LC/MS=885 (M$^+$+1)

Example 22

Preparation of Compound 22

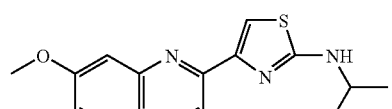

$^1$H NMR (300 MHz, CD$_3$OD) δ 8.25 (d, J=9 Hz, 1H), 8.17 (s, 1H), 7.74 (d, J=2.1 Hz, 1H), 7.68 (s, 1H), 7.55 (d, J=6.9 Hz, 2H), 7.2-7.5 (m, 4H), 6.05 (dt, J=9.6, 17.1 Hz), 5.71 (s, 1H), 5.27 (d, J=17.4 Hz, 1H), 5.09 (d, J=9.6 Hz, 1H), 4.7 (t, J=8.7 Hz, 1H), 4.6 (d, J=12.6 Hz, 1H), 4.51 (s, 1H), 4.06-4.2 (brm, 3H), 4.04 (s, 3H), 2.74 (dd, J=7.8, 13.8 Hz, 1H), 2.57 (m, 1H), 2.28 (m, 1H), 1.36-1.9 (brm, 10H), 1.33 (d, J=6.3 Hz, 6H), 1.04 (s, 9H). $^{31}$P NMR (121.4 MHz, CD$_3$OD) δ 10.2. LC/MS=883 (M$^+$+1)

Example 23

Preparation of Compound 23

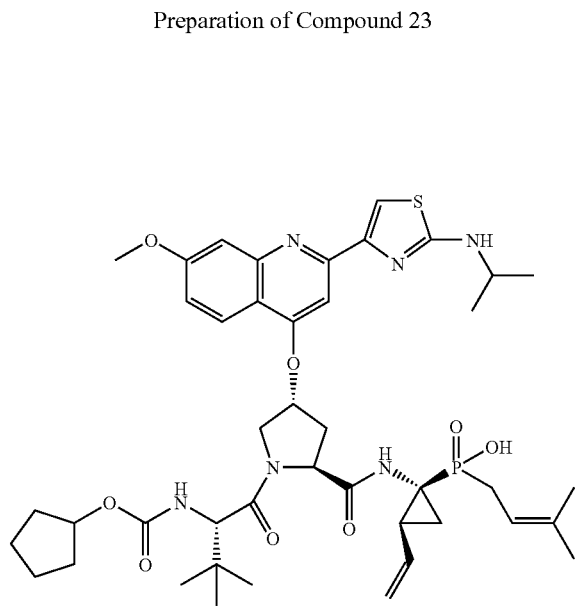

The phosphonous acid IV (363 mg, 1.17 mmol) was suspended in 5 mL of THF and cooled to −40° C. 1N NaN(TMS)$_2$ (1.41 mL, 1.41 mmol) was added dropwise over 15 minutes followed by 1-bromo-3-methylbut-2-ene (164 µl, 1.41 mmol) in 1 mL of THF. The solution was stirred from −40° C. to rt over 45 minutes. The reaction was diluted with EtOAc and quenched with 20 mL of 1N HCl. The organic layer was washed with brine, dried over MgSO$_4$, filtered and concentrated. The crude material was purified using a CombiFlash Chromatography System employing a gradient of 30% EtOAc/Hexane to 100% EtOAc to obtain (1-benzyloxycarbonylamino-2-vinyl-cyclopropyl)-(3-methyl-but-2-enyl)-phosphinic acid ethyl ester (219 mg, 50%) as a brown oil. This oil (135 mg, 0.36 mmol) was suspended in 1 mL of CH$_3$CN and cooled to 0° C. Iodotrimethylsilane (254 µl, 1.79 mmol) was added and the solution was warmed to rt. After 45 minutes, the solution was cooled again to 0° C. and triethylamine (1 mL, 7.33 mmol) and 2 mL of MeOH was added to the reaction. The reaction was warmed to rt and stirred for an additional 20 minutes. The reaction was concentrated, azeotroped 2× with toluene and put on high vacuum for 30 minutes. The crude was coupled with intermediate VII to give compound 23 after HPLC purification. $^1$H NMR (300 MHz, CD$_3$OD): δ 8.30 (d, J=9.5 Hz, 1H), 8.20 (s, 1H), 7.79 (s, 2H), 7.30 (m, 4H), 5.95 (m, 1H), 5.80 (s, 1H), 5.25 (d, J=9.6 Hz, 2H), 5.13 (d, J=9.0 Hz, 2H), 4.75 (m, 2H), 4.45 (bs, 1H), 4.20 (s, 2H), 4.05 (s, 3H), 3.33 (s, 2H), 2.80 (m, 1H), 2.52 (m, 1H), 2.15 (m, 1H), 1.62 (m, 6H), 1.38 (d, 6H), 1.05 (s, 9H). $^{31}$P (121.4 MHz, CD$_3$OD): δ42.837

Example 24

Preparation of Compound 24

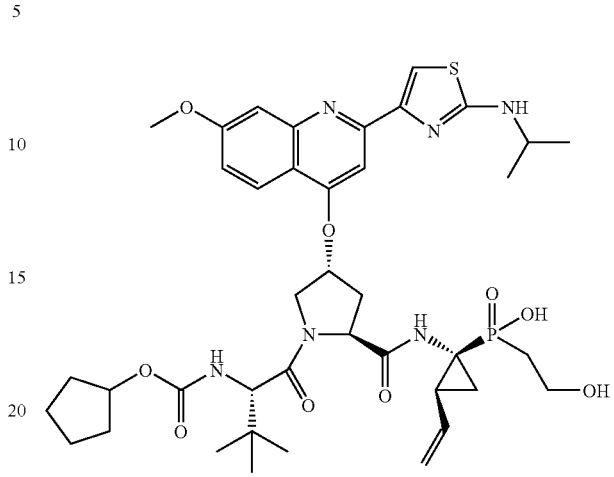

A suspension of sodium borohydride (82 mg, 2.17 mmol) and [(1-Benzyloxycarbonylamino-2-vinyl-cyclopropyl)-ethoxy-phosphinoyl]-acetic acid ethyl ester from example 91 (344 mg, 0.87 mmol) in THF (3.5 mL) was stirred at 50° C. as MeOH (710 µL) was added dropwise over 20 minutes. After 20 minutes at 50° C., the reaction was concentrated and the resulting residue in ethyl acetate (15 mL) was washed with H$_2$O and brine. The aqueous layer was extracted with ethyl acetate and the combined organic layers were dried (MgSO$_4$) and concentrated to yield alcohol (282 mg, 91.8%). The product was used without further purification. $^1$H NMR (300 MHz, CDCl$_3$): δ 7.35 (s, 5H), 5.99 (m, 1H), 5.64 (d, 1H), 5.38 (dd, 1H), 5.07 (s, 2H), 4.12 (m, 2H), 3.91 (m, 2H), 2.96 (bs, 1H), 2.18 (m, 3H), 1.76 (m, 1H), 1.62 (m, 1H), 1.50 (m, 1H), 1.26 (m, 3H). $^{31}$P (121.4 MHz, CDCl$_3$): δ52.755, 49.793.

The alcohol (112 mg, 0.32 mmol) was suspended in 1 mL of CH$_3$CN and cooled to 0° C. Iodotrimethylsilane (225 µl, 1.58 mmol) was added and the solution was warmed to rt. After 45 minutes, the solution was cooled again to 0° C. and triethylamine (1 mL, 7.33 mmol) and 2 mL of MeOH was added to the reaction. The reaction was warmed to rt and stirred for an additional 20 minutes. The reaction was concentrated, azeotroped 2× with toluene and put on high vacuum for 30 minutes. The solid (104 mg, 0.16 mmol) was suspended in 1 mL of DMF. HATU (152 mg, 0.40 mmol), VII (61 mg, 0.32 mmol), and NMM (88 µl, 0.80 mmol) was added. The solution was stirred overnight at rt. The mixture was purified by reverse phase HPLC to obtain 24 (33.3 mg, 25%) as a yellow solid. $^1$H NMR (300 MHz, CD$_3$OD): δ 8.23 (d, J=9.5 Hz, 1H), 8.20 (s, 1H), 7.79 (s, 2H), 7.33 (d, J=8.8 Hz, 1H), 5.95 (m, 1H), 5.78 (s, 1H), 5.22 (d, J=9.6 Hz, 2H), 5.13 (d, J=9.0 Hz, 2H), 4.63 (m, 2H), 4.45 (bs, 1H), 4.20 (m, 3H), 4.05 (s, 3H), 3.83 (m, 2H), 2.80 (m, 1H), 2.78 (s, 3H), 2.45 (m, 1H), 2.20 (m, 1H), 2.15 (m, 1H), 1.62 (m, 2H), 1.50 (m, 6H) 1.38 (d, 6H), 1.05 (s, 9H).

$^{31}$P (121.4 MHz, CD$_3$OD): δ45.011

Example 25

Preparation of Compound 25

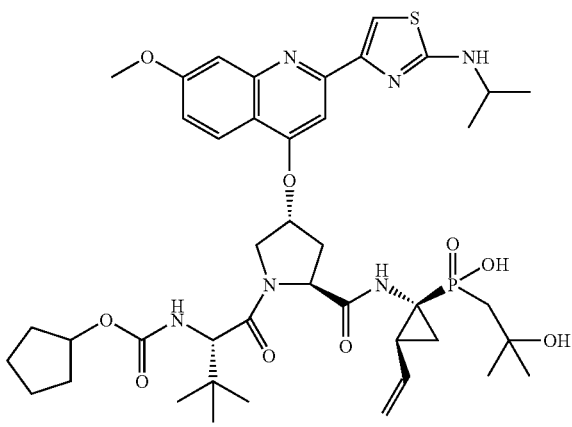

$^1$H NMR (300 MHz, CD$_3$OD) δ 8.29 (d, J=9.6 Hz, 1H), 8.18 (s, 1H), 7.75 (m, 2H), 7.32 (dd, J=3, 9.3 Hz), 6.00 (dt, J=10.2, 16.5 Hz, 1H), 5.78 (s, 1H), 5.27 (d, J=15.6 Hz), 5.10 (d, J=12 Hz, 1H), 4.64 (m, 2H), 4.44 (1H), 4.17 (m, 2H), 4.08 (m, 1H), 4.05 (s, 3H), 2.76 (dd, J=6.6, 13.5 Hz, 1H), 2.45 (m, 1H), 2.32 (m, 1H), 2.09 (m, 2H), 1.37-1.65 (brm, 16H), 1.34 (d, J=6.3 Hz, 6H), 1.05 (s, 9H). $^{31}$P NMR (121.4 MHz, CD$_3$OD) δ 45.7. LC/MS=854.7 (M$^+$+1)

Example 26

Preparation of Compound 26

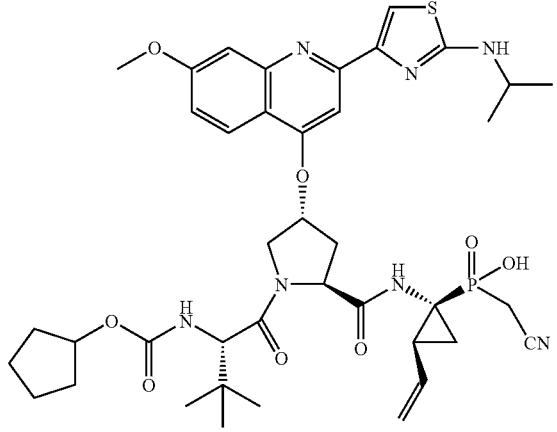

Intermediate IV (467 mg, 1.5 mmol) was dissolved in 5.0 mL of dry DCM. DIEA (523 μl, 3.0 mmol) and 381 μl (3.0 mmol) of TMSCl were added sequentially and the reaction then stirred at rt for 5 min. DIEA (523 μl, 3.0 mmol) and 209 μl (3.0 mmol) of bromoacetonitrile were then added. The reaction was warmed to 40° C. and stirred overnight. The reaction was then diluted with ethyl acetate and concentrated to remove DCM. The organic phase was then washed with sat. NH$_4$Cl, water, and brine. The organic phase was dried over MgSO$_4$. Concentration of the filtrate after vacuum filtration removal of the MgSO$_4$ yielded an orange oil from which the product was isolated by column chromatography (SiO$_2$, neat ethyl acetate) as a clear oil (190 mg, 37%). $^1$H NMR (300 MHz, CDCl$_3$) δ 7.35 (s, 5H), 5.81 (m, 1H), 5.60-5.26 (m, 2H), 5.11 (s, 2H), 4.23 (m, 2H), 2.99 (m, 2H), 2.18 (m, 1H), 1.85-1.70 (m, 1H), 1.65-1.47 (m, 1H), 1.35 (m, 3H). $^{31}$P NMR (121.4 MHz, CDCl$_3$) δ 39.04, 36.33. LC/MS=370 (M$^+$+1)

Deprotection and coupling to dipeptide VII as described above gave 26 (60 mg 40%). $^1$H NMR (300 MHz, CD$_3$OD) 8.30 (d, J=9.3 Hz, 1H), 8.23 (s, 1H), 7.74 (s, 2H), 7.30 (d, J=2.1, 8.7 Hz, 1H), 5.90 (m, 2H), 5.76 (b, 1H), 5.20 (d, J=17.4 Hz, 1H), 5.05 (d, J=11.1 Hz, 1H), 4.61 (m, 2H), 4.55 (s, 1H), 4.18 (m, 2H), 4.11 (s, 1H), 4.04 (s, 3H), 3.0 (m, 2H), 2.70 (m, 1H), 2.60 (m, 1H), 2.00 (m, 1H), 1.41-1.78 (m, 8H), 1.34 (d, J=6.3 Hz, 6H), 1.04 (s, 9H) $^{31}$P NMR (121.4 MHz, CD$_3$OD) δ 24.48

LC/MS=822 (M$^+$+1)

Example 27

Preparation of Compound 27

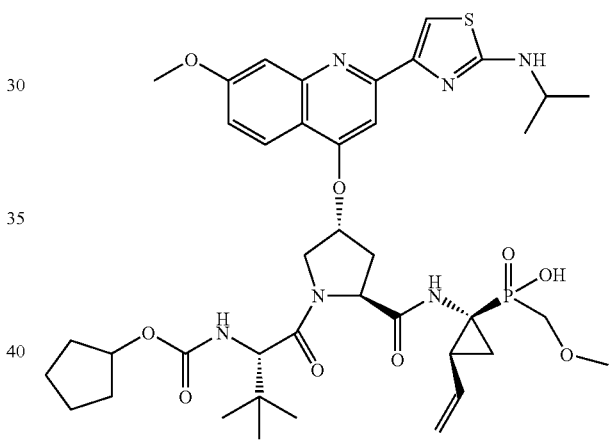

A solution of the phosphonous acid IV (436 mg, 1.40 mmol), Hunig's base (593 μL, 3.40 mmol), and chlorotrimethylsilane (378 μL, 3.12 mmol) in CH$_2$Cl$_2$ (5 mL) was stirred at r.t. for 1 h. After chloro(methoxy)methane (220 μL, 3.17 mmol) was added, the solution was heated at 40° C. for 2 h. The solution was concentrated and the residue in ethyl acetate (30 mL) was washed with H$_2$O (30 mL×2). The aqueous fractions were extracted with ethyl acetate (30 mL), and the combined organic fractions were dried (MgSO$_4$) and concentrated. The residue was purified by column chromatography using hexane:ethyl acetate as eluent to obtain 27 (297 mg, 60%). $^1$H NMR (300 MHz, CDCl$_3$): δ 7.35 (s, 5H), 6.00 (m, 1H), 5.44 (m, 2H), 5.15 (m, 1H), 5.07 (s, 2H), 4.18 (m, 2H), 3.87 (m, 1H), 3.77 (d, J=6.6 Hz, 2H), 3.43 (s, 3H), 2.20 (m, 1H), 2.07 (m, 1H), 1.80 (m, 1H), 1.64 (m, 1H), 1.48 (m, 1H), 1.28 (m, 3H). $^{31}$P (121.4 MHz, CDCl$_3$): δ44.0099, 43.403, 40.648, 40.353.

Deprotection and coupling to dipeptide VII as described above gave 27.

LC/MS=827 (M$^+$+1)

Example 28

Preparation of Compound 28

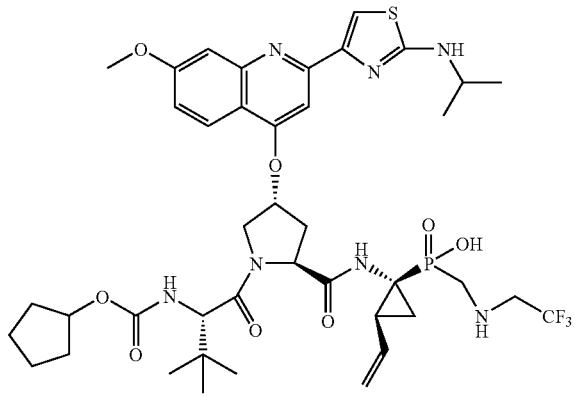

Compound IV (1.64 g, 5.3° mmol) was dissolved in CH$_2$Cl$_2$ (60 mL) and cooled to 0° C. Diisopropylethylamine (1.96 mL) was added and stirred for 15 minutes. Chlorotrimethylsilane (1.40 mL) was added dropwise. The reaction mixture was warmed to r.t. and stirred for 1 h. Ethyl bromoacetate (2.92 mL) was added and the reaction was heated to 45° C. overnight. The reaction mixture was cooled to rt, diluted with CH$_2$Cl$_2$, washed with aqueous NH$_4$Cl, dried with Na$_2$SO$_4$, and concentrated. The crude product was purified by column chromatography to give 1.15 g of [(1-Benzyloxycarbonylamino-2-vinyl-cyclopropyl)-ethoxy-phosphinoyl]-acetic acid ethyl ester in 55% yield.

To a solution of ester (679 mg, 1.72 mmol) in toluene (25 mL) at −78° C. was added 1.0 M DIBAL in CH$_2$Cl$_2$ (6.6 mL, 6.6 mmol) and stirred for 2 h. The mixture was poured into ice cold 6 N HCl (100 mL), extracted with EtOAc, and concentrated. The residue was re-dissolved in CH$_2$Cl$_2$, insoluble material was removed by a filtration through celite, and the filtrate was concentrated to give a colorless oil. The oil was dissolved in CH$_2$Cl$_2$ (20 mL) and then AcOH (0.52 mL), trifluoroethylamine (260 mg), and sodium triacetoxyborohydride (730 mg) were added sequentially. The mixture was stirred at r.t. for 16 h. The reaction was partitioned between CH$_2$Cl$_2$ and saturated NaHCO$_3$. The organic layer was concentrated and purified by column chromatography to give 310 mg of phosphinate as an oil.

To a solution of phosphinate in CH$_3$CN (1 mL) at 0° C. was added iodotrimethylsilane (0.03 mL). The reaction mixture was warmed to rt, stirred for 0.5 h, and cooled to 0° C. Triethylamine (0.2 mL) was added followed by MeOH (2 mL) and the reaction was warmed to rt. The mixture was concentrated and dried under vacuum to give 23 mg of amine as crude product.

Acid VII (35 mg) was dissolved in DMF (0.8 mL). HATU (30 mg) was added and the mixture was cooled to 0° C. DIPEA (0.04 mL) was added and the mixture was stirred at r.t. for 1 h. A solution of the amine in CH$_2$Cl$_2$ (2 mL) was added and stirred for 1 h. The reaction was quenched with H$_2$O and CH$_2$Cl$_2$ was removed in vacuo. The non-volatile residue was purified by HPLC to give 19.9 mg of compound 28. $^1$H NMR (300 MHz, CD$_3$OD): δ 8.28 (d, J=9.3 Hz, 1H), 8.18 (s, 1H), 7.74 (s, 2H), 7.30 (dd, J=2.4, 9.0 Hz, 1H), 5.97 (m, 1H), 5.79 (brs, 1H), 5.23 (d, J=17.7 Hz, 1H), 5.06 (d, J=11.7 Hz, 1H), 4.65 (m, 2H), 4.46 (brs, 1H), 4.15 (m, 2H), 3.90-4.10 (m, 6H), 3.55 (m, 1H), 3.39 (m, 1H), 2.80 (m, 1H), 2.45 (m, 1H), 2.12 (m, 3H), 1.4-1.7 (m, 10H), 1.34 (d, J=6.3 Hz, 6H), 0.95-1.15 (brs, 9H).

Example 29

Preparation of Compound 29

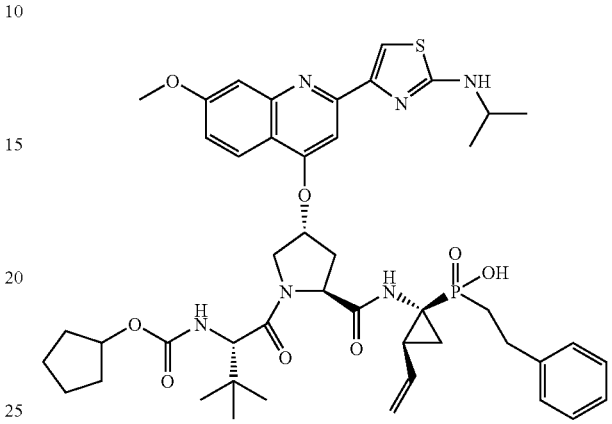

A solution of compound IV (149 mg, 0.482 mmol) in THF (2.41 mL) was cooled to −40° C. To the solution was added a solution of 1M NaHMDS in THF (0.578 mL) and the resulting mixture was stirred for 30 minutes and then 2-bromoethylbenzene (107 mg, 0.578 mmol) was added. The resulting solution was stirred for 2 additional hours until all of the starting materials was consumed as determined by LCMS. The reaction was worked up by removal of the solvent in vacuo. The residue was dissolved in EtOAc and washed with saturated aqueous NH$_4$Cl. The organic layer was dried and the product was purified using silica gel chromatography to give 74 mg of the product as a clear oil. EI MS (m/z) 436.1 [M+Na].

To a solution of benzyl (1S,2S)-1-((S)-ethoxy-(phenethyl)phosphoryl)-2-vinylcyclopropylcarbamate (72 mg, 0.174 mmol) in dry acetonitrile (1.74 mL) was added TMSI (0.124 mL, 0.87 mmol). The reaction was stirred at ambient temperature for 1 hour until LCMS analysis indicated completion of the reaction. The mixture was quenched by addition of TEA (0.243 mL, 1.74 mmol) followed by MeOH (10 mL). The residue was dried and used without further purification.

EI MS (m/z) 252.3 [MH$^+$], 274.1 [M+Na].

A solution of(S)-((1S,2S)-1-amino-2-vinylcyclopropyl)(phenethyl)phosphinic acid (43 mg, 0.171 mmol), carboxylic acid VII (112 mg, 0.171 mmol) in a 1:1 solution of DMF and CH$_2$Cl$_2$ (1.7 mL) was stirred with HATU (98 mg, 0.256 mmol) and DIEA (0.119 mL, 0.685 mmol) for 1 hour until the reaction was complete. The product was purified by reverse phase HPLC (ACN, 0.05% TFA-H$_2$O, 0.05% TFA) to provide the desired product. $^1$H NMR (300 MHz, CD$_3$OD) δ 8.27 (d, 1H, J=9 Hz), 8.16 (s, 1H), 7.75-7.71 (m, 2H), 7.30 (d, 1H, J=11 Hz), 7.27-7.22 (m, 5H), 6.01 (dt, 1H, J=17, 10 Hz), 5.75 (br s, 1H), 5.28 (d, 1H, J=17 Hz), 5.11 (d, 1H, J=11 Hz), 4.68-4.58 (m, 2H), 4.44 (br s, 1H), 4.22-4.10 (m, 2H), 4.04 (s, 3H), 3.05-2.83 (m, 2H), 2.82-2.70 (m, 1H), 2.48-2.37 (m, 1H), 2.18-2.03 (m, 3H), 1.68-1.40 (m, 10H), 1.33 (d, 6H, J=6 Hz), 0.99 (s, 9H); $^{31}$P (121.4 MHz, CD$_3$OD) δ 47.2; EI MS (m/z) 887.4 [MH$^+$].

Example 30

Preparation of Compound 30

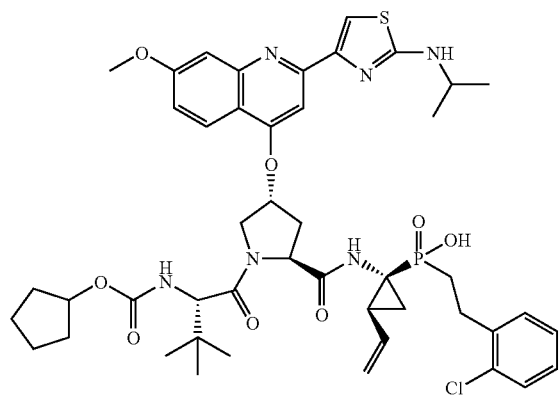

Examples 30 through 33 were prepared by the same method as example 29.

Preparatory reverse phase HPLC afforded compound 30 (10 mg, 33%), a yellow solid. $^1$H NMR (300 MHz, CD$_3$OD): δ 8.27 (d, J=9.4 Hz, 1H), 8.16 (s, 1H), 7.74 (s, 1H), 7.72 (s, 1H), 7.32 (m, 3H), 7.23 (m, 2H) 6.00 (m, 1H), 5.75 (s, 1H), 5.27 (m, 1H), 5.10 (m, 1H) 4.64 (m, 2H), 4.46 (m, 1H), 4.16 (m, 3H), 4.04 (s, 3H), 3.10 (m, 2H), 2.76 (m, 1H), 2.43 (m, 1H), 2.10 (m, 3H), 1.60 (m, 8H) 151.34 (m, 6H), 1.02 (s, 9H). $^{31}$P (121.4 MHz, CD$_3$OD): δ44.597 LC (6 minute run, r.t.=3.82 min) MS (921.6, M+1)

Example 31

Preparation of Compound 31

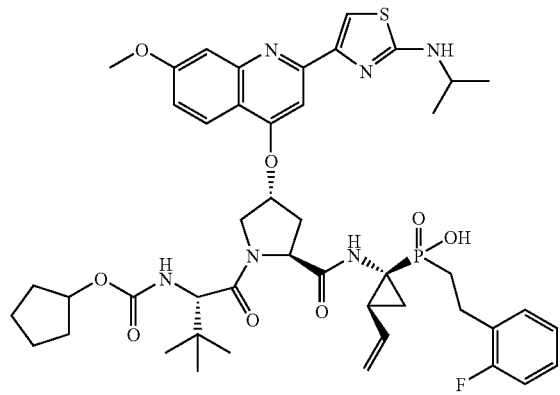

Preparatory reverse phase HPLC purification afforded compound 31 (23 mg, 47%) as a yellow solid. $^1$H NMR (300 MHz, CD$_3$OD): δ 8.22 (d, J=9.2 Hz, 1H), 8.11 (s, 1H), 7.70 (s, 1H), 7.68 (s, 1H), 7.25 (m, 3H), 6.99 (m, 2H) 5.98 (m, 1H), 5.70 (s, 1H), 5.21 (m, 1H), 5.05 (m, 1H) 4.58 (m, 2H), 4.40 (s, 1H), 4.11 (m, 2H), 3.99 (s, 3H), 2.91 (m, 2H), 2.70 (m, 1H), 2.38 (m, 1H), 2.08 (m, 3H), 1.50 (m, 8H) 1.29 (m, 6H), 0.93 (s, 9H). $^{31}$P (121.4 MHz, CD$_3$OD): δ44.896. LC (6 minute run, r.t.=3.70 min) MS (905.5, M+1)

Example 32

Preparation of Compound 32

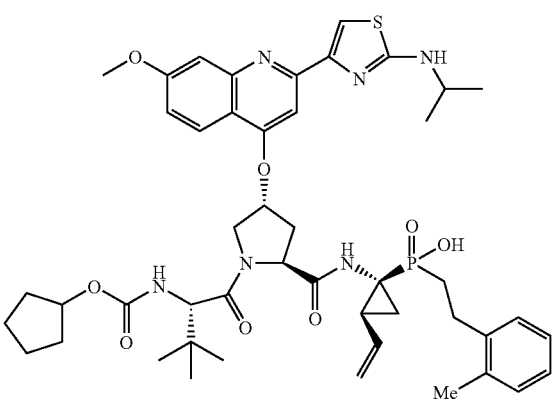

Preparatory reverse phase HPLC purification afforded compound 32 (85 mg, 65%) as a yellow solid. $^1$H NMR (300 MHz, CD$_3$OD): δ 8.215 (d, J=9.3 Hz, 1H), 8.11 (s, 1H), 7.70 (s, 1H), 7.69 (s, 1H), 7.25 (m, 2H), 7.025 (m, 4H) 5.95 (m, 1H), 5.69 (s, 1H), 5.22 (m, 1H), 5.06 (m, 1H) 4.59 (m, 2H), 4.40 (s, 1H), 4.10 (m, 2H), 3.99 (s, 3H), 2.90 (m, 2H), 2.70 (m, 1H), 2.36 (m, 1H), 2.26 (s, 3H) 2.10 (m, 3H), 1.50 (m, 8H) 1.29 (m, 6H), 0.93 (s, 9H). $^{31}$P (121.4 MHz, CD$_3$OD): δ45.420. LC (6 minute run, r.t.=3.77 min) MS (902.6, M+1)

Example 33

Preparation of Compound 33

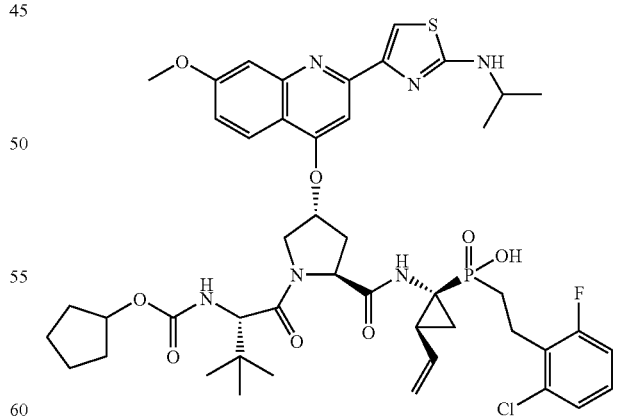

Preparatory reverse phase HPLC purification afforded compound 33 (70 mg, 55%) as a yellow solid. $^1$H NMR (300 MHz, CD$_3$OD): δ 8.25 (d, J=9.1 Hz, 1H), 8.17 (s, 1H), 7.74 (m, 2H), 7.$^{31}$ (m, 1H), 7.21 (m, 2H), 7.04 (m, 1H) 5.95 (m, 1H), 5.75 (bs, 1H), 5.25 (m, 1H), 5.10 (m, 1H) 4.60 (m, 2H), 4.40 (bs, 1H), 4.13 (m, 2H), 4.04 (s, 3H), 3.09 (m, 2H), 2.70 (m, 1H), 2.42 (m, 1H), 2.10 (m, 3H), 1.50 (m, 8H) 1.33 (m, 6H), 0.97 (s, 9H). $^{31}$P (121.4 MHz, CD$_3$OD): δ44.588. LC (6 minute run, r.t.=4.22 min) MS (940.3, M+1).

Example 34

Preparation of Compound 34

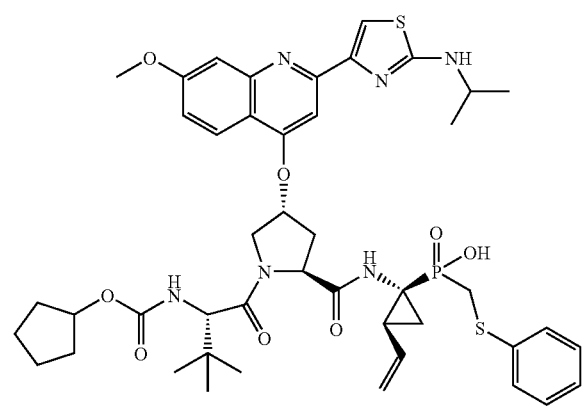

Intermediate IV (1.08 g, 3.5 mmol) was dissolved in CH$_2$Cl$_2$ (40 mL) and cooled to 0° C. Diisopropylethylamine (950 mg, 7.35 mmol) was added and stirred for 15 minutes. Chlorotrimethylsilane (800 mg, 7.35 mmol) was added dropwise. The reaction mixture was warmed to r.t. and stirred for 1 h. Chloromethylsulfanyl-benzene (2.77 g, 17 mmol) was added and the reaction was heated to 45° C. overnight. The reaction mixture was cooled to rt, diluted with CH$_2$Cl$_2$, washed with aqueous NH$_4$Cl, dried with Na$_2$SO$_4$, and concentrated. The crude product was purified by combi-flash to give 222 mg of phosphinate.

To a solution of phosphinate obtained above (222 mg, 0.52 mmol) in CH$_3$CN (1 mL) at 0° C. was added iodotrimethylsilane (0.36 mL, 2.58 mmol). The reaction mixture was warmed to r.t. and stirred for 30 minutes and then cooled to 0° C. 2,6-Lutidine (0.3 mL) and MeOH (0.6 mL) were added and stirred for 10 minutes. The solvent was concentrated and the residue was co-evaporated with toluene (5 mL), and dried under vacuum for 20 minutes to give crude amine. Coupling with acid VII (168 mg, 0.26 mmol) provided 150 mg of compound 34. $^1$H NMR (300 MHz, CD$_3$OD): δ8.27 (d, J=9.6 Hz, 1H), 8.20 (s, 1H), 7.72 (s, 2H), 7.41 (d, J=7.8 Hz, 1H), 7.27 (m, 3H), 7.15 (d, J=7.2 Hz, 1H), 5.94 (m, 1H), 5.74 (s, 1H), 5.28 (d, J=17.1 Hz, 1H), 5.11 (d, J=11.1 Hz, 1H), 4.63 (m, 2H), 4.48 (s, 1H), 4.16 (m, 2H), 3.36 (m, 2H), 2.74 (m, 1H), 2.46 (m, 1H), 2.10 (m, 1H), 1.70-1.40 (m, 8H), 1.30 (m, 6H), 0.97 (s, 9H) $^{31}$P (121.4 MHz, CDCl$_3$): δ 39.174 LC/MS=905.20 (M$^+$+1)

Example 35

Preparation of Compound 35

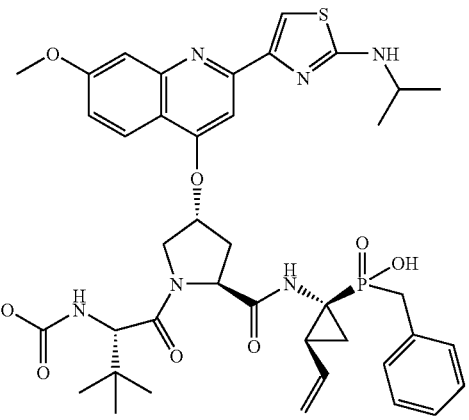

$^1$H NMR (300 MHz, CD$_3$0D) δ 8.29 (d, J=9.3 Hz, 1H), 8.18 (s, 1H), 7.75 (s, 2H), 7.17-7.34 (brm, 6H), 5.96 (dt, J=9.9, 17.1 Hz, 1H), 5.79 (s, 1H), 5.27 (d, J=17.1 Hz, 1H), 5.09 (d, J=10.2 Hz, 1H), 4.69 (m, 2H), 4.46 (s, 1H), 4.07-4.2 (brm, 3H), 4.05 (s, 3H), 3.29 (d, J=15.6 Hz, 2H), 2.78 (dd, J=7.5, 14.1 Hz, 1H), 2.48 (m, 1H), 2.11 (m, 1H), 1.38-1.7 (brm, 10H), 1.34 (d, J=6.3 Hz, 6H), 1.02 (s, 9H). $^{31}$P NMR (121.4 MHz, CD$_3$OD) δ 43.3. LC/MS=872.7 (M$^+$+1), 894.5 (M$^+$+Na)

Example 36

Preparation of Compound 36

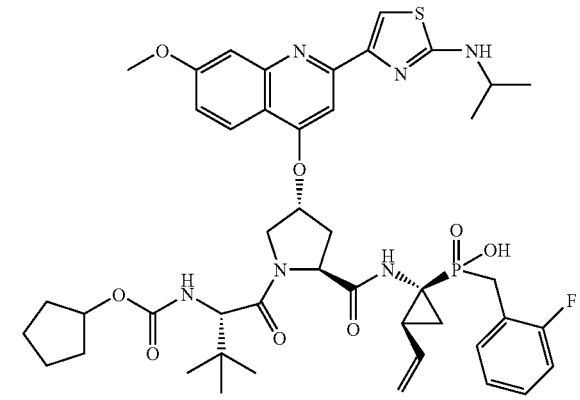

The phosphonous acid IV (409 mg, 1.32 mmol) was suspended in 2.5 mL of CDCl$_3$. The air was removed from the reaction flask by vacuum and replaced with N$_2$. Hunig's Base (552 µl, 3.16 mmol) followed by chlorotrimethylsilyl (368 µl, 2.90 mmol) was added. After 5 minutes, 1-(bromomethyl)-2-fluorobenzene (334 µl, 2.77) was added and the solution was heated at 40° C. After 4 hours, the reaction was concentrated.

The residue was partitioned with EtOAc and H$_2$O and washed with H$_2$O. The organic layer was dried over MgSO$_4$, filtered and concentrated. The crude material was purified using a CombiFlash Chromatography System using a gradient of 50% EtOAc/Hex to 100% EtOAc to obtain (1-benzyloxycarbonylamino-2-vinyl-cyclopropyl)-(2-fluoro-benzyl)-phosphinic acid ethyl ester (142.8 mg, 26%) as a brown oil. $^{1H}$ NMR (300 MHz, CDCl$_3$): δ 7.29-7.48 (m, 6H), 7.16-7.29 (m, 1H), 7.16-6.98 (m, 2H), 6.06 (dt, 0.4H, J=17.1 and 10.2 Hz), 5.76 (dt, 0.6H, J=17.1 and 9.9 Hz), 5.28-5.41 (m, 0.6H), 4.96-5.22 (m, 3.8H), 4.90 (d, 0.6H, J=9.9 Hz), 3.9-4.17 (m, 2H), 3.05-3.53 (m, 2H), 2.11-2.26 (m, 0.4H), 1.91-2.05 (m, 0.6H), 1.70-1.82 (m, 1.4H), 1.50-1.60 (m, 0.6H), 1.05-1.32 (m, 4H). $^{31}$P (121.4 MHz, CDCl$_3$): δ 46.333, (0.4 P), 49.339 (0.6 P). $^{19}$F (121.4 MHz, CDCl$_3$): δ−112.9$^{31}$ (0.6 F), −118.$^{31}$5, 0.4 F).

The residue (142.8 mg, 0.34 mmol) was suspended in 1 mL of CH$_3$CN and cooled to 0° C. Iodotrimethylsilyl(TMSI) (243 µl, 1.71 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The crude was coupled with acid VII (148 mg, 0.23 mmol), HATU (218 mg, 0.58 mmol) and NMM (126 µl, 1.15 mmol) to give 36 (122 mg, 60%) as a yellow solid after Gilson HPLC purification. $^1$H NMR (300 MHz, CD$_3$OD): δ 8.30 (d, J=9.5 Hz, 1H), 8.20 (s, 1H), 7.79 (s, 2H), 7.42 (t, 1H), 7.35 (d, J=8.8 Hz, 1H), 7.22 (m, 1H), 7.15 (m, 2H), 5.95 (m, 1H), 5.78 (s, 1H), 5.35 (d, J=9.6 Hz, 2H), 5.15 (d, J=9.0 Hz, 2H), 4.75 (m, 2H), 4.45 (bs, 1H), 4.20 (s, 2H), 4.05 (s, 3H), 3.33 (m, 2H), 2.80 (m, 1H), 2.52 (m, 1H), 2.20 (m, 1H), 1.62 (m, 6H), 1.38 (d, 6H), 1.05 (s, 9H). $^{31}$P (121.4 MHz, CD$_3$OD): δ42.259.

Example 37

Preparation of Compound 37

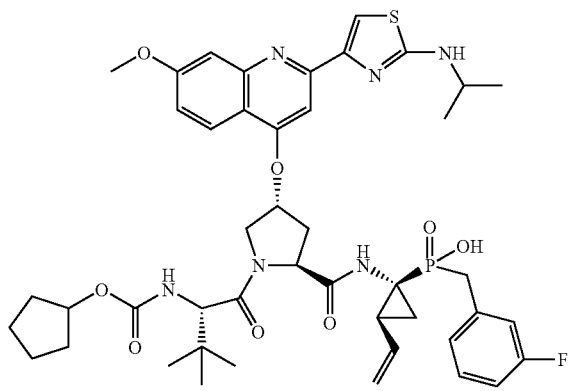

The phosphonous acid IV (350 mg, 1.13 mmol) was suspended in 2.5 mL of CDCl$_3$. The air was removed from the reaction flask by vacuum and replaced with N$_2$. Hunig's Base (472 µl, 2.71 mmol) followed by Chlorotrimethylsilyl ($^{31}$5 µl, 2.48 mmol) was added. After 5 minutes, 1-(bromomethyl)-3-fluorobenzene (449 mg, 2.37) in 500 µl of CDCl$_3$ was added and the solution was heated at 40° C. After 4 hours, the reaction was concentrated. The residue was partitioned with EtOAc and H$_2$O and washed with H$_2$O. The organic layer was dried over MgSO$_4$, filtered and concentrated. The crude material was purified using a CombiFlash Chromatography System using a gradient of 50% EtOAc/Hex to 100% EtOAc to obtain (1-benzyloxycarbonylamino-2-vinyl-cyclopropyl)-(3-fluoro-benzyl)-phosphinic acid ethyl ester (110 mg, 23%) as a brown oil.

The residue (110 mg, 0.26 mmol) was suspended in 1 mL of CH$_3$CN and cooled to 0° C. Iodotrimethylsilyl (TMSI) (187 µl, 1.$^{31}$ mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. Coupling with VII gave compound 37 (86.5 mg, 57%) as a yellow solid. $^{1H}$ NMR (300 MHz, CD$_3$OD): δ 8.30 (d, J=9.5 Hz, 1H), 8.20 (s, 1H), 7.79 (s, 2H), 7.33 (m, 2H), 7.18 (m, 2H), 6.98 (t, 1H), 5.95 (m, 1H), 5.78 (s, 1H), 5.22 (d, J=9.6 Hz, 2H), 5.13 (d, J=9.0 Hz, 2H), 4.65 (m, 2H), 4.42 (bs, 1H), 4.20 (s, 2H), 4.05 (s, 3H), 3.33 (m, 2H), 2.80 (m, 1H), 2.45 (m, 1H), 2.15 (m, 1H), 1.62 (m, 6H), 1.38 (d, 6H), 1.05 (s, 9H). $^{31}$P (121.4 MHz, CD$_3$OD): δ42.855

Example 38

Preparation of Compound 38

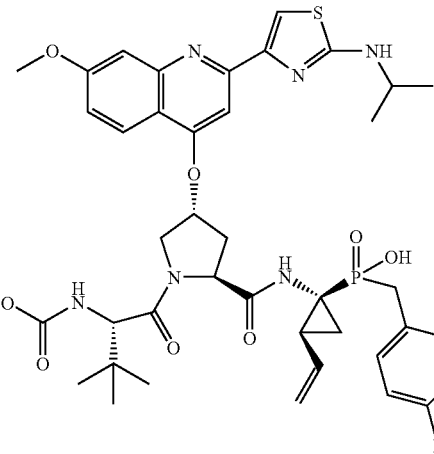

The phosphonous acid IV (404 mg, 1.30 mmol) was suspended in 2.5 mL of CDCl$_3$. The air was removed from the reaction flask by vacuum and replaced with N$_2$. Hunig's Base (543 µl, 3.12 mmol) followed by Chlorotrimethylsilyl (363 µl, 2.86 mmol) was added. After 5 minutes, 1-(bromomethyl)-4-fluorobenzene (337 µl, 2.77 mmol) was added and the solution was heated at 40° C. After 4 hours, the reaction was concentrated. The residue was partitioned with EtOAc and H$_2$O and washed with H$_2$O. The organic layer was dried over MgSO$_4$, filtered and concentrated. The crude material was purified using a CombiFlash Chromatography System using a gradient of 50% EtOAc/Hex to 100% EtOAc to obtain (1-benzyloxycarbonylamino-2-vinyl-cyclopropyl)-(4-fluoro-benzyl)-phosphinic acid ethyl ester (164 mg, 30%) as a brown oil. The crude (151 mg, 0.36 mmol) was suspended in 1 mL of CH$_3$CN and cooled to 0° C. Iodotrimethylsilyl (TMSI) (257 µl, 1.81 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The solid (1-amino-2-vinyl-cyclopropyl)-(4-fluoro-benzyl)-phosphinic acid was used directly.

The acid VII (157 mg, 0.24 mmol) was suspended in 1 mL of DMF. HATU (228 mg, 0.60 mmol), (1-amino-2-vinyl-cyclopropyl)-(4-fluoro-benzyl)-phosphinic acid (92 mg, 0.36 mmol), followed by NMM (132 μl, 1.20 mmol) was added. The solution stirred overnight at rt. The mixture was purified via Gilson HPLC to obtain 38 (133 mg, 62%) as a yellow solid. $^{1H}$ NMR (300 MHz, CD$_3$OD): δ 8.30 (d, J=9.5 Hz, 1H), 8.20 (s, 1H), 7.79 (s, 2H), 7.35 (d, J=8.8 Hz, 1H), 7.05 (t, 2H), 5.95 (m, 1H), 5.78 (s, 1H), 5.35 (d, J=9.6 Hz, 2H), 5.15 (d, J=9.0 Hz, 2H), 4.75 (m, 2H), 4.45 (bs, 1H), 4.20 (s, 2H), 4.05 (s, 3H), 3.33 (m, 2H), 2.80 (m, 1H), 2.52 (m, 1H), 2.20 (m, 1H), 1.62 (m, 6H), 1.38 (d, 6H), 1.05 (s, 9H). $^{31}$P (121.4 MHz, CD$_3$OD): δ43.659

Example 39

Preparation of Compound 39

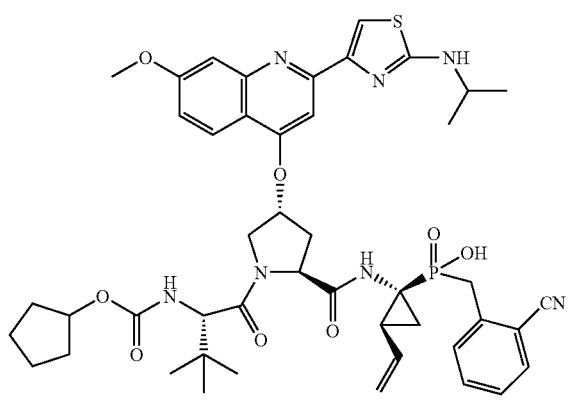

A solution of the phosphonous acid IV (330 mg, 1.07 mmol) and Hunig's Base (392 μl, 2.25 mmol) in CH$_2$Cl$_2$ (9.7 mL) stirred at 0° C. as chlorotrimethylsilyl (285 μl, 2.25 mmol) was added dropwise. The solution was warmed to rt and after 40 minutes 2-(bromomethyl)benzonitrile (461 mg, 2.35 mmol) was added and the solution was heated at 40° C. for 5 h. The solution stirred at rt for 12 h and concentrated. The residue was partitioned with CH$_2$Cl$_2$ and NH$_4$Cl. The organic layer was dried (MgSO$_4$) and concentrated. The crude material was purified with a CombiFlash Chromatography System to give (1-Benzyloxycarbonylamino-2-vinyl-cyclopropyl)-(2-cyano-benzyl)-phosphinic acid ethyl ester (180 mg, 40%). $^{1H}$ NMR (300 MHz, CDCl$_3$): δ 7.58 (m, 4H), 7.33 (m, 5H), 6.18-5.83 (m, 1H), 5.78-5.39 (m, 1H), 5.10 (s, 3H), 4.89 (m, 1H), 4.05 (m, 2H), 3.55 (m, 2H), 2.21 (m, 1H), 1.78 (m, 1H), 1.50 (m, 1H), 1.10 (m, 3H). $^{31}$P (121.4 MHz, CDCl$_3$): δ43.997, 41.885 diastereomers A solution of phosphinate (180 mg, 0.42 mmol) in CH$_3$CN (1 mL) stirred at 0° C. as Iodotrimethylsilyl (301 μl, 2.12 mmol) was added. The solution stirred at rt then was cooled again to 0° C. and triethylamine (1 mL, 7.33 mmol) and MeOH (2 mL) was added. The solution was warmed to rt and stirred for 20 minutes. The solution was concentrated, azeotroped (×2) with toluene and dried on high vacuum for 30 minutes. The solid was used without further purification.

The acid VII (137 mg, 0.21 mmol) was suspended in 3 mL of DMF. HATU (200 mg, 0.53 mmol), amine obtained above (111 mg, 0.42 mmol), followed by NMM (136 μl, 1.05 mmol) was added. The solution stirred overnight at rt. The mixture was purified via Gilson HPLC to obtain 39 (43 mg, 23%) as a yellow solid.
$^{1H}$ NMR (300 MHz, CD$_3$OD): δ 8.29 (d, J=8.7 Hz, 1H), 8.18 (s, 1H), 7.76 (s, 2H), 7.68 (m, 2H), 7.61 (m, 1H), 7.35 (m, 2H), 5.99 (m, 1H), 5.80 (s, 1H), 5.3 (d, J=17.5 Hz, 1H), 5.14 (d, J=10.8 Hz, 1H), 4.68 (m, 2H), 4.52 (bs, 1H), 4.16 (m, 2H), 4.07 (m, 4H), 3.62 (t, J=15.3 Hz, 1H), 3.42 (t, J=15.6 Hz, 1H), 2.83 (m, 1H), 2.66 (m, 1H), 2.18 (m, 1H), 1.62-1.40 (m, 10H) 1.38 (d, J=6.3 Hz, 6H), 1.04 (s, 9H). $^{31}$P (121.4 MHz, CD$_3$OD): δ36.642

LC/MS=898 (M$^+$+1)

Example 40

Preparation of Compound 40

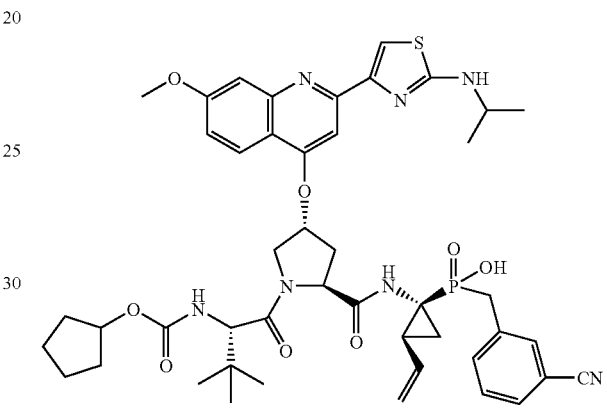

The phosphonous acid IV (320 mg, 1.04 mmol) was suspended in 9.7 mL of CH$_2$Cl$_2$. The solution was cooled to 0° C. Hunig's Base (342 μl, 2.25 mmol) followed by Chlorotrimethylsilyl (285 μl, 2.25 mmol) was added dropwise. The solution was warmed to rt and after 40 minutes 3-(bromomethyl) benzonitrile (461 mg, 2.35 mmol) was added and the solution was heated at 40° C. for 5 h. Then the reaction stirred at rt for 12 h. The residue was partitioned with CH$_2$Cl$_2$ and NH$_4$Cl and washed with NH$_4$Cl. The organic layer was dried over MgSO$_4$, filtered and concentrated. The crude material was purified using a CombiFlash Chromatography System to give (1-Benzyloxycarbonylamino-2-vinyl-cyclopropyl)-(3-cyano-benzyl)-phosphinic acid ethyl ester (190 mg, 42%). $^{1H}$ NMR (300 MHz, CDCl$_3$): δ 7.58 (m, 4H), 7.37 (m, 5H), 6.13 (m, 1H), 5.83-5.78 (m, 1H), 5.65 (m, 1H), 5.39 (m, 1H), 5.10 (s, 2H), 3.98 (m, 2H), 3.25 (m, 2H), 2.15 (m, 1H), 1.78 (m, 1H), 1.41 (m, 1H), 1.10 (m, 3H). $^{31}$P (121.4 MHz, CDCl$_3$): δ44.552, 42.103 diastereomers.

Phosphinate (180 mg, 0.42 mmol) was suspended in 1 mL of CH$_3$CN and cooled to 0° C. Iodotrimethylsilyl(TMSI) (301 μl, 2.12 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The solid was coupled with acid VII (137 mg, 0.21 mmol) in 3 mL of DMF, HATU (200 mg, 0.53 mmol), NMM (136 μl, 1.05 mmol). The solution stirred overnight at rt. The mixture was purified via Gilson HPLC to obtain 40 (40 mg, 22%) as a yellow solid. $^{1H}$ NMR (300 MHz, CD$_3$OD): δ 8.29 (d, J=9.9 Hz, 1H), 8.17 (s, 1H), 7.76 (s, 2H), 7.62 (m, 1H), 7.59 (m, 1H), 7.41 (m, 2H), 7.34 (d, J=8.8 Hz, 1H), 5.89 (m, 1H), 5.78 (s, 1H), 5.24 (d, J=15.9 Hz, 1H), 5.02 (d, J=10.8 Hz, 1H), 4.66 (m, 2H), 4.46 (bs, 1H), 4.15 (m, 20H), 4.05 (m, 4H), 3.22 (m, 2H), 2.78 (m, 1H), 2.49 (m, 1H), 2.09 (m, 1H), 1.62-1.50 (m, 10H) 1.34 (d, J=6.3 Hz, 6H), 1.02 (s, 9H). $^{31}$P (121.4 MHz, CD$_3$OD): δ40.005
LC/MS=898 (M$^+$+1)

Example 41

Preparation of Compound 41

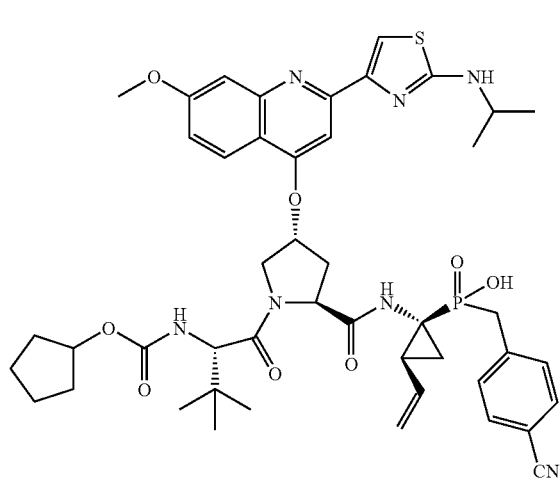

The phosphonous acid IV (330 mg, 1.07 mmol) was suspended in 9.7 mL of CH$_2$Cl$_2$. The solution was cooled to 0° C. Hunig's Base (342 µl, 2.25 mmol) followed by Chlorotrimethylsilyl (285 µl, 2.25 mmol) was added dropwise. The solution was warmed to rt and after 40 minutes 4-(bromomethyl)benzonitrile (7) (461 mg, 2.35 mmol) was added and the solution was heated at 40° C. for 5 h. Then the reaction stirred at rt for 12 h. The residue was partitioned with CH$_2$Cl$_2$ and NH$_4$Cl and washed with NH$_4$Cl. The organic layer was dried over MgSO$_4$, filtered and concentrated. The crude material was purified with a CombiFlash Chromatography System to provide (1-Benzyloxycarbonylamino-2-vinyl-cyclopropyl)-(4-cyano-benzyl)-phosphinic acid ethyl ester (200 mg, 45%). $^{1H}$ NMR (300 MHz, CDCl$_3$): δ 7.58 (m, 4H), 7.37 (m, 5H), 6.13-5.83 (m, 1H), 5.78-5.65 (m, 2H), 5.39 (m, 1H), 5.10 (s, 2H), 3.98 (m, 2H), 3.25 (m, 2H), 2.15 (m, 1H), 1.78 (m, 1H), 1.41 (m, 1H), 1.10 (m, 3H). $^{31}$P (121.4 MHz, CDCl$_3$): δ46.164, 43.998 diastereomers.

Phosphinate (180 mg, 0.42 mmol) was suspended in 1 mL of CH$_3$CN and cooled to 0° C. Iodotrimethylsilyl (TMSI) (301 µl, 2.12 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The solid left was coupled with acid VII (137 mg, 0.21 mmol) in 3 mL of DMF, HATU (200 mg, 0.53 mmol) and NMM (136 µl, 1.05 mmol). The mixture was purified via Gilson HPLC to obtain 41 (55 mg, 30%) as a yellow solid. $^{1H}$ NMR (300 MHz, CD$_3$OD): δ 8.29 (d, J=9.3 Hz, 1H), 8.17 (s, 1H), 7.75 (s, 2H), 7.63 (m, 2H), 7.52 (m, 2H), 7.32 (m, 1H), 5.89 (m, 1H), 5.79 (s, 1H), 5.26 (d, J=17.1 Hz, 1H), 5.06 (d, J=10.8 Hz, 1H), 4.68 (m, 2H), 4.45 (bs, 1H), 4.17 (m, 2H), 4.08 (m, 4H), 3.37 (m, 2H), 2.76 (m, 1H), 2.48 (m, 1H), 2.07 (m, 1H), 1.61-1.40 (m, 10H) 1.34 (d, J=6.3 Hz, 6H), 1.01 (s, 9H). $^{31}$P (121.4 MHz, CD$_3$OD): δ36.642 LC/MS=898 (M$^+$+1)

Example 42

Preparation of Compound 42

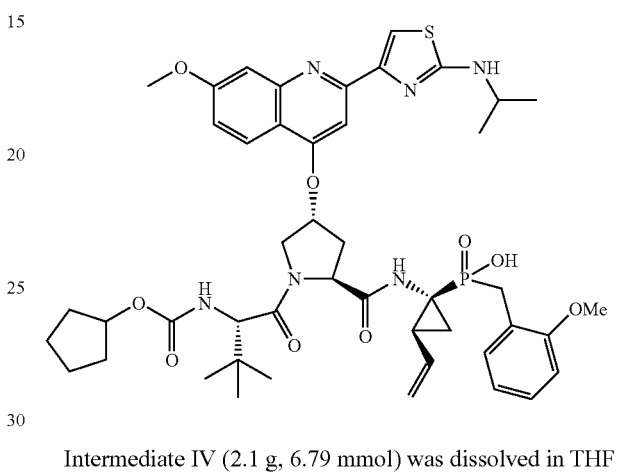

Intermediate IV (2.1 g, 6.79 mmol) was dissolved in THF (20 mL) and cooled to −78° C. A solution of 1 M THF of NaN(TMS)$_2$ (8.83 mL, 8.83 mmol) was added dropwise and the reaction mixture was stirred at −78° C. for 1 h. 2-Methoxybenzyl chloride (1.23 mL, 8.83 mmol) was added and the cold bath was removed. The reaction mixture was stirred at rt for 6 h. The reaction mixture was quenched with NH$_4$Cl and extracted with EtOAc. The organic layers were washed with brine, dried with Na$_2$SO$_4$, filtered, and concentrated. The crude product was purified by combi-flash to give 2.15 g of phosphinate in 74% yield.

To a solution of phosphinate obtained above (2.15 g) in TFA (10 mL) at r.t. was added DMS (3 mL) and stirred overnight. The mixture was concentrated and co-evaporated with toluene. The residue was dissolved in 1/1 iPrOH/heptane and washed with 6 N HCl (3×100 mL). The combined aqueous layers were brought to pH-=10 with NaOH in a cold bath. The aqueous layer was extracted with EtOAc. The organic layers were washed with brine, dried with Na$_2$SO$_4$, and concentrated to give 386 mg of amine which was coupled to intermediate VI in DMF and HATU following standard procedures to give crude product. The crude product was purified by combi-flash to give 1.1 g of tripeptide in 87% yield.

Tripeptide obtained above (1.1 g, 1.18 mmol) was dissolved in CH$_3$CN (10 mL) and cooled to 0° C. Iodotrimethylsilane (0.85 mL, 5.91 mmol) was added dropwise and stirred for 10 minutes. 2,6-Lutidine (0.82 mL) was added. MeOH (10 mL) was added and the reaction mixture was concentrated. The crude product was purified by HPLC to give 645 mg of compound 42.

$^{1H}$ NMR (300 MHz, CD$_3$OD): δ 8.30 (d, J=9.5 Hz, 1H), 8.20 (s, 1H), 7.79 (s, 2H), 7.35 (d, J=8.8 Hz, 1H), 7.05 (t, 2H), 5.95 (m, 1H), 5.78 (s, 1H), 5.35 (d, J=9.6 Hz, 2H), 5.15 (d,

J=9.0 Hz, 2H), 4.75 (m, 2H), 4.45 (bs, 1H), 4.20 (s, 2H), 4.05 (s, 3H), 3.33 (m, 2H), 2.80 (m, 1H), 2.52 (m, 1H), 2.20 (m, 1H), 1.62 (m, 6H), 1.38 (d, 6H), 1.05 (s, 9H). $^{31}$P (121.4 MHz, CD$_3$OD): δ43.659.

Example 43

Preparation of Compound 43

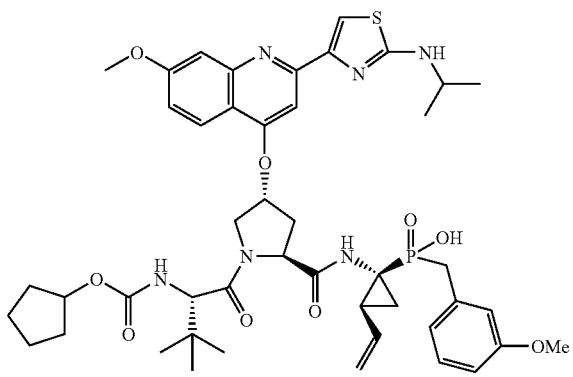

The phosphonous acid IV (373 mg, 1.21 mmol) was suspended in 5 mL of THF and cooled to −40° C. 1N NaN(TMS)$_2$ (1.43 mL, 1.43 mmol) was added dropwise over 15 minutes followed by 1-(chloromethyl)-3-methoxybenzene (212 μl, 1.46 mmol) in 1 mL of THF. The solution stirred from −40° C. to rt overnight. The reaction was diluted with EtOAc and quenched with 20 mL of 1N HCl. The organic layer was washed with brine, dried over MgSO$_4$, filtered and concentrated. The crude material was purified using a CombiFlash Chromatography System using a gradient of 30% EtOAc/Hex to 100% EtOAc to obtain (1-benzyloxycarbonylamino-2-vinyl-cyclopropyl)-(3-methoxy-benzyl)-phosphinic acid ethyl ester (95.9 mg, 19%) as a brown oil, which was suspended in 1 mL of CH$_3$CN and cooled to 0° C. To this mixture, iodotrimethylsilyl (TMSI) (158 μl, 1.11 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The solid (1-Amino-2-vinyl-cyclopropyl)-(3-methoxy-benzyl)-phosphinic acid was coupled with VII (95 mg, 0.16 mmol), HATU (142 mg, 0.38 mmol) and NMM (83 μl, 0.75 mmol) to give compound 43 after Gilson HPLC purification. $^{1H}$ NMR (300 MHz, CD$_3$OD): δ 8.80 (s, 1H), 8.30 (d, J=9.5 Hz, 1H), 8.20 (s, 1H), 7.79 (s, 2H), 7.35 (d, J=8.8 Hz, 1H), 7.18 (m, 1H), 6.85 (m, 2H), 6.78 (m, 1H), 5.95 (m, 1H), 5.78 (s, 1H), 5.50 (s, 1H), 5.35 (d, J=9.6 Hz, 2H), 5.15 (d, J=9.0 Hz, 2H), 4.75 (m, 2H), 4.45 (bs, 1H), 4.20 (s, 2H), 4.05 (s, 3H), 3.80 (s, 3H), 3.33 (m, 2H), 2.80 (m, 1H), 2.52 (m, 1H), 2.20 (m, 1H), 1.62 (m, 6H), 1.38 (d, 6H), 1.05 (s, 9H). $^{31}$P (121.4 MHz, CD$_3$OD): δ43.371

Example 44

Preparation of Compound 44

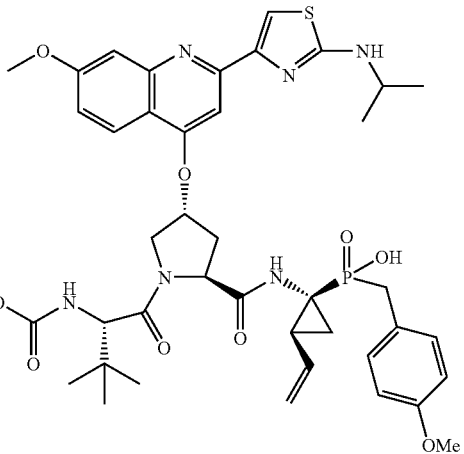

The phosphonous acid IV (341 mg, 1.10 mmol) was suspended in 5 mL of THF and cooled to −40° C. 1N NaN(TMS)$_2$ (1.32 mL, 1.32 mmol) was added dropwise over 15 minutes followed by 1-(chloromethyl)-4-methoxybenzene (180 μl, 1.32 mmol) in 1 mL of THF. The solution stirred from −40° C. to rt overnight. The reaction was diluted with EtOAc and quenched with 20 mL of 1N HCl. The organic layer was washed with brine, dried over MgSO$_4$, filtered and concentrated. The crude material was purified using a CombiFlash Chromatography System using a gradient of 30% EtOAc/Hex to 100% EtOAc to obtain (1-Benzyloxycarbonylamino-2-vinyl-cyclopropyl)-(4-methoxy-benzyl)-phosphinic acid ethyl ester (135 mg, 27%) as a brown oil. The residue was suspended in 1 mL of CH$_3$CN and cooled to 0° C. Iodotrimethylsilyl (TMSI) (215 μl, 1.51 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The solid (1-Amino-2-vinyl-cyclopropyl)-(4-methoxy-benzyl)-phosphinic acid was used directly.

The acid VII (130 mg, 0.20 mmol) was suspended in 1 mL of DMF. HATU (190 mg, 0.50 mmol), (1-Amino-2-vinyl-cyclopropyl)-(4-methoxy-benzyl)-phosphinic acid (80 mg, 0.30 mmol), followed by NMM (110 μl, 1.00 mmol) was added. The solution stirred overnight at rt. The mixture was purified via Gilson HPLC to obtain 44 (85.4 mg, 47%) as a yellow solid. $^{1H}$ NMR (300 MHz, CD$_3$OD): δ 8.80 (s, 1H), 8.30 (d, J=9.5 Hz, 1H), 8.20 (s, 1H), 7.79 (s, 2H), 7.35 (d, J=8.8 Hz, 1H), 7.21 (d, J=8.9 Hz, 2H), 6.85 (d, J=9.2 Hz, 2H), 5.95 (m, 1H), 5.78 (s, 1H), 5.50 (s, 1H), 5.35 (d, J=9.6 Hz, 2H), 5.15 (d, J=9.0 Hz, 2H), 4.75 (m, 2H), 4.45 (bs, 1H), 4.20 (s, 2H), 4.05 (s, 3H), 3.80 (s, 3H), 3.33 (m, 2H), 2.80 (m, 1H), 2.52 (m, 1H), 2.20 (m, 1H), 1.62 (m, 6H), 1.38 (d, 6H), 1.05 (s, 9H). $^{31}$P (121.4 MHz, CD$_3$OD): δ43.939

Example 45

Preparation of Compound 45

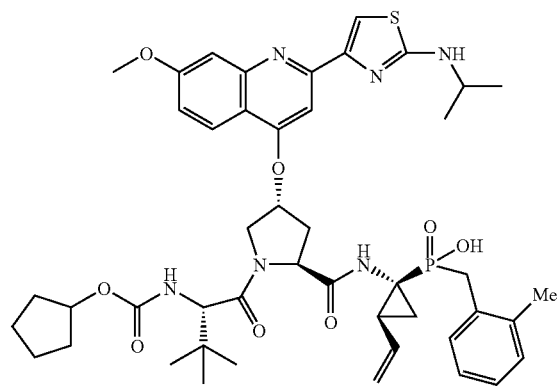

The phosphonous acid IV (330 mg, 1.07 mmol) was suspended in 9.7 mL of CH$_2$Cl$_2$. The solution was cooled to 0° C. Hunig's Base (342 µl, 2.25 mmol) followed by Chlorotrimethylsilyl (285 µl, 2.25 mmol) was added dropwise. The solution was warmed to rt and after 40 minutes 1-(bromomethyl)-3-methylbenzene (435 mg, 2.35 mmol) was added and the solution was heated at 40° C. for 5 h. Then the reaction stirred at rt for 12 h. The residue was partitioned with CH$_2$Cl$_2$ and NH$_4$Cl and washed with NH$_4$Cl. The organic layer was dried over MgSO$_4$, filtered and concentrated. The crude material was purified using a CombiFlash Chromatography System to give (1-Benzyloxycarbonylamino-2-vinyl-cyclopropyl)-(2-methyl-benzyl)-phosphinic acid ethyl ester (190 mg, 43%). $^{1H}$ NMR (300 MHz, CDCl$_3$): δ 7.37 (m, 5H), 7.18 (m, 4H), 6.13 (m, 1H), 5.78 (m, 1H), 5.39 (m, 1H), 5.10 (m, 2H), 3.98 (m, 2H), 3.25 (m, 2H), 2.15 (s, 3H), 1.80 (m, 2H), 1.41 (m, 1H), 1.10 (m, 3H). $^{31}$P (121.4 MHz, CDCl$_3$): δ46.105, 43.225 diastereomers.

Phosphinate (173 mg, 0.42 mmol) was suspended in 1 mL of CH$_3$CN and cooled to 0° C. Iodotrimethylsilyl (TMSI) (301 µl, 2.12 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The solid was used directly without further purification.

The acid VII (137 mg, 0.21 mmol) was suspended in 3 mL of DMF. HATU (200 mg, 0.53 mmol), crude amine obtained above (105 mg, 0.42 mmol), followed by NMM (136 µl, 1.05 mmol) was added. The solution stirred overnight at rt. The mixture was purified via Gilson HPLC to obtain 45 (60 mg, 34%) as a yellow solid. $^{1H}$ NMR (300 MHz, CD$_3$OD): δ 8.29 (d, J=9.9 Hz, 1H), 8.19 (s, 1H), 7.77 (s, 2H), 7.30 (m, 3H), 7.11 (m, 2H), 5.95 (m, 1H), 5.81 (s, 1H), 5.32 (d, J=17.7 Hz, 1H), 5.13 (d, J=10.8 Hz, 1H), 4.67 (m, 2H), 4.44 (bs, 1H), 4.16 (m, 2H), 4.08 (m, 4H), 3.30 (m, 2H), 2.75 (m, 1H), 2.50 (m, 1H), 2.38 (m, 3H), 2.16 (m, 1H), 1.63-1.35 (m, 6H) 1.34 (d, J=6.3 Hz, 6H), 1.03 (s, 9H). $^{31}$P (121.4 MHz, CD$_3$OD): δ42.100

LC/MS=887 (M$^+$+1)

Example 46

Preparation of Compound 46

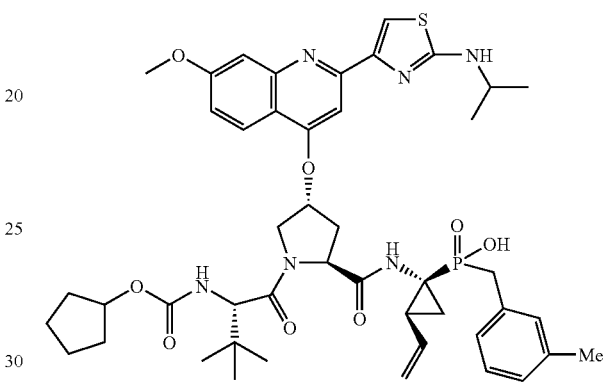

The phosphonous acid IV (330 mg, 1.07 mmol) was suspended in 9.7 mL of CH$_2$Cl$_2$. The solution was cooled to 0° C. Hunig's Base (342 µl, 2.25 mmol) followed by Chlorotrimethylsilyl (285 µl, 2.25 mmol) was added dropwise. The solution was warmed to rt and after 40 minutes 1-(bromomethyl)-3-methylbenzene (435 mg, 2.35 mmol) was added and the solution was heated at 40° C. for 5 h. Then the reaction stirred at rt for 12 h. The residue was partitioned with CH$_2$Cl$_2$ and NH$_4$Cl and washed with NH$_4$Cl. The organic layer was dried over MgSO$_4$, filtered and concentrated. The crude material was purified using a CombiFlash Chromatography System to give (1-Benzyloxycarbonylamino-2-vinyl-cyclopropyl)-(3-methyl-benzyl)-phosphinic acid ethyl ester (200 mg, 45%). $^{1H}$ NMR (300 MHz, CDCl$_3$): δ 7.38 (m, 5H), 7.18 (m, 4H), 6.13 (m, 1H), 5.78 (m, 1H), 5.39 (m, 1H), 5.10 (m, 2H), 4.02 (m, 2H), 3.25 (m, 2H), 2.30 (s, 3H), 1.98 (m, 1H), 1.80 (m, 1H), 1.50 (m, 1H), 1.18 (m, 3H). $^{31}$P (121.4 MHz, CDCl$_3$): δ47.885, 44.001 diastereomers Deprotection and coupling as described for example 45 give compound 46 as a yellow solid. $^{1H}$ NMR (300 MHz, CD$_3$OD): δ 8.29 (d, J=9.0 Hz, 1H), 8.17 (s, 1H), 7.75 (s, 2H), 7.33 (d, J=9.3, 1H), 7.13 (m, 3H), 7.01 (m, 1H), 5.96 (m, 1H), 5.79 (s, 1H), 5.27 (d, J=17.1 Hz, 1H), 5.08 (d, J=9.9 Hz, 1H), 4.68 (m, 2H), 4.46 (bs, 1H), 4.16 (m, 2H), 4.06 (m, 4H), 3.27 (m, 2H), 2.78 (m, 1H), 2.52 (m, 1H), 2.29 (s, 3H), 2.13 (m, 1H), 1.62-1.40 (m, 10H) 1.34 (d, J=6.3 Hz, 6H), 1.03 (s, 9H). $^{31}$P (121.4 MHz, CD$_3$OD): δ42.100 LC/MS 887 (M$^+$+1)

Example 47

Preparation of Compound 47

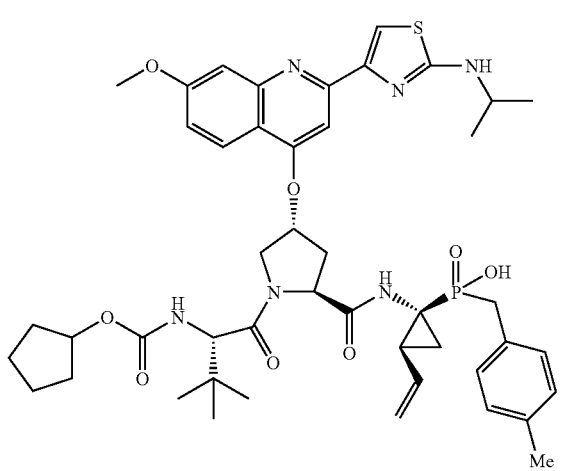

The phosphonous acid IV (330 mg, 1.07 mmol) was suspended in 9.7 mL of $CH_2Cl_2$. The solution was cooled to 0° C. Hunig's Base (342 µl, 2.25 mmol) followed by Chlorotrimethylsilyl (285 µl, 2.25 mmol) was added dropwise. The solution was warmed to rt and after 40 minutes 1-(bromomethyl)-4-methylbenzene (435 mg, 2.35 mmol) was added and the solution was heated at 40° C. for 5 h. Then the reaction stirred at rt for 12 h. The residue was partitioned with $CH_2Cl_2$ and $NH_4Cl$ and washed with $NH_4Cl$. The organic layer was dried over $MgSO_4$, filtered and concentrated. The crude material was purified using a CombiFlash Chromatography System to give (1-Benzyloxycarbonylamino-2-vinyl-cyclopropyl)-(4-methyl-benzyl)-phosphinic acid ethyl ester (195 mg, 44%). $^{1H}$ NMR (300 MHz, $CDCl_3$): δ 7.38 (m, 5H), 7.18 (m, 4H), 6.13 (m, 1H), 5.78 (m, 1H), 5.39 (m, 1H), 5.10 (m, 2H), 4.04 (m, 2H), 3.25 (m, 2H), 2.30 (s, 3H), 1.98 (m, 1H), 1.80 (m, 1H), 1.50 (m, 1H), 1.18 (m, 3H). $^{31}P$ (121.4 MHz, $CDCl_3$): δ45.991, 42.100 diastereomers.

Deprotection and coupling as described for example 45 give compound 47 as a yellow solid.

$^{1H}$ NMR (300 MHz, $CD_3OD$): δ 8.26 (d, J=9.5 Hz, 1H), 8.19 (s, 1H), 7.74 (s, 2H), 7.30 (m, 1H), 7.19 (m, 2H), 7.06 (m, 2H), 5.94 (m, 1H), 5.78 (s, 1H), 5.25 (d, J=17.1 Hz, 1H), 5.06 (d, J=9.0 Hz, 1H), 4.68 (m, 2H), 4.47 (bs, 1H), 4.16 (m, 2H), 4.05 (m, 4H), 3.26 (m, 2H), 2.77 (m, 1H), 2.48 (m, 1H), 2.27 (s, 3H), 2.09 (m, 1H), 1.65-1.43 (m, 8H) 1.34 (d, J=6.3 Hz, 6H), 1.02 (s, 9H). $^{31}P$ (121.4 MHz, $CD_3OD$): δ42.100

LC/MS=887 ($M^+$+1)

Example 48

Preparation of Compound 48

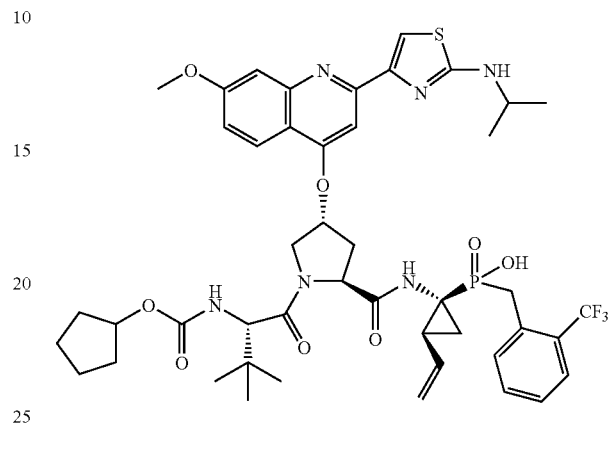

The phosphonous acid IV (330 mg, 1.07 mmol) was suspended in 9.7 mL of $CH_2Cl_2$. The solution was cooled to 0° C. Hunig's Base (342 µl, 2.25 mmol) followed by Chlorotrimethylsilyl (285 µl, 2.25 mmol) was added dropwise. The solution was warmed to rt and after 40 minutes 1-(bromomethyl)-1-(trifluoromethyl)benzene (456 mg, 2.35 mmol) was added and the solution was heated at 40° C. for 48 h. Then the reaction stirred at rt for 12 h. The residue was partitioned with $CH_2Cl_2$ and $NH_4Cl$ and washed with $NH_4Cl$. The organic layer was dried over $MgSO_4$, filtered and concentrated. The crude material was purified using a CombiFlash Chromatography System give (1-Benzyloxycarbonylamino-2-vinyl-cyclopropyl)-(2-trifluoromethyl-benzyl)-phosphinic acid ethyl ester (225 mg, 45%). $^{1H}$ NMR (300 MHz, $CDCl_3$): δ 7.61 (m, 2H), 7.43 (m, 2H), 7.33 (m, 5H), 6.13 (m, 1H), 5.83 (m, 1H), 5.78 (m, 1H), 5.39 (m, 1H), 5.10 (s, 2H), 3.88 (m, 2H), 3.25 (m, 2H), 2.10 (m, 1H), 1.78 (m, 1H), 1.41 (m, 1H), 1.10 (m, 3H). $^{31}P$ (121.4 MHz, $CDCl_3$): δ45.337, 42.005 diastereomers.

Deprotection and coupling as described for example 45 give compound 48 as a yellow solid (80 mg, 45%).

$^{1}H$ NMR (300 MHz, $CD_3OD$): δ 8.28 (d, J=9.3 Hz, 1H), 8.19 (s, 1H), 7.76 (s, 2H), 7.69 (m, 2H), 7.53 (t, J=7.8 Hz, 1H), 7.39 (t, J=7.5 Hz, 1H), 7.32 (d, J=9.3 Hz, 1H), 5.95 (m, 1H), 5.82 (s, 1H), 5.30 (d, J=17.4 Hz, 1H), 5.12 (d, J=11.1 Hz, 1H), 4.69 (m, 2H), 4.43 (bs, 1H), 4.17 (m, 2H), 4.06 (m, 4H), 3.65 (t, J=15.3 Hz, 1H), 3.43 (t, J=16.5 Hz, 1H), 2.79 (m, 1H), 2.53 (m, 1H), 2.17 (m, 1H), 1.70-1.40 (m, 10H), 1.34 (d, J=6.3 Hz, 6H), 1.01 (s, 9H). $^{31}P$ (121.4 MHz, $CD_3OD$): δ40.995. LC/MS 941 ($M^+$+1)

Example 49

Preparation of Compound 49

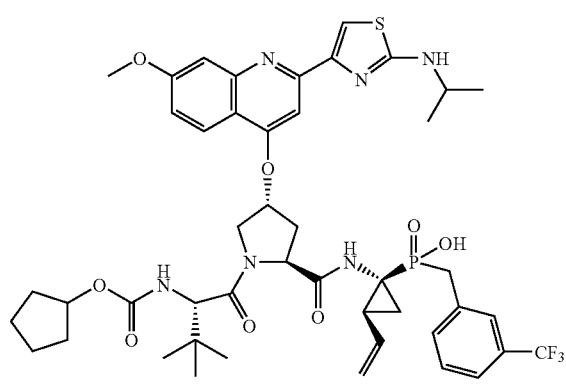

The phosphonous acid IV (330 mg, 1.07 mmol) was suspended in 9.7 mL of $CH_2Cl_2$. The solution was cooled to 0° C. Hunig's Base (342 μl, 2.25 mmol) followed by Chlorotrimethylsilyl (285 μl, 2.25 mmol) was added dropwise. The solution was warmed to rt and after 40 minutes 1-(bromomethyl)-3-(trifluoromethyl)benzene (456 mg, 2.35 mmol) was added and the solution was heated at 40° C. for 48 h. Then the reaction stirred at rt for 12 h. The residue was partitioned with $CH_2Cl_2$ and $NH_4Cl$ and washed with $NH_4Cl$. The organic layer was dried over $MgSO_4$, filtered and concentrated. The crude material was purified using a CombiFlash Chromatography System give (1-Benzyloxycarbonylamino-2-vinyl-cyclopropyl)-(3-trifluoromethyl-benzyl)-phosphinic acid ethyl ester (230 mg, 46%). $^{1H}$ NMR (300 MHz, $CDCl_3$): δ 7.43 (m, 4H), 7.33 (m, 5H), 6.13 (m, 1H), 5.83 (m, 1H), 5.78 (m, 1H), 5.39 (m, 1H), 5.10 (s, 3H), 3.88 (m, 2H), 3.25 (m, 2H), 2.11 (m, 1H), 1.78 (m, 1H), 1.41 (m, 1H), 1.10 (m, 3H). $^{31}$P (121.4 MHz, $CDCl_3$): δ45.337, 42.005 diastereomers.

Deprotection and coupling as described for example 45 give compound 49 as a yellow solid (80 mg, 45%).

$^{1H}$ NMR (300 MHz, $CD_3OD$): δ 8.28 (d, J=9.3 Hz, 1H), 8.18 (s, 1H), 7.75 (s, 2H), 7.65 (m, 1H), 7.59 (m, 1H), 7.46 (m, 2H), 7.$^{31}$ (d, J=9.0 Hz, 1H), 5.87 (m, 1H), 5.80 (s, 1H), 5.23 (d, J=17.1 Hz, 1H), 5.02 (d, J=10.2 Hz, 1H), 4.66 (m, 2H), 4.46 (bs, 1H), 4.18 (m, 2H), 4.07 (m, 4H), 3.38 (m, 2H), 2.81 (m, 1H), 2.51 (m, 3H), 2.10 (m, 1H), 1.63-1.50 (m, 10H), 1.34 (d, J=6.3 Hz, 6H), 1.05 (s, 9H). $^{31}$P (121.4 MHz, $CD_3OD$): δ40.995

LC/MS=941 ($M^+$+1)

Example 50

Preparation of Compound 50

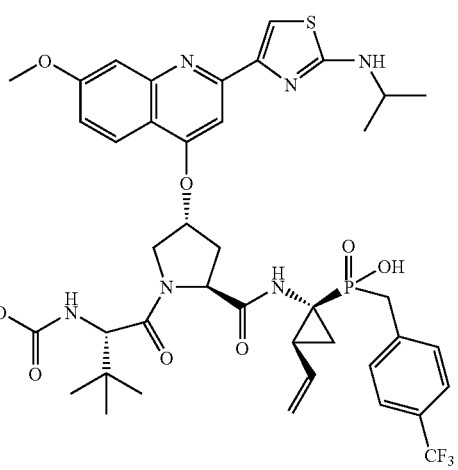

The phosphonous acid IV (330 mg, 1.07 mmol) was suspended in 9.7 mL of $CH_2Cl_2$. The solution was cooled to 0° C. Hunig's Base (342 μl, 2.25 mmol) followed by Chlorotrimethylsilyl (285 μl, 2.25 mmol) was added dropwise. The solution was warmed to rt and after 40 minutes 1-(bromomethyl)-4-(trifluoromethyl)benzene (28) (456 mg, 2.35 mmol) was added and the solution was heated at 40° C. for 48 h. Then the reaction stirred at rt for 12 h. The residue was partitioned with $CH_2Cl_2$ and $NH_4Cl$ and washed with $NH_4Cl$. The organic layer was dried over $MgSO_4$, filtered and concentrated. The crude material was purified using a CombiFlash Chromatography System give (1-Benzyloxycarbonylamino-2-vinyl-cyclopropyl)-(4-trifluoromethyl-benzyl)-phosphinic acid ethyl ester (205 mg, 41%). $^{1H}$ NMR (300 MHz, $CDCl_3$): δ 7.55 (m, 4H), 7.39 (m, 5H), 6.13 (m, 1H), 5.83 (m, 1H), 5.78 (m, 1H), 5.39 (m, 1H), 5.10 (s, 2H), 3.88 (m, 2H), 3.25 (m, 2H), 2.03 (m, 1H), 1.78 (m, 1H), 1.41 (m, 1H), 1.10 (m, 3H). $^{31}$P (121.4 MHz, $CDCl_3$): δ45.337, 42.005 diastereomers.

Deprotection and coupling as described for example 45 give compound 50 as a yellow solid (80 mg, 45%).

$^{1H}$ NMR (300 MHz, $CD_3OD$): δ 8.27 (d, J=9.3 Hz, 1H), 8.19 (s, 1H), 7.75 (s, 2H), 7.51 (m, 4H), 7.27 (m, 1H), 5.92 (m, 1H), 5.81 (s, 1H), 5.23 (d, J=17.1 Hz, 1H), 5.04 (d, J=10.5 Hz, 1H), 4.67 (m, 2H), 4.46 (bs, 1H), 4.17 (m, 2H), 4.04 (m, 4H), 3.35 (m, 2H), 2.80 (m, 1H), 2.49 (m, 1H), 2.08 (m, 1H), 1.62-1.39 (m, 8H), 1.32 (d, J=6.3, 6H), 1.02 (s, 9H). $^{31}$P (121.4 MHz, $CD_3OD$): δ40.995 LC/MS=941 ($M^+$+1)

Example 51

Preparation of Compound 51

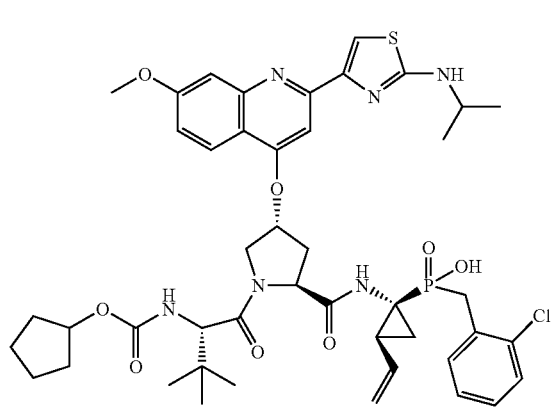

Intermediate IV (13.42 g, 43.4 mmol) was dissolved in CH$_2$Cl$_2$ (300 mL) and cooled to 0° C. and diisopropylethylamine (15.4 mL, 91.1 mmol) was added. Chlorotrimethylsilane (11.4 mL, 91.1 mmol) was added dropwise. The reaction mixture was warmed to r.t. and stirred for 1.5 h. 2-chlorobenzyl chloride (15.6 g, 95.5 mmol) was added and the reaction was heated to 50° C. for 48 h. The reaction mixture was cooled to rt, diluted with CH$_2$Cl$_2$, washed with aqueous NH$_4$Cl, dried with Na$_2$SO$_4$, and concentrated. The crude product was purified by combi-flash to give phosphinate.

The phosphinate (5.0 g, 11.55 mmol) (147 mg, 0.34 mmol) was suspended in 1 mL of CH$_3$CN and cooled to 0° C. Iodotrimethylsilyl (TMSI) (241 µl, 1.70 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The crude was coupled to acid VII to give compound 51. $^{1H}$ NMR (300 MHz, CD$_3$OD): δ 8.30 (d, J=9.5 Hz, 1H), 8.20 (s, 1H), 7.79 (s, 2H), 7.50 (d, J=8.8 Hz, 1H), 7.38 (m, 2H), 7.20 (m, 2H), 5.95 (m, 1H), 5.80 (s, 1H), 5.25 (d, J=9.6 Hz, 2H), 5.15 (d, J=9.0 Hz, 2H), 4.75 (m, 2H), 4.45 (bs, 1H), 4.20 (s, 2H), 4.05 (s, 3H), 3.33 (s, 2H), 2.80 (m, 1H), 2.52 (m, 1H), 2.15 (m, 1H), 1.62 (m, 6H), 1.38 (d, 6H), 1.05 (s, 9H). $^{31}$P (121.4 MHz, CD$_3$OD): δ42.155

Example 52

Preparation of Compound 52

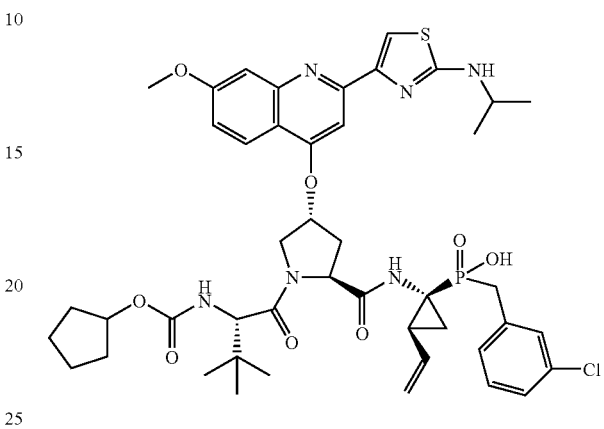

The phosphonous acid IV (369 mg, 1.19 mmol) was suspended in 5 mL of THF and cooled to −40° C. 1N NaN(TMS)$_2$ (1.43 mL, 1.43 mmol) was added dropwise over 15 minutes followed by 1-chloro-3-(chloromethyl)benzene (182 µl, 1.43 mmol) in 1 mL of THF. The solution stirred from −40° C. to rt overnight. The reaction was diluted with EtOAc and quenched with 20 mL of 1N HCl. The organic layer was washed with brine, dried over MgSO$_4$, filtered and concentrated. The crude material was purified using a CombiFlash Chromatography System using a gradient of 30% EtOAc/Hex to 100% EtOAc to obtain (1-benzyloxycarbonylamino-2-vinyl-cyclopropyl)-(3-chloro-benzyl)-phosphinic acid ethyl ester (90.5 mg, 24%) as a brown oil. The crude was suspended in 1 mL of CH$_3$CN and cooled to 0° C. Iodotrimethylsilyl (TMSI) (148 µl, 1.04 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The solid (1-Amino-2-vinyl-cyclopropyl)-(3-chlorobenzyl)-phosphinic acid was used directly. The acid (87 mg, 0.13 mmol) was suspended in 1 mL of DMF. HATU (123 mg, 0.33 mmol), VII (54.6 mg, 0.20 mmol), followed by NMM (71 µl, 0.65 mmol) was added. The solution stirred overnight at rt. The mixture was purified via Gilson HPLC to obtain 52 (68.5 mg, 59%) as a yellow solid. $^{1H}$ NMR (300 MHz, CD$_3$OD): δ 8.30 (d, J=9.5 Hz, 1H), 8.20 (s, 1H), 7.79 (s, 2H), 7.40 (s, 1H), 7.35 (d, J=8.8 Hz, 1H), 7.23 (m, 1H), 6.85 (m, 2H), 6.78 (m, 1H), 5.95 (m, 1H), 5.78 (s, 1H), 5.50 (s, 1H), 5.35 (d, J=9.6 Hz, 2H), 5.15 (d, J=9.0 Hz, 2H), 4.75 (m, 2H), 4.45 (bs, 1H), 4.20 (s, 2H), 4.05 (s, 3H), 3.33 (m, 2H), 2.80 (m, 1H), 2.52 (m, 1H), 2.20 (m, 1H), 1.62 (m, 6H), 1.38 (d, 6H), 1.05 (s, 9H). $^{31}$P (121.4 MHz, CD$_3$OD): δ42.73

Example 53

Preparation of Compound 53

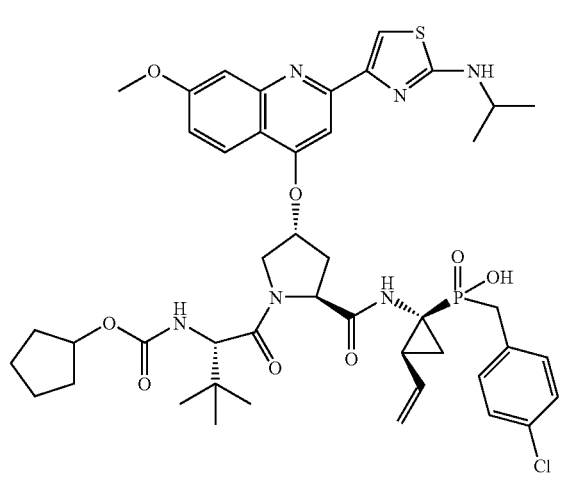

The phosphonous acid IV (370 mg, 1.20 mmol) was suspended in 5 mL of THF and cooled to −40° C. 1N NaN(TMS)$_2$ (1.43 mL, 1.43 mmol) was added dropwise over 15 minutes followed by 1-chloro-4-(chloromethyl)benzene (231 mgl, 1.43 mmol) in 1 mL of THF. The solution stirred from −40° C. to rt overnight. The reaction was diluted with EtOAc and quenched with 20 mL of 1N HCl. The organic layer was washed with brine, dried over MgSO$_4$, filtered and concentrated. The crude material was purified using a CombiFlash Chromatography System using a gradient of 30% EtOAc/Hex to 100% EtOAc to obtain (1-Benzyloxycarbonylamino-2-vinyl-cyclopropyl)-(4-chloro-benzyl)-phosphinic acid ethyl ester (94 mg, 26%) as a brown oil. The residue (94.9 mg, 0.22 mmol) was suspended in 1 mL of CH$_3$CN and cooled to 0° C. Iodotrimethylsilyl (TMSI) (155 μl, 1.09 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. The phosphinic acid was coupled with intermediate VII (96 mg, 0.15 mmol) in 1 mL of DMF, HATU (142 mg, 0.37 mmol), and NMM (821, 0.75 mmol) to give 53 (75.2 mg, 55%) as a yellow solid. $^{1H}$ NMR (300 MHz, CD$_3$OD): δ 8.30 (d, J=9.5 Hz, 1H), 8.20 (s, 1H), 7.79 (s, 2H), 7.30 (m, 4H), 5.95 (m, 1H), 5.80 (s, 1H), 5.25 (d, J=9.6 Hz, 2H), 5.13 (d, J=9.0 Hz, 2H), 4.75 (m, 2H), 4.45 (bs, 1H), 4.20 (s, 2H), 4.05 (s, 3H), 3.33 (s, 2H), 2.80 (m, 1H), 2.52 (m, 1H), 2.15 (m, 1H), 1.62 (m, 6H), 1.38 (d, 6H), 1.05 (s, 9H). $^{31}$P (121.4 MHz, CD$_3$OD): δ42.837

Example 54

Preparation of Compound 54

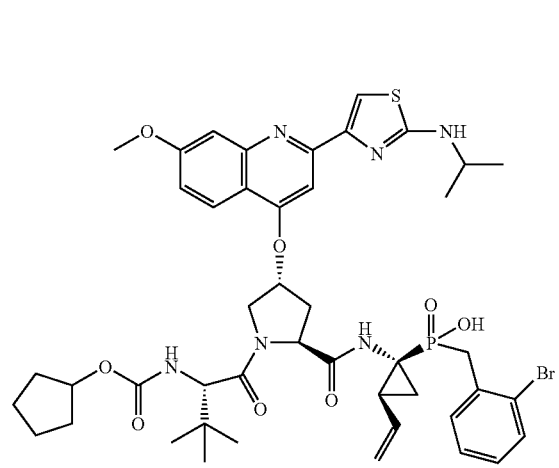

Intermediate IV (398 mg, 1.3 mmol) was dissolved in CH$_2$Cl$_2$ (25 mL) and cooled to 0° C. Diisopropylethylamine (0.5 mL, 2.7 mmol) was added and stirred for 25 minutes. Chlorotrimethylsilane (0.4 mL, 2.7 mmol) was added dropwise. The reaction mixture was warmed to r.t. and stirred for 1 h. 2-Bromobenzyl bromide (1.6 g, 6.4 mmol) was added and the reaction was heated to 45° C. for 18 h. The reaction mixture was cooled to rt, diluted with CH$_2$Cl$_2$, washed with aqueous NH$_4$Cl, dried with Na$_2$SO$_4$, and concentrated. The crude product was purified by combi-flash to give 346 mg of phosphinate in 56% yield.

To a solution of phosphinate obtained above (346 mg, 0.72 mmol) in CH$_3$CN (1 mL) at 0° C. was added iodotrimethylsilane (0.6 mL, 3.6 mmol). The reaction mixture was warmed to r.t. and stirred for 30 minutes and then cooled to 0° C. 2,6-Lutidine (0.5 mL) and MeOH (1 mL) were added and stirred for 10 minutes. The solvent was concentrated and the residue was co-evaporated with toluene (5 mL), and dried under vacuum for 20 minutes to give crude amine. Coupling with acid VII (230 mg, 0.36 mmol) provided 360 mg of compound 54. $^1$H NMR (300 MHz, DMSO): δ 8.30 (s, 1H), 8.20 (s, 1H), 7.88 (s; 1H), 7.79 (s, 1H), 7.54 (d, J=7.5 Hz, 1H), 7.45 (d, J=7.8 Hz, 1H), 7.29 (m, 1H), 7.11 (dd, J=7.8, 7.8 Hz, 1H), 7.01 (d, J=7.5 Hz, 1H), 6.00 (m, 1H), 5.78 (s, 1H), 5.15 (d, J=17.1 Hz, 1H), 5.00 (d, J=11.7 Hz, 1H), 4.60-4.40 (m, 3H), 3.43 (dd, J=15.1, 15.1 Hz, 1H), 3.25 (dd, J=15.9, 15.9 Hz, 2H), 2.58 (m, 1H), 2.32 (m, 1H), 1.94 (m, 1H), 1.70-1.40 (m, 8H), 1.29 (m, 6H), 0.92 (s, 9H). $^{31}$P (121.4 MHz, CDCl$_3$) δ 39.975. LC/MS=951.20 (M$^+$+1), 975.20 (M$^+$+Na)

Example 55

Preparation of Compound 55

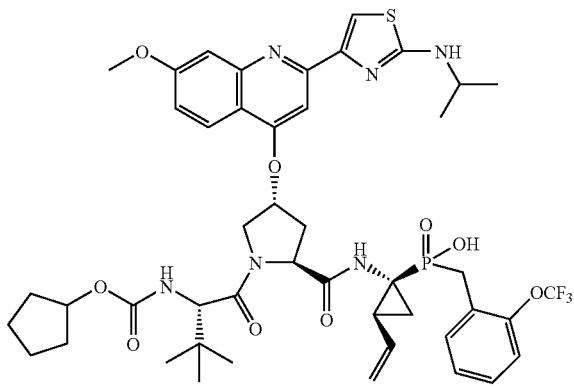

$^{1H}$ NMR (300 MHz, CD$_3$OD): δ 8.28 (d, J=9.3 Hz, 1H), 8.17 (s, 1H), 7.76 (s, 2H), 7.56 (m, 1H), 7.33 (m, 4H), 5.96 (m, 1H), 5.81 (bs, 1H), 5.3 (d, J=17.1 Hz, 1H), 5.12 (d, J=10.5 Hz, 1H), 4.69 (m, 2H), 4.45 (bs, 1H), 4.18 (m, 2H), 4.06 (m, 4H), 3.40 (m, 2H), 2.80 (m, 1H), 2.52 (m, 1H), 2.16 (m, 1H), 1.68-1.50 (m, 10H) 1.34 (d, J=6.3 Hz, 6H), 1.01 (s, 9H). $^{31}$P (121.4 MHz, CD$_3$OD): δ40.042. LC/MS=957 (M$^+$+1)

Example 56

Preparation of Compound 56

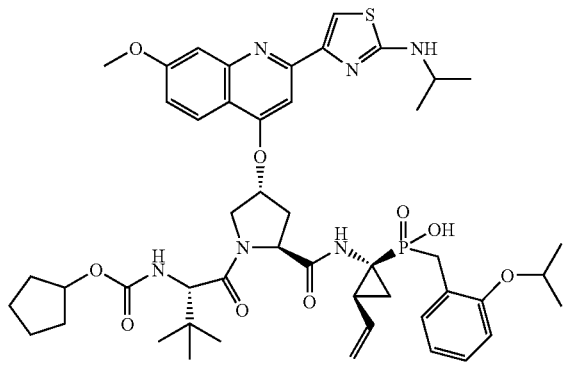

The phosphonous acid IV (1.5 g, 4.85 mmol) was suspended in 40 mL of CH$_2$Cl$_2$. The solution was cooled to 0° C. Hunig's Base (1.73 mL, 10.2 mmol) followed by Chlorotrimethylsilyl (1.28 mL, 10.2 mmol) was added dropwise. The solution was warmed to rt and after 40 minutes 1-Bromomethyl-2-isopropoxy-benzene (2.45 g, 10.7 mmol) was added and the solution was heated at 40° C. for 12 hours. Then the reaction stirred at rt for 12 hours. The residue was partitioned with CH$_2$Cl$_2$ and NH$_4$Cl and washed with NH$_4$Cl. The organic layer was dried over MgSO$_4$, filtered and concentrated. The crude material was purified using a CombiFlash Chromatography System to give (1-Benzyloxycarbonylamino-2-vinyl-cyclopropyl)-(2-isopropoxy-benzyl)-phosphinic acid ethyl ester (1.1 g, 50%). $^{1H}$ NMR (300 MHz, CDCl$_3$): δ 7.33 (m, 5H), 7.10 (m, 2H), 6.89 (m, 2H), 6.18-5.83 (m, 1H), 5.78-5.39 (m, 1H), 5.10 (m, 3H), 4.89 (m, 1H), 4.05 (m, 2H), 3.55 (m, 2H), 2.97 (m, 1H), 2.01 (m, 1H), 1.78 (m, 1H), 1.50 (m, 1H), 1.20 (m, 9H). $^{31}$P (121.4 MHz, CDCl$_3$): δ45.097, 44.785 diastereomers.

The phosphinate (700 mg, 1.07 mmol) was suspended in 1 mL of CH$_3$CN and cooled to 0° C. Iodotrimethylsilyl (TMSI) (727 μl, 5.35 mmol) was added and the solution was warmed to rt. After 45 minutes, the solution was cooled again to 0° C. and triethylamine (2 mL, 14.6 mmol) and 2 mL of MeOH. The solution was warmed to rt and stirred for an additional 20 minutes. The solution was concentrated, azeotroped 2× with toluene and put on high vacuum for 30 minutes. The solid amine was coupled to acid VII to provide compound 56. $^{1H}$ NMR (300 MHz, CD$_3$OD): δ 8.28 (d, J=9.6 Hz, 1H), 8.18 (s, 1H), 7.75 (s, 2H), 7.38 (m, 2H), 7.17 (m, 1H), 6.92 (m, 1H), 6.82 (m, 1H), 5.95 (m, 1H), 5.80 (s, 1H), 5.27 (d, J=17.1 Hz, 1H), 5.06 (d, J=9.0 Hz, 1H), 4.63 (m, 4H), 4.46 (bs, 1H), 4.17 (m, 2H), 4.07 (m, 4H), 3.34 (m, 3H), 2.73 (m, 1H), 2.51 (m, 1H), 2.13 (m, 1H), 1.62 (m, 1H), 1.50 (m, 8H) 1.38 (m, 12H), 1.05 (s, 9H). $^{31}$P (121.4 MHz, CD$_3$OD): δ36.642. LC/MS 931 (M$^+$+1)

Example 57

Preparation of Compound 57

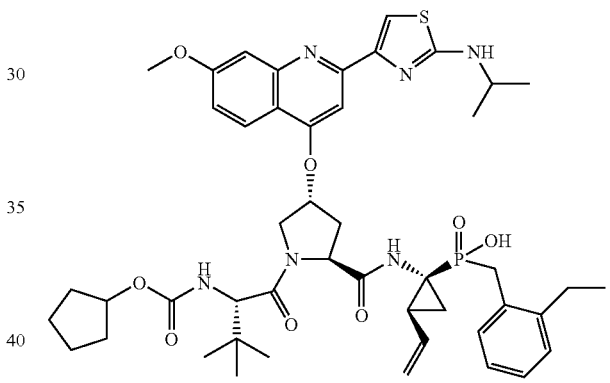

To a solution of (2-ethyl-phenyl)-methanol (3 g, 22 mmol) in ether (10 mL) at 0° C. was added a solution of PBr$_3$ (2.18 g, 8.1 mmol) in ether (3 mL). The reaction mixture was warmed to r.t for 45 minutes and cooled to 0° C. The reaction mixture was treated with 50% aqueous KOH (15 mL) and separated. The organic layer was dried with KOH pellets and concentrated to give 3.9 g of 1-bromomethyl-2-ethyl-benzene.

Intermediate IV (1.29 g, 3.88 mmol) was dissolved in CH$_2$Cl$_2$ (40 mL) and cooled to 0° C. Diisopropylethylamine (1.41 mL, 8.15 mmol) was added and stirred for 15 minutes. Chlorotrimethylsilane (1.1 mL, 8.15 mmol) was added dropwise. The reaction mixture was warmed to r.t. and stirred for 1 h. 2-ethylbenzyl bromide (3.86 g, 19.4 mmol) was added and the reaction was heated to 45° C. overnight. The reaction mixture was cooled to rt, diluted with CH$_2$Cl$_2$, washed with aqueous NH$_4$Cl, dried with Na$_2$SO$_4$, and concentrated. The crude product was purified by combi-flash to give 683 mg of phosphinate in 41% yield.

To a solution of phosphinate obtained above (650 mg, 1.52 mmol) in CH$_3$CN (3 mL) at 0° C. was added iodotrimethylsilane (1.52 g, 7.6 mmol). The reaction mixture was warmed to r.t. for 30 minutes and then cooled to 0° C. 2,6-Lutidine (0.9 mL) and MeOH (1.5 mL) were added and stirred for 10 minutes. The solvent was concentrated and the residue was co-evaporated with toluene (5 mL), and dried under vacuum for 20 minutes to give crude amine which was coupled to VII (500 mg, 0.76 mmol) to give compound 57 (480 mg, 70%). $^1$H NMR (300 MHz, DMSO): δ 8.28 (s, 1H), 8.21 (d, J=9.6 Hz, 1H), 7.88 (s, 1H), 7.79 (s, 1H), 7.32 (d, J=11.1 Hz, 1H), 7.19-7.01 (m, 4H), 6.00 (m, 1H), 5.78 (s, 1H), 5.17 (d, J=17.1 Hz, 1H), 5.02 (d, J=12.3 Hz, 1H), 4.54 (m, 2H), 4.47 (bs, 1H), 4.16 (m, 3H), 3.97 (s, 3H), 3.15 (m, 2H), 2.60 (m, 1H), 2.29 (m, 3H), 1.94 (m, 1H), 1.70-2.40 (m, 8H), 1.30 (m, 6H), 0.92 (s, 9H). $^{31}$P (121.4 MHz, CDCl$_3$): δ 40.942. LC/MS=901.24 (M$^+$+1), 924.17 (M$^+$+Na)

Example 58

Preparation of Compound 58

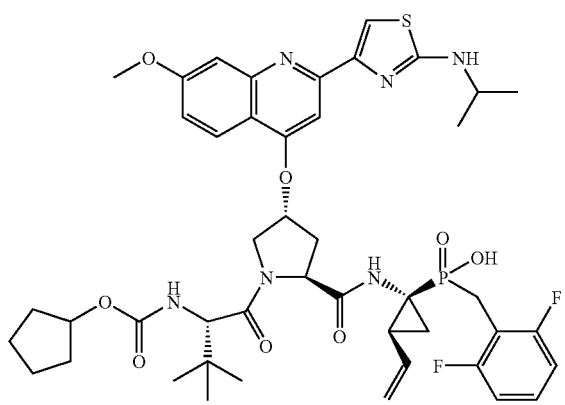

The phosphonous acid IV (327 mg, 1.06 mmol) was suspended in 5 mL of THF and cooled to −40° C. 1N NaN(TMS)$_2$ (1.27 mL, 1.39 mmol) was added dropwise over 15 minutes followed by 2-(bromomethyl)-1,3-difluorobenzene (176 μl, 1.39 mmol) in 1 mL of THF. The solution stirred from −40° C. to rt overnight. The reaction was diluted with EtOAc and quenched with 20 mL of 1N HCl. The organic layer was washed with brine, dried over MgSO$_4$, filtered and concentrated. The crude material was purified using a CombiFlash Chromatography System using a gradient of 30% EtOAc/Hex to 100% EtOAc to obtain (1-benzyloxycarbonylamino-2-vinyl-cyclopropyl)-(2,6-difluoro-benzyl)-phosphinic acid ethyl ester (147 mg, 33%) as a brown oil. The phosphinate (94.7 mg, 0.22 mmol) was suspended in 1 mL of CH$_3$CN and cooled to 0° C. Iodotrimethylsilyl (TMSI) (155 μl, 1.08 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes to provide crude amine, (1-Amino-2-vinyl-cyclopropyl)-(2,6-difluoro-benzyl)-phosphinic acid ethyl ester.

The acid VII (96 mg, 0.15 mmol) was suspended in 1 mL of DMF. HATU (143 mg, 0.37 mmol), amine obtained above (60 mg, 0.22 mmol) was added, followed by the addition of NMM (83 μl, 0.75 mmol). The solution was stirred overnight at rt. The mixture was purified via Gilson HPLC to obtain 58 (67 mg, 53%) as a yellow solid. $^1$H NMR (300 MHz, CD$_3$OD): δ 8.30 (d, J=9.5 Hz, 1H), 8.20 (s, 1H), 7.79 (s, 2H), 7.35 (d, J=9.3 Hz, 1H), 7.33 (m, 1H), 6.94 (m, 2H), 5.95 (m, 1H), 5.80 (s, 1H), 5.25 (d, J=9.6 Hz, 2H), 5.17 (d, J=9.0 Hz, 2H), 4.75 (m, 2H), 4.45 (bs, 1H), 4.20 (s, 2H), 4.05 (s, 3H), 3.40 (m, 2H), 2.80 (m, 1H), 2.52 (m, 1H), 2.15 (m, 1H), 1.62 (m, 6H), 1.38 (d, 6H), 1.05 (s, 9H). $^{31}$P (121.4 MHz, CD$_3$OD): δ40.898

Example 59

Preparation of Compound 59

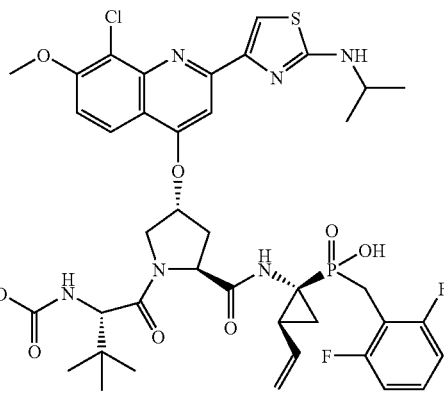

Boc-hydroxyproline methyl ester (5 g, 20.4 mmol) was taken up in DCM (50 mL) and TFA (50 mL). The reaction was stirred at room temp for 1.5 h then concentrated and azeotroped with toluene (2×50 mL). The residue was taken up in DCM (200 mL) and the cyclopentyl carbamate of tert-leucine (5.5 g, 22.4 mmol) was added, followed by HATU (11.6 g, 30.6 mmol) and NMM (9 mL, 81.6 mmol). The reaction was stirred at room temp overnight, then quenched with sat'd NH$_4$Cl solution, washed with water then brine, dried, and concentrated. The residue was then purified by flash chromatography to provide the desired dipeptide (7.56 g).

The methyl ester was taken up in THF (70 mL), water (70 mL), methanol (70 mL) and LiOH—H$_2$O (8.6 g, 204 mmol) was added. The reaction was stirred at room temp for 1 h, then diluted with water and acidified with HCl. The reaction was extracted with ethyl acetate, washed with brine, dried and concentrated to provide the desired acid (5.98 g crude, 82% two steps).

The carboxylic acid (2.62 g, 7.36 mmol) was taken up in THF (75 mL) at 0° C. and TEA (3.1 mL, 22.08 mmol) and ethyl chloroformate (0.70 mL, 7.36 mmol) were added. The reaction was allowed to warm to room temp and stirred 30 minutes. The solids were filtered off and the reaction was concentrated. The residue was taken up in ethyl acetate, washed with 1N HCl, concentrated and purified via flash chromatography to provide the desired lactone (1.81 g, 73%).

This lactone (0.44 g, 1.3 mmol) was taken up in toluene (8 mL) and water (8 mL) in the presence of the amine prepared in example 83 (0.25 g, 0.83 mmol). Sodium ethylhexanoate (0.32 g, 1.95 mmol) was added and the reaction stirred at 80° C. overnight. The reaction was extracted with ethyl acetate, washed with sodium bicarbonate solution, 1N HCl, and brine, dried, concentrated, and purified by flash column to provide the tripeptide (0.25 g, 50%).

The prolinol (0.93 g, 1.45 mmol) was combined with brosyl chloride (0.52 g, 2.03 mmol) and DABCO (0.26 g, 2.32 mmol) in toluene (3 mL) and stirred at room temp for 3 h. The reaction was extracted with ethyl acetate, washed with sodium bicarbonate solution, 1N HCl, brine, concentrated and purified by flash chromatography to provide the brosylate (0.995 g, 80%).

The brosylate (0.995 g, 1.16 mmol) was taken up in NMP (12 mL) and 8-chloro-4-hydroxy-7-methoxy-quinoline-2-carboxylic acid (0.38 g, 1.16 mmol) and cesium carbonate (0.38 g, 1.16 mmol) were added. The reaction was stirred at 60° C. for 4 hours then room temp overnight. The reaction was extracted with ethyl acetate, washed with bicarbonate solution, concentrated and purified by flash chromatography to provide the product (0.86 g, 84%).

This methyl ester (0.86 g, 0.97 mmol) was taken up in THF (10 mL) and water (10 mL) and NaOH (2 mL of 1M solution) were added at 0° C. The reaction was stirred for 1.5 h, diluted with water, acidified with HCl and extracted with ethyl acetate. The organics were dried and concentrated to provide the carboxylic acid. This residue was taken up in THF and TEA (0.15 mL, 1.07 mmol) was added and the mixture cooled to zero. Isobutylchloroformate (0.14 mL, 1.07 mmol) was added and the reaction stirred at room temp for 40 minutes. Diazomethane (2.0 equivalents) was added in ether solution (prepared from MNNG) and the reaction stirred at zero for 30 minutes then for 2 h at room temp. The reaction was then concentrated to provide the diazoketone (0.58 g, 67% two steps).

The diazoketone (0.58 g, 0.646 mmol) was taken up in THF at 0° C. and conc HBr (0.4 mL) was added. The reaction was stirred and monitored by LCMS. Upon full conversion ethyl acetate was added and the mixture was washed with NaHCO$_3$ solution, dried and concentrated. The residue was taken up in IPA (10 mL) and isopropylthiourea (0.15 g, 1.29 mmol) was added. The reaction was heated to 75° C. for 1 h, then concentrated. The resultant residue was taken up in acetonitrile and TMSI (0.5 mL, 3.23 mmol) was added. The reaction was stirred at room temp for 15 minutes, diluted with 0.4 mL of 2,6-lutidine, then quenched with methanol, concentrated and purified by HPLC to provide Compound 59 (443 mg, 73%). $^1$H NMR (300 MHz, CD$_3$OD) δ 8.29 (m, 2H), 7.79 (m, 1H), 7.59 (m, 1H), 7.24 (m, 1H), 6.86 (m, 2H), 5.97 (m, 1H), 5.75 (br s, 1H), 5.32 (m, 1H), 5.09 (m, 1H), 4.77 (m, 1H), 4.60 (m, 1H), 4.40 (br s, 1H), 4.14 (s, 3H), 3.95 (m, 1H), 3.41 (m, 3H), 2.73 (m, 2H), 2.18 (m, 1H), 1.61 (m, 8H), 1.47 (m, 8H), 1.03 (s, 9H). $^{31}$P NMR (121.4 MHz, CD$_3$OD) δ40.279. LCMS: 943 (M+1).

Example 60

Preparation of Compound 60

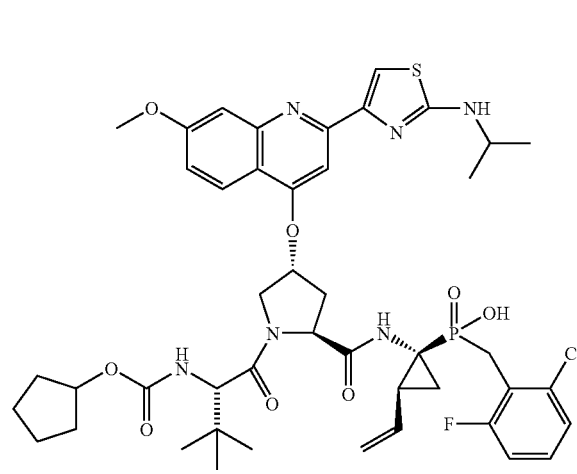

The phosphonous acid IV (1.0 g, 3.24 mmol) was suspended in 30 mL of CH$_2$Cl$_2$. The solution was cooled to 0° C. Hunig's Base (1036 μl, 6.79 mmol) followed by Chlorotrimethylsilyl (863 μl, 6.79 mmol) was added dropwise. The solution was warmed to rt and after 40 minutes 2-Bromomethyl-1-chloro-3-fluoro-benzene (1.58 g, 7.13 mmol) was added and the solution was heated at 40° C. for 12 hours. Then the reaction stirred at rt for 12 hours. The residue was partitioned with CH$_2$Cl$_2$ and NH$_4$Cl and washed with NH$_4$Cl. The organic layer was dried over MgSO$_4$, filtered and concentrated. The crude material was purified using a CombiFlash Chromatography System to give (1-Benzyloxycarbonylamino-2-vinyl-cyclopropyl)-(2-chloro-6-fluoro-benzyl)-phosphinic acid ethyl ester (750 mg, 51%). $^{1H}$ NMR (300 MHz, CDCl$_3$): δ 7.33 (m, 5H), 7.17 (m, 2H), 6.95 (m, 1H), 6.18-5.83 (m, 1H), 5.78-5.39 (m, 1H), 5.10 (m, 3H), 4.89 (m, 1H), 4.05 (m, 2H), 3.55 (m, 2H), 2.21 (m, 1H), 1.78 (m, 1H), 1.50 (m, 1H), 1.10 (m, 3H). $^{31}$P (121.4 MHz, CDCl$_3$): δ45.897, 42.185 diastereomers.

The phosphinate obtained above (730 mg, 1.62 mmol) was suspended in 1 mL of CH$_3$CN and cooled to 0° C. Iodotrimethylsilyl (TMSI) (1112 μl, 8.18 mmol) was added and the solution was warmed to rt. After 45 minutes, the solution was cooled again to 0° C. and triethylamine (2 mL, 14.6 mmol) and 2 mL of MeOH. The solution was warmed to rt and stirred for an additional 20 minutes. The solution was concentrated, azeotroped 2× with toluene and put on high vacuum for 30 minutes. The crude amine was used directly. Coupling with VII gave compound 60. $^{1H}$ NMR (300 MHz, CD$_3$OD): δ 8.23 (d, J=9.5 Hz, 1H), 8.20 (s, 1H), 7.79 (s, 2H), 7.33 (m, 1H), 7.21 (m, 2H), 7.03 (m, 1H), 5.95 (m, 1H), 5.78 (s, 1H), 5.22 (d, J=9.6 Hz, 1H), 5.13 (d, J=9.0 Hz, 1H), 4.63 (m, 2H), 4.45 (bs, 1H), 4.20 (m, 3H), 4.05 (s, 3H), 3.22 (m, 1H), 3.20 (d, 1H), 3.18 (s, 1H), 2.80 (m, 1H), 2.78 (s, 3H), 2.45 (m, 1H), 2.15 (m, 1H), 1.62 (m, 1H), 1.50 (m, 8H) 1.38 (d, 6H), 1.05 (s, 9H). $^{31}$P (121.4 MHz, CD$_3$OD): δ36.642

LC/MS=925 (M$^+$+1)

Example 61

Preparation of Compound 61

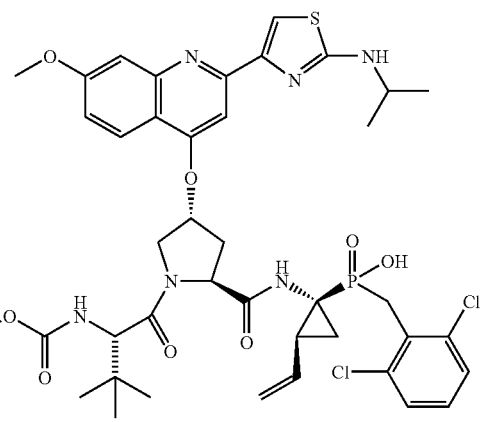

$^{1H}$ NMR (300 MHz, CD$_3$OD): δ 8.28 (d, J=9.3 Hz, 1H), 8.18 (s, 1H), 7.76 (s, 2H), 7.37 (m, 3H), 7.20 (m, 1H), 5.99 (m, 1H), 5.81 (bs, 1H), 5.29 (d, J=17.1 Hz, 1H), 5.11 (d, J=10.5

Hz, 1H), 4.72 (m, 2H), 4.45 (bs, 1H), 4.18 (m, 2H), 4.05 (m, 4H), 3.79 (m, 2H), 2.81 (m, 1H), 2.59 (m, 1H), 2.21 (m, 1H), 1.68-1.50 (m, 10H) 1.38 (d, J=6.3, 6H), 1.04 (s, 9H). $^{31}$P (121.4 MHz, CD$_3$OD): δ41.451 LC/MS 941 (M$^+$+1)

Example 62

Preparation of Compound 62

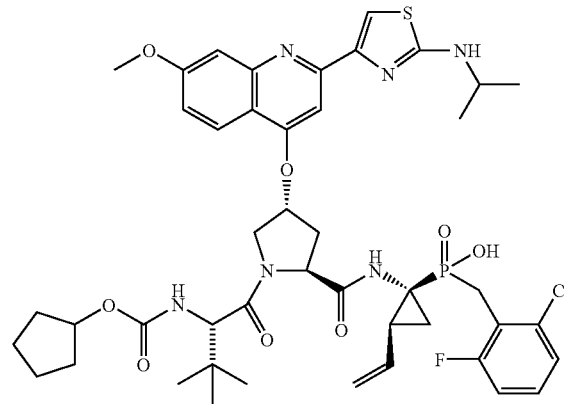

Intermediate IV (2.06 g, 6.7 mmol) was dissolved in CH$_2$Cl$_2$ (60 mL) and cooled to 0° C. Diisopropylethylamine (2.48 mL, 14.3 mmol) was added and stirred for 15 minutes. Chlorotrimethylsilane (1.92 mL, 14.3 mmol) was added dropwise. The reaction mixture was warmed to r.t. and stirred for 1.5 h. 2-Fluoro-6-trifluoromethylbenzyl chloride (8.61 g, 33.5 mmol) was added and the reaction was heated to 45° C. overnight. The reaction mixture was cooled to rt, diluted with CH$_2$Cl$_2$, washed with aqueous NH$_4$Cl, dried with Na$_2$SO$_4$, and concentrated. The crude product was purified by combi-flash to give 1.14 g of phosphinate in 35% yield To a solution of phosphinate obtained above (550 mg, 1.13 mmol) in CH$_3$CN (2 mL) at 0° C. was added iodotrimethylsilane (1.13 g, 5.66 mmol). The reaction mixture was warmed to r.t. and stirred for 30 minutes and then cooled to 0° C. 2,6-Lutidine (0.7 mL) and MeOH (1 mL) were added and stirred for 10 min. The solvent was concentrated and the residue was co-evaporated with toluene (5 mL), and dried under vacuum for 20 minutes to give crude amine, which was coupled to acid VII to give example 62 (339 mg). $^1$H NMR (300 MHz, CD$_3$OD): δ8.28 (d, J=9.3 Hz, 1H), 8.18 (s, 1H), 7.76 (m, 2H), 7.54-7.3° (m, 4H), 5.99 (m, 1H), 5.82 (s, 1H), 5.29 (d, J=17.1 Hz, 1H), 5.13 (m, 1H), 4.71 (m, 2H), 4.43 (s, 1H), 4.22-4.05 (m, 2H), 3.78-3.49 (m, 2H), 3.3 (m, 2H), 2.82 (m, 1H), 2.57 (m, 1H), 2.20 (m, 1H), 1.68-1.48 (m, 8H), 1.34 (m, 6H), 1.01 (s, 9H). $^{31}$P (121.4 MHz, CDCl$_3$): δ40.019 LC/MS=959.37 (M$^+$+1), 981.25 (M$^+$+Na)

Example 63

Preparation of Compound 63

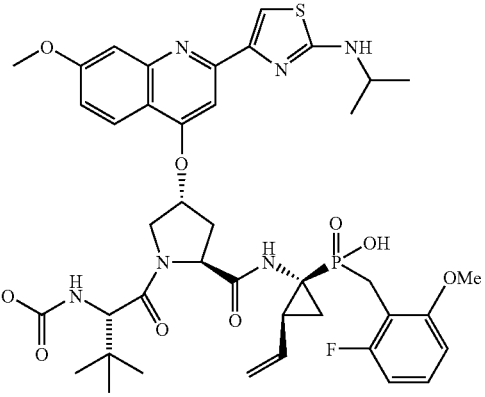

$^{1H}$ NMR (300 MHz, CD$_3$OD): δ 8.28 (d, J=9.6 Hz, 1H), 8.18 (s, 1H), 7.76 (s, 2H), 7.33 (m, 1H), 7.18 (m, 1H), 6.77 (m, 1H), 6.68 (m, 1H), 5.94 (m, 1H), 5.81 (bs, 1H), 5.27 (d, J=16.8 Hz, 1H), 5.08 (d, J=9.0 Hz, 1H), 4.68 (m, 2H), 4.46 (bs, 1H), 4.17 (m, 2H), 4.05 (m, 4H), 3.81 (m, 3H), 3.37 (m, 2H), 2.79 (m, 1H), 2.57 (m, 1H), 2.16 (m, 1H), 1.61-1.50 (m, 10H) 1.38 (d, J=6.3 Hz, 6H), 1.04 (s, 9H). $^{31}$P (121.4 MHz, CD$_3$OD): δ42.834

LC/MS=921 (M$^+$+1)

Example 64

Preparation of Compound 64

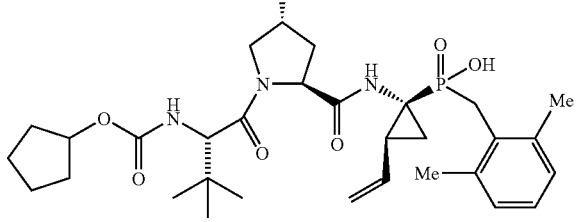

Intermediate IV (948.8 mg, 3.07 mmol) was dissolved in THF (9.5 mL) and cooled to −40° C. 1 M THF solution of NaN(TMS)$_2$ (4 mL, 4 mmol) was added dropwise and the reaction mixture was stirred at −40° C. for 40 minutes. 2,6-Dimethylbenzyl chloride (623.2 mg, 4.03 mmol) in THF (2 mL) was added and the cold bath was removed. The reaction mixture was stirred at rt for 20 h. The reaction mixture was quenched with 1N HCl (50 mL) and extracted with EtOAc (2×50 mL). The organic layers were washed with brine, dried with Na$_2$SO$_4$, filtered, and concentrated. The crude product was purified by combi-flash to give 679.9 mg of phosphinate in 52% yield.

A solution of phosphinate (400.1 mg, 0.94 mmol) in CH$_3$CN (4 mL) was stirred at 0° C. as iodotrimethylsilane (0.67 mL, 4.71 mmol) was added. The reaction mixture was warmed to r.t. and stirred for 1.5 h. The reaction mixture was cooled to 0° C. and TEA (10.76 mL) and MeOH (4 mL) were added. The solution was stirred at r.t. for 0.5 h and concentrated. The residue was triturated with toluene (8 mL) and concentrated. The crude product was dried and used for next step reaction.

The acid VII (408.5 mg, 0.63 mmol) and amine obtained above were dissolved in DMF (5 mL) and cooled to 0° C. HATU (891.2 mg, 2.34 mmol) and NMM (0.52 mL, 4.73 mmol) were added and the mixture was warmed to r.t. and stirred for 3 h. The crude product was purified by HPLC to give 266 mg of 64. $^{1H}$ NMR (300 MHz, CD$_3$OD): δ 8.26 (d, 1H, J=9.0 Hz), 8.20 (s, 1H), 7.74 (br, 2H), 7.30 (dd, 1H, J=9.0 and 2.0 Hz), 6.95 (s, 3H), 6.01 (dt, 1H, J=17.1 and 9.8 Hz), 5.80 (br, 1H), 5.29 (dd, 1H, J=17.1 and 1.9 Hz), 5.13 (dd, 1H, J=9.8 and 1.9 Hz), 4.62-4.77 (m, 2H), 4.46 (br, 1H), 4.05-4.22 (m, 3H), 4.04 (s, 3H), 3.47 (t, 1H, J=15.3 Hz), 3.35 (t, 1H, J=15.3 Hz), 2.81 (dd, 1H, J=13.5 and 7.2 Hz), 2.45-2.57 (m, 1H), 2.39 (s, 6H), 2.12-2.26 (br m, 1H), 1.39-1.70 (m, 10H), 1.34 (d, 6H, J=6.6 Hz), 1.03 (s, 9H). $^{31}$P (121.4 MHz, CD$_3$OD): δ 42.678.

LC/MS=901 (M$^+$+1)

Example 65

Preparation of Compound 65

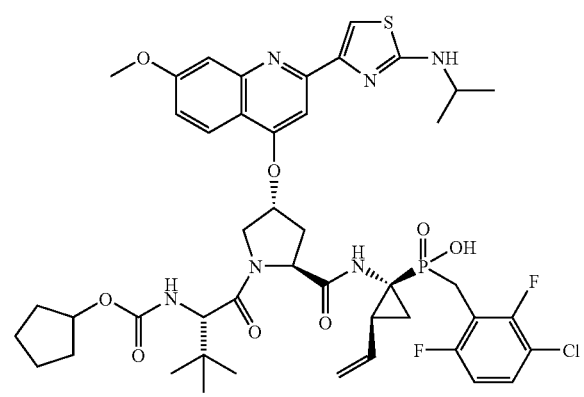

Compound IV (3.9 g, 12.6 mmol) was dissolved in CH$_2$Cl$_2$ (60 mL) and cooled to 0° C. and diisopropylethylamine (4.5 mL, 26.4 mmol) was added. Chlorotrimethylsilane (3.3 mL, 26.4 mmol) was added dropwise. The reaction mixture was warmed to r.t. and stirred for 1 h. 2,6-difluoro-3-chlorobenzyl bromide (4.5 g, 18.8 mmol) was added and the reaction was heated to 42° C. overnight. The reaction mixture was cooled to rt, diluted with CH$_2$Cl$_2$, washed with aqueous NH$_4$Cl, dried with Na$_2$SO$_4$, and concentrated. The crude product was purified by combi-flash to give 3.7 g of phosphinate in 61% yield. The phosphinate was treated with TMSI and coupled with VII to give compound 65. $^{1H}$ NMR (300 MHz, CD$_3$OD): δ 8.23 (d, J=9.5 Hz, 1H), 8.20 (s, 1H), 7.79 (s, 2H), 7.36 (m, 2H), 6.97 (m, 1H), 5.95 (m, 1H), 5.78 (bs, 1H), 5.32 (d, J=9.6 Hz, 1H), 5.18 (d, J=9.0 Hz, 1H), 4.63 (m, 2H), 4.45 (bs, 1H), 4.20 (m, 3H), 4.05 (s, 3H), 3.34 (m, 2H), 2.80 (m, 1H), 2.45 (m, 1H), 2.15 (m, 1H), 1.68-1.50 (m, 8H) 1.38 (d, 6H), 1.05 (s, 9H). $^{31}$P (121.4 MHz, CD$_3$OD): δ40.079 LC/MS=943 (M$^+$+1)

Example 66

Preparation of Compound 66

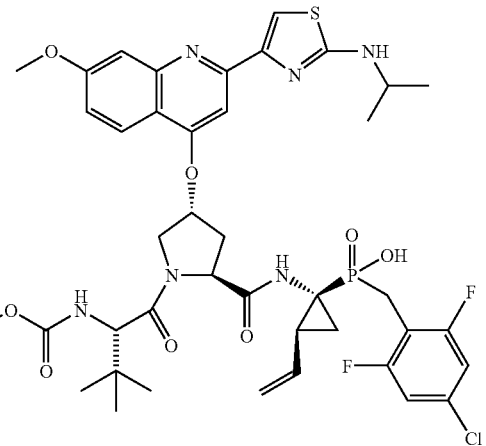

$^{1H}$ NMR (300 MHz, CD$_3$OD): δ 8.23 (d, J=9.5 Hz, 1H), 8.20 (s, 1H), 7.79 (s, 2H), 7.36 (m, 1H), 7.06 (m, 2H), 5.95 (m, 1H), 5.78 (bs, 1H), 5.32 (d, J=9.6 Hz, 1H), 5.18 (d, J=9.0 Hz, 1H), 4.63 (m, 2H), 4.45 (bs, 1H), 4.20 (m, 3H), 4.05 (s, 3H), 3.34 (m, 2H), 2.80 (m, 1H), 2.45 (m, 1H), 2.15 (m, 1H), 1.68-1.50 (m, 8H) 1.38 (d, 6H), 1.05 (s, 9H). $^{31}$P (121.4 MHz, CD$_3$OD): δ40.879

LC/MS=943 (M$^+$+1)

Example 67

Preparation of Compound 67

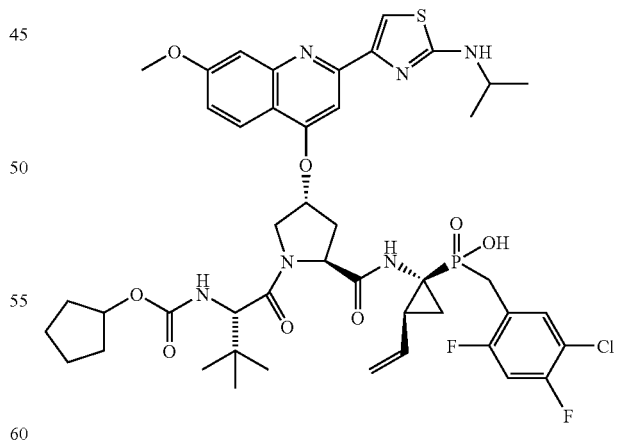

$^1$H NMR (300 MHz, CD$_3$OD): δ 8.28 (d, J=9.3 Hz, 1H), 8.17 (s, 1H), 7.75 (m, 2H), 7.68 (m, 1H), 7.32 (d, J=9.3 Hz, 1H), 7.08 (dd, J=9.6, 9.6 Hz, 1H), 5.94-5.82 (m, 2H), 5.79 (s, 1H), 5.26 (d, J=17.1 Hz, 1H), 5.05 (d, J=10.2 Hz, 1H), 4.65 (m, 2H), 4.15 (m, 3H), 4.05 (s, 3H), 3.$^{31}$ (m, 2H), 2.80 (m, 1H), 2.51 (m, 1H), 2.11 (m, 1H), 1.63-1.49 (m, 8H), 1.34 (m,

6H), 1.00 (s, 9H). $^{31}$P (121.4 MHz, CDCl$_3$): δ40.908 LC/MS=943.27 (M$^+$+1), 965.03 (M$^+$+Na)

Example 68

Preparation of Compound 68

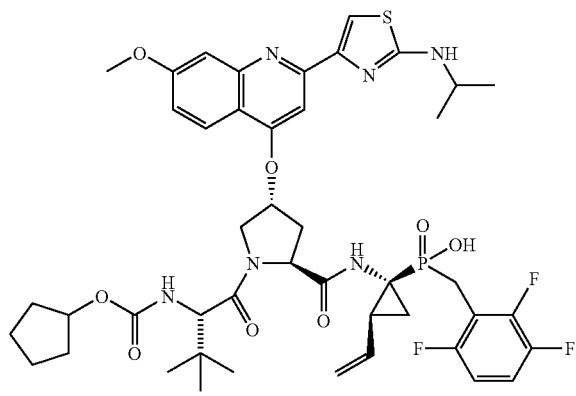

$^1$H NMR (300 MHz, CD$_3$OD) δ 8.28 (d, J=9.3 Hz, 1H), 8.16 (s, 1H), 7.77 (s, 1H), 7.72 (d, J=2.1 Hz, 1H), 7.33 (d, J=12 Hz, 1H), 7.14 (m, 1H), 6.91 (m, 1H), 5.98 (dt, J=10.2, 17.1 Hz, 1H), 5.79 (s, 1H), 5.$^{31}$ (d, J=16.8 Hz, 1H), 5.13 (d, J=11.7 Hz, 1H), 4.71 (t, J=9 Hz), 4.63 (d, J=11.1 Hz, 1H), 4.5 (s, 1H), 4.1-4.2 (brm, 3H), 4.05 (s, 3H), 3.44 (dd, J=5.1, 15.6 Hz, 2H), 2.77 (m, 1H), 2.59 (m, 1H), 2.19 (m, 1H), 1.44-1.7 (m, 10H), 1.34 (d, J=6.3 Hz, 6H), 1.04 (s, 9H). $^{31}$P NMR (121.4 MHz, CD$_3$OD) δ 37.8 LC/MS=927.3 (M$^+$+1)

Example 69

Preparation of Compound 69

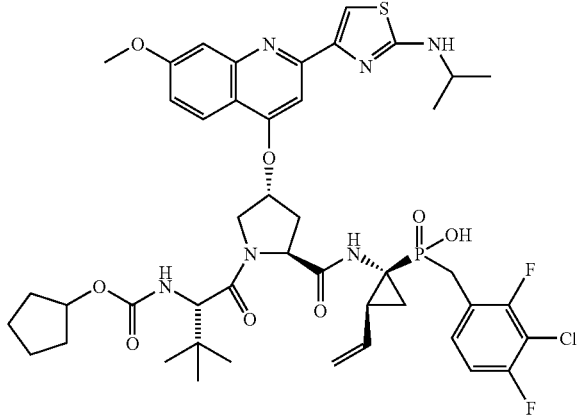

Intermediate IV (15.5 g, 50.3 mmol) was dissolved in CH$_2$Cl$_2$ (300 mL) and cooled to 0° C. and diisopropylethylamine (22 mL, 126 mmol) was added. Chlorotrimethylsilane (17 mL, 126 mmol) was added dropwise. The reaction mixture was warmed to r.t. and stirred for 1 h. 2,3,6-Trifluorobenzyl bromide (37 g, 165 mmol) was added and the reaction was stirred at r.r. overnight. Aqueous NH$_4$Cl (200 mL) was added and stirred for 30 minutes. The two layers were separated and aqueous layer was extracted with CH$_2$Cl$_2$. The combined organic layer was dried with Na$_2$SO$_4$ and concentrated. The crude product was purified by combi-flash to give 7.3 g of phosphinate.

To a solution of phosphinate (7.2 g, 15.8 mmol) in TFA (45 mL) at r.t. was added DMS (10 mL) and stirred overnight. The mixture was concentrated and co-evaporated with toluene. The residue was dissolved in 1/1 iPrOH/heptane and washed with 6 N HCl (3×). The combined aqueous layers were brought to pH=10 with NaOH in a cold bath. The aqueous layer was extracted with EtOAc (3×100 mL). The organic layers were washed with brine, dried with Na$_2$SO$_4$, and concentrated to give 3.8 g of amine which was coupled and deprotected to give compound 69 in 75% yield.

$^1$H NMR (300 MHz, CD$_3$OD): δ8.27 (d, J=9.3 Hz, 1H), 8.18 (s, 1H), 7.76 (d, J=3.0 Hz, 2H), 7.43 (m, 1H), 7.28 (d, J=2.4 Hz, 1H), 7.03 (dd, J=8.7, 8.7 Hz, 1H), 5.91 (m, 1H), 5.81 (s, 1H), 5.27 (d, J=17.1 Hz, 1H), 5.08 (d, J=11.4 Hz, 1H), 4.68 (m, 2H), 4.46 (s, 1H), 4.16 (m, 3H), 3.36 (m, 2H), 2.80 (m, 1H), 2.55 (m, 1H), 2.13 (m, 1H), 1.62-1.46 (m, 8H), 1.34 (d, J=6.3 Hz, 6H), 1.02 (s, 9H). $^{31}$P (121.4 MHz, CDCl$_3$): δ 41.986. LC/MS=943.27 (M$^+$+1), 965.03 (M$^+$+Na)

Example 70

Preparation of Compound 70

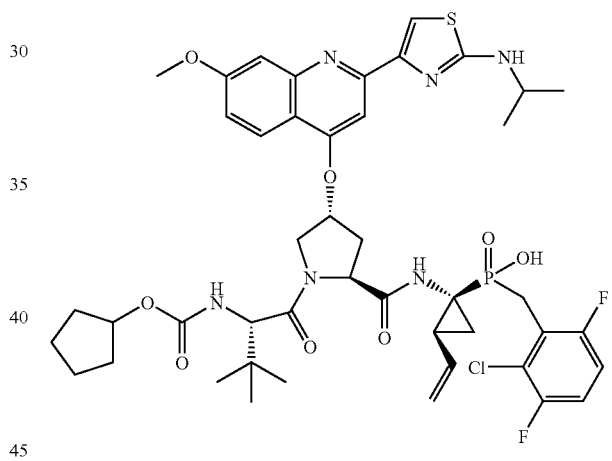

Intermediate IV (380 mg, 0.78 mmol) was dissolved in CH$_2$Cl$_2$ (15 mL) and cooled to 0° C. Diisopropylethylamine (0.4 mL, 2.3 mmol) was added and stirred for 25 minutes. Chlorotrimethylsilane (0.32 mL, 2.3 mmol) was added dropwise. The reaction mixture was warmed to r.t. and stirred for 1 h. 1-Bromomethyl-5-chloro-2,4-difluoro-benzene (940 mg, 3.9 mmol) was added and the reaction was heated to 45° C. for 18 h. The reaction mixture was cooled to rt, diluted with CH$_2$Cl$_2$, washed with aqueous NH$_4$Cl, dried with Na$_2$SO$_4$, and concentrated. The crude product was purified by combi-flash to give 190 mg of phosphinate in 52% yield.

To a solution of phosphinate obtained above (190 mg, 0.41 mmol) in CH$_3$CN (1 mL) at 0° C. was added iodotrimethylsilane (0.3 mL, 2 mmol). The reaction mixture was warmed to r.t. and stirred for 30 minutes and then cooled to 0° C. 2,6-Lutidine (0.23 mL) and MeOH (1 mL) were added and stirred for 10 minutes. The solvent was concentrated and the residue was co-evaporated with toluene (5 mL), and dried under vacuum for 20 minutes to give crude amine. Coupling with acid VII (130 mg, 0.2 mmol) provided compound 70. $^1$H NMR (300 MHz, CD$_3$OD): δ 8.23 (d, J=9.5 Hz, 1H), 8.20 (s, 1H), 7.79 (s, 2H), 7.36 (m, 1H), 7.14 (m, 2H), 5.95 (m, 1H), 5.78 (bs, 1H), 5.32 (d, J=9.6 Hz, 1H), 5.18 (d, J=9.0 Hz, 1H), 4.63 (m, 2H), 4.45 (bs, 1H), 4.20 (m, 3H), 4.05 (s, 3H), 3.34 (m, 2H), 2.80 (m, 1H), 2.45 (m, 1H), 2.15 (m, 1H), 1.68-1.50 (m, 8H) 1.38 (d, 6H), 1.05 (s, 9H). $^{31}$P (121.4 MHz, CD$_3$OD): δ40.578. LC/MS=943 (M$^+$+1)

Example 71

Preparation of Compound 71

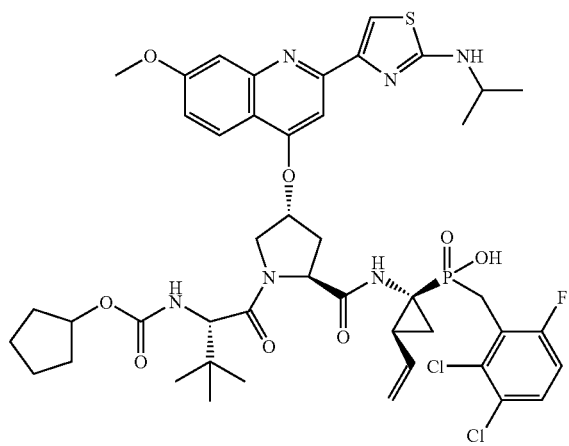

$^{1H}$ NMR (300 MHz, CD$_3$OD): δ 8.28 (d, J=9.6 Hz, 1H), 8.18 (s, 1H), 7.76 (s, 2H), 7.44 (m, 1H), 7.34 (m, 1H), 7.08 (t, d=9.0 Hz, 1H), 5.95 (m, 1H), 5.80 (bs, 1H), 5.29 (d, J=17.4 Hz, 1H), 5.13 (d, J=9.0 Hz, 1H), 4.69 (m, 2H), 4.47 (bs, 1H), 4.18 (m, 2H), 4.06 (m, 4H), 3.58 (m, 2H), 2.79 (m, 1H), 2.57 (m, 1H), 2.19 (m, 1H), 1.68-1.50 (m, 10H) 1.38 (d, J=6.3 Hz, 6H), 1.04 (s, 9H). $^{31}$P (121.4 MHz, CD$_3$OD): δ40.778. LC/MS=959 (M$^+$+1)

Example 72

Preparation of Compound 72

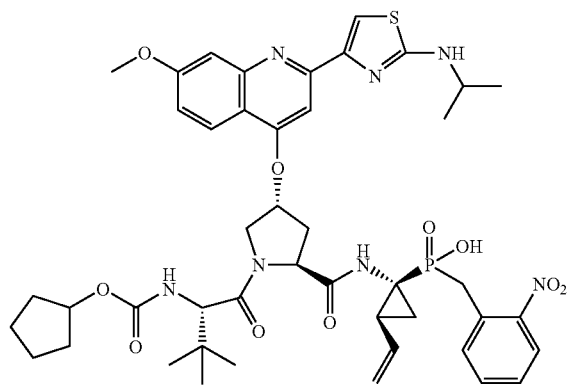

The phosphonous acid IV (1.62 g, 5.27 mmol) was suspended in 5 mL of THF and cooled to −40° C. 1N NaN(TMS)$_2$ (6.32 mL, 6.31 mmol) was added dropwise over 15 minutes followed by 1-(bromomethyl)-2-nitrobenzene (1.36 g, 6.32 mmol) in 1 mL of THF. The solution stirred from −40° C. to rt overnight. The reaction was diluted with EtOAc and quenched with 20 mL of 1N HCl. The organic layer was washed with brine, dried over MgSO$_4$, filtered and concentrated. The crude material was purified using a CombiFlash Chromatography System using a gradient of 30% EtOAc/Hex to 100% EtOAc to obtain (1-Benzyloxycarbonylamino-2-vinyl-cyclopropyl)-(2-nitro-benzyl)-phosphinic acid ethyl ester (196 mg, 8%) as a brown oil.

The phosphinate (196 mg, 0.44 mmol) was suspended in 1 mL of CH$_3$CN and cooled to 0° C. Iodotrimethylsilyl (TMSI) (155 µl, 1.08 mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes to provide (1-Amino-2-vinyl-cyclopropyl)-(2-nitro-benzyl)-phosphinic acid. The acid (124 mg, 0.44 mmol) was coupled with intermediate IV (191 mg, 0.29 mmol), HATU (276 mg, 0.73 mmol), and NMM (160 µl, 1.45 mmol) to give compound 72 (140 mg, 53%) as a yellow solid. $^{1H}$ NMR (300 MHz, CD$_3$OD): δ 8.30 (d, J=9.5 Hz, 1H), 8.20 (s, 1H), 7.79 (s, 2H), 7.35 (d, J=9.3 Hz, 1H), 7.33 (m, 1H), 6.94 (m, 2H), 5.95 (m, 1H), 5.80 (s, 1H), 5.25 (d, J=9.6 Hz, 2H), 5.17 (d, J=9.0 Hz, 2H), 4.75 (m, 2H), 4.45 (bs, 1H), 4.20 (s, 2H), 4.05 (s, 3H), 3.40 (m, 2H), 2.80 (m, 1H), 2.52 (m, 1H), 2.15 (m, 1H), 1.62 (m, 6H), 1.38 (d, 6H), 1.05 (s, 9H). $^{31}$P (121.4 MHz, CD$_3$OD): δ40.898

Example 73

Preparation of Compound 73

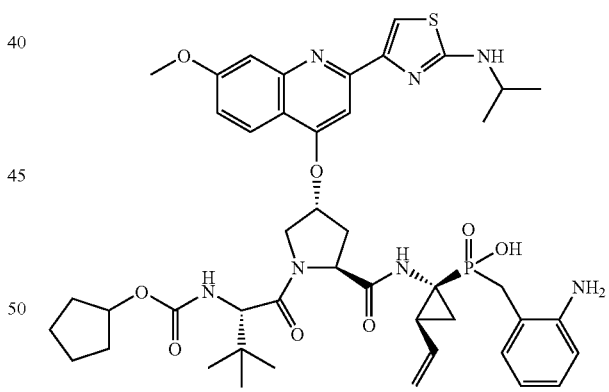

Compound 72 (80 mg, 0.08 mmol) was suspended in EtOH and SnCl$_2$·2H$_2$O (98 mg, 0.44 mmol) was added. The solution was heated to reflux. After 3 hours, the starting material was consumed. The solution was filtered and concentrated. The mixture was purified via Gilson HPLC to obtain 73 (20 mg, 53%) as a yellow solid. $^{1H}$ NMR (300 MHz, CD$_3$OD): δ 8.30 (d, J=9.5 Hz, 1H), 8.20 (s, 1H), 7.79 (s, 2H), 7.35 (d, J=9.3 Hz, 1H), 7.33 (m, 1H), 6.94 (m, 2H), 5.95 (m, 1H), 5.80 (s, 1H), 5.25 (d, J=9.6 Hz, 2H), 5.17 (d, J=9.0 Hz, 2H), 4.75 (m, 2H), 4.45 (bs, 1H), 4.20 (s, 2H), 4.05 (s, 3H), 3.40 (m, 2H), 2.80 (m, 1H), 2.52 (m, 1H), 2.15 (m, 1H), 1.62 (m, 6H), 1.38 (d, 6H), 1.05 (s, 9H). $^{31}$P (121.4 MHz, CD$_3$OD): δ40.898

Example 74

Preparation of Compound 74

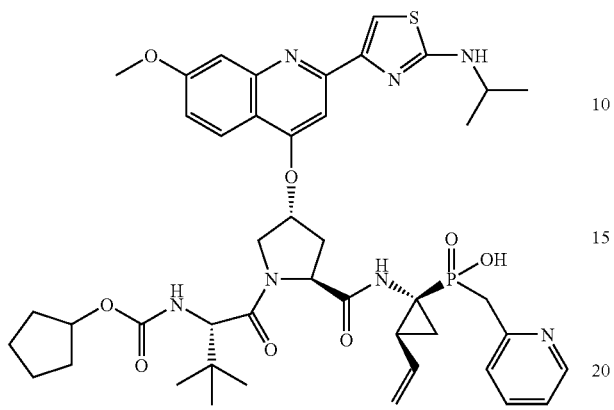

A solution of compound IV (96 mg, 0.31 mmol) in CH$_2$Cl$_2$ (2.82 mL) was added DIEA (0.114 mL, 0.652 mmol) and TMSCl (0.083 mL, 0.652 mmol) at 0° C. The reaction was allowed to warm up to rt and stirred for 1 hour. To the mixture was added a solution of 2-(bromomethyl)pyridine (173 mg, 0.683 mmol) in DIEA (0.054 mL, 0.31 mmol). This reaction was stirred at rt for 2 days when complete consumption of the starting materials was observed by LCMS. The reaction was worked up addition of CH$_2$Cl$_2$ and saturated aqueous NH$_4$Cl. The organic layer was dried in vacuo and purified using silica gel chromatography to give 91 mg of the product as a clear oil. EI MS (m/z) 401.0 [M+H].

A solution of benzyl (1S,2S)-1-((S)-ethoxy(pyridin-2-ylmethyl)phosphoryl)-2-vinylcyclopropylcarbamate (96 mg, 0.239 mmol) in 2.39 mL of aqueous 6N HCl was heated at 70° C. for 7 hours and stirred at rt for 12 hours. The reaction mixture was worked up by removal of all volatiles and was carried on without any further purification. EI MS (m/z) 267.3 [MH$^+$].

A solution of (S)-ethyl ((1S,2S)-1-amino-2-vinylcyclopropyl)(pyridin-2-ylmethyl)phosphinate (64 mg, 0.24 mmol), carboxylic acid VII (157 mg, 0.0.24 mmol) in a 1:1 solution of DMF-CH$_2$Cl$_2$ (1.2 mL) was stirred with HATU (137 mg, 0.36 mmol) and DIEA (0.168 mL, 0.962 mmol) for 2.5 hours when the reaction was complete. The product was purified by silica gel chromatography (EtOAc-EtOAc/MeOH) to provide 82 mg of the desired product. EI MS (m/z) 901.4 [MH$^+$].

A solution of cyclopentyl (S)-1-((2S,4R)-2-(((1S,2S)-1-((S)-ethoxy(pyridin-2-ylmethyl)phosphoryl)-2-vinylcyclopropyl)-carbamoyl)-4-(2-(2-(isopropylamino)thiazol-4-yl)-7-methoxyquinolin-4-yloxy)pyrrolidin-1-yl)-3,3-dimethyl-1-oxobutan-2-ylcarbamate (68 mg, 0.074 mmol) and TMSI (0.053 mL, 0.371 mmol) was stirred in dry acetonitrile (0.74 mL) for 1 hour when the reaction was complete as judged by LCMS. The reaction was quenched using TEA (0.104 mL, 0.742 mmol) followed by addition of MeOH (10 mL). The reaction mixture was dried under reduced pressure and the residue was purified by RP HPLC (ACN, 0.05% TFA-H$_2$O, 0.05% TFA) to provide 42 mg of the desired product. $^1$H NMR (300 MHz, CD$_3$OD) δ 8.60 (d, 1H, J=5 Hz), 8.44 (t, 1H, J=9 Hz), 8.31 (d, 1H, J=9 Hz), 8.17 (s, 1H), 7.98 (d, 1H, J=9 Hz), 7.86 (t, 1H, J=6 Hz), 7.76 (s, 2H), 7.33 (d, 1H, J=11 Hz), 5.83 (br s, 1H), 5.55 (dt, 1H, J=9, 17 Hz), 4.98 (d, 1H, J=17 Hz), 4.78-4.65 (m, 2H), 4.66-4.51 (m, 2H), 4.21-4.07 (m, 3H), 4.05 (s, 3H), 3.54 (d, 1H, J=8 Hz), 3.48 (d, 1H, J=6 Hz), 2.87-2.82 (m, 1H), 2.61-2.45 (m, 1H), 2.08-1.94 (m, 1H), 1.70-1.44 (m, 8H), 1.5-1.35 (m, 2H), 1.34 (d, 6H, J=7 Hz), 1.08 (s, 9H); $^{31}$P (121.4 MHz, CD$_3$OD) δ23.5; EI MS (m/z) 873.7 [MH$^+$].

Example 75

Preparation of Compound 75

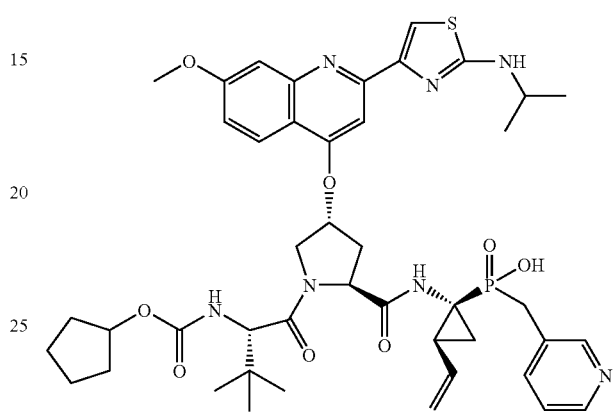

A solution of compound IV (161 mg, 0.521 mmol) in CH$_2$Cl$_2$ (4.7 mL) was added DIEA (0.190 mL, 1.09 mmol) and TMSCl (0.139 mL, 1.09 mmol) at 0° C. The reaction was allowed to warm up to rt and stirred for 1 hour. To the mixture was added a solution of 3-(bromomethyl)pyridine (290 mg, 1.15 mmol) in DIEA (0.091 mL, 0.521 mmol). This reaction was stirred at rt for 3 days when complete consumption of the starting materials was observed by LCMS. The reaction was worked up addition of CH$_2$Cl$_2$ and saturated aqueous NH$_4$Cl. The organic layer was dried in vacuo and purified using silica gel chromatography to give 91 mg of the product as a clear oil. EI MS (m/z) 401.0 [M+H].

A solution of benzyl (1S,2S)-1-((S)-ethoxy(pyridin-3-ylmethyl)phosphoryl)-2-vinylcyclopropylcarbamate (41 mg, 0.102 mmol) in acetonitrile (1.02 mL) was treated with TMSI (0.073 mL, 0.512 mmol) for 2 hours at rt when the reaction was complete. The reaction was quenched by addition of TEA (0.142 mL, 1.02 mmol) and MeOH (10 mL) and the residue was dried and used as is. A solution (S)-((1S,2S)-1-amino-2-vinylcyclopropyl)(pyridin-3-ylmethyl)phosphinic acid (24 mg, 0.10 mmol), carboxylic acid VII (66 mg, 0.100 mmol) in DMF (1.0 mL) was stirred with HATU (57 mg, 0.15 mmol) and DIEA (0.070 mL, 0.403 mmol) for 1 hour when the reaction was complete. The product was purified by RP HPLC (ACN, 0.05% TFA-H$_2$O, 0.05% TFA) to provide 28 mg of the desired product. $^1$H NMR (300 MHz, CD$_3$OD) δ 8.89 (s, 1H), 8.61 (d, 1H, J=5 Hz), 8.52 (d, 1H, J=8 Hz), 8.30 (d, 1H, J=9 Hz), 8.17 (s, 1H), 7.90 (t, 1H, J=6 Hz), 7.76 (s, 2H), 7.32 (d, 1H, J=10 Hz), 5.80 (br s, 1H), 5.77-5.65 (m, 1H), 5.07 (d, 1H, J=17 Hz), 4.79 (d, 1H, J=11 Hz), 4.71-4.63 (m, 2H), 4.49 (br s, 1H), 4.23-4.09 (m, 3H), 4.05 (s, 3H), 3.46-3.23 (m, 2H), 2.90-2.78 (m, 1H), 2.57-2.46 (m, 1H), 2.07-1.93 (m, 1H), 1.70-1.43 (m, 8H), 1.43-1.30 (m, 2H), 1.34 (d, 6H, J=6 Hz), 1.03 (s, 9H); $^{31}$P (121.4 MHz, CD$_3$OD) δ31.7; EI MS (m/z) 874.0 [MH$^+$].

Example 76

Preparation of Compound 76

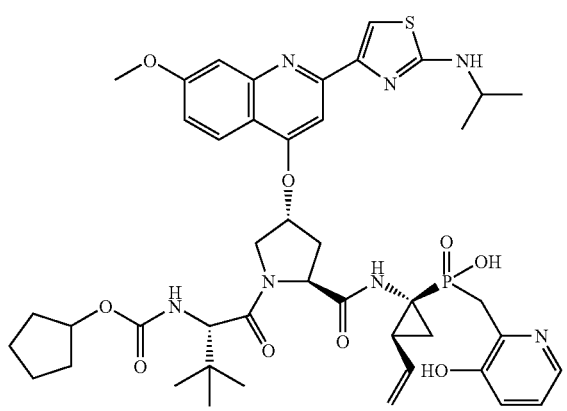

A solution of compound IV (228 mg, 0.737 mmol) in CH$_2$Cl$_2$ (6.7 mL) was added DIEA (0.270 mL, 1.55 mmol) and TMSCl (0.196 mL, 1.55 mmol) at 0° C. The reaction was allowed to warm to rt and was stirred for 1 hour. To the mixture was added 2-bromomethyl-3-hydroxypyridine hydrochloride (436 mg, 1.62 mmol) in DIEA (0.128 mL, 0.737 mmol). This reaction was stirred at room temperature for 1 day, and CH$_2$Cl$_2$ and saturated aqueous NH$_4$Cl were added. The organic layer was dried in vacuo and purified using silica gel chromatography to give 205 mg (67%) of the product as a clear oil. EI MS (m/z) 439.0 [M+H].

A solution of benzyl (1S,2S)-1-((S)-ethoxy((3-hydroxypyridin-2-yl)methyl)phosphoryl)-2-vinylcyclopropyl-carbamate (205 mg, 0.492 mmol) in acetonitrile (4.92 mL) was treated with TMSI (0.350 mL, 2.46 mmol) for 2 hours at rt when the reaction was complete. The reaction was quenched by addition of TEA (0.685 mL, 4.92 mmol) and MeOH (10 mL) and the residue was dried and used as is.

A solution of (S)-((1S,2S)-1-amino-2-vinylcyclopropyl)((3-hydroxypyridin-2-yl)methyl)phosphinic acid (214 mg, 0.328 mmol), carboxylic acid VII (125 mg, 0.493 mmol) in DMF (1.5 mL) was stirred with HATU (188 mg, 0.493 mmol) and DIEA (0.228 mL, 1.30 mmol) for 1 hour when the reaction was complete. The product was purified by RP HPLC (ACN, 0.05% TFA-H$_2$O, 0.05% TFA) to provide 54 mg of the desired product. $^1$H NMR (300 MHz, CD$_3$OD) δ 8.29 (d, 1H, J=9 Hz), 8.17 (s, 1H), 8.11 (d, 1H, J=8 Hz), 7.82 (d, 1H, J=8 Hz), 7.76 (s, 2H), 7.69-7.61 (m, 1H), 7.31 (d, 1H, J=9 Hz), 5.28 (br s, 1H), 5.71 (dt, 1H, J=10, 17 Hz), 5.04 (d, 1H, J=17 Hz), 4.79-4.63 (m, 2H), 4.50 (br s, 1H), 4.25-4.05 (m, 3H), 4.05 (s, 3H), 3.68 (app t, 1H, J=15 Hz), 3.41 (t, 1H, J=16 Hz), 2.95-2.84 (m, 1H), 2.60-2.48 (m, 1H), 2.08-1.97 (m, 1H), 1.70-1.45 (m, 8H), 1.45-1.35 (m, 2H), 1.34 (d, 6H, J=7 Hz), 1.03 (s, 9H); $^{31}$P (121.4 MHz, CD$_3$OD) δ26.7; EI MS (m/z) 889.7 [MH$^+$].

Example 77

Preparation of Compound 77

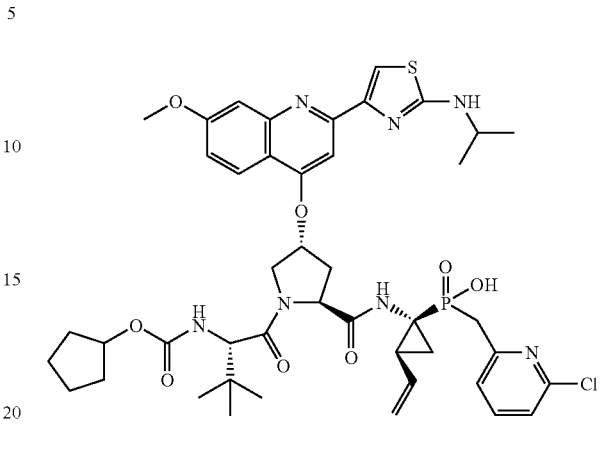

A solution of 3-chloro-6-methylpyridine (220 mg, 1.72 mmol) in carbontetrachloride (4 mL) was heated with NBS (284 mg, 1.60 mmol) and benzoyl peroxide (100 mg) for 3 days. The reaction was worked up by removal of the solvent and resuspension of the production in CH$_2$Cl$_2$. The organic layer was washed with aqueous 2N NaOH (2×50 mL) and dried in vacuo to give 170 mg of the product as a clear oil; EI MS (m/z) 208.0, 210.0 [M+H].

A solution of compound IV (102 mg, 0.330 mmol) in CH$_2$Cl$_2$ (3.0 mL) was added DIEA (0.121 mL, 0.692 mmol) and TMSCl (0.088 mL, 0.692 mmol) at 0° C. The reaction was allowed to warm up to rt and stirred for 1 hour. To the mixture was added 2-(bromomethyl)-6-chloropyridine (102 mg, 0.330 mmol) in DIEA (0.121 mL, 0.692 mmol). This reaction was stirred at rt over night when it was worked up by addition of CH$_2$Cl$_2$ and saturated aqueous NH$_4$Cl. The organic layer was dried in vacuo and purified using silica gel chromatography to give 140 mg (97%) of the product as a clear oil. EI MS (m/z) 457.0 [M+Na].

A solution benzyl (1S,2S)-1-((S)-((6-chloropyridin-2-yl)methyl)(ethoxy)phosphoryl)-2-vinylcyclopropylcarbamate (118 mg, 0.271 mmol) in acetonitrile (2.71 mL) was treated with TMSI (0.193 mL, ⅓₅ mmol) for 1.5 hours at rt when the reaction was complete. The reaction was quenched by addition of TEA (0.377 mL, 2.71 mmol) and MeOH (10 mL) and the residue was dried and used as is; EI MS (m/z) 273.1 [MH$^+$].

A solution of (S)-((1S,2S)-1-amino-2-vinylcyclopropyl)((6-chloropyridin-2-yl)methyl)phosphinic acid (74 mg, 0.271 mmol), carboxylic acid VII (177 mg, 0.271 mmol) in DMF (1.3 mL) was stirred with HATU (155 mg, 0.407 mmol) and DIEA (0.189 mL, 1.09 mmol) for 1 hour when the reaction was complete. The product was purified by RP HPLC (ACN, 0.05% TFA-H$_2$O, 0.05% TFA) to provide 37 mg of the desired product. $^1$H NMR (300 MHz, CD$_3$OD) δ 8.29 (d, 1H, J=9 Hz), 8.17 (s, 1H), 7.77-7.65 (m, 3H), 7.43 (dd, 1H, J=2, 8 Hz), 7.35-7.27 (m, 2H), 5.92-5.75 (m, 2H), 5.23 (d, 1H, J=17 Hz), 5.01 (d, 1H, J=12 Hz), 4.75-4.61 (m, 2H), 4.50 (br s, 1H), 4.20-4.08 (m, 3H), 4.05 (s, 3H), 3.53 (dd, 2H, J=3, 17 Hz), 2.84-2.74 (m, 1H), 2.65-2.53 (m, 1H), 2.16-2.04 (m, 1H), 1.70-1.42 (m, 10H), 1.34 (d, 6H, J=6 Hz), 1.03 (s, 9H); $^{31}$P (121.4 MHz, CD$_3$OD) δ40.7; EI MS (m/z) 907.4 [MH$^+$].

Example 78

Preparation of Compound 78

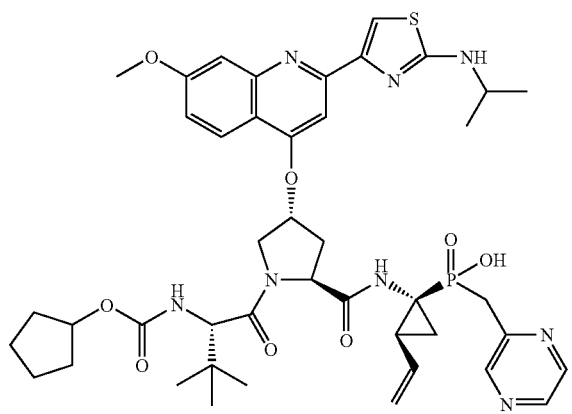

Examples 78 through 81 were prepared in a manner similar to that used to prepare example 74.

The product (Example 78) was afforded as a yellow solid, (48 mg, 15%). $^{1H}$ NMR (300 MHz, CD$_3$OD): δ 8.73 (s, 1H), 8.53 (s, 1H), 8.44 (s, 1H) 8.28 (d, J=9.2 Hz, 1H) 8.195 (s, 1H) 7.76 (s, 2H) 7.31 (d, J=8.8 Hz, 1H) 5.84 (m, 2H), 5.20 (m, 1H), 4.99 (m, 1H), 4.71 (m, 2H), 4.48 (bs, 1H), 4.15 (m, 3H) 4.04 (s, 3H), 3.60 (m, 2H), 2.75 (m, 1H), 2.54 (m, 1H), 2.02 (m, 1H), 1.54 (m, 8H) 1.34 (m, 8H), 1.01 (s, 9H). $^{31}$P (121.4 MHz, CD$_3$OD): δ38.710. LC (6 minute run, r.t.=3.50 min) MS (875.5, M+1)

Example 79

Preparation of Compound 79

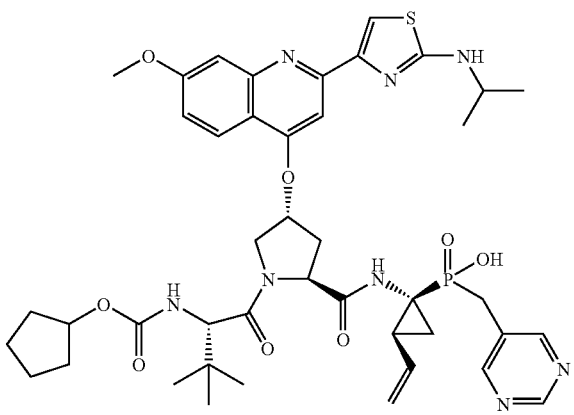

The product, (Example 79) was afforded as a yellow solid (7 mg, 5%).

$^{1H}$ NMR (300 MHz, CD$_3$OD): δ 9.00 (s, 1H) 8.82 (s, 2H) 8.29 (d, J=8.8 Hz, 1H) 8.18 (s, 1H) 7.75 (s, 2H), 7.32, (d, J=8.1 Hz, 1H) 5.80 (m, 2H), 5.18 (m, 1H), 4.95 (m, 1H), 4.66 (m, 2H), 4.47 (bs, 1H), 4.18 (m, 3H), 4.05 (s, 3H) 2.77 (m, 1H), 2.49 (m, 1H), 2.06 (m, 1H), 1.50 (m, 8H), 1.34 (m, 8H), 1.01 (s, 9H). Not enough material for $^{31}$P NMR. LC (6 minute run, r.t.=3.42 min) MS (875.5, M+1)

Example 80

Preparation of Compound 80

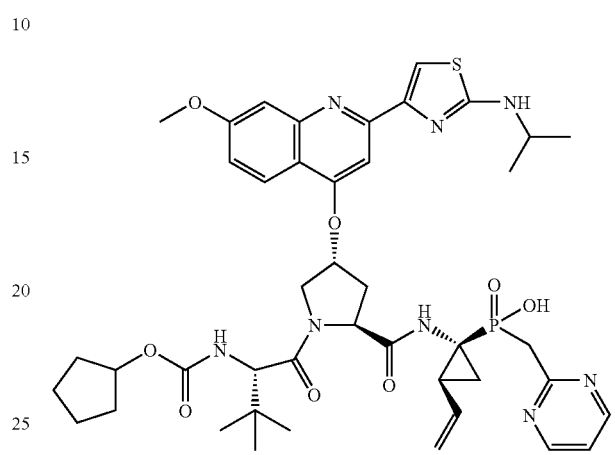

The product, (Example 80) was afforded as a yellow solid (11 mg, 15 $^{1H}$ NMR (300 MHz, CD$_3$OD): δ 8.74 (d, J=4.9 Hz, 2H) 8.29 (d, J=9.4 Hz, 1H) 8.17 (s, 1H) 7.76 (m, 2H), 7.35 (m, 2H) 5.86 (m, 2H), 5.22 (m, 1H), 5.00 (m, 1H), 4.70 (m, 2H), 4.49 (bs, 1H), 4.17 (m, 3H), 4.05 (s, 3H) 3.70 (m, 2H) 2.78 (m, 1H), 2.59 (m, 1H), 2.12 (m, 1H), 1.59 (m, 8H), 1.34 (m, 8H), 1.02 (s, 9H). $^{31}$P (121.4 MHz, CD$_3$OD): δ37.909. LC (6 minute run, r.t.=3.21 min) MS (875.6, M+1)

Example 81

Preparation of Compound 81

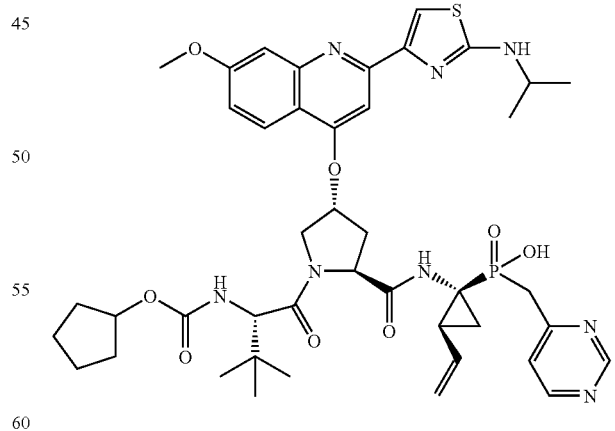

The product (Example 81) was afforded as a yellow solid (85 mg, 51%). $^{1H}$ NMR (300 MHz, CD$_3$OD): δ 9.02 (s, 1H) 8.65 (d, J=5.2 Hz, 1H) 8.28 (d, J=9.5 Hz, 1H) 8.18 (s, 1H) 7.75 (m, 2H), 7.66, (d, J=5.0 Hz, 1H) 7.30 (m, 1H) 5.86 (m, 2H), 5.20 (m, 1H), 5.00 (m, 1H), 4.68 (m, 2H), 4.47 (bs, 1H), 4.17 (m, 3H), 4.05 (s, 3H) 3.57 (m, 2H) 2.78 (m, 1H), 2.56 (m, 1H), 2.08 (m, 1H), 1.60 (m, 8H), 1.34 (m, 8H), 1.02 (s, 9H). $^{31}$P (121.4 MHz, CD$_3$OD): δ 36.81. LC (6 minute run, r.t.=3.21 min) MS (875.5, M+1)

Example 82

Preparation of Compound 82

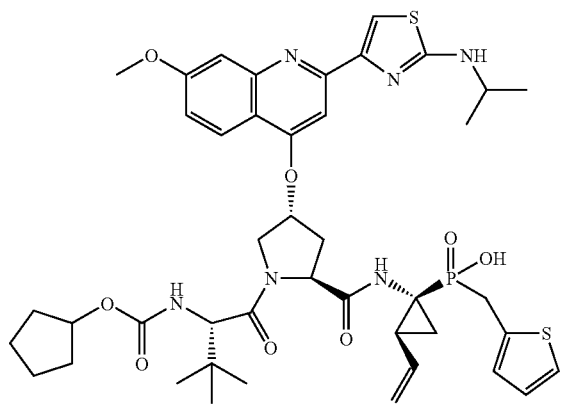

$^1$H NMR (300 MHz, CD$_3$OD) 8.27 (d, J=9.0 Hz, 1H), 8.20 (s, 1H), 7.76 (s, 2H), 7.$^{31}$ (b, 1H), 7.221 (b, 1H), 7.00 (b, 1H), 6.93 (m, 1H), 5.95 (m, 1H), 5.80 ((b, 1H), 5.24 (d, J=17.4 Hz, 1H), 5.07 (d, J=10.2 Hz, 1H), 4.68 (m, 2H), 4.46 (s, 1H), 4.17 (m, 2H), 4.11 (s, 1H), 4.04 (s, 3H), 3.49 (d, 15 Hz, 2H), 2.75 (m, 1H), 2.47 (m, 1H), 2.08 (m, 1H), 1.41-1.62 (m, 8H), 1.34 (d, J=6.3 Hz, 6H), 1.03 (s, 9H). $^{31}$P NMR (121.4 MHz, CD$_3$OD) δ 39.122 LC/MS=879 (M$^+$+1)

Example 83

Preparation of Compound 83

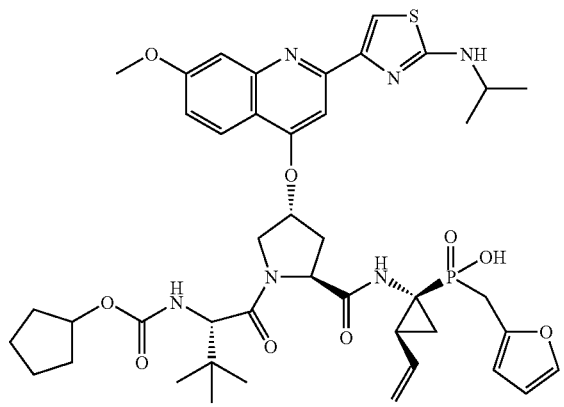

The furfuryl bromide was formed in situ from the furfuryl alcohol in the following manner. Furfuryl alcohol 3.5 mL (41 mmol) was dissolved in 20 mL of dry ether and cooled to 0° C. PBr$_3$ (1.4 mL, 15.1 mmol) dissolved in 4 mL of dry ether was then added at 0° C. After addition, the solution was allowed to warm to rt. After 45 min. at rt, the solution was cooled to 0° C. and 12 mL of 50% aqueous KOH solution was added. The ether layer was then decanted into a dry flask and stored at –20° C. over solid KOH. In a separate flask, 392 mg (1.27 mmol) of IV was dissolved in 5.0 mL of dry DCM. 465 μl (2.67 mmol) of DIEA and 339 μl (2.67 mmol) of TMSCl were added respectively and the reaction then stirred at rt for 5 min. 465 μl (2.67 mmol) of DIEA and 1.7 mL of the ether solution of in situ formed furfurylbromide mentioned above was then added. The reaction was warmed to 40° C. and allowed to go at 40° C. overnight. The reaction was then diluted with ethyl acetate and concentrated to remove DCM. The organic phase was then washed with 1× w/1.0 M Citric Acid, 2× w/water, and 1× w/Brine. The organic phase was dried over MgSO$_4$. Concentration of the filtrate from vacuum filtration removal of the MgSO$_4$ yielded an orange oil from which product 7 was isolated by column chromatography (SiO$_2$, 3:1-Ethylacetate:Hexane) as a clear oil (160 mg, 32% over 2 steps). $^1$H NMR (300 MHz, CDCl$_3$) 7.33 (s, 5H), 6.$^{31}$ (m, 2H), 6.00 (m, 1H), 5.30 (m, 2H), 5.04 (m, 4H), 4.10 (m, 2H), 3.35 (m, 2H), 1.96 (m, 2H)), 1.80 (m, 1H), 1.60 (m, 1H), 1.303 (m, 3H). $^{31}$P NMR (121.4 MHz, CDCl$_3$) δ 44.879, 41.575. LC/MS=390 (M$^+$+1).

A solution of phosphinate obtained above (103 mg, 0.308 mmol) in ACN (7.7 mL) was cooled to 0° C. and TMSI (220 μL, 1.54 mmol) was added in a drop-wise fashion. The reaction was warmed to rt and stirred at rt for one hour. The reaction was cooled back to 0° C. and 2,6-lutidine (360 μL, 3.1 mmol) was added in a drop-wise fashion. This was followed by the addition of Et$_3$N (1 mL, 7.2 mmol) and MeOH (4 mL). The reaction was then concentrated in vacuum and crude was used directly in the next reaction.

Crude residue from step 1, HATU (190 mg, 0.5 mmol), dipeptide VII (130 mg, 0.2 mmol) and n-methylmorpholine (110 μl, 1.0 mmol) were dissolved in 2 mL of DMF and stirred at rt overnight. The crude reaction mixture was then purified by reverse prep HPLC directly to afford 60 mg of 83 (60 mg, 34%) $^1$H NMR (300 MHz, CD$_3$OD) 8.82 (s, 1H), 8.26 (d, J=9.6 Hz, 1H), 8.20 (s, 1H), 7.75 (s, 2H), 7.35 (s, 1H), 7.29 (dd, J=2.1, 9.3 Hz, 1H), 6.30 (m, 2H), 5.95 (m, 1H), 5.80 ((b, 1H), 5.24 (d, J=11.4 Hz, 1H), 5.07 (d, J=12 Hz, 1H), 4.65 (m, 2H), 4.45 (s, 1H), 4.17 (m, 2H), 4.11 (s, 1H), 4.04 (s, 3H), 3.35 (m, 2H), 2.80 (m, 1H), 2.50 (m, 1H), 2.10 (m, 1H), 1.41-1.78 (m, 8H), 1.34 (d, J=6.3 Hz, 6H), 1.04 (s, 9H). $^{31}$P NMR (121.4 MHz, CD$_3$OD) δ 40.029 LC/MS=863 (M$^+$+1)

Example 84

Preparation of Compound 84

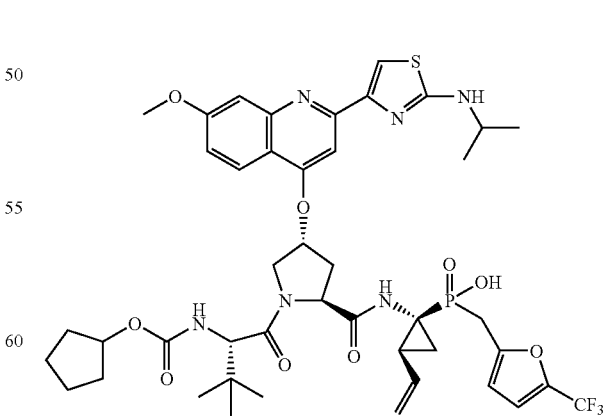

Intermediate IV (360 mg, 1.2 mmol) was dissolved in 5.0 mL of dry DCM. DIEA (418 μl, 2.4 mmol) and 343 μl (2.4 mmol) of TMSCl were added sequentially and the reaction then stirred at rt for 5 min. More DIEA (418 μl, 2.4 mmol) and 343 μl (2.4 mmol) of 5-(trifluoromethyl)furfuryl bromide were then added respectively. The reaction was warmed to 40° C. and allowed to stir at 40° C. overnight. The reaction was then diluted with ethyl acetate and concentrated to remove DCM. The organic phase was then washed with 1× with sat. NH$_4$Cl, 2× with water, and 1× w/brine. The organic phase was dried over MgSO$_4$. Concentration of the filtrate after filtration of the MgSO$_4$ yielded an orange oil from which product was isolated by column chromatography (SiO$_2$, neat ethyl acetate) as a clear oil (313 mg, 56%). Deprotection and coupling to dipeptide VII afforded compound 84.

$^1$H NMR (300 MHz, CD$_3$OD) 8.27 (d, J=8.7 Hz, 1H), 8.20 (s, 1H), 7.75 (s, 2H), 7.35 (s, 1H), 7.29 (d, J=2.1, 9.3 Hz, 1H), 6.86 (b, 1H), 6.48 (b, 1H), 5.90 (b, 1H), 5.79 (b, 1H), 5.25 (d, J=17.4 Hz, 1H), 5.07 (d, J=10.8 Hz, 1H), 4.67 (m, 2H), 4.45 (s, 1H), 4.16 (m, 2H), 4.11 (s, 1H), 4.04 (s, 3H), 3.43 (m, 2H), 2.80 (m, 1H), 2.50 (m, 1H), 2.10 (m, 1H), 1.62-1.33 (m, 8H), 1.34 (d, J=6.3 Hz, 6H), 1.04 (s, 9H). $^{31}$P NMR (121.4 MHz, CD$_3$OD) δ 36.68 LC/MS=931 (M$^+$+1)

Example 85

Preparation of Compound 85

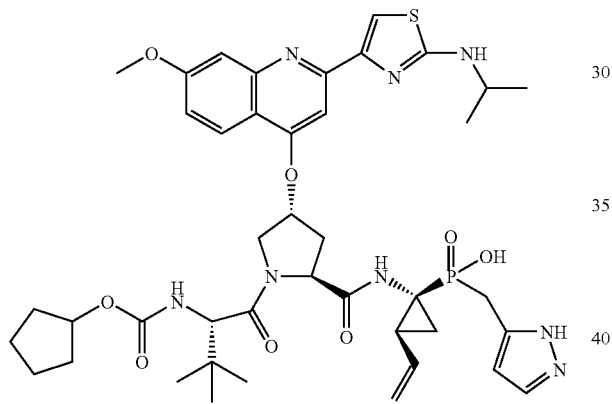

To a solution of 5-methyl-1H-pyrazole (5 g, 61.05 mmol) in CH$_3$CN (50 mL) at 0° C. was added di-tert-butyl dicarbonate (16 g, 73.26 mmol) and DMAP (740 mg, 6.10 mmol). The reaction mixture was warmed to r.t. and stirred for 2 h. The reaction mixture was diluted with EtOAc (30 mL) and washed with 1 N HCl (2×30 mL). The organic layer was washed with saturated NaHCO$_3$ (30 mL) and brine (30 mL), dried with Na$_2$SO$_4$, and concentrated to give 8.7 g of 5-methyl-pyrazole-1-carboxylic acid tert-butyl ester as crude product.

To a solution of 5-methyl-pyrazole-1-carboxylic acid tert-butyl ester in CCl$_4$ (40 mL) was added NBS (3.3 g, 18.5 mmol) and benzoylperoxide (450 mg, 1.86 mmol). The reaction mixture was heated to reflux for 4 h and cooled to r.t. The insoluble material was filtered off and the solution was diluted with EtOAc. The organics were washed with saturated NaHCO$_3$ and H$_2$O, dried with Na$_2$SO$_4$, and concentrated. The crude product was purified by combi-flash to give 1.67 g of 5-bromomethyl-pyrazole-1-carboxylic acid tert-butyl ester in 52% yield.

Intermediate IV (800 mg, 2.56 mmol) was dissolved in CH$_2$Cl$_2$ (30 mL) and cooled to 0° C. Diisopropylethylamine (1 mL, 5.36 mmol) was added and stirred for 15 minutes. Chlorotrimethylsilane (0.8 mL, 5.36 mmol) was added dropwise. The reaction mixture was warmed to r.t. and stirred for 1 h. A solid of 5-bromomethyl-pyrazole-1-carboxylic acid tert-butyl ester (1.67 g, 6.4 mmol) was added and the reaction was heated to 45° C. overnight. The reaction mixture was cooled to rt, diluted with CH$_2$Cl$_2$, washed with aqueous NH$_4$Cl, dried with Na$_2$SO$_4$, and concentrated. The crude product was purified by combi-flash to give 682 mg of phosphinate in 55% yield.

To a solution of phosphinate (682 mg, 1.4 mmol) in CH$_3$CN (2 mL) at 0° C. was added iodotrimethylsilane (1.0 mL, 7 mmol). The reaction mixture was warmed to r.t. and stirred for 30 minutes. An additional amount of iodotrimethylsilane (1 mL, 7 mmol) was added and stirred for 30 minutes. 2,6-Lutidine (0.8 mL) and MeOH (1.6 mL) were added, stirred for 20 minutes, concentrated in vacuo, and dried for 20 minutes to give amine. Coupling with intermediate VII gave phosphinic acid 85. $^1$H NMR (300 MHz, CD$_3$OD): δ 8.30 (d, J=7.8 Hz, 1H), 8.17 (s, 1H) 7.76 (s, 2H), 7.61 (m, 4H), 7.61 (s, 1H), 7.34 (d, J=9.3 Hz, 1H), 6.37 (s, 1H), 5.82 (m, 2H), 5.22 (d J=17.7 Hz, 1H), 5.00 (d J=11.1 Hz, 1H), 4.68 (m, 3H), 4.49 (s, 1H), 4.16 (m, 2H), 4.05 (m, 3H), 3.35 (m, 2H), 2.79 (m, 1H), 2.51 (m, 1H), 2.09 (m, 1H), 1.63-1.48 (m, 8H), 1.34 (m, 6H), 1.02 (s, 9H). LC/MS=863.12 (M$^+$+1)

Example 86

Preparation of Compound 86

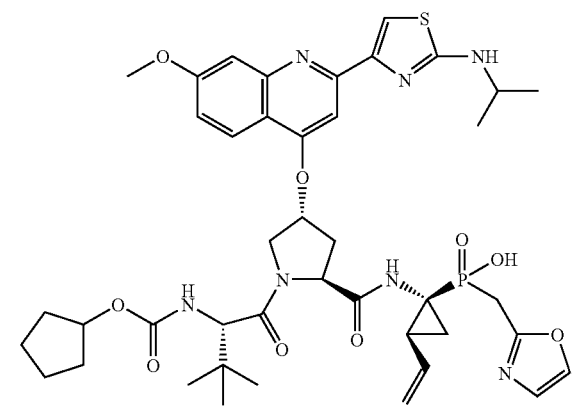

Step 1. To a solution of the phosphinate (structure shown above, 170 mg, 0.44 mmol) in CH$_3$CN at 0° C. was added iodotrimethylsilane (0.$^{31}$ mL, 2.18 mmol). The reaction mixture was warmed to rt, stirred for 1 h, and cooled to 0° C. 2,6-lutidine (0.51 mL) was added followed by addition of MeOH (0.5 mL) and warmed to rt. The mixture was concentrated and dried under vacuum to give the desired amino phosphinic acid as crude product.

Step 2. The intermediate VII (142 mg, 0.22 mmol) and the amino phosphinic acid obtained from step 1 (0.44 mmol) were dissolved in DMF (2 mL). HATU (166 mg, 0.44 mmol) and NMM (0.07 mL, 0.65 mmol) were added and the mixture was stirred at r.t. overnight. The reaction was diluted with CH$_2$Cl$_2$ and washed with 5% LiCl (2×). The organic layer was washed with saturated NaHCO$_3$, dried with Na$_2$SO$_4$, and concentrated. The crude product was purified by HPLC to give 83.2 mg of compound 86. $^1$H NMR (300 MHz, CD$_3$OD): δ 8.28 (d, J=9.3 Hz, 1H), 8.17 (s, 1H), 7.96 (s, 1H), 7.77 (s, 2H), 7.30 (dd, J=2.4, 9.0 Hz, 1H), 7.07 (s, 1H), 5.97 (m, 1H), 5.79 (brs, 1H), 5.23 (d, J=17.7 Hz, 1H), 5.06 (d, J=11.7 Hz, 1H), 4.65 (m, 2H), 4.46 (brs, 1H), 4.15 (m, 3H), 3.97 (s, 3H), 3.6 (d, 2H), 2.80 (m, 1H), 2.45 (m, 1H), 2.12 (m, 1H), 1.4-1.7 (m, 10H), 1.34 (d, J=6.3 Hz, 6H), 0.95-1.15 (brs, 9H); $^{31}$P (121.4 MHz, CD$_3$OD): $\delta$36.884; LC/MS=864(M$^+$+1).

Example 87

Preparation of Compound 87

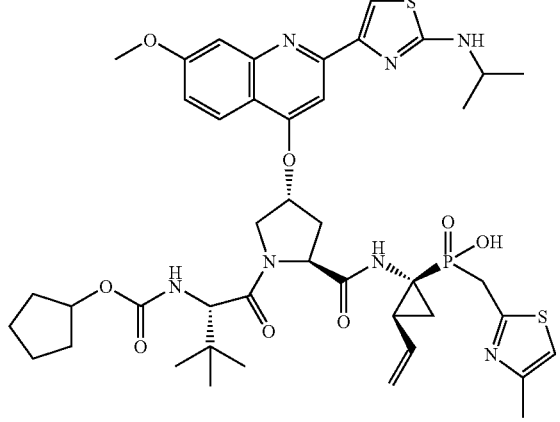

A flask was charged with 1.1 mL (10.2 mmol) of freshly distilled 2,5-dimethylthiazole and 25 mL of dry THF. To this mixture, 4.6 mL (2.8 mmol) of 2.2 M nBuLi was then added dropwise and the reaction stirred at −78° C. for 30 min. The intermediate phosphonus acid IV (prepared from 1.1 g of III, 3.4 mmol) was dissolved in 20 mL of dry THF and added dropwise to the lithium anion solution of 2,5-Dimethylthiazole formed in situ at −78° C. After 30 min the reaction was quenched at −78° C. by the addition of sat. NH$_4$Cl$_{(aq.)}$. The organic phase was diluted with EtOAc and washed with sat. NH$_4$Cl$_{(aq.)}$ and brine. The organic phase was dried over MgSO$_4$. Concentration of the filtrate from vacuum filtration removal of the MgSO$_4$ yielded an orange oil from which product was isolated by column chromatography (SiO$_2$, 3:1-Ethyl Acetate:Hexane) as a clear oil (220 mg, 15% over 2 steps). $^1$H NMR (300 MHz, CDCl$_3$) $\delta$ 7.33 (s, 5H), 6.64 (d, 1H), 5.80 (dt, J=9.9, 17.1 Hz, 1H), 5.18 (b, 4H), 4.10 (m, 2H), 3.60 (m, 2H), 2.0 (m, 1H) 1.80 (m, 2H), 1.20 (m, 3H). $^{31}$P NMR (121.4 MHz, CDCl$_3$) $\delta$ 44.952, 41.135. LC/MS=421 (M$^+$+1)

Deprotection and coupling as described before provide 87. (yield=65 mg, 66%). $^1$H NMR (300 MHz, CD$_3$OD) 8.28 (d, J=9.6 Hz, 1H), 8.27 (s, 1H), 7.77 (s, 2H), 7.45 (s, 1H), 7.31 (dd, J=2.1, 9.3 Hz, 1H), 5.84 (br, 1H), 5.70 (m, 1H), 5.12 (d, J=11.4 Hz, 1H), 4.83 (d, 1H) 4.69 (m, 2H), 4.51 (s, 1H), 4.17 (m, 2H), 4.08 (s, 1H), 4.04 (s, 3H), 3.80 (m, 2H), 2.84 (dd, J=7.2, 14.1 Hz, 1H), 2.45 (m, 4H), 1.41-1.78 (m, 8H), 1.34 (d, J=6.3 Hz, 6H), 1.04 (s, 9H). $^{31}$P NMR (121.4 MHz, CD$_3$OD) $\delta$ 26.015. LC/MS=894 (M$^+$+1)

Example 88

Preparation of Compound 88

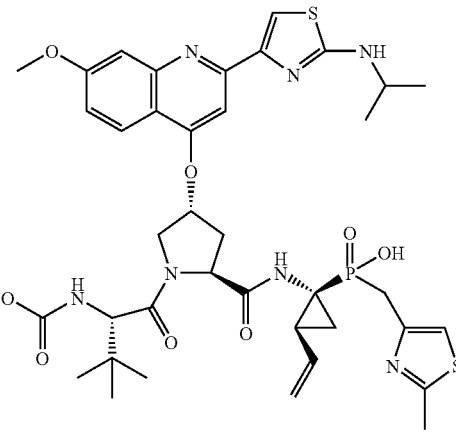

A solution of the phosphonous acid IV (501.3 mg, 1.62 mmol), Hunig's Base (680 μL, 3.90 mmol), and chlorotrimethylsilane (460 μL, 3.62 mmol) in CH$_2$Cl$_2$ (8 mL) was stirred at rt for 20 minutes. A solution of 4-(chloromethyl)-2-methylthiazole (510 mg, 2.77 mmol), tetrabutylammonium iodide (598.4 mg, 1.620 mmol) and Hunig's Base (530 μL, 3.04 mmol) in CH$_2$Cl$_2$ (1.5 mL) was added via a cannula at rt. The resulting solution was stirred at 40° C. for 4.5 days and cooled to rt. The solution was concentrated and the residue dissolved in ethyl acetate (30 mL). The organic layer was washed with H$_2$O (×2) and the aqueous layer extracted with ethyl acetate (30 mL). The organic fractions were dried (MgSO$_4$) and concentrated. The residue was purified with a CombiFlash column chromatography using hexane:ethyl acetate as eluent to obtain phosphinate (449 mg, 66%). $^{1H}$ NMR (300 MHz, CDCl$_3$): $\delta$ 7.35 (s, 2.15H), 7.33 (s, 2.85H), 7.03 (d, J=3.3 Hz, 0.43H), 6.94 (d, 3.9 Hz, 0.57H), 6.72 (s, 0.57H), 6.60 (s, 0.43H), 6.04 (m, 1H), 5.71 (s, 1H), 5.40-5.34 (d, J=17.1 Hz, 1H), 5.29 (s, 2H), 5.10 (m, 3H), 4.76-4.73 (d, J=10.2 Hz, 1H), 4.20 (m, 2H), 3.55 (m, 2H), 3.32 (m, 2H), 2.67 (s, 3H), 2.27 (m, 2H), 1.71 (m, 4H). 1.23 (m, 3H), 1.13 (m, 1H), 0.93 (m, 1H). $^{31}$P (121.4 MHz, CD$_3$OD): $\delta$48.382, 47.151, 44.628, 43.811

Example 89

Preparation of Compound 89

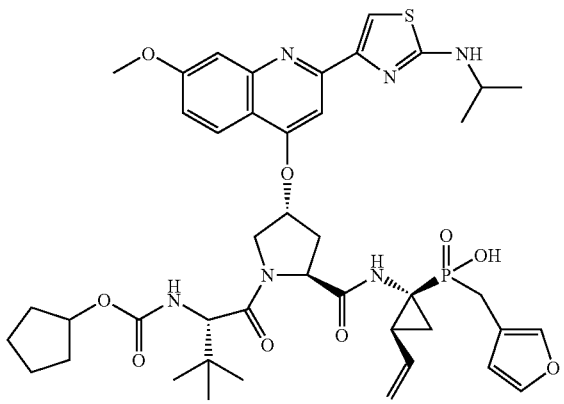

In a manner similar to example 7 (the other furan) Yield=230 mg (40%). $^1$H NMR (300 MHz, CDCl$_3$) 7.33 (s, 5H), 6.41 (d, 1H), 6.00 (m, 1H), 5.30 (m, 1H), 5.08 (m, 3H), 4.05 (m, 2H), 2.96 (m, 2H), 2.08 (m, 1H)), 1.77 (m, 1H), 1.46 (m, 1H), 1.21 (m, 3H). $^{31}$P NMR (121.4 MHz, CDCl$_3$) δ 45.73, 42.55

LC/MS=390 (M$^+$+1)

$^1$H NMR (300 MHz, CD$_3$OD) 8.27 (d, J=9.3 Hz, 1H), 8.19 (s, 1H), 7.75 (s, 2H), 7.42 (m, 1H), 7.30 (m, 1H), 6.46 (s, 1H), 5.95 (m, 1H), 5.80 ((b, 1H), 5.24 (d, J=17.1 Hz, 1H), 5.06 (d, J=10.2 Hz, 1H), 4.67 (m, 2H), 4.45 (s, 1H), 4.17 (m, 2H), 4.11 (s, 1H), 4.04 (s, 3H), 3.06 (d, 15 Hz, 2H), 2.77 (m, 1H), 2.45 (m, 1H), 2.07 (m, 1H), 1.41-1.78 (m, 8H), 1.34 (d, J=6.3 Hz, 6H), 1.04 (s, 9H). $^{31}$P NMR (121.4 MHz, CD$_3$OD) δ 41.17. LC/MS=863 (M$^+$+1)

Example 90

Preparation of Compound 90

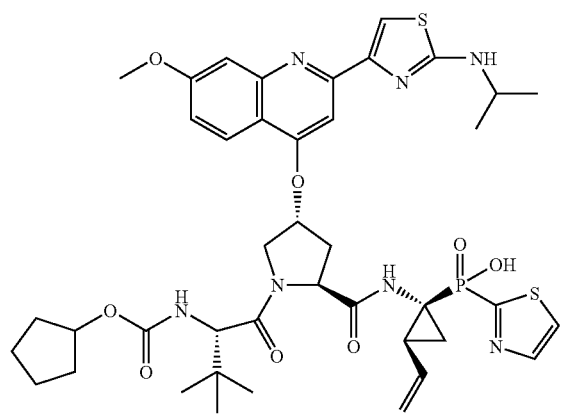

A flask was charged with 13.0 mL of dry ether and 2.95 mL of 2.2 M nBuLi in hexane. The mixture was cooled to −78° C. Freshly distilled bromothiazole 587 μl (6.5 mmol) was then added and the reaction stirred at −78° C. for 20 minutes. The intermediate phosphonus acid IV (prepared from 1.0 g of III, 3.1 mmol) was dissolved in 13.0 mL of THF and then added dropwise to the anion solution at −78° C. After 20 min the reaction was quenched at −78° C. by the addition of sat. NH$_4$Cl$_{(aq.)}$. The organic phase was diluted with EtOAc and washed with sat. NH$_4$Cl$_{(aq.)}$ and brine. The organic phase was dried over MgSO$_4$. Concentration of the filtrate from vacuum filtration removal of the MgSO$_4$ yielded an orange oil from which product was isolated by column chromatography (SiO$_2$, neat Ethyl Acetate) as a clear oil (450 mg, 37% over 2 steps).

$^1$H NMR (300 MHz, CDCl$_3$) δ 8.07 (s, 1H), 7.667 (s, 1H), 7.33 (s, 5H), 6.20-5.90 (m, 1H), 5.82 (s, 1H), 5.55 (d, J=38.1 Hz, 1H), 5.20 (m, 1H), 5.06 (m, 3H), 4.24 (m, 2H), 2.05 (m, 1H), 1.96-1.70 (m, 2H), 1.52 (m, 1H), 1.303 (m, 3H). $^{31}$P NMR (121.4 MHz, CDCl$_3$) δ 28.845, 26.156. LC/MS=393 (M$^+$+1), 415 (M$^+$+Na)

A solution of phosphinate obtained above (300 mg, 0.77 mmol) in ACN (6.5 mL) was cooled to 0° C. and TMSI (764 μL, 5.4 mmol) was added in a drop-wise fashion. The reaction was warmed to rt and stirred for an hour. The reaction was cooled back to 0° C. and 2,6-lutidine (897 μL, 2.6 mmol) was added in a drop-wise fashion. This was followed by the addition of Et$_3$N (2.7 mL, 19.3 mmol) and MeOH (8 mL). The reaction was then concentrated in vacuum and crude was used directly in the next reaction. A solution of dipeptide VII (150 mg, 0.23 mmol) in THF (4 mL) was cooled to −30° C. Et$_3$N (81 μL, 0.58 mmol) was added to this solution followed by ClCO$_2$Et (44 μL, 0.46 mmol). The reaction was stirred at a temperature between −20° C. and −30° C. for 30 min.

A solution of crude from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuum and the residue was dissolved in MeOH (1.5 mL). Compound 90 was isolated from this solution by reverse-phase HPLC as a yellow solid (82 mg, 41%). $^1$H NMR (300 MHz, CD$_3$)D) δ 8.25 (m, 2H), 8.20 (m, 2H), 8.02 (s, 1H), 7.75 (s, 2H), 7.39 (d, J=8.7 Hz, 1H), 5.97 (b, 2H), 5.77 (b, 1H), 5.06 (d, J=11.4 Hz, 1H), 4.63 (m, 2H), 4.44 (s, 1H), 4.17 (m, 2H), 4.08 (s, 1H), 4.04 (s, 3H), 2.75 (b, 1H), 2.57 (b, 1H), 2.10 (b, 1H), 1.7-1.5 (b, 8H), 1.34 (d, J=6.3 Hz, 6H), 1.04 (s, 9H). $^{31}$P NMR (121.4 MHz, CD$_3$CN) δ 18.28 LC/MS=866 (M$^+$+1)

Example 91

Preparation of Compound 91

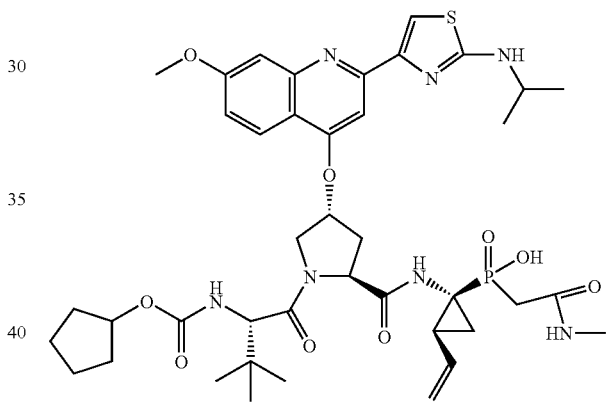

The [(1-Benzyloxycarbonylamino-2-vinyl-cyclopropyl)-ethoxy-phosphinoyl]-acetic acid from examp 11 (290 mg, 0.79 mmol) was suspended in 4 mL of DMF. HATU (901 mg, 2.37 mmol), methylamine (133 mg, 1.97 mmol), followed by NMM (781 μl, 7.11 mmol) was added. After 2 hours, the reaction was concentrated and partitioned with EtOAc and H$_2$O. The aqueous layer was extracted 3× with EtOAc. The organic layer was dried over MgSO4, filtered and concentrated. The material, a brown oil (264 mg, 88%) was used crude.

The residue was suspended in 1 mL of CH$_3$CN and cooled to 0° C. Iodotrimethylsilyl (TMSI) (187 μl, 1.$^{31}$ mmol) was added and the solution was warmed to rt. After 45 minutes, the solution was cooled again to 0° C. and triethylamine (1 mL, 7.33 mmol) and 2 mL of MeOH. The solution was warmed to rt and stirred for an additional 20 minutes. The solution was concentrated, azeotroped 2× with toluene and put on high vacuum for 30 minutes. Coupling with intermediate VII gave 91 as a yellow solid. $^{1H}$ NMR (300 MHz, CD$_3$OD): δ 8.23 (d, J=9.5 Hz, 1H), 8.20 (s, 1H), 7.79 (s, 2H), 7.33 (d, J=8.8 Hz, 1H), 5.95 (m, 1H), 5.78 (s, 1H), 5.22 (d, J=9.6 Hz, 2H), 5.13 (d, J=9.0 Hz, 2H), 4.63 (m, 2H), 4.45 (bs, 1H), 4.20 (m, 3H), 4.05 (s, 3H), 3.22 (m, 1H), 3.20 (d, 1H), 3.18 (s, 1H), 2.80 (m, 1H), 2.78 (s, 3H), 2.45 (m, 1H), 2.15 (m, 1H), 1.62 (m, 2H), 1.50 (m, 6H) 1.38 (d, 6H), 1.05 (s, 9H). $^{31}$P (121.4 MHz, CD$_3$OD): δ36.642

Example 92

Preparation of Compound 92

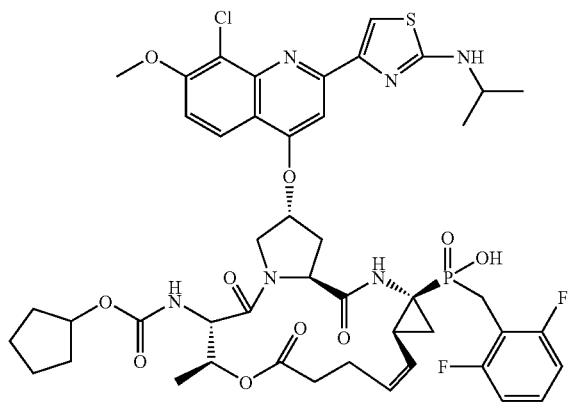

Step 1. Dipeptide compound (Boc deprotected from intermediate XII) (2.86 g, 4.27 mmol) and 2-tert-butoxycarbonylamino-3-hydroxy-butyric acid (958 mg, 4.37 mmol) were dissolved in DMF (18 mL) and cooled to 0° C. TEA (1.09 mL, 8.54 mmol), HOBT (634 mg, 4.7 mmol), and EDCI (1.7 g) were added sequentially. The reaction mixture was stirred at 0° C. for 1 h and warmed to r.t. overnight. The reaction mixture was quenched with H$_2$O and extracted with EtOAc (2×). The organic layer was washed with 5% LiCl, saturated NH$_4$Cl and brine, dried with Na$_2$SO$_4$, and concentrated. The crude product was purified by combi-flash to give 2.21 g of tripeptide in 62% yield. $^{31}$P NMR (121.4 MHz, CDCl$_3$) δ 46.4, 43.9. LC/MS=836.0 (M$^+$+1), 856.0 (M$^+$+Na).

Step 2. Alcohol from step 1 (2.06 g, 2.5 mmol) and Pent-4-enoic acid (0.64 mL, 6.25 mmol) were dissolved in CH$_2$Cl$_2$ (18.75 mL)/DMF (6.25 mL). EDCI (1.8 g, 9.38 mmol) and DMAP (92 mg, 0.75 mmol) were added sequentially. The reaction mixture was stirred at r.t. for 7 h and concentrated. The reaction mixture was diluted with H$_2$O and extracted with EtOAc (2×). The organic layer was washed with 5% LiCl and brine, dried with Na$_2$SO$_4$, and concentrated. The crude product was purified by combi-flash to give 2.16 g of ester product in 96% yield. $^{31}$PNMR (121.4 MHz, CDCl$_3$) δ 44.5, 43.9, 43.2, 42.3. LC/MS=917.9 (M$^+$+1), 856.0 (M$^+$+Na).

Step 3. Ester (2.16 g, 2.36 mmol) was dissolved in CH$_2$Cl$_2$ (236 mL) and degassed with N$_2$ for 20 minutes. Grubb's G1(486 mg, 0.59 mmol) was added and degassed for an additional 20 minutes. The reaction mixture was heated to 50° C. for 5.5 h and cooled to rt. Tris(hydroxymethyl)phosphine (3.66 g, 29.5 mmol) was added followed by addition of TEA (8.2 mL, 59 mmol) and H$_2$O (20 mL). The reaction mixture was heated to 50° C. for 5 h and then r.t. overnight. The two layers were separated. The organic layer was washed with 0.5 N HCl and brine, dried with Na$_2$SO$_4$, and concentrated. The crude product was purified by combi-flash to give 1.48 g of cyclized compound in 71% yield. $^{31}$P NMR (121.4 MHz, CDCl$_3$) δ 44.4, 43.1. LC/MS=888.1 (M$^+$+1), 909.9 (M$^+$+Na)

Step 4. To a solution of cyclic olefin (1.48 g, 1.67 mmol) in CH$_2$Cl$_2$ (10 mL) was added 4 N HCl in 1,4-dioxane (6.26 mL, 25.05 mmol). The reaction mixture was stirred at r.t. for 3.5 h, concentrated, dried under vacuum overnight, and then dissolved in THF (14.3 mL)/H$_2$O (2.4 mL). Compound Carbonic acid cyclopentyl ester 2,5-dioxo-pyrrolidin-1-yl ester (398 mg, 1.75 mmol) and TEA (0.7 mL, 5.01 mmol) were added. The reaction was stirred at r.t. for 2 h and additional Carbonic acid cyclopentyl ester 2,5-dioxo-pyrrolidin-1-yl ester (38 mg) was added. The reaction was stirred for 2 h. The reaction was quenched by adding 0.5 N HCl and diluted with EtOAc. The two layers were separated. The organic layers were washed with 0.5 N HCl and brine, dried with Na$_2$SO$_4$, and concentrated. The crude product was purified by combi-flash to give 1.45 g of cyclopentyl carbamate in 96% yield. $^{31}$P NMR (121.4 MHz, CDCl$_3$) δ 44.4, 43.1. LC/MS=902.0 (M$^+$+1).

Step 5. A solution of cyclopentyl carbamate (1.4 g, 1.55 mmol) and 8-chloro-2-(2-isopropylamino-thiazol-4-yl)-7-methoxy-quinolin-4-ol (542 mg, 1.55 mmol) in NMP (15 mL) was treated with Cs$_2$CO$_3$ (1.26 g, 3.88 mmol). The reaction mixture was heated to 63° C. for 5 h and then cooled to rt. The reaction was diluted with EtOAc and washed with NaHCO$_3$. The organic layer was washed with 5% LiCl and brine, dried with Na$_2$SO$_4$, and concentrated. The crude product was purified by combi-flash to give 1.18 g of desired product in 75% yield.

Step 6. To a solution of product obtained above (1.18 g, 1.16 mmol) in CH$_3$CN (12 mL) at 0° C. was added 2,6-lutidine (1.35 mL, 11.6 mmol) and iodotrimethylsilane (1.66 mL, 11.6 mmol). The reaction mixture was stirred at r.t. for 3 h and cooled to 0° C. 2,6-lutidine (0.27 mL, 2.32 mmol) was added followed by addition of MeOH (5 mL) and warmed to rt for 10 minutes. The mixture was concentrated, dried under vacuum. The crude product was purified by reverse phase combi-flash followed by HPLC to give 1.01 g of 92 in 88% yield. $^1$H NMR (300 MHz, CD$_3$OD) δ8.26 (m, 2H), 7.85 (s, 1H), 7.68 (d, J=9.6 Hz, 1H), 7.26 (t, J=8.1 Hz, 1H), 6.93 (t, J=7.8 Hz, 2H), 5.84 (m, 2H), 5.67 (t, J=10.8 Hz, 1H), 5.08 (dd, J=6.3, 9.9 Hz, 1H), 4.75 (t, J=8.4 Hz, 1H), 4.68 (d, J=11.7 Hz, 1H), 4.42 (d, J=9.9 Hz, 1H), 4.3 (m, 2H), 4.17 (s, 3H), 4.00 (quint., J=6.6 Hz, 1H), 3.55 (t, J=15.3 Hz, 1H), 3.31 (t, J=15.3 Hz, 1H), 2.91 (m, 2H), 2.6 (m, 1H), 2.46 (dd, J=5.4, 16.8 Hz, 1H), 2.30 (m, 1H), 2.20 (m, 1H), 1.4-1.7 (brm, 10H), 1.37 (dd, J=2.1, 6.6 Hz, 6H), 1.25 (d, J=6.3 Hz, 3H), 1.04 (m, 1H). $^{31}$P NMR (121.4 MHz, CD$_3$OD) δ 38.9. LC/MS=985.1 (M$^+$+1)

Example 93

Preparation of Compound 93

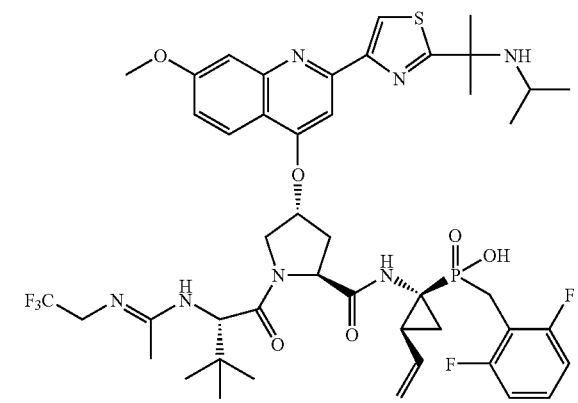

Step 1. Ethyl acetimidate hydrochloride (1.23 g, 9.95 mmol) and 2,2,2-trifluoroethylamine hydrochloride (1.35 g, 9.95 mmol) were dissolved in CH$_2$Cl$_2$ (32 mL)/H$_2$O (3.2 mL). K$_2$CO$_3$ (0.69 g, 4.98 mmol) was added and stirred for 30 minutes. The two layers were separated. The aqueous layer was extracted with CH$_2$Cl$_2$ (2×10 mL). The combined organic layer was dried with Na$_2$SO$_4$ and concentrated to give 1.48 g of N-(2,2,2-Trifluoro-ethyl)-acetimidic acid ethyl ester as a light yellow liquid in 87% yield.

Step 2. The Boc protected tripeptide phosphinate was prepared in a similar manner as described for example 58, which was deprotected as the following. Tripeptide (500 mg, 0.54 mmol) was dissolved in CH$_3$CN (5 mL) and cooled to 0° C. Iodotrimethylsilane (0.77 mL) was added. The reaction mixture was warmed to rt, stirred for 0.5 h, and cooled to 0° C. 2,6-lutidine (1.30 mL) was added followed by addition of MeOH (5 mL). The mixture was concentrated, co-evaporated with CH$_2$Cl$_2$ (2×), and dried in vacuo to give amino phosphinate as a 2,6-lutidine salt. The salt (80 mg, 0.025 mmol) was dissolved in DMF (0.45 mL) and 0.1 N phosphate buffer (0.9 mL). 2 N NaOH (86 µL) was added to adjust pH to 9. A solution of N-(2,2,2-Trifluoro-ethyl)-acetimidic acid ethyl ester (150 mg, 0.89 mmol) in DMF (0.1 mL) was added and stirred for 18 h. The reaction mixture was filtered and the filtrate was purified by HPLC to give 8.8 mg of 93 as a yellow solid.

Example 94

Preparation of Compound 94

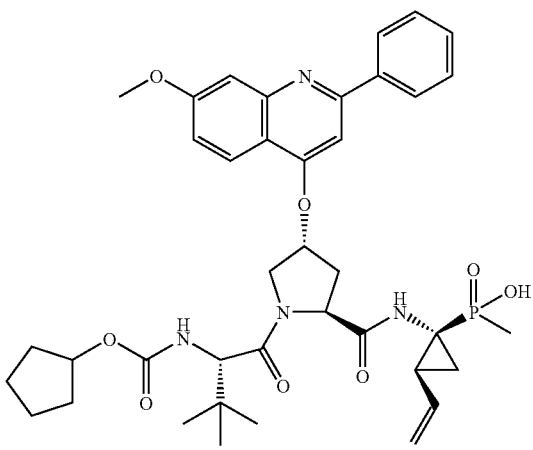

A solution of (1-benzyloxycarbonylamino-2-vinyl-cyclopropyl)-methyl-phosphinic acid ethyl ester (100 mg, 0.308 mmol) in ACN (7.7 mL) was cooled to 0° C. and TMSI (220 µL, 1.54 mmol) was added in a drop-wise fashion. The reaction was warmed to rt and stirred for an hour. The reaction was then cooled to 0° C. and additional TMSI (110 µL, 0.77 mmol) was added in a drop-wise fashion. The reaction was warmed to rt and stirred for 30 min. The reaction was cooled back to 0° C. and 2,6-lutidine (360 µL, 3.1 mmol) was added in a drop-wise fashion. This was followed by the addition of Et$_3$N (1 mL, 7.2 mmol) and MeOH (4 mL). The reaction was then concentrated in vacuum and crude was used directly in the next reaction.

A solution of VI (72 mg, 0.123 mmol) in THF (2 mL) was cooled to −30° C. Et$_3$N (34 µL, 0.246 mmol) was added to this solution followed by ClCO$_2$Et (18 µL, 0.185 mmol). The reaction was stirred at a temperature between −20° C. and −30° C. for 30 min. Additional Et$_3$N (34 µL, 0.246 mmol) and ClCO$_2$Et (18 µL, 0.185 mmol) was added to the reaction. The reaction was stirred for an additional 30 min at a temperature between −20° C. and −30° C. A solution of crude product from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuum and the residue was dissolved in MeOH (1.5 mL). Compound 94 was isolated from this solution by reverse-phase HPLC as a yellow solid (35 mg, 38%). $^1$H NMR (300 MHz, CD$_3$OD) δ 8.25 (d, J=9.3 Hz, 1H), 8.16 (m, 2H), 7.68 (m, 3H), 7.49 (m 1H), 7.39 (m 1H), 7.24 (dd, J=2.1, 9.3 Hz, 1H), 6.45 (m, 1H), 5.97 (m, 2H), 5.69 (s, 1H), 5.26 (d, J=17.1 Hz, 1H), 5.08 (d, J=11.4 Hz, 1H), 4.63 (m, 2H), 4.24 (m, 1H), 4.08 (m, 1H), 4.04 (s, 3H), 2.76 (dd, J=7.2, 14.1 Hz, 1H), 2.43 (ddd, J=3.3, 10.5, 13.8 Hz, 1H), 1.42-1.78 (m, 8H), 1.34 (d, J=6.3 Hz, 3H), 1.34 (m, 1H), 1.15 (m, 1H), 1.04 (s, 9H). $^{31}$P NMR (121.4 MHz, CD$_3$OD) δ 41.2. LC/MS 733 (M$^+$+1), 755 (M$^+$+Na).

Example 95

Preparation of Compound 95

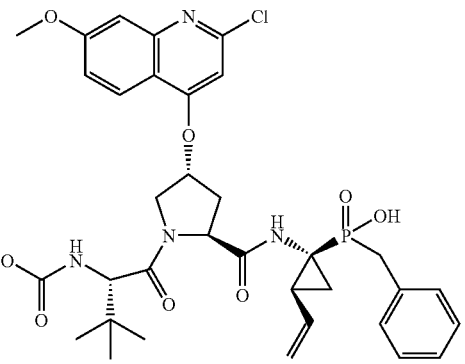

To a mixture of IX (12.38 g, 26.68 mmol) and 2-Amino-7-methoxy-quinolin-4-ol (7.11 g, 37.35 mmol) in NMP (133 mL) was added Cs$_2$CO$_3$ (10.43 g, 32.01 mmol). The reaction mixture was heated to 80° C. overnight and cooled to rt. The mixture was poured into brine (500 mL) and extracted with EtOAc (600 mL). The organic layer was washed with saturated NaHCO$_3$ (300 mL), brine (200 mL), dried with Na$_2$SO$_4$, and concentrated. The crude product was purified by combi-flash to give 4.02 g of 4-(2-Amino-7-methoxy-quinolin-4-yloxy)-pyrrolidine-1,2-dicarboxylic acid 1-tert-butyl ester 2-methyl ester in 26% yield.

A mixture of ester (4.02 g, 9.62 mmol) and 3-methyl-1-nitrosooxy-butane (7.18 mL, 48.5 mmol) in HOAc (21 mL) was stirred at rt for 36 h, poured into H$_2$O (500 mL), and extracted with CH$_2$Cl$_2$ (2×150 mL). The aqueous layer was diluted with brine (200 mL) and extracted with 10% MeOH/CH$_2$Cl$_2$ (2×150 mL). The combined organic layers were dried with Na$_2$SO$_4$ and concentrated. The crude product was purified by combi-flash to give 3.39 g of 4-(2-hydroxy-7-methoxy-quinolin-4-yloxy)-pyrrolidine-1,2-dicarboxylic acid 1-tert-butyl ester 2-methyl ester in 79% yield.

Crude 4-(2-hydroxy-7-methoxy-quinolin-4-yloxy)-pyrrolidine-1,2-dicarboxylic acid 1-tert-butyl ester 2-methyl ester (3.18 g, 7.60 mmol) was dissolved in POCl$_3$ (76 mL) and heated to 40° C. overnight. The reaction mixture was concentrated in vacuo and dissolved in CH$_2$Cl$_2$ (40 mL). 4 N HCl in 1,4-dioxane (40 mL) was added and stirred at r.t. for 1 h. The crude material was partitioned between H$_2$O and CH$_2$Cl$_2$ and pH was adjusted to 11 with NaHCO$_3$ and 1 N NaOH. The aqueous layer was extracted with CH$_2$Cl$_2$ (3×150 mL). The combined organic layer was dried with Na$_2$SO$_4$ and concentrated. The crude product was purified by combi-flash to give 2.05 g of 4-(2-Chloro-7-methoxy-quinolin-4-yloxy)-pyrrolidine-1,2-dicarboxylic acid 1-tert-butyl ester 2-methyl ester.

Amine obtained above (562 mg, 1.67 mmol), 2-Cyclopentyloxycarbonylamino-3,3-dimethyl-butyric acid (489.8 mg, 2.01 mmol) and HATU (1.27 g, 3.34 mmol) were dissolved in DMF (16 mL) and cooled to 0° C. NMM (0.74 mL, 6.73 mmol) was added. The reaction mixture was warmed to r. t. and stirred overnight. The product was partitioned between H$_2$O (300 mL) and EtOAc (3×100 mL). The combined organic layers were washed with H₂O (100 mL), NH₄Cl (100 mL), NaHCO₃ (100 mL), brine (100 mL), dried with Na₂SO₄, filtered, and concentrated. The crude product was purified by combi-flash to give 691.6 mg of dipeptide methyl ester in 71% yield.

Ester (664 mg, 1.18 mmol) was dissolved in THF (4 mL), H₂O (4 mL), and MeOH (4 mL) and LiOH (142.2 mg, 5.94 mmol) was added. The reaction mixture was stirred at r. t. for 2 h. The mixture was diluted with H₂O (15 mL)/EtOAc (20 mL), acidified to pH=2 with 1.0 N HCl, and the two layers were separated. The aqueous layer was extracted with EtOAc (3×50 mL), dried with Na₂SO₄, filtered, and concentrated to give 661 mg of acid. Acid (9³¹ mg, 1.87 mmol), (1-amino-2-vinyl-cyclopropyl)-benzyl-phosphinic acid ethyl ester (548.1 mg, 2.07 mmol) and HATU (1.42 g, 3.74 mmol) were dissolved in DMF (19 mL) and cooled to 0° C. NMM (1.03 mL, 9.37 mmol) was added. The reaction mixture was warmed to r. t. and stirred overnight. The product was partitioned between H₂O (300 mL) and EtOAc (3×100 mL). The combined organic layers were washed with H₂O (100 mL), NH₄Cl (100 mL), NaHCO₃ (100 mL), brine (100 mL), dried with Na₂SO₄, filtered, and concentrated. The crude product was purified by combi-flash to give 1.21 g of tripeptide phosphinate in 81% yield.

Tripeptide phosphinate was dissolved in CH₃CN (1 mL) and cooled to 0° C. Iodotrimethylsilane (72 µL, 0.51 mmol) was added dropwise. The reaction mixture was stirred at 0° C. for 45 min and 2,6-lutidine (0.5 mL) was added. MeOH (0.5 mL) was added and the reaction mixture was concentrated. The crude product was purified by HPLC to give 61.5 mg of 95 in 79% yield. ¹HNMR (300 MHz, CDCl₃) δ: 8.10 (d, J=9.3 Hz, 1H), 7.37-7.17 (m, 6H), 7.14 (dd, J=9.3, 2.1 Hz, 1H), 7.06 (s, 1H), 5.95 (dt, J=17.1, 9.3 Hz, 1H), 5.48 (bs, 1H), 5.32-5.21 (m, 1H), 5.11-5.03 (m, 1H), 4.68-4.51 (m, 3H), 4.22 (s, 1H), 4.06-3.98 (m, 1H), 3.95 (s, 1H), 3.35-3.23 (m, 2H), 2.73-2.62 (m, 1H), 2.41-2.28 (m, 1H), 2.17-2.04 (m, 1H), 1.82-1.33 (m, 10H), 1.03 (s, 9H); ³¹P (121.4 MHz, CDCl₃) δ: 47.5; LCMS (M+1): 767.06.

Example 96

Preparation of Compound 96

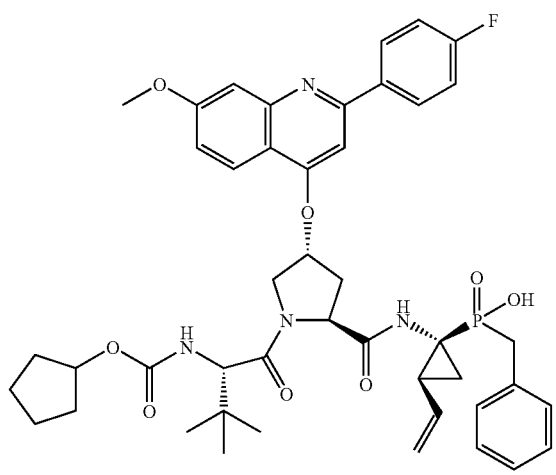

A solution of chloroquinoline from example 95 (51.7 mg, 0.06 mmol) in DMF (0.43 mL) was treated with 4-fluorophenylboronic acid (13.5 mg, 0.10 mmol) and tetrakistriphenylphosphine palladium (7.3 mg). A solution of K₂CO₃ (9 mg, 0.06 mmol) in H₂O (0.22 mL) was added to the above mixture. The reaction mixture was heated at 100° C. in microwave for 1 h. The desired ester (46.7 mg) was obtained after HPLC purification.

Ester (44.8 mg, 0.05 mmol) was dissolved in CH₃CN (0.53 mL) and cooled to 0° C. Iodotrimethylsilane (37.5 µL, 0.27 mmol) was added dropwise. The reaction mixture was stirred at 0° C. for 1 h and 2,6-lutidine (0.3 mL) was added. MeOH (0.3 mL) was added and the reaction mixture was concentrated. The crude product was purified by HPLC to give 17.7 mg of 96 in 41% yield. ¹H NMR (300 MHz, CDCl₃) δ: 8.37 (d, J=9.0 Hz, 1H), 8.20-8.12 (m, 2H), 7.71-7.44 (m, 7H), 7.44-7.18 (m, 3H), 5.96 (dt, J=16.8, 10.2 Hz, 1H), 5.83 (bs, 1H), 5.25 (d, J=16.8 Hz, 1H), 5.11-5.04 (m, 1H), 4.74-4.65 (m, 2H), 4.51-4.42 (m, 1H), 4.22-4.09 (m, 2H), 4.05 (s, 3H), 3.26 (d, J=15.6 Hz, 2H), 2.87-2.76 (m, 1H), 2.54-2.41 (m, 1H), 2.16-2.03 (m, 1H), 1.71-1.28 (m, 10H), 1.02 (s, 9H); ³¹P (121.4 MHz, CDCl₃) δ: 42.3, 32.6; LCMS (M+1): 827.06.

Example 97

Preparation of Compound 97

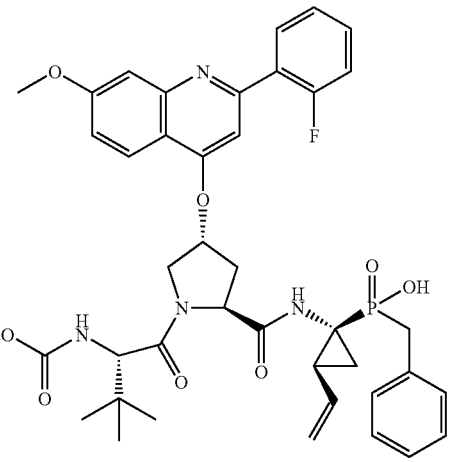

A solution of chloroquinoline from example 95 (78.2 mg, 0.10 mmol) in DMF (0.65 mL) was treated with 2-fluorophenylboronic acid (20.1 mg, 0.15 mmol) and tetrakistriphenylphosphine palladium (6.0 mg). A solution of K₂CO₃ (13.6 mg, 0.10 mmol) in H₂O (0.33 mL) was added to the above mixture. The reaction mixture was heated at 100° C. in microwave for 1 h. The desired ester (73.3 mg) was obtained after HPLC purification.

The phosphinate ester obtained above (73.3 mg, 0.09 mmol) was dissolved in CH₃CN (0.85 mL) and cooled to 0° C. Iodotrimethylsilane (61 µL, 0.43 mmol) was added dropwise. The reaction mixture was stirred at 0° C. for 1 h and 2,6-lutidine (0.3 mL) was added. MeOH (0.3 mL) was added and the reaction mixture was concentrated. The crude product was purified by HPLC to give 97. LCMS (M+1): 827.15

Example 98

Preparation of Compound 98

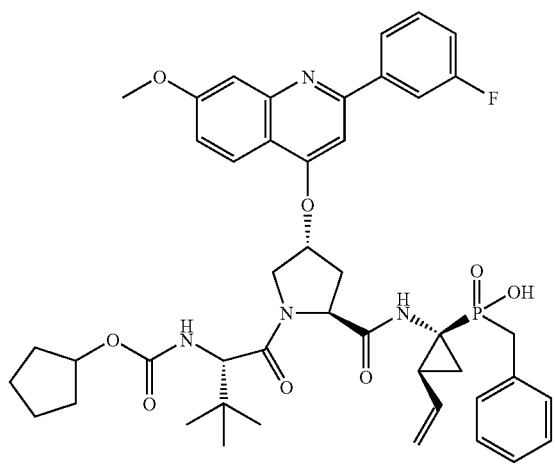

A solution of chloroquinoline from example 95 (78.0 mg, 0.10 mmol) in DMF (0.98 mL) was treated with 3-fluorophenylboronic acid (21.9 mg, 0.16 mmol) and tetrakistriphenylphosphine palladium (6.4 mg). A solution of $K_2CO_3$ (13.5 mg, 0.1 mmol) in $H_2O$ (0.3 mL) was added to the above mixture. The reaction mixture was heated at 100° C. in microwave for 1 h. The crude product was purified by HPLC to give 41 mg of ester in 49% yield.

Ester (41 mg, 0.05 mmol) was dissolved in $CH_3CN$ (0.48 mL) and cooled to 0° C. Iodotrimethylsilane (34 µL, 0.24 mmol) was added dropwise. The reaction mixture was stirred at 0° C. for 1 h and 2,6-lutidine (0.3 mL) was added. MeOH (0.3 mL) was added and the reaction mixture was concentrated. The crude product was purified by HPLC to give 23 mg of acid 98. LCMS (M+1): 827.13.

Example 99

Preparation of Compound 99

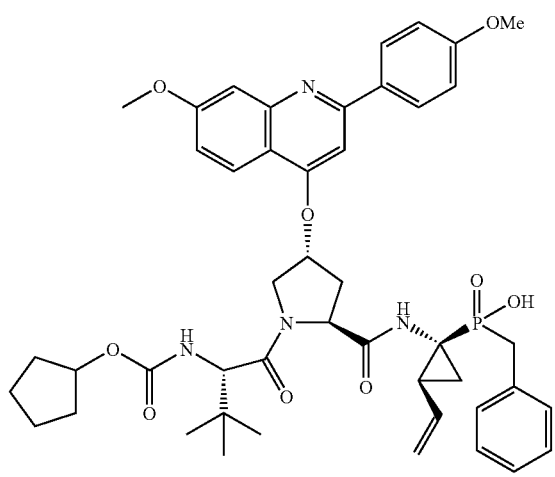

A solution of chloroquinoline from example 95 (78.4 mg, 0.10 mmol) in DMF (0.98 mL) was treated with 4-methoxyphenylboronic acid (23 mg, 0.15 mmol) and tetrakistriphenylphosphine palladium (5.9 mg). A solution of $K_2CO_3$ (13.5 mg, 0.1 mmol) in $H_2O$ (0.3 mL) was added to the above mixture. The reaction mixture was heated at 100° C. in microwave for 1 h. The crude product was purified by HPLC to give 43.8 mg of ester in 51% yield.

Ester (43.8 mg, 0.05 mmol) was dissolved in $CH_3CN$ (0.5 mL) and cooled to 0° C. Iodotrimethylsilane (36.5 µL, 0.26 mmol) was added dropwise. The reaction mixture was stirred at 0° C. for 1 h and 2,6-lutidine (0.3 mL) was added. MeOH (0.3 mL) was added and the reaction mixture was concentrated. The crude product was purified by HPLC to give 29 mg of acid 99.

Example 100

Preparation of Compound 100

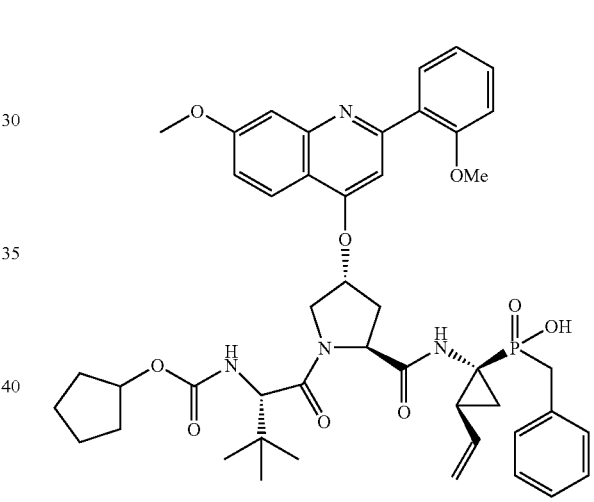

A solution of chloroquinoline from example 95 (79.9 mg, 0.10 mmol) in DMF (0.98 mL) was treated with 2-methoxyphenylboronic acid (24.4 mg, 0.16 mmol) and tetrakistriphenylphosphine palladium (5.9 mg). A solution of $K_2CO_3$ (13.7 mg, 0.1 mmol) in $H_2O$ (0.33 mL) was added to the above mixture. The reaction mixture was heated at 100° C. in microwave for 1 h. The crude product was purified by HPLC to give 29.9 mg of ester in 36% yield.

Ester (29.9 mg, 0.03 mmol) was dissolved in $CH_3CN$ (0.35 mL) and cooled to 0° C. Iodotrimethylsilane (25 µL, 0.18 mmol) was added dropwise. The reaction mixture was stirred at 0° C. for 1 h and 2,6-lutidine (0.3 mL) was added. MeOH (0.3 mL) was added and the reaction mixture was concentrated. The crude product was purified by HPLC to give 19 mg of acid 100.

Example 101

Preparation of Compound 101

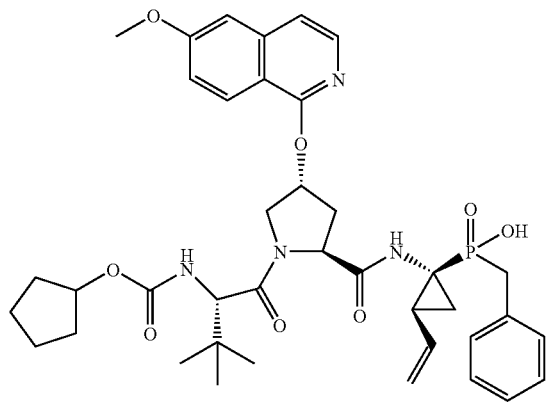

Dipeptides in examples 101-103 are known in prior literature. Each was coupled to the benzyl phospiniate P1 by the same method used in example 35. Prep HPLC afforded (Example 101) (22 mg, 24%). $^{1H}$ NMR (300 MHz, CD$_3$OD): δ 8.14 (d, J=8.8 Hz, 1H), 7.90 (d, J=6.0 Hz, 1H), 7.30 (m, 8H), 5.91 (m, 1H), 5.84 (bs, 1H), 5.21 (m, 1H), 5.05 (m, 1H) 4.63 (m, 2H), 4.50 (m, 1H), 4.03 (m, 1H), 3.94 (s, 3H), 3.32 (m, 2H), 2.65 (m, 1H), 2.33 (m, 1H), 2.11 (m, 1H), 1.60 (m, 10H) 1.03 (s, 9H). $^{31}$P (121.4 MHz, CD$_3$OD): δ42.175. LC (6 minute run, r.t.=4.15 min) MS (733.7, M+1)

Example 102

Preparation of Compound 102

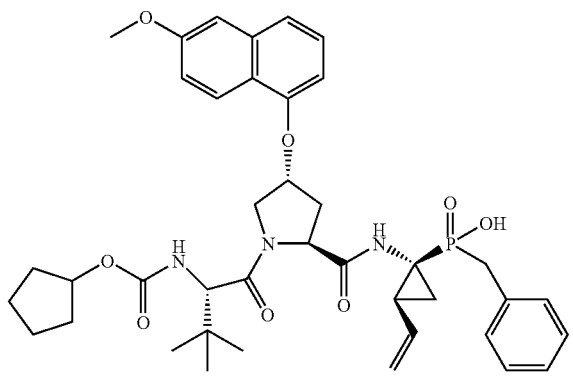

Prep HPLC afforded (Example 102) (29 mg, 26%). $^{1H}$ NMR (300 MHz, CD$_3$OD): δ 8.07 (d, J=9.2 Hz, 1H), 7.30 (m, 8H), 7.00 (d, J=8.9 Hz, 1H) 6.82 (d, J=6.1 Hz, 1H) 5.92 (m, 1H), 5.30 (m, 2H), 5.05 (m, 1H) 4.83 (bs, 1H) 4.58 (m, 1H), 4.42 (m, 1H), 4.03 (m, 1H), 3.90 (s, 3H), 3.32 (m, 2H), 2.65 (m, 1H), 2.28 (m, 1H), 2.06 (m, 1H), 1.60 (m, 10H) 1.03 (s, 9H). $^{31}$P (121.4 MHz, CD$_3$OD): δ42.159. LC (6 minute run, r.t.=4.32 min) MS (732.7, M+1)

Example 103

Preparation of Compound 103

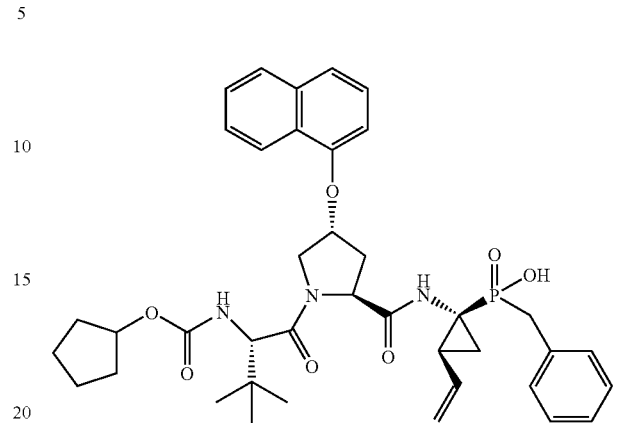

Prep HPLC afforded (Example 103) (15 mg, 19%). $^{1H}$ NMR (300 MHz, CD$_3$OD): δ 8.18 (d, J=8.0 Hz, 1H), 7.80 (d, J=8.2 Hz, 1H), 7.30 (m, 8H), 6.97 (d, J=7.6 Hz, 1H) 5.92 (m, 1H), 5.30 (m, 2H), 5.05 (m, 1H) 4.83 (bs, 1H) 4.56 (m, 1H), 4.45 (m, 1H), 4.05 (m, 1H), 3.32 (m, 2H), 2.67 (m, 1H), 2.28 (m, 1H), 2.07 (m, 1H), 1.60 (m, 10H) 1.03 (s, 9H). $^{31}$P (121.4 MHz, CD$_3$OD): δ42.125 LC (6 minute run, r.t.=4.37 min) MS (702.7, M+1)

Example 104

Preparation of Compound 104

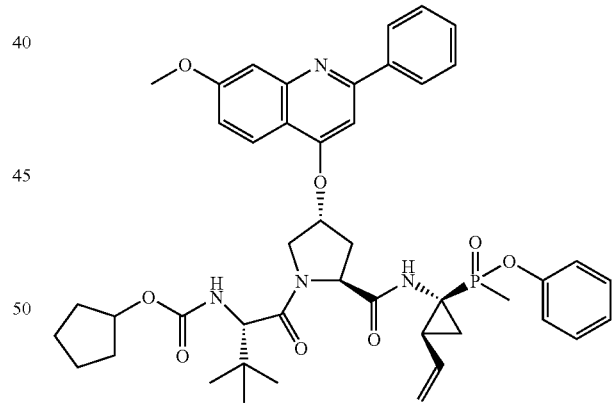

Compound 94 (100 mg, 0.14 mmol) was dissolved in pyridine (3 mL) followed by the addition of phenol (129 mg, 1.37 mmol) and the solution was heated at 60° C. for 10 min. To the heated solution was added dicyclohexylcarbodiimide (169 mgs, 0.82 mmol) and the reaction mixture was further heated for 3 h. The reaction mixture was then cooled to rt and the solvents were removed under reduced pressure. The reaction mixture was dilued with EtOAc and the solids were filtered. Solvent was removed under reduced pressure and the crude product was purified on combi-flash EtOAc/Hex to afford 23 mg of phosphinate prodrug in 21% yield. $^1$H NMR (300 MHz, CDCl$_3$): δ 8.07-7.99 (m, 2H), 7.55-7.00 (m, 11H), 5.89-5.83 (m, 1H), 5.45-4.91 (m, 4H), 4.33-3.96 (m, 5H), 2.56 (m, 2H), 1.97-0.90 (m, 28H). $^{31}$P (121.4 MHz, CDCl$_3$): 51.6 (s, $^{31}$P), 48.86 (s, $^{31}$P); LC/MS: M+Na=8$^{31}$.

Example 105

Preparation of Compound 105

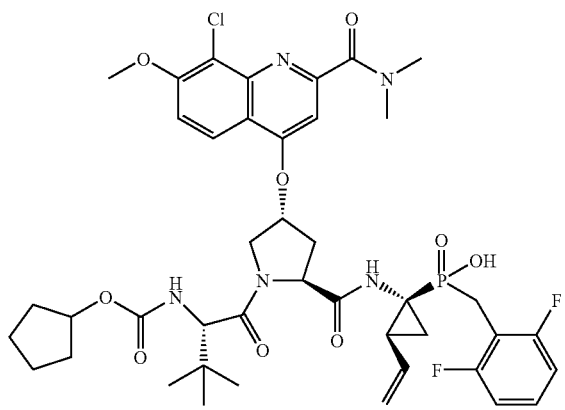

Step 1. The 8-chloro-4-hydroxy-7-methoxy-quinoline-2-carboxylic acid (500 mg, 1.97 mmol) and 2.0 M dimethylamine in THF (2 mL, 3.94 mmol) were dissolved in DMF (20 mL). HATU (1.5 g, 3.94 mmol) and NMM (697 mg, 6.89 mmol) were added and the mixture was stirred at r.t. overnight. The reaction was diluted with EtOAc and acidified with 1 N HCl. The two layers were separated. The organic layer was washed with 2% LiCl, saturated NaHCO$_3$ and brine, dried with Na$_2$SO$_4$, and concentrated to give 8-chloro-4-hydroxy-7-methoxy-quinoline-2-carboxylic acid dimethylamide.

A solution of brosylate example 58 (100 mg, 0.11 mmol) and phenol obtained above (35 mg, 0.11 mmol) in NMP (5 mL) was treated with Cs$_2$CO$_3$ (76 mg, 0.22 mmol). The reaction mixture was heated to 80° C. for 3 h and cooled to rt. The reaction was diluted with EtOAc and washed with H$_2$O. The aqueous layer was brought to pH=4 with 1 N HCl and extracted with 5% MeOH/EtOAc (2×). The combined organic layers were dried with Na$_2$SO$_4$ and concentrated to give 58 mg of phosphinate. To a solution of phosphinate (58 mg, 0.06 mmol) in CH$_3$CN (0.5 mL) at 0° C. was added iodotrimethylsilane (0.05 mL, 0.32 mmol). The reaction mixture was warmed to r.t. and stirred for 30 minutes and then cooled to 0° C. 2,6-Lutidine (0.32 mL) and MeOH (0.5 mL) were added and stirred for 10 minutes. The solvent was concentrated and the crude product was purified by HPLC to give acid 105. $^1$H NMR (300 MHz, CD$_3$OD): δ8.20 (d, J=9.3 Hz, 1H), 7.48 (d, J=8.7 Hz, 1H), 7.28 (m, 1H), 7.14 (s, 1H), 6.95 (m, 2H), 6.00 (m, 1H), 5.52 (m, 1H), 5.38 (m, 1H), 5.12 (m, 1H), 4.62 (m, 2H), 4.$^{31}$ (bs, 1H), 4.17 (s, 3H), 4.06 (m, 3H), 3.20 (m, 6H), 2.74 (m, 1H), 2.42 (m, 1H), 2.20 (m, 1H), 1.70-1.40 (m, 8H), 1.30 (m, 2H), 1.01 (s, 9H). LC/MS=874.13 (M$^+$+1), 896.27 (M$^+$+Na)

Example 106

Preparation of Compound 106

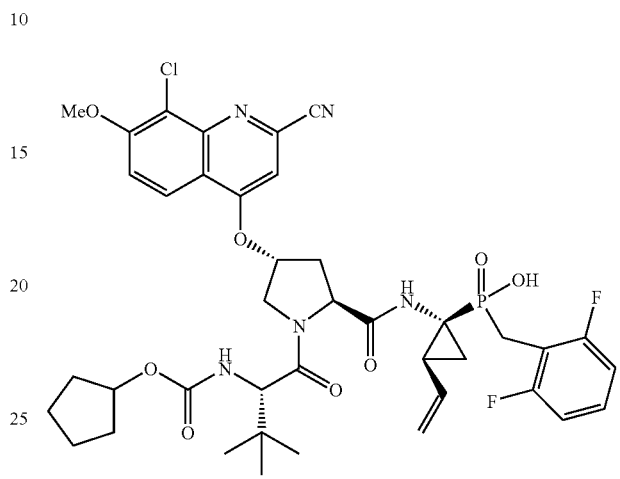

8-Chloro-4-hydroxy-7-methoxy-quinoline-2-carboxylic acid (115 mg, 0.45 mmol) and ammoniumchloride (36 mg, 0.68 mmol) were dissolved in DMF (4 mL). HATU (342 mg, 0.9 mmol) and NMM (159 mg, 1.58 mmol) were added and the mixture was stirred at r.t. overnight. An additional amount of ammoniumchloride (72 mg, 13.5 mmol) was added and heated to 53° C. for 18 h. The reaction mixture was cooled to r.t. and concentrated to give 8-chloro-4-hydroxy-7-methoxy-quinoline-2-carboxylic acid amide as a yellow solid.

A solution of brosylate example 58 (380 mg, 0.44 mmol) and 8-chloro-4-hydroxy-7-methoxy-quinoline-2-carboxylic acid amide (100 mg, 0.4 mmol) in NMP (3 mL) was treated with Cs$_2$CO$_3$ (287 mg, 0.88 mmol). The reaction mixture was heated to 80° C. overnight and then cooled to rt. The reaction mixture was diluted with EtOAc and washed with H$_2$O. The aqueous layer was brought to pH=4 with 1 N HCl and extracted with EtOAc (2×). The combined organic layers were dried with Na$_2$SO$_4$ and concentrated. 334 mg of crude product was obtained.

To a solution of crude product obtained above (78 mg, 0.09 mmol) in CH$_3$CN (0.5 mL) at 0° C. was added iodotrimethylsilane (89 mg, 0.45 mmol). The reaction mixture was stirred at 0° C. for 20 minutes. 2,6-Lutidine (0.06 mL) and MeOH (0.5 mL) were added, stirred for 20 minutes, concentrated in vacuo, and dried for 20 minutes to give acid, which was treated with TFAA to provide 106. $^1$H NMR (300 MHz, CD$_3$OD): δ8.21 (d, J=9.6 Hz, 1H), 7.56 (d, J=9.6 Hz, 2H), 7.44 (s, 1H), 7.28 (m, 1H), 6.96 (m, 2H), 5.96 (m, 1H), 5.54 (s, 1H), 5.30 (d, J=17.1 Hz, 1H), 5.11 (d, J=12.0 Hz, 1H), 4.69-4.56 (m, 2H), 4.36 (bs, 1H), 4.17-4.00 (m, 6H), 3.38 (m, 2H), 2.74 (m, 1H), 2.45 (m, 1H), 2.20 (m, 1H), 1.67-1.54 (m, 8H), 1.47 (m, 2H), 1.02 (s, 9H). $^{31}$P (121.4 MHz, CDCl$_3$): δ 41.479. LC/MS=874.13 (M$^+$+1), 896.27 (M$^+$+Na)

Example 107

Preparation of Compound 107

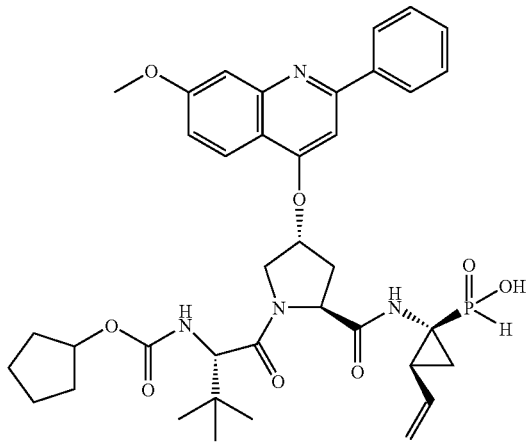

A solution of the acid VI (160 mg, 0.27 mmol), HATU (256 mg, 0.67 mmol), acid (example 9) (80 mg, 0.54 mmol), and NMM (148 µl, 1.35 mmol) stirred in DMF (1 mL) overnight at rt. The solution was concentrated and purified with a Gilson HPLC to obtain 107 (25.3 mg, 13%) as a white solid. $^{1H}$ NMR (300 MHz, CD$_3$OD): δ 8.39 (d, J=9.0 Hz, 1H), 8.10 (d, J=9.3 Hz, 2H), 7.79 (m, 2H), 7.63 (s, 1H), 7.58 (s, 1H), 7.39 (d, J=8.8 Hz, 1H), 5.87 (m, 2H), 5.30 (d, J=9.6 Hz, 1H), 5.18 (d, J=9.0 Hz, 1H) 4.78 (m, 3H), 4.20 (s, 1H), 4.05 (s, 3H), 2.80 (m, 1H), 2.50 (m, 1H), 2.10 (m, 1H), 1.62 (m, 2H,) 1.40 (m, 2H) 1.05 (s, 9H). $^{31}$P (121.4 MHz, CD$_3$OD): δ23.135

Example 108

Preparation of Compound 108

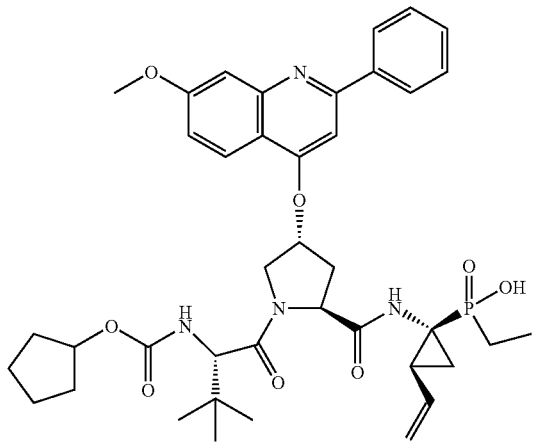

The P1 phosphinate amine was prepared as described in example 2 and coupled with VI. $^1$H NMR (300 MHz, CD$_3$OD) δ8.36 (d, J=9.3 Hz, 1H), 8.1 (m, 2H), 7.76 (m, 3H), 7.65 (s, 1H), 7.55 (d, J=2.1 Hz, 1H), 7.38 (dd, J=2.4, 9.3 Hz, 1H), 5.96 (dt, J=9.9, 17.1 Hz, 1H), 5.85 (s, 1H), 5.26 (d, J=16.8 Hz, 1H), 5.08 (d, J=12 Hz, 1H), 4.66 (m, 2H), 4.46 (s, 1H), 4.16 (s, 1H), 4.08 (m, 1H), 4.06 (s, 3H), 2.78 (dd, J=6.6, 14.1 Hz, 1H), 2.43 (ddd, J=3.9, 10.2, 14.1 Hz, 1H), 2.08 (m, 1H), 1.83 (m, 2H), 1.39-1.65 (brm, 10H), 1.14 (dt, J=7.8, 18.3 Hz, 3H), 1.04 (s, 9H). $^{31}$P NMR (121.4 MHz, CD$_3$OD) δ 50.6
LC/MS=746.8 (M$^+$+1)

Example 109

Preparation of Compound 109

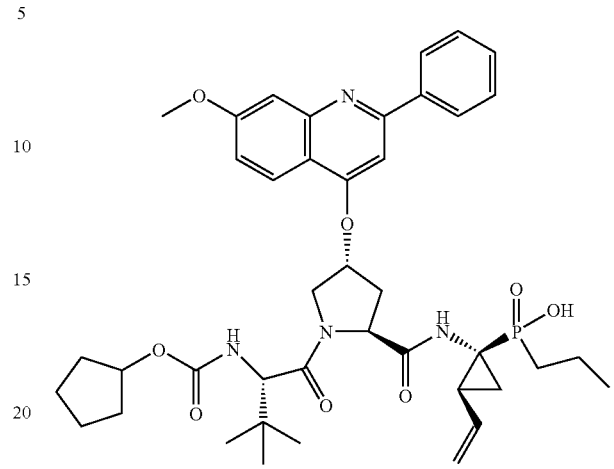

The P1 phosphinate amine was prepared as described in example 10 and coupled with VI. $^{1H}$ NMR (300 MHz, CD$_3$OD): δ 8.38 (d, J=9.6 Hz, 1H), 8.11 (m, 2H), 7.76 (m, 3H), 7.65 (m 1H), 7.55 (m 1H), 7.24 (dd, J=2.1, 9.6 Hz, 1H), 6.02 (m, 1H), 5.81 (m, 1H), 5.22 (d, J=9.6 Hz, 1H), 5.09 (d, J=9.0 Hz, 1H), 4.63 (m, 2H), 4.45 (bs, 1H), 4.20 (m, 1H), 4.07 (m, 4H), 2.80 (m, 1H), 2.41 (m, 1H), 2.10 (m, 1H), 1.89-1.33 (m, 13H), 1.05 (m, 12H). $^{31}$P (121.4 MHz, CD$_3$OD): δ48.663
LC/MS=761 (M$^+$+1)

Example 110

Preparation of Compound 110

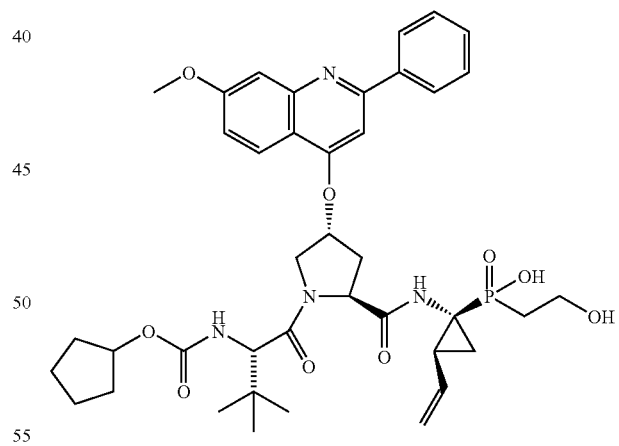

The acid VI (82 mg, 0.14 mmol) was suspended in 1 mL of DMF. HATU (133 mg, 0.35 mmol), (1-Amino-2-vinyl-cyclopropyl)-(2-hydroxy-ethyl)-phosphinic acid (example 24) (53 mg, 0.28 mmol), followed by NMM (77 µl, 0.70 mmol) was added. The solution stirred overnight at rt. The mixture was purified via Gilson HPLC to obtain 110 (28.3 mg, 27%) as a white solid. $^{1H}$ NMR (300 MHz, CD$_3$OD): δ 8.39 (d, J=9.0 Hz, 1H), 8.10 (d, J=9.3 Hz, 2H), 7.79 (m, 2H), 7.63 (s, 1H), 7.58 (s, 1H), 7.39 (d, J=8.8 Hz, 1H), 5.87 (m, 2H), 5.30 (d, J=9.6 Hz, 1H), 5.18 (d, J=9.0 Hz, 1H) 4.78 (m, 3H), 4.20 (s, 1H), 4.05 (s, 3H), 3.80 (m, 1H), 2.80 (m, 1H), 2.50 (m, 1H), 2.20 (m, 1H), 2.10 (m, 1H), 1.62 (m, 2H,) 1.40 (m, 2H) 1.20 (d, 3H), 1.05 (s, 9H). $^{31}$P (121.4 MHz, CD$_3$OD): δ44.493

Example 111

Preparation of Compound 111

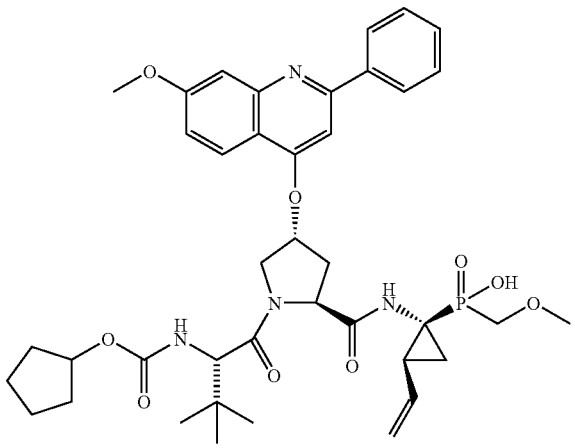

A solution of the acid VI (100 mg, 0.17 mmol), HATU (161 mg, 0.42 mmol), amine example x (65 mg, 0.34 mmol), and NMM (93 µl, 0.85 mmol) stirred in DMF (1 mL) overnight at rt. The solution was concentrated and purified with a Gilson HPLC to obtain 111 (97 mg, 75%) as a white solid. $^{1H}$ NMR (300 MHz, CD$_3$OD): δ 8.39 (d, J=9.0 Hz, 1H), 8.10 (d, J=9.3 Hz, 2H), 7.79 (m, 2H), 7.63 (s, 1H), 7.58 (s, 1H), 7.39 (d, J=8.8 Hz, 1H), 5.87 (m, 2H), 5.30 (d, J=9.6 Hz, 1H), 5.18 (d, J=9.0 Hz, 1H) 4.78 (m, 3H), 4.20 (s, 1H), 4.05 (s, 3H), 2.80 (m, 1H), 2.50 (m, 1H), 2.10 (m, 1H), 1.62 (m, 2H,) 1.40 (m, 2H) 1.05 (s, 9H). $^{31}$P (121.4 MHz, CD$_3$OD): δ37.043

Example 112

Preparation of Compound 112

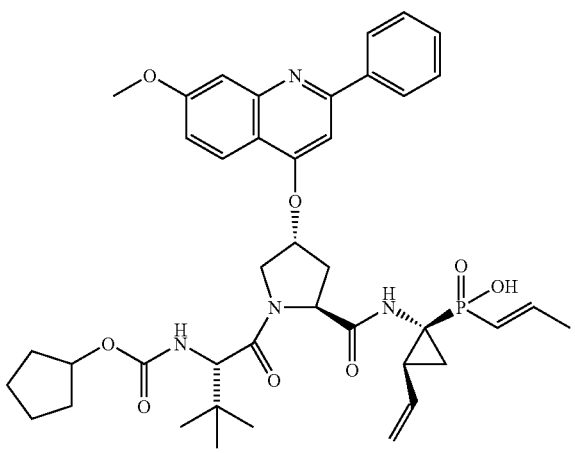

The P1 phosphinate amine was prepared as described in example 17 and coupled with VI. $^{1H}$ NMR (300 MHz, CD$_3$CN): δ 8.25 (d, J=9.0 Hz, 1H), 8.06 (m, 2H), 7.80 (m 1H), 7.63 (m 3H), 7.31 (m, 2H), 6.50 (m, 1H), 5.89 (m, 2H), 5.64 (bs, 1H), 5.04 (d, J=16.5 Hz, 1H), 4.91 (d, J=10.5 Hz, 1H), 4.62 (m, 3H), 4.20 (m, 1H), 3.98 (m, 4H), 2.67 (m, 1H), 2.39 (m, 1H), 1.90 (m, 1H), 1.89-1.23 (m, 12H), 1.05 (s, 9H). $^{31}$P (121.4 MHz, CD$_3$CN): δ33.463. LC/MS=759 (M$^+$+1)

Example 113

Preparation of Compound 113

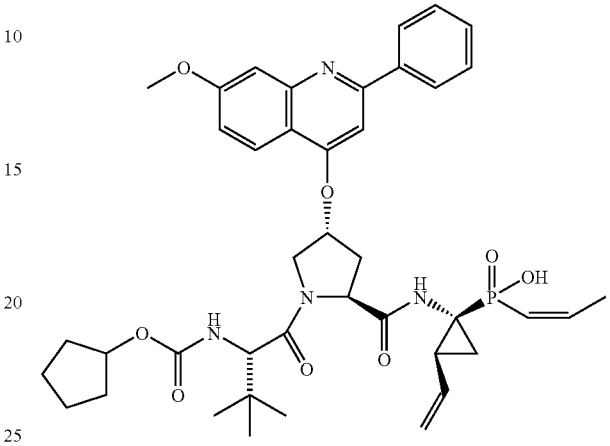

The P1 phosphinate amine was prepared as described in example 18 and coupled with VI. $^{1H}$ NMR (300 MHz, CD$_3$OD): δ 8.36 (d, J=9.6 Hz, 1H), 8.08 (m, 2H), 7.76 (m, 3H), 7.65 (m 1H), 7.55 (m 1H), 7.39 (dd, J=2.1, 9.6 Hz, 1H), 6.63-6.41 (m, 1H), 5.96 (m, 2H), 5.81 (bs, 1H), 5.25 (d, J=16.8 Hz, 1H), 5.07 (d, J=12.0 Hz, 1H), 4.65 (m, 2H), 4.44 (bs, 1H), 4.15 (m, 1H), 4.04 (m, 4H), 2.77 (m, 1H), 2.43 (m, 1H), 2.10 (m, 3H), 1.69-1.33 (m, 8H), 1.05 (s, 9H). $^{31}$P (121.4 MHz, CD$_3$OD): δ33.412

LC/MS=759 (M$^+$+1)

Example 114

Preparation of Compound 114

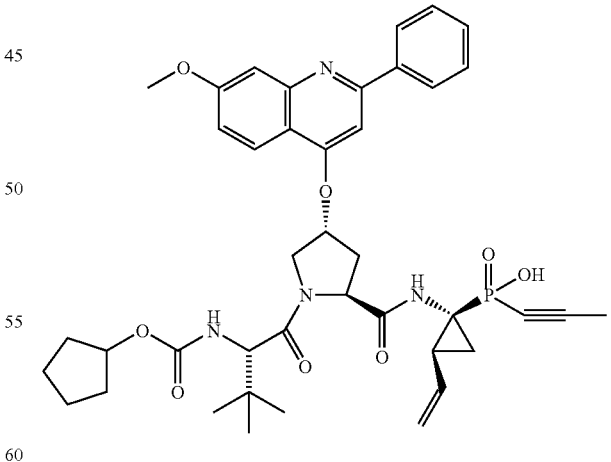

$^{1H}$ NMR (300 MHz, CD$_3$OD): δ 8.37 (d, J=9.0 Hz, 1H), 8.09 (m, 2H), 7.77 (m, 3H), 7.67 (m 1H), 7.53 (m 1H), 7.38 (m, 1H), 5.98 (m, 1H), 5.84 (bs, 1H), 5.24 (d, J=16.8 Hz, 1H), 5.07 (d, J=10.2 Hz, 1H), 4.70 (m, 2H), 4.46 (bs, 1H), 4.17 (m, 1H), 4.06 (m, 4H), 2.80 (m, 1H), 2.54 (m, 1H), 2.21 (m, 1H), 1.98 (m, 3H), 1.69-1.33 (m, 8H), 1.05 (s, 9H). $^{31}$P (121.4 MHz, CD$_3$OD): δ10.616. LC/MS=757 (M$^+$+1)

Example 115

Preparation of Compound 115

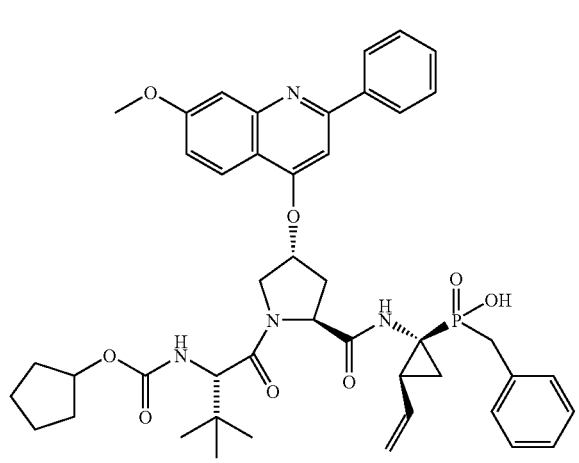

The P1 phosphinate amine was prepared as described in example 35 and coupled with VI. $^{1}H$ NMR (300 MHz, CD$_3$OD): δ 8.38 (d, J=9.3 Hz, 1H), 8.10 (m, 2H), 7.77 (m, 3H), 7.65 (m 1H), 7.55 (m 1H), 7.24 (m, 1H), 5.98 (m, 1H), 5.87 (bs, 1H), 5.27 (d, J=17.1 Hz, 1H), 5.08 (d, J=10.5 Hz, 1H), 4.72 (m, 2H), 4.46 (bs, 1H), 4.17 (m, 1H), 4.07 (m, 4H), 2.83 (m, 1H), 2.48 (m, 1H), 2.09 (m, 1H), 1.97 (m, 3H), 1.69-1.33 (m, 10H), 1.05 (s, 9H). $^{31}$P (121.4 MHz, CD$_3$OD): δ40.676. LC/MS=809 (M$^+$+1)

Example 116

Preparation of Compound 116

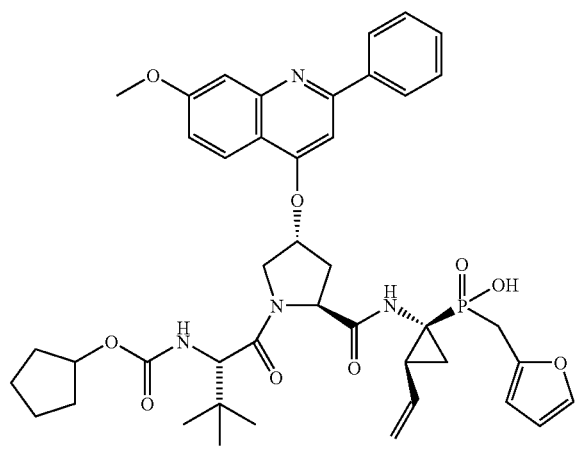

The P1 phosphinate amine was prepared as described in example 83 and coupled with VI. $^1$H NMR (300 MHz, CD$_3$OD) δ 8.39 (d, J=9.6 Hz, 1H), 8.10 (dd, J=1.2 Hz, 5.4 Hz, 2H), 7.77 (m, 5H), 7.68 (s, 1H), 7.55 (s, 1H), 7.38 (m, 2H), 6.30 (m, 2H), 5.89 (m, 1H), 5.82 (s, 1H), 5.20 (d, J=17.1 Hz, 1H), 5.07 (d, J=8 Hz, 1H), 4.75 (m, 2H), 4.51 (b, 1H), 4.17 (s, 1H), 4.07 (s, 3H), 3.35 (m, 2H), 2.78 (m, 1H), 2.50 (m, 1H), 2.10 (m, 1H), 1.41-1.78 (m, 8H), 1.04 (s, 9H). $^{31}$P NMR (121.4 MHz, CD$_3$OD) δ 39.32.
LC/MS 799 (M$^+$+1).

Example 117

Preparation of Compound 117

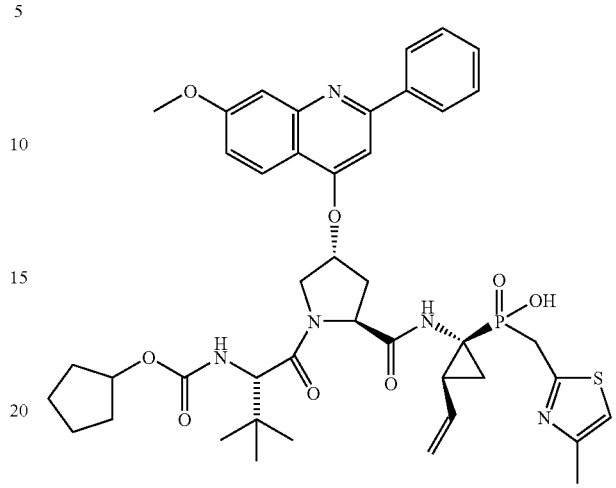

The P1 phosphinate amine was prepared as described in example 87 and coupled with VI. $^1$H NMR (300 MHz, CD$_3$OD) δ 8.39 (d, J=9.6 Hz, 1H), 8.10 (dd, J=1.2 Hz, 5.4 Hz, 2H), 7.77 (m, 5H), 7.68 (s, 1H), 7.55 (d, J=2.1 Hz, 1H), 7.42 (m, 2H), 5.89 (br, 1H), 5.75 (m, 1H), 5.10 (d, J=17.1 Hz, 1H), 4.80 (d, 1H) 4.69 (m, 2H), 4.51 (b, 1H), 4.17 (s, 1H), 4.07 (s, 3H), 3.72 (m, 2H), 2.78 (m, 1H), 2.50 (m, 4H), 2.17 (m, 1H), 1.41-1.78 (m, 8H), 1.04 (s, 9H). $^{31}$P NMR (121.4 MHz, CD$_3$OD) δ 24.93. LC/MS 830 (M$^+$+1)

Example 118

Preparation of Compound 118

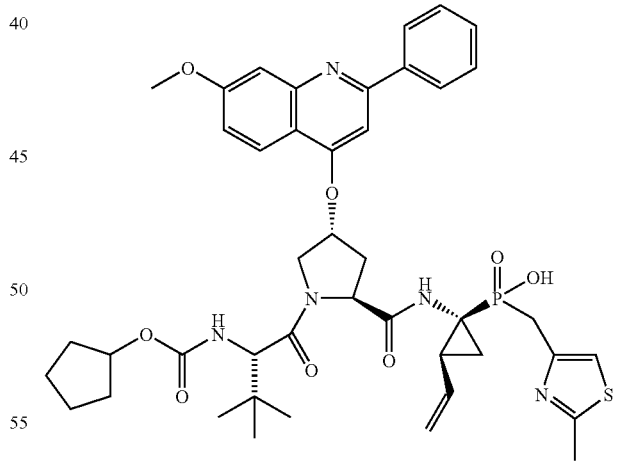

The P1 phosphinate amine was prepared as described in example 88 and coupled with VI. $^{1H}$ NMR (300 MHz, CD$_3$OD): δ 8.37 (d, 1H, J=9.3 Hz), 8.05-8.17 (m, 2H), 7.70-7.83 (m, 3H), 7.68 (s, 1H), 7.50-7.62 (m, 2H), 7.35 (dd, 1H, J=–9.3 and 2.1 Hz), 5.89 (br, 1H), 5.72 (dt, 1H, J=17.1 and 9.9 Hz), 5.09 (d, 1H, J=17.1 Hz), 4.70-5.04 (m, 4H), 4.51 (br, 1H), 4.21 (br, 1H), 4.04-4.18 (m, 1H), 4.05 (s, 3H), 3.36-3.50 (m, 2H), 2.82-2.94 (m, 1H), 2.80 (s, 3H), 2.50-2.65 (m, 1H), 2.09 (br m, 1H), 1.32-1.80 (m, 9H), 1.05 (s, 9H). $^{31}$P (121.4 MHz, CD$_3$OD): δ 33.449. LC/MS=830 (M$^+$+1)

Example 119

Preparation of Compound 119

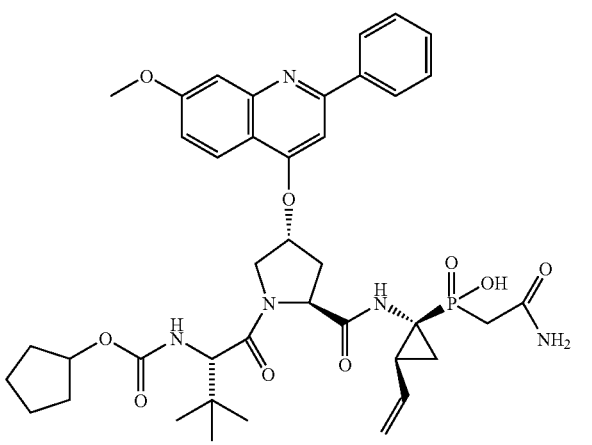

The acid VI (85 mg, 0.14 mmol) was suspended in 1 mL of DMF. HATU (133 mg, 0.35 mmol), (1-amino-2-vinyl-cyclopropyl)-carbamoylmethyl-phosphinic acid (59 mg, 0.29 mmol), followed by NMM (77 µl, 0.70 mmol) was added. The solution stirred overnight at rt. The mixture was purified via Gilson HPLC to obtain 119 (30 mg, 27%) as a white solid. $^{1}H$ NMR (300 MHz, CD$_3$OD): δ 8.39 (d, J=9.0 Hz, 1H), 8.10 (d, J=9.3 Hz, 2H), 7.79 (m, 2H), 7.63 (s, 1H), 7.58 (s, 1H), 7.39 (d, J=8.8 Hz, 1H), 5.87 (m, 2H), 5.83 (s, 1H), 5.22 (d, J=9.6 Hz, 1H), 5.13 (d, J=9.0 Hz, 1H), 4.78 (m, 2H), 4.50 (s, 1H), 4.20 (s, 1H), 4.05 (s, 3H), 3.15 (m, 1H), 2.80 (m, 1H), 2.50 (m, 1H), 2.10 (m, 1H), 1.62 (m, 4H), 1.40 (m, 2H), 1.05 (s, 9H). $^{31}$P (121.4 MHz, CD$_3$OD): δ36.428

Example 120

Preparation of Compound 120

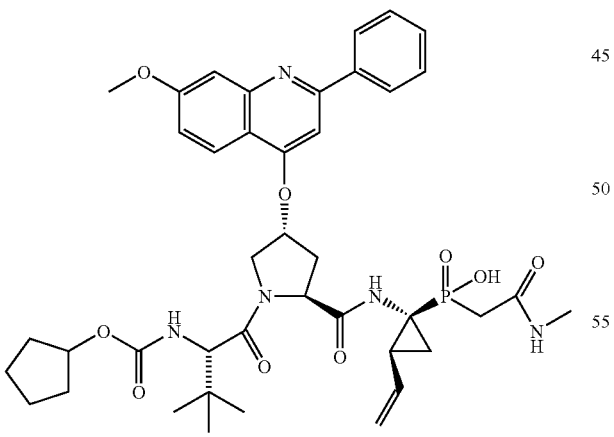

The acid VI (76 mg, 0.13 mmol) was suspended in 1 mL of DMF. HATU (123 mg, 0.32 mmol), (1-amino-2-vinyl-cyclopropyl)-methylcarbamoylmethyl-phosphinic acid (56 mg, 0.26 mmol), followed by NMM (71 µl, 0.65 mmol) was added. The solution stirred overnight at rt. The mixture was purified via Gilson HPLC to obtain 120 (93 mg, 91%) as a white solid. $^{1}H$ NMR (300 MHz, CD$_3$OD): δ 8.39 (d, J=9.0 Hz, 1H), 8.10 (d, J=9.3 Hz, 2H), 7.79 (m, 2H), 7.63 (s, 1H), 7.58 (s, 1H), 7.39 (d, J=8.8 Hz, 1H), 5.87 (m, 2H), 5.30 (d, J=9.6 Hz, 1H), 5.18 (d, J=9.0 Hz, 1H) 4.78 (m, 3H), 4.20 (s, 1H), 4.05 (s, 3H), 3.30 (m, 1H), 3.20 (d, 1H), 3.18 (m, 3H), 2.87 (s, 3H), 2.80 (m, 1H), 2.50 (m, 1H), 2.10 (m, 1H), 1.62 (m, 2H,) 1.40 (m, 2H) 1.20 (d, 3H), 1.05 (s, 9H). $^{31}$P (121.4 MHz, CD$_3$OD): δ37.802

Example 121

Preparation of Compound 121

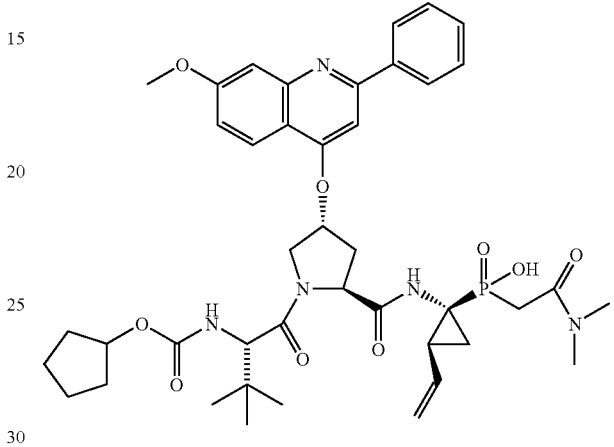

The acid VI (100 mg, 0.17 mmol) was suspended in 1 mL of DMF. HATU (161 mg, 0.42 mmol), (1-amino-2-vinyl-cyclopropyl)-dimethylcarbamoylmethyl-phosphinic acid (78 mg, 0.34 mmol), followed by NMM (93 µl, 0.85 mmol) was added. The solution stirred overnight at rt. The mixture was purified via Gilson HPLC to obtain 121 (112 mg, 82%) as a white solid. $^{1}H$ NMR (300 MHz, CD$_3$OD): δ 8.39 (d, J=9.0 Hz, 1H), 8.10 (d, J=9.3 Hz, 2H), 7.79 (m, 2H), 7.63 (s, 1H), 7.58 (s, 1H), 7.39 (d, J=8.8 Hz, 1H), 5.87 (m, 2H), 5.30 (d, J=9.6 Hz, 1H), 5.18 (d, J=9.0 Hz, 1H) 4.78 (m, 3H), 4.20 (s, 1H), 4.05 (s, 3H), 3.30 (m, 1H), 3.20 (d, 1H), 3.18 (m, 3H), 2.87 (s, 3H), 2.80 (m, 1H), 2.50 (m, 1H), 2.10 (m, 1H), 1.62 (m, 2H,) 1.40 (m, 2H) 1.05 (s, 9H). $^{31}$P (121.4 MHz, CD$_3$OD): δ37.043.

Example 122

Preparation of Compound 122

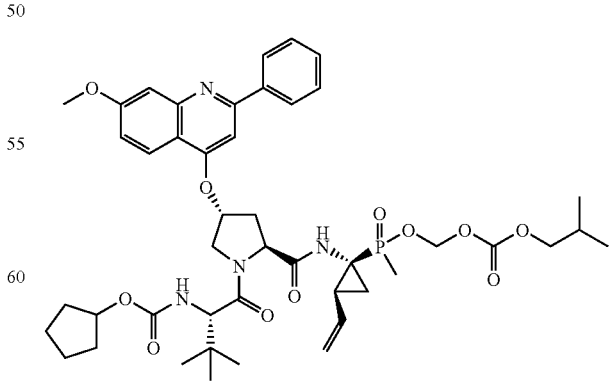

Compound 94 (200 mg, 0.27 mmol) was dissolved in ACN (5 mL) followed by the addition of TEA (1 mL) and the solution was heated at 70° C. for 10 min. To the heated solution, isobutylchloro-methylcarbonate was added and the reaction mixture was further heated for 5 h. The reaction mixture was then cooled to rt and the solvents were removed under reduced pressure. The crude product was purified by reverse phase prep HPLC followed by lyophilization to afford 102 mg of phosphinate prodrug in 49% yield.

$^1$H NMR (300 MHz, CD$_3$OD): δ 8.01-7.95 (m, 3H), 7.57-7.48 (m, 3H), 7.39 (s, 1H), 7.26 (m, 1H), 7.09 (m, 1H), 6.78-6.70 (m, 1H), 5.98-5.55 (m, 4H), 5.35-5.10 (m, 2H), 4.74-4.64 (s, 1H), 4.55-4.52 (m, 2H), 4.29-4.26 (m, 1H), 4.07-4.03 (m, 1H), 3.95-3.81 (m, 4H), 3.34-3.$^{31}$ (m, 1H), 2.69-2.63 (m, 1H), 2.38-2.13 (m, 2H), 1.99-1.33 (m, 12H), 1.$^{31}$-0.80 (m, 18H). $^{31}$P (121.4 MHz, CD$_3$OD): 53.15 (s, $^{31}$P); LC/MS: M+1=863.

Example 123

Preparation of Compound 123

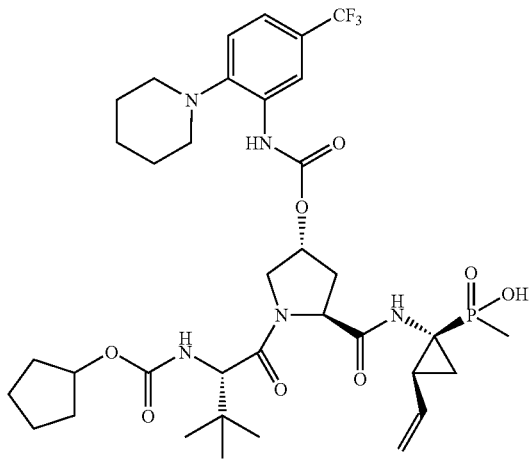

Step 1. To dipeptide (1.0 g, 2.70 mmol) dissolved in 20 mL of THF was added DSC (1.38 g, 5.40 mmol) followed by NaH (60% dispersion in mineral oil) (270 mg, 6.75 mmol). The reaction was refluxed for 6 hs, quenched by adding 120 mL of 1M solution of HCl in water, extracted by EtOAc and dried using anhydrous magnesium sulfate. The organic phase was concentrated under vacuo, dissolved in 6 mL of DCM and added to a microwave flask. To the solution was added 2-piperidin-1-yl-5-trifluoromethyl-phenylamine (1.98 mg, 8.10 mmol). The microwave flask was sealed and put on the microwave apparatus. The reaction was heated to 65° C. for 1 hour. The reaction was purified by silica gel chromatography using SiO$_2$ (eluted with 0% to 100% EtOAc/hexane) to give crude as a yellow solid (1.0 g, 58%). LC/MS=641 (M$^+$+1)

Step 2. To crude (100 mg, 0.156 mm) dissolved in 1.5 mL of pyridine was added NaI (467 mg, 3.12 mm). The reaction was heated to 115° C. for 6 hours. After cooled back to rt, pyridine was removed under high vacuo. The crude was dissolved in 2 mL of H$_2$O and washed by diethyl ether (2×5 mL) and was adjusted to pH=2 by adding 3 M HCl solution in water. The crude acid was isolated by extracting with EtOAc (2×30 mL) and used for next step without further purification. To the crude acid was added (1-Amino-2-vinyl-cyclopropyl)-methyl-phosphinic acid (example 1) (50 mg, 0.$^{31}$2 mm), HATU (148 mg, 0.390 mm), NMM (79 mg, 0.78 mm) and DMF (5 mL). The reaction was stirring at rt for 12 hours. The reaction solution was filtrated and purified by reverse phase HPLC (eluted with 10% to 75% H$_2$O/CH$_3$CN) to give 123 as a white solid (45 mg, 37%). $^1$H NMR (300 MHz, CD$_3$CN): δ 7.39 (m, 3H), 6.11 (br, 1H), 5.85 (m, 1H), 5.41 (bs, 2H), 5.21 (m, 1H), 5.03 (m, 1H), 4.90-4.40 (m, 6H), 4.33 (m, 1H), 3.90 (m, 1H), 2.95-2.80 (m, 6H), 2.45-2.35 (m, 2H), 2.17-2.07 (m, 1H), 1.85-1.33 (m, 17H), 1.02 (s, 9H). $^{31}$P NMR (121.4 MHz, CD$_3$CN): δ51.297. LC/MS: 770 (M$^+$+1).

Example 124

Preparation of Compound 124

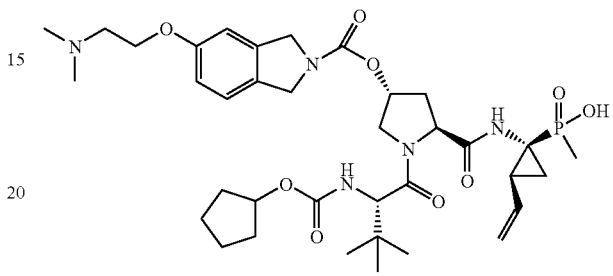

Step 1. The 5-Hydroxy-1,3-d1Hydro-isoindole-2-carboxylic acid tert-butyl ester (2.00 g, 0.85 mmol) and 2-chloro-N,N-dimethylethylamine hydrochloride (1.47 g, 1.02 mmol) were dissolved in 20 mL of CH$_3$CN. Cesium carbonate (6.92 g, 2.12 mmol) was added and the solution was heated to 65° C. for 18 hours. The mixture was cooled to rt and the solid was filtered off. The filtrate was concentrated and the residue was dissolved in 15% MeOH/CH$_2$Cl$_2$, washed with H$_2$O (×2), dried with Na$_2$SO$_4$, filtered, and concentrated. The crude product was purified using silica gel column chromatography CH$_2$Cl$_2$/MeOH to give amine (2.50 g, 19%) as a brown waxy solid. $^{1H}$ NMR (300 MHz, CDCl$_3$): δ 7.16 (m, 1H), 6.85 (m, 2H), 5.30 (s, 1H), 4.61 (t, 4H), 4.08 (m, 2H), 2.77 (m, 2H), 2.35 (s, 6H), 1.51 (s, 9H).

Step 2. The amine (480 mg, 1.57 mmol) was treated with 5 mL of 4 N HCl/1,4-dioxane and 2 mL of CH$_2$Cl$_2$. The reaction mixture was stirred overnight at rt. The solution was concentrated and co-evaporated with toluene (×2), CHCl$_3$ and dried under vacuum to give diamine (416 mg, 95%) as a dark solid.

Step 3. Dipeptide, 1-(2-Cyclopentyloxycarbonylamino-3,3-dimethyl-butyryl)-4-hydroxy-pyrrolidine-2-carboxylic acid methyl ester (200 mg, 0.54 mmol) was dissolved in 2 mL of CH$_2$Cl$_2$ and CDI (109 mg, 0.67 mmol) was added. The mixture was stirred at rt for 5 hours. A mixture of triethylamine (0.24 mL, 1.72 mmol) and diamine (377 mg, 1.35 mmol) in 1 mL of CH$_2$Cl$_2$ was added to the reaction. The reaction mixture was stirred at rt overnight. The solution was concentrated and the product was partitioned between H$_2$O and 15% MeOH/CH$_2$Cl$_2$ (×3). The organic layer was concentrated and purified using a Gilson HPLC to give ester (277 mg, 85%). $^{1H}$ NMR (300 MHz, CDCl$_3$): δ 7.16 (d, J=8.3 Hz, 1H), 7.08 (d, J=8 Hz, 1H), 6.85 (m, 2H), 6.73 (s, 1H), 5.38 (s, 1H), 5.21 (d, J=9.5 Hz, 1H), 4.72 (t, 2H), 4.66 (m, 2H), 4.25 (m, 2H), 4.05 (m, 2H), 3.79 (s, 3H), 2.79 (m, 2H), 2.54 (m, 1H), 2.47 (s, 6H), 2.22 (m, 1H), 1.61 (m, 1H), 1.55 (m, 2H), 1.45 (m, 2H), 1.04 (s, 9H).

Step 4. Ester (275 mg, 0.46 mmol) was dissolved in 4 mL of H$_2$O/CH$_3$CN (1/1) and NaOH (183 mg, 4.60 mmol) was added. The reaction mixture was stirred for 1 hour at rt. The CH$_3$CN was removed in vacuo and the aqueous layer was acidified using 1 N HCl. The product was extracted with 15% MeOH/CH$_2$Cl$_2$ (×3), dried over Na$_2$SO$_4$, filtered and concentrated. The crude product (201 mg, 75%) was coupled to phosphinic acid (example 1) to give 124 (52 mg, 21%) as a white foam. $^{1H}$ NMR (300 MHz, CD$_3$OD): δ 7.29 (d, J=8.6 Hz, 1H), 7.19 (d, J=8.2 Hz, 1H), 7.01 (m, 2H), 5.96 (m, 1H), 5.$^{31}$ (s, 1H), 5.12 (d, J=10.7 Hz, 1H), 4.68 (t, 2H), 4.50 (t, 1H), 4.38 (s, 1H), 4.14 (s, 1H), 3.84 (d, 1H), 3.62 (m, 2H), 3.$^{31}$ (s, 3H), 2.98 (m, 6H), 2.44 (m, 1H), 2.21 (m, 1H), 2.18 (m, 1H), 1.61 (m, 1H), 1.55 (m, 2H), 1.45 (m, 2H), 1.04 (s, 9H); $^{31}$P (121.4 MHz, CD$_3$OD): δ 47.57.

Example 125

Preparation of Compound 125

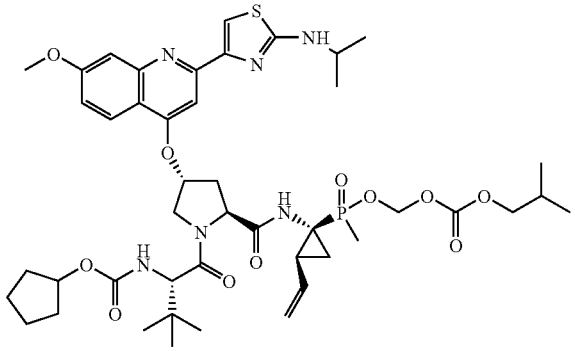

Phosphinic acid (10 mg, 1.3 μmol) was dissolved in H$_2$O (0.2 mL) and treated with 0.1 N NaOH to adjust pH=11. The mixture was lyophilized, dissolved in NMP (0.3 mL), and heated to 60° C. TEA (7 μL) and isobutylchloromethylcarbonate (19 mg, 0.013 mmol) were added. The reaction mixture was stirred at 60° C. for 1 h. The reaction mixture was cooled to r.t. and purified by HPLC to give 4.5 mg of 125 in 39% yield. $^1$H NMR (300 MHz, CD$_3$OD): δ 8.30 (d, J=9.3 Hz, 1H), 8.20 (s, 1H), 7.80 (m, 2H), 7.35 (d, J=9.0 Hz, 1H), 6.05-5.60 (m, 4H), 5.40 (m, 1H), 5.20 (m, 1H), 4.65 (m, 2H), 4.45 (broad, s, 1H), 4.20-4.00 (m, 7H), 2.80 (m, 1H), 2.45 (m, 1H), 2.20 (m, 1H), 1.80-1.45 (m, 10H), 1.40-1.22 (m, 14H), 1.00 (m, 10H); $^{31}$P (121.4 MHz, CD$_3$OD): δ 57.17, 52.94; LC/MS: 913.

Example 126

Preparation of Compound 126

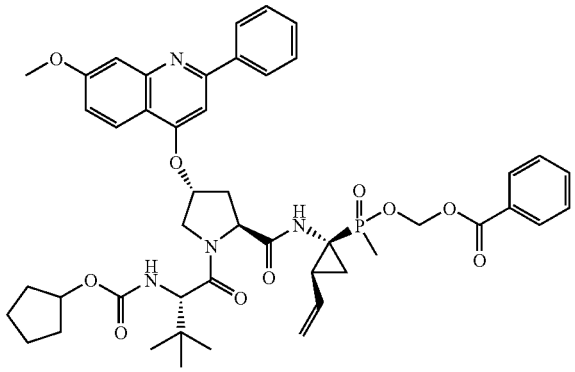

Following experimental procedures similar to those described for the preparation of compound 125, 18.4 mg of compound 126 was prepared. $^{1H}$ NMR (300 MHz, CD$_3$OD): δ 7.91-8.15 (m, 5H), 7.$^{31}$-7.66 (m, 7H), 7.23 (s, 1H), 7.07 (d, 1H, J=8.7 Hz), 5.79-6.10 (m, 3H), 5.45-5.56 (br m, 1H), 5.34 and 5.28 (two d, 1H, J=~11 Hz), 5.17 and 5.08 (two d, 1H, J=~11 Hz), 4.73 (br m, 1H), 4.46-4.57 (br m, 2H), 4.26 (s, 1H), 3.98-4.08 (m, 1H), 3.95 and 3.91 (two s, 3H), 2.56-2.70 (m, 1H), 2.23-2.38 (m, 1H), 2.09-2.23 (m, 1H), 1.37-1.83 (m, 13H), 1.05 and 1.02 (two s, 9H). $^{31}$P (121.4 MHz, CD$_3$OD): δ 57.517, 53.031. LC/MS=867 (M$^+$+1)

Example 127

Preparation of Compound 127

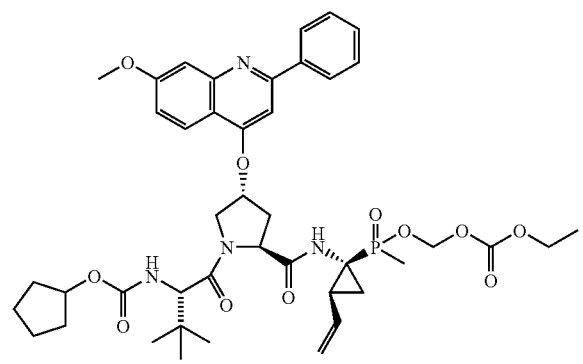

Compound 94 (200 mg, 0.27 mmol) was dissolved in ACN (5 mL) followed by the addition of TEA (1 mL) and the solution was heated at 70° C. for 10 min. To the heated solution, isobutylchloromethylcarbonate was added and the reaction mixture was further heated for 5 h. The reaction mixture was then cooled to rt and the solvents were removed under reduced pressure. The crude product was purified by reverse phase prep HPLC followed by lyophilization to afford 102 mg of phosphinate prodrug in 49% yield. $^1$H NMR (300 MHz, CDCl$_3$): δ 8.06-8.01 (m, 3H), 7.56-7.48 (m, 4H), 7.21-7.01 (m, 3H), 6.14-6.08 (m, 1H), 5.87-4.98 (m, 6H), 4.59-3.97 (s, 8H), 3.34-3.$^{31}$ (m, 1H), 2.58-2.52 (m, 2H), 2.20-1.96 (m, 1H), 1.70-1.04 (m, 26H). $^{31}$P (121.4 MHz, CDCl$_3$): 51.12 (s, $^{31}$P); LC/MS: M+1=835, M+Na=857.

Example 128

Preparation of Compound 128

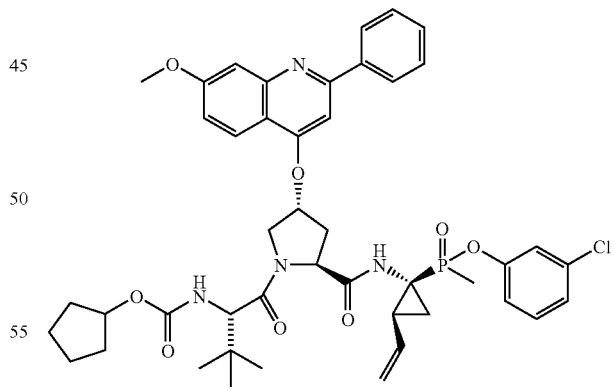

Compound 94 (100 mg, 0.14 mmol) was dissolved in pyridine (3 mL) followed by the addition of m-Cl phenol (175 mg, 1.37 mmol) and the solution was heated at 60° C. for 10 min. To the heated solution was added dicyclohexylcarbodiimide (169 mgs, 0.82 mmol) and the reaction mixture was further heated for 3 h. The reaction mixture was then cooled to rt and the solvents were removed under reduced pressure. Dilute the reaction mixture with EtOAc and filter the solids. Remove solvent under reduced pressure and purify the crude product on combi-flash EtOAc/Hex to afford 46 mg of phosphinate prodrug in 40% yield. ¹H NMR (300 MHz, CDCl₃): δ 8.10-7.99 (m, 2H), 7.57-6.99 (m, 10H), 5.89-5.83 (m, 1H), 5.41-4.93 (m, 4H), 4.73-3.96 (m, 5H), 3.15-2.80 (m, 2H), 2.56 (m, 1H), 2.05-0.91 (m, 27H). ³¹P (121.4 MHz, CDCl₃): 51.12 (s, ³¹P); LC/MS: M+1=843.

Example 129

Preparation of Compound 129

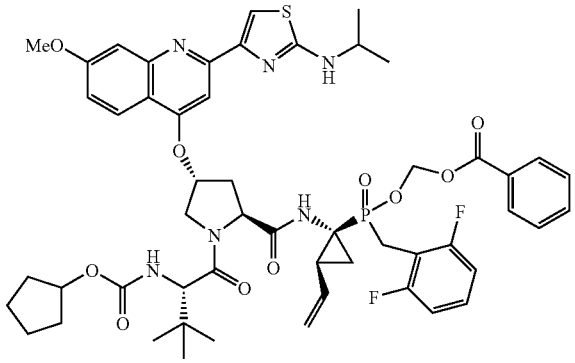

Acid compound 58 (128 mg, 0.14 mmol) was dissolved in CH₃CN (2.5 mL) and heated to 65° C. for 10 minutes. TEA (0.2 mL, 1.41 mmol) and BOMCl (480 mg, 2.82 mmol) were added. The reaction mixture was stirred at 65° C. for 24 h and cooled to rt. The reaction was quenched with H₂O and organic solvents were evaporated. The aqueous layer was extracted with EtOAc. The aqueous layer was brought to pH=2 and extracted with EtOAc. The combined organic layers were dried with Na₂SO₄, filtered and concentrated. The crude product was purified by HPLC to give 10 mg of 129.

Example 130

Preparation of Compound 130

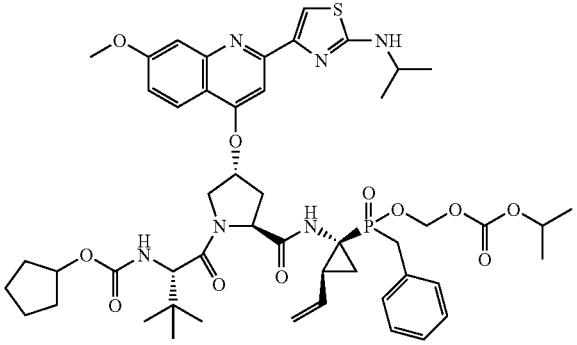

To a solution of compound 35 (725 mg, 0.831 mmol) in CH₃CN (20 mL) was added TEA (1.16 mL, 0.831 mmol) and the solution was heated at 70° C. for 10 min. POC—Cl was then added to the reaction mixture, and heating was continued for 5 h. The mixture was concentrated under reduced pressure and purified on reverse phase HPLC to afford 219 mgs of the phosphinate prodrug in 27% yield. ¹H NMR (300 MHz, CD₃OD): δ 8.89 (s, 1H), 8.30 (m, 1H), 8.18 (s, 1H), 7.76 (s, 1H), 7.35-7.23 (m, 6H), 6.03-5.77 (m, 2H), 5.57-5.28 (m, 3H), 5.15-5.01 (m, 2H), 4.86-4.65 (m, 2H), 4.45 (s, 1H), 4.22-4.05 (m, 5H), 3.65-3.20 (m, 2H), 2.81-2.74 (m, 2H), 2.50-2.44 (m, 2H), 2.18-2.15 (m, 1H), 1.77-1.23 (m, 23H), 1.19-0.97 (m, 10H). ³¹P (121.4 MHz, CD₃OD): 48.55; LC/MS: M+1=989.

Example 131

Preparation of Compound 131

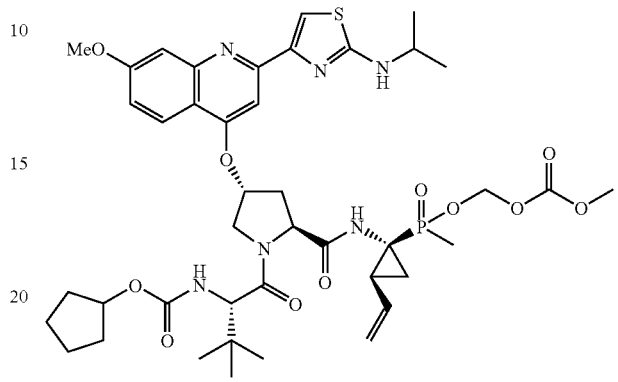

Following experimental procedures similar to those described for the preparation of compound 130, 15 mg of compound 131 was prepared. ¹H NMR (300 MHz, CD₃OD): δ 8.05 (d, 1H, J=9.6 Hz), 7.48 and 7.46 (two s, 1H), 7.43 (s, 1H), 7.36 (d, 1H), 7.04 (dd, 1H, J=9.6 Hz), 5.76-6.06 (m, 1H), 5.56-5.76 (m, 2H), 5.48 (br, 1H), 5.26-5.38 (m, 1H), 5.14 (appt t, 1H, J=~12 Hz), 4.78 (br, 1H), 4.46-4.57 (m, 2H), 4.28 (s, 1H), 4.06 (br d, 1H, J=~11 Hz), 3.95 (s, 3H), 3.88-4.00 (m, 1H), 3.80 and 3.72 (two s, 3H), 2.94 (br m, 0.5H), 2.62-2.75 (m, 1.5H), 2.22-2.42 (m, 1H), 2.06-2.22 (m, 1H), 1.42-1.84 (m, 10H), 1.32 (d, 6H, J=6.6 Hz), 1.27-1.36 (m, 1H), 1.20 (appt t, 1H, J=7.4 Hz), 1.06 and 1.04 (two s, 9H). ³¹P (121.4 MHz, CD₃OD): δ 57.608, 53.232. LC/MS=885 (M⁺+1)

Example 132

Preparation of Compound 132

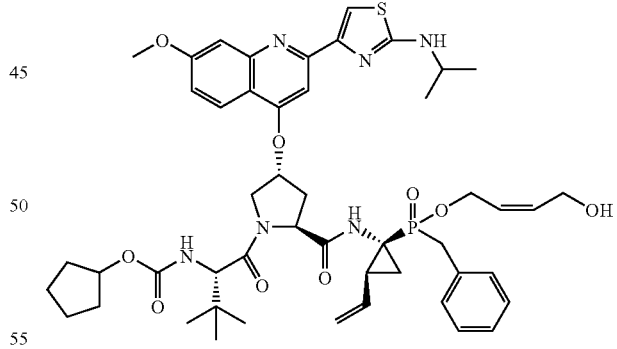

Phosphinic acid (500 mg, 5.73 mmol) and alcohol (1.87 g, 57.3 mmol) were dissolved in DMF (3 mL). PyBop (843 mg, 20.06 mmol), TEA (0.4 mL, 28.65 mmol), and DMAP (14 mg, 1.15 mmol) were added. The reaction mixture was stirred at r.t. for 3 h and concentrated. The product was partitioned between brine and CH₂Cl₂ (3×). The organic layer was dried with Na₂SO₄ and concentrated. The residue was purified by combi-flash to give 406 mg of intermediate sily ether in 60% yield. The resulting silyl ether (406 mg, 3.44 mmol) was dissolved in THF (3 mL) and 1.0 M TBAF in THF (0.43 mL, 4.3 mmol) was added. The reaction mixture was stirred for 1 h and concentrated. The product was partitioned between H₂O and CH₂Cl₂. The organic layer was concentrated and purified by HPLC to give 227 mg of 132 in 70% yield. ¹H NMR (300 MHz, CDCl₃): δ 8.80 (s, 1H), 8.20 (m, 1H), 7.80 (m, 2H), 7.65 (m, 3H), 7.45-7.17 (m, 6H), 5.80-5.65 (m, 2H), 5.40-5.05 (m, 4H), 4.65 (m, 2H), 4.40-3.95 (m, 8H), 3.60-3.20 (m, 3H), 2.70 (m, 1H), 2.00 (m, 1H), 1.80-1.35 (m, 13H), 1.05-0.95 (m, 16H); ³¹P (12.1.4 MHz, CDCl₃): δ 50.24, 48.92; LC/MS: 943.

Example 133

Preparation of Compound 133

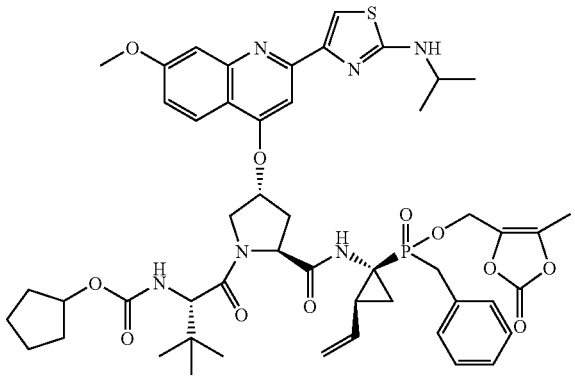

Step 1. 4,5-dimethyl-2-oxo-1,3-dioxole (5 g, 43.82 mmol), NBS (8.19 g, 46.01 mmol), and benzoyl peroxide (20 mg) were dissolved in CCl₄ (30 mL) and heated to 80° C. for 1.5 h. The reaction mixture was cooled to r.t and the solid was filtered off. The filtrate was concentrated. The residue was purified by silica gel column to give 8.29 g of 4-bromomethyl-5-methyl-2-oxo-1,3-dioxole as a yellow oil. TEA (12 mL, 86.1 mmol) was added dropwise to a solution of 4-bromomethyl-5-methyl-2-oxo-1,3-dioxole (6 g, ³¹0.09 mmol) and formic acid (3.36 mL) in CH₃CN (96 mL) while keeping the temperature under 20° C. The mixture was stirred at r.t. for 2 h and concentrated. The product was partitioned between H₂O and EtOAc (3×). The organic layer was dried with Na₂SO₄, concentrated and dried in vacuo to give crude formate. The resulting formate was dissolved in MeOH (40 mL) and 0.5 mL of concentrated HCl was added. The mixture was stirred at r.t. for 5 h, concentrated, and co-evaporated with toluene. The crude product was purified by silica gel column to give 2.8 g of 4-hydroxymethyl-5-methyl-2-oxo-1,3-dioxole in 69% yield. ¹H NMR (300 MHz, CDCl₃): δ 4.40 (s, 2H), 2.60 (broad, s, 1H), 2.20 (s, 3H).

Phosphinic acid (150 mg, 0.17 mmol) and 4-hydroxymethyl-5-methyl-2-oxo-1,3-dioxole (112 mg, 0.85 mmol) were dissolved in DMF (1 mL). PyBop (179 mg, 0.34 mmol), TEA (0.07 mL, 0.51 mmol), and DMAP (7 mg) was added. The mixture was stirred at r.t. overnight. The product was partitioned between aqueous NaHCO₃ and EtOAc (3×). The organic layer was washed with NH₄Cl and brine, dried with Na₂SO₄, and concentrated. The crude product was purified by HPLC followed by silica gel column to give 40 mg of (133) in 24% yield. ¹H NMR (300 MHz, CDCl₃): δ 8.00 (d, J=9.3 Hz, 1H), 7.5 (s, 1H), 7.40 (m, 2H), 7.30-7.20 (m, 5H), 7.00 (d, J=8.7 Hz, 1H), 5.95-5.80 (m, 2H), 5.40-5.10 (m, 5H), 5.00 (broad, s, 1H), 4.70-4.40 (m, 5H), 4.00 (s, 5H), 3.70 (m, 1H), 3.30 (m, 2H), 2.80 (m, 1H), 2.60 (m, 1H), 2.00-1.35 (m, 16H), 1.05 (m, 12H); ³¹P (121.4 MHz, CDCl₃): δ 50.81, 47.39; LC/MS: M+1=985

Example 134

Preparation of Compound 134

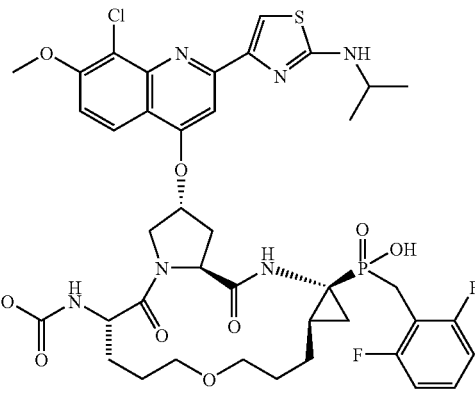

Step 1. The 2-tert-butoxycarbonylamino-pentanedioic acid 1-benzyl ester (4.06 g, 12 mmol) and TEA (5 mL, 35.87 mmol) were dissolved in THF (60 mL) and cooled to 0° C. Ethylchloroformate (3.4 mL, 35.7 mmol) was added dropwise. The mixture was stirred at 0° C. for 5 minutes and warmed to r.t. for 1 h. NaBH₄ (1.88 g, 49.7 mmol) was added followed by addition of 1 drop of H₂O. The reaction mixture was stirred at r.t. overnight. 4 N HCl was added at 0° C. and extracted with EtOAc (100 mL). The aqueous layer was washed with H₂O (100 mL), NaOH (2×100 mL), H₂O (100 mL) and brine (100 mL). The organic layer was dried with Na₂SO₄, filtered, and concentrated. The crude product was purified by combi-flash to give 2.89 g of 2-tert-butoxycarbonylamino-5-hydroxy-pentanoic acid benzyl ester in 75% yield.

To a solution of alcohol 2-tert-butoxycarbonylamino-5-hydroxy-pentanoic acid benzyl ester (1.64 g, 5.07 mmol) in ether (15 mL) was added Ag₂O (4.08 g, 17.61 mmol) and allyl bromide (2.6 mL, 29.87 mmol). The reaction mixture was stirred at r.t. overnight. The reaction mixture was filtered through celite and concentrated. The crude product was purified by combi-flash to give 940 mg of 5-allyloxy-2-tert-butoxycarbonylamino-pentanoic acid benzyl ester.

Step 2. To a solution of 5-allyloxy-2-tert-butoxycarbonylamino-pentanoic acid benzyl ester (5.95 g, 16.38 mmol) in CH₂Cl₂ (100 mL) was added 4 N HCl in 1,4-dioxane (100 mL, 400 mmol). The reaction mixture was stirred at r.t. for 2 h, concentrated, and dried under vacuo to give amine HCl salt. The resulting amine HCl salt was dissolved in THF (150 mL) and H₂O (25 mL). TEA (7 mL, 50.2 mmol) and carbonic acid cyclopentyl ester 2,5-dioxo-pyrrolidin-1-yl ester (3.92 g, 17.25 mmol) were added. The reaction mixture was stirred at r.t. for 1 h. H₂O (200 mL) was added and the organic solvent was reduced on rotavap. The remaining mixture was extracted with EtOAc (3×150 mL). The combined organic layer was washed with 1 N HCl, H₂O and brine, dried with Na₂SO₄, concentrated, and dried to give 6.41 g of ester as crude product.

Ester (6.41 g, 17.07 mmol) was dissolved in THF (65 mL)/H₂O (75 mL), and LiOH (1.63 g, 38.85 mmol) was added. The reaction mixture was stirred at r. t. overnight and diluted with EtOAc. The reaction mixture was acidified to pH=2 with 1 N HCl and separated. The aqueous layer was extracted with EtOAc (3×150 mL). The combined organic layers were washed with brine, dried with Na₂SO₄, concentrated and dried under vacuum to give 4.87 g of 5-allyloxy-2-cyclopentyloxycarbonylamino-pentanoic acid.

Step 3. To a solution of intermediate XII (2.25 g, 3.07 mmol) in CH₂Cl₂ (20 mL) was added 4 N HCl in 1,4-dioxane (20 mL, 80 mmol). The reaction mixture was stirred at r.t. for 1 h, concentrated, and dried under vacuo to give amine HCl salt. The resulting amine HCl salt and acid (1.05 g, 3.67 mmol) were dissolved in DMF (30 mL). HATU (2.36 g, 6.20 mmol) and NMM (1.56 g, 15.46 mmol) were added and the mixture was stirred at r.t. for 2 h. The reaction was diluted with EtOAc and washed with 20% LiCl (2×100 mL). The organic layer was washed with aqueous NH$_4$Cl (200 mL), dried with Na$_2$SO$_4$, and concentrated. The crude product was purified by combi-flash to give 2.5 g of diene in 94% yield.

Step 4. Diene (2.59 g, 2.87 mmol) was dissolved in CH$_2$Cl$_2$ (300 mL) and degassed with N$_2$ for 20 minutes. Grubb's G1 (664.5 mg, 0.73 mmol) was added and degassed for an additional 20 minutes. The reaction mixture was heated to 45° C. overnight and cooled to r.t. Tris(hydroxymethyl)phosphine (5.03 g, 40.54 mmol) was added followed by addition of TEA (11.2 mL, 80.35 mmol) and H$_2$O (47 mL). The reaction mixture was heated to 45° C. for 4 h and then r.t. overnight. The two layers were separated. The organic layer was washed with 0.5 N HCl, brine, dried with Na$_2$SO$_4$, and concentrated. The crude product was purified by combi-flash to give 1.03 g of macrocyclic phosphinate.

Step 5. A solution of phosphinate (1.00 g, 1.15 mmol) and 8-chloro-2-(2-isopropylamino-thiazol-4-yl)-7-methoxy-quinolin-4-ol (469 mg) in NMP (12 mL) was treated with Cs$_2$CO$_3$ (1.20 g). The reaction mixture was heated to 70° C. overnight and then cooled to rt. The reaction was diluted with 5% LiCl (150 mL) and extracted with EtOAc (3×150 mL). The combined organic layers were washed with brine, dried with Na$_2$SO$_4$, and concentrated. The crude product was purified by combi-flash to give 964.3 mg of desired product.

To a solution of product obtained above (964.3 mg, 0.98 mmol) in DME (10 mL)/H$_2$O (1 mL) was added p-tosylhydrazide (1.37 g, 7.36 mmol) and NaOAc (1.22 g, 14.8 mmol). The reaction mixture was heated to 95° C. for 2 h and cooled to rt. The mixture was diluted with EtOAc (125 mL) and washed with saturated NaHCO$_3$ (2×50 mL). The aqueous layer was extracted with EtOAc (25 mL). The combined organic layer was washed with brine (25 mL), dried with Na$_2$SO$_4$, and concentrated. The crude product was purified by combi-flash to give 437.6 mg of 134. $^1$H NMR (300 MHz, CD$_3$OD): δ 8.36 (d, J=8.9 Hz, 1H), 8.19 (s, 1H), 7.90 (s, 1H), 7.64 (d, J=9.7 Hz, 1H), 7.2 (m, 1H), 6.86 (m, 2H), 5.9 (bs, 1H), 4.77 (m, 1H), 4.63 (m, 1H), 4.40 (m, 1H), 4.3-3.95 (m, 8H), 3.60 (bs, 3H), 3.55-3.35 (m, 5H), 2.81 (m, 1H), 2.68 (m, 1H) 2.15-1.1 (m, 25H). LC/MS=959.29 (M$^+$+1 LC/MS=959.29 (M$^+$+1).

Example 135

Preparation of Compound 135

The fully protected phosphinate (synthesized as described in example 58 with Boc protection group) was treated with HCl to remove the Boc protection group. The resulting amine was used to prepare compound 135-141. To a solution of this amine (390 mg, 0.47 mmol) in EtOAc (50 mL) was added saturated NaHCO$_3$ (60 mL) and stirred vigorously. Cyclopentyl acetylchloride (76 mg, 0.52 mmol) in EtOAc (1 mL) was added and stirred for 15 minutes. The two layers were separated. The organic layer was washed with brine and concentrated. The dried residue was dissolved in CH$_3$CN (5 mL) and cooled to 0° C. Iodotrimethylsilane (0.60 mL, 2.37 mmol) was added. The reaction mixture was warmed to rt, stirred for 0.5 h, and cooled to 0° C. 2,6-lutidine (1.5 mL, 4.73 mmol) was added followed by addition of MeOH (5 mL). The mixture was concentrated in vacuo. The residue was purified by HPLC to give 337.2 mg of compound 135. $^1$H NMR (300 MHz, CD$_3$OD): δ 8.25 (d, J=9.0 Hz, 1H), 8.15 (s, 1H), 7.76 (s, 1H), 7.73 (d, J=2.1 Hz, 1H), 7.32 (dd, J=2.4, 9.0 Hz, 1H), 7.23 (t, J=7.8 Hz, 1H), 6.90 (t, J=7.8 Hz, 2H), 5.99 (m, 1H), 5.78 (brs, 1H), 5.30 (d, J=15.3 Hz, 1H), 5.12 (d, J=11.7 Hz, 1H), 4.67 (m, 2H), 4.50 (m, 1H), 4.14 (m, 2H), 4.05 (s, 3H), 3.40 (m, 2H), 2.75 (m, 1H), 2.63 (m, 1H), 2.0-2.4 (m, 3H), 1.91 (m, 1H), 1.4-1.7 (m, 8H), 1.34 (d, J=6.3 Hz, 6H), 0.95-1.15 (brs, 11H); $^{31}$P (121.4 MHz, CD$_3$OD): δ42.091; LC/MS=907 (M$^+$+1).

Example 136

Preparation of Compound 136

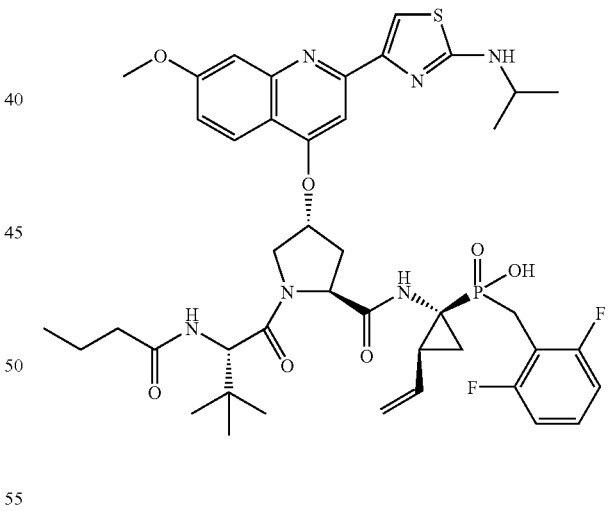

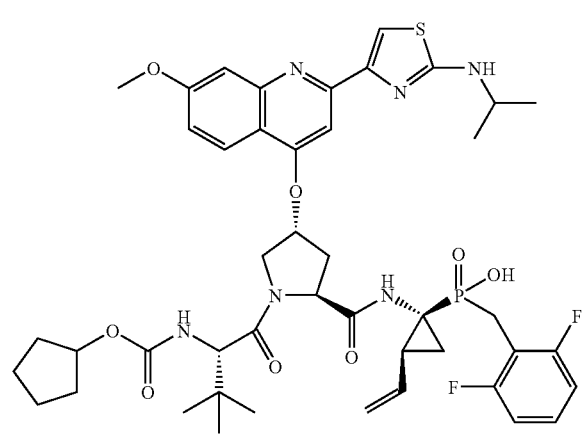

Following experimental procedures similar to those described for the preparation of compound 135, compound 136 was prepared. $^1$H NMR (300 MHz, CD$_3$OD): δ 8.25 (d, J=9.0 Hz, 1H), 8.17 (s, 1H), 7.76 (s, 1H), 7.75 (d, J=2.1 Hz, 1H), 7.33 (dd, J=2.1, 9.0 Hz, 1H), 7.26 (t, J=7.8 Hz, 1H), 6.93 (t, J=7.8 Hz, 2H), 5.97 (m, 1H), 5.80 (brs, 1H), 5.$^{31}$ (d, J=15.9 Hz, 1H), 5.12 (d, J=12.0 Hz, 1H), 4.66 (m, 2H), 4.49 (t, 1H), 4.14 (m, 2H), 4.06 (s, 3H), 3.41 (d, 2H), 2.77 (m, 1H), 2.56 (m, 1H), 2.22 (m, 1H), 2.06 (m, 2H), 1.62 (m, 1H), 1.47 (m, 1H), 1.2-1.4 (m, 8H), 1.07 (s, 9H), 0.80 (t, J=7.4 Hz, 3H); $^{31}$P (121.4 MHz, CD$_3$OD): δ41.043.

Example 137

Preparation of Compound 137

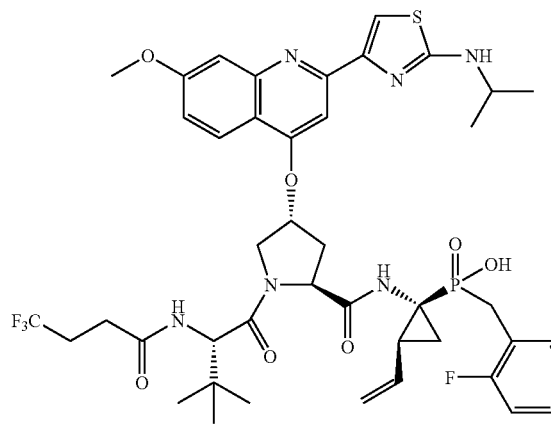

Following experimental procedures similar to those described for the preparation of compound 135, compound 137 was prepared. $^1$H NMR (300 MHz, CD$_3$OD): δ 8.26 (d, J=9.0 Hz, 1H), 8.17 (s, 1H), 7.76 (s, 1H), 7.75 (d, J=2.7 Hz, 1H), 7.32 (dd, J=2.7, 9.2 Hz, 1H), 7.26 (t, J=7.8 Hz, 1H), 6.93 (t, J=7.8 Hz, 2H), 5.97 (m, 1H), 5.81 (brs, 1H), 5.$^{31}$ (dd, J=1.4, 17.0 Hz, 1H), 5.12 (dd, J=1.4, 10.5 Hz, 1H), 4.70 (m, 2H), 4.41 (t, 1H), 4.14 (m, 2H), 4.05 (s, 3H), 3.41 (d, 2H), 2.79 (m, 1H), 2.57 (m, 1H), 2.33 (m, 2H), 2.19 (m, 1H), 2.04 (m, 2H), 1.64 (m, 1H), 1.46 (m, 1H), 1.34 (d, J=6.3 Hz, 6H), 1.06 (s, 9H); $^{31}$P (121.4 MHz, CD$_3$OD): δ41.952.

Example 138

Preparation of Compound 138

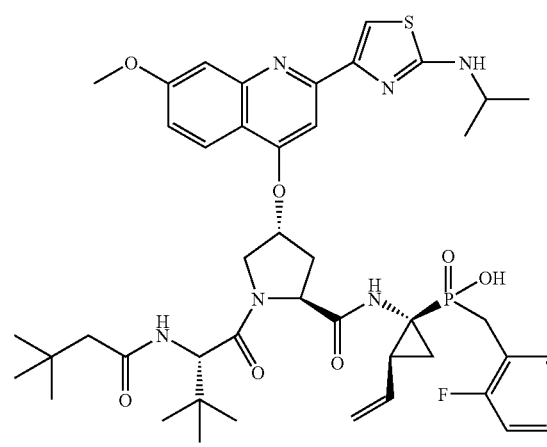

Following experimental procedures similar to those described for the preparation of compound 135, compound 138 was prepared. $^1$H NMR (300 MHz, CD$_3$OD): δ 8.25 (d, J=9.3 Hz, 1H), 8.18 (s, 1H), 7.76 (s, 2H), 7.33 (dd, J=2.4, 9.0 Hz, 1H), 7.26 (t, J=7.8 Hz, 1H), 6.93 (t, J=7.8 Hz, 2H), 5.97 (m, 1H), 5.79 (brs, 1H), 5.32 (d, J=15.9 Hz, 1H), 5.13 (d, J=12.0 Hz, 1H), 4.67 (m, 2H), 4.48 (t, 1H), 4.14 (m, 2H), 4.05 (s, 3H), 3.42 (d, 2H), 2.78 (m, 1H), 2.57 (m, 1H), 2.20 (m, 1H), 1.98 (d, J=12.6 Hz, 1H), 1.90 (d, J=12.6 Hz, 1H), 1.64 (m, 1H), 1.48 (m, 1H), 1.34 (d, J=9.6 Hz, 6H), 1.06 (s, 9H, 0.80 (s, 9H); $^{31}$P (121.4 MHz, CD$_3$OD): δ41.077; LC/MS=895 (M$^+$+1).

Example 139

Preparation of Compound 139

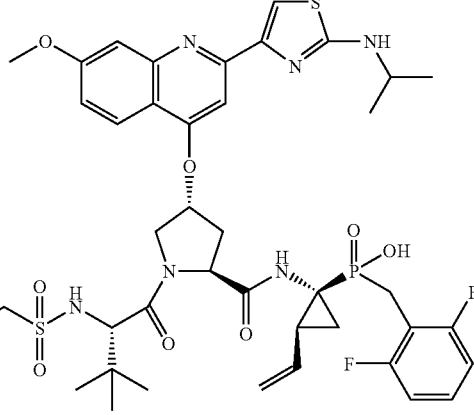

Following experimental procedures similar to those described for the preparation of compound 135, compound 139 was prepared. $^1$H NMR (300 MHz, CD$_3$OD): δ 8.27 (d, J=9.6 Hz, 1H), 8.16 (s, 1H), 7.74 (s, 2H), 7.34 (dd, J=2.1, 9.3 Hz, 1H), 7.25 (t, J=7.8 Hz, 1H), 6.92 (t, J=7.8 Hz, 2H), 5.96 (m, 1H), 5.79 (brs, 1H), 5.30 (d, J=17.1 Hz, 1H), 5.12 (d, J=10.5 Hz, 1H), 4.72 (t, 1H), 4.52 (d, 1H), 4.14 (m, 2H), 4.05 (s, 3H), 3.41 (d, 2H), 3.00 (t, J=8.3 Hz, 2H), 2.59 (m, 3H), 2.19 (m, 1H), 2.04 (m, 2H), 1.63 (m, 1H), 1.47 (m, 1H), 1.34 (d, J=6.3 Hz, 6H), 1.10 (s, 9H); $^{31}$P (121.4 MHz, CD$_3$OD): δ38.190 40.829.

Example 140

Preparation of Compound 140

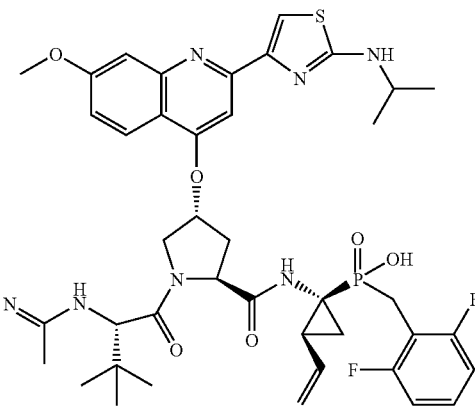

Step 1. Ethyl acetimidate hydrochloride (1.23 g, 9.95 mmol) and 2,2,2-trifluoroethylamine hydrochloride (1.35 g, 9.95 mmol) were dissolved in CH$_2$Cl$_2$ (32 mL)/H$_2$O (3.2 mL). K$_2$CO$_3$ (0.69 g, 4.98 mmol) was added and stirred for 30 minutes. The two layers were separated. The aqueous layer was extracted with CH$_2$Cl$_2$ (2×10 mL). The combined organic layer was dried with Na$_2$SO$_4$ and concentrated to give 1.48 g of the desired amidate as a light yellow liquid in 87% yield.

Step 2. The phosphinate (500 mg, 0.54 mmol) was dissolved in CH$_3$CN (5 mL) and cooled to 0° C. Iodotrimethylsilane (0.77 mL) was added. The reaction mixture was warmed to rt, stirred for 0.5 h, and cooled to 0° C. 2,6-lutidine (1.30 mL) was added followed by addition of MeOH (5 mL). The mixture was concentrated, co-evaporated with CH$_2$Cl$_2$ (2×), and dried in vacuo to give the desired amino phosphinic acid as the 2,6-lutidine salt.

Step 3. The amino phosphinic acid obtained from step 2 (80 mg, 0.025 mmol) was dissolved in DMF (0.45 mL) and 0.1 N phosphate buffer (0.9 mL). 2 N NaOH (86 µL) was added to adjust pH to 9. A solution of the amidate obtained from step 1 (150 mg, 0.89 mmol) in DMF (0.1 mL) was added and stirred for 18 h. The reaction mixture was filtered and the filtrate was purified by HPLC to give 8.8 mg of compound 140. $^1$H NMR (300 MHz, CD$_3$OD): δ 8.27 (d, J=9.6 Hz, 1H), 8.16 (s, 1H), 7.74 (s, 2H), 7.34 (dd, J=2.1, 9.3 Hz, 1H), 7.25 (t, J=7.8 Hz, 1H), 6.92 (t, J=7.8 Hz, 2H), 5.97 (m, 1H), 5.79 (brs, 1H), 5.30 (d, J=17.1 Hz, 1H), 5.12 (d, J=10.5 Hz, 1H), 4.72 (t, 1H), 4.52 (d, 1H), 4.14 (m, 2H), 4.05 (s, 3H), 3.41 (d, 2H), 3.3° (s, 3H), 3.01 (t, J=8.3 Hz, 2H), 2.80 (m, 1H), 2.59 (m, 5H), 2.19 (m, 1H), 1.63 (m, 1H), 1.47 (m, 1H), 1.34 (d, J=6.3 Hz, 6H), 1.10 (s, 9H); $^{31}$P (121.4 MHz, CD$_3$OD): δ40.829.

Example 141

Preparation of Compound 141

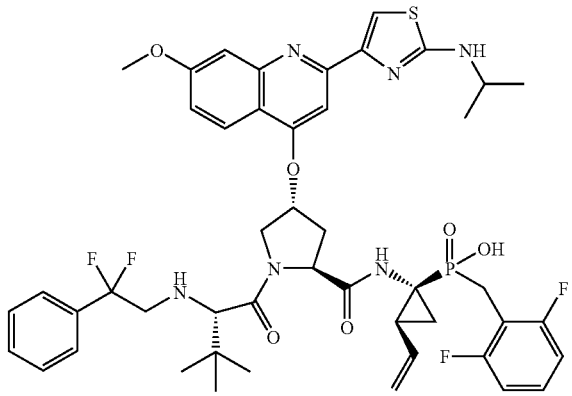

Step 1. A mixture of α-ketoester Oxo-phenyl-acetic acid methyl ester (820 mg, 5 mmol) and Deoxo-Fluor (2.43 g, 11 mmol) was heated to 45° C. and stirred under N$_2$ for 16 h. The mixture was cooled to rt, poured into ice water, and added CH$_2$Cl$_2$ (40 mL). The CH$_2$Cl$_2$ layer was collected and concentrated. The crude product was purified by combi-flash to give 536 mg of the corresponding difluoro ester as colorless oil. To a solution of the difluoro ester (536 mg, 2.88 mmol) in toluene (20 mL) at −78° C. was added 1.0 M DIBAL in CH$_2$Cl$_2$ and stirred for 2 h at −78° C. The reaction mixture was poured into ice cold 6 N HCl (100 mL) and extracted with CH$_2$Cl$_2$. The organic layers were filtered through celite, concentrated to a volume of 40 mL, and used for the next step reaction.

Step 2. To a solution of amino phosphinic acid (example 140, step 2) (65 mg, 0.02 mmol) in CH$_2$Cl$_2$ (1 mL) was added a solution of aldehyde obtained from step 1 in CH$_2$Cl$_2$/toluene (1 mL). TFA (50 µL) and NaBH(OAc)$_3$ (21 mg) were added and stirred for 16 h. Additional NaBH(OAc)$_3$ (63 mg) and the solution of aldehyde in CH$_2$Cl$_2$/toluene (2 mL) were added. The reaction mixture was stirred for 24 h. The reaction was diluted with CH$_2$Cl$_2$ (30 mL) and washed with saturated NaHCO$_3$. The organic layers were washed with 0.1 N HCl and concentrated. The residue was dissolved in CH$_2$Cl$_2$, filtered through Acrodisk, and concentrated. The crude product was purified by HPLC to give 28.2 mg of (141). $^1$H NMR (300 MHz, CD$_3$OD): δ 8.15 (s, 1H), 8.10 (d, J=9.3 Hz, 1H), 7.76 (s, 1H), 7.56 (s, 1H), 7.44 (d, J=7.2 Hz, 1H), 7.33 (t, J=8.1 Hz, 2H), 7.26 (t, J=7.8 Hz, 1H), 7.05-7.20 (m, 3H), 6.92 (t, J=7.8 Hz, 2H), 5.97 (m, 1H), 5.84 (brs, 1H), 5.3 (d, J=16.8 Hz, 1H), 5.12 (d, J=10.5 Hz, 1H), 4.85 (m, 2H), 4.43 (d, 1H), 4.13 (m, 2H), 3.98 (s, 3H), 3.41 (d, 2H), 3.22 (m, 2H), 2.85 (m, 1H), 2.60 (m, 1H), 2.21 (m, 1H), 1.65 (m, 1H), 1.50 (m, 1H), 1.34 (d, J=6.3 Hz, 6H), 1.09 (s, 9H); $^{31}$P (121.4 MHz, CD$_3$OD): δ40.804.

Example 142

Preparation of Compound 142

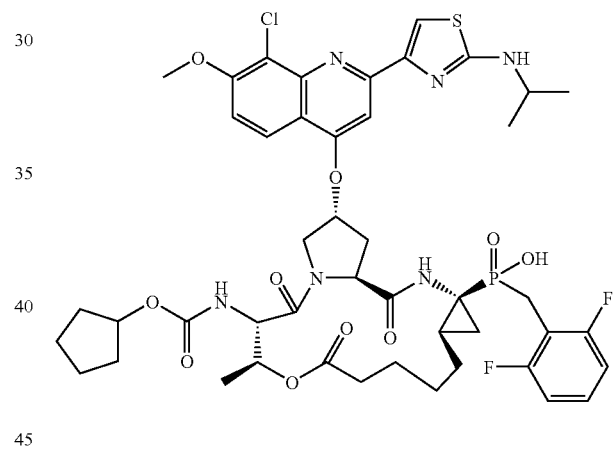

To a solution of 92 (600 mg, 0.61 mmol) in DME (9.1 mL) and H$_2$O (1.02 mL) was added p-tosylhydrazide (856 mg, 4.57 mmol) and NaOAc (749 mg, 9.14 mmol). The reaction mixture was heated to 95° C. for 3 h and cooled to room temperature. The mixture was concentrated, dissolved in CH$_2$Cl$_2$, washed with H$_2$O, and then slightly acidic H$_2$O. The organic layer was dried over Na$_2$SO$_4$ and concentrated. The crude product was purified by reverse phase combi-flash followed by HPLC to give acid 142 (366 mg, 61%) as a yellow solid. $^1$H NMR (300 MHz, CD$_3$OD) δ8.31 (s, 1H), 8.30 (d, J=9 Hz, 1H), 7.87 (s, 1H), 7.67. (d, J=9.3 Hz, 1H), 7.28 (m, 1H), 6.96 (t, J=7.8 Hz, 2H), 5.84 (s, 1H), 4.95 (dd, J=6, 10.2 Hz, 1H), 4.76 (d, J=11.4 Hz, 1H), 4.71 (d, J=8.4 Hz, 1H), 4.35 (d, J=10.5 Hz, 1H), 4.20 (m, 2H), 4.17 (s, 3H), 4.04 (quint., J=6.6 Hz, 1H), 3.49 (t, J=15 Hz, 1H), 3.33, (t, J=15 Hz, 1H), 2.88 (dd, J=7.5, 14.7 Hz, 1H), 2.56-2.74 (brm, 2H), 2.29 (m, 1H), 1.92 (m, 2H), 1.40-1.79 (brm, 10H), 1.37 (dd, J=1.8, 6.6 Hz, 6H), 1.31 (m, 4H), 1.23 (d, J=6 Hz, 3H), 1.00 (m, 1H). $^{31}$P NMR (121.4 MHz, CD$_3$OD) δ 39.8. LC/MS=987.1 (M$^+$+1)

Example 143

Preparation of Compound 143

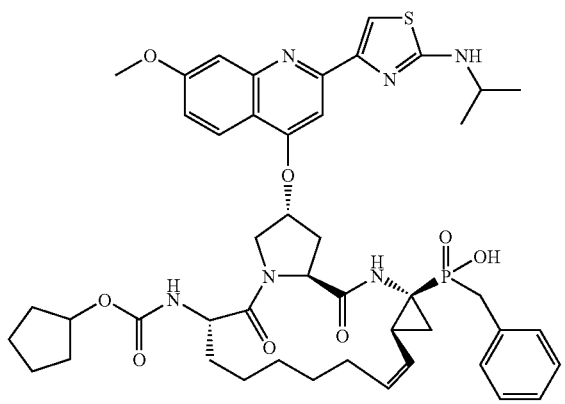

Step 1. A mixture of the intermediate VIII (1.96 g, 5.36 mmol), benzyl-(1-benzyloxycarbonylamino-2-vinyl-cyclopropyl)-phosphinic acid ethyl ester (730 mg, 2.75 mmol), sodium 2-ethylhexanoic acid (300 mg), toluene (5 mL) and water (10 mL) was stirred at 80° C. for 16 h. The resulting reaction mixture was partitioned between ethyl acetate and 5% aqueous sodium bicarbonate. The organic layer was washed sequentially with ice-cold 0.5 N NaOH, 1 N HCl and brine, and then concentrated, affording the desired product (1.15 g, 66%) as an oil.

Step 2. To a solution of the alcohol obtained from step 1 (1.15 g, 1.82 mmol) and DABCO (410 mg, 3.66 mmol) in toluene (2 mL) was added a solution of 4-bromobenzenesulfonyl chloride (840 mg, 3.38 mmol) in toluene (2 mL) and stirred at rt for 1 h. The reaction mixture was diluted with ethyl acetate, washed sequentially with ice-cold 0.5 N NaOH, 1N HCl and brine and then concentrated, affording the brosylated product (1.38 g, 89%).

Step 3. A solution of the intermediate obtained from step 2 (589 mg, 0.69 mmol) in $CH_2Cl_2$ (60 mL) was purged with nitrogen for 5 min. A ruthenium catalyst (G1, 110 mg, 0.14 mmol) was added and the mixture was stirred at 50° C. for 16 h. After cooling, tri(hydroxymethyl)phosphine (860 mg, 6.9 mmol), triethylamine (0.96 mL, 6.9 mmol) and water (20 mL) were added and the mixture was vigorously stirred for 4 h. The organic layer was taken, washed with 1N HCl and then brine, and concentrated. The residue was purified by Combiflash, affording 328 mg of the desired macrocycle as oil.

Step 4. A mixture of the brosylated compound obtained from step 3 (348 mg, 0.42 mmol), 2-(2-isopropylamino-thiazol-4-yl)-7-methoxy-quinolin-4-ol (133 mg, 0.42 mmol) and cesium carbonate (210 mg, 0.63 mmol) in NMP (3 mL) was stirred at 60° C. for 3 h. Acetic acid (0.1 mL) was added and the mixture was diluted with water (0.5 mL) and DMF (2 mL). The crude solution was subjected to HPLC purification, affording the desired product (132 mg, 35%).

Step 5. To a suspension of the compound obtained from step 4 (170 mg, 0.19 mmol) in $CH_3CN$ (10 mL) was added bromotrimethylsilane (0.2 mL). The reaction mixture was stirred at rt for 3 h and then heated to 50° C. for 1 h. The reaction was cooled to r.t. and MeOH (1 mL) was added. The mixture was concentrated and the residue was dissolved in DMF (5 mL). The crude product was purified by HPLC and the desired fractions containing the desired amino phosphinic acid were combined, and concentrated to a volume of 20 mL, which was used for the next reaction.

Step 6. The compound obtained from step 5 was in acidic water. Triethylamine (1 mL) was added to bring the solution to pH=9. Cyclopentyl chloroformate (0.1 mL) was added dropwise while stirring until the starting material was completely converted to product. The mixture was concentrated to a volume of 10 mL. The product was partitioned between EtOAc and saturated $NH_4Cl$. The aqueous layer was extracted with EtOAc. The combined organic layers were concentrated. The residue was purified by HPLC to give 16 mg of compound 143 as a yellow fluffy powder. $^1H$ NMR (300 MHz, $CD_3OD$): δ8.33 (d, J=9.0 Hz, 1H), 8.18 (s, 1H), 7.74 (s, 1H), 7.73 (s, 1H), 7.13-7.33 (m, 6H), 5.83 (brs, 1H), 5.70 (dd, J=8.6, 18.3 Hz, 1H), 5.28 (t, J=9.6 Hz, 1H), 4.73 (t, J=8.7 Hz, 1H), 4.40 (brs, 1H), 4.03-4.22 (m, 3H), 4.02 (s, 3H), 3.39 (t, J=15.9 Hz, 1H), 3.18 (t, J=15.9 Hz, 1H), 2.80 (m, 1H), 2.61 (m, 1H), 2.26 (m, 1H), 1.82 (m, 3H), 1.2-1.7 (m, 23H); $^{31}P$ (121.4 MHz, $CD_3OD$): δ42.259; LC/MS=885 ($M^+$+1).

Example 144

Preparation of Compound 144

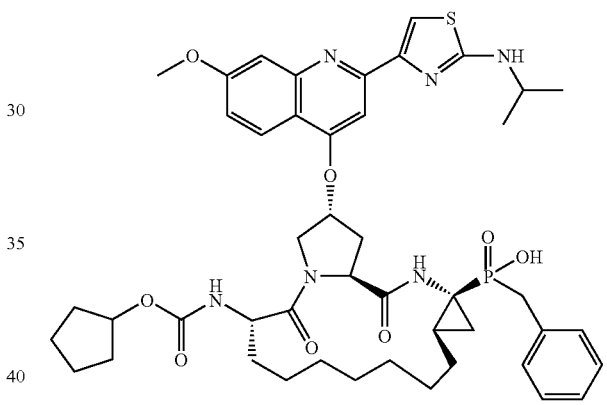

Step 1. To a solution of the phosphinate (step 4, example 143, 132 mg, 0.15 mmol) and 2,4,6-triisopropylbenzenesulfonylhydrazide (440 mg) in THF (10 mL) was added TEA (0.2 mL). The reaction mixture was heated to 55° C. for 4 h. An additional hydrazide (440 mg) and TEA (0.2 mL) were added and stirred for 16 h at 55° C. More hydrazide (400 mg) and TEA (0.2 mL) were added and stirred for 4 h. The reaction mixture was concentrated and the residue was chromatographed affording a fraction containing a mixture of the starting material, the desired product, and the benzenesulfinic acid byproduct. After removal of the solvents, the material was re-dissolved in THF. The hydrazide (440 mg) and TEA (0.4 mL) were sequentially added. The reaction mixture was stirred at 55° C. for 16 h. To drive the reaction to completion, additional hydrazide (660 mg) and TEA (0.4 mL) were added, and stirred for 6 h at 55° C. The reaction mixture was concentrated and the residue was chromatographed affording a fraction containing the desired product. After removal of the solvents, the residue was partitioned between $CH_2Cl_2$ (100 mL) and ice-cold 0.5 N NaOH (20 mL). The $CH_2Cl_2$ layer was washed with 0.5 N NaOH (20 mL) and brine (30 mL) and concentrated. 93 mg of the desired saturated macrocycle was obtained as a yellow solid.

Step 2. To a solution of the saturated macrocycle obtained from step 1 (93 mg, 0.1 mmol) in $CH_2Cl_2$ (10 mL) was added bromotrimethylsilane (0.2 mL) and stirred at r.t for 2 h. 2,6-Lutidine (0.1 mL) was added and stirred at r.t for 16 h. LCMS showed the desired product with tert-Boc protected phosphinic acid as a minor product. Additional bromotrimethylsilane (0.1 mL) was added. The mixture was heated to reflux for 1 h. MeOH (3 mL) was added and concentrated. The crude product was dissolved in DMF (5 mL) and H₂O (0.5 mL) and purified by HPLC to give 27 mg of the desired amino phosphinic acid as a fluffy solid.

Step 3. To a solution of the amino phosphinic acid obtained from step 2 and triethylamine (0.2 mL) in CH₃CN (10 mL) and H₂O (1 mL) was added cyclopentyl chloroformate (50 μL). The reaction mixture was stirred at r.t. for 0.5 h. Additional cyclopentyl chloroformate (50 μL) was added and stirred for 1 h. After removal of the solvents, the residue was dissolved in DMF (1.8 mL) and H₂O (0.2 mL) and purified by HPLC to give 12 mg of compound 144.

¹H NMR (300 MHz, CD₃OD): δ8.28 (d, J=9.0 Hz, 1H), 8.18 (s, 1H), 7.75 (s, 1H), 7.74 (s, 1H), 7.13-7.33 (m, 6H), 5.82 (brs, 1H), 4.85 (d, J=12.3 Hz, 1H), 4.68 (t, J=8.7 Hz, 1H), 4.24 (brs, 1H), 4.04-4.23 (m, 3H), 4.03 (s, 3H), 3.34 (t, J=15.9 Hz, 1H), 3.22 (t, J=15.9 Hz, 1H), 2.78 (m, 1H), 2.49 (m, 1H), 1.1-2.0 (m, 27H); ³¹P (121.4 MHz, CD₃OD): δ44.791; LC/MS=887 (M⁺+1).

Example 145

Preparation of Compound 145

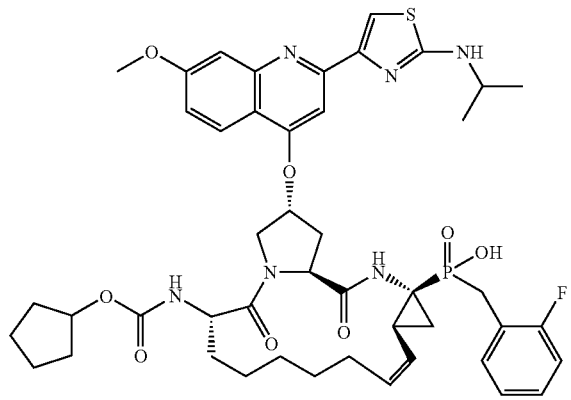

To a yellow solution of VIII (1.67 g, 4.56 mmol) and amine (1-amino-2-vinyl-cyclopropyl)-(2-fluoro-benzyl)-phosphinic acid ethyl ester (972 mg, 3.5 mmol) in toluene (10 mL) was added a solution of sodium 2-ethyl hexanoate (871 mg, 5.25 mmol) in H₂O (30 mL). The reaction mixture was heated to 80° C. overnight and cooled to rt. The reaction mixture was diluted with EtOAc, washed with saturated NaHCO₃, 0.5 N HCl, brine, dried with Na₂SO₄, and concentrated. The crude product was purified by combi-flash to give 1.47 g of alcohol in 65% yield. ¹H NMR (300 MHz, CDCl₃): δ7.68 (s1H) 7.43-7.34 (m, 2H), 7.24-6.98 (m, 2H), 6.07-5.98 (m, 1H), 5.82-5.60 (m, 2H), 5.³¹ (m, 1H), 5.19-5.09 (m, 2H), 5.03-5.00 (m, 1H), 4.96-4.91 (m, 2H), 4.83 (m, 1H), 4.69 (m, 1H), 4.51-4.37 (m, 2H), 4.34-4.29 (m, 2H), 4.09-4.02 (m, 3H), 3.89-3.79 (m, 3H), 3.69 (m, 2H), 3.43-3.09 (m, 2H), 2.39-2.07 (m, 2H), 2.02-2.00 (m, 1H), 1.83-1.52 (m, 2H), 1.43 (s, 9H), 1.38-1.21 (m, 2H), 1.16 (m, 3H); ³¹P (121.4 MHz, CDCl₃): δ45.47 (s, ³¹P), 42.84 (s, ³¹P). LC/MS: M+1=650.

Alcohol (992 mg, 1.53 mmol) and DABCO (550 mg, 4.89 mmol) were dissolved in toluene (8 mL). A toluene (8 mL) solution of brosylchloride (1.25 g, 4.89 mmol) was added dropwise. The reaction mixture was stirred at r. t. for 3 h. The reaction was diluted with EtOAc and quenched with saturated NaHCO₃. The two layers were separated and the organic layer was washed with 0.5 N HCl, brine, dried with Na₂SO₄, filtered, and concentrated. The crude product was purified by combi-flash to give 764 mg of brosylate in 58% yield. ¹H NMR (300 MHz, CDCl₃): δ7.81-7.7 (m, 4H), 7.63 (m, 1H), 7.38 (m, 1H), 7.26-6.96 (m, 5H), 6.10-6.04 (m, 1H), 5.80-5.70 (m, 1H), 5.28 (m, 1H), 5.18-4.87 (m, 6H), 4.64 (m, 1H), 4.30-3.78 (m, 7H), 3.29-3.06 (m, 4H), 2.76-2.60 (m, 2H), 2.36-2.28 (m, 2H), 2.22-2.05 (m, 2H), 1.74-1.56 (m, 3H), 1.43 (s, 9H), 1.39-1.10 (m, 4H); ³¹P (121.4 MHz, CDCl₃): δ 46.34 (s, ³¹P), 43.32 (s, ³¹P). LC/MS: M+1=870.

Brosylate (760 mg, 0.87 mmol) was dissolved in CH₂Cl₂ (56 mL) and degassed with N₂ for 20 minutes. Grubb's G1 (180 mg, 0.22 mmol) was added and degassed for an additional 20 minutes. The reaction mixture was heated to 50° C. overnight and cooled to rt. Tris(hydroxymethyl)phosphine (1.35 g, 11 mmol) was added followed by addition of TEA (3.1 mL, 22 mmol) and H₂O (10 mL). The reaction mixture was heated to 50° C. for 4 h and then r.t. overnight. The two layers were separated. The organic layer was washed with 0.5 N HCl, brine, dried with Na₂SO₄, and concentrated. The crude product was purified by combi-flash to give 487 mg of cyclized olefin in 66% yield. ¹HNMR (300 MHz, CDCl₃): δ7.82-7.68 (m, 4H), 7.47-7.40 (m, 1H), 7.32-6.96 (m, 3H), 6.60-6.54 (m, 1H), 5.66-4.98 (m, 6H), 4.46-3.97 (m, 8H), 3.84-3.74 (m, 1H), 3.44-3.13 (m, 3H), 2.53-2.32 (m, 4H), 2.09-1.07 (m, 18H); ³¹P (121.4 MHz, CDCl₃): δ45.34 (s, ³¹P), 43.41 (s, ³¹P). LC/MS: M+1=842. A solution of olefin (798 mg, 0.95 mmol) and 2-(2-isopropylamino-thiazol-4-yl)-7-methoxy-quinolin-4-ol (300 mg, 0.95 mmol) in NMP (10 mL) was treated with Cs₂CO₃ (310 mg, 0.95 mmol). The reaction mixture was heated to 65° C. overnight and then cooled to rt. The reaction was diluted with EtOAc and washed with H₂O. The aqueous layer was brought to pH=4 with 1 N HCl and extracted with EtOAc (2×). The combined organic layers were dried with Na₂SO₄ and concentrated. The crude product was purified by combi-flash to give 625 mg of desired product in 72% yield. ¹H NMR (300 MHz, CDCl₃): δ8.02-7.98 m, 1H), 7.47 (s, 1H), 7.34-6.96 (m, 7H), 5.69-5.60 (m, 1H), 5.40-5.25 (m, 4H), 4.51-4.07 (m, 3H), 4.03-3.71 (m, 8H), 3.54-3.36 (m, 4H), 3.16-3.05 (m, 2H), 2.85-2.68 (m, 2H), 2.40-1.07 (m, 28H); ³¹P (121.4 MHz, CDCl₃): δ45.15 s, ³¹P), 44.29 (s, ³¹P). LC/MS: M+1=919.

To a solution of product obtained above (625 mg, 0.68 mmol) in CH₃CN (10 mL) at 0° C. was added iodotrimethylsilane (0.5 mL, 3.4 mmol). The reaction mixture was stirred at 0° C. for 5 minutes. 2,6-Lutidine (0.48 mL) was added and stirred for 1 h. TEA (2 mL) and MeOH (3 mL) were added and stirred for 30 minutes. The mixture was concentrated, co-evaporated with toluene and CH₃CN, and dried for 20 minutes to give crude acid. The crude acid was dissolved in CH₃CN (5 mL). Saturated Na₂CO₃ in H₂O (5 mL) was added and stirred for 5 minutes. The THF solution of the freshly prepared cyclopentylchloroformate was added. The reaction was completed within 0.5 h and concentrated. The residue was dissolved in EtOAc and 1.0 N HCl was added to adjust pH=2. The two layers were separated and the organic layer was concentrated. The crude product was purified by HPLC to give 327 mg of product 145 in 53% yield. ¹H NMR (300 MHz, CDCl₃): δ8.89 (s, 1H), 7.34 (d, J=9.5 Hz, 1H), 8.18 (s, 1H), 7.76-7.73 (m, 2H), 7.39-7.02 (m, 5H), 5.84 (br s, 1H), 5.77 (dt, J=8.9 Hz, 9.1 Hz, 1H), 5.29 (t, J=9.5 Hz, 1H), 4.86 (s, 1H), 4.72 (t, J=9.2 Hz, 1H), 4.38 (s, 1H), 4.22-4.03 (m, 6H), 3.57-3.43 (m, 1H), 3.32-3.17 (m, 1H), 2.85-2.78 (m, 2H), 2.66-2.58 (m, 1H), 2.31-2.23 (m, 1H), 1.94-1.82 (m, 3H), 1.58-1.33 (m, 24H); $^{31}$P (121.4 MHz, CD$_3$OD): δ 41.98 (s, $^{31}$P). LC/MS: M+1=903.

Example 146

Preparation of Compound 146

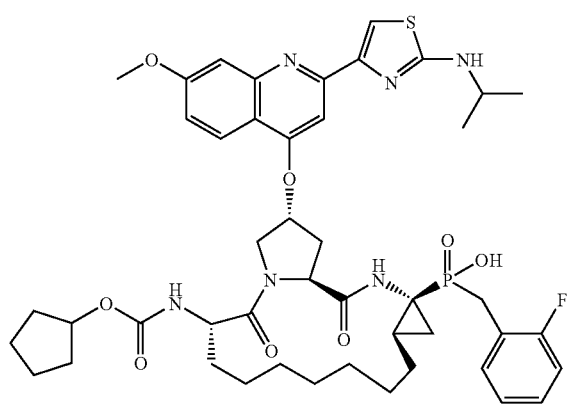

To a solution of 145 (30 mg, 0.033 mmol) in DME (1 mL)/H$_2$O (0.1 mL) was added p-tosylhydrazide (31 mg, 0.17 mmol) and NaOAc (19 mg, 0.23 mmol). The reaction mixture was heated to 95° C. for 2 h and cooled to rt. A few drops of 3 N HCl was added to adjust pH=2. The crude product was purified by HPLC to give 4 mg of acid 146. $^1$H NMR (300 MHz, CD$_3$OD): δ8.31 (d, J=9.4 Hz, 1H), 8.18 (s, 1H), 7.75 (s, 2H), 7.39-7.04 (m, 5H), 5.84 (br s, 1H), 4.81-4.68 (m, 3H), 4.44 (s, 1H), 4.25-4.04 (m, 7H), 3.47-3.23 (m, 2H), 2.84-2.77 (m, 2H), 2.55-2.52 (m, 2H), 1.95-1.33 (m, 30H); $^{31}$P (121.4 MHz, CD$_3$OD): δ43.74 s), $^{31}$P). LC/MS: M+1=905.

Example 147

Preparation of Compound 147

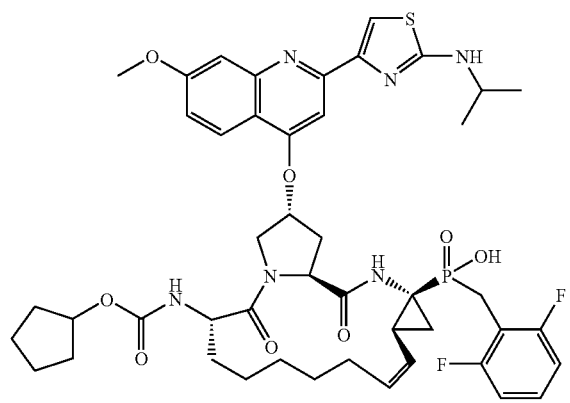

Compound 147 was prepared as described for example 145 with the phosphinate in example 58. $^1$H NMR (300 MHz, CD$_3$OD) δ 8.32 (d, 1H, J=10 Hz), 8.19 (s, 1H), 7.81-7.72 (m, 2H), 7.35-7.20 (m, 2H), 6.94 (t, 2H, J=8 Hz), 5.85 (br s, 1H), 5.74 (app q, 1H, J=8 Hz), 5.32 (t, 1H, J=10 Hz), 4.74 (t, 1H, J=8 Hz), 4.40 (br s, 1H), 4.23-4.05 (m, 3H), 4.04 (s, 3H), 3.58 (t, 1H, J=14 Hz), 3.36-3.22 (m, 1H), 2.90-2.77 (m, 1H), 2.70-2.58 (m, 1H), 2.37-2.24 (m, 1H), 1.93-1.76 (m, 2H), 1.69-1.37 (m, 17H), 1.34 (d, 6H, J=7 Hz); $^{19}$F NMR (282.6 MHz, CD$_3$OD) δ-114.6; $^{31}$P (121.4 MHz, CD$_3$OD) δ 40.7; EI MS (m/z) 920.6 [MH$^+$].

Example 148

Preparation of Compound 148

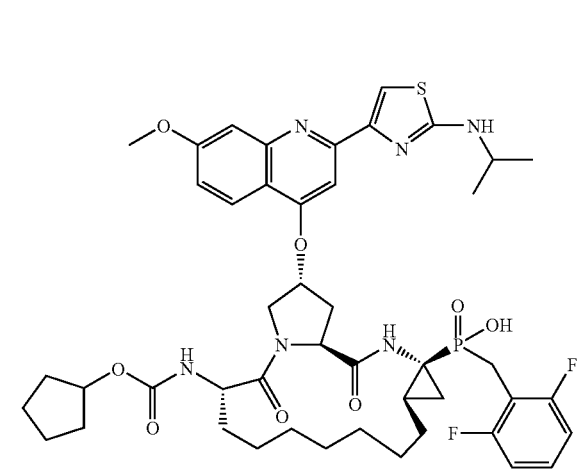

Compound was prepared as described for 146. LC/MS: 923 (M+1).

Example 149

Preparation of Compound 149

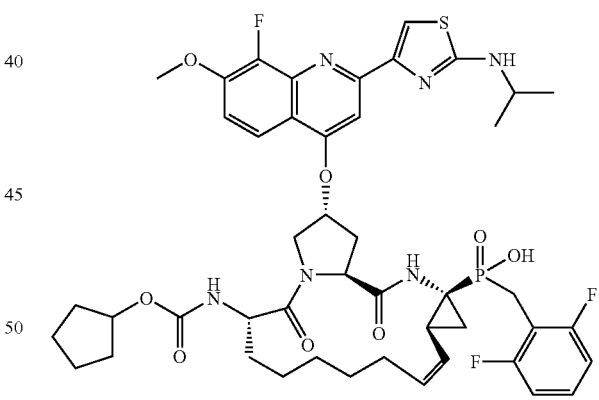

The brosylate from example 147 (1.49 g, 1.73 mmol) and the fluoro-quinoline (synthesis described below) (0.58 g, 1.73 mmol) were taken up in NMP (18 mL) with cesium carbonate (0.57 g, 1.73 mmol). The reaction was stirred at 60° C. for 15 h, cooled, and taken up in ethyl acetate. The mixture was washed with bicarbonate solution and water, dried, concentrated and purified by flash chromatography to provide the desired Boc-amine (0.942 g, 57%).

This Boc-amine (0.942 g, 0.098 mmol) was taken up in DCM (10 mL) and 4N HCl in dioxane (2.5 mL) was added. The mixture was stirred at room temp for 1 h, then concentrated. The residue was taken up in acetonitrile (10 mL) and water (10 mL). Cyclopentylchloroformate (5 equivalents)

and sodium carbonate (0.125 g, 1.17 mmol) were added and the reaction stirred at room temp for 1.5 h. The reaction mixture was partitioned with H₂O and ethyl acetate, washed with brine, dried (MgSO₄) and concentrated. This residue was taken up in acetonitrile (10 mL) and subjected to TMSI (0.70 mL, 4.93 mmol) for 15 minutes at which time 2,6-lutidine (10 eq.) was added. The reaction was quenched with methanol, concentrated and purified by HPLC to provide the desired phosphinate compound 149 (533 mg, 58% 3 steps) $^{1H}$ NMR (300 MHz, CD₃OD): δ 8.62 (s, 1H), 8.18 (m, 2H), 7.74 (s, 1H), 7.61 (m, 1H), 7.25 (m, 1H), 6.93 (m, 2H), 5.79 (m, 2H), 5.36 (m, 1H), 4.76 (m, 2H), 4.38 (m, 1H), 4.16 (m, 1H), 4.12 (s, 3H), 4.05 (m, 1H), 2.81 (m, 2H), 2.65 (m, 1H), 2.32 (m, 1H), 1.86 (m, 1H), 1.60 (m, 22H), 1.37 (d, J=6.4 Hz, 6H). $^{31}$P NMR (75 MHz, CD₃OD) δ 40.807. LCMS: 940 (M−1).

The quinoline was prepared in the following manner: 2-fluoro-3-methoxybenzoic acid (10 g, 58.8 mmol) and Hunig's base (12.3 mL, 70.5 mmol) were taken up in toluene (50 mL) and tert-butanol (50 mL) and stirred over activated 4 angstrom molecular sieves for 1 h. Diphenylphosphorylazide (15.2 mL, 70.5 mmol) was added and the reaction warmed to reflux overnight. The mixture was cooled, filtered and concentrated. The residue was then taken up in ethyl acetate, washed with water and brine, dried and concentrated to provide 15.6 g of crude material. This Boc-aniline was then subjected to 4N HCl in dioxane (260 mL) for 1 h at room temp. The reaction was concentrated, then taken up in ethyl acetate, washed with sodium bicarbonate solution followed by brine, dried, and concentrated to provide the aniline (10 g). This crude aniline (10 g, 71 mmol)) was taken up in methanol (200 mL) and dimethylacetylene dicarboxylate (10.4 mL, 85 mmol) was added. The mixture was refluxed for 2 h, then concentrated and purified by column chromatography (ethyl acateta/hexanes) to provide the desired product (11.64 g, 58%). This olefin (11.6 g) was taken up in diphenyl ether (80 mL). A sand bath was prepared and warmed to 350° C. The reaction was placed in this warm sand bath and the internal temperature was monitored. When the internal temperature reached 240° C., a 5 minute timer was started. After this time, the reaction was removed from the sand bath and allowed to cool. A brown solid precipitated out and this was filtered and washed extensively with diethyl ether to provide 8-fluoro-4-hydroxy-7-methoxy-quinoline-2-carboxylic acid (5.5 g).

This methyl ester (3.95 g, 15.7 mmol) was taken up in THF (50 mL), water (50 mL), and methanol (50 mL) and LiOH (3.3 g, 79 mmol) was added. The reaction was stirred at room temp for 1 h then acidified using HCl. The product precipitated from solution and was then filtered and dried via lyophilization to provide the acid (3.57 g, 96%).

This acid (3.57 g, 15 mmol) was taken up in THF (150 mL) at zero 0° C. Triethylamine (4.6 mL, 33.1 mmol) and isobutylchloroformate (4.3 mL, 33.1 mmol) was added and the mixture stirred for 1 h. At this time, diazomethane (2.2 equivalents) in ether solution was added (prepared from MNNG). The reaction was stirred at 0° C. for 30 minutes and warmed to room temp for 2 h. The mixture was then concentrated to provide the diazoketone quinoline with isobutyl carbonate protecting the hydroxyl. This diazoketone (15 mmol) was taken up in THF (100 mL) and conc HBr (8.5 mL, 75.3 mmol) was added at 0° C. The reaction was stirred for 1 h, then taken up in ethyl acetate, washed with bicarbonate solution, dried, and concentrated. The residue was taken up in isopropanol and isopropylthiourea (3.5 g, 30 mmol) was added. The reaction was heated to 75° C. for 1 h, then cooled overnight. The orange solid was filtered and dried to provide the aminothiazolequinoline (1.7 g, 33%). $^{1H}$ NMR (300 MHz, CD₃OD): δ 8.62 (s, 1H), 8.18 (m, 2H), 7.74 (s, 1H), 7.61 (m, 1H), 7.25 (m, 1H), 6.93 (m, 2H), 5.79 (m, 2H), 5.36 (m, 1H), 4.76 (m, 2H), 4.38 (m, 1H), 4.16 (m, 1H), 4.12 (s, 3H), 4.05 (m, 1H), 2.81 (m, 2H), 2.65 (m, 1H), 2.32 (m, 1H), 1.86 (m, 1H), 1.60 (m, 22H), 1.37 (d, J=6.4 Hz, 6H). $^{31}$P NMR (75 MHz, CD₃OD) δ 40.807. LC/MS: 940 (M−1).

Example 150

Preparation of Compound 150

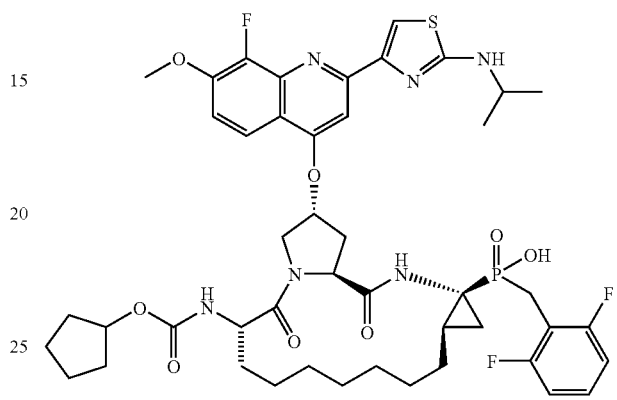

Compound 149 (528 mg, 0.56 mmol) was taken up in DME (5 mL) and water (0.5 mL). Sodium acetate (0.69 g, 8.43 mmol) and tosyl hydrazide (0.785 g, 4.21 mmol) were added and the reaction heated at 95° C. The reaction was monitored by LCMS and determined to be complete after 5 h at which time it was cooled to 0° C. and HCl (1.4 mL of 6N solution) was added and the reaction was concentrated. The residue purified by HPLC to provide the desired saturated product compound 150 (390 mg, 74%). ¹H NMR (300 MHz, CD₃OD) δ 8.16 (m, 2H), 7.72 (s, 1H), 7.64 (m, 1H), 7.27 (m, 1H), 6.95 (m, 2H), 5.81 (br s, 1H), 4.75 (m, 2H), 4.47 (m, 1H), 4.28 (m, 1H), 4.12 (s, m, 4H), 4.04 (m, 1H), 2.80 (m, 1H), 2.59 (m, 1H), 1.98 (m, 1H), 1.82 (m, 2H), 1.37 (m, $^{31}$H). $^{31}$P NMR (121.4 MHz, CD₃OD) δ 42.381. LCMS: 942 (M+1).

Example 151

Preparation of Compound 151

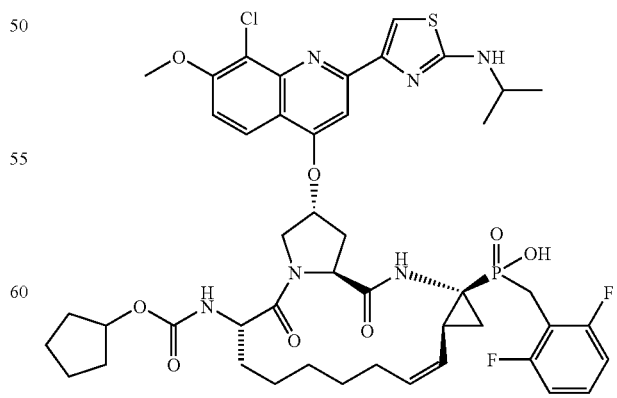

Step 1. To a mixture of intermediate VIII (22.03 g, 60.12 mmol) and (1-amino-2-vinyl-cyclopropyl)-(2,6-difluorobenzyl)-phosphinic acid ethyl ester (described in Example 58, 12.97 g, 40.48 mmol) in toluene (160 mL) was added sodium 2-ethylhexanoate (10.01 g, 60.26 mmol) and H₂O (240 mL). The reaction mixture was heated to 80° C. and stirred for 48 h. The reaction mixture was cooled to room temperature, diluted with EtOAc (400 mL), and separated. The aqueous layer was extracted with EtOAc (200 mL). The combined organic layers were washed with 1 N HCl (400 mL), NaHCO₃ (300 mL), brine (400 mL), dried with Na₂SO₄, and concentrated in vacuo. The coupling product (23.25 g) was obtained as crude product. LCMS (M+1): 667.97

Step 2. The product obtained above (23.25 g, 34.82 mmol) and DABCO (6.26 g, 55.79 mmol) were dissolved in toluene (55 mL). A toluene (15 mL) solution of 4-bromobenzene-sulfonyl chloride (12.48 g, 48.9 mmol) was added. The reaction mixture was stirred at r. t. overnight whereupon additional 4-bromo-benzenesulfonyl chloride (7.14 g, 39.12 mmol) and DABCO (3.13 g, 27.9 mmol) were added. The reaction was stirred for 3 h. The reaction mixture was diluted with EtOAc (350 mL) and 0.5 N HCl (400 mL) was added. The two layers were separated. The organic layers were washed with brine (400 mL), dried with Na₂SO₄, filtered, and concentrated in vacuo. The crude product was purified by silica gel chromatography (EtOAc-hexanes) to give 20.38 g of brosylate. LCMS (M+1): 887.75

Step 3. Brosylate (11.96 g, 13.49 mmol) was dissolved in CH₂Cl₂ (1.33 L) and the solution was degassed for 30 min. The solution was heated to 40° C. and Grubb's G1 catalyst (2.78 g, 3.38 mmol) was added. The reaction was heated to 45° C. and stirred overnight. Additional Grubb's G1 catalyst (567 mg) was added and stirred for 7 h at 45° C. Trishydroxymethylphosphine (25.24 g, 0.17 mol), TEA (57 mL, 0.34 mol), and H₂O (200 mL) were added and the reaction mixture was refluxed overnight whereupon it was cooled to rt and the two layers were separated. The organic layer was washed with H₂O (2×200 mL) and brine (400 mL), dried with Na₂SO₄, and concentrated in vacuo. The crude product was purified by silica gel chromatography (EtOAc-hexanes) to give 5.79 g of macrocyclic olefin in 50% yield. LCMS (M+1): 857.88

Step 4. Macrocyclic olefin (5.78 g, 6.74 mmol) and 8-chloro-4-hydroxy-7-methoxy-quinoline-2-carboxylic acid methyl ester (2.17 g, 8.10 mmol) were dissolved in NMP (68 mL) and Cs₂CO₃ (2.21 g, 6.77 mmol) was added. The reaction mixture was heated to 70° C. and stirred for 6 h. Additional Cs₂CO₃ (219 mg, 0.68 mmol) was added and stirred at 70° C. for 5 h. The reaction mixture was cooled to r.t. and stirred overnight. The mixture was poured into H₂O/brine (900 mL/100 mL) and extracted with EtOAc (3×250 mL). The organic layer was washed with 2% LiCl (300 mL), NaHCO₃ (300 mL), brine (300 mL), dried with Na₂SO₄, filtered, and concentrated. The crude product was purified by silica gel chromatography (EtOAc-hexanes) to give 4.11 g of ester in 69% yield. LCMS (M+1): 889.14

Step 5. To a solution of ester obtained above (4.11 g, 4.62 mmol) in CH₂Cl₂ (23 mL) was added 4 N HCl in 1,4-dioxane (23 mL). The reaction mixture was stirred at r.t for 1.5 h and concentrated in vacuo. The crude HCl salt was dissolved in CH₃CN (46 mL)/saturated Na₂CO₃ (46 mL) and a solution of cyclopentylchloroformate in THF (46 mL) was added. The reaction was completed within 20 min. The organic was decanted from the solid that precipitated and concentrated in vacuo after washing the solid with CH₃CN and CH₂Cl₂. The solid that precipitated was dissolved in H₂O (250 mL) and extracted with CH₂Cl₂ (2×125 mL). The combined organic layers were washed with brine, dried with Na₂SO₄, and concentrated in vacuo. The crude product was purified by silica gel chromatography (EtOAc-hexanes) to give 4.00 g of cyclopentyl carbamate. LCMS (M+1): 901.13

Step 6. Cyclopentyl carbamate (4.39 g, 4.87 mmol) was dissolved in THF (48 mL)/H₂O (48 mL) and cooled to 0° C. NaOH (200 mg, 5.0 mmol) was added. The reaction mixture was stirred at 0° C. for 40 min and additional NaOH (200 mg, 5.0 mmol) was added. The reaction was stirred for 15 min. The reaction mixture was diluted with H₂O (200 mL), acidified to pH=2 with 1 N HCl, and extracted with EtOAc (3×300 mL). The combined organic layers were dried with Na₂SO₄, filtered, concentrated, and dried under vacuum to give 4.26 g of acid in 98% yield.

Step 7. To a solution of acid (2.20 g, 2.48 mmol) in THF (25 mL) at 0° C. was added TEA (0.38 mL, 2.73 mmol) and stirred for 5 min. Isobutylchloroformate (0.36 mL, 2.75 mmol) was added dropwise and the reaction mixture was stirred for 40 min at 0° C. An ether solution of diazomethane (5 mL, 5 mmol) was added and the reaction mixture was warmed to r.t. and stirred for 2 h. The mixture was concentrated and the residue was dissolved in EtOAc (400 mL). The EtOAc layer was washed with saturated NaHCO₃ (150 mL), H₂O (150 mL), brine (150 mL), dried with Na₂SO₄, and concentrated to give 2.22 g of crude diazoketone product. LCMS (M+1): 911.33

Step 8. Diazoketone (2.22 g, 2.44 mmol) was dissolved in THF (25 mL) and cooled to 0° C., whereupon aqueous HBr (1.38 mL, 48%, 12.2 mmol) was added dropwise and the reaction was stirred for 1.5 h. The reaction mixture was diluted with EtOAc (400 mL) and washed with NaHCO₃. The aqueous layer was extracted with EtOAc (150 mL). The combined organic layers were dried with Na₂SO₄, filtered, concentrated, and dried under vacuum to give 2.36 g of α-bromoketone. LCMS (M+1): 965.01

Step 9. A mixture of α-bromoketone (2.36 g, 2.44 mmol) and isopropyl-thiourea (580 mg, 4.91 mol) in 2-propanol (25 mL) was heated to 75° C. and stirred for 1.5 h. The reaction mixture was cooled to r. t. and concentrated. The residue was dissolved in EtOAc (300 mL) and washed with NaHCO₃ (350 mL). The aqueous layer was extracted with EtOAc (200 mL). The combined organic layers were washed with brine (200 mL), dried with Na₂SO₄, and concentrated to give 2.64 g of ester product. LCMS (M+1): 983.31

Step 10. Ester (2.64 g, 2.68 mmol) was dissolved in CH₃CN (18 mL) and cooled to 0° C. Iodotrimethylsilane (1.95 mL, 13.7 mmol) was added dropwise. The reaction mixture was warmed to r.t. and stirred for 35 min. 2,6-lutidine (4 mL) and MeOH (4 mL) were added and the reaction mixture was concentrated. The crude product was purified by HPLC to give 1.78 g of Compound 151. $^1$H NMR (300 MHz, CDCl₃) δ 8.38 (d, J=9.3 Hz, 1H), 8.30 (s, 1H), 7.60 (d, J=9.3 Hz, 1H), 7.32-7.19 (m, 1H), 6.99-6.87 (m, 2H), 5.84 (bs, 1H), 5.73 (bq, J—8.9 Hz, 1H), 5.32 (dd, J=9.9, 9.9 Hz, 1H), 4.96-4.82 (m, 1H), 4.80-4.71 (m, 1H), 4.27 (bs, 1H), 4.20-3.78 (m, 3H), 4.16 (s, 3H), 3.66-3.52 (m, 1H), 3.36-3.22 (m, 1H), 2.92-2.73 (m, 2H), 2.73-2.59 (m, 1H), 2.35-2.22 (m, 1H), 1.93-1.71 (m, 2H) 1.71-1.20 (m, 17H) 1.38 (d, J=6.6 Hz, 6H). $^{31}$P NMR (121.4 MHz, CD₃OD) δ40.5; LCMS (M+1): 955.43.

Example 152

Preparation of Compound 152

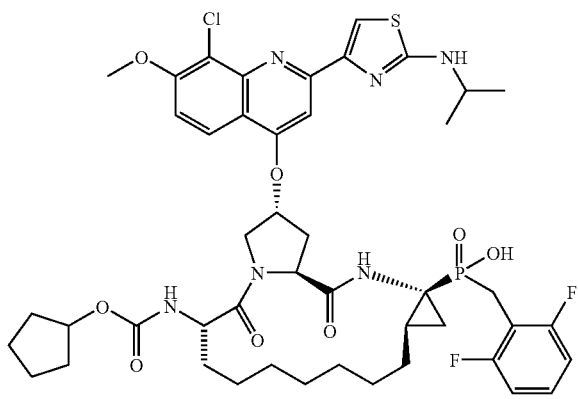

Step 1. Intermediate XI (17.42 g, 28.30 mmol) was dissolved in THF (136 mL) and cooled to 0° C. To the solution was added N-methylmorpholine (4.7 mL, 42.7 mmol). After 10 min at 0° C., i-butylchloroformate (4.05 mL, 30.96 mmol) was added dropwise. After an additional 1 h, (1-amino-2-vinyl-cyclopropyl)-(2,6-difluoro-benzyl)-phosphinic acid ethyl ester (described in Example 58, 8.94 g, 29.70 mmol) was slowly added as a soln in THF (20 mL). The suspension was warmed to rt and after 2 h it was partitioned between $H_2O$ (400 mL) and ethylacetate (200 mL). The aqueous layer was extracted with ethylacetate (200 mL×2) and the combined organic layers were washed with HCl (1N, 225 mL) and $H_2O$ (200 mL). The acid wash and aqueous wash were combined and back-extracted with ethylacetate (175 mL×2, 100 mL×2). The combined organic layers were washed with brine (400 mL), dried over $Na_2SO_4$, and concentrated in vacuo providing 25.06 g of diene product in 98.5% crude yield. LCMS (M+1): 898.06

Step 2. The crude diene product (12.91 g, 14.36 mmol) was dissolved in $CH_2Cl_2$ (1440 mL) and the solution was degassed for 30 min. The solution was heated to 40° C. and Grubb's G1 catalyst (2.95 g, 3.59 mmol) was added. The reaction was refluxed for 17 h whereupon tris-hydroxymethylphosphine (22.3 g, 18.0 mmol), TEA (50 mL, 35.9 mmol), and $H_2O$ (400 mL) were added and the reaction mixture was heated to reflux for an additional 16 h. The reaction mixture was cooled to r.t. and the two layers were separated. The organic layer was washed with $H_2O$ (400 mL) and brine (300 mL), dried over $MgSO_4$, and concentrated. The crude residue was purified by silica-gel chromatography to afford 8.30 g of macrocyclic olefin product in 66% yield. LCMS (M+1): 870.09.

Step 3. The macrocyclic olefin (7.34 g, 8.42 mmol) was dissolved in ethylacetate (105 mL) and rhodium on alumina (5% wt, 2.945 g, 0.40 wt %) was added. The system was evacuated and flushed with $H_2$ (1 atm, 3×). To the system, after 3 h, was added more rhodium on alumina (5% wt, 842 mg, 0.10 wt %) and it evacuated and flushed with $H_2$ (1 atm, 3×). After an additional 1 h the suspension was filtered and concd in vacuo providing 6.49 g of reduced macrocycle in 88% crude yield. LCMS (M+1): 872.04.

Step 4. The brosylate macrocycle (6.49 g, 7.67 mmol) was dissolved in N-methylpyrrolidinone (25.0 mL) and 8-chloro-2-(2-isopropylamino-thiazol-4-yl)-7-methoxy-quinolin-4-ol (2.564 g, 7.33 mmol) followed by $Cs_2CO_3$ (4.40 g, 13.50 mmol)were added. The mixture was heated to 65° C. for 6 h then diluted with ethylacetate (200 mL) and washed with LiCl (5%, 250 mL). The aqueous layer was extracted with ethylacetate (100 mL×2) and the combined organic layers were washed with brine (150 mL), dried over $Na_2SO_4/MgSO_4$, and concentrated in vacuo. The crude residue was purified via silica-gel chromatography (ethylacetate-methanol) affording 4.39 g of aminothiazole product in 58% yield. LCMS (M+1): 985.28.

Step 5. Phosphinate ester (23.7 g, 24.05 mmol) was dissolved in $CH_3CN$ (240 mL) and cooled to 0° C. Iodotrimethylsilane (17.4 mL, 122.3 mmol) was added at a fast drop-wise pace followed by, after 10 min, 2,6-lutidine (17.0 mL, 146.4 mmol). The reaction mixture was slowly warmed to r.t. and stirred for 1 h then cooled back down to 0° C. and 2,6-Lutidine (11.1 mL, 95.6 mmol) followed by MeOH (24 mL) were added. The solution was concentrated in vacuo and the crude residue was purified by HPLC to afford 12.68 g of Compound 152 in 55% yield. $^1H$ NMR (300 MHz, $CDCl_3$) δ 8.35 (d, J=9.3 Hz, 1H), 8.28 (s, 1H), 7.85 (s, 1H), 7.64 (d, J=9.6 Hz, 1H), 7.35-7.22 (m, 1H), 7.02-6.89 (m, 2H), 5.85 (bs, 1H), 4.82-4.71 (m, 2H), 4.33 (bs, 1H), 4.28-3.99 (m, 3H), 4.16 (s, 3H), 3.57-3.28 (m, 2H), 2.90-2.78 m, 1H), 2.63-2.50 (m, 1H), 2.08-1.91 (m, 1H), 1.91-170 (m, 2H), 1.70-1.13 (m, 22H), 1.37 (d, J=6.9 Hz, 6H); $^{31}P$ NMR (121.4 MHz, $CD_3OD$) δ42.4; LCMS (M+1): 957.35.

Example 153

Preparation of Compound 153

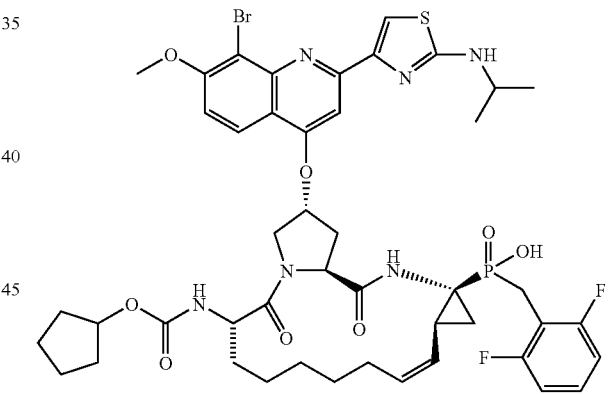

The brosylate from example 147 (603.2 mg, 0.70 mmol) and 8-bromo-4-hydroxy-7-methoxy-quinoline-2-carboxylic acid methyl ester (263.4 mg, 0.84 mmol) were dissolved in NMP (7.0 mL) and $Cs_2CO_3$ (251.5 mg, 0.77 mmol) was added. The reaction mixture was heated to 70° C. and stirred overnight. The reaction mixture was cooled to r.t. and poured into $H_2O$ (175 mL)/brine (25 mL) and extracted with EtOAc (3×100 mL). The organic layer was washed with 2% LiCl (125 mL), $NaHCO_3$ (150 mL), brine (100 mL), dried with $Na_2SO_4$, filtered, and concentrated to give 655 mg of crude product. LCMS (M+1): 934.94.

To a solution of product obtained above (655 mg, 0.70 mmol) in $CH_2Cl_2$ (3.6 mL) was added 4 N HCl in 1,4-dioxane (3.4 mL). The reaction mixture was stirred at r.t for 1 h and concentrated in vacuo. The crude HCl salt was dissolved in $CH_3CN$ (7 mL)/saturated $Na_2CO_3$ (7 mL) and a solution of cyclopentylchloroformate in THF was added. The reaction was completed within 20 min. The organic was decanted from the Na$_2$CO$_3$ that precipitated and concentrated in vacuo after washing the solid with CH$_3$CN and CH$_2$Cl$_2$. The solid Na$_2$CO$_3$ was dissolved in H$_2$O (75 mL) and extracted with CH$_2$Cl$_2$ (2×75 mL). The combined organic layers were washed with brine (75 mL), dried with Na$_2$SO$_4$, and concentrated. The crude product was purified by combi-flash to give 473 mg of cyclopentyl carbamate in 71% yield. LCMS (M+1): 945.10.

Methyl ester obtained above (473 mg, 0.5 mmol) was dissolved in THF (1.6 mL)/H$_2$O (1.7 mL) and cooled to 0° C. LiOH (60.4 mg, 2.52 mmol) in H$_2$O (1.7 mL) was added. The reaction mixture was stirred at 0° C. for 40 min and additional NaOH (200 mg, 5.0 mmol) was added. The reaction was stirred for 15 min. The reaction mixture was diluted with H$_2$O (20 mL), acidified to pH=1 with 1 N HCl, and extracted with EtOAc (3×25 mL). The combined organic layers were dried with Na$_2$SO$_4$, filtered, concentrated, and dried under vacuum to give acid.

To a solution of acid (466 mg, 0.50 mmol) in THF (5 mL) at 0° C. was added TEA (77 µL, 0.55 mmol) and stirred for 5 min. Isobutylchloroformate (72 µL, 0.55 mmol) was added dropwise and the reaction mixture was stirred for 1 h at 0° C. An ether solution of diazomethane (2.70 mL, 1.08 mmol) was added and the reaction mixture was warmed to r.t. and stirred for 2 h. The mixture was concentrated and the residue was dissolved in EtOAc (75 mL). The EtOAc layer was washed with saturated NaHCO$_3$ (60 mL), H$_2$O (50 mL), brine (50 mL), dried with Na$_2$SO$_4$, and concentrated to give crude product.

Diazoketone crude (478 mg, 0.5 mmol) was dissolved in THF (5 mL) and cooled to 0° C., HBr (0.29 mL, 2.52 mmol) was added dropwise and the reaction was stirred for 15 min. The reaction mixture was diluted with EtOAc (200 mL) and washed with NaHCO$_3$ (75 mL). The aqueous layer was extracted with EtOAc (20 mL). The combined organic layers were dried with Na$_2$SO$_4$, filtered, concentrated, and dried under vacuum to give 403.4 mg of bromoketone. LCMS (M+1): 1008.91.

A mixture of bromoketone (403.4 mg, 0.4 mmol) and iso-propyl-thiourea (94.4 mg, 0.8 mol) in 2-propanol (25 mL) was heated to 75° C. and stirred for 0.5 h. The reaction mixture was cooled to r. t. and concentrated. The residue was dissolved in CH$_2$Cl$_2$ (150 mL) and washed with NaHCO$_3$ (30 mL). The aqueous layer was extracted with CH$_2$Cl$_2$ (150 mL). The combined organic layers were washed with brine (50 mL), dried with Na$_2$SO$_4$, and concentrated to give 424.1 mg of desired product. LCMS (M+1): 1029.17.

Ester obtained above (424.1 mg, 0.41 mmol) was dissolved in CH$_3$CN (4.1 mL) and cooled to 0° C. Iodotrimethylsilane (0.3 mL, 2.07 mmol) was added dropwise. The reaction mixture was warmed to r.t. and stirred for 20 min and cooled to 0° C. 2,6-lutidine (0.5 mL) and MeOH (0.5 mL) were added and the reaction mixture was concentrated. The crude product was purified by HPLC to give 232.1 mg of compound 153 in 46% yield. $^1$H NMR (300 MHz, CDCl$_3$) δ: 8.43 (d, J=9.0 Hz, 1H), 8.33 (s, 1H), 7.90 (s, 1H), 7.60 (d, J=9.3 Hz, 1H), 7.35-7.21 (m, 1H), 6.95 (dd, J=7.8, 7.5 Hz, 2H) 5.88 (s, 1H), 5.84-5.71 (m, 1H), 5.34 (dd, J=9.3, 9.0 Hz, 1H), 4.77 (dd, J=8.4, 7.5 Hz, 1H), 4.24-4.01 (m, 7H), 3.60 (t, J=15.3 Hz, 1H), 3.32 (t, J=15.3 Hz, 1H), 2.95-2.75 (m, 2H), 2.75-2.58 (m, 1H), 2.37-2.23 (m, 1H), 1.96-1.61 (m, 2H), 1.61-1.15 (m, 17H) 1.38 (d, J=−6.6 Hz, 6H); $^{31}$P (121.4 MHz, CD$_3$OD) δ40.9; LCMS (M+): 1001.20.

Example 154

Preparation of Compound 154

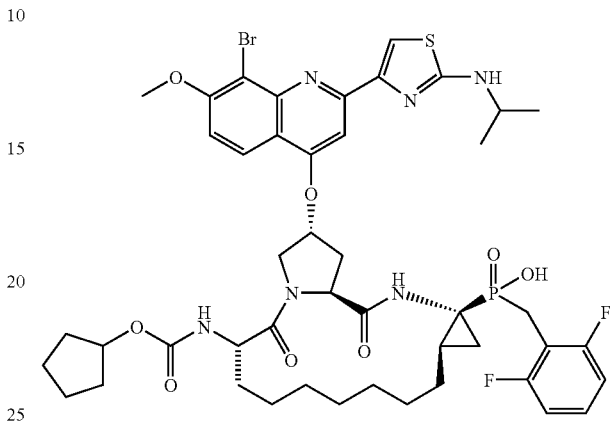

A mixture of 153 (221.3 mg, 0.22 mmol), sodium acetate (274.1 mg, 3.34 mmol), and p-tosylhydrazine ($^{31}$0.7 mg, 1.67 mmol) in DME (2 mL) and H$_2$O (0.2 mL) was heated to 95° C. for 1.5 h. The reaction mixture was cooled to r.t. and treated with 4 N HCl (0.8 mL). The crude product was purified by HPLC to give 101 mg of 154 in 47% yield. $^1$H NMR (300 MHz, CDCl$_3$) δ 8.40 (d, J=9.3 Hz, 1H), 8.29 (s, 1H), 7.88 (s, 1H), 7.63 (d, J=9.6 Hz, 1H), 7.33-7.21 (m, 1H), 6.96 (t, J=7.8 Hz, 2H) 5.86 (bs, 1H), 4.83-4.70 (m, 1H), 4.$^{31}$-4.00 (m, 5H), 4.17 (s, 3H), 3.57-3.47 (m, 1H), 3.47-3.33 (m, 1H), 2.90-2.78 (m, 1H), 2.64-2.52 (m, 1H), 2.06-1.92 (m, 1H), 1.90-1.69 (m, 2H), 1.69-1.12 (m, 22H), 1.37 (d, J=6.6 Hz, 6H); $^{31}$P (121.4 MHz, CD$_3$OD) δ42.2.

Example 155

Preparation of Compound 155

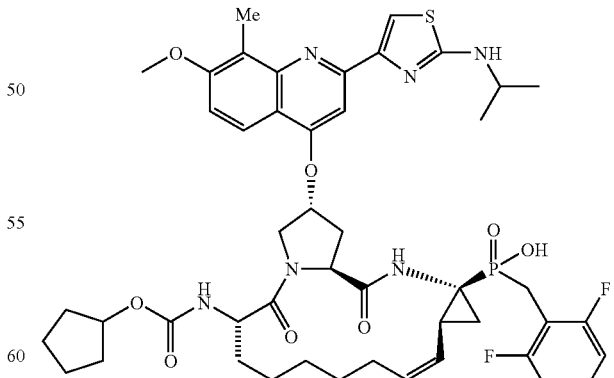

A solution of macrocyclic phosphinate (example 147) (212.6 mg, 0.25 mmol) and 2-(2-isopropylamino-thiazol-4-yl)-7-methoxy-8-methyl-quinolin-4-ol (82.0 mg, 0.25 mmol)

in NMP (3 mL) was treated with Cs₂CO₃ (81.3 mg, 0.25 mmol). The reaction mixture was heated to 70° C. overnight and then cooled to rt. The reaction was diluted with 5% LiCl (10 mL) and extracted with EtOAc (3×10 mL). The combined organic layers were washed with brine, dried with Na₂SO₄, and concentrated. The crude product was purified by combiflash to give 166.1 mg of desired product in 70% yield.

To a solution of compound obtained above (1.383 g, 1.45 mmol) in CH₂Cl₂ (7.5 mL) was added 4 N HCl in 1,4-dioxane (7.5 mL, 30 mmol). The reaction mixture was stirred at r.t. for 2 h, concentrated, dried under vacuum for 20 minutes, and then dissolved in CH₃CN (15 mL). Saturated NaHCO₃ in H₂O (15 mL) was added and stirred for 5 minutes. The freshly prepared cyclopentylchloroformate (7.7 mmol) in THF (15 mL) was added. The reaction was completed within 1 h. The solvent was removed on rotavap and the residue was diluted with EtOAc. The mixture was brought to pH=2 with 1 N HCl and the two layers were separated. The organic layers were washed with brine, dried with Na₂SO₄, filtered, and concentrated. Cyclopentayl carbamate (1.21 g) was obtained as crude product.

To a solution of cyclopentayl carbamate (194.9 mg, 0.20 mmol) in CH₃CN (2 mL) at 0° C. was added 5 equivalents of iodotrimethylsilane. The reaction mixture was stirred at 0° C. for 35 minutes. 2,6-lutidine (0.4 mL) was added and stirred for 5 minutes. MeOH (0.4 mL) was added and stirred for 20 minutes. The mixture was concentrated and the crude acid was purified by HPLC to give 97.4 mg of acid 155 in 51% yield. LC/MS 935.40 (M⁺+1)

Example 156

Preparation of Compound 156

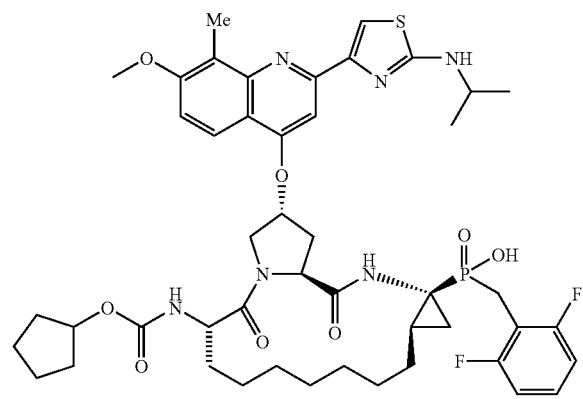

To a solution of 155 (46.8 mg, 0.05 mmol) in DME (0.5 mL)/H₂O (0.05 mL) was added p-tosylhydrazide (69.7 mg, 0.80 mmol) and NaOAc (61.8 mg, 0.75 mmol). The reaction mixture was heated to 95° C. for 2.5 h and cooled to rt. A few drops of 3 N HCl was added to adjust pH=2. The crude product was purified by HPLC to give 20.6 mg of acid 156 in 44% yield. LC/MS=937.33 (M⁺+1)

Example 157

Preparation of Compound 157

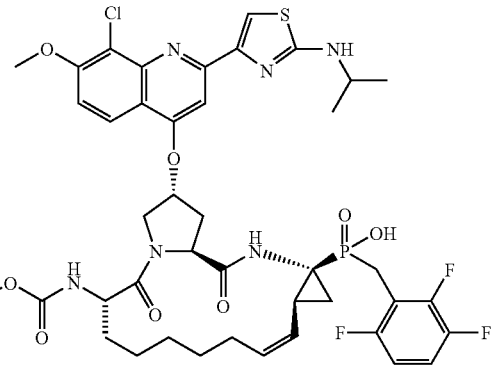

The acid XI (3.09 g, 5.03 mmol) and NMM (0.78 mL, 7.06 mmol) were dissolved in THF (40 mL) and cooled to 0° C. Isobutylchloroformate (0.69 mL, 5.3 mmol) was added dropwise and stirred at 0° C. for 1 h. (1-Amino-2-vinyl-cyclopropyl)-(2,3,6-trifluoro-benzyl)-phosphinic acid ethyl ester (prepared as described in example 68 with DMS) (1.75 g, 5.48 mmol) was added slowly and the mixture was stirred at r.t. for 1.5 h. The reaction was diluted with EtOAc and washed with 1 N HCl, saturated NaHCO₃/brine, dried with Na₂SO₄ and concentrated. The crude product was purified by combiflash to give 2.7 g of compound diene in 59% yield.

Diene compound (2.7 g, 2.94 mmol) was dissolved in CH₂Cl₂ (300 mL) and degassed with N₂ for 20 minutes. Grubb's G1 (970 mg, 1.18 mmol) was added and degassed for an additional 20 minutes. The reaction mixture was heated to 45° C. overnight and cooled to rt. Tris(hydroxymethyl)phosphine (9 g) was added followed by addition of TEA (20 mL) and H₂O (40 mL). The reaction mixture was heated to 50° C. overnight. The two layers were separated. The organic layer was washed with 0.5 N HCl, brine, dried with Na₂SO₄, and concentrated. The crude product was purified by combi-flash to give 2.01 g of macrocyclic compound in 77% yield.

A solution of macrocyclic compound (2.0 g, 2.25 mmol) and 8-chloro-2-(2-isopropylamino-thiazol-4-yl)-7-methoxyquinolin-4-ol (786 mg, 2.25 mmol) in NMP (11 mL) was treated with Cs₂CO₃ (880 mg, 2.7 mmol). The reaction mixture was heated to 60° C. for 1 h. Additional Cs₂CO₃ (1.13 g, 3.47 mmol) was added and stirred at 60° C. for 1.5 h. The temperature was lowered to 40° C. overnight and then cooled to rt. The reaction was diluted with EtOAc and washed with 5% LiCl (3×) and brine. The organic layer was dried with Na₂SO₄ and concentrated. The crude product was directly used for next step reaction.

The residue (2.07 g, 2.07 mmol) was dissolved in CH₃CN (20 mL) at 0° C. To this mixture was added iodotrimethylsilane (1.48 mL, 10.39 mmol). The reaction mixture was stirred at 0° C. for 5 minutes. 2,6-Lutidine (1.44 mL, 12.46 mmol) was added and stirred for 1.5 h. MeOH was added and stirred for 30 minutes. The mixture was concentrated and re-dissolved in minimal MeOH and divided into two portions. One portion was purified by HPLC to give 404 mg of 157. LC/MS=973 (M⁺+1)

Example 157X

Preparation of Compound 157X

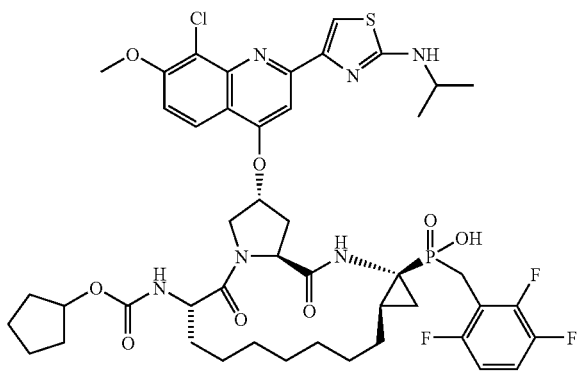

Compound 157 was reduced to give 157X as described for example 156. LC/MS=975 (M⁺+1)

Example 158

Preparation of Compound 158

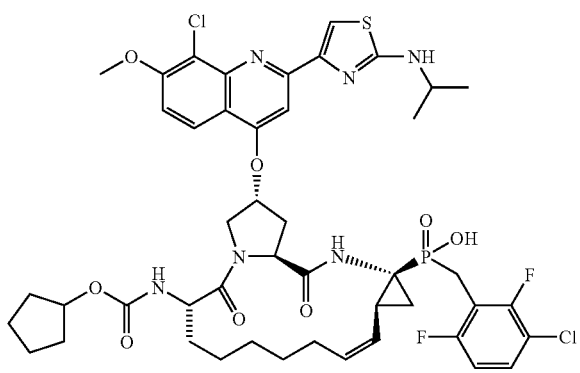

To a solution of (1-benzyloxycarbonylamino-2-vinyl-cyclopropyl)-(3-chloro-2,6-difluoro-benzyl)-phosphinic acid ester (example 65) (8 g, 17.1 mmol) in TFA (46 mL, 614 mmol) at 0° C. was added DMS (12.1 mL, 164.2 mmol). The reaction mixture was stirred at r.t. overnight. The reaction mixture was poured into ice cold 4 N HCl (500 mL) and extracted with 1/1 iPrOH/heptane (500 mL). The organic layers were washed with 4 N HCl (5×500 mL). The combined aqueous layers were brought to pH=10 in a cold bath. The aqueous layer was extracted with EtOAc (5×500 mL). The organic layers were washed with brine, dried with $Na_2SO_4$, and concentrated to give 4.1 g of amine in 66% yield.

The acid from intermediate X (8.4 g, 13.86 mmol) and amine obtained above (3.9 g, 11.55 mmol) were dissolved in DMF (100 mL). HATU (10.97 g, 28.88 mmol) and NMM (5.9 g, 57.75 mmol) were added and the mixture was stirred at r.t. for 2 h. The reaction was diluted with EtOAc and washed with 20% LiCl (2×500 mL). The organic layer was washed with aqueous $NH_4Cl$ (500 mL), dried with $Na_2SO_4$, and concentrated. The crude product was purified by combi-flash to give 8.2 g of tripeptide. $^1$H NMR (300 MHz, $CDCl_3$): δ 7.74 (m, 4H), 7.24 (m, 1H), 6.83 (m, 1H), 6.07 (m, 1H), 5.78 (m, 2H), 5.25 (m, 1H), 5.17 (m, 1H), 4.98 (m, 1H), 4.67 (d, 1H), 4.38 (m, 2H), 4.18 (m, 2H), 4.12 (m, 2H), 3.83 (m, 2H), 3.65 (m, 2H), 3.32 (m, 3H), 2.24 (m, 3H), 2.04 (m, 4H), 1.80 (m, 2H), 1.63 (m, 1H), 1.51 (m, 2H), 1.42 (m, 9H), 1.25 (m, 3H). $^{31}$P (121.4 MHz, $CDCl_3$): δ45.110, 44.254 diastereomers.

Tripeptide (5.0 g, 5.43 mmol) was dissolved in $CH_2Cl_2$ (600 mL) and degassed with $N_2$ for 30 minutes. Grubb's G1 (1.34 g, 1.63 mmol) was added and degassed for an additional 30 minutes. The reaction mixture was heated to 45° C. overnight and cooled to rt. Tris(hydroxymethyl)phosphine (9.9 g, 80.1 mmol) was added and stirred for 20 minutes. TEA (16.5 g, 162.9 mmol) was added and stirred for 20 minutes followed by addition of $H_2O$ (60 mL). The reaction mixture was heated to 50° C. for 4 h and then r.t. overnight. The two layers were separated. The organic layer was washed with 0.5 N HCl, brine, dried with $Na_2SO_4$, and concentrated. The crude product was purified by combi-flash to give 2.1 g of cyclized compound. $^1$H NMR (300 MHz, $CDOD_3$); δ 7.87 (m, 4H), 7.40 (m, 1H), 7.03 (m, 1H), 6.75 (m, 1H), 5.78 (m, 1H), 5.60 (m, 1H), 5.40 (m, 1H), 5.11 (m, 1H), 4.90 (m, 1H), 4.37 (m, 3H), 3.83 (m, 2H), 3.75 (m, 2H), 3.51 (m, 1H) 3.22 (m, 2H), 2.24 (m, 3H), 2.04 (m, 4H), 1.80 (m, 2H), 1.63 (m, 1H), 1.51 (m, 2H), 1.42 (m, 9H), 1.25 (m, 3H). $^{31}$P (121.4 MHz, $CDOD_3$): δ45.978, 45.613 diastereomers.

A solution of cyclic phosphinate (2.1 g, 2.35 mmol) and 8-chloro-2-(2-isopropylamino-thiazol-4-yl)-7-methoxy-quinolin-4-ol (820 mg, 2.35 mmol) in NMP (50 mL) was treated with $Cs_2CO_3$ (1.53 g, 4.7 mmol). The reaction mixture was heated to 80° C. for 6 h and then cooled to rt. The reaction was diluted with EtOAc and washed with $H_2O$. The aqueous layer was brought to pH=4 with 1 N HCl and extracted with 10% MeOH/EtOAc (2×200 mL). The combined organic layers were concentrated. The crude material was dissolved in $CH_2Cl_2$ (1 L), dried with $Na_2SO_4$ and concentrated. The crude product was dried in vacuo and carried on for next step reaction.

To a solution of crude product obtained above (1.5 g, 1.5 mmol) in $CH_2Cl_2$ (5 mL) was added 4 N HCl in 1,4-dioxane (5 mL, 20 mmol). The reaction mixture was stirred at r.t. for 0.5 h, concentrated, dried under vacuum for 20 minutes, and then dissolved in $CH_3CN$ (20 mL). $Na_2CO_3$ (1.5 g, 18 mmol) in $H_2O$ (30 mL) was added and stirred for 5 minutes. A THF solution of the freshly prepared cyclopentylchloroformate (1.11 g, 7.5 mmol) was added. The reaction was completed within 1 h. The solvent was removed on rotavap and the residue was diluted with EtOAc. The mixture was brought to pH=2 with 1 N HCl and the two layers were separated. The organic layers were washed with brine, dried with $Na_2SO_4$, filtered, and concentrated. The crude product was dried under vacuo overnight and dissolved in $CH_3CN$ (3 mL)/$CH_2Cl_2$ (1 mL). The reaction mixture was cooled to 0° C. and iodotrimethylsilane (1.1 mL, 7.5 mmol) was added. The reaction mixture was warmed to r.t and stirred for 30 minutes and cooled to 0° C. 2,6-Lutidine (1 mL) and MeOH (1 mL) were added and stirred for 10 minutes. The mixture was concentrated and the crude product was purified by HPLC to give 560 mg of product 158. $^1$H NMR (300 MHz, $CD_3OD$): δ 8.91 (s, 1H), 8.36 (d, J=9.0 Hz, 2H), 8.30 (s, 1H), 7.85 (s, 1H), 7.65 (d, J=9.6 Hz, 2H), 7.39 (m, 1H), 7.00 (t, J=9.0 Hz, 1H), 5.85 (s, 1H), 5.77 (m, 1H), 5.33 (m, 1H), 4.78 (m, 1H), 4.38 (m, 1H), 4.22 (m, 2H), 4.07 (s, 3H), 3.75 (m, 1H), 3.38 (m, 2H), 2.85 (m, 1H), 2.57 (m, 1H) 1.98-1.37 (m, 21H), 1.33 (m, 6H).

$^{31}$P NMR (121.4 MHz, CD$_3$OD): δ40.231; LC/MS=989 (M$^+$+1)

Example 159

Preparation of Compound 159

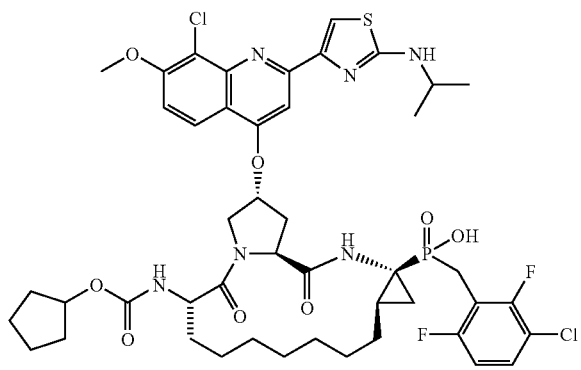

To a solution of 158 (771 mg, 0.79 mmol) in DME (5 mL)/H$_2$O (0.4 mL) was added p-tosylhydrazide (737 mg, 3.96 mmol) and NaOAc (650 mg, 7.93 mmol). The reaction mixture was heated to 95° C. for 1.5 h and cooled to rt. A few drops of 3 N HCl was added to adjust pH=2. The crude product was purified by HPLC to give 587 mg of acid 159 in 76% yield. $^1$H NMR (300 MHz, CD$_3$OD): δ 8.89 (s, 1H), 8.39 (d, J=9.5 Hz, 2H), 8.25 (s, 1H), 7.82 (s, 1H), 7.60 (d, J=9.5 Hz, 2H), 7.40 (m, 1H), 7.01 (m, 1H), 5.84 (s, 1H), 4.75 (m, 1H), 4.38 (m, 1H), 4.22 (m, 2H), 4.07 (s, 3H), 3.75 (m, 1H), 3.38 (m, 2H), 2.83 (m, 1H), 2.58 (m, 1H), 2.31 (m, 1H) 1.82 (m, 1H), 1.58 (m, 23H), 1.35 (m, 6H). $^{31}$P (121.4 MHz, CD$_3$OD): δ41.136; LC/MS=991 (M$^+$+1)

Example 160

Preparation of Compound 160

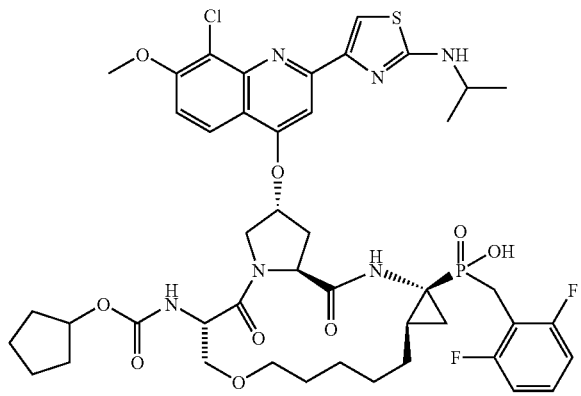

Step 1. A solution of N-Boc-L-serine (10.26 g, 50 mmol) in DMSO (200 mL) was treated with NaH (4 g, 100 mmol). The mixture was stirred at rt for 1 h and 5-bromo 1-pentene (6 mL, 50 mmol) was added. An additional NaH (4 g, 100 mmol) was added and the reaction mixture was stirred overnight. The reaction was diluted with EtOAc (200 mL) and quenched slowly with H$_2$O. EtOAc (200 mL) was added and 1 N HCl was added to adjust pH=2. The two layers were separated. The organic layer was washed with H$_2$O and brine, dried with Na$_2$SO$_4$, filtered, and concentrated. The residue was treated with 0.1 N NaOH (200 mL) and extracted with hexane (2×200 mL). The aqueous layer was brought to pH 2 with 1 N HCl and extracted with EtOAc (2×200 mL). The organic layer was dried with Na$_2$SO$_4$ and concentrated to give 8 g of acid. $^1$H NMR (300 MHz, CDCl$_3$): δ 5.7 (m, 1H), 5.36 (d, J=8.4 Hz, 1H), 5.11 (s, 1H), 4.92 (m, 2H), 4.41 (q, J=5.7 Hz, 1H), 3.82 (dd, J=9.9, 21.6 Hz, 1H), 3.52 (m, 2H), 3.34 (m, 3H), 2.21 (m, 1H), 1.95 (m, 3H), 1.52 (dt, J=7.8, 14.4 Hz, 2H), 1.34 (s, 9H). LC/MS=369.9 (M$^+$+1), 392.0 (M$^+$+Na)

Step 2. Intermediate IX (6.0 g, 12.9 mmol) was treated with 4 N HCl/1,4-dioxane (32 mL) and stirred for 1 h. The reaction mixture was concentrated and dried under vacuum for 20 minutes. The crude amine HCl salt was dissolved in DMF (70 mL) and acid (7.1 g, 25.8 mmol) was added. HATU (12 g, 32.25 mmol) and NMM (6.6 g, 64.5 mmol) were added. The reaction mixture was stirred at r.t. overnight. The reaction was diluted with EtOAc (300 mL), washed with 1 N HCl (200 mL), saturated NaHCO$_3$, brine, dried with Na$_2$SO$_4$, and concentrated. The crude product was purified by combi-flash to give 7.5 g of dipeptide. $^1$H NMR (300 MHz, CDCl$_3$): δ 7.76 (m, 4H), 5.81 (m, 2H), 5.35 (m, 1H), 5.19 (m, 1H), 5.01 (m, 2H), 4.73 (m, 1H), 4.48 (m, 1H), 4.03 (m, 1H), 3.79 (m, 1H), 3.68 (m, 3H), 3.63 (m, 1H), 3.43 (m, 3H), 2.41 (m, 1H), 2.11 (m, 2H), 1.67 (m, 2H), 1.48 (m, 9H).

To a solution of dipeptide (7.1 g, 11.5 mmol) in CH$_2$Cl$_2$ (5 mL) was added 4 N HCl in 1,4-dioxane (29 mL, 115 mmol). The reaction mixture was stirred at r.t. for 1 h and concentrated in vacuo for 20 minutes. Cyclopentanol (4.9 g, 57.5 mmol) was dissolved in THF (70 mL) and phosgene (9.7 g, 97.8 mmol) in toluene was added. The reaction was stirred for 1.5 h and concentrated to half volume to remove phosgene. The crude amine HCl salt was dissolved in EtOAc (200 mL). Na$_2$CO$_3$ (17.1 g, 138 mmol) in H$_2$O (100 mL) was added and stirred for 5 minutes. The THF solution of the freshly prepared cyclopentylchloroformate was added. The reaction was completed within 1.5 h. The two layers were separated. The organic layers were washed with brine, dried with Na$_2$SO$_4$, filtered, and concentrated. The crude product was purified by combi-flash to give 3.9 g of product. $^1$H NMR (300 MHz, CDCl$_3$): δ 7.76 (m, 4H), 5.81 (m, 2H), 5.35 (m, 1H), 5.19 (m, 1H), 5.01 (m, 2H), 4.73 (m, 1H), 4.48 (m, 1H), 4.03 (m, 1H), 3.79 (m, 1H), 3.68 (m, 3H), 3.63 (m, 1H), 3.43 (m, 3H), 2.41 (m, 1H), 2.11 (m, 2H), 1.67-1.31 (m, 10H).

Ester obtained above (3.9 g, 6.2 mmol) was dissolved in THF (30 mL), H$_2$O (30 mL), and MeOH (10 mL) and LiOH (1.3 g, 31 mmol) was added. The reaction mixture was stirred at r. t. for 1 h and diluted with EtOAc. The reaction mixture was acidified to pH=2 with 1 N HCl and separated. The aqueous layer was extracted with EtOAc. The combined organic layers were washed with brine, dried with Na$_2$SO$_4$, concentrated and dried under vacuum to give acid. The crude acid and amine (Example 147, step 1) (2.1 g, 6.8 mmol) were dissolved in DMF (50 mL). HATU (5.9 g, 15.5 mmol) and NMM (3.1 g, 31 mmol) were added and the mixture was stirred at r.t. for 2 h. The reaction was diluted with EtOAc and washed with 1 N HCl, saturated NaHCO$_3$/brine, dried with Na$_2$SO$_4$ and concentrated. The crude product was purified by comi-flash to give 3.7 g of desired diene compound. $^1$H NMR (300 MHz, CDCl$_3$): δ 7.76 (m, 4H), 7.19 (m, 1H), 6.82 (m, 1H), 5.95-5.62 (m, 3H), 5.49-5.20 (m, 3H), 5.19 (m, 1H), 5.01 (m, 2H), 4.73 (m, 1H), 4.48 (m, 1H), 4.19-3.82 (m, 3H), 3.79-3.21 (m, 7H), 2.41 (m, 1H), 2.23 (m, 1H), 2.11 (m, 2H), 1.83-1.31 (m, 12H). 1.09 (m, 3H). $^{31}$P NMR (121.4 MHz, CDCl$_3$): δ45.168, 43.313 diastereomers.

Diene (3.7 g, 4.3 mmol) was dissolved in CH$_2$Cl$_2$ (400 mL) and degassed with N$_2$ for 30 minutes. Grubb's G1 (1.1 g, 1.3 mmol) was added and degassed for an additional 30 minutes.

The reaction mixture was heated to 45° C. for 3 h and cooled to rt. Tris(hydroxymethyl)phosphine (8.0 g, 64.5 mmol) was added followed by addition of TEA (13.1 g, 129 mmol) and H$_2$O (30 mL). The reaction mixture was stirred overnight and two layers were separated. The organic layer was washed with 0.5 N HCl, brine, dried with Na$_2$SO$_4$, and concentrated. The crude product was purified by combi-flash to give 1.7 g of cyclized compound. $^1$H NMR (300 MHz, CDCl$_3$): δ 7.76 (m, 4H), 7.19 (m, 1H), 6.82 (m, 1H), 5.81 (m, 1H), 5.58 (m, 1H), 5.19 (m, 1H), 5.01 (m, 2H), 4.73 (m, 1H), 4.48 (m, 1H), 4.19-3.82 (m, 3H), 3.79-3.21 (m, 7H), 2.41 (m, 1H), 2.23 (m, 1H), 2.11 (m, 2H), 1.83-1.31 (m, 12H). 1.09 (m, 3H). $^{31}$P NMR (121.4 MHz, CDCl$_3$): δ45.768, 41.813 diastereomers.

A solution of cyclized compound (1.7 g, 1.9 mmol) and 8-chloro-2-(2-isopropylamino-thiazol-4-yl)-7-methoxy-quinolin-4-ol (0.62 g, 1.8 mmol) in NMP (40 mL) was treated with Cs$_2$CO$_3$ (1.3 g, 3.8 mmol). The reaction mixture was heated to 80° C. for 6 h and then cooled to rt. The reaction was diluted with EtOAc and washed with H$_2$O. The aqueous layer was brought to pH=4 and extracted with 5% MeOH/EtOAc (2×200 mL). The combined organic layers were dried with Na$_2$SO$_4$ and concentrated. The residue was purified by combi-flash to give 1.6 g of product. Ester obtained above (1.6 g, 1.6 mmol) was dissolved in CH$_3$CN (3 mL) and cooled to 0° C. Iodotrimethylsilane (1.6 g, 8.1 mmol) was added dropwise. The reaction mixture was warmed to r.t. and stirred for 0.5 h. The reaction was cooled to 0° C. and 2,6-lutidine (1 mL) was added. MeOH (1 mL) was added and the reaction mixture was concentrated. The crude product was purified by HPLC to give 600 mg of acid, which was reduced with p-tosyl hydrazide (758 mg, 4.1 mmol) and NaOAc (672 mg, 8.2 mmol) to give 160 (390 mg). $^1$H NMR (300 MHz, CD$_3$OD): δ 8.32 (d, J=9.6 Hz, 1H), 8.26 (s, 1H), 7.86 (s, 1H), 7.65 (d, J=9.3 Hz, 1H), 7.26 (m, 1H), 6.92 (t, J=6.9 Hz, 2H), 5.86 (s, 1H), 4.75 (m, 1H), 4.65 (m, 1H), 4.48 (m, 2H), 4.21 (m, 1H), 4.18 (s, 3H), 4.07 (m, 1H), 3.75 (m, 6H), 3.53 (m, 2H), 2.83 (m, 1H), 2.58 (m, 1H), 1.87 (m, 3H), 1.68-1.36 (m, 17H), 1.36 (m, 6H). $^{31}$P NMR (121.4 MHz, CD$_3$OD): δ42.637. LC/MS=959 (M$^+$+1)

Example 161

Preparation of Compound 161

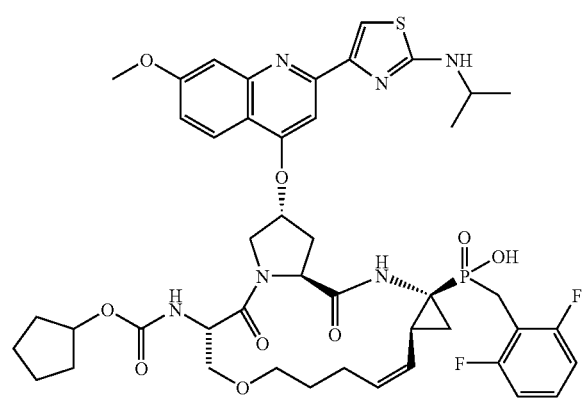

Step 1. 2-Oxa-5-aza-bicyclo[2.2.1]heptan-3-one amine HCl salt (1.0 g, 6.7 mmol) and acid (Example 160, step 1) (2.73 g, 10 mmol) were dissolved in CH$_2$Cl$_2$ (60 mL)/DMF (7 mL). HATU (7.64 g, 20.1 mmol) and NMM (2.94 mL, 26.80 mmol) were added and the mixture was stirred at r.t. for 1 h. The reaction was diluted with CH$_2$Cl$_2$ and washed with 5% LiCl (2×). The organic layer was washed with saturated NaHCO$_3$, dried with Na$_2$SO$_4$, and concentrated. The crude product was purified by comi-flash followed by HPLC to give 725 mg of compound in 29% yield.

Step 2. To a yellow solution of product from step 1 (725 mg, 1.97 mmol) and amine example 58 (1.0 g, 3.30 mmol) in toluene (5 mL) was added a solution of sodium hexanoate (327 mg, 1.97 mmol) in H$_2$O (15 mL). The reaction mixture was heated to 70° C. for 60 h. The reaction mixture was diluted with EtOAc, washed with saturated NH$_4$Cl (2×), saturated NaHCO$_3$ (2×) and brine. The organic layer was dried with Na$_2$SO$_4$, concentrated, and dried under vacuum to give 520 mg of alcohol as crude product. Alcohol (520 mg, 0.78 mmol) and DABCO (279 mg, 2.48 mmol) were dissolved in toluene (4 mL). A toluene (4 mL) solution of brosylchloride (635 mg, 2.48 mmol) was added dropwise. The reaction mixture was stirred at r. t. for 1 h. The reaction was diluted with EtOAc and quenched with saturated NaHCO$_3$. The two layers were separated and the organic layer was washed with 0.5 N HCl, brine, dried with Na$_2$SO$_4$, filtered, and concentrated. The crude product was purified by combi-flash to give 621 mg of brosylate in 90% yield. $^{31}$P NMR (121.4 MHz, CDCl$_3$) δ47.0, 44.5, 42.8, 41.6. LC/MS=890.4 (M$^+$+1)

Step 3. Brosylate (620 mg, 0.70 mmol) was dissolved in CH$_2$Cl$_2$ (70 mL) and degassed with N$_2$ for 20 minutes. Grubb's G1 (144 mg, 0.18 mmol) was added and degassed for an additional 20 minutes. The reaction mixture was heated to 50° C. for 5.5 h and cooled to rt. Tris(hydroxymethyl)phosphine (1.09 g) was added followed by addition of TEA (2.44 mL) and H$_2$O (10 mL). The reaction mixture was heated to 50° C. for 6 h and then r.t. overnight. The two layers were separated. The organic layer was washed with 0.5 N HCl and brine, dried with Na$_2$SO$_4$, and concentrated. The crude product was purified by combi-flash to give 504 mg of olefin in 84% yield. $^1$H NMR (300 MHz, CDCl$_3$): δ $^{31}$P (121.4 MHz, CDCl$_3$): δ

Step 4. A solution of compound olefin (504 mg, 0.59 mmol) and 2-(2-isopropylamino-thiazol-4-yl)-7-methoxy-quinolin-4-ol (185 mg, 0.59 mmol) in NMP (5.9 mL) was treated with Cs$_2$CO$_3$ (191 mg, 0.59 mmol). The reaction mixture was heated to 63° C. for 7 h and then cooled to rt overnight. The reaction was diluted with EtOAc and washed with NaHCO$_3$. The organic layer was washed with 5% LiCl and brine, dried with Na$_2$SO$_4$, and concentrated. The crude product (551 mg) was used directly for next step reaction.

To a solution of crude product obtained above (551 mg, 0.59 mmol) in CH$_3$CN (5.9 mL) at 0° C. was added iodotrimethylsilane (0.42 mL, 2.94 mmol). The reaction mixture was warmed to r.t, stirred for 30 minutes, and cooled to 0° C. 2,6-lutidine (0.69 mL, 5.87 mmol) was added followed by addition of MeOH (3 mL) and warmed to rt. The mixture was concentrated, dried under vacuum, and then dissolved in CH$_3$CN (3 mL). Saturated Na$_2$CO$_3$ in H$_2$O (3 mL) was added and stirred for 5 minutes. A THF solution of the freshly prepared cyclopentylchloroformate (4.11 mmol) was added. The reaction was completed within 1 h. The solvent was removed on rotavap. The residue was worked up and purified by HPLC to give 180 mg of 161. $^1$H NMR (300 MHz, CD$_3$OD) δ8.27 (d, J=9.6 Hz, 1H), 8.2 (s, 1H), 7.76 (m, 2H), 7.32 (dd, J=2.4, 9.3 Hz, 1H), 7.26 (m, 1H), 6.94 (t, J=7.5 Hz, 2H), 5.84 (s, 1H), 5.67 (dd, J=8.4, 9.9 Hz, 1H), 5.45 (t, J=9.9 Hz, 1H), 4.77 (t, J=8.1 Hz, 1H), 4.69 (d, J=12 Hz, 1H), 4.54 (m, 2H), 4.17 (m, 3H), 4.03 (s, 3H), 3.26-3.73 (brm, 7H), 2.81 (dd, J=7.8, 14.1 Hz, 1H), 2.5-2.7 (brm, 2H), 2.38 (m, 1H), 2.2

(m, 1H), 1.4-1.7 (brm, 10H), 1.36 (d, J=15.6 Hz). $^{31}$P NMR (121.4 MHz, CD$_3$OD) δ 40.9. LC/MS=925.5 (M$^+$+1)

Example 162

Preparation of Compound 162

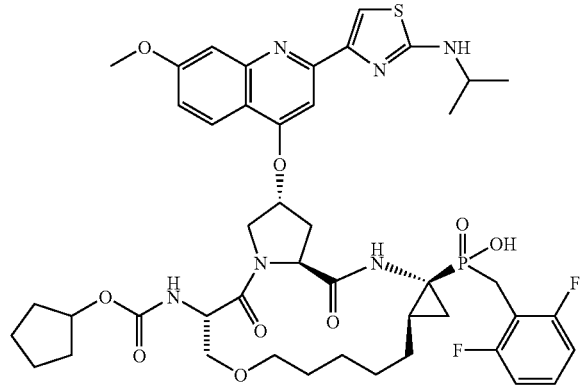

To a solution of 161 (103 mg, 0.11 mmol) in DME (18 mL)/H$_2$O (1.8 mL) was added p-tosylhydrazide (156 mg, 0.84 mmol) and NaOAc (138 mg, 1.68 mmol). The reaction mixture was heated to 95° C. for 3 h and cooled to rt. The mixture was concentrated, dissolved in CH$_2$Cl$_2$, and washed with H$_2$O. The aqueous layer was extracted with CH$_2$Cl$_2$ (2×). The organic layer was dried with Na$_2$SO$_4$ and concentrated. The crude product was purified by HPLC to give 74 mg of acid 162 in 71% yield. $^1$H NMR (300 MHz, CD$_3$OD) δ8.25 (d, J=9 Hz, 1H), 8.19 (s, 1H), 7.74 (d, J=3.6 Hz, 2H), 7.34 (dd, J=2.1, 9.3 Hz, 1H), 7.26 (qd, J=2.1, 8.7 Hz, 1H), 6.95 (t, J=7.8 Hz, 2H), 5.84 (s, 1H), 4.7 (t, J=8.4 Hz, 1H), 4.61 (brs, 2H), 4.52 (dd, J=3.0, 3.6 Hz, 1H), 4.17 (m, 2H), 4.03 (s, 3H), 3.67 (m, 3H), 3.45 (m, 1H), 3.33 (m, 2H), 2.82 (dd, J=7.8, 14.4 Hz, 1H), 2.53 (ddd, J=3.9, 8.7, 13.5 Hz, 1H), 1.4-2.0 (brm, 19H), 1.34 (d, J=6.3 Hz). $^{31}$P NMR (121.4 MHz, CD$_3$OD) δ 42.9 LC/MS=927.6 (M$^+$+1).

Example 163

Preparation of Compound 163

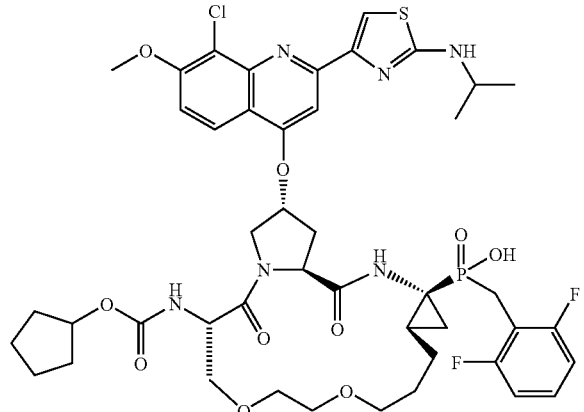

A solution of 2-allyloxy-ethanol (20 g, 196 mmol) in pyridine (3.48 mL, 43 mmol) was added to PBr$_3$ (7.45 mL, 78.4 mmol) at 0° C. The reaction mixture was stirred overnight at rt. The white precipitate was filtered. The organic was diluted with ether, washed saturated NaHCO$_3$ and brine, dried with Na$_2$SO$_4$, filtered, and concentrated. The crude product was purified by combi-flash to give 6.3 g of 3-(2-bromo-ethoxy)-propene in 85% yield. $^1$H NMR (300 MHz, CDCl$_3$): δ5.85 (m, 1H), 5.19-5.38 (m, 2H), 4.15 (d, 2H), 3.78 (dd, 2H), 3.48 (dd, 2H). LC/MS=165 (M$^+$+1), 187 (M$^+$+Na)

A solution of N-Boc-L-serine (7 g, 34 mmol) in DMSO (100 mL) was treated with 60% of NaH (1.36 g, 34 mmol). The mixture was stirred at rt for 1 h and compound 3-(2-bromo-ethoxy)-propene (5.6 g, 34 mmol) was added. An additional NaH (1.36 g, 34 mmol) was added and the reaction mixture was stirred overnight. The reaction was cooled to 0° C., diluted with EtOAc, and quenched slowly with 1N HCl to pH=4. The two layers were separated. The organic layer was washed with H$_2$O and brine, dried with Na$_2$SO$_4$, filtered, and concentrated. The residue was treated with 0.3 N NaOH and extracted with hexane twice. The aqueous layer was brought to pH=4 with 1 N HCl and extracted with EtOAc. The organic layer was dried with Na$_2$SO$_4$ and concentrated to give 3.75 g of acid. $^1$H NMR (300 MHz, CDCl$_3$): δ 5.90 (m, 1H), 5.19-5.38 (m, 2H), 4.42 (m, 1H), 4.15 (dd, 2H), 3.98 (dd, 2H), 3.60 (d, 2H), 3.70 (d, 2H). LC/MS=289.9 (M$^+$+1)

To a solution of intermediate XI (4 g, 5.45 mmol) in CH$_2$Cl$_2$ (30 mL) was added 4 N HCl in 1,4-dioxane (32 mL, 129 mmol). The reaction mixture was stirred at r.t. for 0.5 h, concentrated, dried under vacuum for 20 minutes to give amine HCl salt. The resulting amine HCl salt and acid obtained above (2.4 g, 8.42 mmol) were dissolved in DMF (30 mL). HATU (5 g, 13.1 mmol) and NMM (2.8 mL, 26 mmol) were added and the mixture was stirred at r.t. overnight. The crude product was purified by combi-flash to give 3.65 g of tripeptide in 75% yield. $^1$H NMR (300 MHz, CDCl$_3$): δ7.80 (m, 4H), 7.18 (m, 1H), 6.89 (m, 2H), 5.98 (m, 2H), 5.42-5.02 (m, 5H), 4.78 (m, 1H), 4.58 (m, 1H), 4.20-3.31 (m, 12H), 2.82 (s, 2H), 2.58-2.21 (m, 2H), 1.80 (m, 1H), 1.42 (s, 9H), 1.38-1.08 (m, 5H). $^{31}$P (121.4 MHz, CDCl$_3$): δ44.89, 44.82. LC/MS=905.80 (M$^+$+1), 928.13 (M$^+$+Na)

To a solution of tripeptide (3.65 g, 4 mmol) in CH$_2$Cl$_2$ (20 mL) was added 4 N HCl in 1,4-dioxane (20 mL, 80 mmol). The reaction mixture was stirred at r.t. for 0.5 h, concentrated, dried under vacuum for 20 minutes, and then dissolved in EtOAc (50 mL). Na$_2$CO$_3$ (5.9 g, 48 mmol) in H$_2$O (25 mL) was added and stirred for 5 minutes. A THF solution of the freshly prepared cyclopentylchloroformate (2.93 g, 19.73 mmol) was added. The reaction was completed within 1.5 h. The solvent was removed on rotavap and the residue was diluted with EtOAc. The mixture was brought to pH=2 with 1 N HCl and the two layers were separated. The organic layers were washed with brine, dried with Na$_2$SO$_4$, filtered, and concentrated. Cyclopentyl carbamate (3.5 g) was obtained. $^1$H NMR (300 MHz, CDCl$_3$): $^1$H NMR (300 MHz, CDCl$_3$): δ 7.78 (m, 4H), 7.18 (m 1H), 6.90 (m, 2H), 6.18-5.85 (m, 2H), 5.58-4.90 (m, 5H), 4.78 (m, 1H), 4.60 (m, 1H), 4.20-3.25 (m, 13H), 2.81 (s, 2H), 2.60-2.20 (m, 2H), 1.9-1.3 (m, 9H), 1.30-1.05 (m, 5H) $^{31}$P (121.4 MHz, CDCl$_3$): δ 44.70, 42.66. LC/MS=917.93 (M$^+$+1), 940.98 (M$^+$+Na)

Cyclopentyl carbamate (3.26 g, 3.56 mmol) was dissolved in CH$_2$Cl$_2$ (450 mL) and degassed with N$_2$ for 30 minutes. Grubb's G1 (880 mg, 1.07 mmol) was added and degassed for an additional 30 minutes. The reaction mixture was heated to 45° C. overnight and cooled to rt. Tris(hydroxymethyl)phosphine (6.7 g, 53.4 mmol) was added followed by addition of TEA (15 mL, 107 mmol) and H$_2$O (50 mL). The reaction mixture was heated to reflux overnight. The two layers were separated. The organic layer was washed with 0.5 N HCl, brine, dried with Na$_2$SO$_4$, and concentrated. The crude product was purified by combi-flash to give 2.73 g of cyclic tripeptide.

A solution of cyclic tripeptide (1.75 g, 1.97 mmol) and intermediate X (622 mg, 1.78 mmol) in NMP (35 mL) was treated with Cs$_2$CO$_3$ (1.24 g, 3.82 mmol). The reaction mixture was heated to 80° C. for 6 h and then kept at rt overnight. The reaction was diluted with EtOAc and washed with H$_2$O. The aqueous layer was brought to pH=4 with 1 N HCl and extracted with 5% MeOH/EtOAc (2×). The combined organic layers were dried with Na$_2$SO$_4$ and concentrated. The crude product was purified by combi-flash to give 2.0 g of olefin intermediate.

To a solution of olefin intermediate (487 mg, 0.49 mmol) in CH$_3$CN (2.5 mL) at 0° C. was added iodotrimethylsilane (0.34 mL, 2.4 mmol). The reaction mixture was warmed to r.t. and stirred for 30 minutes and then cooled to 0° C. 2,6-Lutidine (0.34 mL) and MeOH (2.5 mL) were added and stirred for 10 minutes. The solvent was concentrated and the crude product was purified by HPLC to give 246 mg of acid 163. $^1$H NMR (300 MHz, CD$_3$OD): δ 8.32 (d, J=11.4 Hz, 2H), 7.86 (s, 1H), 7.67 (d, J=9.3 Hz, 1H), 7.28 (m, 1H), 6.96 (dd, J=7.8, 7.8 Hz, 2H), 5.85 (s, 1H), 4.67 (m, 1H), 4.56 (m, 2H), 4.47 (bs, 1H), 4.24 (m, 1H), 4.17 (s, 3H), 4.03 (m, 1H), 3.99-3.46 (m, 10H), 3.32 (m, 3H), 2.87 (m, 1H), 2.61 (m, 1H), 2.04-1.25 (m, 18H). $^{31}$P (121.4 MHz, CD$_3$OD): δ42.463. LC/MS=975.30 (M$^+$+1)

Example 164

Preparation of Compound 164

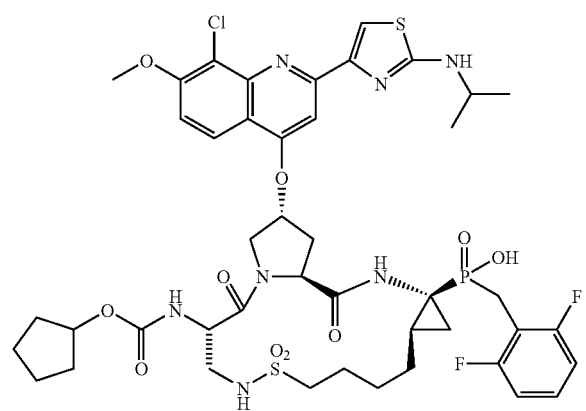

A solution of 2.17 g (9.36 mmol) of methyl 2-t-butoxycarbonylamino-3-aminopropanoate and 1.56 mL (11.19 mmol) of triethylamine in CH$_2$Cl$_2$ (20 mL) was stirred at 0° C. as a solution of 3-butenesulfonyl chloride in CH$_2$Cl$_2$ (3 mL) was added by canula. After 30 min, the mixture was stirred at rt for 14 h and concentrated. The viscous residue was dissolved in ethyl acetate (50 mL) and washed with 0.3 M aq. HCl. The aqueous fraction was extracted with ethyl acetate (30 mL). The organic fractions were washed with water (×1) and brine (×1), dried (MgSO$_4$), and concentrated. The residue was purified by combiflash (120 g column) using hexanes and ethyl acetate to obtain 1.54 g (49%) of the sulfonamide as light yellow solids.

Methyl 3-(3-butenylsulfonamido)-2-t-butoxycarbonylamino-propanoate (1.54 g, 4.58 mmol) was dissolved in 4 N HCl in dioxane and the solution was stirred at rt for 1 h and concentrated. After drying the residue in high vacuum for 20 min, the residue and triethylamine (1.92 mL, 13.78 mmol) were dissolved in H$_2$O (23 mL) and THF (23 mL) and cyclopentyloxycarbonyloxy-succinamide (1.10 g, 4.83 mmol) was added to the solution. The solution was stirred at rt for 3.5 h and concentrated to a half volume before dilution with H$_2$O (30 mL). The product was extracted with ethyl acetate (50 mL×2) and the extracts were washed with H$_2$O (50 mL×1) and saturated aq. NH$_4$Cl (50 mL×1), dried (MgSO$_4$), and concentrated to afford 1.52 g (95%). The methyl ester (1.52 g, 4.36 mmol) and LiOH (522.5 mg, 21.82 mmol) were dissolved in H$_2$O (20 mL), methanol (20 mL), and THF (20 mL) at 0° C. and the resulting mixture was stirred at rt for 9 h. The solution was concentrated to remove THF and methanol, the resulting concentrated solution was diluted with H$_2$O (30 mL) and washed with ethyl acetate (30 mL×1). After the aqueous fraction was acidified with 6 N HCl (5 mL), the product was extracted with ethyl acetate (40 mL×3). The extracts were washed with brine (40 mL×1), dried (MgSO$_4$), and concentrated to obtain 1.30 g (89%) of the acid.

The dipeptide XII (3.20 g, 4.36 mmol) was dissolved in 16.5 mL of 4 N HCl in dioxane and stirred at rt for 1 h. The resulting solution was concentrated and dried in vacuum. A solution of the resulting residue in DMF (7 mL) was added to a solution of the acid (1.30 g, 3.89 mmol), HATU (2.22 g, 5.83 mmol), and N-methylmorpholine (1.5 mL, 13.64 mmol) in DMF (8 mL) at rt. After 2 h, the solution was stirred with 5% aq. LiCl solution (60 mL) for 20 min and the mixture was further diluted with H$_2$O (50 mL) before extraction with ethyl acetate (100 mL×2). The organic extracts were washed with 1 N HCl (100 mL×1), saturated aq. NaHCO$_3$ (100 mL×1), and brine (100 mL×1), dried (MgSO$_4$), and concentrated. The residue was purified by combiflash chromatography (120 g column) to obtain 1.31 g (35.5%) of the tripeptide.

A solution of the tripeptide (1.30 g, 1.37 mmol) in CH$_2$Cl$_2$ (260 mL) was degassed for 30 min and Grubbs G1 (283 mg, 0.344 mmol) was added to the solution. The solution was refluxed for 5 h at 45° C. bath and additional catalyst (112 mg, 0.137 mmol) was added before heating for additional 4 h. To the solution were added tris(hydroxymethyl)phosphine (2.98 g, 24 mmol), triethylamine (6.7 mL, 48.07 mmol), and H$_2$O (55 mL). The resulting mixture was stirred at 50° C. bath for 3 h. The mixture was diluted with H$_2$O (200 mL) and saturated aq. NH$_4$Cl (200 mL) and the two layers were separated. The aqueous fraction was further extracted with CH$_2$Cl$_2$ (100 mL×2). The organic fractions were washed with H$_2$O (250 mL×1), dried (MgSO$_4$), and concentrated. The residue was purified by combiflash chromatography to obtain 456 mg (36%) of the major product.

The obtained product (456 mg, 0.495 mmol) was dissolved in NMP (5 mL) and 8-chloro-2-(2-isopropylaminothiazol-4-yl)-7-methoxy-quinolin-4-ol (173 mg, 0.495 mmol) and Cs$_2$CO$_3$ (323 mg, 0.991 mmol) were added to the solution. The resulting mixture was stirred at 70° C. bath for 16 h and diluted with ethyl acetate (25 mL) before stirring with 5% aq.

LiCl solution (20 mL) for 30 min. After the two phases were separated, the aqueous fraction was extracted with ethyl acetate (30 mL×1). The organic fractions were washed with H₂O (×1), dried (MgSO₄), and concentrated. The residue was purified by combiflash chromatography using CH₂Cl₂ and methanol to obtain 259 mg of the product with some impurities.

A mixture of the impure product (286 mg, 0.250 mmol), tosylhydrazide (350 mg, 1.88 mmol), and sodium acetate (308 mg, 3.75 mmol) in DME (2.5 mL) and H₂O (0.25 mL) was refluxed at 95° C. bath for 3 h. Additional tosylhydrazide (350 mg, 1.88 mmol), and sodium acetate (308 mg, 3.75 mmol) were added to the mixture and the mixture was refluxed for 1.5 h. The mixture was diluted with H₂O (50 mL) and saturated aq. NaHCO₃ (50 mL), and extracted with ethyl acetate (40 mL×2). The extracts were washed with H₂O (×1), dried (MgSO₄), and concentrated. The residue was purified by reverse-phase combiflash chromatography (43 g column) using H₂O and acetonitrile with 0.05% TFA. The combined fractions were concentrated to remove acetonitrile, and the product was extracted with ethyl acetate (×2) from the resulting aq. solution was diluted with saturated aq. saturated NaHCO₃ to obtain 135 mg of the product with some impurities.

A solution of the impure product (135 mg, 0.130 mmol) and 2,6-lutidine (0.19 mL, 1.63 mmol) in acetonitrile (3 mL) was stirred at 0° C. as TMSI (0.18 mL, 1.27 mmol) was added. After the mixture was stirred at rt for 2 h, methanol (2 mL) was added and the solution was stirred for 1 h at rt. The solution was concentrated and the residue was purified by reverse-phase HPLC. The product containing fractions were pooled, concentrated and freeze-dried to obtain 74.6 mg (51%) as TFA salt. $^{1H}$ NMR (300 MHz, CD₃OD): δ 8.26 (d, 1H, J=9.3 Hz), 8.24 (s, 1H), 7.78 (s, 1H), 7.60 (s, 1H), 7.24 (appt quint, 1H, J=7.2 Hz), 6.92 (t, 1H, J=7.5 Hz), 5.83 (br, 1H), 4.67-4.78 (m, 2H), 4.74 (dd, 1H), 4.40 (br, 1H), 4.21 (d, 1H, J=12.0 Hz), 4.15 (s, 3H), 3.99 (hept, 1H, J=6.3 Hz), 3.07-3.54 (m, 6H), 2.89 (dd, 1H, J=12.9 and 6.9 Hz), 2.44-2.59 (m, 1H), 1.92-2.26 (m, 3H), 1.15-1.81 (m, 16H), 1.38 (d, 6H, J=6.3 Hz). $^{31}$P (121.4 MHz, CD₃OD): δ 40.177. $^{19}$F (282 MHz, CD₃OD): δ –77.$^{31}$ 1 (CF₃COOH salt), –114.754. LC/MS=1008 (M⁺+1)

Example 165

Preparation of Compound 165

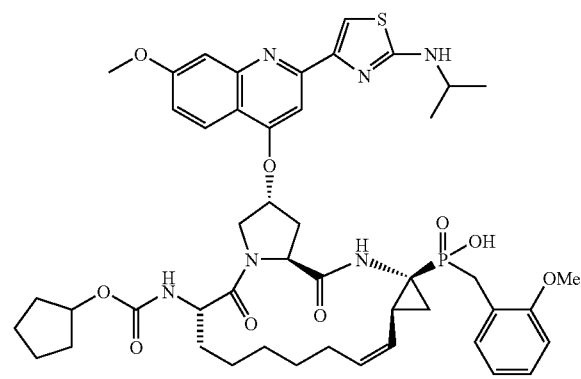

Step 1. To a yellow solution of VIII (477 mg, 1.30 mmol) and (1-amino-2-vinyl-cyclopropyl)-(2-methoxy-benzyl)-phosphinic acid ethyl ester (Example 42) (274 mg, 0.93 mmol) in toluene (4.5 mL) was added a solution of sodium 2-ethyl-hexanoate (77 mg, 0.46 mmol) in H₂O (4.5 mL). The reaction mixture was heated to 70° C. for 22 h. Additional 2-ethyl-hexanoate (100 mg) was added, stirred for 22 h at 70° C. and cooled to rt. The reaction mixture was diluted with EtOAc, washed with saturated NH₄Cl (2×), saturated NaHCO₃ (2×) and brine. The organic layer was dried with Na₂SO₄ and concentrated. The crude product was purified by column chromatography to give 468 mg of alcohol. LC/MS=661.9 (M⁺+1), 683.9 (M⁺+Na)

Step 2. Alcohol (468 mg, 0.71 mmol) and DABCO (255 mg, 2.27 mmol) were dissolved in toluene (3.5 mL). A toluene (3.5 mL) solution of brosyl chloride (580 mg, 2.27 mmol) was added dropwise. The reaction mixture was stirred at r. t. for 1 h. The reaction was diluted with EtOAc and quenched with saturated NaHCO₃. The two layers were separated and the organic layer was washed with 0.5 N HCl, brine, dried with Na₂SO₄, filtered, and concentrated. The crude product was purified by combi-flash to give 402 mg of brosylate in 49% yield. $^{31}$P NMR (121.4 MHz, CDCl₃) δ46.5, 44.1. LC/MS=881.4 (M⁺+1), 903.8 (M⁺+Na)

Step 3. To a solution of brosylate (402 mg, 0.46 mmol) in CH₂Cl₂ (3.4 mL) was added 4 N HCl in 1,4-dioxane (3.4 mL, 17 mmol). The reaction mixture was stirred at r.t. for 2 h, concentrated, dried under vacuum overnight, and then dissolved in THF (3.4 mL). The freshly prepared cyclopentyl-chloroformate (2.33 mmol) in THF (4.6 mL) was added. TEA (0.32 mL, 2.28 mmol) was added to the reaction mixture. The reaction was completed within 1 h. The reaction was quenched by adding saturated NH₄Cl and diluted with EtOAc. The two layers were separated. The organic layers were washed with saturated NH₄Cl and brine, dried with Na₂SO₄, and concentrated. The crude product was purified by column chromatography to give 349 mg of cyclopentyl carbamate in 86% yield. $^{31}$P NMR (121.4 MHz, CDCl₃) δ 46.4, 44.1. LC/MS=893.8 (M⁺+1), 915.6 (M⁺+Na)

Step 4. Cyclopentyl carbamate (349 mg, 0.39 mmol) was dissolved in CH₂Cl₂ (28 mL) and degassed with N₂ for 20 minutes. Grubb's G1 (80 mg, 0.10 mmol) was added and degassed for an additional 20 minutes. The reaction mixture was heated to 50° C. for 6.5 h. Additional Grubb's G1 (40 mg) was added and heated to 60° C. for 8 h. More Grubb's G1 (40 mg) was added, stirred at 50° C. for 5 h, and cooled to rt. Tris(hydroxymethyl)phosphine (1.21 g) was added followed by addition of TEA (2.7 mL) and H₂O (5 mL). The reaction mixture was heated to 50° C. for 6 h and then r.t. overnight. The two layers were separated. The organic layer was washed with 0.5 N HCl and brine, dried with Na₂SO₄, and concentrated. The crude product was purified by combi-flash to give 210 mg of compound olefin in 62% yield.
LC/MS=865.5 (M⁺+1), 887.5 (M⁺+Na)

Step 5. A solution of compound olefin (210 mg, 0.24 mmol) and 2-(2-isopropylamino-thiazol-4-yl)-7-methoxy-quinolin-4-ol (77 mg, 0.24 mmol) in NMP (2.4 mL) was treated with Cs₂CO₃ (79 mg, 0.24 mmol). The reaction mixture was heated to 65° C. for 6 h and then cooled to rt overnight. The reaction was diluted with EtOAc and washed with NaHCO₃. The organic layer was washed with 5% LiCl and brine, dried with Na₂SO₄, and concentrated. The crude product (229 mg, 0.24 mmol) was dissolved in CH₃CN (3 mL), 2,6-lutidine was added at 0° C. was added, followed by iodotrimethylsilane (0.52 mL, 3.65 mmol). The reaction mixture was warmed to rt, stirred for 3 h, and cooled to 0° C. 2,6-lutidine (0.2 mL) was added followed by addition of MeOH (2.5 mL) and warmed to rt. The mixture was concentrated and purified by HPLC to give 98 mg of product 165 in 44% yield. $^1$H NMR (300 MHz, CD$_3$OD) δ8.13 (d, J=9.3 Hz, 1H), 7.99 (s, 1H), 7.55 (s, 2H), 7.09 (m, 2H), 7.00 (m, 1H), 6.73 (d, J=8.4 Hz, 1H), 6.67 (t, J=7.5 Hz, 1H), 5.63 (s, 1H), 5.45 (q, J=9 Hz, 1H), 5.08 (t, J=9.9 Hz, 1H), 4.7 (d, J=12 Hz, 1H), 4.55 (t, J=9.3 Hz, 1H), 4.24 (s, 1H), 3.99 (m, 2H), 3.89 (dd, J=2.4, 11.7 Hz, 1H), 3.83 (s, 3H), 3.62 (s, 3H), 3.29 (t, J=15 Hz, 1H), 3.10 (t, J=15 Hz, 1H), 2.6 (dd, J=7.5, 14.1 Hz, 1H), 2.6 (m, 1H), 2.42 (ddd, J=3.6, 9.6, 13.5 Hz, 1H), 2.05 (m, 1H), 1.64 (m, 2H), 1.22-1.46 (brm, 17H), 1.16 (d, J=6.5 Hz, 6H).

$^{31}$P NMR (121.4 MHz, CD$_3$OD) δ43.4
LC/MS=914.6 (M$^+$+1)

Example 166

Preparation of Compound 166

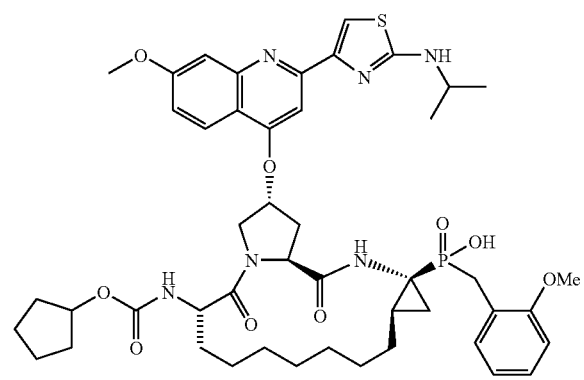

To a solution of 165 (887 mg, 0.97 mmol) in DME (87 mL)/H$_2$O (8.7 mL) was added p-tosyl hydrazide (1.45 g, 7.28 mmol) and NaOAc (1.19 g, 14.57 mmol). The reaction mixture was heated to 95° C. for 4 h and cooled to rt. The mixture was concentrated, dissolved in CH$_2$Cl$_2$, and washed with H$_2$O. The aqueous layer was extracted with CH$_2$Cl$_2$ (2×). The organic layer was dried with Na$_2$SO$_4$, concentrated, and dried under vacuum for 30 minutes. The residue was dissolved in DME (60 mL) and H$_2$O (6 mL). NaOAc (1.19 g, 14.57 mmol) and p-tosylhydrazide (1.45 g, 7.28 mmol) were added. The reaction mixture was heated to 95° C. for 6 h and cooled to rt. The reaction was worked up and purified by HPLC to give 318 mg of acid 166 in 36% yield. $^1$H NMR (300 MHz, CD$_3$OD) δ8.23 (d, J=9.6 Hz, 1H, 8.18 (s, 1H), 7.69 (s, 1H), 7.31 (dt, J=1.8, 7.2 Hz, 1H), 7.25 (dd, J=2.1, 9.3 Hz, 1H), 7.18 (t, J=7.8 Hz, 1H), 6.92 (d, J=8.1 Hz, 1H), 6.87 (t, J=7.5 Hz, 1H), 5.79 (s, 1H), 4.8 (d, J=11.7 Hz, 1H), 4.69 (t, J=8.7 Hz, 1H), 4.47 (s, 1H), 4.23 (dd, J=2.7, 10.2 Hz, 1H), 4.15 (t, J=6.3 Hz, 1H), 4.1 (d, J=11.1 Hz, 1H), 3.98 (s, 3H), 3.81 (s, 3H), 3.43 (t, J=15 Hz, 1H), 3.32 (t, J=15 Hz, 1H), 2.76 (dd, J=8.1, 14.4 Hz, 1H), 2.49 (ddd, J=3.6, 9, 13.2 Hz, 1H), 1.98 (m, 1H), 1.79 (m, 2H), 1.34 (d, J=6.3 Hz, 1H), 1.2-1.7 (m, 22H). $^{31}$P NMR (121.4 MHz, CD$_3$OD) δ45.5. LC/MS=915.3 (M$^+$+1).

Example 167

Preparation of Compound 167

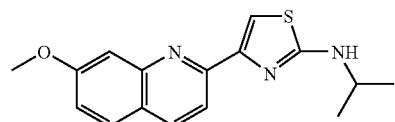
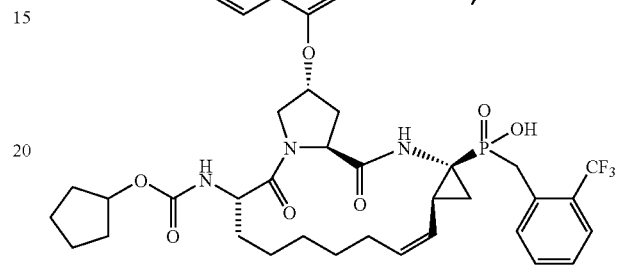

The product (Example 167) was afforded as a yellow solid. $^1$H NMR (300 MHz, CD$_3$OD): δ8.32 (d, J=9.3 Hz, 1H), 8.18 (s, 1H), 7.71 (m, 2H), 7.67 (m, 2H), 7.53 (m, 1H), 7.37 (m, 2H), 5.86 (s, 1H), 5.75 (m, 1H), 5.34 (m, 1H), 4.73 (m, 1H), 4.11 (m, 3H), 4.04 (s, 3H) 3.72 (m, 1H), 3.38 (m, 1H), 2.80 (m, 3H), 2.64 (m, 1H), 2.31 (m, 1H) 1.80 (m, 1H), 1.65-1.2 (m, 24H); $^{31}$P NMR (121.4 MHz, CD$_3$OD): δ39.599. LC (6 minute run, r.t.=3.67 min) MS (954.6, M+1)

Example 168

Preparation of Compound 168

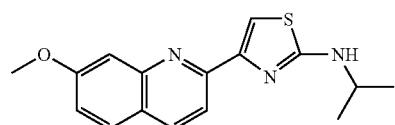
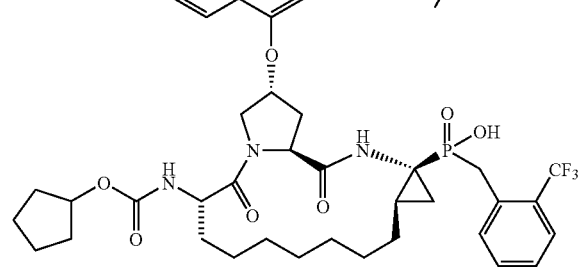

The product (Example 168) was obtained as a yellow solid. $^1$H NMR (300 MHz, CD$_3$OD): δ8.29 (d, J=9.5 Hz, 1H), 8.17 (s, 1H), 7.69 (m, 4H), 7.56 (m, 1H), 7.37 (m, 2H), 5.86 (s, 1H), 4.80 (m, 1H), 4.74 (m, 1H) 4.38 (s, 1H) 4.11 (m, 3H), 4.04 (s, 3H) 3.30-3.62 (m, 3H), 2.80 (m, 1H), 2.59 (m, 1H), 2.01 (m, 1H) 1.78 (m, 1H), 1.65-1.2 (m, 26H). $^{31}$P NMR (121.4 MHz, CD$_3$OD): δ41.418 LC (6 minute run, r.t.=3.65 min) MS (956.5, M+1).

Example 169

Preparation of Compound 169

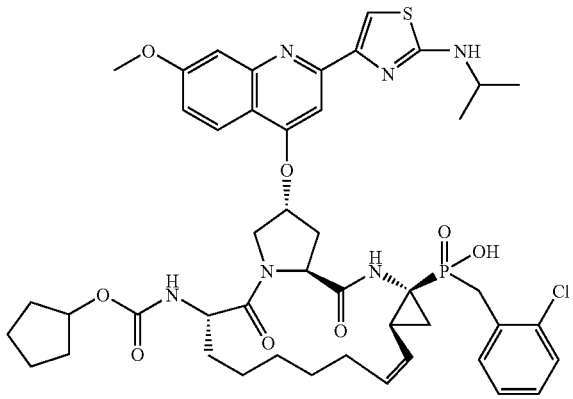

To a solution of phosphinate (described in Example 51) (5.0 g, 11.55 mmol) in TFA (31 mL, 416 mmol) at r.t. was added DMS (8.2 mL, 111 mmol) and stirred overnight. The reaction mixture was poured into ice cold 4 N HCl (350 mL) and extracted with 1/1 iPrOH/heptane (420 mL). The organic layers were washed with 4 N HCl (5×500 mL). The combined aqueous layers were brought to pH=10 in a cold bath. The aqueous layer was extracted with EtOAc (5×500 mL). The organic layers were washed with brine, dried with Na$_2$SO$_4$, and concentrated to give 2.9 g of amine in 84% yield. $^1$H NMR (300 MHz, CDCl$_3$): 7.58 (m, 1H), 7.41 (m, 1H), 7.18 (m, 2H), 5.96 (m, 1H), 5.60 (m, 1H), 5.19 (m, 2H), 5.09 (m, 1H), 4.03 (m, 2H), 3.44 (m, 2H), 1.83 (m, 1H), 1.32 (m, 3H), 1.19 (m, 2H). $^{31}$P NMR (121.4 MHz, CDCl$_3$): δ49.684, 47.512

To a yellow solution of VIII (3.5 g, 9.56 mmol) and amine (2.2 g, 7.36 mmol) in toluene (20 mL) was added a solution of sodium hexanoate (1.83 g, 11.04 mmol) in H$_2$O (60 mL). The reaction mixture was heated to 80° C. for 40 h and cooled to rt. The reaction mixture was diluted with EtOAc, washed with saturated NaHCO$_3$, 0.5 N HCl, brine, dried with Na$_2$SO$_4$, and concentrated. The crude product was purified by combi-flash to give 4.4 g of alcohol in 69% yield. $^1$H NMR (300 MHz, CDCl$_3$): δ 7.48 (m, 1H), 7.36 (m, 1H), 7.18 (m, 2H), 6.07 (m, 1H), 5.78 (m, 2H), 5.50 (m, 1H), 5.30 (m, 1H), 5.17 (m, 1H), 4.67 (d, 1H), 4.48 (m, 2H), 4.33 (m, 2H), 4.12 (m, 2H), 3.83 (m, 2H), 3.65 (m, 2H), 3.32 (m, 3H), 2.24 (m, 3H), 2.04 (m, 4H), 1.80 (m, 2H), 1.63 (m, 1H), 1.51 (m, 2H), 1.42 (m, 9H), 1.25 (m, 3H). $^{31}$P NMR (121.4 MHz, CDCl$_3$): δ45.191, 43.161 diastereomers.

Alcohol (1.4 g, 2.1 mmol) and DABCO (750 mg, 6.7 mmol) were dissolved in toluene (20 mL). A toluene solution of brosylchloride (1.7 g, 6.7 mmol) was added dropwise. The reaction mixture was stirred at r. t. for 3 h. The reaction was diluted with EtOAc and quenched with saturated NaHCO$_3$. The two layers were separated and the organic layer was washed with 0.5 N HCl, brine, dried with Na$_2$SO$_4$, filtered, and concentrated. The crude product was purified by combi-flash to give 1.3 g of brosylate in 70% yield. $^1$H NMR (300 MHz, CDCl$_3$): δ 7.74 (m, 4H), 7.48 (m, 1H), 7.36 (m, 1H), 7.18 (m, 2H), 6.07 (m, 1H), 5.78 (m, 2H), 5.25 (m, 1H), 5.17 (m, 1H), 4.98 (m, 1H), 4.57 (d, 1H), 4.48 (m, 2H), 4.33 (m, 2H), 4.12 (m, 2H), 3.83 (m, 2H), 3.65 (m, 2H), 3.32 (m, 3H), 2.24 (m, 3H), 2.04 (m, 4H), 1.80 (m, 2H), 1.63 (m, 1H), 1.51 (m, 2H), 1.42 (m, 9H), 1.25 (m, 3H). $^{31}$P NMR (121.4 MHz, CDCl$_3$): δ46.216, 43.654 diastereomers.

Brosylate (1.48 g, 1.61 mmol) was dissolved in CH$_2$Cl$_2$ (200 mL) and degassed with N$_2$ for 20 minutes. Grubb's G1 (413 mg, 0.5 mmol) was added and degassed for an additional 20 minutes. The reaction mixture was heated to 45° C. overnight and cooled to rt. Tris(hydroxymethyl)phosphine (3.4 g, 27.4 mmol) was added followed by addition of TEA (8 mL, 50 mmol) and H$_2$O (20 mL). The reaction mixture was heated to 50° C. for 4 h and then r.t. overnight. The two layers were separated. The organic layer was washed with 0.5 N HCl, brine, dried with Na$_2$SO$_4$, and concentrated. The crude product was purified by combi-flash to give 907 mg of cyclic phosphinate. $^1$H NMR (300 MHz, CDCl$_3$): δ 7.76 (m, 4H), 7.40 (m, 1H), 7.30 (m, 1H), 7.12 (m, 2H), 5.78 (m, 1H), 5.60 (m, 1H), 5.40 (m, 1H), 5.07 (m, 1H), 4.90 (m, 1H), 4.37 (m, 3H), 3.83 (m, 2H), 3.75 (m, 2H), 3.51 (m, 1H) 3.22 (m, 2H), 2.24 (m, 3H), 2.04 (m, 4H), 1.80 (m, 2H), 1.63 (m, 2H), 1.51 (m, 2H), 1.42 (m, 9H), 1.25 (m, 3H). $^{31}$P NMR (121.4 MHz, CDCl$_3$): δ45.216, 44.153 diastereomers.

A solution of cyclic phosphinate (857 mg, 1.0 mmol) and phenol ($^{31}$6 mg, 1.0 mmol) in NMP (10 mL) was treated with Cs$_2$CO$_3$ (651.6 mg, 2.0 mmol). The reaction mixture was heated to 65° C. overnight and then cooled to rt. The reaction was diluted with EtOAc and washed with H$_2$O. The aqueous layer was brought to pH=4 with 1 N HCl and extracted with 5% MeOH/EtOAc (2×50 mL). The combined organic layers were dried with Na$_2$SO$_4$ and concentrated. The crude product was purified by combi-flash to give 670 mg of desired product. $^1$H NMR (300 MHz, CDCl$_3$): $^1$H NMR (300 MHz, CDCl$_3$): δ 8.02 (d, J=9.1 Hz, 1H), 7.47 (s, 1H), 7.37 (m, 2H), 7.15 (m, 2H), 7.02 (m, 2H), 5.69 (m, 1H), 5.40 (m, 1H), 5.35 (m, 1H), 5.28 (m, 1H), 4.82 (m, 1H), 4.69 (m, 2H), 4.39 (m, 1H), 4.18 (m, 4H), 3.98 (s, 3H), 3.90 (m, 2H), 3.80 (m, 2H), 3.42 (m, 1H), 3.23 (m, 1H), 2.71 (m, 1H), 2.40 (m, 3H) 2.02 (m, 2H), 1.76 (m, 2H), 1.36 (m, 9H), 1.30 (m, 6H), 1.15 (m, 3H). $^{31}$P NMR (121.4 MHz, CDCl$_3$): δ45.152, 44.291 diastereomers.

To a solution of product obtained above (670 mg, 0.72 mmol) in CH$_3$CN (2 mL) at 0° C. was added iodotrimethylsilane (717 mg, 3.58 mmol). The reaction mixture was stirred at 0° C. for 20 min. 2,6-Lutidine (1 mL) and MeOH (1 mL) were added, stirred for 20 min, concentrated in vacuo, and dried for 20 minutes to give crude acid. Cyclopentanol (308 mg, 3.58 mmol) was dissolved in THF (7.8 mL) and phosgene (3.2 mL, 6.09 mmol) in toluene was added. The reaction was stirred for 1 h and concentrated to half volume to remove phosgene. The crude acid was dissolved in CH$_3$CN (20 mL). Na$_2$CO$_3$ (1.1 g, 8.64 mmol) in H$_2$O (10 mL) was added and stirred for 5 minutes. The THF solution of the freshly prepared cyclopentylchloroformate was added. The reaction was completed within 1 h and concentrated. The residue was dissolved in EtOAc and 1.0 N HCl was added to adjust pH=2. The two layers were separated and the organic layer was concentrated. The crude product was purified by HPLC to give product 169. $^1$H NMR (300 MHz, CD$_3$OD): δ 8.89 (s, 1H), 8.34 (d, J=9.5 Hz, 2H), 8.18 (s, 1H), 7.76 (m, 2H), 7.39 (m, 1H), 7.30 (m, 1H), 7.21 (m, 2H), 5.83 (s, 1H), 5.70 (m, 1H), 5.31 (m, 1H), 4.73 (m, 1H), 4.40 (m, 1H), 4.16 (m, 2H), 4.02 (m, 4H), 3.72 (m, 1H), 3.38 (m, 2H), 2.81 (m, 1H), 2.62 (m, 1H), 2.29 (m, 1H) 1.95-1.37 (m, 21H), 1.34 (m, 6H). $^{31}$P NMR (121.4 MHz, CD$_3$OD): δ41.998

LC/MS=919 (M$^+$+1)

Example 170

Preparation of Compound 170

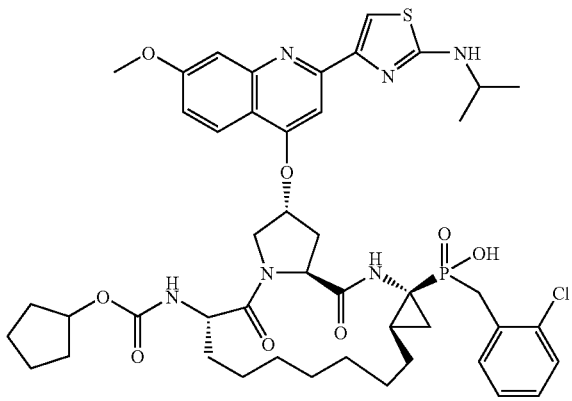

To a solution of 169 (50 mg, 0.05 mmol) in DME (1 mL)/H₂O (0.1 mL) was added p-tosyl hydrazide (76 mg, 0.41 mmol) and NaOAc (66 mg, 0.81 mmol). The reaction mixture was heated to 95° C. for 1.5 h and cooled to rt. A few drops of 3 N HCl was added to adjust pH=2. The crude product was purified by HPLC to give 25 mg of acid 170. $^1$H NMR (300 MHz, CD₃OD): δ 8.89 (s, 1H), 8.30 (d, J=9.4 Hz, 2H), 8.16 (s, 2H), 7.75 (m, 3H), 7.41 (m, 4H), 7.22 (m, 3H), 5.84 (s, 1H), 4.74 (m, 2H), 4.42 (m, 1H), 4.18 (m, 2H), 4.07 (m, 4H), 3.52 (m, 1H), 3.$^{31}$ (m, 2H), 2.77 (m, 1H), 2.52 (m, 1H), 2.00 (m, 1H), 1.81 (m, 1H), 1.58 (m, 21H), 1.35 (m, 6H). $^{31}$P NMR (121.4 MHz, CD₃OD): δ44.041

LC/MS=921 (M⁺+1)

Example 171

Preparation of Compound 171

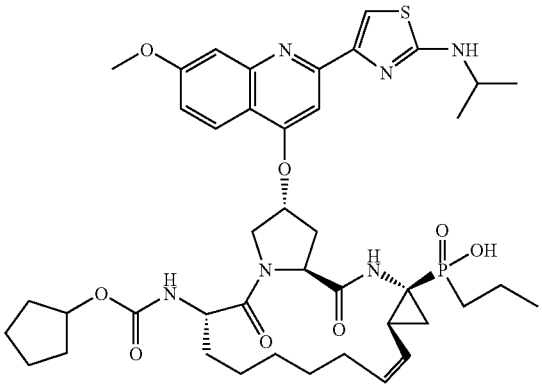

Step 1. A solution of the 4-Hydroxy-pyrrolidine-1,2-dicarboxylic acid 1-tert-butyl ester (460 mg, 1.99 mmol) and Et₃N (417 μl, 2.99 mmol) in THF (13 mL) was stirred at −43° C. as ethyl chloroformate (209 μl, 2.19 mmol) was added. The mixture was stirred between −40° C. and −25° C. for 30 minutes. To this mixture a solution of (1-Amino-2-vinyl-cyclopropyl)-phosphonic acid diethyl ester (480 mg, 2.19 mmol) in THF (13 mL) was added drop-wise while the internal temperature was kept below −35° C. The solution was allowed to warm to rt and quenched with H₂O. Reaction mixture was extracted with EtOAc. Combined organic washes were then extracted with brine, 1N HCl (2×) and then brine. Organic layer was dried over MgSO₄. The crude product (760 mg, 88%) was used without further purification. LC/MS 433 (M⁺+1), 454.9 (M⁺+Na)

Step 2. To a solution of ester (760 mg, 1.75 mmol) in CH₂Cl₂ (4.40 mL) was added 4N HCl/Dioxane (4.40 mL, 17.5 mmol). The reaction was stirred at rt for 2 h. The reaction was concentrated and the residue was dried under vacuum for 2 h. The crude amine was used without further purification.

LC/MS=333.3 (M⁺ free base+1), 454.9 (M⁺ free base+Na)

Step 3. To a solution of amine (644 mg, 1.75 mmol), 2-tert-Butoxycarbonylamino-non-8-enoic acid and HATU (665 mg, 1.75 mmol) in CH₂Cl₂ (13.125 mL) and DMF (4.375 mL) was added N-methyl-morpholine (524 μL, 4.77 mmol). The reaction was stirred at rt for 30 min. The reaction was quenched with 5% LiCl (20 mL), and the mixture was stirred until the two layers were separated. After the mixture was extracted with EtOAc (75 mL) the aqueous layer was further extracted with EtOAc. The combined organic layers were washed with saturated NaHCO₃, brine, and then dried over MgSO₄. The filtrate was concentrated and the residue was purified using column chromatography to obtain tripeptide (440 mg, 43%). $^{31}$P NMR (121.4 MHz, CDCl₃): δ22.3. LC/MS=586.0 (M⁺+1), 607.9 (M⁺+Na).

Step 4. A solution of tripeptide (2.4 g, 4.10 mmol) in CH₂Cl₂, which had been degassed by bubbling N₂ through it for 20 min, and Grubb's G1 catalyst (844 mg, 1.025 mmol) was heated to 40° C. After the reaction had stirred at 40° C. for 4 h, additional Grubbs G1 catalyst (150 mg, 0.18 mmol) was added and the solution continued to stir at 40° C. overnight. Additional Grubbs G1 catalyst (132 mg, 0.16 mmol) was added and the solution was refluxed in a 50° C. oil bath. After 4 h, tris-(hydroxymethyl)phosphine (8.48 g, 68.34 mmol) was added and the solution was stirred for 10 minutes before Et₃N (19 mL, 136 mmol) was added, followed by H₂O (20 mL). After the mixture was stirred under N₂ at 50° C. for 2 h, another portion of H₂O (10 mL) was added and the mixture was heated an additional 4 h at 50° C. and then stirred overnight at rt. The aqueous phase was removed and the organic phase was washed with H₂O, 0.5 N HCl, and saturated NaHCO₃. The organic phase was then dried over MgSO₄ and concentrated. The residue was purified using column chromatography to yield olefin (1.85 g, 81%). $^{31}$P NMR (121.4 MHz, CDCl₃): δ22.160. LC/MS=558.0 (M⁺+1), 579.8 (M⁺+Na).

Step 5. A solution of olefin (1.85 g, 3.32 mmol) and sodium iodide (4.98 g, 33.2 mmol) in pyridine (33.2 mL) was heated at 105° C. for 10 h. The reaction was then at rt for 2 days. Additional sodium iodide (1.50 g, 10.0 mmol) was added and the solution was heated at 105° C. for 2 h. The reaction was then cooled to rt.

To this solution was added 4-Di(methylamino)pyridine (41 mg, 0.33 mmol) and acetic anhydride (4.10 mL, 43.16 mmol). The reaction was stirred at rt for 2 h, and then frozen overnight. The solution was defrosted and EtOAc was added. Saturated NaHCO₃ was added to adjust the pH to 7-8, and then the layers were separated. The organic layer was extracted with H₂O and the combined aqueous layers were acidified to pH 1-2 with 1N HCl. The aqueous layers were extracted with 200 mL of ethyl acetate (4×) and the combined organic layers were washed with brine, dried over MgSO₄, and concentrated. The residue was purified using reverse phase HPLC to give monoacid (1.15 g, 61%) as a white solid.

³¹P NMR (121.4 MHz, CDCl₃): δ21.3, 20.9. LC/MS=571.8 (M⁺+1).

Step 6. To a solution of oxalyl chloride (589 μl, 6.75 mmol) in toluene (16.9 mL), dimethylformamide (26 μl, 0.34 mmol) was added drop-wise. The resulting solution was stirred at rt for 10 minutes. The monoacid (965 mg, 1.69 mmol) in toluene (8 mL) was added drop-wise to the previous solution and the resulting mixture was stirred for 30 minutes at rt. The mixture was concentrated and placed under high vacuum for 20 minutes. The residue was dissolved in THF (16.9 mL) and cooled to −35° C. n-Propylmagnesium chloride (845 μl, 1.69 mmol) was added drop-wise and the reaction stirred at −30° C. for 30 minutes. Additional n-propylmagnesium chloride (845 μl, 1.69 mmol) was added and the reaction was warmed to −25° C. and stirred for 20 minutes. Additional n-propylmagnesium chloride (845 μl, 1.69 mmol) was added and the reaction was stirred at −25° C. for 20 minutes. More n-propylmagnesium chloride (845 μl, 1.69 mmol) was added and stirred an addition 15 minutes at −25° C. A final addition of n-propylmagnesium chloride (845 μl, 1.69 mmol) was conducted and the solution stirred at −30° C. Saturated NH₄Cl was used to quench the reaction at −30° C. The reaction was warmed to rt and diluted with EtOAc. The organic layer was washed with saturated NH₄Cl and brine, dried over MgSO₄ and concentrated Desired product (468 mg, 46%) was isolated from the residue by column chromatography, as white foam. LC/MS=598.0 (M⁺+1), 619.9 (M⁺+Na).

Step 7. To a solution of product obtained above in CH₂Cl₂ (9.8 mL) was added 4N HCl/Dioxane (4.90 mL, 19.58 mmol) and stirred for 1.5 h at rt. The solution was concentrated and dried under high vacuum. The white solid was used without further purification. LC/MS=497.8 (M+free base+1), 519.9 (M⁺ free base+Na).

Step 8. A solution of amine in CH₃CN (7.83 mL), H₂O (783 μl) and Et₃N (273 mL, 1.96 mmol) stirred for 5 minutes before cyclopentyl chloroformate (173 μl, 1.17 mmol) was added drop-wise. The reaction stirred at rt for 35 minutes and was concentrated and taken up in ethyl acetate. The organic phase was washed with saturated NH₄Cl and brine. The organic layer was dried over MgSO₄ and concentrated. Cyclopentyl carbamate was purified from the residue by column chromatography (388 mg, 86% over 2 steps). ³¹P NMR (121.4 MHz, CDCl₃): δ50.2, 49.6, 48.8, 47.9. LC/MS=609.8 (M⁺+1), 6³¹.0 (M⁺+Na).

Step 9. A solution of cyclopentyl carbamate (388 mg, 0.64 mmol) in THF (9.54 mL) and MeOH (6.36 mL) was stirred at 0° C. as a solution of LiOH (27 mg, 0.64 mmol) in H₂O (3.16 mL) was added drop-wise. The reaction was then stirred for 45 minutes. The reaction was quenched with saturated NH₄Cl and extracted with CH₂Cl₂. The organic layer was dried over MgSO₄ and concentrated. The resulting alcohol was placed on high vacuum and used without further purification.

Step 10. To a solution of the alcohol (361 mg, 0.64 mmol) and DABCO (200 mg, 1.78 mmol) in toluene (1.27 mL) was added 4-bromobenzenesulfonyl chloride (455 mg, 1.78 mmol) in toluene (1.27 mL). The reaction was stirred at rt for 2 h. The reaction was diluted with toluene and quenched with 1M Na₂CO₃. The organic layer was then extracted with 1M Na₂CO₃, diluted with a small volume of THF and washed with 0.5M HCl. The organic layer was then washed with H₂O, dried over MgSO₄ and concentrated. Brosylate was purified from the residue by column chromatography (323 mg, 65%) as a white foam/semi-crystalline solid. LC/MS=685.5 (M⁺+1).

Step 11. A solution of brosylate (100 mg, 0.13 mmol), 2-(2-Isopropylamino-thiazol-4-yl)-7-methoxy-quinolin-4-ol (40 mg, 0.13 mmol) and Cs₂CO₃ (42 mg, 0.13 mmol) in 1-methyl-2-pyrrolidinone (2 mL) was stirred at 60° C. for 10 h, and then overnight at rt. The reaction was then re-heated to 60° C. and stirred for another 5 h. The reaction was diluted with EtOAc and washed with a 1:1 solution of H₂O and saturated NaHCO₃ and then brine. The organic layer was dried over Na₂SO₄ and concentrated. The residue was placed on high vacuum overnight. The crude (110 mg, 0.03 mmol) and 2,6-lutidine (148 μl, 1.27 mmol) in CH₃CN (2 mL) was stirred at 0° C. as iodotrimethylsilane (181 μl, 1.27 mmol) was added drop-wise. The reaction was stirred at rt for 3.5 h. The reaction was then cooled to 0° C. and additional 2,6-lutidine (74 μl, 0.64 mmol) and iodotrimethylsilane (91 μl, 0.64 mmol) was added. The reaction was warmed to rt for 1 h. The reaction was cooled to 0° C. and then Et₃N (200 μl) and MeOH (2.5 mL) was added. The reaction was concentrated and 171 (47.6 mg, 45%) was isolated from the residue by HPLC as a yellow solid. ¹H NMR (300 MHz, CD₃OD) δ8.30 (d, J=9 Hz, 1H), 8.18 (s, 1H), 7.72 (s, 2H), 7.27 (dd, J=2.4, 9.3 Hz, 1H), 5.79 (s, 1H), 5.60 (dd, J=8.1, 17.7 Hz, 1H), 5.21 (t, J=9.6 Hz, 1H), 4.58 (s, 1H), 4.69 (t, J=9.3 Hz, 1H), 4.39 (s, 1H), 4.04-4.22 (brm, 3H), 4.01 (s, 3H), 2.8 (m, 1H), 2.77 (dd, J=7.2, 14.4 Hz, 1H), 2.56 (ddd, J=4.2, 9.9, 14.1 Hz, 1H), 2.20 (m, 1H), 1.2-1.9 (brm, 23H), 1.34 (d, J=6.3 Hz, 6H), 1.01 (t, J=7.5 Hz, 3H). ³¹P NMR (121.4 MHz, CD₃OD) δ 48.2. LC/MS=836.8 (M⁺+1).

Example 172

Preparation of Compound 172

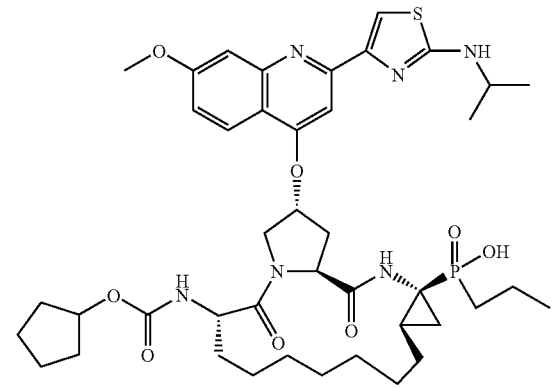

A reaction vessel containing a solution of brosylate (40 mg, 0.05 mmol) and 5% Rh/Al₂O₃ (12 mg) in EtOAc (2 mL) was evacuated under vacuum and the atmosphere was replaced with H₂. This evacuation/re-pressurization cycle was repeated 2 more times. The reaction was then stirred under H₂ at rt for 16 h. The reaction was filtered through a plug of Celite 541 and the filtrate was concentrated. Saturated compound (22 mg, 55%) was isolated from the residue by column chromatography as a white solid. ³¹P NMR (121.4 MHz, CDCl₃) δ 54.2, 50.8. LC/MS=787.5 (M⁺+1).

Replacement and deprotection as described for Example 171 gave compound 172. ¹H NMR (300 MHz, CD₃OD): δ8.28 (d, J=9.3 Hz, 1H), 8.17 (s, 1H), 7.74 (s, 2H), 7.31 (dd, J=2.1, 9 Hz, 1H), 5.81 (s, 1H), 4.81 (d, J=12 Hz, 1H), 4.67 (t, J=8.7 Hz, 1H), 4.42 (s, 1H), 4.17 (m, 2H), 4.02 (dd, J=2.7, 12.3 Hz, 1H), 4.03 (s, 3H), 2.80 (dd, J=7.8, 15 Hz, 1H), 2.49

(ddd, J=3.9, 9.3, 13.8 Hz, 1H), 1.25-1.9 (brm, 29H), 1.34 (d, J=6.3 Hz, 6H), 1.06 (t, J=7.5 Hz, 3H). $^{31}$P NMR (121.4 MHz, CD$_3$OD) δ 50.3. LC/MS=839.3 (M$^+$+1).

Example 173

Preparation of Compound 173

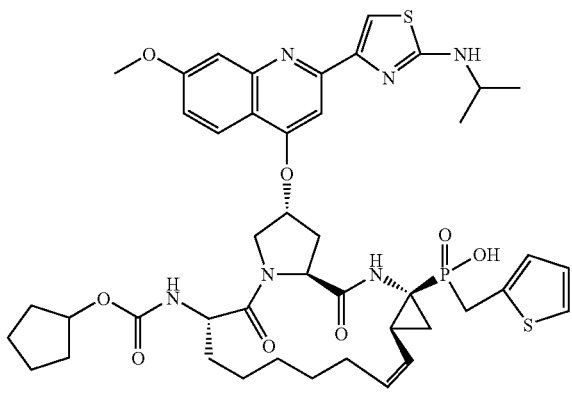

A solution of the thiophen-2-yl-methanol (3.0 mL, 31.7 mmol) in 15 mL of ether was stirred at 0° C. as PBr$_3$ was added over 5 minutes. After 1.5 h at 0° C., 50% aq. KOH (15 mL) was added and the organic layer was separated, which was dried over KOH pellet for 1 h at freezer. The crude solution of 2-bromomethyl-thiophene was used for the next reaction.

A solution of IV (2.78 g, 8.98 mmol) and DIEA (3.75 mL, 21.53 mmol) in 30 mL of CH$_2$Cl$_2$ was stirred at r.t. as TMSCl (2.55 mL, 20.09 mmol) was added. After 30 min, the crude bromide (16 mL) was added and the solution was stirred at 40° C. for 16 h. The solution was concentrated and the residue in water (50 mL) was extracted with ethyl acetate (50 mL×2). After the organic fraction was washed with water (50 mL), it was dried (MgSO$_4$) and concentrated. The residue was purified with a combi-flash column chromatography using hexane:ethyl acetate as eluent to obtain phosphinate (2.191 g, 60%) as a mixture of two diastereomers.

A solution of phosphinate obtained above (2.032 g, 5.01 mmol) in 16 mL of TFA and 4 mL of Me$_2$S was stirred at r.t. for 6 h. The solution was concentrated at 25° C. and the residue in ethyl acetate (60 mL) was washed with ice-cold 1 N NaOH (60 mL×2) and brine (60 mL). The aqueous fractions were extracted with ethyl acetate (60 mL). The combined organic fractions were dried (MgSO$_4$) and concentrated to obtain 1.22 g (90%) of amine.

To a mixture of VIII (845 mg, 2.31 mmol) and amine (404.8 mg, 1.49 mmol) in toluene (2.7 mL) was added sodium 2-ethyl-hexanoate (164 mg, 0.99 mmol) and H$_2$O (5.5 mL). The reaction mixture was heated to 80° C. and stirred for 19 h. An additional amount of VIII (150 mg) in toluene (1 mL) was added and stirred at 80° C. for 7 h. The reaction mixture was cooled to rt, quenched with 1 N HCl (50 mL), and extracted with EtOAc (2×40 mL). The combined organic layers were washed with 1 N HCl (40 mL). The aqueous layer was neutralized with 2 N NaOH (60 mL) before extraction with EtOAc (50 mL). The combined organic layers were washed with saturated NaHCO$_3$ (2×50 mL) and brine (20 mL), dried with Na$_2$SO$_4$, and concentrated. The crude product was purified by combi-flash to give 740.5 mg of tripeptide alcohol in 78% yield.

Alcohol (740.8 mg, 1.16 mmol) and DABCO (209.2 mg, 1.87 mmol) were dissolved in toluene (1.1 mL). A solution of brosylchloride (476.8 mg, 1.87 mmol) in toluene (0.8 mL) was added dropwise. The reaction mixture was stirred at r. t. for 2 h. The reaction was diluted with EtOAc (35 mL) and washed with 1 N Na$_2$CO$_3$. The organic layers were washed with 1 N HCl (30 mL) and H$_2$O (2×30 mL), dried with Na$_2$SO$_4$, filtered, and concentrated. The crude product was purified by combi-flash to give 915.9 mg of brosylate in 92% yield.

Brosylate (915.9 mg, 1.07 mmol) was dissolved in CH$_2$Cl$_2$ (150 mL) and degassed with N$_2$ for 20 minutes. Grubb's G1 (221.2 mg, 0.27 mmol) was added and degassed for an additional 20 minutes. The reaction mixture was heated to 50° C. overnight and cooled to rt. Tris(hydroxymethyl)phosphine (1.67 g, 3.45 mmol) was added followed by addition of TEA (3.75 mL, 26.9 mmol) and H$_2$O (30 mL). The reaction mixture was stirred at rt for 5 h. The two layers were separated. The organic layer was washed with H$_2$O, 0.5 N HCl and saturated NaHCO$_3$, dried with Na$_2$SO$_4$, and concentrated. The crude product was purified by combi-flash to give 753.4 mg of cyclic phosphinate in 85% yield.

A solution of cyclic phosphinate (753.4 mg, 0.91 mmol) and 2-(2-isopropylamino-thiazol-4-yl)-7-methoxy-quinolin-4-ol (301.3 mg, 0.96 mmol) in NMP (10 mL) was treated with Cs$_2$CO$_3$ (364.1 mg, 1.12 mmol). The reaction mixture was heated to 70° C. for 12 h and then cooled to rt. The reaction mixture was diluted with EtOAc (50 mL) and H$_2$O (70 mL) and filtered through celite. The two layers were separated. The organic layer was washed with H$_2$O (70 mL) and saturated NaHCO$_3$ (2×70 mL). The aqueous layer was extracted with EtOAc (50 mL). The combined organic layers were dried with Na$_2$SO$_4$ and concentrated. The crude product was purified by combi-flash on C18 column to give 470.3 mg of compound.

To a solution of the product obtained above (470.3 mg, 0.52 mmol) in CH$_2$Cl$_2$ (3.25 mL) was added 4 N HCl in 1,4-dioxane (3.25 mL, 13 mmol). The reaction mixture was stirred at r.t. for 2.5 h and concentrated. The residue was triturated with CH$_3$CN and concentrated. The residue was dried under vacuum for 20 minutes to give crude amine HCl salt. The resulting crude amine HCl salt was dissolved in CH$_3$CN (5 mL) and cooled to 0° C. Na$_2$CO$_3$ (360 mg, 3.4 mmol) in H$_2$O (5 mL) was added and stirred for 5 minutes. A solution of the freshly prepared cyclopentylchloroformate in CH$_3$CN (5 mL, 2.64 mmol) was added. The reaction was completed within 1 h and concentrated. The residue was dissolved in EtOAc (40 mL) and washed with H$_2$O (40 mL) and brine (20 mL). The aqueous layers were extracted with EtOAc (20 mL). The combined organic layers were dried with Na$_2$SO$_4$ and concentrated. The crude product was purified by HPLC to give 286.9 mg of product cyclopetantyl carbamate in 60% yield.

A solution of cyclopetantyl carbamate (87.9 mg, 0.096 mmol) and 2,6-lutidine (0.07 mL, 0.6 mmol) in CH$_3$CN (3 mL) was stirred at 0° C. as iodotrimethylsilane (0.07 mL, 0.49 mmol) was added. The reaction mixture was warmed to r.t.

and stirred for 3.5 h. The reaction mixture was cooled to 0° C. and additional iodotrimethylsilane (0.01 mL) and 2,6-lutidine (0.01 mL) were added. The mixture was stirred at r.t. for 1 h. MeOH (1 mL) was added and stirred for 1 h. The mixture was concentrated and the crude product was purified by HPLC to give 71.2 mg of 173 in 74% yield. 1H NMR (300 MHz, CD$_3$OD): δ 8.29 (d, 1H, J=9.3 Hz), 8.19 (s, 1H), 7.70 (s, 2H), 7.20-7.28 (m, 2H), 6.91-6.97 (m, 2H), 5.79 (br, 1H), 5.65 (appt q, 1H, J=~9 Hz), 5.23 (t, 1H, J=~9 Hz), 4.88 (d, 1H, J=12 Hz), 4.71 (t, 1H, J=8.4 Hz), 4.42 (br, 1H), 4.11-4.24 (m, 2H), 4.06 (d, 1H, J=9.9 Hz), 3.99 (s, 3H), 3.64 (t, 1H, J=15.6 Hz), 3.38 (t, 1H, J=-15.6 Hz), 2.72-2.90 (m, 2H), 2.55-2.66 (m, 1H), 2.17-2.30 (m, 1H), 1.81 (brm, 2H), 1.17-1.70 (m, 17H), 1.34 (d, 6H, J=6.3 Hz). $^{31}$P (121.4 MHz, CD$_3$OD): δ 38.644. LC/MS=891 (M$^+$+1)

Example 174

Preparation of Compound 174

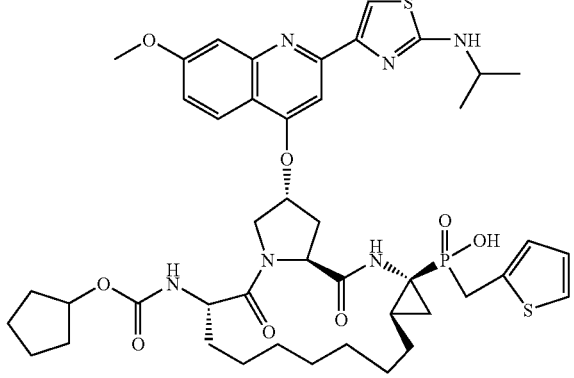

A solution of olefin from Example 173 (193.6 mg, 0.21 mmol) and p-tosyl hydrazide (1.26 g, 4.22 mmol) in THF (8 mL) was heated to 60° C. as TEA (0.59 mL, 4.23 mmol) in THF (1 mL) was added in 10 minutes. The reaction mixture was stirred at 60° C. for 27 h. An additional hydrazide (1.26 g, 4.22 mmol) and TEA (0.59 mL, 4.23 mmol) were added and stirred for 24 h at 60° C. The reaction was cooled to r.t and filtered off some solid. The filtrate was concentrated and the residue was purified by combi-flash to give 100.5 mg of a mixture containing the starting material with the desired product. The resulting mixture was dissolved in THF (5 mL). Hydrazide (655.2 mg, 2.20 mmol) and TEA (0.31 mL, 2.22 mmol) were added. The mixture was stirred at 60° C. for 20 h. The reaction mixture was concentrated and the residue was dissolved in CH$_2$Cl$_2$. The solid was filtered off and the filtrate was concentrated. The residue was purified by combi-flash to give 68.1 mg of saturated compound which was hydrolyzed with 2,6-lutidine (0.1 mL, 0.86 mmol) in CH$_3$CN (3 mL) and CH$_2$Cl$_2$ (1.5 mL) was stirred at 0° C. as iodotrimethylsilane (0.1 mL, 0.7 mmol) was added. The reaction mixture was warmed to r.t. and stirred for 1.5 h. MeOH (1 mL) was added and stirred at r.t for 0.5 h. The mixture was concentrated and the crude product was purified by HPLC to give 51.3 mg of acid 174. $^1$H NMR (300 MHz, CD$_3$OD): δ 8.22 (d, 1H, J=9.3 Hz), 8.19 (s, 1H), 7.69 (s, 2H), 7.25 (appt d, 2H, J=3.8 Hz), 7.01 (br, 1H), 6.91-6.98 (m, 1H), 5.78 (br, 1H), 4.80 (d, 1H, J=11.7 Hz), 4.67 (t, 1H, J=8.4 Hz), 4.45 (br, 1H), 4.03-4.27 (m, 3H), 3.98 (s, 3H), 3.57 (t, 1H, J=15.6 Hz), 3.44 (t, 1H, J=15.6 Hz), 2.70-2.82 (m, 1H), 2.42-2.54 (m, 1H), 1.08-1.96 (m, 25H), 1.34 (d, 6H, J=6.3 Hz). $^{31}$P NMR (121.4 MHz, CD$_3$OD): δ 41.072. LC/MS=893 (M$^+$+1)

Example 175

Preparation of Compound 175

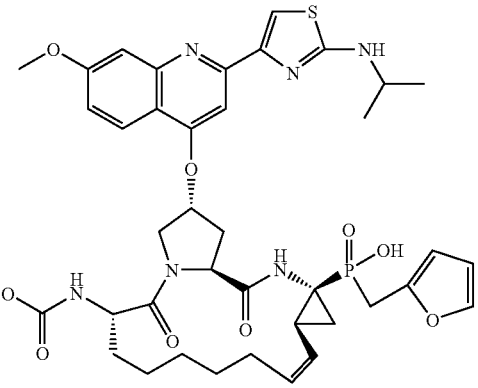

A solution of the lactone (VIII) (860 mg, 2.35 mmol), the amine (prepared in Example 83) (300 mg, 1.18 mmol) and sodium 2-ethylhexanoate (60 mg, 0.35 mmol) was stirred in toluene (10 mL) and H$_2$O (10 mL) at 80° C. for 12 h and then rt for 72 h. Ethyl acetate (50 mL) was added to the solution and it was washed with saturated sodium carbonate (20 mL), 1M HCl (20 mL) and then brine (15 mL). The organic layer was dried and concentrated.

To a solution of the resultant diene alcohol (700 mg, 1.13 mmol) and DABCO (200 mg, 1.58 mmol) in toluene (2 mL) was added 4-bromotoluenesulfonyl chloride (400 mg, 1.81 mmol) in toluene (5 mL). The solution was stirred at rt for 1.5 h after which the reaction was diluted with toluene and quenched with 1M Na$_2$CO$_3$. The organic layer was washed with 1M Na$_2$CO$_3$, diluted with ethyl acetate, washed again with 0.5M HCl and then H$_2$O, dried and concentrated. The crude material was purified by flash chromatography to give the desired brosylate. This diene (290 mg, 0.35 mmol) was placed in degassed CH$_2$Cl$_2$ (40 mL) and Grubb's G1 catalyst (7.1 mg, 0.09 mmol) was added. The reaction mixture was stirred at 40° C. for 15 h. An additional 5 mol % catalyst was added and the solution continued to stir at 40° C. for 1.5 h. Additional Grubb's G1 (5 mol %) was added and the solution continued to stir at 40° C. for 1.5 h. Tris(hydroxymethyl) phosphine (750 g, 1.12 mmol), triethylamine (1.7 mL) and H$_2$O (25 mL) were added. The solution was stirred 3 h at 40° C. and then at room temp overnight. The solution was then washed with H$_2$O; the organic layer was dried and concentrated. The crude material was purified by HPLC to yield the desired metathesis product (264 mg). A solution of this macrocyclic brosylate (260 mg, 0.32 mmol), Cs$_2$CO$_3$ (104 mg, 0.32 mmol) and aminothiazolequinoline (101 mg, 0.32 mmol) in N-methylpyrrolidone (3 mL) was heated at 60° C. for 5 h. The reaction mixture was diluted with ethyl acetate and quenched with saturated sodium bicarbonate. The organic phase was washed with saturated bicarbonate solution and brine, then dried and concentrated. The material was purified by column chromatography to provide the product (128 mg, 42% over 2 steps).

A solution of the Boc-amine (128 mg, 0.14 mmol) was stirred in CH$_2$Cl$_2$ (1 mL) as trifluoroacetic acid (500 µl) was added. The solution was stirred at rt for 1 h. The solution was concentrated and azeotroped with toluene (2×). The residue was stirred in THF (1 mL), and cyclopentylchloroformate (0.72 mmol), triethylamine (240 µl, 1.73 mmol) in THF (500 µl) were added and left at room temp for 1 hour. The reaction mixture was partitioned with H₂O and ethyl acetate, washed with brine, dried (MgSO₄) and concentrated. The crude material was purified with by column chromatography to give the cyclopentyl carbamate (68 mg, 66%).

To a solution of this ethyl phosphinate (68 mg, 0.08 mmol) in CH₃CN (1 mL) was added TMSI (54 µl, 0.38 mmol). After 30 minutes, 2,6-lutidine (500 µl) was added, followed by methanol. The reaction mixture was concentrated and azeotroped. The crude material was purified by HPLC to give Compound 175 (15 mg, 23%). ¹H NMR (300 MHz, CD₃OD): δ 8.31 (d, J=9.4 Hz, 1H), 8.17 (s, 1H), 7.75 (m, 2H), 7.43 (m, 1H), 7.36 (m, 1H), 6.36 (m, 1H), 6.28 (m, 1H), 5.85 (m, 1H), 5.73 (m, 1H), 5.28 (m, 1H), 4.73 (m, 1H), 4.35 (m, 1H), 4.18 (m, 2H), 4.04 (s, 3H), 2.79 (m, 2H), 2.60 (m, 1H), 2.26 (m, 1H) 1.83 (m, 4H), 1.59 (m, 9H), 1.35 (m, 6H). ³¹P NMR (121.4 MHz, CD₃OD): 40.291; LCMS: 875.39 (M+1).

Example 176

Preparation of Compound 176

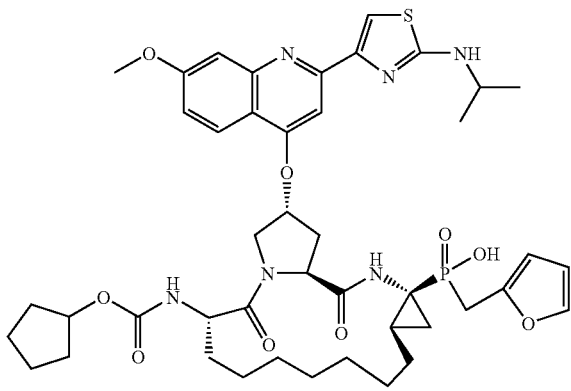

The methathesis product from Example 175 (1.2 g, 1.48 mmol) was taken up in ethyl acetate (15 mL) and Degusssa-type Rhodium on Alumina (0.6 g, 50% w/w) was added. The reaction vessel was evacuated and placed under hydrogen atmosphere, stirred at rt for 5 h. When the reaction was complete, the solution was filtered through celite and concentrated to provide 1.08 g which was used directly in the next step.

This brosylate (1.08 g, 1.33 mmol), was taken up in N-methylpyrrolidinone (15 mL) and the aminothiazolequinoline (0.42 g, 1.33 mmol) and cesium carbonate (0.43 g, 1.33 mmol) were added. The reaction mixture was heated at 60° C. for 4 h, and then stirred at room temperature overnight. Ethyl acetate was added and the organic layer was washed with saturated sodium bicarbonate solution, dried, and concentrated. The residue was purified by flash chromatography to provide the desired product (0.45 g, 38% in two steps).

This Boc-amine (0.45 g, 0.5 mmol) was taken up in acetonitrile (5 mL), and TMSI (0.36 mL, 2.5 mmol) was added. The reaction mixture was stirred at room temperature for 15 minutes (LCMS analysis showed full conversion). 2,6-Lutidine (0.2 mL) was added, followed by quenching with methanol, concentrating and azeotroping with toluene (3×20 mL). The residue was then taken up in acetonitrile/water (5 mL each). Sodium carbonate (0.64 g, 6 mmol) and cyclopentyl chloroformate (5 equiv.) were added, and the reaction mixture was stirred at room temperature for 1.5 h. LCMS showed full conversion and the reaction was then concentrated, filtered, and purified by HPLC to provide compound 176 (180 mg, 41%). ¹H NMR (300 MHz, CD₃OD): δ 8.30 (d, 1H, J=9.4 Hz), 8.07 (s, 1H), 7.75 (s, 2H), 7.43 (m, 1H), 7.35 (m, 1H), 6.37 (m, 1H), 6.29 (m, 1H), 5.83 (m, 1H), 4.79 (m, 1H), 4.65 (m, 1H), 4.41 (m, 1H), 4.18 (m, 3H), 4.04 (s, 3H), 2.79 (m, 1H), 2.51 (m, 1H), 1.89 (m, 2H), 1.76 (m, 2H), 1.42 (m, 24H), 1.34 (d, 6H, J=6.7 Hz). ³¹P NMR (121.4 MHz, CD₃OD): δ42.676. LCMS: 877.16 (M+1).

Example 177

Preparation of Compound 177

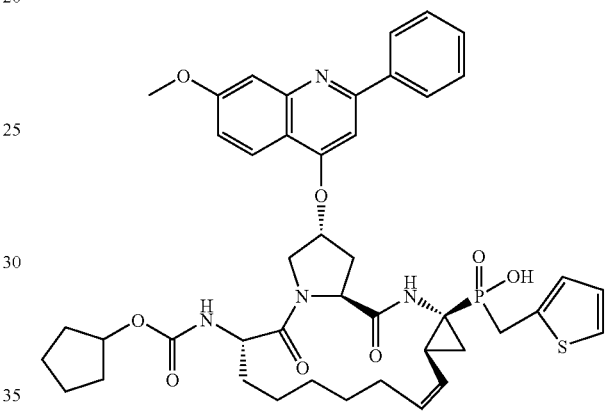

A solution of cyclic brosylate (Example 173) (448.5 mg, 0.54 mmol) and 7-methoxy-2-phenyl-quinolin-4-ol (145 mg, 0.58 mmol) in NMP (6.8 mL) was treated with Cs₂CO₃ (224 mg, 0.69 mmol). The reaction mixture was heated to 70° C. for 8 h and then cooled to rt. The reaction mixture was diluted with EtOAc (80 mL) and washed with H₂O (2×100 mL) followed by saturated NaHCO₃ (2×100 mL). The aqueous layer was extracted with EtOAc (80 mL). The combined organic layers were dried with Na₂SO₄ and concentrated. The crude product was purified by combi-flash to give 295.7 mg of desired product in 65% yield.

To a solution of product obtained above (295.7 mg, 0.35 mmol) in CH₂Cl₂ (2.2 mL) was added 4 N HCl in 1,4-dioxane (2.2 mL, 8.8 mmol). The reaction mixture was stirred at r.t. for 2 h and concentrated. The residue was triturated with CH₃CN and concentrated. The residue was dried under vacuum for 20 minutes to give crude amine HCl salt. Cyclopentanol (0.16 mL, 1.76 mmol) was dissolved in THF (6 mL) and 20% phosgene in toluene (1.5 mL, 2.84 mmol) was added. The reaction was stirred for 1 h and concentrated. The residue was dissolved in CH₂Cl₂ and concentrated to give crude cyclopentylchloroformate. The crude amine HCl salt was dissolved in CH₃CN (2 mL) and cooled to 0° C. Na₂CO₃ (225 mg, 2.12 mmol) in H₂O (3 mL) was added and stirred for 5 minutes. A solution of the freshly prepared cyclopentylchloroformate in CH₃CN (4 mL) was added. The reaction was completed within 1 h and concentrated. The residue was dissolved in EtOAc (30 mL) and washed with H₂O (30 mL) and brine (20 mL). The aqueous layer was extracted with EtOAc (20 mL). The combined organic layers were dried with Na$_2$SO$_4$ and concentrated. The crude product was purified by combi-flash to give 255.9 mg of product.

A solution of product obtained above (97.5 mg, 0.11 mmol) and 2,6-lutidine (0.08 mL, 0.69 mmol) in CH$_3$CN (2 mL) was stirred at 0° C. as iodotrimethylsilane (0.08 mL, 0.56 mmol) was added. The reaction mixture was stirred at 0° C. for 6 h and then warmed to r.t for 30 minutes. MeOH (1 mL) was added and stirred for 20 minutes. The mixture was concentrated and the crude product was purified by HPLC to give 96.1 mg of acid 177 in 90% yield. $^1$H NMR (300 MHz, CD$_3$OD): δ 8.43 (d, 1H, J=9.3 Hz), 8.09 (dd, 2H, J=8.0 and 1.7 Hz), 7.71-7.82 (m, 3H), 7.67 (s, 1H), 7.55 (d, 1H, J=2.4 Hz), 7.38 (dd, 1H, J=9.3 and 2.4 Hz), 7.18-7.23 (m, 1H), 6.90-6.96 (m, 2H), 5.89 (br, 1H), 5.64 (appt q, 1H, J=~9 Hz), 5.24 (appt t, 1H, J=9.9 Hz), 4.96 (1H), 4.74 (dd, 1H, J=9.3 and 7.5 Hz), 4.42 (br, 1H), 4.18 (d, 1H), 4.07 (d, 1H), 4.03 (s, 3H), 3.62 (t, 1H, J=15.3 Hz), 3.36 (t, 1H, J=15.3 Hz), 2.74-2.88 (m, 2H), 2.55-2.67 (m, 1H), 2.17-2.29 (m, 1H), 1.80 (br m, 1H), 1.16-1.69 (m, 18H). $^{31}$P NMR (121.4 MHz, CD$_3$OD): δ 38.060. LC/MS=827 (M$^+$+1)

Example 178

Preparation of Compound 178

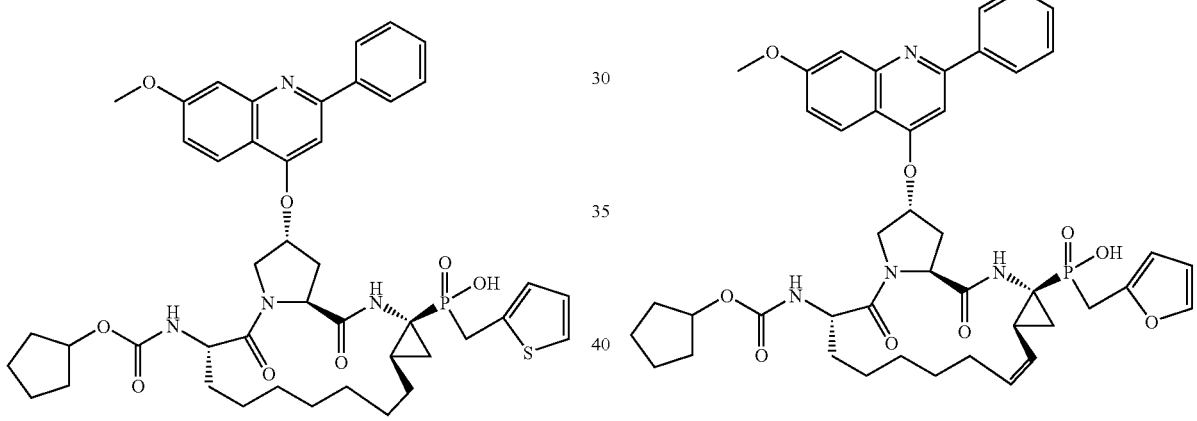

A solution of ethyl phosphinate (Example 177, 158.1 mg, 0.18 mmol) and p-tosyl hydrazide (551.9 mg, 1.85 mmol) in THF (6 mL) was heated to 70° C. as TEA (0.26 mL) in THF (1 mL) was added in 10 minutes. The reaction mixture was stirred at 60° C. overnight. An additional hydrazide (555 mg) and TEA (0.26 mL) in THF (1 mL) were added, and stirred for 16 h at 60° C. More hydrazide (552 mg) and TEA (0.26 mL) in THF (1 mL) were added, and stirred at 60° C. for 9 h. The mixture was stored in freezer for 5.5 days. Hydrazide (1.11 g) and TEA (0.52 mL) were added, and stirred at 60° C. for 20 h. The reaction mixture was concentrated and the residue was diluted with EtOAc before washing with 0.5 N NaOH (2×50 mL). The aqueous layer was extracted with EtOAc (2×25 mL). The organic layers were washed with brine, dried with Na$_2$SO$_4$, and concentrated. The residue was purified by combi-flash to give 88.3 mg of a mixture containing 10% of product. The resulting mixture was dissolved in CH$_3$CN (5 mL). Hydrazide (618 mg, 2.07 mmol) and TEA (0.29 mL) were added. The mixture was stirred at 60° C. overnight. The reaction mixture was concentrated and the residue was dissolved in EtOAc (30 mL). The solution was washed with ice cold 1 N NaOH (2×20 mL) and brine. The aqueous layer was extracted with EtOAc (2×20 mL). The combined organic layers were dried with Na$_2$SO$_4$ and concentrated. The residue was purified by thin layer chromatography to give 71.5 mg of saturated compound. A solution of saturated compound (71.5 mg, 0.08 mmol) and 2,6-lutidine (0.06 mL, 0.52 mmol) in CH$_3$CN (2 mL) was stirred at 0° C. as iodotrimethylsilane (0.06 mL, 0.42 mmol) was added. The reaction mixture was warmed to r.t. and stirred for 2 h. MeOH (1 mL) was added and stirred for 1 h. The mixture was concentrated and the crude product was purified by HPLC to give 49.2 mg of acid 178. $^1$H NMR (300 MHz, CD$_3$OD): δ 8.36 (d, 1H, J=9.3 Hz), 8.09 (dd, 2H, J=8.1 and 1.5 Hz), 7.68-7.81 (m, 3H), 7.66 (s, 1H), 7.56 (d, 1H, J=2.1 Hz), 7.37 (dd, 1H, J=9.3 and 2.1 Hz), 7.24 (d, 1H, J=4.8 Hz), 7.00 (br, 1H), 6.95 (dd, 1H, J=4.8 and 3.3 Hz), 5.89 (br, 1H), 4.87 (d, 1H, J=12 Hz), 4.71 (t, 1H, J=8.4 Hz), 4.43 (br, 1H), 4.24 (m, 1H), 4.09 (m, 1H), 4.02 (s, 3H), 3.56 (t, 1H, J=15.6 Hz), 3.43 (t, 1H, J=15.6 Hz), 2.81 (dd, 1H, J=14.1 and 7.5 Hz), 2.44-2.56 (m, 1H), 1.10-1.96 (m, 25H). $^{31}$P NMR (121.4 MHz, CD$_3$OD): δ 41.123. LC/MS=829 (M$^+$+1)

Example 179

Preparation of Compound 179

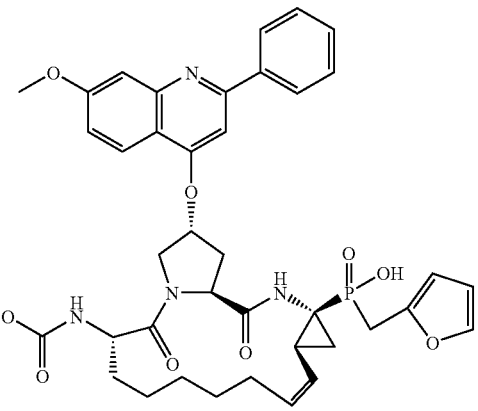

A solution of the brosylate from Example 175 (255 mg, 0.31 mmol), Cs$_2$CO$_3$ (102 mg, 0.31 mmol) and phenylquinoline (79 mg, 0.31 mmol) stirred in N-methylpyrrolidone (3 mL) at 60° C. After 4 h, the reaction was diluted with ethyl acetate and quenched with saturated NaHCO$_3$. The organic layer was washed with saturated NaHCO$_3$ (2×) and brine. The organic layer was dried and concentrated. The material was purified by column chromatography to provide the desired product (114 mg, 41%).

A solution of the Boc-amine (114 mg, 0.14 mmol) and trifluoroacetic acid (500 µl) in CH$_2$Cl$_2$ (1 mL) was stirred at rt for 1 h. The solution was then concentrated, and azeotroped with toluene (2×). The residue was stirred in THF (1 mL), and cyclopentyl chloroformate (0.69 mmol) and triethylamine (230 µl, 1.66 mmol) in THF (500 µl) were sequentially added. The solution was stirred at rt for 1 hour. The reaction mixture was partitioned between water and ethyl acetate. The organic layer was washed with brine, dried (MgSO$_4$) and concentrated. The crude material was purified by column chromatography to give the ethyl phosphinate (86 mg, 76%).

A solution of the ethyl phosphinate (39 mg, 0.04 mmol) and TMSI (30 µl, 0.23 mmol) in CH$_3$CN (1 mL) was stirred for 30 minutes, and then 2,6-Lutidine (500 µl) was added. The solution was concentrated and azeotroped with methanol and toluene. The crude material was purified by HPLC to give compound 179 (21 mg, 56%). $^1$H NMR (300 MHz, CD$_3$OD): δ 8.40 (d, 1H, J=9.4 Hz), 8.08 (m, 1H), 7.73 (m, 5H), 7.52 (m, 1H), 7.38 (m, 2H), 6.33 (m, 1H), 6.22 (m, 1H), 5.91 (m, 1H), 5.73 (m 1H), 5.26 (m, 1H), 4.71 (m, 1H), 4.35 (m, 1H), 4.15 (m, 1H), 5.24 (s, m, 4H), 2.80 (m, 2H), 2.62 (m, 1H), 2.26 (m, 1H), 1.81 (m, 2H), 1.50 (m, 14H). $^{31}$P NMR (121.4 MHz) δ 40.245. LCMS. 812 (M+1).

Example 180

Preparation of Compound 180

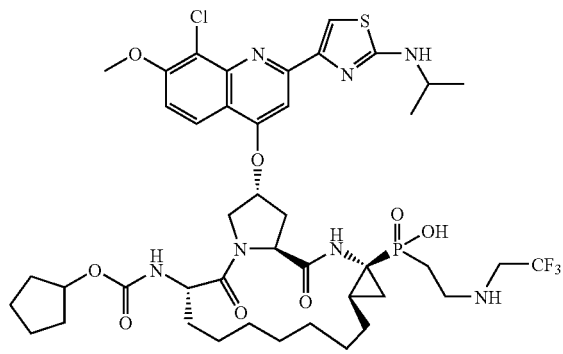

Following experimental procedures similar to those described for the preparation of compound 152, compound 180 was prepared. $^1$H NMR (300 MHz, CD$_3$OD) δ 8.34 (d, J=9.6 Hz, 1H), 8.31 (s, 1H), 7.86 (s, 1H), 7.65 (d, J=9.6 Hz, 1H), 5.84 (bs, 1H), 4.84 (m, 1H), 4.67 (t, J=7.5 Hz, 1H), 4.33 (bs, 1H), 4.17 (m, 1H), 4.16 (s, 3H), 4.03 (m, 2H), 3.47 (m, 2H), 2.83 (m, 1H), 2.58 (m, 1H), 2.0-2.3 (m, 2H), 1.6-2.0 (m, 2H), 1.2-1.6 (m, 31H) $^{31}$P NMR (121.4 MHz, CD$_3$OD) δ38.831; LCMS (M+1): 956.2.

Example 181

Preparation of Compound 181

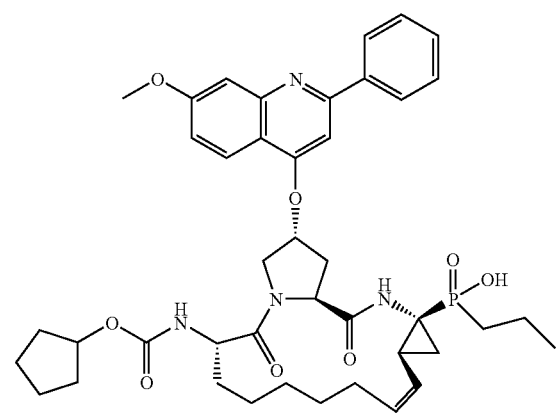

A solution of brosylate (Example 171) (182 mg, 0.23 mmol), Cs$_2$CO$_3$ (76 mg, 0.23 mmol) and 7-Methoxy-2-phenyl-quinolin-4-ol (58 mg, 0.23 mmol) in 1-methyl-2-pyrrolidinone (2.3 mL) was stirred at 65° C. for 3.5 h. The solution was diluted with EtOAc and quenched with 2.5% NaHCO$_3$ solution. The organic phase was washed with 2.5% NaHCO$_3$ solution (2×) and brine, dried over MgSO$_4$, and concentrated.

A solution of crude product (93 mg, 0.12 mmol) and 2,6-lutidine (81 µl, 0.70 mmol) in CH$_3$CN (3 mL) was stirred at 0° C. as iodotrimethylsilane (99 µl, 0.70 mmol) was added dropwise. The solution was warmed to rt and stirred for 1.5 h. The solution was cooled back to 0° C., and additional 2,6-Lutidine (40 µl, 0.35 mmol) and iodotrimethylsilane (49 µl, 0.35 mmol) were added. The solution was then stirred again at rt for 1.5 h. The solution was cooled to 0° C., and Et$_3$N (500 µl) and MeOH (1 mL) were added. The reaction mixture was concentrated and 181 (70 mg, 78%) was obtained from the residue by HPLC purification as a white solid. $^1$H NMR (300 MHz, CD$_3$OD): δ8.42 (d, J=9.3 Hz, 1H), 8.08 (d, J=6.9 Hz, 2H), 7.76 (m, 3H), 7.66 (s, 1H), 7.55 (s, 1H), 7.35 (d, J=9.3 Hz, 1H), 5.88 (s, 1H), 5.54 (q, J=9 Hz, 1H), 5.18 (t, J=9.6 Hz, 1H), 4.9 (s, 1H), 4.73 (t, J=8.7 Hz, 1H), 4.42 (s, 1H), 4.17 (d, J=11.4 Hz, 1H), 4.07 (d, J=11.7 Hz, 1H), 4.02 (s, 3H), 2.80 (m, 2H), 2.58 (m, 1H), 2.20 (m, 1H), 1.2-2.0 (brm, 21H), 1.00 (t, J=7.2 Hz, 3H). $^{31}$P NMR (121.4 MHz, CD$_3$OD): δ 46.5 LC/MS=773.8 (M$^+$+1).

Example 182

Preparation of Compound 182

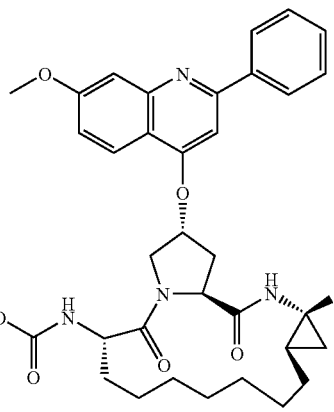

A solution of phosphinate (Example 181, 81 mg, 0.10 mmol) and 2,4,6-triisopropylbenzene-sulfonylhydrazide (292 mg, 0.98 mmol) in THF (3 mL) was stirred at 60° C. as Et$_3$N (137 µl, 0.98 mmol) was added dropwise over 5 minutes. After 1 h, the reaction was cooled and additional 2,4,6-triisopropylbenzene-sulfonylhydrazide (292 mg, 0.98 mmol) was added. This was followed by the slow addition of more Et$_3$N (137 µl, 0.98 mmol). After 1 h, more 2,4,6-triisopropylbenzene-sulfonylhydrazide (292 mg, 0.98 mmol) and Et$_3$N (137 µl, 0.98 mmol) was added. After 1 h, the reaction was diluted with EtOAc and washed with saturated NH$_4$Cl (2×). THF was added to the organic layer and it was extracted with saturated NH$_4$Cl, saturated Na$_2$CO$_3$, and H$_2$O. The resulting mono-phasic solution was extracted with EtOAc. Combined organic washes were extracted with brine, and dried over MgSO$_4$ and concentrated. Saturated phosphinate (70 mg, 87%) was purified from the residue by HPLC to yield a glassy white solid. LC/MS=802.7 (M$^+$+1), 824.4 (M$^+$+Na)

A solution of saturated phosphinate (70 mg, 0.09 mmol) and 2,6-lutidine (61 μl, 0.52 mmol) in CH$_3$CN (3 mL) was cooled to 0° C. and iodotrimethylsilane (75 μl, 0.52 mmol) was added drop-wise. The solution was stirred at rt for 1 h. The reaction was then cooled to 0° C. and additional 2,6-lutidine (30 μl, 0.26 mmol) and iodotrimethylsilane (37 μl, 0.26 mmol) was added. The solution then warmed again to rt and stirred for 3 h. The reaction was cooled to 0° C. and Et$_3$N (500 μl) and MeOH (1 mL) was added. The reaction was concentrated and 182 (46 mg, 69%) was isolated from the residue by HPLC as an off-white solid. $^1$H NMR (300 MHz, CD$_3$OD) δ8.37 (d, J=9 Hz, 1H), 8.08 (m, 2H), 7.76 (m, 3H), 7.66 (s, 1H), 7.55 (s, 1H), 7.39 (dd, J=1.8, 9.3 Hz, 1H), 5.89 (1H), 4.69 (t, J=9 Hz, 1H), 4.43 (s, 1H), 4.24 (d, J=7.5 Hz, 1H), 4.09 (d, J=12 Hz, 1H), 4.04 (s, 3H), 2.82 (dd, J=7.2, 14.4 Hz), 2.50 (ddd, J=4.2, 9.3, 13.8 Hz, 1H), 1.2-2.0 (brm, 28H), 1.05 (t, J=7.2 Hz, 3H). $^{31}$P NMR (121.4 MHz, CD$_3$OD): δ 50.36. LC/MS=775.3 (M$^+$+1)

Example 183

Preparation of Compound 183

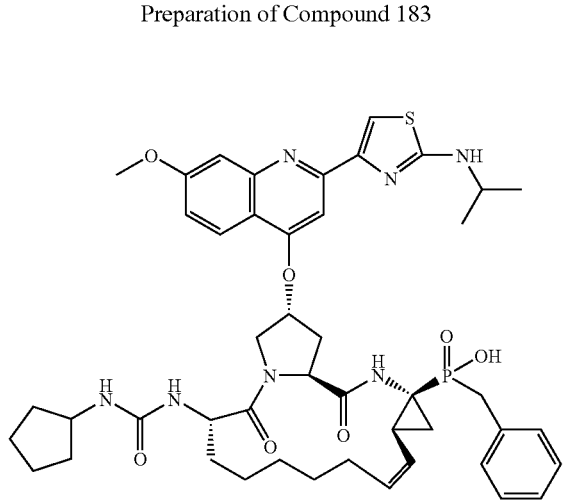

Step 1. To a solution of the BOC-protected phosphinate (described in Example 143, 2.22 g, 2.46 mmol) in CH$_2$Cl$_2$ (10 mL) was added 4 N HCl in 1,4-dioxane (50 mL, 200 mmol). The reaction mixture was stirred at r.t. for 3.5 h, concentrated, co-evaporated with CH$_2$Cl$_2$, and dried under vacuum to give the desired amine as a brown solid.

Step 2. To a solution of the amine obtained from step 1 (60 mg, 0.075 mmol) in CH$_2$Cl$_2$ (0.7 mL) at 0° C. was added 6.8 M cyclopentylisocyanate in CH$_2$Cl$_2$ (0.2 mL, 0.062 mmol). The reaction mixture was stirred for 1 h, kept in −20° C. freezer overnight, and concentrated. The residue was purified by combi-flash to give 50.6 mg of intermediate ester. The resulting ester (50 mg) was dissolved in CH$_3$CN (2 mL) and cooled to 0° C. Iodotrimethylsilane (0.2 mL) was added. The reaction mixture was warmed to rt, stirred for 0.5 h, and cooled to 0° C. TEA (0.5 mL) was added followed by addition of MeOH (2 mL). The mixture was concentrated and purified by HPLC to give 11.6 mg of compound 183. $^1$H NMR (300 MHz, CD$_3$OD): δ8.35 (d, J=9.3 Hz, 1H), 8.19 (s, 1H), 7.74 (s, 2H), 7.15-7.42 (m, 6H), 5.82 (brs, 1H), 5.68 (dd, J=8.6, 18.3 Hz, 1H), 5.27 (t, J=9.6 Hz, 1H), 4.83 (d, J=12.0 Hz, 1H), 4.72 (t, J=8.7 Hz, 1H), 4.$^{31}$ (d, J=8.7 Hz, 1H), 4.07-4.23 (m, 2H), 4.03 (s, 3H), 3.51 (m, 1H), 3.38 (t, J=15.9 Hz, 1H), 3.17 (t, J=15.9 Hz, 1H), 2.79 (m, 1H), 2.61 (m, 1H), 2.25 (m, 1H), 1.2-1.9 (m, 26H); $^{31}$P NMR (121.4 MHz, CD$_3$OD): δ42.114; LC/MS=884 (M$^+$+1).

Example 184

Preparation of Compound 184

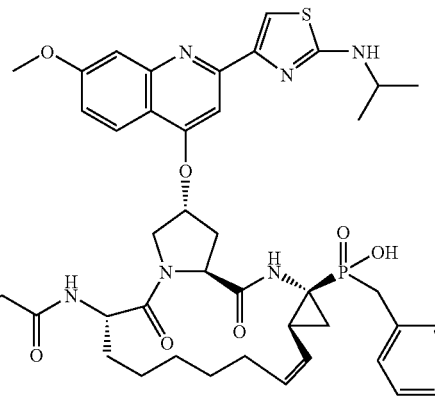

4-Trifluorobutyric acid (15.5 mg, 0.11 mmol) and the amine HCl salt (Example 183, 70 mg, 0.084 mmol) were dissolved in CH$_2$Cl$_2$ (1 mL)/DMF (0.5 mL). HATU (47.88 mg, 0.13 mmol) and DIPEA (0.06 mL, 0.34 mmol) were added and the mixture was stirred at r.t. for 15 minutes. The reaction mixture was concentrated, re-dissolved in EtOAc, washed with 5% LiCl, saturated NaHCO$_3$ and brine, and concentrated. The crude product was purified by combi-flash to give 33.4 mg of intermediate ester. The resulting ester (33.4 mg, 0.036 mmol) was dissolved in CH$_3$CN (2 mL) and cooled to 0° C. Iodotrimethylsilane (0.2 mL) was added. The reaction mixture was warmed to rt, stirred for 0.5 h, and cooled to 0° C. TEA (0.5 mL) was added followed by addition of MeOH (2 mL). The mixture was concentrated and purified by HPLC to give 17.7 mg of compound 184. $^1$H NMR (300 MHz, CD$_3$OD): δ8.29 (d, J=9.3 Hz, 1H), 8.18 (s, 1H), 7.75 (s, 2H), 7.15-7.42 (m, 6H), 5.85 (brs, 1H), 5.73 (dd, J=8.6, 18.3 Hz, 1H), 5.30 (t, J=9.6 Hz, 1H), 4.69 (dd, J=7.5, 9.3 Hz, 1H), 4.30 (d, J=9.6 Hz, 1H), 4.05-4.22 (m, 2H), 4.04 (s, 3H), 3.51 (m, 1H), 3.39 (t, J=15.3 Hz, 1H), 3.18 (t, J=15.3 Hz, 1H), 2.81 (m, 2H), 2.61 (m, 1H), 2.25 (m, 3H), 2.02 (m, 2H), 1.50 (m, 3H), 1.4-1.6 (m, 8H), 1.34 (d, J=6.3 Hz, 6H); ³¹P NMR (121.4 MHz, CD₃OD): δ42.563; LC/MS=897 (M⁺+1).

Example 185

Preparation of Compound 185

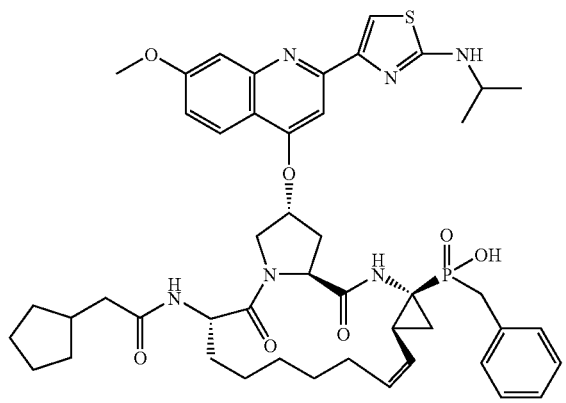

Following experimental procedures similar to those described for the preparation of compound 184, compound 185 was prepared. ¹H NMR (300 MHz, CD₃OD): δ8.29 (d, J=9.3 Hz, 1H), 8.19 (s, 1H), 7.76 (s, 2H), 7.15-7.38 (m, 6H), 5.84 (brs, 1H), 5.73 (dd, J=8.6, 18.3 Hz, 1H), 5.29 (t, J=9.6 Hz, 1H), 4.94 (d, J=12.0 Hz, 1H), 4.69 (t, J=8.7 Hz, 1H), 4.36 (d, J=8.7 Hz, 1H), 4.07-4.23 (m, 2H), 4.05 (s, 3H), 3.38 (t, J=15.9 Hz, 1H), 3.18 (t, J=15.9 Hz, 1H), 2.82 (m, 2H), 2.61 (m, 1H), 2.25 (m, 1H), 2.02 (d, J=7.5 Hz, 2H), 1.85 (m, 3H), 1.2-1.9 (m, 23H); ³¹P NMR (121.4 MHz, CD₃OD): δ42.453; LC/MS=883 (M⁺+1).

Example 186

Preparation of Compound 186

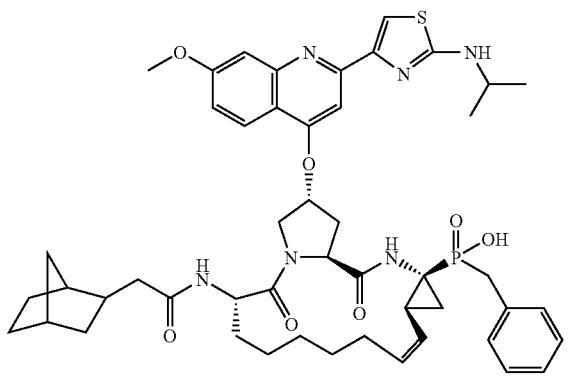

Following experimental procedures similar to those described for the preparation of compound 184, compound 186 was prepared. LC/MS=909 (M⁺+1).

Example 187

Preparation of Compound 187

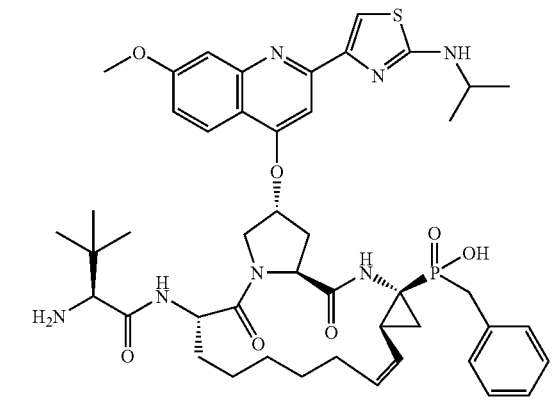

To a solution of amine (Example 185) (130 mg, 0.16 mmol) and Boc-L-tert-leucine (45 mg, 0.20 mmol) were dissolved in CH₂Cl₂ (2 mL)/DMF (0.5 mL). HATU (93 mg, 0.24 mmol) and DIPEA (0.13 mL, 0.45 mmol) were added and the mixture was stirred at r.t. for 15 minutes. The reaction mixture was concentrated, re-dissolved in EtOAc, washed with 5% LiCl, saturated NaHCO₃ and brine, and concentrated. The crude product was purified by combi-flash to give 133 mg of tetrapeptide in 81% yield.

The tetrapeptidic intermediate (133 mg, 0.13 mmol) was dissolved in CH₃CN (2 mL) and cooled to 0° C. Iodotrimethylsilane (0.2 mL) was added. The reaction mixture was warmed to rt, stirred for 0.5 h, and cooled to 0° C. TEA (0.4 mL) was added followed by addition of MeOH (2 mL). The mixture was concentrated and purified by HPLC to give 82.6 mg of 187 in 57% yield. ¹H NMR (300 MHz, CD₃OD): δ8.24 (d, J=9.3 Hz, 1H), 8.21 (s, 1H), 7.78 (s, 2H), 7.36 (dd, J=2.4, 9.0 Hz, 1H) 7.15-7.38 (m, 5H), 5.86 (brs, 1H), 5.78 (dd, J=8.6, 18.3 Hz, 1H), 5.33 (t, J=9.6 Hz, 1H), 4.86 (d, J=12.0 Hz, 1H), 4.67 (t, J=8.7 Hz, 1H), 4.54 (d, J=8.7 Hz, 1H), 4.1-4.25 (m, 2H), 4.06 (s, 3H), 3.47 (s, 1H), 3.36 (t, J=15.9 Hz, 1H), 3.19 (t, J=15.9 Hz, 1H), 2.82 (m, 2H), 2.61 (m, 1H), 2.32 (m, 1H), 2.02 (d, J=7.5 Hz, 1H), 1.98 (m, 2H), 1.23-1.7

(m, 8H), 1.34 (d, J=6.3 Hz, 6H), 0.83 (s, 9H); $^{31}$P NMR (121.4 MHz, CD$_3$OD): δ42.485; LC/MS=886 (M$^+$+1).

Example 188

Preparation of Compound 188

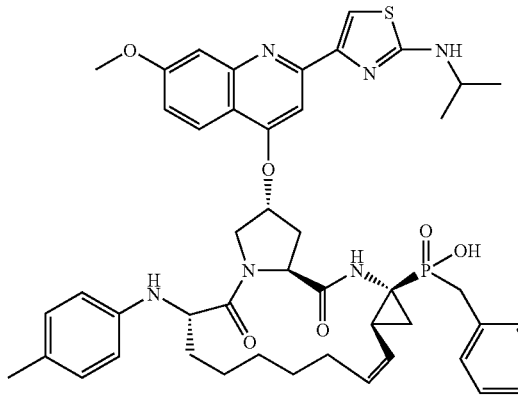

To a mixture of the amine prepared as shown in Example 185 (60 mg, 0.075 mmol) and p-tolylboronic acid (20 mg, 0.15 mmol) in CH$_2$Cl$_2$ (4 mL) was added molecular sieves (150 mg), TEA (0.2 mL), and Cu(OAc)$_2$ sequentially. The reaction mixture was stirred under air with drying tube for 18 h, diluted with CH$_2$Cl$_2$, and filtered through celite. The filtrate was concentrated and purified by HPLC to give 100 mg of intermediate ester. The ester (100 mg, 0.075 mmol) and 2,6-lutidine (0.09 mL, 0.75 mmol) were dissolved in CH$_3$CN (2 mL) and cooled to 0° C. Iodotrimethylsilane (0.05 mL, 0.38 mmol) was added. The reaction mixture was warmed to rt, stirred for 1 h, and cooled to 0° C. MeOH (0.2 mL) was added and warmed to rt. The mixture was concentrated and purified by HPLC to give 4.6 mg of 188 as a yellow solid. $^1$H NMR (300 MHz, CD$_3$OD): δ8.19 (s, 1H) 7.96 (d, J=9.0 Hz, 1H), 7.81 (s, 1H), 7.74 (s, 1H), 7.25-7.35 (m, 6H), 6.61 (m, 4H), 5.84 (brs, 1H), 5.78 (dd, J=8.6, 18.3 Hz, 1H), 5.36 (t, J=9.6 Hz, 1H), 4.64 (t, J=8.7 Hz, 1H), 4.30-4.47 (m, 2H), 4.10-4.25 (m, 2H), 4.08 (s, 3H), 3.39 (t, J=15.9 Hz, 1H), 3.18 (t, J=15.9 Hz, 1H), 2.75 (m, 1H), 2.63 (m, 1H), 2.28 (m, 1H), 1.98 (s, 3H), 1.7-2.1 (m, 3H), 1.2-1.7 (m, 14H); $^{31}$P NMR (121.4 MHz, CD$_3$OD): δ42.409; LC/MS=863 (M$^+$+1).

Example 189

Preparation of Compound 189

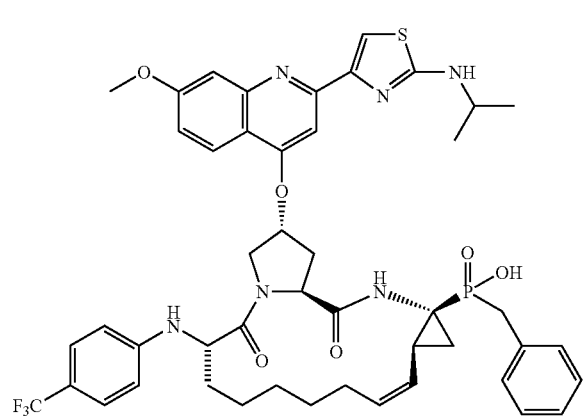

Following experimental procedures similar to those described for the preparation of compound 184, compound 189 was prepared. $^1$H NMR (300 MHz, CD$_3$OD): δ8.20 (s, 1H) 8.13 (d, J=9.0 Hz, 1H), 7.82 (s, 1H), 7.80 (s, 1H), 7.20-7.38 (m, 6H), 6.88 (d, J=8.1 Hz, 2H), 6.50 (d, J=8.1 Hz, 2H), 5.94 (brs, 1H), 5.77 (dd, J=8.6, 18.3 Hz, 1H), 5.36 (t, J=9.6 Hz, 1H), 4.74 (t, J=8.7 Hz, 1H), 4.60 (d, J=12.3 Hz, 1H), 4.43 (m, 1H), 4.10-4.25 (m, 2H), 4.07 (s, 3H), 3.36 (t, J=15.9 Hz, 1H), 3.20 (t, J=15.9 Hz, 1H), 2.63-2.82 (m, 2H), 2.24 (m, 1H), 1.7-2.1 (m, 3H), 1.2-1.7 (m, 14H); $^{31}$P NMR (121.4 MHz, CD$_3$OD): δ42.592; LC/MS=917 (M$^+$+1).

Example 190

Preparation of Compound 190

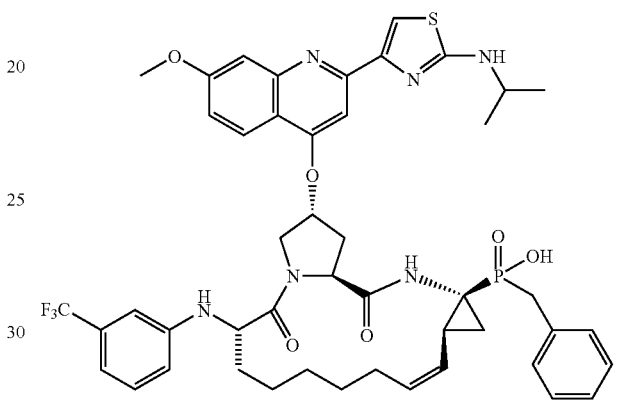

Following experimental procedures similar to those described for the preparation of compound 184, compound 190 was prepared. $^1$H NMR (300 MHz, CD$_3$OD): δ8.18 (s, 1H) 7.99 (d, J=9.3 Hz, 1H), 7.76 (s, 1H), 7.75 (s, 1H), 7.15-7.33 (m, 6H), 6.90 (m, 2H), 6.78 (d, J=7.5 Hz, 1H), 6.72 (d, J=7.5 Hz, 1H), 5.89 (brs, 1H), 5.75 (dd, J=8.6, 18.3 Hz, 1H), 5.34 (t, J=9.6 Hz, 1H), 4.72 (t, J=8.7 Hz, 1H), 4.49 (brs, 1H), 4.44 (d, J=12.3 Hz, 1H), 4.10-4.30 (m, 2H), 4.07 (s, 3H), 3.35 (t, J=15.9 Hz, 1H), 3.19 (t, J=15.9 Hz, 1H), 2.63-2.82 (m, 2H), 2.24 (m, 1H), 1.7-2.1 (m, 3H), 1.2-1.7 (m, 14H); $^{31}$P NMR (121.4 MHz, CD$_3$OD): δ42.205; LC/MS=917 (M$^+$+1).

Example 191

Preparation of Compound 191

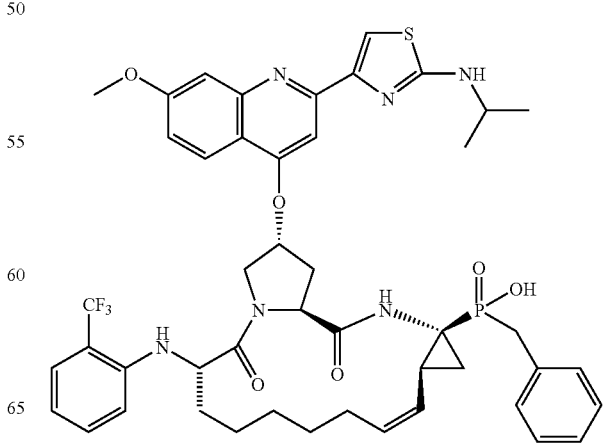

Following experimental procedures similar to those described for the preparation of compound 184, compound 191 was prepared. $^1$H NMR (300 MHz, CD$_3$OD): δ8.16 (s, 1H) 8.12 (d, J=9.3 Hz, 1H), 7.75 (s, 1H), 7.74 (s, 1H), 7.15-7.33 (m, 6H), 7.08 (t, J=7.2 Hz, 1H), 6.81 (d, J=7.2 Hz, 1H), 6.63 (d, J=7.2 Hz, 1H), 5.88 (brs, 1H), 5.75 (dd, J=8.6, 18.3 Hz, 1H), 5.40 (t, J=9.6 Hz, 1H), 4.78 (t, J=8.7 Hz, 1H), 4.64 (m, 1H), 4.39 (d, J=12.3 Hz, 1H), 4.10-4.30 (m, 2H), 4.06 (s, 3H), 3.35 (t, J=15.9 Hz, 1H), 3.21 (t, J=15.9 Hz, 1H), 2.63-2.82 (m, 2H), 2.24 (m, 1H), 1.7-2.1 (m, 3H), 1.2-1.7 (m, 14H); $^{31}$P NMR (121.4 MHz, CD$_3$OD): δ 42.896; LC/MS=917 (M$^+$+1).

Example 192

Preparation of Compound 192

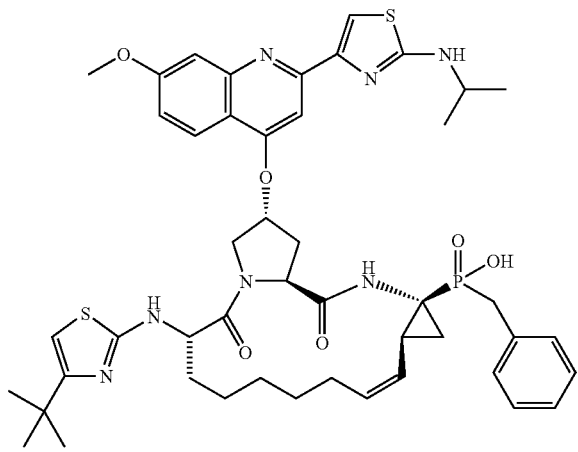

To a solution of the amine prepared as step 1 of Example 185 (70 mg, 0.087 mmol) in THF (2 mL) was added thiocarbonyl diimidazole and stirred at r.t. for 1 h. 2.0 M ammonium in MeOH (1 mL) was added and stirred at 50° C. for 1 h in a capped vial and concentrated. The residue was dissolved in CH$_2$Cl$_2$ (2 mL), the α-bromoketone (35 μL) was added, stirred at 50° C. for 1 h, and concentrated. The crude product was purified by combi-flash to give 80 mg of the phosphinate. Deprotection with iodotrimethylsilane (0.1 mL) provided 192. $^1$H NMR (300 MHz, CD$_3$OD): δ8.20 (S, 1H), 8.16 (d, J=9.3 Hz, 1H), 7.80 (s, 1H), 7.77 (s, 1H), 7.73 (s, 1H), 7.18-7.38 (m, 6H), 5.95 (brs, 1H), 5.79 (dd, J=8.6, 18.3 Hz, 1H), 5.39 (t, J=9.6 Hz, 1H), 4.82 (t, J=8.7 Hz, 1H), 4.72 (brs, 1H), 4.44 (d, J=12.3 Hz, 1H), 4.24 (dd, J=12.6, 3.3 Hz, 1H), 4.17 (m, 1H), 4.03 (s, 3H), 3.39 (t, J=15.9 Hz, 1H), 3.18 (t, J=15.9 Hz, 1H), 2.82 (m, 1H), 2.61 (m, 1H), 2.24 (m, 1H), 1.91 (m, 2H), 1.65 (m, 1H), 1.2-1.7 (m, 23H); $^{31}$P NMR (121.4 MHz, CD$_3$OD): δ42.306.

Example 193

Preparation of Compound 193

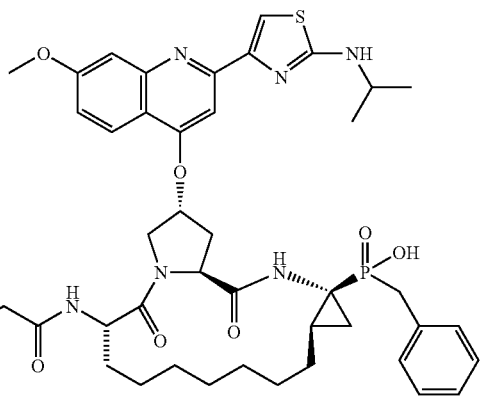

A mixture of compound 184 (308 mg, 0.305 mmol), tosyl hydrizde (425 mg, 2.28 mmol) and sodium acetate (375 mg, 4.58 mmol) in a mixed solvents of 1,2-dimethoxyethane (5.5 mL) and water (0.6 mL) was stirred at 95° C. for 3 h. The reaction mixture was then concentrated to a volume of 3 mL and filtered. The filtrate was purified by HPLC, affording 250 mg (81%) of compound 193. $^1$H NMR (300 MHz, CD$_3$OD): δ8.27 (d, J=9.6 Hz, 1H), 8.17 (s, 1H), 7.76 (s, 2H), 7.2-7.4 (m, 6H), 5.84 (brs, 1H), 4.83 (d, J=12.3 Hz, 1H), 4.65 (t, J=8.7 Hz, 1H), 4.39 (m, 1H), 4.24 (brs, 1H), 4.04-4.23 (m, 3H), 4.15 (m, 2H), 3.39 (t, J=15.9 Hz, 1H), 3.28 (t, J=15.9 Hz, 1H), 2.78 (m, 1H), 2.49 (m, 1H), 2.30 (m, 2H), 1.7-2.1 (m, 5H), 1.1-1.7 (m, 19H); $^{31}$P NMR (121.4 MHz, CD$_3$OD): δ44.910; LC/MS=899 (M$^+$+1).

Example 194

Preparation of Compound 194

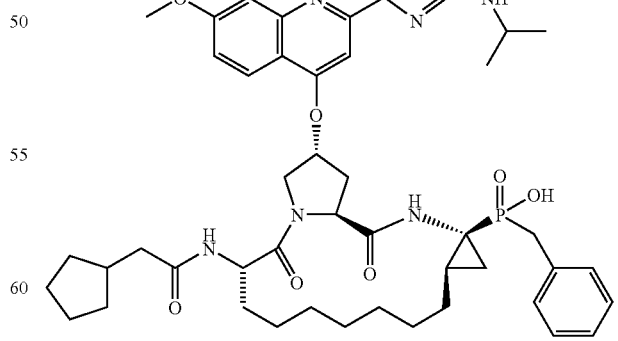

Following experimental procedures similar to those described for the preparation of compound 184, compound 194 was prepared. $^1$H NMR (300 MHz, CD$_3$OD): δ8.26 (d, J=9.3 Hz, 1H), 8.18 (s, 1H), 7.75 (s, 2H), 7.20-7.35 (m, 6H), 5.82 (brs, 1H), 4.84 (d, J=12.3 Hz, 1H), 4.64 (t, J=8.7 Hz, 1H), 4.44 (m, 1H), 4.15 (m, 3H), 4.05 (s, 3H), 3.34 (t, J=15.9 Hz, 1H), 3.22 (t, J=15.9 Hz, 1H), 2.77 (m, 1H), 2.48 (m, 1H), 2.04 (d, 2H), 1.7-2.0 (m, 3H), 1.1-1.7 (m, 26H), 1.00 (m, 2H); $^{31}$P NMR (121.4 MHz, CD$_3$OD): δ44.979; LC/MS=885 (M$^+$+1).

Example 195

Preparation of Compound 195

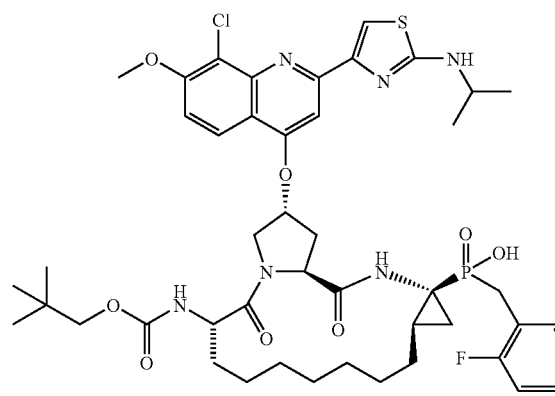

The fully protected macrocyclic phosphinate (synthesized as described in Example 152 with the Boc protection group) was treated with HCl to remove the Boc protection group. The resulting amine was used to prepare compounds 195-200

To a solution of this amine (34 mg, 0.04 mmol) in EtOAc (2 mL) was added saturated NaHCO$_3$ (2 mL) and stirred vigorously. 2,2-Dimethylpropyl chloroformate (7 μL) was added and stirred for 15 minutes. The two layers were separated. The organic layer was washed with brine and concentrated. The dried residue was dissolved in CH$_3$CN (1 mL) and cooled to 0° C. Iodotrimethylsilane (0.20 mL) was added. The reaction mixture was stirred for 0.5 h at 0° C. 2,6-lutidine (0.6 mL) was added followed by addition of MeOH (3 mL). The mixture was concentrated in vacuo. The residue was purified by HPLC to give 25.2 mg of compound 195. LC/MS=959.1 (M$^+$+1).

Example 196

Preparation of Compound 196

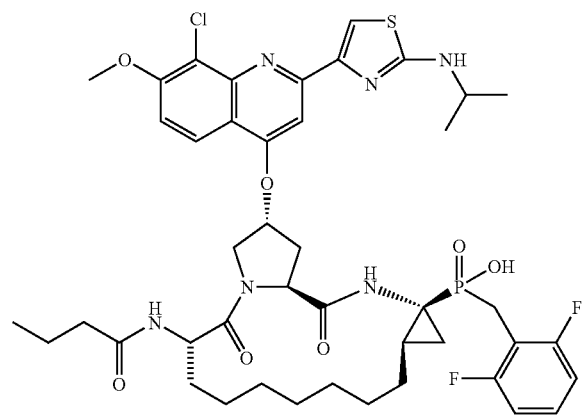

Following experimental procedures similar to those described for the preparation of compound 184, compound 196 was prepared. LC/MS=915.2 (M$^+$+1).

Example 197

Preparation of Compound 197

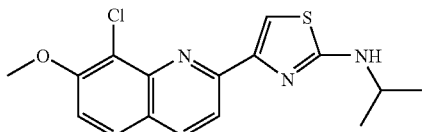

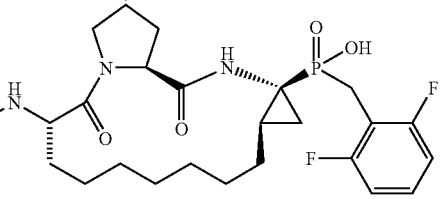

Following experimental procedures similar to those described for the preparation of compound 184, compound 197 was prepared. LC/MS=955.1 (M$^+$+1).

Example 198

Preparation of Compound 198

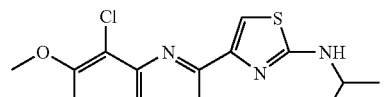

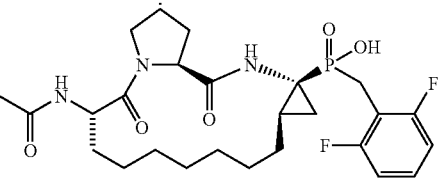

Following experimental procedures similar to those described for the preparation of compound 184, compound 198 was prepared. LC/MS=983.1 (M$^+$+1).

Example 199

Preparation of Compound 199

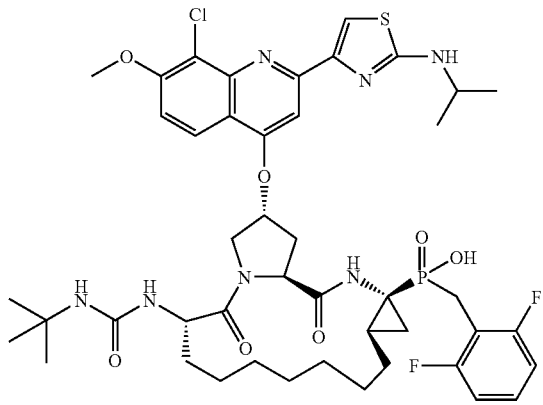

Following experimental procedures similar to those described for the preparation of compound 184, compound 199 was prepared. LC/MS=944.3 (M$^+$+1).

Example 200

Preparation of Compound 200

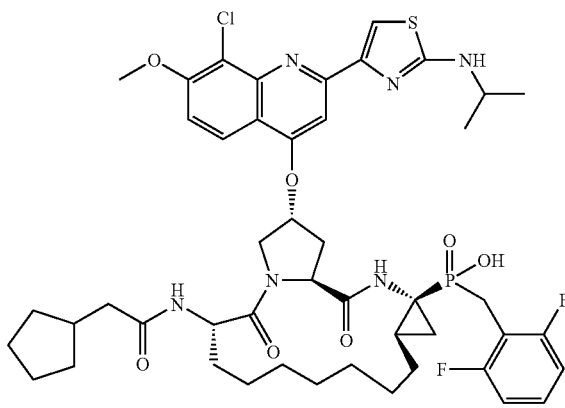

Compound 200 was prepared using a method similar to that described for compound 194. LCMS (M+1): 955.24.

Example 201

Preparation of Compound 201

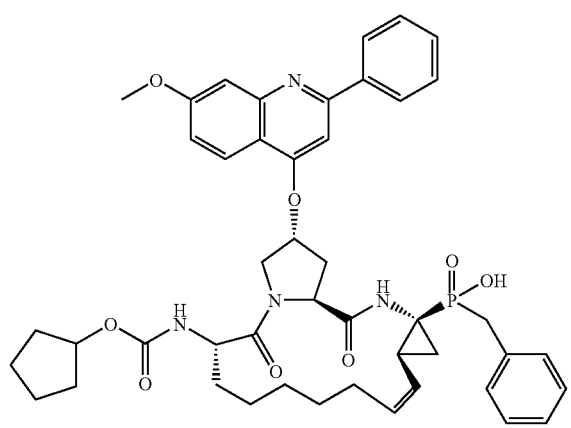

Compound 201 was prepared using a method similar to that described for compound 177. LCMS (M+1): 821.36.

Example 202

Preparation of Compound 202

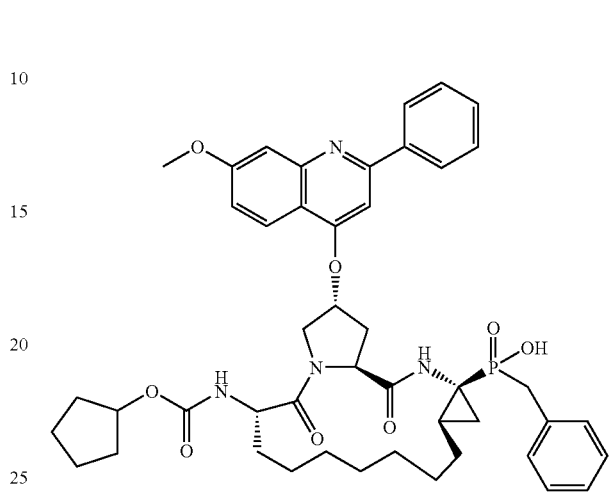

Compound 202 was prepared using a method similar to that described for compound 178. LCMS (M+1): 823.37.

Example 203

Preparation of Compound 203

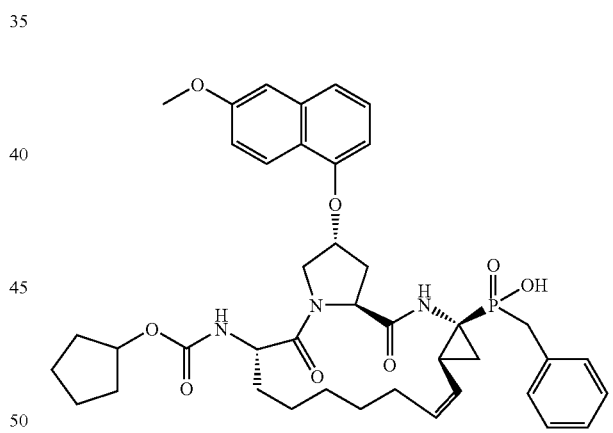

Compound 203 was prepared using the same method as described for compound 153. Displacement of the brosylate was performed using 6-methoxy-1-naphthol. The subsequent steps were analogous to previously described methods. The final product was purified by reverse phase HPLC (A: water/0.05% TFA, B: acetonitrile/0.5% TFA). $^1$H NMR (300 MHz, CD$_3$OD): δ8.13 (d, J=9 Hz, 1H), 7.40-7.35 (m, 2H), 7.30-7.16 (m, 6H), 7.01 (d, J=11 Hz, 1H), 6.85-6.80 (m, 1H), 5.73 (q, J=11 Hz, 1H), 5.42-5.34 (m, 2H), 4.85-4.76 (m, 1H), 4.64-4.55 (m, 2H), 4.32 (d, J=8 Hz, 1H), 4.06-3.97 (m, 1H), 3.90 (s, 3H), 3.39-3.11 (m, 2H), 2.87-2.70 (m, 1H), 2.70-2.57 (m, 1H), 2.45-2.24 (m, 2H), 1.95-1.25 (m, 19H). $^{31}$P NMR (121.4 MHz, CD$_3$OD): δ43.13.

EI MS (m/z) 743.7 [M+H]$^+$, 765.7 [M+Na]$^+$.

Example 204

Preparation of Compound 204

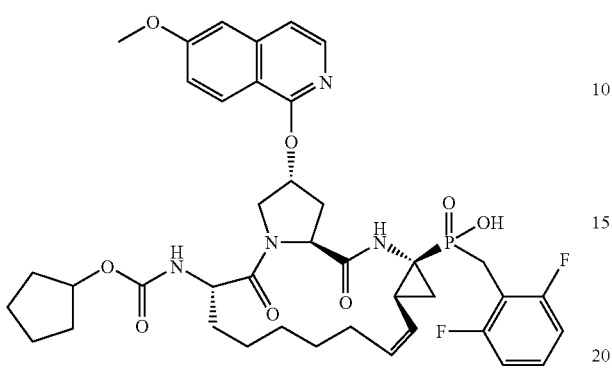

Compound 204 was afforded as a white solid. $^1$H NMR (300 MHz, CD$_3$OD): δ8.33 (m, 1H), 7.90 (m, 1H), 7.55 (m, 1H), 7.31 (m, 3H), 6.94 (m, 2H), 5.90 (bs, 1H), 5.73 (m, 1H), 5.33 (m, 1H), 4.74 (m, 2H), 4.42 (bs, 1H), 4.13 (m, 2H), 4.00 (s, 3H), 3.57 (m, 1H), 2.76 (m, 2H), 2.57 (m, 1H) 2.$^{31}$ (m, 1H), 1.86 (m, 2H) 1.65-1.2 (m, 18H); $^{31}$P NMR (121.4 MHz, CD$_3$OD): δ39.386 LC (6 minute run, r.t.=4.79 min) MS (781.2, M+1)

Example 205

Preparation of Compound 205

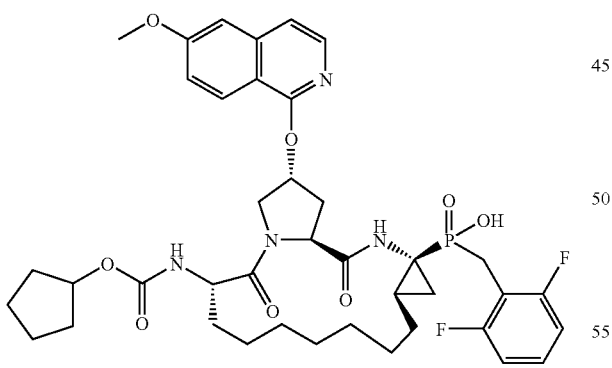

Compound 205 was afforded as a white solid. $^1$H NMR (300 MHz, CD$_3$OD): δ8.28 (d, J=9.2 Hz, 1H), 7.90 (d, J=6.4 Hz, 1H), 7.$^{31}$ (d, J=6.8 Hz, 1H), 7.$^{31}$ (m, 3H), 6.98 (m, 2H), 5.89 (bs, 1H), 4.74 (m, 2H), 4.42 (bs, 1H), 4.24 (m, 1H) 4.08 (m, 1H), 3.98 (s, 3H) 3.40 (m, 2H), 2.76 (m, 1H), 2.48 (m, 1H) 1.99 (m, 1H), 1.79 (m, 2H) 1.65-1.2 (m, 22H); $^{31}$P NMR (121.4 MHz, CD$_3$OD): δ41.217. LC (6 minute run, r.t.=4.74 min) MS (783.2, M+1)

Example 206

Preparation of Compound 206

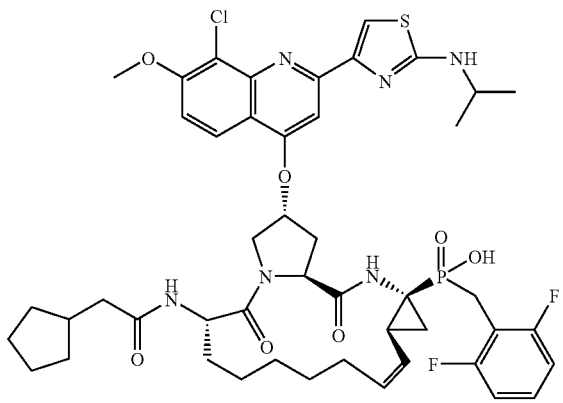

Compound 206 was prepared using a method similar to that described for compound 185. LCMS (M+1): 953.32

Example 207

Preparation of Compound 207

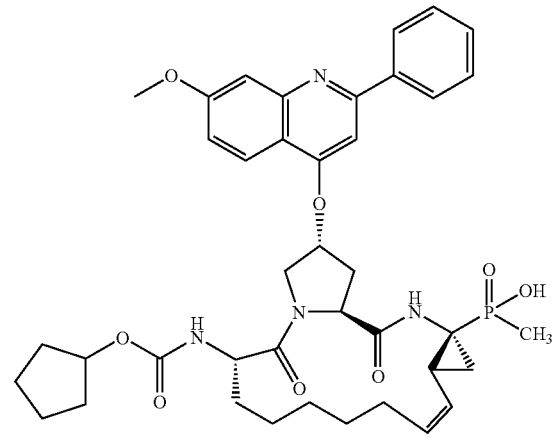

Compound 207 was prepared using procedures similar to those described herein. LCMS (M+1): 745.

Example 208

Preparation of Compound 208

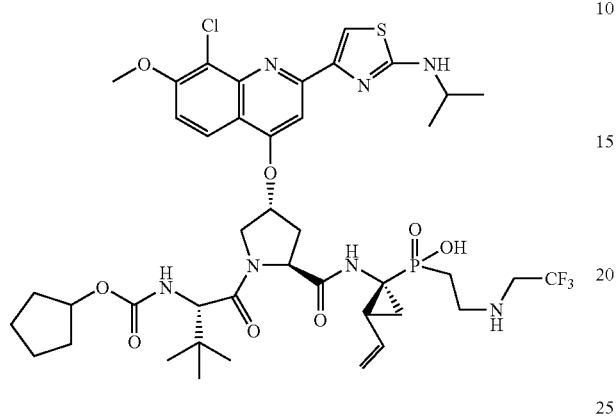

Compound 208 was prepared using procedures similar to those described herein. LCMS (M+1): 942.

Example 209

Preparation of Compound 209

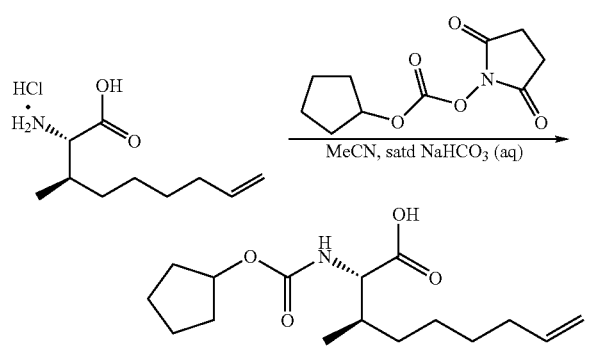

a. Amino acid (702 mg, 3.16 mmol) was slurried in MeCN (31 mL) and satd NaHCO$_3$ (aq, 32 mL) was added followed by N-cyclopentyloxy-(Carbonyloxy) succinimde (1.00 g, 4.41 mmol), portion-wise. After 2 h at room temperature, the mixture was concd in vacuo and partitioned between ethylacetate (40 mL)/H$_2$O (30 mL) whereupon it was acidified with HCl (IN) to pH=1. The aqueous layer was drawn off and extracted with ethylacetate (80 mL×2). The combined organic layers were washed with brine (80 mL), dried over Na$_2$SO$_4$, and concd in vacuo affording 1.32 g of (R)-3-methyl-8-nonenoic acid product contaminated with N-Cyclopentyloxy(Carbonyloxy) succinimide. LCMS (M+1): 297.88.

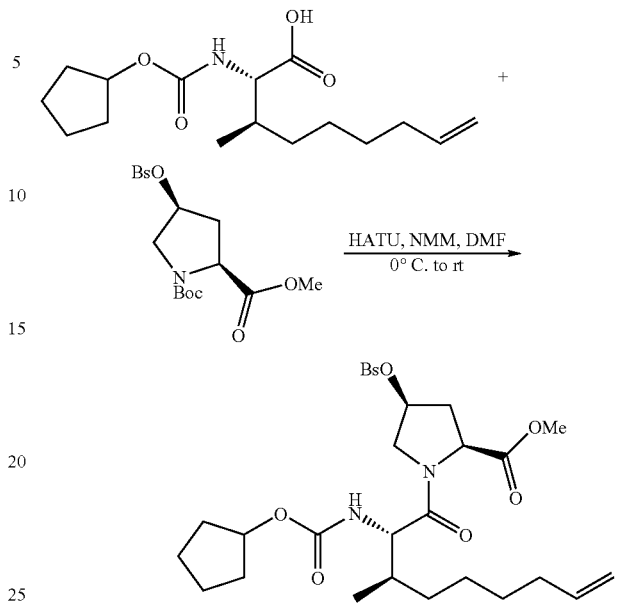

b. N-boc-4-cis-brosylproline methylester (1.77 g, 3.80 mmol) was dissolved in DCM (16 mL) and HCl (4N in dioxane, 16 mL) was added slowly. After 1.5 hours at room temperature the solution was concentrated in vacuo and the crude solid was dissolved in DMF (32 mL). To this solution was added crude (R)-3-methyl-8-nonenoic acid (1.32 g, 3.16 mmol), and HATU (2.40 g, 6.32 mmol). The slurry was cooled to 0° C. and N-methylmorpholine (1.75 mL, 15.92 mmol) was added drop-wise whereupon the cold bath was removed. After 16 hours at room temperature, the soln was poured into LiCl (2%, aq, 250 mL) and extracted with ethylacetate (100 mL×3). The combined organic layers were washed with LiCl (2%, aq, 25 mL), satd NaHCO$_3$ (100 mL), satd NH$_4$Cl (100 mL), brine (100 mL), dried over MgSO$_4$, and concd in vacuo. The crude residue was purified via silica-gel chromatography (ethylacetate-hexanes) to afford 1.99 g of amide product in 98% yield. LCMS (M+1): 644.87.

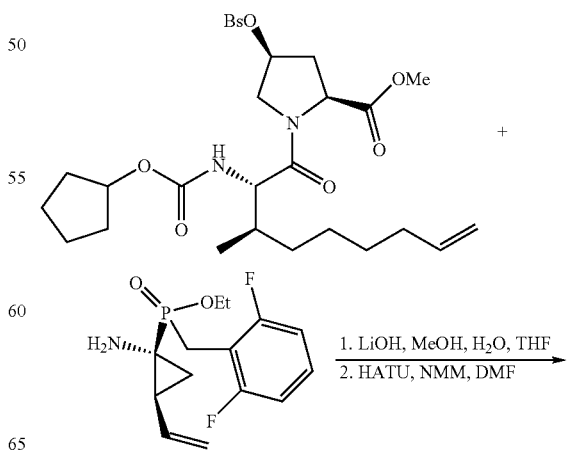

-continued

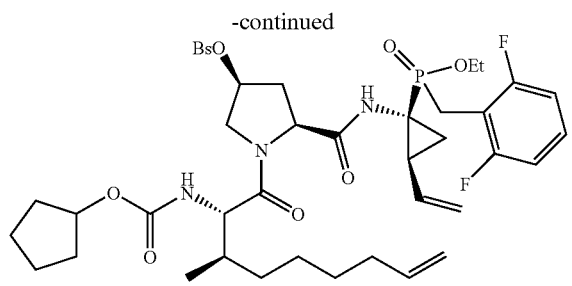

c. To a soln of proline methylester (1.98 g, 3.07 mmol) in THF (10 mL) and MeOH (10 mL) was added a solution of LiOH (379 mg, 0.915 mmol, 10 mL $H_2O$) dropwise. After 2 hours at room temperature, the resulting suspension was diluted with $H_2O$ and acidified to pH=1. The aqueous was extracted with ethylacetate (50 mL×4). The combined organic layers were washed with brine (75 mL), dried over $MgSO_4$, and concentrated in vacuo. The crude solid was dissolved in DMF (30 mL) and aminophosphinate (1.13 g, 3.74 mmol) was added followed by HATU (2.34 g, 6.14 mmol). The slurry was cooled to 0° C. and N-methylmorpholine (1.70 mL, 15.46 mmol) was added drop-wise whereupon the cold bath was removed. After 16 hours at room temperature, the solution was poured into LiCl (5%, aq, 200 mL) and extracted with ethylacetate (100 mL×3). The combined organic layers were washed with LiCl (5%, aq, 100 mL), HCl (0.5 N, 100 mL), satd $NaHCO_3$ (100 mL), brine (100 mL), dried over $MgSO_4$, and concentrated in vacuo. The crude residue was purified via silica-gel chromatography (ethylacetate-hexanes) to afford 2.17 g of amide product in 78% yield. LCMS (M+1): 912.02.

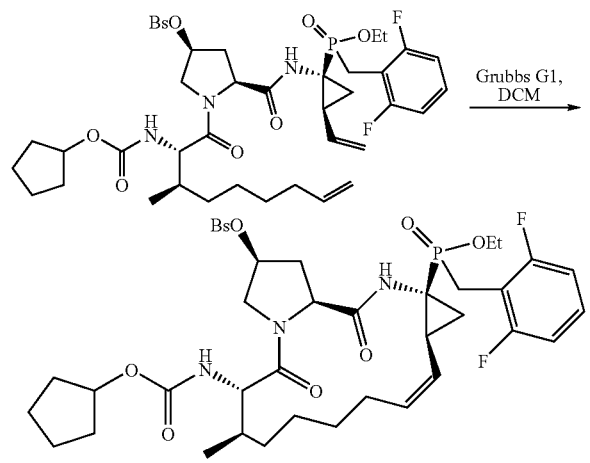

c. Phosphinate-diene was dissolved in $CH_2Cl_2$ (237 mL) and the solution was degassed for 30 minutes. The solution was heated to reflux and Grubb's G1 catalyst (492 mg, 0.598 mmol) was added. After 20 hours at reflux, trishydroxymethylphosphine (3.71 g, 29.90 mmol), TEA (8.6 mL, 59.8 mmol), and $H_2O$ (100 mL) were added and the reaction mixture was refluxed overnight. After cooling to room temperature, the layers were separated. The organic layer was washed with $H_2O$ (100 mL), ½ satd $NaHCO_3$ (100 mL×2), LiCl (5%, aq, 100 mL), brine (100 mL), dried over $MgSO_4$, and concentrated in vacuo. The crude residue was purified by silica-gel chromatography (ethylacetate-hexanes) to afford 1.32 g of product in 63% yield. LCMS (M+1): 884.01.

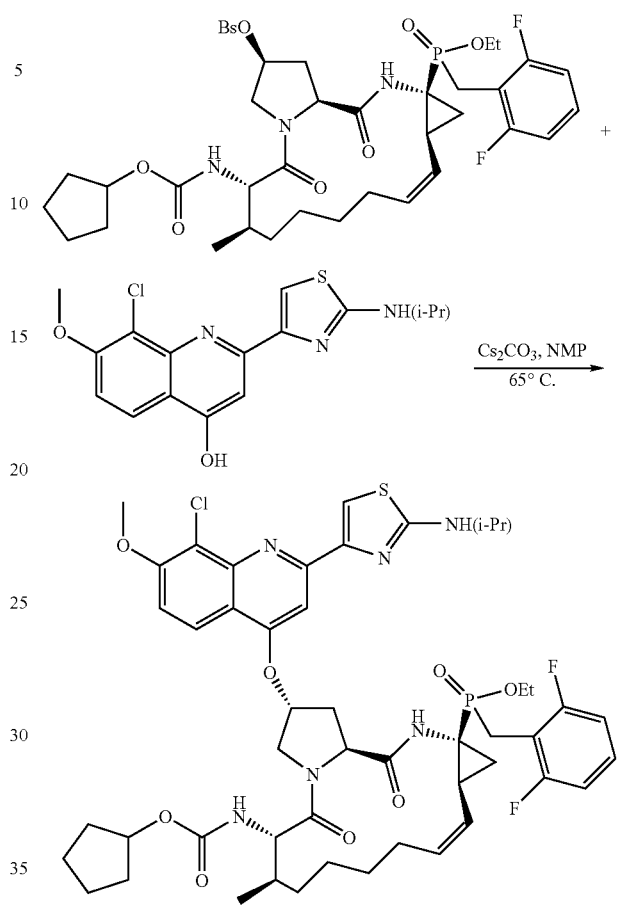

d. Macrocycle (1.32 g, 1.49 mmol), hydroxyquinoline (523 mg, 1.49 mmol), and $Cs_2CO_3$ (973 mg, 2.98 mmol) were slurried in NMP (5.0 mL) and heated to 65° C. for 8 hours. The mixture was poured into LiCl (5%, aq, 50 mL) and extracted with ethylacetate (30 mL×3). The combined organic layers were washed with LiCl (5%, aq, 35 mL×3), satd $NaHCO_3$ (40 mL), ½ satd $NaHCO_3$ (50 mL), brine (50 mL), dried over $Na_2SO_4$, and concd in vacuo. The crude residue was purified via silica-gel chromatography (ethylacetate-hexanes) to afford 1.13 g of aminothiazole in 76% yield. LCMS (M+1): 997.31.

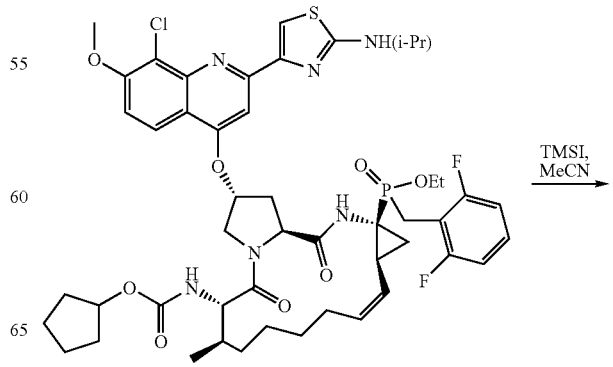

-continued

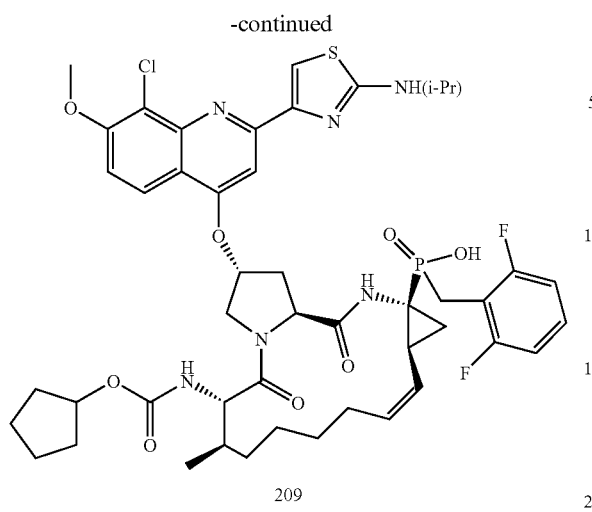

209 e. Aminothiazole (1.13 g, 1.13 mmol) was dissolved in MeCN (11.2 mL) and cooled to 0° C. (precipitation was observed). To the cooled slurry was added trimethylsilyliodide (800 μL, 5.62 mmol) drop-wise, whereupon the cold-bath was removed. After 35 minutes at room temperature, the solution was cooled to 0° C. and 2,6-lutidine (1.3 mL, 11.2 mmol) was added followed by MeOH (1.3 mL). The soln was concentrated in vacuo and purified via reverse-phase HPLC (MeCN—H$_2$O with 0.1% TFA) affording 1.002 g of phosphinic acid in 80% yield. $^1$H NMR (300 MHz, CD$_3$OD) δ 8.33 (d, J=9.9 Hz, 1H), 8.32 (s, 1H), 7.87 (s, 1H), 7.65 (d, J=9.3 Hz, 1H), 7.33-7.21 (m, 1H), 6.94 (dd, J=7.8, 7.5 Hz, 2H), 5.85 (s, 1H), 5.76-5.66 (m, 1H), 5.35 (dd, J=9.9 Hz, 1H), 4.73 (dd, J=9.3, 7.5 Hz, 1H), 4.18 (s, 3H), 4.15-4.01 (m, 3H), 3.83-3.77 (m, 1H), 3.64 (s, 3H), 3.62-3.55 (m, 1H), 2.92-2.81 (m, 1H), 2.78-2.58 (m, 2H), 2.48-2.32 (m, 1H), 2.07-1.91 (m, 1H), 1.84-1.76 (m, 1H), 1.75-1.22 (m, 23H), 1.19-1.01 (m, 2H), 0.97-0.90 (m, 3H); (M+1): 969.42.

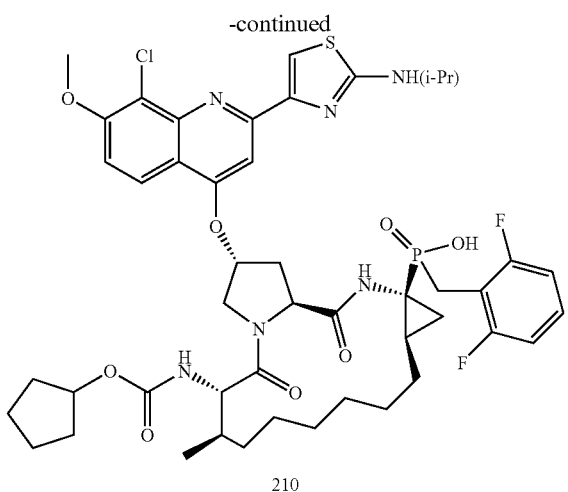

210

Phosphinic acid (702 mg, 0.632 mmol), sodium acetate (778 mg, 9.48 mmol), and tosylhydrazide (886 mg, 4.76 mmol), were slurried in DME (5.75 mL) and H$_2$O (575 μL) and heated to 95° C. for 1.5 hours. After which, more sodium acetate (160 mg, 1.95 mmol) and tosylhydrazide (177 mg, 0.95 mmol) were added and the mixture was heated at 95° C. for another 1.2 hours. It was concd in vacuo, dissolved in MeOH, filtered, and purified via reverse-phase HPLC (MeCN—H$_2$O with 0.1% TFA) affording 371 mg of phosphinic acid in 53% yield. $^1$H NMR (300 MHz, CD$_3$OD) δ 8.32 (t, J=4.5 Hz, 2H), 7.88 (s, 1H), 7.66 (d, J=9.3 Hz, 1H), 7.38-7.25 (m, 1H), 6.98 (dd, J=7.8 Hz, 2H), 5.85 (s, 1H), 4.73 (dd, J=8.7, 8.4 Hz, 2H), 4.17 (s, 3H), 4.12-3.98 (m, 3H), 3.79 (d, J=10.5 Hz, 1H), 3.73-3.67 (m, 1H), 3.57-3.50 (m, 1H), 3.43 (d, J=10.5 Hz, 1H), 2.94-2.85 (m, 1H), 2.58-2.47 (m, 1H), 2.04-1.91 (m, 1H), 1.85-1.04 (m, 24H) 1.37 (d, J=6.6 Hz, 6H), 0.90 (d, J=6.6 Hz, 3H); LCMS (M+1): 971.28.

Example 211

Preparation of Compound 211

Example 210

Preparation of Compound 210

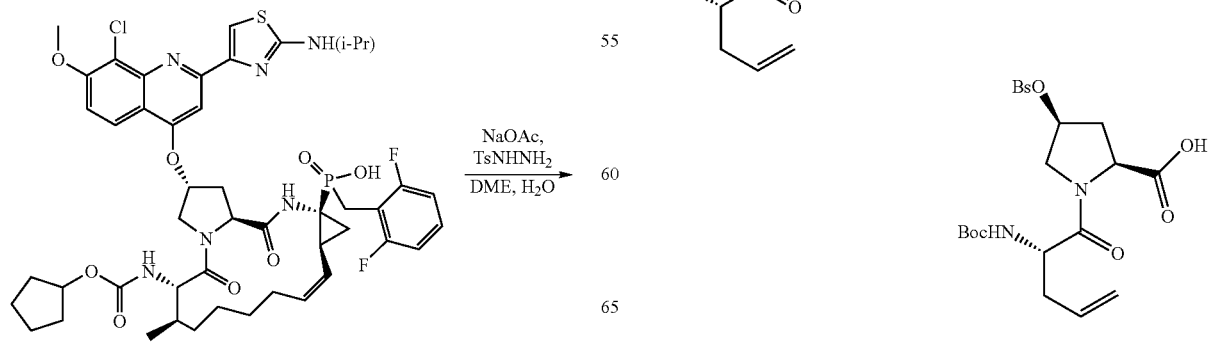

a. Proline methylester (4.85 g, 8.67 mmol) was dissolved in MeOH (30 mL) and THF (30 mL). To the organic soln was slowly added a solution of lithium hydroxide (3.60 g, 86.7 mmol) in H₂O (30 mL). The mixture was stirred at room temperature for 1 hour, whereupon it was diluted with H₂O (20 mL), acidified with HCl (1N) to pH=2, and extracted with ethylacetate (40 mL×3). The combined organic layers were dried over MgSO₄ and concd in vacuo affording 4.55 g of acid in 96% crude yield.

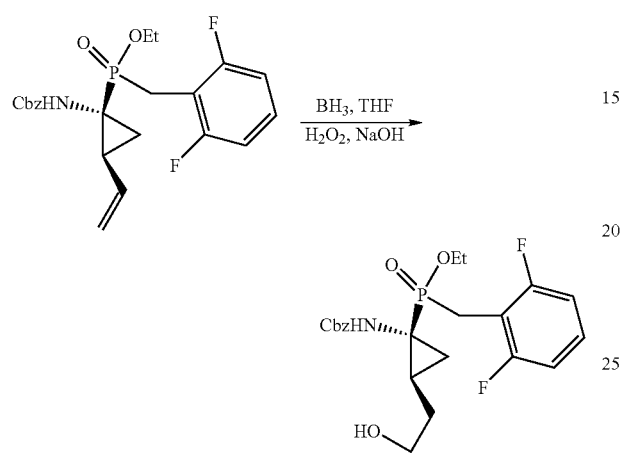

b. Vinylcyclopropane phosphinate (5.90 g, 13.6 mmol) was dissolved in THF (100 mL) and borane-THF complex (1.0 M in THF, 13.6 mL, 13.6 mmol) was slowly added. After 2 hours at room temperature, hydrogen peroxide (30% in water, 1.4 mL, 13.6 mmol) was slowly added followed by sodium hydroxide (1.0 M, 17.7 mL, 17.7 mmol) and the mixture was stirred for an additional 1 hour at room temperature. The mixture was then diluted with H₂O (100 ml) and extracted with ethylacetate (100 mL×3). The combined organic layers were washed with brine (100 mL), dried over Na₂SO₄, and concd in vacuo. The crude residue was purified via silica-gel chromatography (ethylacetate-hexanes) to afford 4.19 g of alcohol in 68% yield.

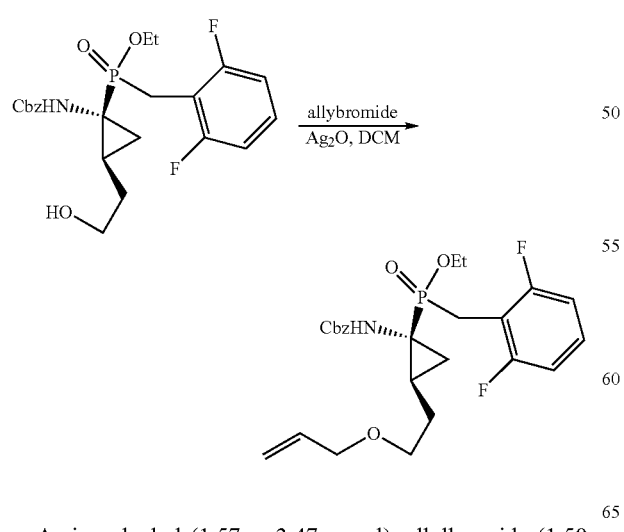

c. Amino alcohol (1.57 g, 3.47 mmol), allylbromide (1.50 mL, 17.3 mmol), and mol sieves (4 Å) were stirred in DCM (17 mL) for 30 min. To the mixture was added silver oxide (2.80 g, 12.14 mmol) and it was stirred at room temperature overnight. The mixture was filtered and concentrated in vacuo. The crude residue was purified via silica-gel chromatography (ethylacetate-hexanes) to afford 465 mg of allylated product in 27% yield.

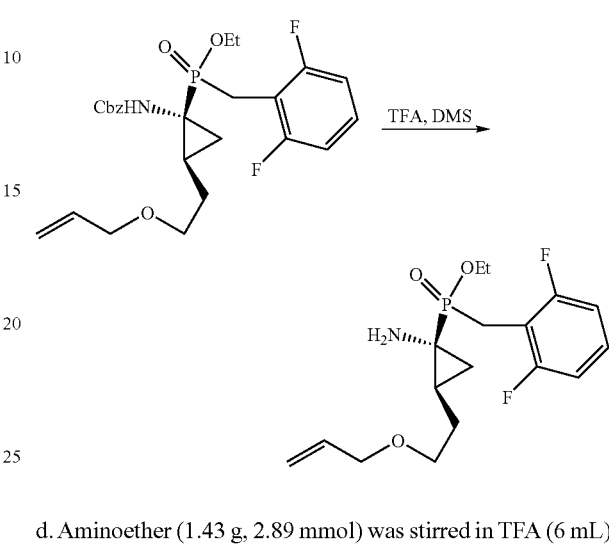

d. Aminoether (1.43 g, 2.89 mmol) was stirred in TFA (6 mL) and dimethylsulfide (2 mL) at room temperature overnight. The solution was diluted with isopropylacetate (30 mL)/heptanes (30 mL) and extracted with HCl (1N, 30 mL×2). The organic layer was further diluted with heptanes (30 mL) and extracted with HCl (1 N, 30 mL). The dilution with heptanes and extraction with HCl was repeated 2×. The combined aqueous layers were basified with sodium hydroxide to pH=12 and extracted with ethylacetate (100 mL×3). The combined organic layers were washed with brine (100 mL), dried over Na₂SO₄, and concentrated in vacuo to afford 754 mg of amine in 72% yield. LCMS (M+1): 360.07.

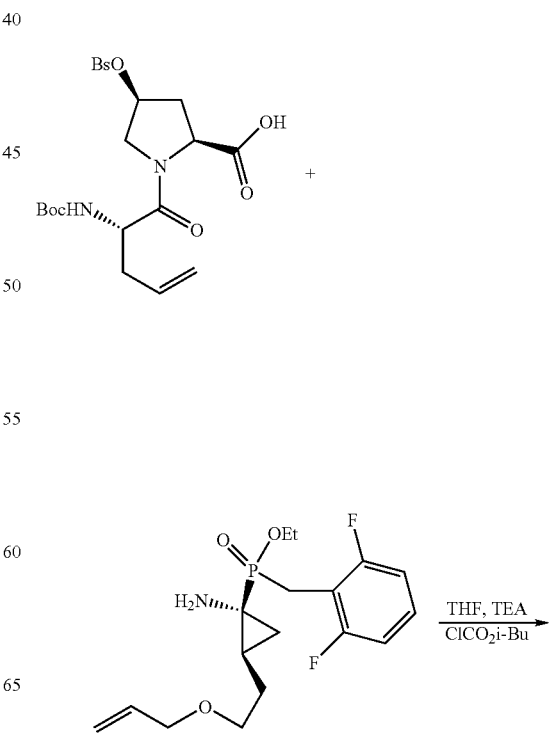

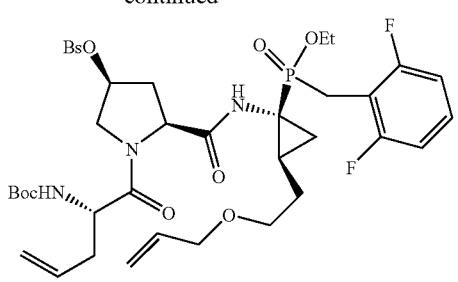

e. Proline acid (303 mg, 0.555 mmol) and TEA (85 μL, 0.61 mmol) were dissolved in THF (4.0 mL) and cooled to 0° C. To the solution was added isobutylchloroformate (80 μL, 0.61 mmol). After an additional 40 minutes at 0° C., the amine (200 mg, 0.555 mmol) was added as a solution in THF (1.5 mL) and the mixture was allowed to warm to room temperature. Following 2 hours at room temperature, the mixture was diluted with satd NaHCO$_3$ and extracted with ethylacetate. The combined organic layers were washed with brine, dried over MgSO$_4$ and concd in vacuo. The crude residue was purified via silica-gel chromatography (ethylacetate-hexanes) to afford 306 mg of amide product in 62% yield. LCMS (M+1): 889.87.

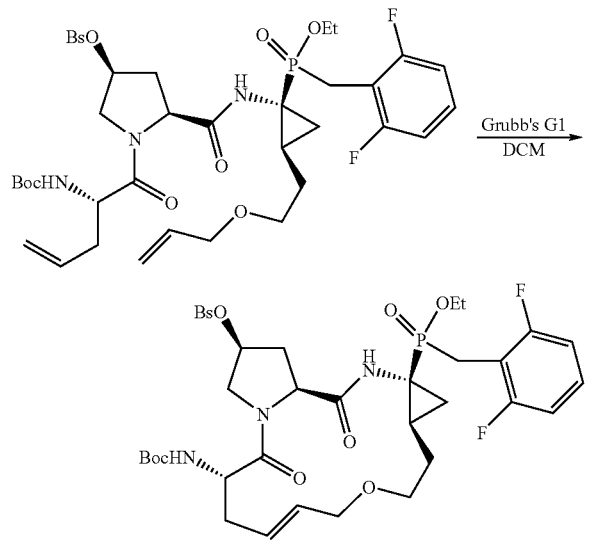

211 f. Phosphinate-diene (986 mg, 1.11 mmol) was dissolved in DCM (100 mL) and the solution was degassed for 30 minutes. The solution was heated to reflux and Grubb's G1 catalyst (250 mg, 0.31 mmol) was added. After 16 hours at reflux, more Grubb's G1 catalyst (45 mg, 0.055 mmol) was added. After an additional 3 hours at reflux more Grubb's G1 catalyst (45 mg, 0.055 mmol) was added. After an additional 3 hours at reflux trishydroxymethylphosphine (2.3 g, 18.5 mmol), TEA (5.1 mL, 37 mmol), and H$_2$O (20 mL) were added and the reaction mixture was refluxed overnight. After cooling to room temperature, the layers were separated. The aqueous layer was washed with DCM (50 mL), dried over Na$_2$SO$_4$, and concentrated in vacuo. The crude residue was purified via silica-gel chromatography (ethylacetate-hexanes) to afford 440 mg of product in 46% yield. LCMS (M+1): 859.93.

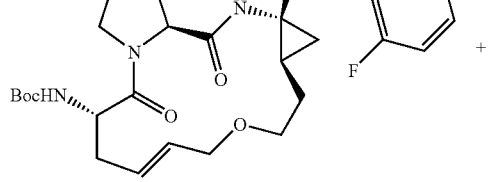

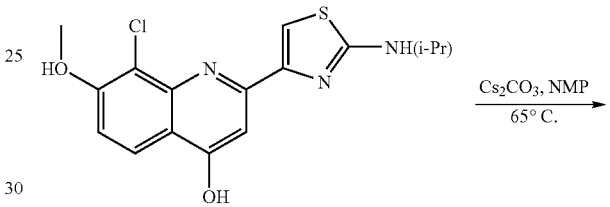

g. Macrocycle (532 mg, 0.62 mmol), hydroxyquinoline (216 mg, 0.62 mmol), and Cs$_2$CO$_3$ (404 mg, 1.24 mmol) were slurried in NMP (6.0 mL) and heated to 65° C. for 8 hours. The mixture was poured into LiCl (5%, aq, 60 mL) and extracted with ethylacetate (30 mL×3). The combined organic layers were washed with LiCl (5%, aq, 35 mL×3), satd NaHCO$_3$ (40 mL), brine (50 mL), dried over Na$_2$SO$_4$, and concd in vacuo. The crude residue was purified via silica-gel chromatography (methanol-ethylacetate) to afford 456 mg of aminothiazole in 76% yield. LCMS (M+1): 973.27.

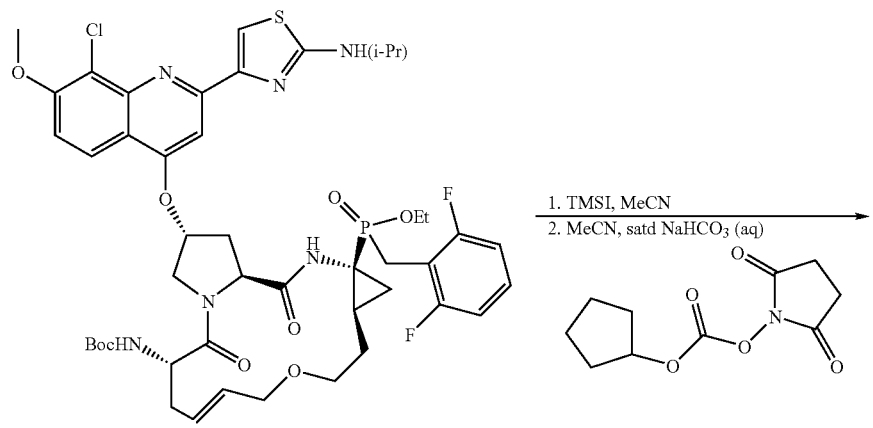

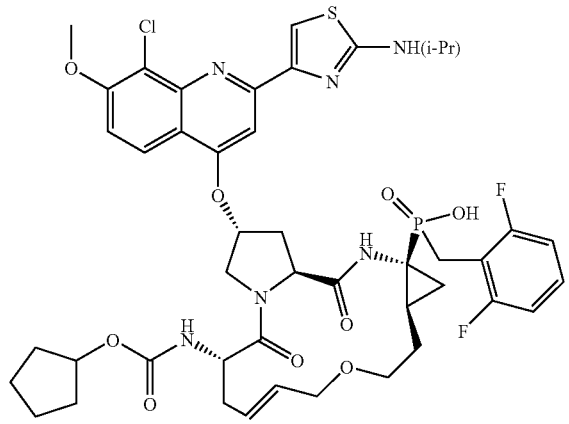

h. Macrocycle (456 mg, 0.468 mmol) was dissolved in MeCN (5.0 mL) and TMSI (0.34 mL, 2.35 mmol) was added dropwise. After 10 minutes at room temperature, 2,6-lutidine (0.27 mL, 2.33 mmol) was added followed by MeOH (0.27 mL) and the solution was concd in vacuo. The crude residue was dissolved in MeCN (3.0 mL) and satd NaHCO$_3$ (3.0 mL) was added. To the bilayer was added N-Cyclopentyloxy(Carbonyloxy) succinimide (127 mg, 0.56 mmol). After 2 hours at rt the layers were separated and the aqueous layer was acidified to pH=2 and extracted with ethylacetate (7 mL×3). The combined organic layers were concd in vacuo and the crude residue was dissolved in DMF and purified directly by reverse-phase preparative HPLC (Column: Phemomenex Gemini 5u, C18, 110A, 75×30 mm, Gradient: 30-95% acetonitrile-water with 0.1% TFA) affording 216 mg of phosphinic acid in 48% yield. LCMS (M+1): 957.20.

Example 212
Preparation of Compound 212

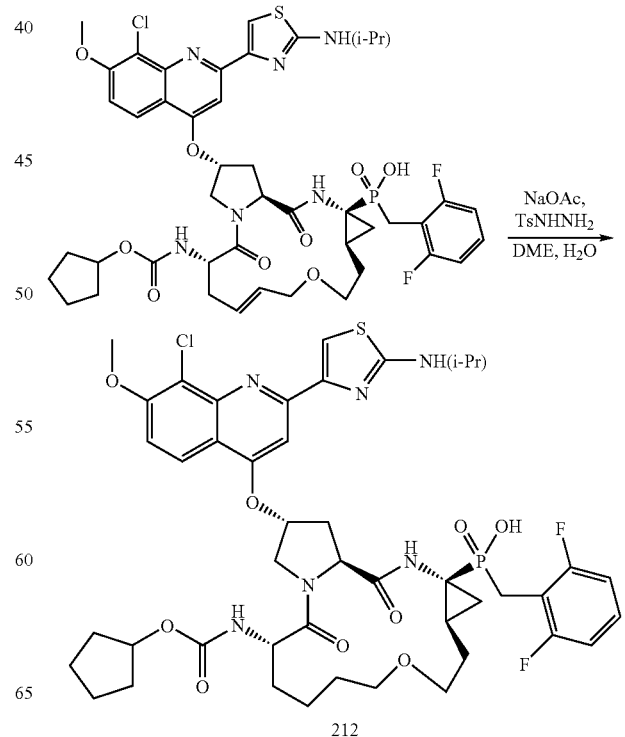

Phosphinic acid (210 mg, 0.22 mmol), sodium acetate (270 mg, 3.29 mmol), and tosylhydrazide (310 mg, 1.65 mmol), were slurried in DME (5.0 mL) and H$_2$O (500 μL) and heated to 95° C. for 2 hours. The mixture was cooled to 0° C. and HCl (6N, 550 μL, 3.29 mmol) was added and it was concentrated in vacuo, dissolved in MeOH, filtered, and purified via reverse-phase HPLC (Column: Phemomenex Gemini 5u, C18, 110A, 75×30 mm, Gradient: 30-95% acetonitrile-water with 0.1% TFA) affording 170 mg of phosphinic acid in 80% yield. LCMS (M+1): 959.33.

Example 213

Preparation of Compound 213

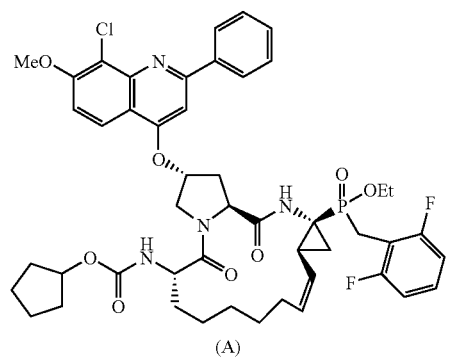

(A)

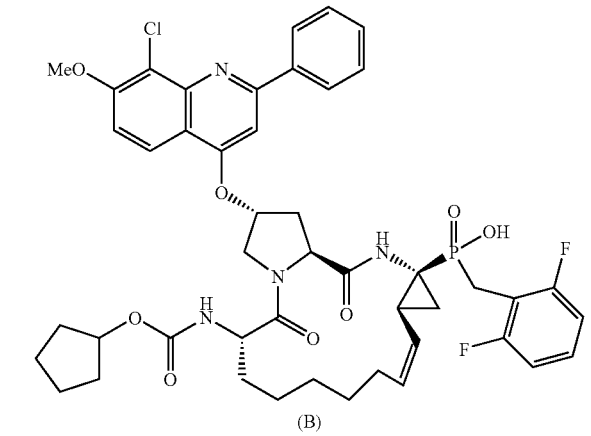

(B)

Example 213

Preparation of Compound 213

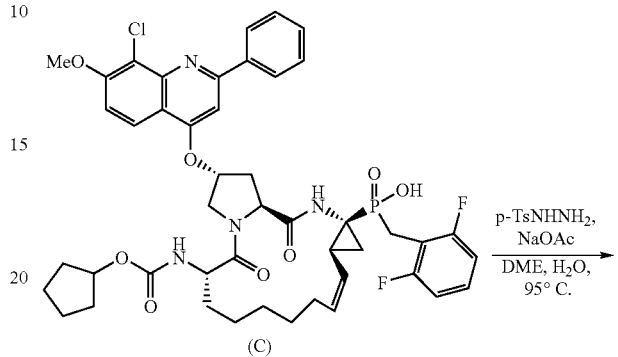

(C)

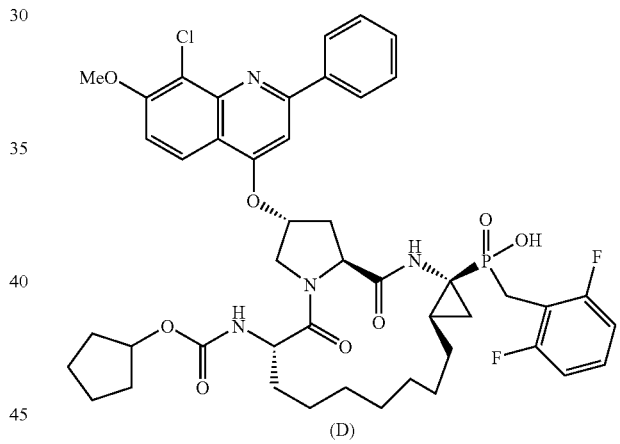

(D)

To a solution of (A) (250 mg, 0.272 mmol) in CH$_3$CN (3 mL, 0.1 M) at 0° C. was added iodotrimethylsilane (194 μL, 1.36 mmol). The reaction mixture was stirred at 0° C. for 5 minutes. 2,6-Lutidine (315 μL, 2.72 mmol) was added and stirred for 1.5 hours. MeOH was added and stirred for 30 minutes. The mixture was concentrated and re-dissolved in minimal MeOH and purified by reverse phase HPLC to afford 190 mgs (70%) of (B) as a TFA salt. $^1$H NMR (300 MHz, CDCl$_3$): δ8.15-8.0 (m, 4H), 7.49 (d, J=7.3, 3H), 7.26-7.04 (m, 5H), 6.74 (dd, J=7.1 Hz, J=8.2 Hz, 2H), 5.68 (d, J=8.2 Hz, 1H), 5.48 (m, 1H), 4.85 (m, 1H), 4.62-4.36 (m, 3H), 4.25-3.99 (m, 5H), 3.48 (t, J=15.3 Hz, 1H), 3.21 (t, J=16.5 Hz, 1H), 2.60 (m, 1H), 2.16 (m, 1H), 1.73-1.23 (m, 22H); $^{31}$P (75 MHz, CDCl$_3$): δ42.04. LC/MS: M+1=891.

To a solution of (C) (35 mg, 0.039 mmol) in DME (1 mL)/H$_2$O (0.1 mL) was added p-tosylhydrazide (37 mg, 0.196 mmol) and NaOAc (32 mg, 0.39 mmol). The reaction mixture was heated to 95° C. for 1.5 hour and cooled to room temperature. A few drops of 1 N HCl was added to adjust the pH=2. The crude product was purified by reverse phase HPLC to give 12.4 mg of acid (D) in 36% yield. $^1$H NMR (300 MHz, CDCl$_3$): δ8.32-8.24 (m, 2H), 7.92 (d, J=6.4 Hz, 2H), 7.56-7.27 (m, 5H), 7.00 (m, 1H), 6.71-6.66 (m, 2H), 5.73 (s, 1H), 5.54 (d, J=7.3 Hz, 1H), 4.76-4.73 (m, 2H), 4.47-4.43 (m, 2H), 4.14 (s, 3H), 3.39 (t, J=15.6 Hz, 1H), 3.24 (t, J=14.6 Hz, 1H), 2.61 (m, 1H), 1.79-1.19 (m, 31H); $^{31}$P (75 MHz, CDCl$_3$) δ 42.77 (s, 1P). LC/MS: M+1=893.

Example 214
Preparation of Compounds 214-225
Using procedures similar to those described herein, the following compounds 214-225 can also be prepared.
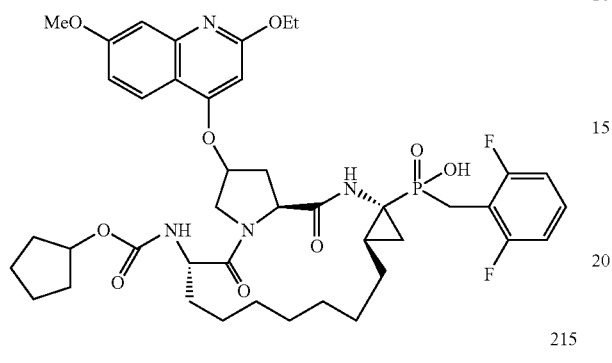
214
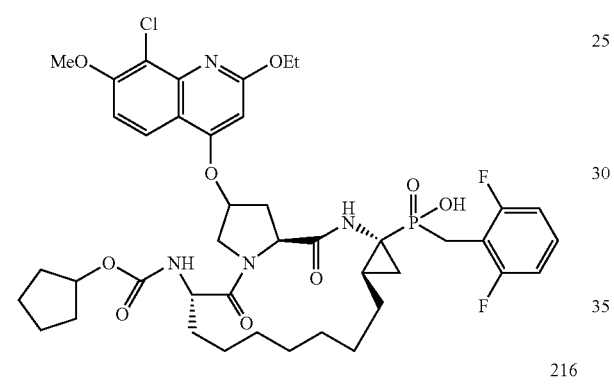
215
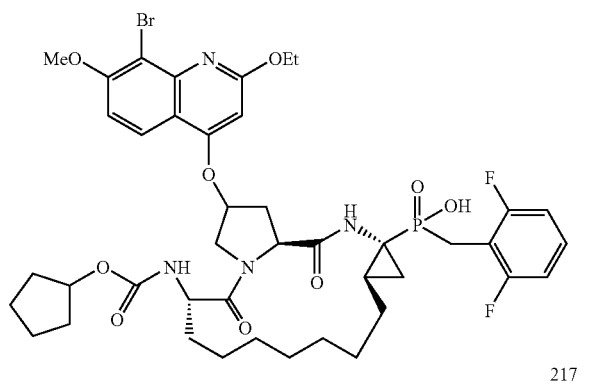
216
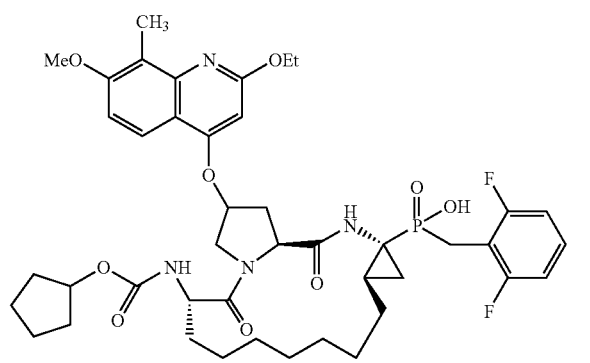
217
-continued
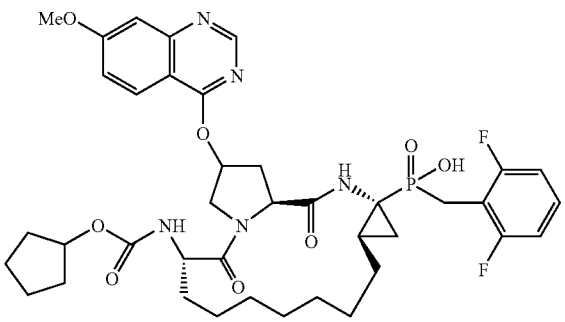
218
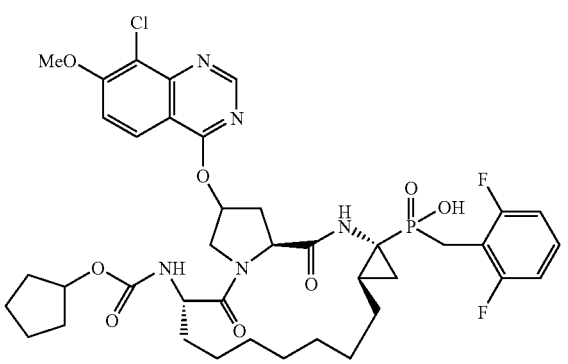
219
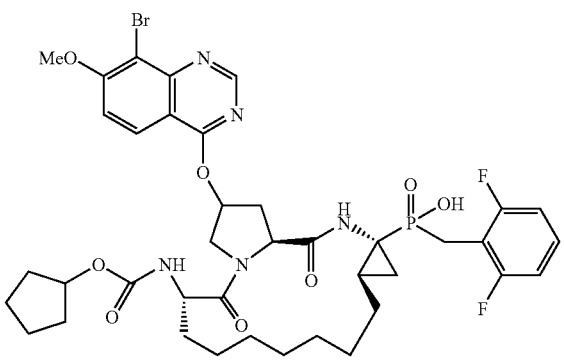
220
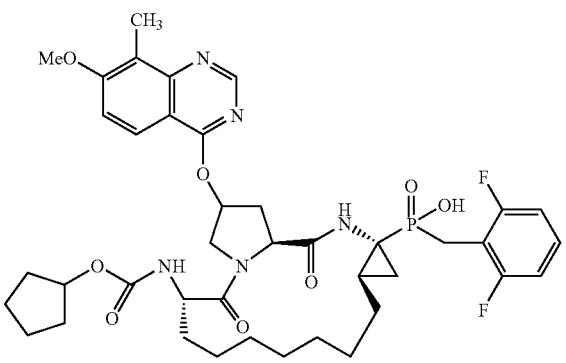
221

-continued

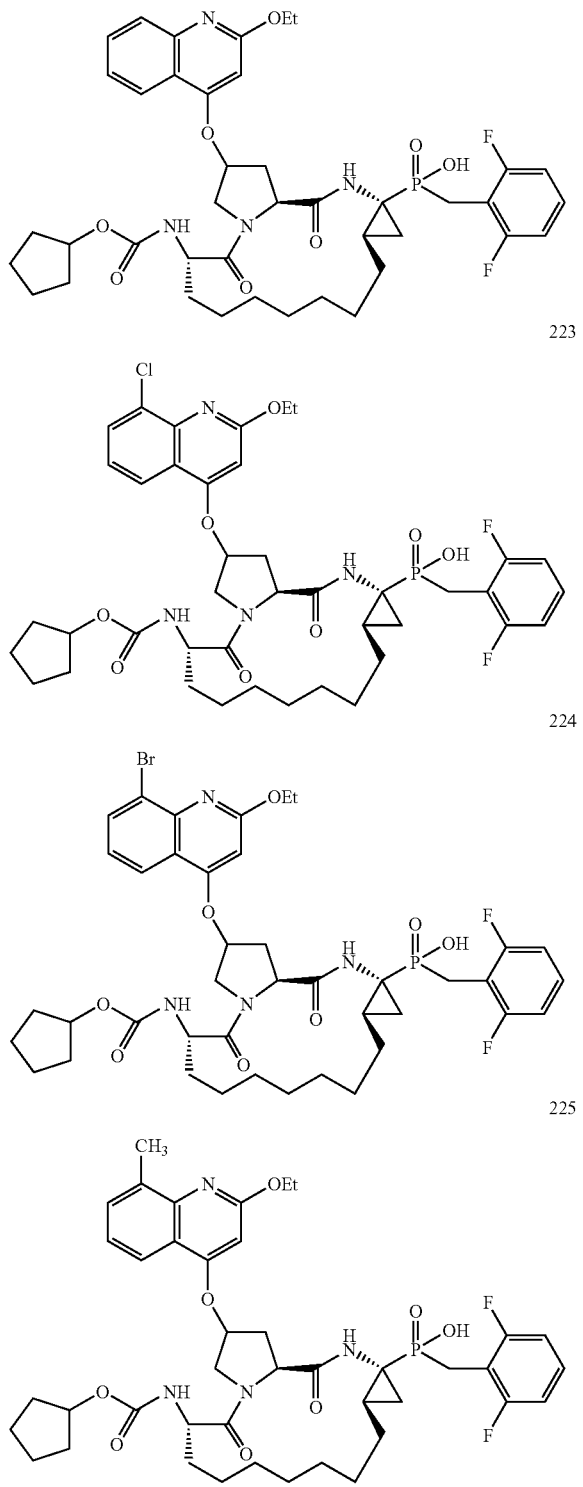

Biological Assays

NS3 Enzymatic Potency: Purified NS3 protease is complexed with NS4A peptide and then incubated with serial dilutions of compound (DMSO used as solvent). Reactions are started by addition of dual-labeled peptide substrate and the resulting kinetic increase in fluorescence is measured. Non-linear regression of velocity data is performed to calculate $IC_{50}$s. Activity is initially tested against genotype 1b protease. Depending on the potency obtained against genotype 1b, additional genotypes (1a, 2a, 3) and/or protease inhibitor resistant enzymes (D168Y, D168V, or A156T mutants) may be tested. BILN-2061 is used as a control during all assays. Representative compounds of the invention were evaluated in this assay and were typically found to have $IC_{50}$ values of less than about 1 μm.

Replicon Potency and Cytotoxicity: Huh-luc cells (stably replicating Bartenschlager's I389luc-ubi-neo/NS3-3'/ET genotype 1b replicon) are treated with serial dilutions of compound (DMSO is used as solvent) for 72 hours. Replicon copy number is measured by bioluminescence and non-linear regression is performed to calculate $EC_{50}$s. Parallel plates treated with the same drug dilutions are assayed for cytotoxicity using the Promega CellTiter-Glo cell viability assay. Depending on the potency achieved against the 1b replicon, compounds may be tested against a genotype 1a replicon and/or inhibitor resistant replicons encoding D168Y or A156T mutations. BILN-2061 is used as a control during all assays. Representative compounds of the invention were evaluated in this assay and were typically found to have $EC_{50}$ values of less than about 5 μm.

Effect of Serum Proteins on Replicon Potency

Replicon assays are conducted in normal cell culture medium (DMEM+10% FBS) supplemented with physiologic concentrations of human serum albumin (40 mg/mL) or α-acid glycoprotein (1 mg/mL). $EC_{50}$s in the presence of human serum proteins are compared to the $EC_{50}$ in normal medium to determine the fold shift in potency.

Enyzmatic Selectivity: The inhibition of mammalian proteases including Porcine Pancreatic Elastase, Human Leukocyte Elastase, Protease 3, and Cathepsin D are measured at $K_m$ for the respective substrates for each enzyme. $IC_{50}$ for each enzyme is compared to the $IC_{50}$ obtained with NS3 1b protease to calculate selectivity. Representative compounds of the invention have shown activity.

MT-4 Cell Cytotoxicity: MT4 cells are treated with serial dilutions of compounds for a five day period. Cell viability is measured at the end of the treatment period using the Promega CellTiter-Glo assay and non-linear regression is performed to calculate $CC_{50}$.

Compound Concentration Associated with Cells at $EC_{50}$: Huh-luc cultures are incubated with compound at concentrations equal to $EC_{50}$. At multiple time points (0-72 hours), cells are washed 2× with cold medium and extracted with 85% acetonitrile; a sample of the media at each time-point will also be extracted. Cell and media extracts are analyzed by LC/MS/MS to determine the Molar concentration of compounds in each fraction. Representative compounds of the invention have shown activity.

Solubility and Stability: Solubility is determined by taking an aliquot of 10 mM DMSO stock solution and preparing the compound at a final concentration of 100 μM in the test media solutions (PBS, pH 7.4 and 0.1 N HCl, pH 1.5) with a total DMSO concentration of 1%. The test media solutions are incubated at room temperature with shaking for 1 hr. The solutions will then be centrifuged and the recovered supernatants are assayed on the HPLC/UV. Solubility will be calculated by comparing the amount of compound detected in the defined test solution compared to the amount detected in DMSO at the same concentration. Stability of compounds after a 1 hour incubation with PBS at 37° C. will also be determined.

Stability in Cryopreserved Human, Dog, and Rat Hepatocytes: Each compound is incubated for up to 1 hour in hepatocyte suspensions (100 μl, 80,000 cells per well) at 37° C. Cryopreserved hepatocytes are reconstituted in the serum-free incubation medium. The suspension is transferred into 96-well plates (50 μL/well). The compounds are diluted to 2 μM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data will also be scaled up to represent intrinsic hepatic clearance and/or total hepatic clearance.

Stability in Hepatic S9 Fraction from Human, Dog, and Rat: Each compound is incubated for up to 1 hour in S9 suspension (500 μl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability: Compounds are assayed via a contract service (Absorption Systems, Exton, Pa.). Compounds are provided to the contractor in a blinded manner. Both forward (A-to-B) and reverse (B-to-A) permeability will be measured. Caco-2 monolayers are grown to confluence on collagen-coated, microporous, polycarbonate membranes in 12-well Costar Transwell® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation and at 1 hr and 2 hr after incubation, a 200-μL aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 μM. The spiked plasma and phosphate buffer is placed into opposite sides of the assembled dialysis cells, which will then be rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left( \frac{C_f}{C_b + C_f} \right)$$

Where $C_f$ and $C_b$ are free and bound concentrations determined as the post-dialysis buffer and plasma concentrations, respectively CYP450 Profiling:

Each compound is incubated with each of 5 recombinant human CYP450 enzymes, including CYP1A2, CYP2C9, CYP3A4, CYP2D6 and CYP2C19 in the presence and absence of NADPH. Serial samples will be taken from the incubation mixture at the beginning of the incubation and at 5, 15, 30, 45 and 60 min after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds will be incubated for up to 2 hour in plasma (rat, dog, monkey, or human) at 37° C. Compounds are added to the plasma at final concentrations of 1 and 10 μg/mL. Aliquots are taken at 0, 5, 15, 30, 60, and 120 min after adding the compound. Concentration of compounds and major metabolites at each timepoint are measured by LC/MS/MS.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

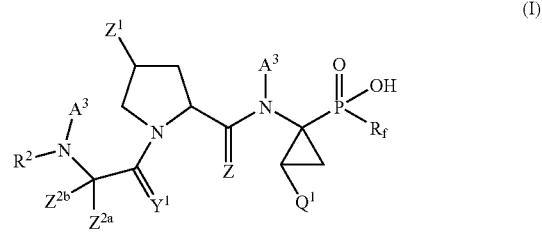

or a pharmaceutically acceptable salt thereof, wherein:

$R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is selected from, a) —C($Y^1$)($A^3$), b) (C2-10)alkyl, (C3-7)cycloalkyl or (C1-4)alkyl-(C3-7)cycloalkyl, where said cycloalkyl and alkyl-cycloalkyl may be optionally mono-, di- or tri-substituted with (C1-3)alkyl, or where said alkyl, cycloalkyl and alkyl-cycloalkyl may optionally be mono- or di-substituted with substituents selected from hydroxy and O—(C1-4)alkyl, or where each of said alkyl-groups may optionally be mono-, di- or tri-substituted with halogen, or where each of said cycloalkyl groups being 5-, 6- or 7-membered, one or two —CH$_2$— groups not being directly linked to each other may be optionally substituted replaced by —O— such that the O-atom is linked to the N atom to which $R^2$ is attached via at least two C-atoms, c) phenyl, (C1-3)alkyl-phenyl, heteroaryl or (C1-3)alkyl-heteroaryl,
wherein the heteroaryl-groups are 5- or 6-membered having from 1 to 3 heteroatoms selected from N, O and S, wherein said phenyl and heteroaryl groups may optionally be mono-, di- or trisubstituted with substituents selected from halogen, —OH, (C1-4)alkyl, O—(C1-4)alkyl, S—(C1-4)alkyl, —$NH_2$, —$CF_3$, —NH((C1-4)alkyl) and N((C1-4)alkyl)$_2$, —$CONH_2$ and —CONH—(C1-4)alkyl; and wherein said (C1-3) alkyl may optionally be substituted with one or more halogen; or
d) —S(O)$_2$(A$^3$);
$R^3$ is H or (C1-6)alkyl;
$Y^1$ is independently O, S, N(A$^3$), N(O)(A$^3$), N(OA$^3$), N(O)(OA$^3$) or N(N(A$^3$)(A$^3$));
Z is O, S, or NR$^3$;
$Z^1$ is:

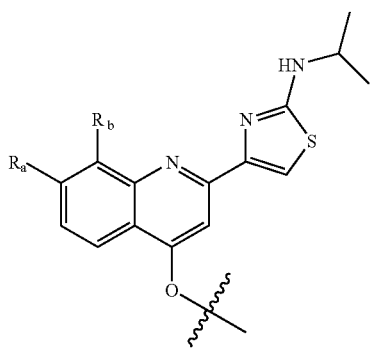

$R_a$ is H or (C1-6)alkoxy;
$R_b$ is H, F, Cl, Br, I, or (C1-6)alkyl;
$Z^{2b}$ is H, (C1-6)alkyl, (C2-8)alkenyl, (C2-8)alkynyl;
$Q^1$ and $Z^{2a}$ taken together with the atoms to which they are attached form a heterocycle, which heterocycle may optionally be substituted with one or more oxo (=O) or A$^3$;
$A^3$ is independently selected from PRT, H, —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, —C(A$^2$)$_3$, —C(A$^2$)$_2$—C(O)A$^2$, —C(O)A$^2$, —C(O)OA$^2$, —O(A$^2$), —N(A$^2$)$_2$, —S(A$^2$), —$CH_2$P(Y$^1$)(A$^2$)(OA$^2$), —$CH_2$P(Y$^1$)(A$^2$)(N(A$^2$)$_2$), —$CH_2$P(Y$^1$)(OA$^2$)(OA$^2$), —OCH$_2$P(Y$^1$)(OA$^2$)(OA$^2$), —OCH$_2$P(Y$^1$)(A$^2$)(OA$^2$), —OCH$_2$P(Y$^1$)(A)(N(A$^2$)$_2$), —C(O)OCH$_2$P(Y$^1$)(OA$^2$)(OA$^2$), —C(O)OCH$_2$P(Y$^1$)(A$^2$)(OA$^2$), —C(O)OCH$_2$P(Y$^1$)(A$^2$)(N(A$^2$)$_2$), —$CH_2$P(Y$^1$)(OA$^2$)(N(A$^2$)$_2$), —OCH$_2$P(Y$^1$)(OA$^2$)(N(A$^2$)$_2$), —C(O)OCH$_2$P(Y$^1$)(OA$^2$)(N(A$^2$)$_2$), —$CH_2$P(Y$^1$)(N(A$^2$)$_2$)(N(A$^2$)$_2$), —C(O)OCH$_2$P(Y$^1$)(N(A$^2$)$_2$)(N(A$^2$)$_2$), —OCH$_2$P(Y$^1$)(N(A$^2$)$_2$)(N(A$^2$)$_2$), —(CH$_2$)$_m$-heterocycle, —(CH$_2$)$_m$C(O)Oalkyl, —O—(CH$_2$), —O—C(O)—Oalkyl, —O—(CH$_2$)$_n$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide,
wherein each A$^3$ maybe optionally substituted with 1 to 4
—R$^1$, —P(Y$^1$)(OA$^2$)(OA$^2$), —P(Y$^1$)(OA$^2$)(N(A$^2$)$_2$), —P(Y$^1$)(A$^2$)(OA$^2$), —P(Y$^1$)(A$^2$)(N(A$^2$)$_2$), or P(Y$^1$)(N(A$^2$)$_2$)(N(A$^2$)$_2$), —C(=O)N(A$^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, arylthio, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$;
$A^2$ is independently selected from PRT, H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A$^3$; m is 0 to 6; and
$R_f$ is H, alkyl, alkenyl, alkynyl, aryl, heteroaryl, or cycloalkyl, which R$_f$ is optionally substituted with one or more R$_g$;
each R$_g$ is independently halo, hydroxy, cyano, arylthio, cycloalkyl, aryl, heteroaryl, alkoxy, NR$_h$R$_i$, —C(=O)NR$_h$R$_i$, wherein each aryl and heteroaryl is optionally substituted with one or more alkyl, halo, hydroxy, cyano, nitro, amino, alkoxy, alkoxycarbonyl, alkanoyloxy, haloalkyl, or haloalkoxy; and each R$_h$ and R$_i$ is independently H, alkyl, or haloalkyl.

2. The compound of claim 1 wherein $Z^1$ is selected from the following structures:

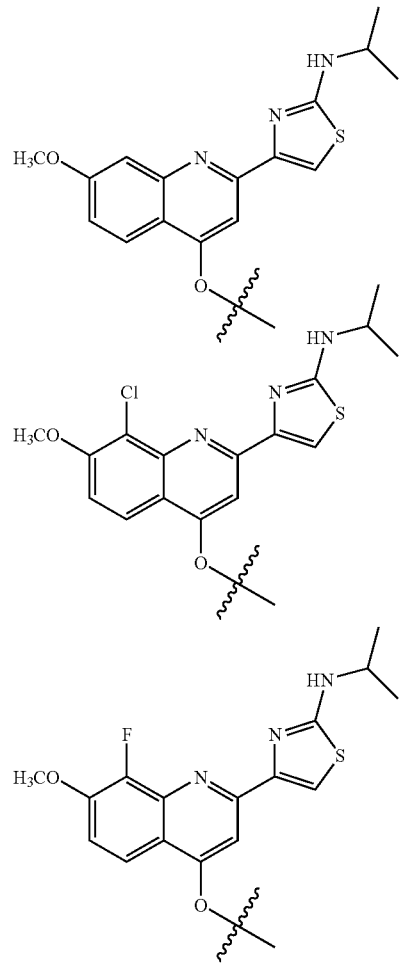

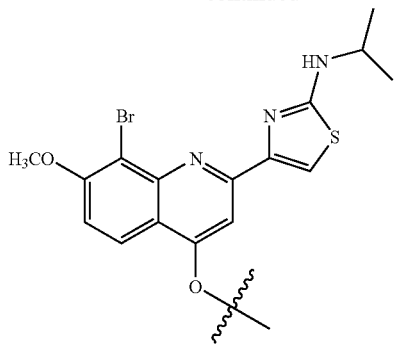

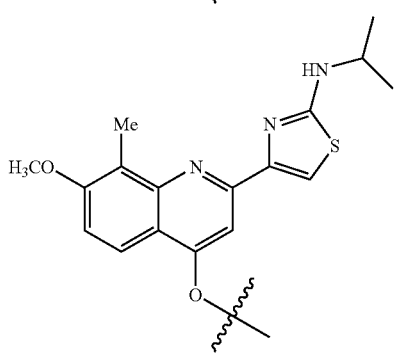

3. The compound of claim 1 wherein $R_f$ is alkyl, alkenyl, or alkynyl, which $R_f$ is substituted with aryl that is optionally substituted with one or more alkyl, halo, hydroxy, cyano, nitro, amino, alkoxy, alkoxycarbonyl, alkanoyloxy, haloalkyl, or haloalkoxy.

4. The compound of claim 1 wherein $R_f$ is alkyl, which is substituted with aryl that is optionally substituted with one or more alkyl, halo, hydroxy, cyano, nitro, amino, alkoxy, alkoxycarbonyl, alkanoyloxy, haloalkyl, or haloalkoxy.

5. The compound of claim 1 wherein $R_f$ is (C1-6)alkyl substituted with a phenyl ring that is optionally substituted with 1, 2, or 3 alkyl, halo, hydroxy, cyano, nitro, amino, alkoxy, alkoxycarbonyl, alkanoyloxy, haloalkyl, or haloalkoxy.

6. The compound of claim 1 wherein $R_f$ is benzyl or phenethyl that is optionally substituted with 1, 2, or 3 alkyl, halo, hydroxy, cyano, nitro, amino, alkoxy, alkoxycarbonyl, alkanoyloxy, haloalkyl, or haloalkoxy.

7. The compound of claim 1 wherein $R_f$ is H, methyl, ethyl, propyl, butyl, cyclopropylmethyl, 3-butenyl, 2-methylpropyl, isopropyl, vinyl, cis-1-propenyl, trans-1-propenyl, cis-1-butenyl, 2-methylpropenyl, 2-phenylvinyl, 2-phenylethynyl, 3-methyl-2-butenyl, 2-hydroxyethyl, 2-hydroxy-2-methylpropyl, cyanomethyl, methoxymethyl, N-(2,2,2-trifluoroethyl)-2-aminoethyl, phenethyl, 2-chlorophenethyl, 2-fluorophenethyl, 2-methylphenethyl, 2-chloro-6-fluorophenethyl, phenylthiomethyl, benzyl, 4-fluorobenzyl, 3-fluorobenzyl, 2-fluorobenzyl, 4-cyanobenzyl, 3-cyanobenzyl, 2-cyanobenzyl, 4-methoxybenzyl, 3-methoxybenzyl, 2-methoxybenzyl, 2-bromobenzyl, 2-trifluoromethoxybenzyl, 2-isopropoxybenzyl, 2-methylbenzyl, 3-methylbenzyl, 4-methylbenzyl, 2-ethylbenzyl, 4-trifluoromethylbenzyl, 3-trifluoromethylbenzyl, 2-trifluoromethylbenzyl, 4-chlorobenzyl, 3-chlorobenzyl, 2-chlorobenzyl, 2,6-difluorobenzyl, 2-chloro-6-fluorobenzyl, 2,6-dichlorobenzyl, 2-methoxy-6-fluorobenzyl, 2,6-dimethylbenzyl, 2,6-difluoro-3-chlorobenzyl, 2,6-difluoro-4-chlorobenzyl, 2-chloro-3,6-difluorobenzyl, 2,3,6-trifluorobenzyl, 3-chloro-2,4-difluorobenzyl, 2-chloro-3,6-difluorobenzyl, 2,3-dichloro-6-fluorobenzyl, 2-nitrobenzyl, 2-aminobenzyl, 2-thienylmethyl, 2-furylmethyl, 3-furylmethyl, 5-trifluoromethylfur-2-ylmethyl 5-pyrazolylmethyl, 2-oxazolylmethyl, 4-methylthiazol-2-ylmethyl, 3-pyridyl, 2-pyridylmethyl, 3-hydroxy-2-pyridylmethyl, 6-chloro-2-pyridylmethyl, 2-pyrazinylmethyl, 5-pyrimidinylmethyl, 2-pyrimidinylmethyl, 4-pyrimidinylmethyl, phenyl, 2-thiazolyl, N,N-dimethylaminocarbonylmethyl, N-methylaminocarbonylmethyl, aminocarbonylmethyl, 1-propynyl, or 2-methylthiazol-4-ylmethyl.

8. The compound of claim 1 which is a compound of formula (III):

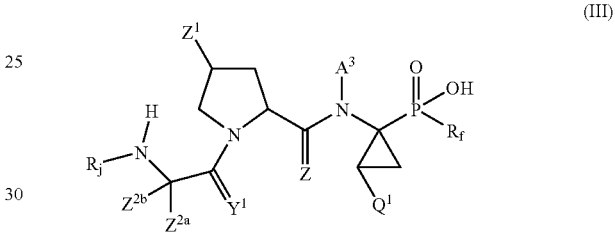

or a pharmaceutically acceptable salt thereof, wherein:

$R_j$ is cyclopentyloxycarbonyl, 1-[N-(2,2,2-trifluoroethyl)imino]ethyl, α,α-difluorophenethyl, cyclopentylacetyl, butanoyl, 4,4,4-trifluorobutanoyl, 3,3,3-trifluoropropylsulfonyl, 3,3-dimethylbutanoyl, cyclopentylaminocarbonyl, 2-norbornanylacetyl, 2-amino-3,3-dimethylbutanoyl, 4-methylphenyl, 4-trifluoromethylphenyl, 3-trifluoromethylphenyl, 2-trifluoromethylphenyl, 3,3,3-trifluoropropanoyl, 5,5,5-trifluoropentanoyl, tert-butylaminocarbonyl, 2,2-dimethylpropoxycarbonyl, or 4-tert-butylthiazol-2-yl.

9. The compound of claim 1 wherein $Q^1$ and $Z^{2a}$ taken together with the atoms to which they are attached form a 12-18 membered heterocycle, which heterocycle may optionally be substituted with one or more oxo (=O) or A3.

10. The compound of claim 1 which is a compound of formula (IX):

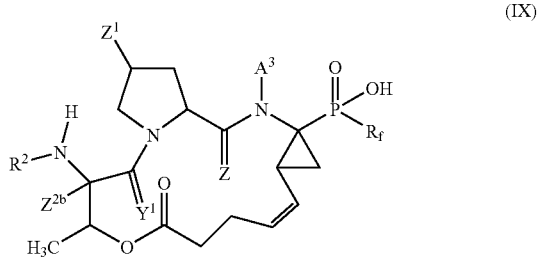

or a pharmaceutically acceptable salt, thereof.

11. The compound of claim 1 which is a compound of formula (X):

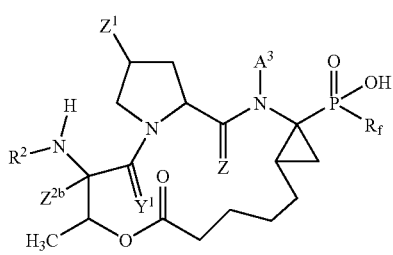

(X)

or a pharmaceutically acceptable salt thereof.

12. The compound of claim 1 which is a compound of formula (XI):

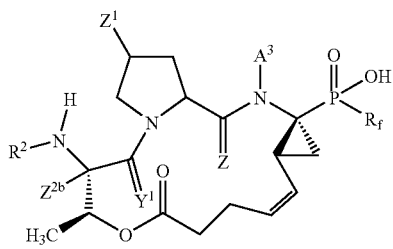

(XI)

or a pharmaceutically acceptable salt thereof.

13. The compound of claim 1 which is a compound of formula (XII):

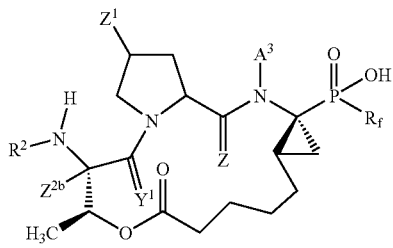

(XII)

or a pharmaceutically acceptable salt thereof.

14. The compound of claim 1 which is a compound of formula (XIII):

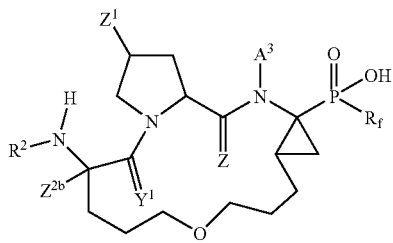

(XIII)

or a pharmaceutically acceptable salt thereof.

15. The compound of claim 1 which is a compound of formula (XIV):

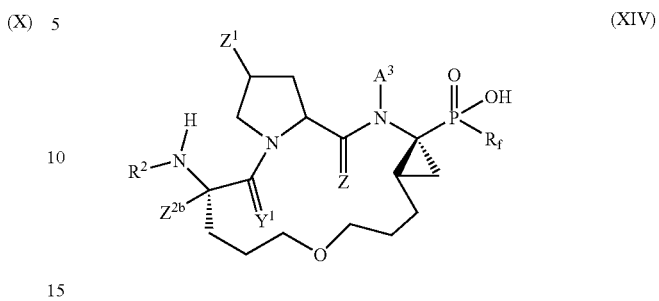

(XIV)

or a pharmaceutically acceptable salt thereof.

16. The compound of claim 1 which is a compound of formula (IV):

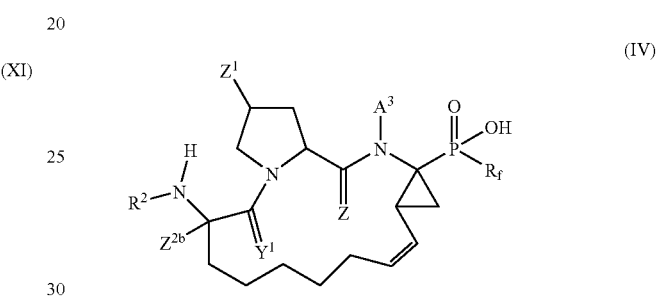

(IV)

or a pharmaceutically acceptable salt thereof.

17. The compound of claim 1 which is a compound of formula (V):

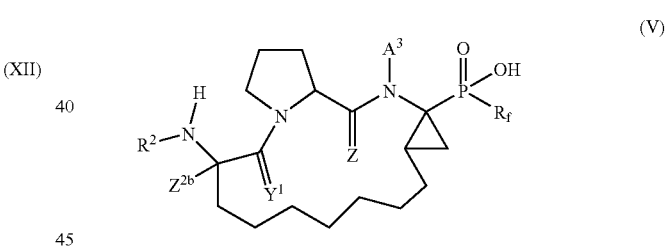

(V)

or a pharmaceutically acceptable salt thereof.

18. The compound of claim 16 which is a compound of formula (VI):

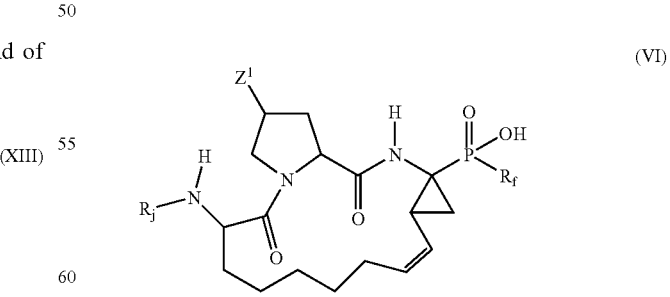

(VI)

or a pharmaceutically acceptable salt thereof, wherein:

$R_j$ is cyclopentyloxycarbonyl, 1-[N-(2,2,2-trifluoroethyl)imino]ethyl, α,α-difluorophenethyl, cyclopentylacetyl, butanoyl, 4,4,4-trifluorobutanoyl, 3,3,3-trifluoropropylsulfonyl, 3,3-dimethylbutanoyl, cyclopentylaminocarbonyl, 2-norbornanylacetyl, 2-amino-3,3-dimethylbutanoyl, 4-methylphenyl, 4-trifluoromethylphenyl, 3-trifluoromethylphenyl, 2-trifluoromethylphenyl, 3,3,3-trifluoropropanoyl, 5,5,5-trifluoropentanoyl, tert-butylaminocarbonyl, 2,2-dimethylpropoxycarbonyl, or 4-tert-butylthiazol-2-yl.

19. The compound of claim 17 which is a compound of formula (VII):

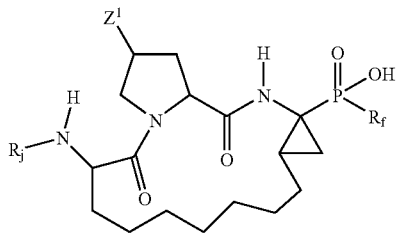

(VII)

or a pharmaceutically acceptable salt wherein:

$R_j$ is cyclopentyloxycarbonyl, 1-[N-(2,2,2-trifluoroethyl)imino]ethyl, α,α-difluorophenethyl, cyclopentylacetyl, butanoyl, 4,4,4-trifluorobutanoyl, 3,3,3-trifluoropropylsulfonyl, 3,3-dimethylbutanoyl, cyclopentylaminocarbonyl, 2-norbornanylacetyl, 2-amino-3,3-dimethylbutanoyl, 4-methylphenyl, 4-trifluoromethylphenyl, 3-trifluoromethylphenyl, 2-trifluoromethylphenyl, 3,3,3-trifluoropropanoyl, 5,5,5-trifluoropentanoyl, tert-butylaminocarbonyl, 2,2-dimethylpropoxycarbonyl, or 4-tert-butylthiazol-2-yl.

20. The compound of claim 1 which is a compound of formula (XV):

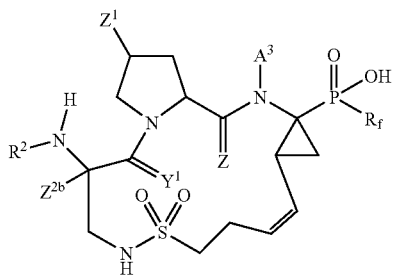

(XV)

or a pharmaceutically acceptable salt thereof.

21. The compound of claim 1 which is a compound of formula (XVI):

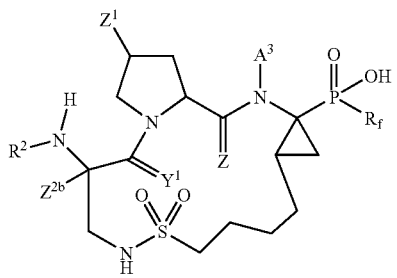

(XVI)

or a pharmaceutically acceptable salt thereof.

22. The compound of claim 1 which is a compound of formula (XVII):

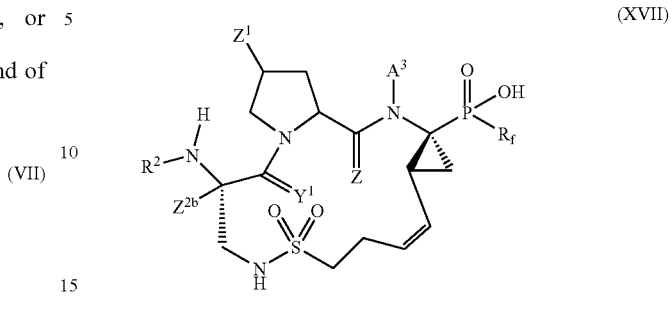

(XVII)

or a pharmaceutically acceptable salt thereof.

23. The compound of claim 1 which is a compound of formula (XVIII):

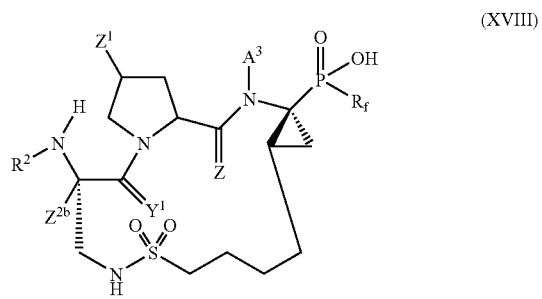

(XVIII)

or a pharmaceutically acceptable salt thereof.

24. The compound of claim 1 which is a compound of formula (XIX):

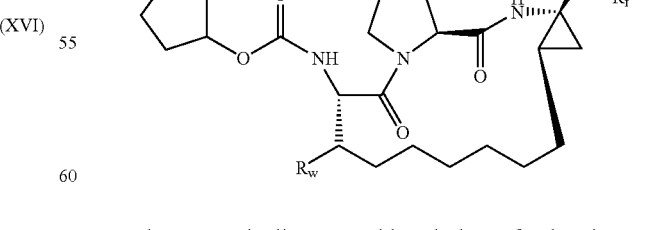

(XIX)

or a pharmaceutically acceptable salt thereof; wherein:

$R_a$ is H or (C1-6)alkoxy;

$R_b$ is H, F, Cl, Br, I, or (C1-6)alkyl;

$R_f$ is alkyl, which is substituted with aryl that is optionally substituted with one or more alkyl, halo, hydroxy, cyano, nitro, amino, alkoxy, alkoxycarbonyl, alkanoyloxy, haloalkyl, or haloalkoxy; and $R_w$ is H or (C1-6)alkyl.

25. The compound of claim 1 which is a compound of formula (XX):

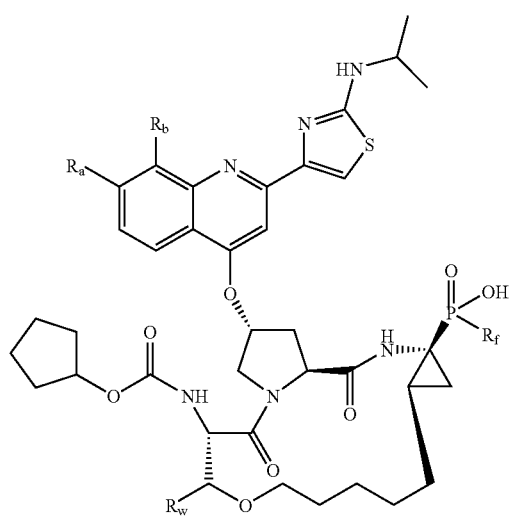

(XX)

or a pharmaceutically acceptable salt thereof; wherein:

$R_a$ is H or (C1-6)alkoxy;

$R_b$ is H, F, Cl, Br, I, or (C1-6)alkyl;

$R_f$ is alkyl, which is substituted with aryl that is optionally substituted with one or more alkyl, halo, hydroxy, cyano, nitro, amino, alkoxy, alkoxycarbonyl, alkanoyloxy, haloalkyl, or haloalkoxy; and $R_w$ is H or (C1-6)alkyl.

26. The compound of claim 24 or 25 wherein $R_a$ is (C1-6) alkoxy.

27. The compound of claim 24 or 25 wherein $R_a$ is methoxy.

28. The compound of claim 24 wherein $R_b$ is H, F, Cl, Br, I, or (C1-6)alkyl.

29. The compound of claim 24 wherein $R_b$ is H.

30. The compound of claim 24 wherein $R_b$ is F, Cl, Br, or I.

31. The compound of claim 24 wherein $R_b$ is Cl.

32. The compound of claim 24 wherein $R_b$ is (C1-6)alkyl.

33. The compound of claim 24 wherein $R_f$ is (C1-6)alkyl substituted with a phenyl ring that is optionally substituted with 1, 2, or 3 alkyl, halo, hydroxy, cyano, nitro, amino, alkoxy, alkoxycarbonyl, alkanoyloxy, haloalkyl, or haloalkoxy.

34. The compound of claim 24 wherein $R_f$ is benzyl or phenethyl that is optionally substituted with 1, 2, or 3 alkyl, halo, hydroxy, cyano, nitro, amino, alkoxy, alkoxycarbonyl, alkanoyloxy, haloalkyl, or haloalkoxy.

35. The compound of claim 24 wherein is 2,6-difluorobenzyl.

36. The compound of claim 24 wherein $R_w$ is methyl.

37. The compound of claim 24 wherein $R_w$ is hydrogen.

38. A compound of formula (XXI):

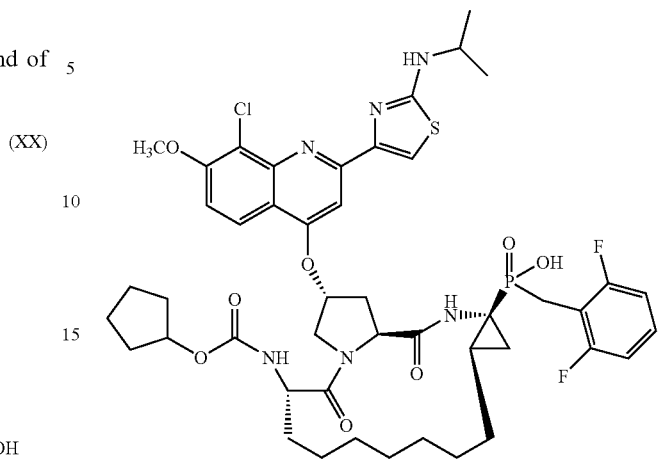

(XXI)

or a pharmaceutically acceptable salt thereof.

39. A compound of formula (XXII):

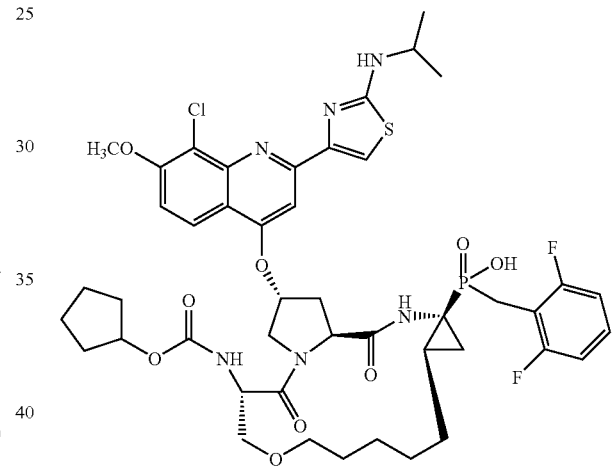

(XXII)

or a pharmaceutically acceptable salt thereof.

40. A compound of formula (XXIII):

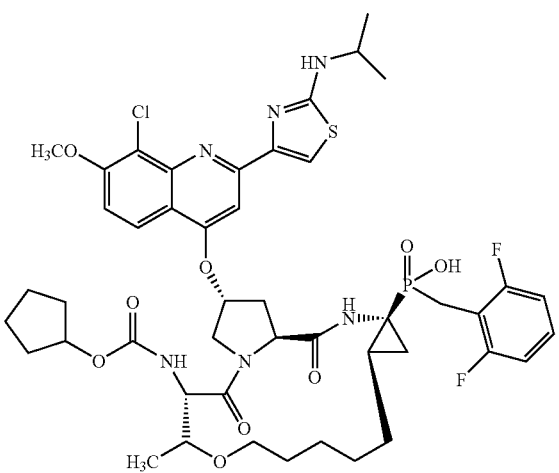

(XXIII)

or a pharmaceutically acceptable salt thereof.

41. The compound of claim 1 which is a compound of formula (XXIV):

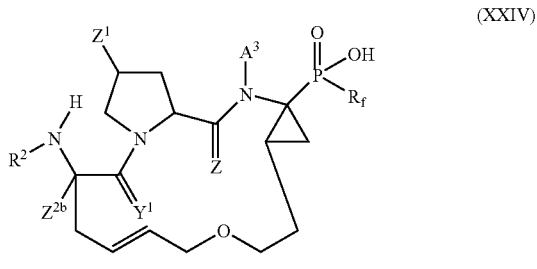

(XXIV)

or a pharmaceutically acceptable salt thereof.

42. The compound of claim 1 which is a compound of formula (XXV):

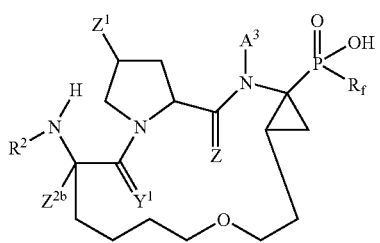

(XXV)

or a pharmaceutically acceptable salt thereof.

43. The compound of claim 1 which is a compound of formula (XXVI):

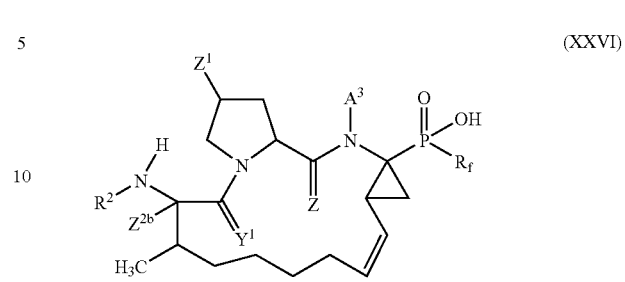

(XXVI)

or a pharmaceutically acceptable salt thereof.

44. A pharmaceutical composition comprising the compound of claim 1 and at least one pharmaceutically acceptable carrier.

45. The pharmaceutical composition according to claim 44, further comprising a nucleoside analogue.

46. The pharmaceutical composition according to claim 45, further comprising an interferon or pegylated interferon.

47. The pharmaceutical composition according to claim 46, wherein said nucleoside analogue is selected from ribavirin, viramidine, levovirin, a L-nucleoside, and isatoribine and said interferon is α-interferon or pegylated interferon.

* * * * *